US011479762B1

(12) United States Patent
Joyce et al.

(10) Patent No.: US 11,479,762 B1
(45) Date of Patent: Oct. 25, 2022

(54) COMPOSITIONS, SYSTEMS, AND METHODS FOR GENOME EDITING

(71) Applicant: Inari Agriculture Technology, Inc., Cambridge, MA (US)

(72) Inventors: Adam Patrick Joyce, Stow, MA (US); Michael Andreas Kock, Rheinfelden (DE)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 708 days.

(21) Appl. No.: 16/557,581

(22) Filed: Aug. 30, 2019

Related U.S. Application Data

(60) Provisional application No. 62/725,910, filed on Aug. 31, 2018.

(51) Int. Cl.
| | | |
|---|---|---|
| *C12N 9/22* | (2006.01) | |
| *C12N 15/11* | (2006.01) | |
| *C12N 15/82* | (2006.01) | |

(52) U.S. Cl.
CPC ............... *C12N 9/22* (2013.01); *C12N 15/11* (2013.01); *C12N 15/8202* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | |
|---|---|---|
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,790,490 B2 | 10/2017 | Zhang et al. |
| 9,896,696 B2 | 2/2018 | Begemann et al. |
| 2015/0059010 A1 | 2/2015 | Cigan et al. |
| 2015/0082478 A1 | 3/2015 | Cigan et al. |
| 2015/0344912 A1 | 12/2015 | Kim et al. |
| 2016/0138008 A1 | 5/2016 | Doudna et al. |

FOREIGN PATENT DOCUMENTS

WO 2016166340 A1 10/2016

OTHER PUBLICATIONS

Begemann et al., "Characterization and Validation of a Novel Group of Type V, Class 2 Nucleases for in vivo Genome Editing", bioRxiv, 2017, pp. 1-9, https://doi.org/10.1101/192799.
Burstein et al., "New CRISPR-Cas Systems from Uncultivated Microbes", published as Nature, 2017, pp. 237-241, vol. 542, No. 7640 doi:10.1038/nature21059.
Cong et al., "Multiplex Genome Engineering Using CRISPR/Cas Systems", Science, 2013, pp. 819-823, vol. 339, No. 6121.
Di Tomasso et al., "The ARiBo Tag: A Reliable Tool for Affinity Purification of RNAs under Native Conditions", Nucleic Acids Research, 2011, pp. 1-10, vol. 39, No. 3, e18.
Hendel et al., "Chemically Modified Guide RNAs Enhance CRISPR-Cas Genome Editing in Human Primary Cells", published as Nature Biotechnology, 2015, pp. 985-989, vol. 33, No. 9.
Kieft et al., "A General Method for Rapid and Nondenaturing Purification of RNAs", RNA, 2004, pp. 988-995, vol. 10.
Lee et al., "RNA-protein Analysis Using a Conditional CRISPR Nuclease", Proceedings of the National Academy of Sciences USA, Apr. 2013, pp. 5416-5421 , vol. 110, No. 14.
Leppek et al., "An Optimized Streptavidin-Binding RNA Aptamer for Purification of Ribonucleoprotein Complexes Identifies Novel ARE-Binding Proteins", Nucleic Acids Research, 2014, pp. 1-15, vol. 42, No. 2.
Park et al., "Extension of the crRNA Enhances Cpf1 Gene Editing in vitro and in vivo", Nature Communications, 2018, pp. 1-12, doi: 10.1038/s41467-018-05641-3.
Parrott et al., "RNA Aptamers for the MS2 Bacteriophage Coat Protein and the Wild-Type RNA Operator have Similar Solution Behaviour", Nucleic Acids Research, 2000, pp. 489-497, vol. 28, No. 2.
Ran et al., "Genome Engineering Using the CRISPR-Cas9 System", Nature Protocols, 2013, pp. 2281-2308, vol. 8, No. 11.
Shmakov et al., "Discovery and Functional Characterization of Diverse Class 2 CRISPR-Cas Systems", Molecular Cell, 2015, pp. 385-397, vol. 60.
Srisawat et al., "RNA Affinity Tags for Purification of RNAs and Ribonucleoprotein Complexes", Methods, Feb. 2002, pp. 156-161, vol. 26, No. 2.
Zetsche et al., "Cpf1 is a Single RNA-Guided Endonuclease of a Class 2 CRISPR-Cas System", Cell, 2015, pp. 759-771, vol. 163.

*Primary Examiner* — Suzanne M Noakes
*Assistant Examiner* — Jae W Lee
(74) *Attorney, Agent, or Firm* — McKee, Voorhees & Sease, PLC

(57) ABSTRACT

This disclosure provides compositions, recombinant expression constructs, and engineered systems that include a polynucleotide including or encoding a Cas12a tracrRNA, and methods for their use. The materials and methods of the disclosure are especially suited to sequence-specific genome editing of eukaryotic genomic sequences.

15 Claims, 14 Drawing Sheets
Specification includes a Sequence Listing.

LbCpf1 putative tracr 1 (19/36=52.8% identity)

Tracr 1 (84 nt)  5' ACTTATACTAAATTTTAACTGTATACTTTCCCAAAATACCATAGGCTCTCTGAATCTCTTAACCCAGATTCCAAGGGCTTTTTT 3'
                     |  || ||| | |    || | | || | |    |||
DR (36 nt)       5' ATCTACACTTAGTAGAAATTATTTAATCTTTGAAAC 3'  (Reverse Complement)

LbCpf1 putative tracr 2 (18/36=50% identity)

Tracr 2 (65 nt)  5' AATTGCAAATCTTTGAAATAATGCAGACTTAAATTTATAAATTCATGGAATAAGGTGATTTTATT 3'
                    |  | ||  |  | ||||| ||  |   |||  |
DR (36 nt)       5' ATCTACACTTAGTAGAAATTATTTAATCTTTGAAAC 3'  (Reverse Complement)

Figure 3

AsCpf1 putative tracr (18/35=51.4% identity)

Tracr 2 (72nt) 5' CATTGTCTAACCTGCAAACCTCCAACTTACTATTGCTAAGGAGTATATATTTTGTATAAAAGGTCTTTTTTC 3'
                                                  |   |  | |     |  |||||||||||  |
DR (35 nt)                                     5' ATCTACAAGAGTAGAAATTAAAAAGGTCTTTTGAC 3' (Reverse Complement)

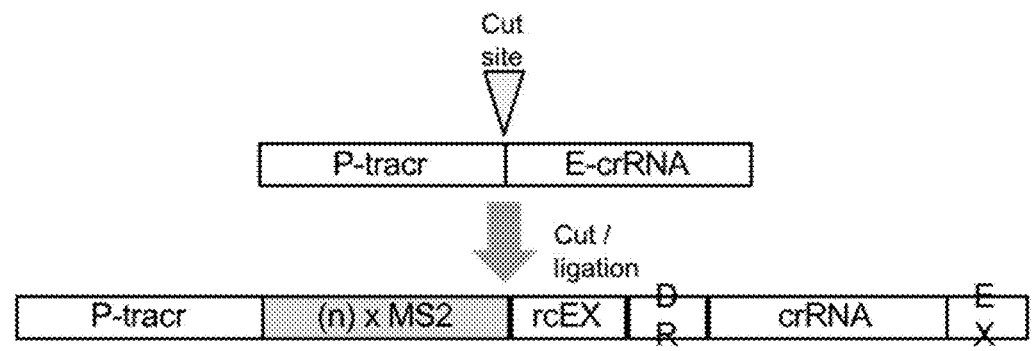
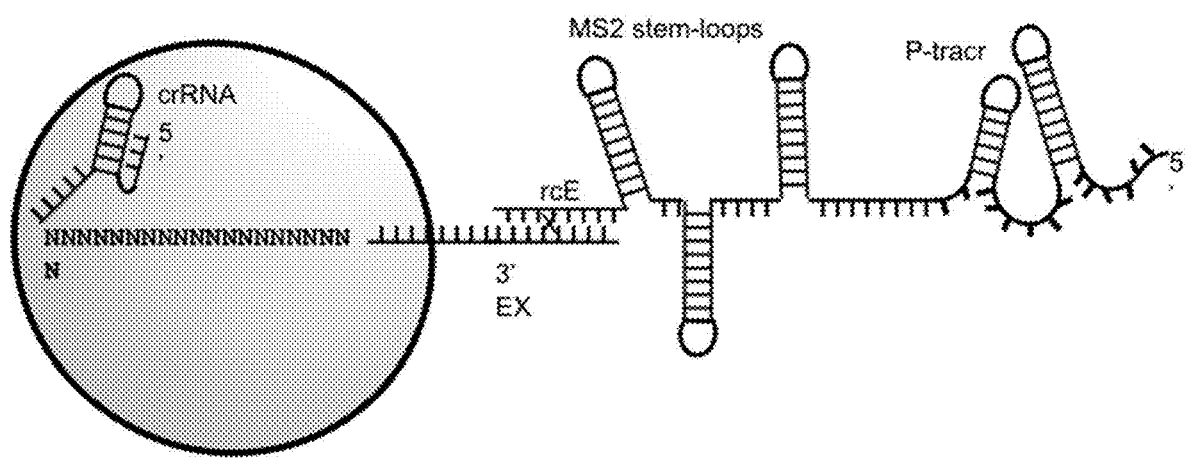
Figure 11

COMPOSITIONS, SYSTEMS, AND METHODS FOR GENOME EDITING

REFERENCE TO RELATED APPLICATIONS AND

This application claims benefit of priority to U.S. Provisional Patent Application No. 62/725,910 filed 31 Aug. 2018, which is incorporated herein by reference in its entirety.

INCORPORATION OF SEQUENCE LISTINGS

A sequence listing containing the file named "10015US1_ST25.txt" which is 527121 bytes (measured in MS-Windows®), comprises 203 biological sequences, and was created on 29 Aug. 2019, is electronically filed herewith via the USPTO's EFS system, and is herein incorporated by reference in its entirety.

A replacement sequence listing containing the file named "10015US1.1_ST25.txt" which is 529404 bytes (measured in MS-Windows®), which comprises 203 biological sequences, which was created on 30 Sep. 2019, and which does not go beyond the disclosure of the originally filed sequence listing file named "10015US1_ST25.txt," is herein incorporated by reference in its entirety.

FIELD

Aspects of this disclosure relate to biotechnology, in particular compositions and methods for genome editing.

BACKGROUND

Recent advances in genome editing technologies have provided opportunities for precise modification of the genome in many types of organisms, including plants and animals. For example, technologies based on genome editing proteins, such as zinc finger nucleases, TALENs, and CRISPR systems are advancing rapidly and it is now possible to target genetic changes to specific DNA sequences in the genome.

CRISPR technology for editing the genes of eukaryotes is disclosed in U.S. Patent Application Publications 2016/0138008A1 (now U.S. Pat. No. 1,022,711) and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 (Cas12a) endonucleases and corresponding guide RNAs and PAM sites are disclosed in U.S. Pat. No. 9,790,490 and U.S. patent application Ser. No. 15/566,528 (national phase of PCT Application PCT/EP2016/058442, published as WO 2016/166340), now published as U.S. Patent Application Publication 2018/0282713. Other CRISPR nucleases useful for editing genomes include C2c1 and C2c3 (see Shmakov et al. (2015) *Mol. Cell*, 60:385-397) and CasX and CasY (see Burstein et al. (2016) Nature, doi:10.1038/nature21059). Plant RNA promoters for expressing CRISPR guide RNA and plant codon-optimized CRISPR Cas9 endonuclease are disclosed in U.S. patent application Ser. No. 15/120,110, published as U.S. Patent Application Publication 2017/0166912, national phase application claiming priority to International Patent Application PCT/US2015/018104 (published as WO 2015/131101 and claiming priority to U.S. Provisional Patent Application 61/945,700). Methods of using CRISPR technology for genome editing in plants are disclosed in U.S. Patent Application Publications U.S. 2015/0082478A1 and U.S. 2015/0059010A1 and in International Patent Application PCT/US2015/038767 A1 (published as WO 2016/007347, claiming priority to U.S. Provisional Patent Application 62/023,246, with U.S. National Phase application U.S. Ser. No. 15/325,116, now published as U.S. Patent Application Publication 2017/0306349).

U.S. Pat. No. 9,790,490 and Zetsche et al. (2015) *Cell*, 163:759-771 teach that a tracrRNA is not required for nuclease cleavage activity of Cpf1 (Cas12a) effector protein complexes and suggest deletion of such sequences from engineered genome editing systems. This disclosure demonstrates that the presence of the tracrRNA as such has a beneficial effect on Cas12a editing efficiency and that the tracrRNA can be usefully employed in genome editing.

SUMMARY

Disclosed herein are polynucleotides, DNA expression systems, compositions, and methods of use thereof, useful for genome editing.

In one aspect, the invention provides a method of tethering a functional RNA molecule to a Cas12a crRNA, the method including hybridizing (a) a functional RNA molecule including a Cas12a tracrRNA and a functional RNA moiety; and (b) a Cas12a crRNA that includes a 3' extension capable of hybridizing with a segment of the functional RNA molecule; thereby tethering the functional RNA molecule to the Cas12a crRNA. In embodiments, the functional RNA molecule is transcribed from a DNA molecule that encodes the Cas12a tracrRNA and the functional RNA moiety; in embodiments, DNA encoding the functional RNA moiety is inserted or integrated at a native (naturally occurring) or artificial (engineered) restriction endonuclease cleavage site that is located in or adjacent to (typically within the 3' region of) the DNA encoding the Cas12a tracrRNA. In embodiments, the crRNA 3' extension includes nucleotides that when base-paired form about one helical turn, or at least 10 contiguous nucleotides. In embodiments, the Cas12a tracrRNA further includes a 5' extension. The functional RNA moiety is characterized by one or more functions. Embodiments of the RNA moiety include RNA sequences for annealing to one or more polynucleotides, RNA sequences that provide structures for binding to other molecules (including proteins or small molecule ligands) or that are catalytically active, or RNA sequences that serve as directly or indirectly detectable labels. In many embodiments of the method, the Cas12a crRNA is complexed with, or is capable of complexing with, a Cas12a nuclease to form a Cas12a ribonucleoprotein complex containing the functional RNA molecule; thus, in embodiments, the method further includes the step of associating or complexing a Cas12a nuclease with a Cas12a crRNA that has (e.g., in a preceding or simultaneous step), or will have (e.g., in a subsequent step) the functional RNA molecule tethered to it. In embodiments, the Cas12a nuclease is one having a naturally occurring sequence (e.g., a native sequence of a Cas12a nuclease such as, but not limited to, LbCas12a, AsCas12a, and FnCas12a); in other embodiments, the Cas12a nuclease includes a modification, such as an amino acid sequence modification or a chemical modification.

In a related aspect, the invention provides a modified Cas12a ribonucleoprotein complex including: (a) a Cas12a nuclease; (b) a functional RNA molecule including a Cas12a tracrRNA and a functional RNA moiety; and (c) a Cas12a crRNA that includes a 3' extension capable of hybridizing with a segment of the functional RNA molecule. In embodiments, the Cas12a nuclease is one having a naturally occurring sequence (e.g., a native sequence of a Cas12a nuclease such as, but not limited to, LbCas12a, AsCas12a, and FnCas12a); in other embodiments, the Cas12a nuclease includes a modification, such as an amino acid sequence modification or a chemical modification. In a preferred embodiment the expression and/or presence of the Cas12a tracrRNA enhances the genome editing capability of the Cas12a nuclease.

In another aspect, the invention provides a method of inserting a nucleotide sequence encoded by a donor polynucleotide at a specific locus in a target DNA, the method including: (a) annealing a donor polynucleotide to the modified Cas12a ribonucleoprotein complex of claim 12, wherein the functional RNA moiety includes an RNA sequence for annealing to the donor polynucleotide, and wherein the Cas12a crRNA includes a spacer sequence that corresponds to a specific target locus in a target DNA, thus forming a donor: RNP complex; and (b) contacting the target DNA with the donor: RNP complex; whereby the nucleotide sequence encoded by the donor polynucleotide is inserted at the specific target locus in the target DNA. In embodiments, the donor polynucleotide includes single-stranded DNA, optionally including chemical modifications. In embodiments, the donor polynucleotide includes double-stranded DNA, optionally including chemical modifications. In embodiments, the donor polynucleotide encodes coding sequence, non-coding sequence (e.g., a non-coding sequence or regulatory element that modifies expression of a target gene located at or near the target locus), or both coding and non-coding sequence. In embodiments, the target DNA is genomic DNA, e.g., genomic DNA or nuclear DNA of a eukaryote. In embodiments, the target DNA is mitochondrial or plastid DNA.

In another aspect, the invention provides a DNA expression system including (a) DNA sequence for a first promoter; and (b) operably linked and heterologous to the first promoter a DNA encoding a first RNA molecule including a Cas12a tracrRNA and including a restriction endonuclease cleavage site (native or engineered) that is suitable for insertion of a sequence coding for a functional RNA moiety. In embodiments, the DNA expression system further includes: (c) optionally, a DNA sequence for a second promoter; (d) operably linked and heterologous to the first promoter or the second promoter, a DNA encoding a Cas12a crRNA that includes a 3' extension capable of hybridizing with a segment of the first RNA molecule; and (e) optionally, a terminator; in embodiments, the first promoter and the DNA encoding the first RNA molecule, and the DNA encoding a Cas12a crRNA that includes a 3' extension are contained in a single construct, and in other embodiments, the first promoter and the DNA encoding the first RNA molecule are contained in a first construct, and the second promoter and the DNA encoding a Cas12a crRNA that includes a 3' extension are contained in a second construct. Where the DNA expression system is provided in a first construct and a second construct, these can be provided in a single vector or in separate vectors. In some embodiments wherein the DNA expression system includes DNA encoding a Cas12a crRNA, the first promoter drives expression of both the DNA encoding the first RNA molecule and the DNA encoding the Cas12a crRNA. In some embodiments, the Cas12a tracrRNA further includes a 5' extension. In many embodiments of the DNA expression system, the Cas12a crRNA is capable of complexing with a Cas12a nuclease to form a Cas12a ribonucleoprotein complex. In a preferred embodiment the expression and/or presence of the Cas12a tracrRNA enhances the genome editing capability of the Cas12a nuclease.

In another aspect, the invention provides a DNA expression system including: (a) DNA sequence for a first promoter; and (b) operably linked and heterologous to the first promoter, a DNA encoding a functional RNA molecule including a Cas12a tracrRNA and a functional RNA moiety. The functional RNA moiety is characterized by one or more functions. Embodiments of the RNA moiety include RNA sequences for annealing to one or more polynucleotides, RNA sequences that provide structures for binding to other molecules (including proteins or small molecule ligands) or that are catalytically active, or RNA sequences that serve as directly or indirectly detectable labels. In embodiments, the DNA expression system further includes: (c) optionally, a DNA sequence for a second promoter; (d) operably linked and heterologous to the first promoter or the second promoter, a DNA encoding a Cas12a crRNA that includes a 3' extension capable of hybridizing with a segment of the functional RNA molecule; and (e) optionally, a terminator. In embodiments wherein the DNA expression system includes the DNA encoding the Cas12a crRNA, the DNA expression system can be provided in a single construct (e.g., where the first promoter drives expression of both the DNA encoding the functional RNA molecule and the DNA encoding the Cas12a crRNA). In embodiments wherein the DNA expression system includes the second promoter, the second promoter can be operably linked to the DNA encoding the crRNA (e.g., in a second construct). In embodiments where the DNA expression system is provided in two constructs, these can be in a single vector or in separate vectors. In embodiments, the Cas12a tracrRNA further includes a 5' extension. In many embodiments of the DNA expression system, the Cas12a crRNA is capable of complexing with, a Cas12a nuclease to form a Cas12a ribonucleoprotein complex containing the functional RNA molecule. In embodiments, the Cas12a nuclease is one having a naturally occurring sequence (e.g., a native sequence of a Cas12a nuclease such as, but not limited to, LbCas12a, AsCas12a, and FnCas12a); in other embodiments, the Cas12a nuclease includes a modification, such as an amino acid sequence modification or a chemical modification. In a preferred embodiment the expression and/or presence of the Cas12a tracrRNA enhances the genome editing capability of the Cas12a nuclease.

In another aspect, the invention provides an engineered system including: (a) a Cas12a nuclease; and (b) at least one engineered Cas12a crRNA, or a polynucleotide encoding the engineered Cas12a crRNA, wherein the engineered Cas12a crRNA includes (i) at least one direct repeat sequence or fragment thereof that is capable of associating with the Cas12a nuclease, and (ii) a spacer sequence that is designed to hybridize with a target sequence in a eukaryotic cell, wherein the at least one direct repeat sequence or fragment thereof is adjacent to and 5' to the spacer sequence; and (c) a Cas12a tracrRNA including a nucleotide sequence that has at least 50% complementarity with, the nucleotide sequence of the at least one direct repeat of the engineered Cas12a crRNA. In another aspect, the invention further provides an engineered system including: (a) a Cas12a nuclease; and (b) at least one engineered Cas12a crRNA, or a polynucleotide encoding the engineered Cas12a crRNA, wherein the engineered Cas12a crRNA includes (i) at least one direct repeat sequence or fragment thereof that is capable of associating with the Cas12a nuclease, and (ii) a spacer sequence that is designed to hybridize with a target sequence in a eukaryotic cell, wherein the at least one direct repeat sequence or fragment thereof is adjacent to and 5' to the spacer sequence; and (c) a Cas12a tracrRNA including a naturally occurring putative Cas12a tracrRNA sequence that is identified from the same genomic region as the Cas12a nuclease by at least the following steps: (i) identifying in the genomic region flanking the DNA encoding the Cas12a nuclease at least one nucleotide sequence that includes a CRISPR array including direct repeats, and (ii) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat. In yet another aspect, the invention provides an engineered system including: (a) one or more nucleotide sequences encoding a Cas12a nuclease; and (b) one or more nucleotide sequences encoding at least one engineered Cas12a crRNA that is designed to form a complex with the Cas12a nuclease and that includes a spacer sequence designed to hybridize with a target sequence in a eukaryotic cell; and (c) one or more nucleotide sequences encoding at least one Cas12a tracrRNA. In yet another aspect, the invention provides an engineered system including: (a) a Cas12a nuclease, or one or more nucleotide sequences encoding the Cas12a nuclease; and (b) at least one engineered Cas12a crRNA designed to form a complex with the Cas12a nuclease and including a spacer sequence designed to hybridize with a target sequence in a eukaryotic cell, or one or more nucleotide sequences encoding the at least one engineered Cas12a crRNA polynucleotide; and (c) at least one tracrRNA, or one or more nucleotide sequences encoding the at least one Cas12a tracrRNA. In embodiments of these engineered systems, the engineered Cas12a crRNA, or the polynucleotide (such as a pre-processed Cas12a crRNA precursor transcript) encoding the engineered Cas12a crRNA, further includes at least one direct repeat sequence or fragment thereof capable of associating with the Cas12a nuclease, wherein the at least one direct repeat sequence or fragment thereof is adjacent to and 3' to the spacer sequence. In embodiments of these engineered systems, the engineered Cas12a crRNA further includes a 3' extension adjacent to the spacer sequence. In embodiments of these engineered systems, the eukaryotic cell is a non-human animal cell (e.g., a cell of an animal selected from the group consisting of invertebrates, vertebrates, insects, arthropods, mollusks, fish, reptiles, amphibians, birds, mammals, primates, and non-human primates), a human cell, a plant cell, or a fungal cell. In embodiments of these engineered systems, the eukaryotic cell is in vitro, ex vivo, or in vivo.

In another aspect, the invention provides an engineered system including one or more vectors including: (a) a first regulatory element (such as a promoter) that is heterologous to and operably linked to one or more nucleotide sequences encoding a Cas12a nuclease; and (b) a second regulatory element (such as a promoter) that is heterologous to and operably linked to one or more nucleotide sequences encoding at least one engineered Cas12a crRNA that is designed to form a complex with the Cas12a nuclease and that includes a spacer sequence designed to hybridize with a target sequence in a eukaryotic cell; and (c) a third regulatory element (such as a promoter) that is heterologous to and operably linked to one or more nucleotide sequences encoding at least one Cas12a tracrRNA; wherein components (a) and (b) and (c) are located on the same vector or on different vectors of the system. In embodiments each of the regulatory elements includes one or more expression elements (such as a promoter, an enhancer, or an intron) that is functional in a eukaryotic cell.

In another aspect, the invention provides an engineered system including one or more vectors including: (a) a first expression cassette including at least a first promoter that is heterologous to and operably linked to one or more nucleotide sequences encoding a Cas12a nuclease and—optionally—a first transcription terminator sequence; and (b) a second expression cassette including at least a second promoter that is heterologous to operably linked to one or more nucleotide sequences encoding at least one engineered Cas12a crRNA that is designed to form a complex with the Cas12a nuclease and that includes a spacer sequence designed to hybridize with a target sequence in a eukaryotic cell and—optionally—a second transcription terminator sequence; and (c) a third expression cassette including at least a third promoter that is heterologous to operably linked to one or more nucleotide sequences encoding at least one Cas12a tracrRNA and—optionally—a third transcription terminator sequence, wherein components (a) and (b) and (c) are located on the same vector or on different vectors of the system. In embodiments each of the promoters and each of the transcription terminator sequences is functional in a eukaryotic cell. In embodiments, each of the promoters is heterologous to the nucleotide sequence of which the promoter drives expression.

Further aspects of the invention are related to the engineered systems disclosed and claimed herein. These aspects include compositions (e.g., a delivery particle or a delivery liquid) that include one or more of the engineered systems. Embodiments of the compositions include those wherein the Cas12a tracrRNA is present in a molar excess, relative to the amount of Cas12a nuclease. Specific embodiments of the compositions include those wherein the Cas12a tracrRNA is present in a molar amount that is at least 10-fold greater than the molar amount of the Cas12a nuclease. Additional aspects of the invention include a method of modifying a locus of interest having a target sequence of a eukaryotic cell including delivering one or more of the engineered systems to the locus of interest, wherein the spacer sequence hybridizes with the target sequence, whereby modification of the locus of interest occurs. In embodiments of the method, the locus of interest is within a eukaryotic cell. In embodiments of the method, the eukaryotic cell is a non-human animal cell (e.g., a cell of an animal selected from the group consisting of invertebrates, vertebrates, insects, arthropods, mollusks, fish, reptiles, amphibians, birds, mammals, primates, and non-human primates), a human cell, a plant cell, or a fungal cell. In embodiments of the method, the eukaryotic cell is in vitro, ex vivo, or in vivo. In embodiments of the method, the modification of the locus of interest is an insertion of at least one nucleotide, a deletion of at least one nucleotide, a change of at least one nucleotide (such as creation of a point mutation in the locus), non-homologous end-joining (NHEJ), or homology-dependent repair (HDR).

In another aspect, the invention provides a method of editing a genetic locus with a Cas12a nuclease, including contacting DNA that includes the genetic locus with: (a) a Cas12a nuclease; and (b) an engineered Cas12a crRNA that includes a spacer sequence that is designed to hybridize with a target sequence in the genetic locus; and (c) a Cas12a tracrRNA, thereby editing the genetic locus; wherein the efficiency of editing of the genetic locus is increased compared to a control method in which the DNA that includes the genetic locus is contacted with the Cas12a nuclease and the Cas12a crRNA, but not the Cas12a tracrRNA. In embodiments, the efficiency of editing is assessed by quantifying the amount of Cas12a nuclease required to obtain a given percentage of edited target sequences (or percentage of cells containing the edited target sequences); efficiency is increased where a given editing efficiency is achieved using a lower amount of Cas12a nuclease. In embodiments of the method, the Cas12a tracrRNA is provided in a molar excess, relative to the Cas12a nuclease. In embodiments of the method, the Cas12a tracrRNA is provided in a molar amount that is at least 10-fold greater than the molar amount of the Cas12a nuclease.

In a related aspect, the invention further provides a composition for modifying a genetic locus in a eukaryotic cell, including: (a) a eukaryotic cell containing a genetic locus to be modified; and (b) a Cas12a nuclease, or a polynucleotide encoding the Cas12a nuclease; and (c) an engineered Cas12a crRNA that includes a spacer sequence corresponding to a specific sequence in the genetic locus, or a polynucleotide encoding the Cas12a crRNA; and (d) a Cas12a tracrRNA, or a polynucleotide encoding the Cas12a tracrRNA, wherein the Cas12a tracrRNA is provided in molar excess relative to the Cas12a nuclease. In embodiments of the composition, the Cas12a tracrRNA is identified from the same genomic region as the Cas12a nuclease by at least the following steps: (a) identifying in the genomic region flanking the DNA encoding the Cas12a nuclease at least one nucleotide sequence that includes a CRISPR array including direct repeats; (b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat. In embodiments of the composition, the Cas12a tracrRNA is present in a molar excess, relative to the Cas12a nuclease. In embodiments of the composition, the Cas12a tracrRNA is present in a molar amount that is at least 10-fold greater than the molar amount of the Cas12a nuclease.

The DNA expression systems, engineered systems, compositions, and methods disclosed herein can be employed with Cas12a nucleases or modified variants thereof. In embodiments, the Cas12a nuclease is any one of the Cas12a ("Cpf1") nucleases disclosed in U.S. Pat. No. 9,790,490 or in U.S. patent application Ser. No. 15/566,528 (national phase entry of International Application No. PCT/EP2016/058442, published as WO2016166340), or in U.S. Pat. No. 9,896,696 which are specifically incorporated herein by reference. In embodiments, the Cas12a nuclease is a Cas12a ("Cpf1") nuclease identified from *Francisella novicida* U112 (FnCas12a or "FnCpf1"), from *Acidaminococcus* sp. BV3L6 (AsCas12a or "AsCpf1"), or from Lachnospiraceae bacterium ND2006 (LbCas12a or "LbCpf1"), or is an orthologue thereof, such as an orthologue having at least 50% sequence identity to FnCas12a ("FnCpf1"); see, e.g., the FnCpf1 nuclease contained in the FnCpf1 locus having SEQ ID NO:211 in U.S. Pat. No. 9,790,490, incorporated herein by reference. In embodiments, a Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, Smithella sp. SCADC, *Acidaminococcus* sp. BV3L6, Lachnospiraceae bacterium MA2020, Candidatus Methanoplasma *termitum*, *Eubacterium eligens*, *Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease selected from the group consisting of (1) a variant LbCpf1 that differs from a wild type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease includes orthologues of LbCas12a, AsCas12a, or FnCas12a. In embodiments, the Cas12a nuclease is a deactivated Cas12a nuclease, a tagged or labelled Cas12a nuclease, or a Cas12a fusion; examples are described elsewhere in this disclosure. The systems and compositions including a tracrRNA and methods of use thereof that are disclosed herein can also be employed with related Cas nucleases, including Csm nucleases, e.g., ObCsm1 (GenBank accession number OGX23684), SmCsm1 (GenBank accession number KF067988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

Related aspects of the invention include eukaryotes and eukaryotic cells containing a genomic modification obtained by use of the polynucleotides, compositions, engineered systems, and methods of use thereof disclosed herein. Embodiments include non-human animals and non-human animal cells, non-human animal stem cells, human cells, human stem cells, and human somatic (non-gametic) cells; isolated tissue (e.g., nervous tissue, epithelial tissue, liver, spleen, pancreas, muscle tissue, bone, connective tissue, endocrine system tissues, and tumours) or cells (e.g., blood cells, erythrocytes, leukocytes, lymphocytes, liver cells, bone cells, immune cells, T cells, B cells, dendritic cells, and tumour cells) or cell organelles (e.g., mitochondria or chloroplasts, either isolated or contained within the eukaryotic cell, tissue, or organism) obtained from a non-human animal or from a human; engineered hybridoma cells; fungi, fungal cells, plants, plant tissue, plant cells, and seeds having such a genomic modification, e.g., a genomic modification including a heterologous nucleotide sequence encoded by a donor polynucleotide and integrated into a specific locus in the genome, wherein the donor polynucleotide is provided in a donor: RNP complex that includes the donor polynucleotide ("donor") annealed to a modified Cas12a ribonucleoprotein ("RNP") that includes: (a) a Cas12a nuclease; (b) a functional RNA molecule including a Cas12a tracrRNA and a functional RNA moiety, wherein the functional RNA moiety includes an RNA sequence for annealing to the donor polynucleotide and optionally an RNA sequence for annealing to the crRNA 3' extension; and (c) a Cas12a crRNA that includes a 3' extension capable of hybridizing with a segment of the functional RNA molecule. Additional aspects of the invention include progeny plants or progeny seeds obtained from a plant, plant cell, plant tissue, or seed having a genomic modification obtained by use of the polynucleotides, compositions, and methods of use disclosed herein. Also encompassed by the invention are raw plant materials, processed plant products, and commodity plant products obtained from a plant, plant cell, plant tissue, or seed (or from progeny plants or seeds thereof) having a genomic modification obtained by use of the polynucleotides, compositions, and methods of use disclosed herein.

BRIEF DESCRIPTION OF THE DRAWINGS

FIG. 3 illustrates the alignments of the reverse complement of the LbCpf1 direct repeat (DR) sequence, ATCTACACTTAGTAGAAATTATTTAATCTTTGAAAC (SEQ ID NO:5), with the LbCpf1 tracrRNA 1 ("putative tracrRNA 1") (SEQ ID NO:2) (top, showing 52.8% identity between the two sequences) and the LbCpf1 tracrRNA 2 ("putative tracrRNA 2") (SEQ ID NO:4) (bottom, showing 50.0% identity between the two sequences), as described in detail in Example 1.

FIG. 6 illustrates the alignment of the reverse complement of the AsCpf1 direct repeat (DR) sequence, ATCTACAAGAGTAGAAATTAAAAAGGTCTTTTGAC (SEQ ID NO:8) with the AsCpf1 tracrRNA ("putative tracrRNA") (SEQ ID NO:7), showing 51.4% identity between the two sequences as described in detail in Example 1.

FIG. 9B (right) schematically depicts an alternative design wherein the DNA expression system includes (a) DNA sequence for a first promoter; (b) operably linked and heterologous to the first promoter, a DNA encoding a first RNA molecule including a Cas12a tracrRNA or putative tracrRNA and including a restriction endonuclease cleavage site that is suitable for insertion of a sequence coding for a functional RNA moiety; and (c) operably linked and heterologous to the first promoter, a DNA encoding a Cas12a crRNA including multiple guide RNAs (Cas12a crRNAs), and including a 3' extension capable of hybridizing with a segment of the first RNA molecule, as described in detail in Example 3.

FIG. 9C (right) further schematically depicts an expression construct for expressing a guide RNA (Cas12a crRNA), as described in detail in Example 3.

FIG. 10 (bottom) schematically depicts a second DNA expression system, described in detail in Example 3, and similar to that shown in FIG. 10 (top), except that the guide RNA includes multiple guide RNAs, and includes a 3' extension capable of hybridizing with a segment of the first RNA molecule; the 3'-most direct repeat is optional.

FIG. 11 (top) schematically depicts construction of the DNA encoding the functional RNA molecule by cleavage at an HphI restriction endonuclease cleavage site ("cut site") in or adjacent to a Lb Cas12a tracrRNA ("P-tracr") and before the LbCas12a crRNA with a 3' extension ("E-crRNA"), insertion of DNA encoding multiple copies of an MS2 aptamer ("(n) x MS2") as well as sequence for annealing ("rcEX") to the crRNA 3' extension ("EX"), and ligation to form the DNA encoding the functional RNA molecule, which can be complexed with the Cas12a nuclease to form the ribonucleoprotein depicted in FIG. 11 (bottom).

DETAILED DESCRIPTION OF THE INVENTION

Figure 1:
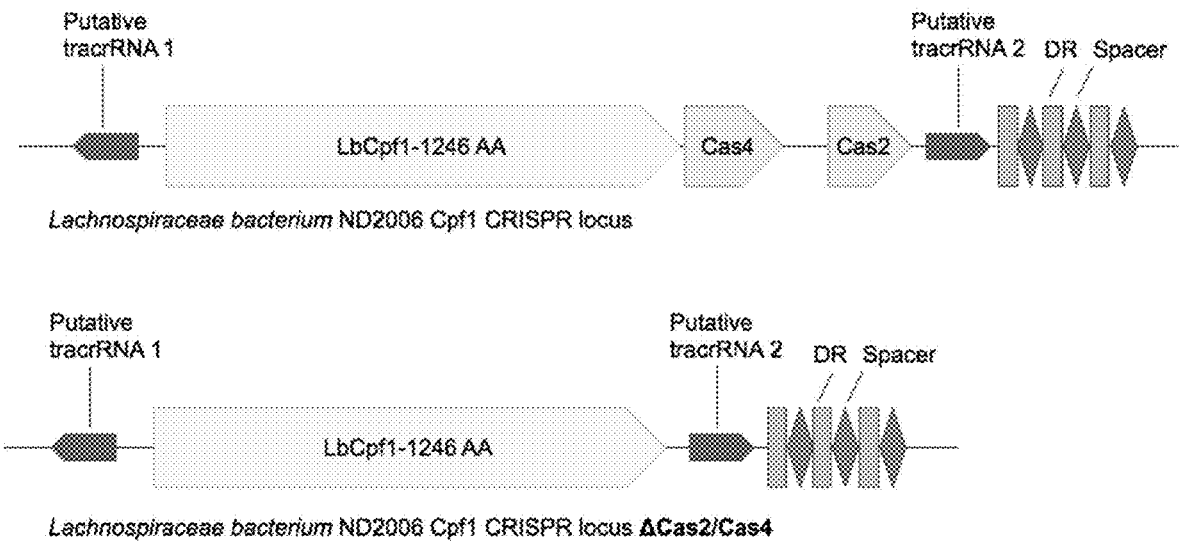
FIG. 1 illustrates schematics of the Lachnospiraceae bacterium ND2006 Cas12a ("LbCpf1") CRISPR locus and Cas12a tracrRNA ("putative tracrRNA") location as described in detail in Example 1. The schematics are shown with (upper figure) and without (lower figure) the Cas4 and Cas2 components of the locus. The direct repeats ("DR") are indicated by upright rectangles and the spacer sequences indicated by diamonds.

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art. Where a term is provided in the singular, the inventors also contemplate aspects of the invention described by the plural of that term. As used herein, the terms "comprise," "comprises," "comprising," "include," "includes," and "including" can be interchanged and are to be construed as at least having the features to which they refer while not excluding any additional unspecified features. The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

By "polynucleotide" is meant a nucleic acid molecule containing multiple nucleotides and refers to "oligonucleotides" (defined here as a polynucleotide molecule between 2-25 nucleotides in length) and polynucleotides of 26 or more nucleotides. Polynucleotides are generally described as single- or double-stranded. Where a polynucleotide contains double-stranded regions formed by intra- or intermolecular hybridization, the length of each double-stranded region is conveniently described in terms of the number of base pairs. Aspects of this invention include the use of polynucleotides or compositions containing polynucleotides; embodiments include one or more oligonucleotides or polynucleotides or a mixture of both, including single- or double-stranded RNA or single- or double-stranded DNA or double-stranded DNA/RNA hybrids or chemically modified analogues or a mixture thereof. In various embodiments, a polynucleotide includes a combination of ribonucleotides and deoxyribonucleotides (e.g., synthetic polynucleotides consisting mainly of ribonucleotides but with one or more terminal deoxyribonucleotides or synthetic polynucleotides consisting mainly of deoxyribonucleotides but with one or more terminal dideoxyribonucleotides), or includes non-canonical nucleotides such as inosine, thiouridine, or pseudouridine. In embodiments, the polynucleotide includes chemically modified nucleotides (see, e.g., Verma and Eckstein (1998) *Annu. Rev. Biochem.*, 67:99-134); for example, the naturally occurring phosphodiester backbone of an oligonucleotide or polynucleotide can be partially or completely modified with phosphorothioate, phosphorodithioate, or methylphosphonate internucleotide linkage modifications; modified nucleoside bases or modified sugars can be used in oligonucleotide or polynucleotide synthesis; and oligonucleotides or polynucleotides can be labelled with a fluorescent moiety (e.g., fluorescein or rhodamine or a fluorescence resonance energy transfer or FRET pair of chromophore labels) or other label (e.g., biotin or an isotope). Modified nucleic acids, particularly modified RNAs, are disclosed in U.S. Pat. No. 9,464,124, incorporated by reference in its entirety herein.

"CRISPR (Clustered Regularly Interspaced Short Palindromic Repeats)/Cas (CRISPR-associated) systems," or CRISPR systems, are adaptive defense systems originally discovered in bacteria and archaea. CRISPR systems use RNA-guided nucleases termed CRISPR-associated or "Cas" endonucleases (e.g., Cas9 or Cas12a ("Cpf1")) to cleave foreign DNA. In atypical CRISPR/Cas system, a Cas endonuclease is directed to a target nucleotide sequence (e.g., a site in the genome that is to be sequence-edited) by sequence-specific, non-coding "guide RNAs" that target single- or double-stranded DNA sequences. In microbial hosts, CRISPR loci encode both Cas endonucleases and "CRISPR arrays" of the non-coding RNA elements that determine the specificity of the CRISPR-mediated nucleic acid cleavage.

Two classes (1 and 2) of CRISPR systems have been identified across a wide range of bacterial hosts. The well characterized class 2 CRISPR systems use a single Cas endonuclease (rather than multiple Cas proteins). One class 2 CRISPR system includes a type II Cas endonuclease such as Cas9, a CRISPR RNA ("crRNA"), and a trans-activating crRNA ("tracrRNA"). A "trans-activating crRNA" or "tracrRNA" is a trans-encoded small RNA that is partially homologous to repeats within a CRISPR array. At least in the case of Cas9 type CRISPR systems, both a tracrRNA and a crRNA are required for the CRISPR array to be processed and for the nuclease to cleave the target DNA sequence. In contrast, Cas12a type CRISPR systems have been reported to function without a tracrRNA, with the Cas12a CRISPR arrays processed into mature crRNAs without the requirement of a tracrRNA; see Zetsche et al. (2015) *Cell,* 163: 759-771 and U.S. Pat. No. 9,790,490. The Cas9 crRNA contains a "spacer sequence", typically an RNA sequence of about 20 nucleotides (in various embodiments this is 20, 21, 22, 23, 24, 25, or up to about 30 contiguous nucleotides in length) that corresponds to (e.g., is identical or nearly identical to, or alternatively is complementary or nearly complementary to) a target DNA sequence of about equivalent length. The Cas9 crRNA also contains a region that binds to the Cas9 tracrRNA to form a partially double-stranded structure which is cleaved by RNase III, resulting in a crRNA:tracrRNA hybrid or duplex. The crRNA:tracrRNA hybrid then directs the Cas9 endonuclease to recognize and cleave the target DNA sequence; in some examples, a tracrRNA and crRNA (e.g., a crRNA including a spacer sequence) can be included in a chimeric nucleic acid referred to as a "single guide RNA" (sgRNA).

The Cas12a ("Cpf1") CRISPR system includes the type V endonuclease Cas12a (also known as "Cpf1"). Cas12a nucleases are characterized as having only a RuvC nuclease domain, in contrast to Cas9 nucleases which have both RuvC and HNH nuclease domains. Cas12a nucleases are generally smaller proteins than Cas9 nucleases, and can function with a smaller guide RNA (e.g., a crRNA having at least one spacer flanked by direct repeats), which are practical advantages in that the nuclease and guide RNAs are more economical to produce and potentially more easily delivered to a cell. Examples of Cas12a nucleases include AsCas12a or "AsCpf1" (from *Acidaminococcus* sp.) and LbCas12a or "LbCpf1" (from Lachnospiraceae bacteria). In contrast to Cas9 type CRISPR systems, Cas12a-associated ("Cpf1"-associated) CRISPR arrays have been reported to be processed into mature crRNAs without the requirement of a tracrRNA, i.e., the naturally occurring Cas12a (Cpf1) CRISPR system was reported to require only the Cas12a (Cpf1) nuclease and a Cas12a crRNA to cleave the target DNA sequence; see Zetsche et al. (2015) *Cell,* 163:759-771; U.S. Pat. No. 9,790,490.

The term "tracrRNA" sequence or analogous terms includes any polynucleotide sequence that has sufficient complementarity with a crRNA sequence to hybridize. Embodiments of tracrRNA sequences useful in the compositions, engineered systems, and methods provided by this disclosure include those described as a "putative transactivating crRNA" or "putative tracrRNA" in U.S. Pat. No. 9,490,490 (e.g., in FIGS. 46, 48-51, and 54 of U.S. Pat. No. 9,490,490, and SEQ IDS NO: 28, 31, 34, 40, 43, 44, 47, and 50 of U.S. Pat. No. 9,490,490) and its priority documents, all of which are incorporated by reference herein. Embodiments of methods of identifying orthologues of CRISPR-Cas system enzymes may involve identifying tracrRNA sequences in genomes of interest.

The term "Cas12a tracrRNA" as used herein means a naturally occurring Cas12a tracrRNA or an engineered derivative thereof. In a preferred embodiment, the term "Cas12a tracrRNA" refers to a naturally occurring Cas12a tracrRNA has a nucleotide sequence that includes or comprises: (a) a nucleotide sequence or region of about 60 to about 100 contiguous nucleotides that has more than 50% identity to the direct repeat (DR) or tracr mate sequence in the Cas12a crRNA, preferably also has (b) secondary structure, and preferably also has (c) a transcriptional terminator. In some embodiments, a naturally occurring Cas12a tracrRNA has a nucleotide sequence that includes or comprises: (a) a nucleotide sequence or region of about 60 to about 100 contiguous nucleotides that has more than 50% identity to the direct repeat (DR) or tracr mate sequence in the Cas12a crRNA, and preferably also has (b) secondary structure, but is not associated with a transcriptional terminator. In some embodiments, the Cas12a tracrRNA is physically associated with the corresponding Cas12a crRNA and/or with the corresponding Cas12a nuclease. In other embodiments, the Cas12a tracrRNA is not physically associated with the corresponding Cas12a crRNA and/or with the corresponding Cas12a nuclease.

A naturally occurring tracrRNA sequence can be identified from a genome as DNA sequence encoding a RNA molecule (a "putative tracrRNA") that is predicted to be or putatively transcribed (or that may be determined to be transcribed, e.g., by RNA analysis) from a CRISPR genomic region, specifically from a locus that flanks the DNA encoding the CRISPR nuclease and that includes a predicted transcriptional terminator in the direction of transcription; is about 60 to about 100 nucleotides in length, e.g., 60-80 nucleotides, 60-85 nucleotides, 60-90 nucleotides, or 65-95 nucleotides; and is not a direct repeat in the CRISPR array, but rather has a nucleotide sequence of sufficient complementarity with a crRNA sequence to hybridize, e.g., of at least 50% identity to or at least 50% complementarity to the direct repeat in a CRISPR array. Steps for identifying tracrRNA sequences have been described, e.g., in U.S. Pat. No. 9,790,490, incorporated here by reference: "Identification of tracr sequences may relate to the following steps: Search for the direct repeats or tracr mate sequences in a database to identify a CRISPR region comprising a CRISPR enzyme. Search for homologous sequences in the CRISPR region flanking the CRISPR enzyme in both the sense and antisense directions. Look for transcriptional terminators and secondary structures. Identify any sequence that is not a direct repeat or a tracr mate sequence but has more than 50% identity to the direct repeat or tracr mate sequence as a potential tracr sequence. Take the potential tracr sequence and analyze for transcriptional terminator sequences associated therewith." RNA sequencing can be used to further characterize such sequences identified as potential or putative tracrRNAs.

In embodiments, an engineered Cas12a tracrRNA is used in place of or as a substitute for a naturally occurring tracrRNA or putative tracrRNA identified from a genome. In embodiments, an engineered Cas12a tracrRNA is designed based on guidelines similar to those employed for identifying a naturally occurring tracrRNA or putative tracrRNA identified from a genome. In embodiments, an engineered Cas12a tracrRNA is designed to have a sequence of about 60 to about 100 ribonucleotides and to have at least 50% complementarity to the sequence of the direct repeat of the Cas12a crRNA with which the engineered Cas12a tracrRNA is meant to be used. Engineered Cas12a tracrRNAs can be expressed with any of the systems described in this disclosure, e.g., in an expression construct using any of the promoters, terminator, or other expression elements described herein.

The genomic DNA sequence targeted for editing or modification must generally be adjacent to a "protospacer adjacent motif" ("PAM") that is specific for a given Cas endonuclease; however, PAM sequences are short and relatively non-specific, appearing throughout a given genome. CRISPR endonucleases identified from various prokaryotic species have unique PAM sequence requirements; examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). Some endonucleases, e.g., Cas9 endonucleases, are associated with G-rich PAM sites, e.g., 5'-NGG, and perform blunt-end cleaving of the target DNA at a location three nucleotides upstream from (5' from) the PAM site. Cas12a (Cpf1) CRISPR systems cleave the target DNA adjacent to a short T-rich PAM sequence, e.g., 5'-TTN, in contrast to the G-rich PAM sequences identified for Cas9 systems. Examples of Cas12a PAM sequences include those for the naturally occurring *Acidaminococcus* sp. BV3L6 Cpf1 (AsCpf1) and Lachnospiraceae bacterium ND2006 Cpf1 (LbCpf1) TTTV, where V can be A, C, or G. In some instances, Cas12a can also recognize a 5'-CTA PAM motif. Other examples of potential Cas12a PAM sequences include TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide). Various methods (including in silico and/or wet lab methods) for identification of the appropriate PAM sequence are known in the art and are routine, and any convenient method can be used. A PAM sequence can be identified using a PAM depletion assay. Cas12a cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e.g., Zetsche et al. (2015) *Cell,* 163:759-771.

For the purposes of gene editing, CRISPR arrays can be designed to contain one or multiple guide RNAs designed to target a DNA sequence for editing, where the guide RNA includes at least one spacer sequence that corresponds to a specific locus of about equivalent length in the target DNA; see, for example, Cong et al. (2013) *Science,* 339:819-823; Ran et al. (2013) *Nature Protocols,* 8:2281-2308. As used herein "guide RNA" or "gRNA" refers to a nucleic acid that comprises or includes a nucleotide sequence (sometimes referred to a "spacer sequence") that corresponds to (e.g., is identical or nearly identical to, or alternatively is complementary or nearly complementary to) a target DNA sequence (e.g., a contiguous nucleotide sequence that is to be modified) in a genome; the guide RNA functions in part to direct the CRISPR nuclease to a specific location on the genome. In embodiments, a gRNA is a CRISPR RNA ("crRNA"), such as the engineered Cas12a crRNAs described in this disclosure. For nucleases (such as a Cas9 nuclease) that require a combination of a trans-activating crRNA ("tracrRNA") and a crRNA for the nuclease to cleave the target nucleotide sequence, the gRNA can be a tracrRNA:crRNA hybrid or duplex, or can be provided as a single guide RNA (sgRNA). At least 16 or 17 nucleotides of gRNA sequence corresponding to a target DNA sequence are required by Cas9 for DNA cleavage to occur; for Cas12a (Cpf1) at least 16 nucleotides of gRNA sequence corresponding to a target DNA sequence are needed to achieve detectable DNA cleavage and at least 18 nucleotides of gRNA sequence corresponding to a target DNA sequence were reported necessary for efficient DNA cleavage in vitro; see Zetsche et al. (2015) *Cell,* 163:759-771. Cas12a (Cpf1) endonuclease and corresponding guide RNAs and PAM sites are disclosed in U.S. Pat. No. 9,790,490, which is incorporated herein by reference in its entirety and particularly for its disclosure of DNA encoding Cas12a (Cpf1) endonucleases and guide RNAs and PAM sites. In practice, guide RNA sequences are generally designed to contain a spacer sequence of between 17-24 contiguous nucleotides (frequently 19, 20, or 21 nucleotides) with exact complementarity (e.g., perfect base-pairing) to the targeted gene or nucleic acid sequence; guide RNAs having spacers with less than 100% complementarity to the target sequence can be used (e.g., a gRNA with a spacer having a length of 20 nucleotides and between 1-4 mismatches to the target sequence), but this can increase the potential for off-target effects. The design of effective guide RNAs for use in plant genome editing is disclosed in U.S. Patent Application Publication 2015/0082478 A1, the entire specification of which is incorporated herein by reference. Chemically modified sgRNAs have been demonstrated to be effective in Cas9 genome editing; see, for example, Hendel et al. (2015) *Nature Biotechnol.,* 33:985-991.

CRISPR-type genome editing has value in various aspects of agriculture research and development. CRISPR elements, e.g., CRISPR endonucleases and CRISPR single-guide RNAs, are useful in effecting genome editing without remnants of the CRISPR elements or selective genetic markers occurring in progeny. Alternatively, genome-inserted CRISPR elements are useful in plant lines adapted for multiplex genetic screening and breeding. For instance, a plant species can be created to express one or more of a CRISPR endonuclease such as a Cas12a-type endonuclease or combinations with unique PAM recognition sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for trait introgression. Multiple endonucleases can be provided in expression cassettes with the appropriate promoters to allow multiple genome editing in a spatially or temporally separated fashion in either in chromosome DNA or episome DNA.

CRISPR technology for editing the genes of eukaryotes is disclosed in U.S. Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cas12a (Cpf1) endonuclease and corresponding guide RNAs and PAM sites are disclosed in U.S. Pat. No. 9,790,490 and U.S. patent application Ser. No. 15/566,528 (national phase of PCT Application PCT/EP2016/058442, published as WO 2016/166340). Plant RNA promoters for expressing CRISPR guide RNA and plant codon-optimized CRISPR Cas9 endonuclease are disclosed in U.S. patent application Ser. No. 15/120,110, published as U.S. Patent Application Publication 2017/0166912, national phase application claiming priority to International Patent Application PCT/US2015/018104 (published as WO 2015/131101 and claiming priority to U.S. Provisional Patent Application 61/945,700). Methods of using CRISPR technology for genome editing in plants are disclosed in in U.S. Patent Application Publications U.S. 2015/0082478A1 and U.S. 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety.

Endonucleases such as Cas9 and Cas12a (Cpf1) can be provided to a cell in different forms. In an embodiment, an endonuclease is provided as a ribonucleoprotein (RNP) complex, e.g., a preassembled RNP that includes the endonuclease complexed with a polynucleotide including the gRNA or encoding a gRNA, or a preassembled RNP that includes a polynucleotide that encodes the endonuclease (and optionally encodes the gRNA, or is provided with a separate polynucleotide including the gRNA or encoding a gRNA), complexed with a protein. In embodiments, the endonuclease is a fusion protein, i.e., wherein the endonuclease is covalently bound through a peptide bond to a cell-penetrating peptide, a nuclear localization signal peptide, a chloroplast transit peptide, or a mitochondrial targeting peptide; such fusion proteins are conveniently encoded in a single nucleotide sequence, optionally including codons for linking amino acids. In embodiments, the endonuclease or a polynucleotide that encodes the endonuclease is provided as a complex with a cell-penetrating peptide or other transfecting agent. In embodiments, the endonuclease or a polynucleotide that encodes the endonuclease is complexed with, or covalently or non-covalently bound to, a further element, e.g., a carrier molecule, an antibody, an antigen, a viral movement protein, a polymer, a detectable label (e.g., a moiety detectable by fluorescence, radioactivity, or enzymatic or immunochemical reaction), a quantum dot, or a particulate or nanoparticulate. In embodiments, the endonuclease or a polynucleotide that encodes the endonuclease is provided in a solution, or is provided in a liposome, micelle, emulsion, reverse emulsion, suspension, or other mixed-phase composition. Similarly, editing complexes such as those disclosed herein (or compositions including such editing complexes) can be provided in combination with further elements (e.g., a carrier molecule, an antibody, an antigen, a viral movement protein, a polymer, a detectable label, a quantum dot, or a particulate or nanoparticulate) or provided in a suitable form (e.g., in a solution, liposome, micelle, emulsion, reverse emulsion, suspension, or other mixed-phase composition).

By "integration of heterologous sequence" is meant integration or insertion of one or more nucleotides, resulting in a sequence (including the inserted nucleotide(s) as well as at least some adjacent nucleotides of the genomic sequence flanking the site of insertion at a double-strand break effected by a CRISPR endonuclease) that is heterologous (e.g., would not otherwise or does not normally occur at the site of insertion). The term "heterologous" is also used to refer to a given sequence in relationship to another, e.g., the sequence of a donor DNA is heterologous to the sequence at the site of the double-strand break wherein the donor DNA is integrated. The term "heterologous" is also used to refer to components of a synthetic polynucleotide construct, where the components do not naturally occur together; for example, an expression cassette or construct can include a promoter to drive expression of a downstream sequence, where the promoter is heterologous to that downstream sequence. As used herein, the terms "heterologous promoter", "heterologous terminator", "heterologous coding sequence", and the like refer to discrete genetic sequences such as promoters and other expression-related genetic elements (e.g., promoters, enhancers, introns, terminators, silencers, and insulators), that are not normally associated with a particular nucleic acid in nature. For example, a "promoter that is heterologous to a coding region" is a promoter that is not normally associated with the coding region in nature.

By "capable of specifically binding to" is meant an agent that binds substantially or preferentially only to a defined target (such as an oligonucleotide or polynucleotide to a specific nucleic acid). In some examples, an oligonucleotide or polynucleotide capable of specifically binding to a target nucleic acid is complementary to the target nucleic acid. However, exact complementarity is not required for specific binding. The term "capable of hybridizing" refers to the ability of two polynucleotides to hybridize or "anneal", i.e., to form Watson-Crick base pairs; one of skill in the art would understand that the ability to hybridize requires a sufficient degree of complementarity between the two polynucleotides under given conditions (e.g., temperature) and that the degree of complementarity can be estimated using algorithms in the art.

By "complementary" is meant sequences with at least sufficient complementarity to permit enough base-paring for two nucleic acids to hybridize (for example, for a tether to hybridize with or bind to a gRNA or donor DNA), which in some examples may be under typical physiological conditions for the cell. In some examples, the oligonucleotide or polynucleotide is at least 80% complementary to the target, for example, at least 85%, 90%, 95%, 96%, 97%, 98%, 99%, or 100% complementary to the target.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available at ncbi[dot]nlm[dot]nih[dot]gov/BLAST. See, e.g., Altschul et al. (1990) *Mol. Biol.*, 215:403-410. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.*, 70: 173-187 (1997). Also, the GAP program using the Needleman and Wunsch alignment method can be utilized to align sequences. See *Mol. Biol.*, 48: 443-453 (1970).

The term "operably linked" refers to a juxtaposition wherein the components so described are in a relationship permitting them to function in their intended manner. For instance, a promoter is operably linked to a coding sequence if the promoter affects its transcription or expression.

By "native" is meant naturally occurring in a genome, such as a prokaryotic or eukaryotic genome. A "native" restriction endonuclease cleavage site means a restriction endonuclease cleavage site that is found in a naturally existing genome, such as a restriction endonuclease cleavage site that is naturally found within genomic DNA encoding the tracrRNA, in contrast to an artificial or engineered restriction endonuclease cleavage site that is created through recombinant nucleic acid technology.

By "engineered" is meant artificial, synthetic, or not occurring in nature. For example, a polynucleotide that includes two DNA sequences that are heterologous to each other can be engineered or synthesized by recombinant nucleic acid techniques.

By a "complex" is meant two or more associated components, such as two or more associated nucleic acids and/or proteins. A complex may include two or more covalently linked nucleic acids and/or proteins, two or more non-covalently linked nucleic acids and/or proteins, or a combination thereof. In an example, a complex includes a nuclease (such as a Cas12a nuclease) and an appropriate crRNA; such a complex can optionally include one or more polynucleotides, such as the tracrRNA molecules described herein, donor polynucleotides, and functional RNA moieties. In some examples, a complex includes a gRNA (such as a crRNA) and a donor polynucleotide (or a template for production of a donor polynucleotide), which may be covalently or non-covalently linked. In other examples, a complex includes a nuclease and a donor DNA, which may be covalently linked. In further example, a complex includes one or more CRISPR nuclease polypeptides, a gRNA, and a donor DNA (or a template for production of donor DNA).

By "covalently linked" is meant that two elements (such as a gRNA and a tether or a gRNA and a donor DNA) are joined by a covalent bond, for example, an internucleotide linkage such as a phosphodiester bond, a phosphorothioate bond, a phosphothioate bond, or a peptide bond.

By "non-covalently linked" is meant that two elements (such as two discrete polynucleotides, or a polypeptide and a polynucleotide) interact non-covalently, for example by hydrogen bonding, such as Watson-Crick base pairing. Other non-covalent interactions include non-Watson-Crick pairing, electrostatic interactions, van der Waals forces, 7r-effects, and hydrophobic effects.

By "in vivo" is meant that the systems, compositions, and methods of this disclosure are applied to or within a living organism, such as a living intact non-human animal, a living human, or a living plant or seed. By "in vitro" is meant that the systems, compositions, and methods of this disclosure are applied to cells or tissue maintained alive independently of an intact multicellular organism, such as a living intact non-human animal, a living intact human, or a living intact plant or seed; examples of in vitro embodiments include those where the systems, compositions, and methods of this disclosure are applied to stable or transient animal or plant cell lines in culture and tissue samples in culture. In vitro embodiments further include prokaryotic cell cultures. By "ex vivo" is meant occurring in cells, tissue, or organs (e.g., blood, blood cells, T cells, liver cells or tissue, skin, bone, muscle, eggs or ovules, sperm, pollen, etc.) removed from a living non-human animal, human, or plant and at least temporarily maintained alive in culture. Ex vivo cells or tissues may be returned to a living intact multicellular organism, such as the living non-human animal, human, or plant from which the cells or tissue were originally removed. In an embodiment, the systems, compositions, and methods of this disclosure are applied to human T-cells for the purpose of generating chimeric antigen receptor T cells ("CAR-T cells"), which may be delivered to a human as a therapeutic; see, e.g., Liu et al., *Frontiers Immunol.*, 10:456, available at doi: 10.3389/fimmu.2019.00456. Ex vivo cells or tissues may be grown into differentiated tissue or even differentiated organs, or undifferentiated tissue or callus. Ex vivo plant cells or plant tissues may be grown into intact plants.

Method of Tethering a Functional RNA Molecule to a Cas12a crRNA or a Cas12a Ribonucleoprotein An aspect of this invention provides a method of tethering a functional RNA molecule to a Cas12a crRNA, optionally to a Cas12a ribonucleoprotein including a Cas12a nuclease and a Cas12a crRNA. In embodiments, the method includes the step of hybridizing (a) a functional RNA molecule including a Cas12a tracrRNA and a functional RNA moiety; and (b) a Cas12a crRNA that includes a 3' extension capable of hybridizing with a segment of the functional RNA molecule; thereby tethering the functional RNA molecule to the Cas12a crRNA. In embodiments, the method includes the step of hybridizing (a) a functional RNA molecule including a Cas12a tracrRNA and a functional RNA moiety; and (b) a naturally occurring Cas12a crRNA that optionally includes a 3' extension capable of hybridizing with a segment of the functional RNA molecule; thereby tethering the functional RNA molecule to the Cas12a crRNA. In embodiments, the method includes the step of hybridizing (a) a functional RNA molecule including a Cas12a tracrRNA and a functional RNA moiety; and (b) an engineered Cas12a crRNA that optionally includes a 3' extension capable of hybridizing with a segment of the functional RNA molecule; thereby tethering the functional RNA molecule to the Cas12a crRNA.

Embodiments of a "Cas12a tracrRNA" include an RNA molecule having the nucleotide sequence of a naturally occurring tracrRNA identified from a native Cas12a locus. For example, a naturally occurring Cas12a tracrRNA can be identified from a genome using the techniques described by Zetsche et al. (2015) *Cell*, 163:759-771, and in U.S. Pat. No. 9,790,490. A naturally occurring Cas12a tracrRNA can be identified from a genome as DNA sequence encoding a RNA molecule that: is predicted to be or putatively transcribed (or that may be determined to be transcribed, e.g., by RNA analysis) from a Cas12a CRISPR genomic region, specifically from a locus that flanks the DNA encoding the Cas12a CRISPR nuclease; that preferably but not necessarily includes a predicted transcriptional terminator in the direction of transcription; that is about 60 to about 100 nucleotides in length, e.g., 60-80 nucleotides, 60-85 nucleotides, 60-90 nucleotides, or 65-95 nucleotides; and that is not a direct repeat in the Cas12a CRISPR array, but rather has a nucleotide sequence that permits the transcribed tracrRNA to hybridize to the crRNA (i.e., the transcribed tracrRNA has sufficient complementarity to a crRNA sequence to hybridize to the crRNA). In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4. In embodiments, the transcribed tracrRNA has a nucleotide sequence having at least 50% identity (e.g., at least 50%, at least 51%, at least 52%, at least 53%, at least 54%, at least 55%, at least 56%, at least 57%, at least 58%, at least 59%, or at least 60% sequence identity) to the sequence of the direct repeat. In embodiments, the Cas12a tracrRNA has a sequence that is selected from the group consisting of SEQ ID NOs:1, 3, 6, 139-146, and 149-169. An alternative embodiment of a "Cas12a tracrRNA" includes an RNA molecule having or including a nucleotide sequence based on the nucleotide sequence of a naturally occurring tracrRNA identified from a native Cas12a locus. Examples include RNA molecules that include the nucleotide sequence of a tracrRNA (or putative tracrRNA) identified from a native Cas12a locus but that further include one or more modifications such as (a) additional nucleotides, e.g., an extension at the 3' terminus, (b) insertion, deletion, or substitution of one or more nucleotides within the naturally occurring tracrRNA sequence, preferably maintaining the secondary structure of the tracrRNA, and (c) chemical modifications, e.g., addition of a detectable label.

In embodiments of the method, the functional RNA molecule is provided by transcription of a DNA molecule including DNA encoding the Cas12a tracrRNA and DNA encoding the functional RNA moiety, wherein the DNA encoding the functional RNA moiety is inserted at a restriction endonuclease cleavage site in or adjacent to the DNA encoding the Cas12a tracrRNA. In embodiments, the restriction endonuclease cleavage site is located within the 3' region of the DNA encoding the Cas12a tracrRNA, or within a short distance (e.g., within about 40, about 30, about 20, or about 10 nucleotides) of the 3' end of the Cas12a tracrRNA. In embodiments, the restriction endonuclease cleavage site occurs natively in the Cas12a tracrRNA, that is to say, occurs in a naturally occurring DNA sequence that encodes a predicted or putative Cas12a tracrRNA. In other embodiments, the restriction endonuclease cleavage site is artificial or engineered; a non-limiting example includes a naturally occurring DNA sequence that encodes a predicted or putative Cas12a tracrRNA and further includes at least one nucleotide that is artificially added, deleted, or substituted to provide an engineered restriction endonuclease cleavage site located in or adjacent to the sequence encoding the tracrRNA.

In embodiments of the method, the crRNA 3' extension includes nucleotides that when base-paired form about one helical turn. In embodiments, the crRNA 3' extension includes at least 10 contiguous nucleotides. In embodiments, the crRNA 3' extension improves hybridization of the Cas12a crRNA to the Cas12a tracrRNA. In some embodiments, the Cas12a tracrRNA further includes a 5' extension, such as the 5' extensions disclosed by Park et al. (2018) *Nature Communications*, doi: 10.1038/s41467-018-05641-3.

The functional RNA molecule includes a Cas12a tracrRNA and at least one functional RNA moiety. In embodiments, the functional RNA moiety is a nucleotide sequence inserted at a restriction endonuclease cleavage site in or adjacent to the DNA encoding the Cas12a tracrRNA. Non-limiting embodiments of functional RNA moieties include: (a) an RNA sequence for annealing to a donor polynucleotide (e.g., a single- or double-stranded DNA containing a nucleotide template for HDR-mediated editing, or a single- or double-stranded polynucleotide including a nucleotide sequence to be integrated by an NHEJ mechanism at a double-stranded break effected, for example, by the Cas12a nuclease); (b) an RNA sequence for annealing to the crRNA 3' extension; (c) a terminator sequence; (d) an RNA aptamer; (e) a ribozyme or catalytically active RNA; (f) a detectable label, such as a fluorescent tag; (g) a bar-coding sequence, or short nucleotide sequence useful for marking and identifying DNA that contains the bar-coding sequence; and (h) an RNA sequence forming at least partially double-stranded RNA. In an embodiment, the functional RNA moiety includes RNA forming at least partially double-stranded RNA capable of silencing a gene (e.g., RNA that forms one or more stem-loops where the stem includes double-stranded RNA of at least about 18 base-pairs designed to silence a target gene, or RNA that has the secondary structure of a microRNA precursor and is processed to a mature microRNA designed to silence a target gene). In embodiments, the functional RNA moiety is a terminator, e.g., a terminator functional in eukaryotic cells, such as a U6 poly-T terminator, an SV40 terminator, an hGH terminator, a BGH terminator, an rbGlob terminator, a synthetic terminator functional in a eukaryotic cell, a 3' element from an *Agrobacterium* sp. gene, a 3' element from a non-human animal gene, a 3' element from a human gene, and a 3' element from a plant gene, wherein the 3' element terminate transcription of an RNA transcript located immediately 5' to the 3' element. Non-limiting examples of RNA aptamers include an MS2 aptamer (see Parrott et al. (2000) *Nucleic Acids Res.*, 28(2):489-497), an ARiBo tag (see Di Tomasso et al. (2011) *Nucleic Acids Res.*, 39(3):e18; doi: 10.1093/nar/gkq1084), a streptavidin-binding aptamer (see Leppek and Stoecklin (2014) *Nucleic Acids Res.*, 452(2): e13; doi: 10.1093/nar/gkt956), a Csy4 aptamer (see Lee et al. (2013) *Proc. Natl. Acad. Sci. USA*, 110(14):5416-5421; doi: 10.1073/pnas.1302807110, and a Sephadex aptamer (see Srisawat and Engelke (2002) *Methods*, 26(2):156-161; doi: 10.1016/S1046-2023(02)00018-X. Many aptamers are useful for affinity purification and tagging; for example, a two-element affinity tag useful for preparing large quantities of RNA includes a variant of the hepatitis delta virus (HW) ribozyme that is activated by imidazole and a hairpin loop from a thermostable SRP RNA that forms a high-affinity and kinetically stable complex with the *Thermotoga maritima* Ffh-M domain protein (see Keift and Batey (2004) *RNA*, 10(6): 988-995; doi: 10.1261/rna.7040604).

In embodiments, the method includes the step of hybridizing in vitro (a) a functional RNA molecule including a Cas12a tracrRNA and a functional RNA moiety; and (b) a Cas12a crRNA that includes a 3' extension capable of hybridizing with a segment of the functional RNA molecule. In embodiments, the method includes the step of hybridizing in vitro (a) a functional RNA molecule including a Cas12a tracrRNA and a functional RNA moiety; and (b) a naturally occurring or an engineered Cas12a crRNA that optionally includes a 3' extension capable of hybridizing with a segment of the functional RNA molecule. In some embodiments, a heating (melting) step and a cooling step are employed during the hybridization. In some embodiments, the hybridization is carried out at room temperature, without additional heating or cooling steps.

In many embodiments of the method, the Cas12a crRNA is complexed with, or is capable of complexing with, a Cas12a nuclease to form a Cas12a ribonucleoprotein complex containing the functional RNA molecule. Complexing of the Cas12a crRNA with the Cas12a nuclease can occur prior to, concurrently with, or after hybridization of the functional RNA molecule with the Cas12a crRNA. In embodiments, the method includes the step of hybridizing (a) a functional RNA molecule including a Cas12a tracrRNA and a functional RNA moiety; and (b) a naturally occurring Cas12a crRNA that optionally includes a 3' extension capable of hybridizing with a segment of the functional RNA molecule; following this hybridization, the Cas12a nuclease is added to form the Cas12a ribonucleoprotein. In embodiments, the method includes the step of hybridizing (a) a functional RNA molecule including a Cas12a tracrRNA and a functional RNA moiety; and (b) an engineered Cas12a crRNA that optionally includes a 3' extension capable of hybridizing with a segment of the functional RNA molecule; following this hybridization, the Cas12a nuclease is added to form the Cas12a ribonucleoprotein. A related aspect of the invention is therefore a modified Cas12a ribonucleoprotein complex including (a) a Cas12a nuclease; (b) a functional RNA molecule including a Cas12a tracrRNA and a functional RNA moiety; and (c) a naturally occurring or an engineered Cas12a crRNA that optionally includes a 3' extension capable of hybridizing with a segment of the functional RNA molecule.

In embodiments of the method wherein the Cas12a crRNA is complexed with, or is capable of complexing with, a Cas12a nuclease, or in embodiments of the modified Cas12a ribonucleoprotein complex thus formed, the Cas12a nuclease is any one of the Cas12a ("Cpf1") nucleases disclosed in U.S. Pat. No. 9,790,490 or in U.S. patent application Ser. No. 15/566,528 (national phase entry of International Application No. PCT/EP2016/058442, published as WO2016166340), or in U.S. Pat. No. 9,896,696 which are specifically incorporated herein by reference. In specific embodiments, the Cas12a nuclease is a Cas12a ("Cpf1") nuclease identified from *Francisella novicida* U112 (FnCas12a or "FnCpf1"), from *Acidaminococcus* sp. BV3L6 (AsCas12a or "AsCpf1"), or from Lachnospiraceae bacterium ND2006 (LbCas12a or "LbCpf1"), or is an orthologue thereof, such as an orthologue having at least 50% sequence identity to FnCas12a ("FnCpf1"); see, e.g., the FnCpf1 nuclease contained in the FnCpf1 locus having SEQ ID NO:211 in U.S. Pat. No. 9,790,490, incorporated herein by reference. In embodiments, a Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease selected from the group consisting of (1) a variant LbCpf1 that differs from a wild type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease includes orthologues of LbCas12a, AsCas12a, or FnCas12a. In embodiments, the Cas12a nuclease is deactivated. In embodiments, the Cas12a nuclease includes at least one modification selected from the group consisting of: (a) a localization or signal peptide (e.g., a nuclear localization signal (NLS), a chloroplast or plastid transit peptide (CTP), or a mitochondrial targeting peptide (MTP)); (b) a detectable label (e.g., a fluorescent dye); (c) a cell-penetrating peptide; (d) an endosomal escape peptide; and (e) an affinity tag. In embodiments, the Cas12a nuclease includes at least one modification selected from a fluorescent protein (e.g., green fluorescent protein (GFP), YFP, RFP, CFP, mCherry, tdTomato, mScarlett), a histidine tag (e.g., a 6×His tag), a hemagglutinin (HA) tag, a FLAG tag, a Myc tag, horseradish peroxidase (HRP), alkaline phosphatase (AP), beta-galactosidase (GAL), glucose-6-phosphate dehydrogenase, beta-N-acetylglucosaminidase, beta-glucuronidase, invertase, xanthine oxidase (XO), firefly luciferase (LUC), and glucose oxidase (GO). The systems and compositions including a tracrRNA and methods of use thereof that are disclosed herein can also be employed with related Cas nucleases, including Csm nucleases, e.g., ObCsm1 (GenBank accession number OGX23684), SmCsm1 (GenBank accession number KF067988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

A Method of Integrating a Sequence Encoded by a Donor Polynucleotide at a Specific Locus Another aspect of the invention provides a method of integrating or inserting a nucleotide sequence encoded by a donor polynucleotide at a specific locus in a target DNA, wherein the method includes the steps of: (1) annealing a donor polynucleotide to a modified Cas12a ribonucleoprotein complex, wherein the modified Cas12a ribonucleoprotein complex includes: (a) a Cas12a nuclease; (b) a functional RNA molecule including a Cas12a tracrRNA and a functional RNA moiety; and (c) a Cas12a crRNA that includes a 3' extension capable of hybridizing with a segment of the functional RNA molecule; wherein the functional RNA moiety includes an RNA sequence for annealing to the donor polynucleotide; and wherein the Cas12a crRNA includes a spacer sequence that corresponds to a specific target locus in a target DNA, thus forming a donor: RNP complex; and (2) contacting the target DNA with the donor: RNP complex; whereby the nucleotide sequence encoded by the donor polynucleotide is integrated or inserted at the specific target locus in the target DNA.

In embodiments, the Cas12a nuclease that forms part of the modified Cas12a ribonucleoprotein complex is any one of the Cas12a ("Cpf1") nucleases disclosed in U.S. Pat. No. 9,790,490 or in U.S. patent application Ser. No. 15/566,528 (national phase entry of International Application No. PCT/EP2016/058442, published as WO2016166340), or in U.S. Pat. No. 9,896,696 which are specifically incorporated herein by reference. In specific embodiments, the Cas12a nuclease is a Cas12a ("Cpf1") nuclease identified from *Francisella novicida* U112 (FnCas12a or "FnCpf1"), from *Acidaminococcus* sp. BV3L6 (AsCas12a or "AsCpf1"), or from Lachnospiraceae bacterium ND2006 (LbCas12a or "LbCpf1"), or is an orthologue thereof, such as an orthologue having at least 50% sequence identity to FnCas12a ("FnCpf1"); see, e.g., the FnCpf1 nuclease contained in the FnCpf1 locus having SEQ ID NO:211 in U.S. Pat. No. 9,790,490, incorporated herein by reference. In embodiments, a Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease selected from the group consisting of (1) a variant LbCpf1 that differs from a wild type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization or signal peptide (e.g., a nuclear localization signal (NLS), a chloroplast or plastid transit peptide (CTP), or a mitochondrial targeting peptide (MTP)); (b) a detectable label (e.g., a fluorescent dye); (c) a cell-penetrating peptide; (d) an endosomal escape peptide; and (e) an affinity tag. The methods including the use of a tracrRNA as disclosed herein can also be employed with related Cas nucleases, including Csm nucleases, e.g., ObCsm1 (GenBank accession number OGX23684), SmCsm1 (GenBank accession number KF067988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

Embodiments of a "Cas12a tracrRNA" include an RNA molecule having the nucleotide sequence of a naturally occurring tracrRNA identified from a native Cas12a locus. For example, a naturally occurring Cas12a tracrRNA can be identified from a genome using the techniques described by Zetsche et al. (2015) *Cell*, 163:759-771, and in U.S. Pat. No. 9,790,490. A naturally occurring Cas12a tracrRNA can be identified from a genome as DNA sequence encoding a RNA molecule that: is predicted to be or putatively transcribed (or that may be determined to be transcribed, e.g., by RNA analysis) from a Cas12a CRISPR genomic region, specifically from a locus that flanks the DNA encoding the Cas12a CRISPR nuclease; that preferably but not necessarily includes a predicted transcriptional terminator in the direction of transcription; that is about 60 to about 100 nucleotides in length, e.g., 60-80 nucleotides, 60-85 nucleotides, 60-90 nucleotides, or 65-95 nucleotides; and that is not a direct repeat in the Cas12a CRISPR array, but rather has a nucleotide sequence that permits the transcribed tracrRNA to hybridize to the crRNA (i.e., the transcribed tracrRNA has sufficient complementarity to a crRNA sequence to hybridize to the crRNA). In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4. In embodiments, the transcribed tracrRNA has a nucleotide sequence having at least 50% identity (e.g., at least 50%, at least 51%, at least 52%, at least 53%, at least 54%, at least 55%, at least 56%, at least 57%, at least 58%, at least 59%, or at least 60% sequence identity) to the sequence of the direct repeat. In embodiments, the Cas12a tracrRNA has a sequence that is selected from the group consisting of SEQ ID NOs:1, 3, 6, 139-146, and 149-169. An alternative embodiment of a "Cas12a tracrRNA" includes an RNA molecule having or including a nucleotide sequence based on the nucleotide sequence of a naturally occurring tracrRNA identified from a native Cas12a locus. Examples include RNA molecules that include the nucleotide sequence of a tracrRNA (or putative tracrRNA) identified from a native Cas12a locus but that further include one or more modifications such as (a) additional nucleotides, e.g., an extension at the 3' terminus, (b) insertion, deletion, or substitution of one or more nucleotides within the naturally occurring tracrRNA sequence, preferably maintaining the secondary structure of the tracrRNA, and (c) chemical modifications, e.g., addition of a detectable label.

In embodiments, the functional RNA moiety includes an RNA sequence for annealing to the donor polynucleotide. The RNA sequence for annealing to the donor polynucleotide has a length and degree of sequence identity that in combination are sufficient to allow hybridization of the functional RNA moiety and the donor polynucleotide at physiological conditions. For convenience and economy, in some embodiments, the RNA sequence for annealing to the donor polynucleotide is short, about 10 nucleotides in length, and has exact (100%) sequence complementarity to a segment of the donor polynucleotide of equivalent length. In other embodiments, the RNA sequence for annealing to the donor polynucleotide is greater than 10 nucleotides in length, and has at least 50%, at least 60%, at least 70%, at least 80%, at least 90%, or at least 95% sequence complementarity to a segment of the donor polynucleotide of equivalent length.

In embodiments, the donor polynucleotide includes single-stranded DNA, optionally including chemical modifications. In other embodiments, the donor polynucleotide includes double-stranded DNA, optionally including chemical modifications. In some embodiments, the donor polynucleotide includes both DNA and RNA, for example as a duplex formed by a DNA strand and an RNA strand. In embodiments, the donor polynucleotide is designed to include a template for genome editing via homology-dependent repair (HDR); the template generally includes a "core sequence" that is to replace a sequence of the genome of about the same size, as well as "homology arms" that flank the core sequence on either side and have a sequence complementary to the genomic regions flanking the genomic sequence to be replaced or edited. In other embodiments, the donor polynucleotide does not include homology arms or does not include a core sequence and homology arms, for example in embodiments where the donor polynucleotide is used to make a deletion.

In general, a donor polynucleotide including a template encoding a nucleotide change over a region of less than about 50 nucleotides is conveniently provided in the form of single-stranded DNA; larger donor templates (e.g., more than 100 nucleotides) are often conveniently provided as double-stranded DNAs. Thus in some embodiments, the donor polynucleotide is about 25 nucleotides, 50 nucleotides, 60 nucleotides, 70 nucleotides 80 nucleotides, 90 nucleotides, 100 nucleotides, 200 nucleotides, 300 nucleotides, 400 nucleotides, 500 nucleotides, 600 nucleotides, 700 nucleotides, 800 nucleotides, 900 nucleotides, 1000 nucleotides, 1200 nucleotides, 1500 nucleotides, 1800 nucleotides, 2000 nucleotides, 2500 nucleotides, 3000 nucleotides, 5000 nucleotides, 10,000 nucleotides, or more (such as about 25-200 nucleotides, 50-300 nucleotides, 100-500 nucleotides, 200-800 nucleotides, 700-2000 nucleotides, 1000-2500 nucleotides, 2000-5000 nucleotides, 4000-8000 nucleotides, or 6000-10,000 nucleotides).

The target DNA or target sequence (i.e., the DNA to be edited) is in many embodiments genomic DNA or chromosomal DNA of a eukaryotic cell or eukaryotic organism. In embodiments, the target DNA is mitochondrial DNA or plastid DNA. In embodiments, the target DNA includes recombinant DNA, for example, a transgene stably integrated in the genome of a eukaryote, such as of a plant. Target sequences and eukaryotic cells are described in detail below under the section headed "Related Disclosure".

DNA Expression Systems (I)

Another aspect of the invention provides a DNA expression system including: (a) DNA sequence for a first promoter; and (b) operably linked and heterologous to the first promoter, a DNA sequence encoding a first RNA molecule including a Cas12a tracrRNA and including a restriction endonuclease cleavage site that is suitable for insertion of a sequence coding for a functional RNA moiety.

The first promoter is heterologous to the DNA encoding a first RNA molecule including a Cas12a tracrRNA and including a restriction endonuclease cleavage site. The first promoter is selected for operability in the context (in vitro or in vivo) in which the DNA expression system is to be used. Thus, in certain embodiments, the first promoter is a promoter that functions in prokaryotic cells, such as in bacterial cells. In preferred embodiments, the first promoter is a promoter that functions in eukaryotic cells, such as in non-human animal (e.g., mammalian, human) or human or plant or fungal cells; in embodiments, the first promoter is one identified from a eukaryotic genome, such as a non-human animal or human or plant or fungal genome. In embodiments, the first promoter is a promoter selected from the group consisting of pol III promoters, pol II promoters, and pol I promoters. In embodiments, the first promoter is a promoter selected from the group consisting of a U6 promoter, an H1 promoter, a Rous sarcoma virus (RSV) LTR promoter, a cytomegalovirus (CMV) promoter, an SV40 promoter, a dihydrofolate reductase promoter, a beta-actin promoter, a phosphoglycerol kinase (PGK) promoter, and an EF1a promoter. For use in plants, useful promoters include constitutive, conditional, inducible, and temporally or spatially specific promoters (e.g., a tissue specific promoter, a developmentally regulated promoter, or a cell cycle regulated promoter). In embodiments, the promoter is a pol II promoter. In embodiments, the promoter is a constitutive promoter that drives DNA expression in plant cells; in embodiments, the promoter drives DNA expression in the nucleus or in an organelle such as a chloroplast or mitochondrion. Examples of constitutive promoters include a CaMV 35S promoter as disclosed in U.S. Pat. Nos. 5,858, 742 and 5,322,938, a rice actin promoter as disclosed in U.S. Pat. No. 5,641,876, a maize chloroplast aldolase promoter as disclosed in U.S. Pat. No. 7,151,204, and an opaline synthase (NOS) and octapine synthase (OCS) promoter from *Agrobacterium tumefaciens*. In embodiments, the promoter is a promoter from figwort mosaic virus (FMV), a RUBISCO promoter, or a pyruvate phosphate dikinase (PDK) promoter, which is active in the chloroplasts of mesophyll cells. Other contemplated promoters include cell-specific or tissue-specific or developmentally regulated promoters, for example, a promoter that limits the expression of the DNA expression system to germline or reproductive cells (e.g., promoters of genes encoding DNA ligases, recombinases, replicases, or other genes specifically expressed in germline or reproductive cells). In embodiments, the first promoter is a plant U6 spliceosomal RNA promoter, which can be native to the genome of the plant cell or from a different species, e.g., a U6 promoter from maize, tomato, or soybean such as those disclosed in U.S. patent application Ser. No. 15/120,110, published as U.S. Patent Application Publication 2017/0166912, national phase application claiming priority to PCT/US2015/018104 (published as WO 2015/131101 and claiming priority to U.S. Provisional Patent Application 61/945,700), or a homologue thereof; in an example, such a promoter is operably linked to DNA sequence encoding a first RNA molecule including a Cas12a tracrRNA and including a restriction endonuclease cleavage site that is suitable for insertion of a sequence coding for a functional RNA moiety, followed by a suitable 3' element such as a U6 poly-T terminator. In another embodiment, the first promoter is a plant U3, 7SL (signal recognition particle RNA), U2, or U5 promoter, or chimerics thereof, e.g., as described in U.S. patent application Ser. No. 15/120,110, published as U.S. Patent Application Publication 2017/0166912, national phase application claiming priority to PCT/US2015/018104 (published as WO 2015/131101 and claiming priority to U.S. Provisional Patent Application 61/945,700). All of the patent publications referenced in this paragraph are incorporated herein by reference in their entirety. Additional non-limiting embodiments of promoters functional in plants are provided in Example 5.

Embodiments of a "Cas12a tracrRNA" include an RNA molecule having the nucleotide sequence of a naturally occurring tracrRNA identified from a native Cas12a locus. For example, a naturally occurring Cas12a tracrRNA can be identified from a genome using the techniques described by Zetsche et al. (2015) *Cell*, 163:759-771, and in U.S. Pat. No. 9,790,490. A naturally occurring Cas12a tracrRNA can be identified from a genome as DNA sequence encoding a RNA molecule that: is predicted to be or putatively transcribed (or that may be determined to be transcribed, e.g., by RNA analysis) from a Cas12a CRISPR genomic region, specifically from a locus that flanks the DNA encoding the Cas12a CRISPR nuclease; that preferably includes a predicted transcriptional terminator in the direction of transcription; that is about 60 to about 100 nucleotides in length, e.g., 60-80 nucleotides, 60-85 nucleotides, 60-90 nucleotides, or 65-95 nucleotides; and that is not a direct repeat in the Cas12a CRISPR array, but rather has a nucleotide sequence that permits the transcribed tracrRNA to hybridize to the crRNA (i.e., the transcribed tracrRNA has sufficient complementarity to a crRNA sequence to hybridize to the crRNA). In embodiments, the Cas tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4. In embodiments, the transcribed tracrRNA has a nucleotide sequence having at least 50% identity (e.g., at least 50%, at least 51%, at least 52%, at least 53%, at least 54%, at least 55%, at least 56%, at least 57%, at least 58%, at least 59%, or at least 60% sequence identity) to the sequence of the direct repeat. In embodiments, the Cas12a tracrRNA has a sequence that is selected from the group consisting of SEQ ID NOs:1, 3, 6, 139-146, and 149-169. An alternative embodiment of a "Cas12a tracrRNA" includes an RNA molecule having or including a nucleotide sequence based on the nucleotide sequence of a naturally occurring tracrRNA identified from a native Cas12a locus. Examples include RNA molecules that include the nucleotide sequence of a tracrRNA (or putative tracrRNA) identified from a native Cas12a locus but that further include one or more modifications such as (a) additional nucleotides, e.g., an extension at the 3' terminus, (b) insertion, deletion, or substitution of one or more nucleotides within the naturally occurring tracrRNA sequence, preferably maintaining the secondary structure of the tracrRNA, and (c) chemical modifications, e.g., addition of a detectable label. In embodiments of the DNA expression system, the Cas12a tracrRNA further includes a 5' extension, such as the 5' extensions disclosed by Park et al. (2018) *Nature Communications*, doi: 10.1038/s41467-018-05641-3.

In one application, the DNA expression system is useful for expression of an RNA molecule that includes a Cas12a tracrRNA and a functional RNA moiety. Thus, the DNA expression system includes a DNA sequence that encodes a first RNA molecule including a Cas12a tracrRNA, and that includes a restriction endonuclease cleavage site that is suitable for insertion of a sequence coding for an RNA moiety. In embodiments, the restriction endonuclease cleavage site is located in or adjacent to the DNA encoding the Cas12a tracrRNA. In embodiments, the restriction endonuclease cleavage site is located within the DNA encoding the Cas12a tracrRNA. In preferred embodiments, the restriction endonuclease cleavage site is located within the 3' region of the DNA encoding the Cas12a tracrRNA, or within a short distance (e.g., within about 40, about 30, about 20, or about 10 nucleotides) of the 3' end of the Cas12a tracrRNA. In many embodiments, the restriction endonuclease recognizes and binds to the DNA at the same location at which the endonuclease cuts the DNA. In some embodiments, the restriction endonuclease cleavage site (that is, where the restriction endonuclease cuts) can be at a location on the DNA at a short distance from where the restriction endonuclease recognizes and binds to the DNA. In embodiments, the restriction endonuclease cleavage site occurs natively in the Cas12a tracrRNA, that is to say, occurs in a naturally occurring DNA sequence that encodes a predicted or putative Cas12a tracrRNA. In other embodiments, the restriction endonuclease cleavage site is artificial or engineered; in a non-limiting example includes a naturally occurring DNA sequence that encodes a predicted or putative Cas12a tracrRNA and further includes at least one nucleotide that is artificially added, deleted, or substituted to provide an engineered restriction endonuclease cleavage site located in or adjacent to the sequence encoding the tracrRNA. In embodiments, the DNA expression system further includes a terminator located 3' to the DNA sequence encoding the tracrRNA.

In embodiments, the DNA expression system further includes: (a) optionally, a DNA sequence for a second promoter; (b) operably linked and heterologous to the first promoter or the second promoter, a DNA encoding a Cas12a crRNA that includes a 3' extension capable of hybridizing with a segment of the first RNA molecule (wherein the segment can be within or part of the tracrRNA that is part of the first RNA molecule); and (c) optionally, a terminator. The optional second promoter is selected for operability in the context (in vitro or in vivo) in which the DNA expression system is to be used. Thus, in certain embodiments, the second promoter is a promoter that functions in prokaryotic cells, such as in bacterial cells. In preferred embodiments, the second promoter is a promoter that functions in eukaryotic cells, such as in non-human animal (e.g., mammalian, human) or human or plant or fungal cells; in embodiments, the first promoter is one identified from a eukaryotic genome, such as a non-human animal or human or plant or fungal genome. In embodiments, the second promoter is a promoter such as those described as suitable for the first promoter. In embodiments, the first promoter and the second promoter, if present, are different promoters. In embodiments, the first promoter and the DNA encoding the first RNA molecule, and the DNA encoding a Cas12a crRNA that includes a 3' extension are contained in a single construct. In some embodiments where the DNA expression system includes the second promoter, the first promoter and the DNA encoding the first RNA molecule are contained in a first construct, and the second promoter and the DNA encoding a Cas12a crRNA that includes a 3' extension are contained in a second construct; in such embodiments, the first construct and the second construct can be provided (a) in a single vector, or (b) in separate vectors. In other embodiments, the first promoter drives expression of both the DNA encoding the first RNA molecule and the DNA encoding the Cas12a crRNA.

In embodiments where the DNA expression system further includes a terminator located 3' to the DNA sequence encoding the tracrRNA, the terminator is functional in the cell wherein the DNA expression system is to be used. By "terminator" is meant a DNA segment near the 3' end of an expression cassette that acts as a signal to terminate transcription and directs polyadenylation of the resultant mRNA. Such a 3' element is also sometimes referred to as a "3'-untranslated region" or "3'-UTR" or a "polyadenylation signal". Non-limiting embodiments of terminators functional in eukaryotic cells include a U6 poly-T terminator, an SV40 terminator, an hGH terminator, a BGH terminator, an rbGlob terminator, a synthetic terminator functional in a eukaryotic cell, a 3' element from an *Agrobacterium* sp. gene, a 3' element from a non-human animal gene, a 3' element from a human gene, and a 3' element from a plant gene, wherein the 3' element terminate transcription of an RNA transcript located immediately 5' to the 3' element. Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in U.S. Patent Application Publication 2002/0192813 A1, incorporated herein by reference. Cas12a tracrRNAs (such as putative Cas12a tracrRNAs identified as described herein) may have associated endogenous pol III terminators which can be used in the DNA expression systems disclosed herein. In embodiments, the DNA expression system includes a heterologous promoter operably linked to a DNA sequence that encodes a first RNA molecule that includes a Cas12a tracrRNA and that includes a restriction endonuclease cleavage site that is suitable for insertion of a sequence coding for an RNA moiety, and further includes an endogenous pol III terminator (e.g., the terminator naturally associated with a putative Cas12a tracrRNA), or a heterologous terminator. In preferred embodiments of the various DNA expression systems disclosed herein, the terminator is functional in a eukaryotic cell, such as a plant cell; in embodiments, the terminator is one identified from eukaryotic genomic sequence, such as a plant genomic sequence. In embodiments, the terminator has a sequence selected from the group consisting of SEQ ID NOs:72-100.

In embodiments of the DNA expression system, the Cas12a crRNA is capable of complexing with a Cas12a nuclease to form a Cas12a ribonucleoprotein complex or system. In embodiments, the Cas12a nuclease is any one of the Cas12a ("Cpf1") nucleases disclosed in U.S. Pat. No. 9,790,490 or in U.S. patent application Ser. No. 15/566,528 (national phase entry of International Application No. PCT/EP2016/058442, published as WO2016166340), or in U.S. Pat. No. 9,896,696 which are specifically incorporated herein by reference. In specific embodiments, the Cas12a nuclease is a Cas12a ("Cpf1") nuclease identified from *Francisella novicida* U112 (FnCas12a or "FnCpf1"), from *Acidaminococcus* sp. BV3L6 (AsCas12a or "AsCpf1"), or from Lachnospiraceae bacterium ND2006 (LbCas12a or "LbCpf1"), or is an orthologue thereof, such as an orthologue having at least 50% sequence identity to FnCas12a ("FnCpf1"); see, e.g., the FnCpf1 nuclease contained in the FnCpf1 locus having SEQ ID NO:211 in U.S. Pat. No. 9,790,490, incorporated herein by reference. In embodiments, a Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease selected from the group consisting of (1) a variant LbCpf1 that differs from a wild type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag. In embodiments of the DNA expression system, the first promoter has a DNA sequence selected from the group consisting of SEQ ID NOs:16-71 and the Cas12a tracrRNA has a nucleotide sequence including a sequence selected from the group consisting of SEQ ID NOs:1, 3, 6, 139-146, and 149-169. In embodiments of the DNA expression system, the first promoter has a DNA sequence selected from the group consisting of SEQ ID NOs:16-71, the Cas12a tracrRNA has a nucleotide sequence including a sequence selected from the group consisting of SEQ ID NOs:1, 3, 6, 139-146, and 149-169, and the optional first terminator has a sequence selected from the group consisting of SEQ ID NOs:72-100. The systems including a tracrRNA as disclosed herein can also be employed with related Cas nucleases, including Csm nucleases, e.g., ObCsm1 (GenBank accession number OGX23684), SmCsm1 (GenBank accession number KF067988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

DNA Expression Systems (II)

Another aspect of the invention provides a DNA expression system including: (a) DNA sequence for a first promoter; and (b) operably linked and heterologous to the first promoter, a DNA sequence encoding a functional RNA molecule including a Cas12a tracrRNA and a functional RNA moiety. In embodiments, the DNA expression system includes (a) DNA sequence for a first promoter; and (b) operably linked and heterologous to the first promoter, a DNA sequence encoding a functional RNA molecule including a Cas12a tracrRNA and a functional RNA moiety, and (c) a terminator 3' to and operably linked to the DNA encoding a functional RNA molecule. In embodiments, the DNA expression system further includes: (a) optionally, a DNA sequence for a second promoter; (b) operably linked and heterologous to the first promoter or the second promoter, a DNA encoding a Cas12a crRNA that includes a 3' extension capable of hybridizing with a segment of the functional RNA molecule; and (c) optionally, a terminator.

The first promoter is heterologous to the DNA sequence encoding a functional RNA molecule including a Cas12a tracrRNA and a functional RNA moiety. Where the DNA expression system further includes a DNA encoding a Cas12a crRNA that includes a 3' extension capable of hybridizing with a segment of the functional RNA molecule, the first promoter is also heterologous to this DNA. The optional second promoter is heterologous to the DNA encoding a Cas12a crRNA that includes a 3' extension capable of hybridizing with a segment of the functional RNA molecule. Each promoter is selected for operability in the context (in vitro or in vivo) in which the DNA expression system is to be used. Thus, in embodiments, the first promoter (and the optional second promoter) is a promoter that functions in prokaryotic cells, such as in bacterial cells. In preferred embodiments, the first promoter is a promoter that functions in eukaryotic cells, such as in non-human animal (e.g., mammalian, human) or human or plant or fungal cells; in embodiments, the first promoter is one identified from a eukaryotic genome, such as a non-human animal or human or plant or fungal genome. In embodiments, the first promoter is a promoter selected from the group consisting of pol III promoters, pol II promoters, and pol I promoters. In embodiments, the first promoter is a promoter selected from the group consisting of a U6 promoter, an H1 promoter, a Rous sarcoma virus (RSV) LTR promoter, a cytomegalovirus (CMV) promoter, an SV40 promoter, a dihydrofolate reductase promoter, a beta-actin promoter, a phosphoglycerol kinase (PGK) promoter, and an EF1a promoter. In embodiments, the first promoter (and the optional second promoter) is a promoter that functions in eukaryotic cells, such as in plant cells. For use in plants, useful promoters include constitutive, conditional, inducible, and temporally or spatially specific promoters (e.g., a tissue specific promoter, a developmentally regulated promoter, or a cell cycle regulated promoter). In embodiments, the promoter is a pol II promoter. In embodiments, the promoter is a constitutive promoter that drives DNA expression in plant cells; in embodiments, the promoter drives DNA expression in the nucleus or in an organelle such as a chloroplast or mitochondrion. Examples of constitutive promoters include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and an opaline synthase (NOS) and octapine synthase (OCS) promoter from *Agrobacterium tumefaciens*. In embodiments, the promoter is a promoter from figwort mosaic virus (FMV), a RUBISCO promoter, or a pyruvate phosphate dikinase (PDK) promoter, which is active in the chloroplasts of mesophyll cells. Other contemplated promoters include cell-specific or tissue-specific or developmentally regulated promoters, for example, a promoter that limits the expression of the DNA expression system to germline or reproductive cells (e.g., promoters of genes encoding DNA ligases, recombinases, replicases, or other genes specifically expressed in germline or reproductive cells). In embodiments, the first promoter is a plant U6 spliceosomal RNA promoter, which can be native to the genome of the plant cell or from a different species, e.g., a U6 promoter from maize, tomato, or soybean such as those disclosed in U.S. patent application Ser. No. 15/120,110, published as U.S. Patent Application Publication 2017/0166912, national phase application claiming priority to PCT/US2015/018104 (published as WO 2015/131101 and claiming priority to U.S. Provisional Patent Application 61/945,700), or a homologue thereof; in an example, such a promoter is operably linked to DNA sequence encoding a functional RNA molecule including a Cas12a tracrRNA and a functional RNA moiety, followed by a suitable 3' element such as a U6 poly-T terminator. In another embodiment, the first promoter is a plant U3, 7SL (signal recognition particle RNA), U2, or U5 promoter, or chimerics thereof, e.g., as described in U.S. patent application Ser. No. 15/120,110, published as U.S. Patent Application Publication 2017/0166912, national phase application claiming priority to PCT/US2015/018104 (published as WO 2015/131101 and claiming priority to U.S. Provisional Patent Application 61/945,700). All of the patent publications referenced in this paragraph are incorporated herein by reference in their entirety.

Embodiments of a "Cas12a tracrRNA" include an RNA molecule having the nucleotide sequence of a naturally occurring tracrRNA identified from a native Cas12a locus. For example, a naturally occurring Cas12a tracrRNA can be identified from a genome using the techniques described by Zetsche et al. (2015) *Cell*, 163:759-771, and in U.S. Pat. No. 9,790,490. A naturally occurring Cas12a tracrRNA can be identified from a genome as DNA sequence encoding a RNA molecule that: is predicted to be or putatively transcribed (or that may be determined to be transcribed, e.g., by RNA analysis) from a Cas12a CRISPR genomic region, specifically from a locus that flanks the DNA encoding the Cas12a CRISPR nuclease; that preferably includes a predicted transcriptional terminator in the direction of transcription; that is about 60 to about 100 nucleotides in length, e.g., 60-80 nucleotides, 60-85 nucleotides, 60-90 nucleotides, or 65-95 nucleotides; and that is not a direct repeat in the Cas12a CRISPR array, but rather has a nucleotide sequence that permits the transcribed tracrRNA to hybridize to the crRNA (i.e., the transcribed tracrRNA has sufficient complementarity to a crRNA sequence to hybridize to the crRNA). In embodiments, the Cas tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4. In embodiments, the transcribed tracrRNA has a nucleotide sequence having at least 50% identity (e.g., at least 50%, at least 51%, at least 52%, at least 53%, at least 54%, at least 55%, at least 56%, at least 57%, at least 58%, at least 59%, or at least 60% sequence identity) to the sequence of the direct repeat. In embodiments, the Cas12a tracrRNA has a sequence that is selected from the group consisting of SEQ ID NOs:1, 3, 6, 139-146, and 149-169. An alternative embodiment of a "Cas12a tracrRNA" includes an RNA molecule having or including a nucleotide sequence based on the nucleotide sequence of a naturally occurring tracrRNA identified from a native Cas12a locus. Examples include RNA molecules that include the nucleotide sequence of a tracrRNA (or putative tracrRNA) identified from a native Cas12a locus but that further include one or more modifications such as (a) additional nucleotides, e.g., an extension at the 3' terminus, (b) insertion, deletion, or substitution of one or more nucleotides within the naturally occurring tracrRNA sequence, preferably maintaining the secondary structure of the tracrRNA, and (c) chemical modifications, e.g., addition of a detectable label. In embodiments of the DNA expression system, the Cas12a tracrRNA further includes a 5' extension, such as the 5' extensions disclosed by Park et al. (2018) *Nature Communications*, doi: 10.1038/s41467-018-05641-3.

In embodiments where the DNA expression system further includes a terminator located 3' to and operably linked to the DNA encoding a functional RNA molecule, the terminator is functional in the cell wherein the DNA expression system is to be used. By "terminator" is meant a DNA segment near the 3' end of an expression cassette that acts as a signal to terminate transcription and directs polyadenylation of the resultant mRNA. Such a 3' element is also sometimes referred to as a "3'-untranslated region" or "3'-UTR" or a "polyadenylation signal". Non-limiting embodiments of terminators functional in eukaryotic cells include a U6 poly-T terminator, an SV40 terminator, an hGH terminator, a BGH terminator, an rbGlob terminator, a synthetic terminator functional in a eukaryotic cell, a 3' element from an *Agrobacterium* sp. gene, a 3' element from a non-human animal gene, a 3' element from a human gene, and a 3' element from a plant gene, wherein the 3' element terminate transcription of an RNA transcript located immediately 5' to the 3' element. Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in U.S. Patent Application Publication 2002/0192813 A1, incorporated herein by reference. Cas12a tracrRNAs (such as putative Cas12a tracrRNAs identified as described herein) may have associated endogenous pol III terminators which can be used in the DNA expression systems disclosed herein. In embodiments, the DNA expression system includes: (a) DNA sequence for a first promoter; (b) operably linked and heterologous to the first promoter, a DNA sequence encoding a functional RNA molecule including a Cas12a tracrRNA and a functional RNA moiety; and (c) an endogenous pol III terminator (e.g., the terminator naturally associated with a putative Cas12a tracrRNA), or a heterologous terminator. In preferred embodiments of the various DNA expression systems disclosed herein, the terminator is functional in a eukaryotic cell, such as a plant cell; in embodiments, the terminator is one identified from eukaryotic genomic sequence, such as a plant genomic sequence.

In embodiments of the DNA expression system, the first promoter and the DNA encoding the functional RNA molecule, and the DNA encoding a Cas12a crRNA that includes a 3' extension are contained in a single construct. In embodiments of the DNA expression system that include the optional second promoter, the first promoter and the DNA encoding the functional RNA molecule are contained in a first construct, and the second promoter and the DNA encoding a Cas12a crRNA that includes a 3' extension are contained in a second construct; in such embodiments, the first construct and the second construct can be provided (a) in a single vector, or (b) in separate vectors. In embodiments, the first promoter drives expression of both the DNA encoding the functional RNA molecule and the DNA encoding the Cas12a crRNA.

The DNA expression system is useful for expressing a functional RNA molecule including a Cas12a tracrRNA and a functional RNA moiety. Non-limiting embodiments of functional RNA moieties include: (a) an RNA sequence for annealing to a donor polynucleotide (e.g., a single- or double-stranded DNA containing a nucleotide template for HDR-mediated editing, or a single- or double-stranded polynucleotide including a nucleotide sequence to be integrated by an NHEJ mechanism at a double-stranded break effected, for example, by the Cas12a nuclease); (b) an RNA sequence for annealing to the crRNA 3' extension; (c) a terminator sequence; (d) an RNA aptamer; (e) a ribozyme or catalytically active RNA; (f) a detectable label, such as a fluorescent tag; (g) a bar-coding sequence, or short nucleotide sequence useful for marking and identifying DNA that contains the bar-coding sequence; and (h) an RNA sequence forming at least partially double-stranded RNA. In an embodiment, the functional RNA moiety includes RNA forming at least partially double-stranded RNA capable of silencing a gene (e.g., RNA that forms one or more stem-loops where the stem includes double-stranded RNA of at least about 18 base-pairs designed to silence a target gene, or RNA that has the secondary structure of a microRNA precursor and is processed to a mature microRNA designed to silence a target gene). Non-limiting examples of RNA aptamers include an MS2 aptamer (see Parrott et al. (2000) *Nucleic Acids Res.,* 28(2):489-497), an ARiBo tag (see Di Tomasso et al. (2011) *Nucleic Acids Res.,* 39(3):e18; doi: 10.1093/nar/gkq1084), a streptavidin-binding aptamer (see Leppek and Stoecklin (2014) *Nucleic Acids Res.,* 452(2):e13; doi: 10.1093/nar/gkt956), a Csy4 aptamer (see Lee et al. (2013) *Proc. Natl. Acad. Sci. USA,* 110(14):5416-5421; doi: 10.1073/pnas.1302807110, and a Sephadex aptamer (see Srisawat and Engelke (2002) *Methods,* 26(2):156-161; doi: 10.1016/S1046-2023(02)00018-X. Many aptamers are useful for affinity purification and tagging; for example, a two-element affinity tag useful for preparing large quantities of RNA includes a variant of the hepatitis delta virus (HW) ribozyme that is activated by imidazole and a hairpin loop from a thermostable SRP RNA that forms a high-affinity and kinetically stable complex with the *Thermotoga maritima* Ffh-M domain protein (see Keift and Batey (2004) *RNA,* 10(6): 988-995; doi: 10.1261/rna.7040604).

In embodiments of the DNA expression system, the Cas12a crRNA is capable of complexing with a Cas12a nuclease to form a Cas12a ribonucleoprotein complex containing the functional RNA molecule including a Cas12a tracrRNA and a functional RNA moiety. In embodiments, the Cas12a nuclease is any one of the Cas12a ("Cpf1") nucleases disclosed in U.S. Pat. No. 9,790,490 or in U.S. patent application Ser. No. 15/566,528 (national phase entry of International Application No. PCT/EP2016/058442, published as WO2016166340), or in U.S. Pat. No. 9,896,696 which are specifically incorporated herein by reference. In specific embodiments, the Cas12a nuclease is a Cas12a ("Cpf1") nuclease identified from *Francisella novicida* U112 (FnCas12a or "FnCpf1"), from *Acidaminococcus* sp. BV3L6 (AsCas12a or "AsCpf1"), or from Lachnospiraceae bacterium ND2006 (LbCas12a or "LbCpf1"), or is an orthologue thereof, such as an orthologue having at least 50% sequence identity to FnCas12a ("FnCpf1"); see, e.g., the FnCpf1 nuclease contained in the FnCpf1 locus having SEQ ID NO:211 in U.S. Pat. No. 9,790,490, specifically incorporated herein by reference. In embodiments, a Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide;

and (e) an affinity tag. In embodiments of the DNA expression system, the first promoter has a DNA sequence selected from the group consisting of SEQ ID NOs:16-71 and the Cas12a tracrRNA has a nucleotide sequence including a sequence selected from the group consisting of SEQ ID NOs:1, 3, 6, 139-146, and 149-169. In embodiments of the DNA expression system, the first promoter has a DNA sequence selected from the group consisting of SEQ ID NOs:16-71, the Cas12a tracrRNA has a nucleotide sequence including a sequence selected from the group consisting of SEQ ID NOs:1, 3, 6, 139-146, and 149-169, and the optional first terminator has a sequence selected from the group consisting of SEQ ID NOs:72-100. The systems including a tracrRNA as disclosed herein can also be employed with related Cas nucleases, including Csm nucleases, e.g., ObCsm1 (GenBank accession number OGX23684), SmCsm1 (GenBank accession number KF067988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

Engineered Systems

Another aspect of the invention provides a first engineered system including: (a) a Cas12a nuclease; and (b) at least one engineered Cas12a crRNA, or a polynucleotide encoding the engineered Cas12a crRNA, wherein the engineered Cas12a crRNA includes (i) at least one direct repeat sequence or fragment thereof that is capable of associating with the Cas12a nuclease, and (ii) a spacer sequence that is designed to hybridize with a target sequence in a eukaryotic cell, wherein the at least one direct repeat sequence or fragment thereof is adjacent to and 5' to the spacer sequence; and (c) a Cas12a tracrRNA including a nucleotide sequence that has at least 50% complementarity with, the nucleotide sequence of the at least one direct repeat of the engineered Cas12a crRNA.

In another aspect, the invention provides a second engineered system including: (a) a Cas12a nuclease; and (b) at least one engineered Cas12a crRNA, or a polynucleotide encoding the engineered Cas12a crRNA, wherein the engineered Cas12a crRNA includes (i) at least one direct repeat sequence or fragment thereof that is capable of associating with the Cas12a nuclease, and (ii) a spacer sequence that is designed to hybridize with a target sequence in a eukaryotic cell, wherein the at least one direct repeat sequence or fragment thereof is adjacent to and 5' to the spacer sequence; and (c) a Cas12a tracrRNA including a naturally occurring putative Cas12a tracrRNA sequence that is identified from the same genomic region as the Cas12a nuclease by at least the following steps: (i) identifying in the genomic region flanking the DNA encoding the Cas12a nuclease at least one nucleotide sequence that includes a CRISPR array including direct repeats, and (ii) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat.

In embodiments of the first or second engineered systems, the Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag. The systems including a tracrRNA as disclosed herein can also be employed with related Cas nucleases, including Csm nucleases, e.g., ObCsm1 (GenBank accession number OGX23684), SmCsm1 (GenBank accession number KF067988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

In embodiments of the first or second engineered systems, the Cas12a tracrRNA includes a nucleotide sequence that has at least 50% complementarity with, the nucleotide sequence of the at least one direct repeat of the engineered Cas12a crRNA; such a Cas12a tracrRNA can include a naturally occurring putative Cas12a tracrRNA sequence identified from a native Cas12a locus. For example, a naturally occurring putative Cas12a tracrRNA sequence can be identified from a genome using the techniques described by Zetsche et al. (2015) *Cell*, 163:759-771, and in U.S. Pat. No. 9,790,490. A naturally occurring putative Cas12a tracrRNA sequence can be identified from a genome as DNA sequence encoding a RNA molecule that: is predicted to be or putatively transcribed (or that may be determined to be transcribed, e.g., by RNA analysis) from a Cas12a CRISPR genomic region, specifically from a locus that flanks the DNA encoding the Cas12a CRISPR nuclease; that preferably includes a predicted transcriptional terminator in the direction of transcription; that is about 60 to about 100 nucleotides in length, e.g., 60-80 nucleotides, 60-85 nucleotides, 60-90 nucleotides, or 65-95 nucleotides; and that is not a direct repeat in the Cas12a CRISPR array, but rather has a nucleotide sequence that permits the transcribed tracrRNA to hybridize to the crRNA (i.e., the naturally occurring putative Cas12a tracrRNA sequence has sufficient complementarity to a crRNA sequence to hybridize to the crRNA). In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4. In embodiments, the naturally occurring putative Cas12a tracrRNA sequence has a nucleotide sequence having at least 50% identity (e.g., at least 50%, at least 51%, at least 52%, at least 53%, at least 54%, at least 55%, at least 56%, at least 57%, at least 58%, at least 59%, or at least 60% sequence identity) to the sequence of the direct repeat. In embodiments of the first or second engineered systems, the Cas12a tracrRNA has a nucleotide sequence including a sequence selected from the group consisting of SEQ ID NOs:1, 3, 6, 139-146, and 149-169. An alternative embodiment of a "Cas12a tracrRNA" includes an RNA molecule having or including a nucleotide sequence based on the nucleotide sequence of a naturally occurring putative Cas12a tracrRNA sequence identified from a native Cas12a locus. Examples include RNA molecules that include the nucleotide sequence of a naturally occurring putative Cas12a tracrRNA sequence identified from a native Cas12a locus but that further include one or more modifications such as (a) additional nucleotides, e.g., an extension at the 3' terminus, (b) insertion, deletion, or substitution of one or more nucleotides within the naturally occurring tracrRNA sequence, preferably maintaining the secondary structure of the tracrRNA, and (c) chemical modifications, e.g., addition of a detectable label. In embodiments of the first or second engineered systems, the Cas12a tracrRNA further includes a 5' extension, such as the 5' extensions disclosed by Park et al. (2018) *Nature Communications*, doi: 10.1038/s41467-018-05641-3.

In embodiments of the first or second engineered systems, the engineered Cas12a crRNA includes a spacer sequence that is designed to hybridize with a target sequence in a eukaryotic cell. Target sequences and eukaryotic cells are described in detail below under the section headed "Related Disclosure". In embodiments of the first or second engineered systems, the "polynucleotide encoding the engineered Cas12a crRNA" is a naturally occurring polynucleotide, e.g., a pre-processed transcript that includes at least the Cas12a crRNA and often includes additional nucleotides that are removed during processing. In embodiments of the first or second engineered systems, the "polynucleotide encoding the engineered Cas12a crRNA" is an engineered or recombinant polynucleotide. In embodiments of the first or second engineered systems, the engineered Cas12a crRNA, or the polynucleotide encoding the engineered Cas12a crRNA, further includes at least one direct repeat sequence or fragment thereof capable of associating with the Cas12a nuclease, wherein the at least one direct repeat sequence or fragment thereof is adjacent to and 3' to the spacer sequence. In some embodiments of the first or second engineered systems wherein the engineered Cas12a crRNA further includes at least one direct repeat sequence or fragment thereof capable of associating with the Cas12a nuclease, wherein the at least one direct repeat sequence or fragment thereof is adjacent to and 3' to the spacer sequence, the Cas12a tracrRNA has a nucleotide sequence that has at least about 50% or preferably greater than 50% complementarity to the at least one direct repeat sequence or fragment adjacent to and 3' to the spacer sequence.

In embodiments of the first or second engineered systems, the engineered Cas12a crRNA, or the polynucleotide encoding the engineered Cas12a crRNA, further includes: (a) at least one direct repeat sequence or fragment thereof capable of associating with the Cas12a nuclease, wherein the at least one direct repeat sequence or fragment thereof is adjacent to and 3' to the spacer sequence; and (b) a 3' extension adjacent to the spacer sequence. In embodiments of the first or second engineered systems, the 3' extension includes nucleotides that when base-paired form about one helical turn. In embodiments of the first or second engineered systems, the 3' extension includes at least 10 contiguous nucleotides. In embodiments of the first or second engineered systems wherein the engineered Cas12a crRNA further includes a 3' extension adjacent to the spacer sequence, the Cas12a tracrRNA includes a nucleotide sequence having sufficient complementarity (e.g., about 50% or greater than 50%) to the engineered Cas12a crRNA's 3' extension to allow hybridization between the tracrRNA and the engineered Cas12a crRNA. In embodiments, the polynucleotide encoding the engineered Cas12a crRNA is a pre-processed Cas12a crRNA precursor transcript that includes, in 5' to 3' direction, a first direct repeat or fragment thereof, the spacer, and a 3' extension; in some embodiments, the 3' extension includes a second direct repeat or fragment thereof, and/or includes at least 10 contiguous nucleotides, and/or includes nucleotides that when base-paired form about one helical turn; in some embodiments, such a pre-processed Cas12a crRNA precursor transcript is processed (e.g., in vivo or in vitro), resulting in a processed Cas12a crRNA that has had the 3' extension nucleotides excised.

In another aspect, the invention provides a third engineered system including: (a) one or more nucleotide sequences encoding a Cas12a nuclease; and (b) one or more nucleotide sequences encoding at least one engineered Cas12a crRNA that is designed to form a complex with the Cas12a nuclease and that includes a spacer sequence designed to hybridize with a target sequence in a eukaryotic cell; and (c) one or more nucleotide sequences encoding at least one Cas12a tracrRNA.

In another aspect, the invention provides a fourth engineered system including: (a) a Cas12a nuclease, or one or more DNA or RNA nucleotide sequences encoding the Cas12a nuclease; and (b) at least one engineered Cas12a crRNA designed to form a complex with the Cas12a nuclease and including a spacer sequence designed to hybridize with a target sequence in a eukaryotic cell, or one or more DNA or RNA nucleotide sequences encoding the at least one engineered Cas12a crRNA polynucleotide; and (c) at least one tracrRNA, or one or more DNA or RNA nucleotide sequences encoding the at least one Cas12a tracrRNA.

In embodiments of the third or fourth engineered systems, the Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum*, *Eubacterium eligens*, *Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag. The systems including a tracrRNA as disclosed herein can also be employed with related Cas nucleases, including Csm nucleases, e.g., ObCsm1 (GenBank accession number OGX23684), SmCsm1 (GenBank accession number KF067988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

In embodiments of the third or fourth engineered systems, the engineered Cas12a crRNA includes a spacer sequence that is designed to hybridize with a target sequence in a eukaryotic cell. Target sequences and eukaryotic cells are described in detail below under the section headed "Related Disclosure". In embodiments of the third or fourth engineered systems, the "polynucleotide encoding the engineered Cas12a crRNA" is a naturally occurring polynucleotide, e.g., a pre-processed transcript that includes at least the Cas12a crRNA and often includes additional nucleotides that are removed during processing. In embodiments of the third or fourth engineered systems, the "polynucleotide encoding the engineered Cas12a crRNA" is an engineered or recombinant polynucleotide. In embodiments of the third or fourth engineered systems, the at least one engineered Cas12a crRNA, or a polynucleotide encoding the at least one engineered Cas12a crRNA, further includes at least one direct repeat sequence or fragment thereof capable of associating with the Cas12a nuclease, wherein the at least one direct repeat sequence or fragment thereof is adjacent to and 3' to the spacer sequence. In embodiments of the third or fourth engineered systems, the engineered Cas12a crRNA, or a polynucleotide encoding the engineered Cas12a crRNA, further includes at least one direct repeat sequence or fragment thereof capable of associating with the Cas12a nuclease, wherein the at least one direct repeat sequence or fragment thereof is adjacent to and 3' to the spacer sequence. In embodiments of the third or fourth engineered systems where the engineered Cas12a crRNA further includes at least one direct repeat sequence or fragment thereof capable of associating with the Cas12a nuclease, wherein the at least one direct repeat sequence or fragment thereof is adjacent to and 3' to the spacer sequence, the Cas12a tracrRNA has a nucleotide sequence that has at least about 50% or preferably greater than 50% complementarity to the at least one direct repeat sequence or fragment adjacent to and 3' to the spacer sequence. In embodiments of the third or fourth engineered systems, the engineered Cas12a crRNA further includes a 3' extension adjacent to the spacer sequence; in some embodiments, the 3' extension includes nucleotides that when base-paired form about one helical turn; in some embodiments, the 3' extension includes at least 10 contiguous nucleotides. In embodiments of the third or fourth engineered systems where the engineered Cas12a crRNA further includes a 3' extension adjacent to the spacer sequence, the Cas12a tracrRNA has a nucleotide sequence having sufficient complementarity (e.g., about 50% or greater than 50%) to the engineered Cas12a crRNA's 3' extension to allow hybridization between the Cas12a tracrRNA and the engineered Cas12a crRNA.

In embodiments of the third or fourth engineered systems, the at least one tracrRNA, or the one or more nucleotide sequences encoding the at least one Cas12a tracrRNA, includes a nucleotide sequence that has at least 50% complementarity with, the nucleotide sequence of the at least one direct repeat of the engineered Cas12a crRNA. In embodiments of the third or fourth engineered systems, the at least one tracrRNA, or the one or more nucleotide sequences encoding the at least one Cas12a tracrRNA, includes a nucleotide sequence of a naturally occurring putative Cas12a tracrRNA sequence identified from a native Cas12a locus, such as a nucleotide sequence of a naturally occurring putative Cas12a tracrRNA sequence identified from a genome using the techniques described by Zetsche et al. (2015) *Cell*, 163:759-771, and in U.S. Pat. No. 9,790,490. A naturally occurring putative Cas12a tracrRNA sequence can be identified from a genome as DNA sequence encoding a RNA molecule that: is predicted to be or putatively transcribed (or that may be determined to be transcribed, e.g., by RNA analysis) from a Cas12a CRISPR genomic region, specifically from a locus that flanks the DNA encoding the Cas12a CRISPR nuclease; that preferably includes a predicted transcriptional terminator in the direction of transcription; that is about 60 to about 100 nucleotides in length, e.g., 60-80 nucleotides, 60-85 nucleotides, 60-90 nucleotides, or 65-95 nucleotides; and that is not a direct repeat in the Cas12a CRISPR array, but rather has a nucleotide sequence that permits the transcribed tracrRNA to hybridize to the crRNA (i.e., the naturally occurring putative Cas12a tracrRNA sequence has sufficient complementarity to a crRNA sequence to hybridize to the crRNA). In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4. In embodiments of the third or fourth engineered systems, the at least one tracrRNA, or the one or more nucleotide sequences encoding the at least one Cas12a tracrRNA, has a nucleotide sequence having at least 50% identity (e.g., at least 50%, at least 51%, at least 52%, at least 53%, at least 54%, at least 55%, at least 56%, at least 57%, at least 58%, at least 59%, or at least 60% sequence identity) to the sequence of the direct repeat. In embodiments of the third or fourth engineered systems, the at least one tracrRNA, or the one or more nucleotide sequences encoding the at least one Cas12a tracrRNA, has a nucleotide sequence including a sequence selected from the group consisting of SEQ ID NOs:1, 3, 6, 139-146, and 149-169. An alternative embodiment of a "Cas12a tracrRNA" includes an RNA molecule having or including a nucleotide sequence based on the nucleotide sequence of a naturally occurring putative Cas12a tracrRNA sequence identified from a native Cas12a locus. Examples include RNA molecules that include the nucleotide sequence of a naturally occurring putative Cas12a tracrRNA sequence identified from a native Cas12a locus but that further include one or more modifications such as (a) additional nucleotides, e.g., an extension at the 3' terminus, (b) insertion, deletion, or substitution of one or more nucleotides within the naturally occurring tracrRNA sequence, preferably maintaining the secondary structure of the tracrRNA, and (c) chemical modifications, e.g., addition of a detectable label. In embodiments of the third or fourth engineered systems, the at least one tracrRNA, or the one or more nucleotide sequences encoding the at least one Cas12a tracrRNA, further includes a 5' extension, such as the 5' extensions disclosed by Park et al. (2018) *Nature Communications*, doi: 10.1038/s41467-018-05641-3.

In another aspect, the invention provides a fifth engineered system including one or more vectors including: (a) a first regulatory element that is heterologous to and operably linked to one or more nucleotide sequences encoding a Cas12a nuclease; and (b) a second regulatory element that is heterologous to and operably linked to one or more nucleotide sequences encoding at least one engineered Cas12a crRNA that is designed to form a complex with the Cas12a nuclease and that includes a spacer sequence designed to hybridize with a target sequence in a eukaryotic cell; and (c) a third regulatory element that is heterologous to and operably linked to one or more nucleotide sequences encoding at least one Cas12a tracrRNA; wherein components (a) and (b) and (c) are located on the same vector or on different vectors of the system.

In embodiments of the fifth engineered system, the first regulatory element, the second regulatory element, and the third regulatory element each include a promoter that is functional in the eukaryotic cell. Each promoter is selected for operability in the context (in vitro or in vivo) in which the DNA expression system is to be used. Thus, in embodiments, the first regulatory element, the second regulatory element, and the third regulatory element each include a promoter that functions in prokaryotic cells, such as in bacterial cells. In preferred embodiments, the first regulatory element, the second regulatory element, and the third regulatory element each include a promoter that functions in eukaryotic cells, such as in non-human animal (e.g., mammalian, human) or human or plant or fungal cells; in embodiments, the first regulatory element, the second regulatory element, and the third regulatory element each include a promoter identified from a eukaryotic genome, such as a non-human animal or human or plant or fungal genome. In embodiments of the fifth engineered system, any one or more of the regulatory elements also includes other elements that regulate expression, such as, but not limited to, enhancers and introns, examples of which are provided in Table 3. In embodiments of the fifth engineered system, the first regulatory element, the second regulatory element, and the third regulatory element each include a promoter selected from the group consisting of pol III promoters, pol II promoters, and pol I promoters. In embodiments of the fifth engineered system, the first regulatory element, the second regulatory element, and the third regulatory element each include a promoter selected from the group consisting of a U6 promoter, an H1 promoter, a Rous sarcoma virus (RSV) LTR promoter, a cytomegalovirus (CMV) promoter, an SV40 promoter, a dihydrofolate reductase promoter, a beta-actin promoter, a phosphoglycerol kinase (PGK) promoter, and an EF1a promoter. In embodiments, the first regulatory element, the second regulatory element, and the third regulatory element each include a promoter selected from the group consisting of pol III promoters, pol II promoters, and pol I promoters. In embodiments, the first regulatory element, the second regulatory element, and the third regulatory element each include a promoter selected from the group consisting of a U6 promoter, an H1 promoter, a Rous sarcoma virus (RSV) LTR promoter, a cytomegalovirus (CMV) promoter, an SV40 promoter, a dihydrofolate reductase promoter, a beta-actin promoter, a phosphoglycerol kinase (PGK) promoter, an EF1a promoter. In embodiments, the first regulatory element, the second regulatory element, and the third regulatory element each include a promoter that functions in eukaryotic cells, such as in plant cells. For use in plants, useful promoters include constitutive, conditional, inducible, and temporally or spatially specific promoters (e.g., a tissue specific promoter, a developmentally regulated promoter, or a cell cycle regulated promoter). In embodiments, the promoter is a pol II promoter. In embodiments, the promoter is a constitutive promoter that drives DNA expression in plant cells; in embodiments, the promoter drives DNA expression in the nucleus or in an organelle such as a chloroplast or mitochondrion. Examples of constitutive promoters include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and an opaline synthase (NOS) and octapine synthase (OCS) promoter from *Agrobacterium tumefaciens*. In embodiments, the promoter is a promoter from figwort mosaic virus (FMV), a RUBISCO promoter, or a pyruvate phosphate dikinase (PDK) promoter, which is active in the chloroplasts of mesophyll cells. Other contemplated promoters include cell-specific or tissue-specific or developmentally regulated promoters, for example, a promoter that limits the expression of the DNA expression system to germline or reproductive cells (e.g., promoters of genes encoding DNA ligases, recombinases, replicases, or other genes specifically expressed in germline or reproductive cells). In embodiments, the first regulatory element, the second regulatory element, and/or the third regulatory element includes a plant U6 spliceosomal RNA promoter, which can be native to the genome of the plant cell or from a different species, e.g., a U6 promoter from maize, tomato, or soybean such as those disclosed in U.S. patent application Ser. No. 15/120,110, published as U.S. Patent Application Publication 2017/0166912, national phase application claiming priority to PCT/US2015/018104 (published as WO 2015/131101 and claiming priority to U.S. Provisional Patent Application 61/945,700), or a homologue thereof; in an embodiment of the fifth engineered system, such a promoter is operably linked to DNA sequence encoding one or more nucleotide sequences encoding at least one Cas12a tracrRNA, followed by a suitable 3' element such as a U6 poly-T terminator. In another embodiment, the first promoter is a plant U3, 7SL (signal recognition particle RNA), U2, or U5 promoter, or chimerics thereof, e.g., as described in U.S. patent application Ser. No. 15/120,110, published as U.S. Patent Application Publication 2017/0166912, national phase application claiming priority to PCT/US2015/018104 (published as WO 2015/131101 and claiming priority to U.S. Provisional Patent Application 61/945,700). All of the patent publications referenced in this paragraph are incorporated herein by reference in their entirety. In embodiments of the fifth engineered system, the eukaryotic cell is a plant cell, and wherein the third regulatory element includes a promoter having a nucleotide sequence selected from the group consisting of SEQ ID NOs:16-71. In embodiments of the fifth engineered system, the at least one Cas12a tracrRNA is at least one Cas12a tracrRNA having a nucleotide sequence including a sequence selected from the group consisting of SEQ ID NOs:1, 3, 6, 139-146, and 149-169. In specific embodiments of the fifth engineered system, the eukaryotic cell is a plant cell, the third regulatory element includes a promoter having a nucleotide sequence selected from the group consisting of SEQ ID NOs:16-71, and the at least one Cas12a tracrRNA is at least one Cas12a tracrRNA having a nucleotide sequence including a sequence selected from the group consisting of SEQ ID NOs:1, 3, 6, 139-146, and 149-169.

In embodiments of the fifth engineered system, the Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag. The systems including a tracrRNA as disclosed herein can also be employed with related Cas nucleases, including Csm nucleases, e.g., ObCsm1 (GenBank accession number OGX23684), SmCsm1 (GenBank accession number KF067988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

In embodiments of the fifth engineered system, the at least one engineered Cas12a crRNA includes a spacer sequence designed to hybridize with a target sequence in a eukaryotic cell. Target sequences and eukaryotic cells are described in detail below under the section headed "Related Disclosure". In embodiments of the fifth engineered system, the at least one engineered Cas12a crRNA, or the one or more nucleotide sequences encoding the at least one engineered Cas12a crRNA, further includes at least one direct repeat sequence or fragment thereof that is capable of associating with the Cas12a nuclease and is adjacent to and 5' to the spacer sequence. In embodiments of the fifth engineered system, the engineered Cas12a crRNA, or a polynucleotide encoding the engineered Cas12a crRNA, further includes at least one direct repeat sequence or fragment thereof capable of associating with the Cas12a nuclease, wherein the at least one direct repeat sequence or fragment thereof is adjacent to and 3' to the spacer sequence. In embodiments of the fifth engineered system where the engineered Cas12a crRNA further includes at least one direct repeat sequence or fragment thereof capable of associating with the Cas12a nuclease, wherein the at least one direct repeat sequence or fragment thereof is adjacent to and 3' to the spacer sequence, the Cas12a tracrRNA has a nucleotide sequence that has at least about 50% or preferably greater than 50% complementarity to the at least one direct repeat sequence or fragment adjacent to and 3' to the spacer sequence. In embodiments of the fifth engineered system, the engineered Cas12a crRNA further includes a 3' extension adjacent to the spacer sequence; in some embodiments, the 3' extension includes nucleotides that when base-paired form about one helical turn; in some embodiments, the 3' extension includes at least 10 contiguous nucleotides. In embodiments of the fifth engineered system where the engineered Cas12a crRNA further includes a 3' extension adjacent to the spacer sequence, the Cas12a tracrRNA has a nucleotide sequence having sufficient complementarity (e.g., about 50% or greater than 50%) to the engineered Cas12a crRNA's 3' extension to allow hybridization between the Cas12a tracrRNA and the engineered Cas12a crRNA.

In embodiments of the fifth engineered system, the at least one tracrRNA, or the one or more nucleotide sequences encoding at least one Cas12a tracrRNA, includes a nucleotide sequence that has at least 50% complementarity with, the nucleotide sequence of a direct repeat sequence or fragment thereof that is capable of associating with the Cas12a nuclease and is adjacent to and 5' to the spacer sequence of the engineered Cas12a crRNA. In embodiments of the fifth engineered system, the at least one tracrRNA, or the one or more nucleotide sequences encoding the at least one Cas12a tracrRNA, includes a nucleotide sequence of a naturally occurring putative Cas12a tracrRNA sequence identified from a native Cas12a locus, such as a nucleotide sequence of a naturally occurring putative Cas12a tracrRNA sequence identified from a genome using the techniques described by Zetsche et al. (2015) Cell, 163:759-771, and in U.S. Pat. No. 9,790,490. A naturally occurring putative Cas12a tracrRNA sequence can be identified from a genome as DNA sequence encoding a RNA molecule that: is predicted to be or putatively transcribed (or that may be determined to be transcribed, e.g., by RNA analysis) from a Cas12a CRISPR genomic region, specifically from a locus that flanks the DNA encoding the Cas12a CRISPR nuclease; that preferably includes a predicted transcriptional terminator in the direction of transcription; that is about 60 to about 100 nucleotides in length, e.g., 60-80 nucleotides, 60-85 nucleotides, 60-90 nucleotides, or 65-95 nucleotides; and that is not a direct repeat in the Cas12a CRISPR array, but rather has a nucleotide sequence that permits the transcribed tracrRNA to hybridize to the crRNA (i.e., the naturally occurring putative Cas12a tracrRNA sequence has sufficient complementarity to a crRNA sequence to hybridize to the crRNA). In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4. In embodiments of the fifth engineered system, the at least one tracrRNA, or the one or more nucleotide sequences encoding the at least one Cas12a tracrRNA, has a nucleotide sequence having at least 50% identity (e.g., at least 50%, at least 51%, at least 52%, at least 53%, at least 54%, at least 55%, at least 56%, at least 57%, at least 58%, at least 59%, or at least 60% sequence identity) to the sequence of the direct repeat. In embodiments of the fifth engineered system, the at least one tracrRNA, or the one or more nucleotide sequences encoding the at least one Cas12a tracrRNA, has a nucleotide sequence including a sequence selected from the group consisting of SEQ ID NOs:1, 3, 6, 139-146, and 149-169. An alternative embodiment of a "Cas12a tracrRNA" includes an RNA molecule having or including a nucleotide sequence based on the nucleotide sequence of a naturally occurring putative Cas12a tracrRNA sequence identified from a native Cas12a locus. Examples include RNA molecules that include the nucleotide sequence of a naturally occurring putative Cas12a tracrRNA sequence identified from a native Cas12a locus but that further include one or more modifications such as (a) additional nucleotides, e.g., an extension at the 3' terminus, (b) insertion, deletion, or substitution of one or more nucleotides within the naturally occurring tracrRNA sequence, preferably maintaining the secondary structure of the tracrRNA, and (c) chemical modifications, e.g., addition of a detectable label. In embodiments of the fifth engineered system, the at least one tracrRNA, or the one or more nucleotide sequences encoding the at least one Cas12a tracrRNA, further includes a 5' extension, such as the 5' extensions disclosed by Park et al. (2018) *Nature Communications*, doi: 10.10381s41467-018-05641-3.

Another aspect of the invention provides a sixth engineered system including one or more vectors including: (a) a first expression cassette including at least a first promoter that is heterologous to and operably linked to one or more nucleotide sequences encoding a Cas12a nuclease and—optionally—a first transcription terminator sequence; and (b) a second expression cassette including at least a second promoter that is heterologous to operably linked to one or more nucleotide sequences encoding at least one engineered Cas12a crRNA that is designed to form a complex with the Cas12a nuclease and that includes a spacer sequence designed to hybridize with a target sequence in a eukaryotic cell and—optionally—a second transcription terminator sequence; and (c) a third expression cassette including at least a third promoter that is heterologous to operably linked to one or more nucleotide sequences encoding at least one Cas12a tracrRNA and—optionally—a third transcription terminator sequence, wherein components (a) and (b) and (c) are located on the same vector or on different vectors of the system.

In embodiments of the sixth engineered system, the first promoter, the second promoter, and the third promoter are each a promoter that is functional in the eukaryotic cell, and wherein the first transcription terminator, the second transcription terminator, and the third transcription terminator are each a transcription terminator that is functional in the eukaryotic cell. In embodiments, the first promoter, the second promoter, and the third promoter are each a promoter selected from the group consisting of pol III promoters, pol II promoters, and pol I promoters. In embodiments of the sixth engineered system, the first promoter, the second promoter, and the third promoter are each a promoter selected from the group consisting of a U6 promoter, an H1 promoter, a *Rous sarcoma* virus (RSV) LTR promoter, a cytomegalovirus (CMV) promoter, an SV40 promoter, a dihydrofolate reductase promoter, a beta-actin promoter, a phosphoglycerol kinase (PGK) promoter, an EF1a promoter. In embodiments of the sixth engineered system, the first promoter, the second promoter, and the third promoter are each a promoter with a nucleotide sequence selected from the group consisting of SEQ ID NOs:16-71. In embodiments of the sixth engineered system, the first transcription terminator, the second transcription terminator, and the third transcription terminator are each selected from the group consisting of a U6 poly-T terminator, an SV40 terminator, an hGH terminator, a BGH terminator, an rbGlob terminator, a synthetic terminator functional in a eukaryotic cell, a 3' element from an *Agrobacterium* sp. gene, a 3' element from a non-human animal gene, a 3' element from a human gene, and a 3' element from a plant gene, wherein the 3' element terminate transcription of an RNA transcript located immediately 5' to the 3' element. In embodiments of the sixth engineered system, the first transcription terminator, the second transcription terminator, and the third transcription terminator are each a transcription terminator having a sequence selected from the group consisting of SEQ ID NOs:72-100.

In embodiments of the sixth engineered system, the Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag. The systems including a tracrRNA as disclosed herein can also be employed with related Cas nucleases, including Csm nucleases, e.g., ObCsm1 (GenBank accession number OGX23684), SmCsm1 (GenBank accession number KF067988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

In embodiments of the sixth engineered system, the at least one tracrRNA, or the one or more nucleotide sequences encoding at least one Cas12a tracrRNA, includes a nucleotide sequence that has at least 50% complementarity with the nucleotide sequence of a direct repeat sequence or fragment thereof that is capable of associating with the Cas12a nuclease and is adjacent to and 5' to the spacer sequence of the engineered Cas12a crRNA. In embodiments of the sixth engineered system, the at least one tracrRNA, or the one or more nucleotide sequences encoding the at least one Cas12a tracrRNA, includes a nucleotide sequence of a naturally occurring putative Cas12a tracrRNA sequence identified from a native Cas12a locus, such as a nucleotide sequence of a naturally occurring putative Cas12a tracrRNA sequence identified from a genome using the techniques described by Zetsche et al. (2015) *Cell,* 163:759-771, and in U.S. Pat. No. 9,790,490. A naturally occurring putative Cas12a tracrRNA sequence can be identified from a genome as DNA sequence encoding a RNA molecule that: is predicted to be or putatively transcribed (or that may be determined to be transcribed, e.g., by RNA analysis) from a Cas12a CRISPR genomic region, specifically from a locus that flanks the DNA encoding the Cas12a CRISPR nuclease; that preferably includes a predicted transcriptional terminator in the direction of transcription; that is about 60 to about 100 nucleotides in length, e.g., 60-80 nucleotides, 60-85 nucleotides, 60-90 nucleotides, or 65-95 nucleotides; and that is not a direct repeat in the Cas12a CRISPR array, but rather has a nucleotide sequence that permits the transcribed tracrRNA to hybridize to the crRNA (i.e., the naturally occurring putative Cas12a tracrRNA sequence has sufficient complementarity to a crRNA sequence to hybridize to the crRNA). In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4. In embodiments of the sixth engineered system, the at least one tracrRNA, or the one or more nucleotide sequences encoding the at least one Cas12a tracrRNA, has a nucleotide sequence having at least 50% identity (e.g., at least 50%, at least 51%, at least 52%, at least 53%, at least 54%, at least 55%, at least 56%, at least 57%, at least 58%, at least 59%, or at least 60% sequence identity) to the sequence of the direct repeat. In embodiments of the sixth engineered system, the at least one tracrRNA, or the one or more nucleotide sequences encoding the at least one Cas12a tracrRNA, has a nucleotide sequence including a sequence selected from the group consisting of SEQ ID NOs:1, 3, 6, 139-146, and 149-169. An alternative embodiment of a "Cas12a tracrRNA" includes an RNA molecule having or including a nucleotide sequence based on the nucleotide sequence of a naturally occurring putative Cas12a tracrRNA sequence identified from a native Cas12a locus. Examples include RNA molecules that include the nucleotide sequence of a naturally occurring putative Cas12a tracrRNA sequence identified from a native Cas12a locus but that further include one or more modifications such as (a) additional nucleotides, e.g., an extension at the 3' terminus, (b) insertion, deletion, or substitution of one or more nucleotides within the naturally occurring tracrRNA sequence, preferably maintaining the secondary structure of the tracrRNA, and (c) chemical modifications, e.g., addition of a detectable label. In embodiments of the sixth engineered system, the at least one tracrRNA, or the one or more nucleotide sequences encoding the at least one Cas12a tracrRNA, further includes a 5' extension, such as the 5' extensions disclosed by Park et al. (2018) *Nature Communications*, doi: 10.1038/s41467-018-05641-3.

In embodiments of the sixth engineered system, the at least one engineered Cas12a crRNA includes a spacer sequence designed to hybridize with a target sequence in a eukaryotic cell. Target sequences and eukaryotic cells are described in detail below under the section headed "Related Disclosure". In embodiments, the eukaryotic cell is a non-human animal cell, a human cell, a plant cell, or a fungal cell. In embodiments of the sixth engineered system, the eukaryotic cell is in vitro, ex vivo, or in vivo.

Disclosure Related to the Engineered Systems

The disclosure of this section is related to embodiments of the first, second, third, fourth, fifth, and sixth engineered systems.

In embodiments of any one of the first, second, third, fourth, fifth, and sixth engineered systems, the Cas12a nuclease is: (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum*, *Eubacterium eligens*, *Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag. The systems including a tracrRNA as disclosed herein can also be employed with related Cas nucleases, including Csm nucleases, e.g., ObCsm1 (GenBank accession number OGX23684), SmCsm1 (GenBank accession number KF067988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

In embodiments of any one of the first, second, third, fourth, fifth, and sixth engineered systems, the at least one Cas12a tracrRNA has a nucleotide sequence selected from SEQ ID NOs:1, 3, 6, 139-146, and 149-169. In embodiments of any one of the first, second, third, fourth, fifth, and sixth engineered systems, the genomic sequence encoding the Cas12a nuclease and the genomic sequence encoding the Cas12a tracrRNA occur naturally within the same region in a genome; in embodiments, the genomic sequence encoding the Cas12a tracrRNA is located preferably within about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 kilobases of the DNA segment(s) encoding the Cas12a nuclease. In embodiments of any one of the first, second, third, fourth, fifth, and sixth engineered systems, the target sequence is located 3' of a Protospacer Adjacent Motif (PAM) and the PAM sequence is TTN, where N is A/C/G or T and the Cas12a nuclease is FnCpf1, or the PAM sequence is TTTV, where V is A/C or G and the Cas12a nuclease is PaCpf1p, LbCpf1 or AsCpf1.

In embodiments of any one of the first, second, fourth, fifth, and sixth engineered systems, the Cas12a tracrRNA is a putative Cas12a tracrRNA that is identified from the same genomic region as the Cas12a nuclease by at least the following steps: (a) identifying in the genomic region flanking the DNA encoding the Cas12a nuclease at least one nucleotide sequence that includes a CRISPR array including direct repeats; (b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat. In embodiments, the genomic sequence encoding the Cas12a tracrRNA is located preferably within about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 kilobases of the DNA segment(s) encoding the Cas12a nuclease. In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4.

In embodiments of any one of the first, second, fourth, fifth, and sixth engineered systems, the Cas12a tracrRNA is provided: (a) as DNA encoding a first RNA molecule including the Cas12a tracrRNA and including a restriction endonuclease cleavage site that is suitable for insertion of a sequence coding for a functional RNA moiety; or (b) as a functional RNA molecule including the Cas12a tracrRNA and a functional RNA moiety, or as a polynucleotide encoding the functional RNA molecule; or (c) by a DNA expression system including: (i) DNA sequence for a first promoter; and (ii) operably linked and heterologous to the first promoter, a DNA sequence encoding a first RNA molecule including a Cas12a tracrRNA and including a restriction endonuclease cleavage site that is suitable for insertion of a sequence coding for a functional RNA moiety; or (d) by a DNA expression system including: (a) DNA sequence for a first promoter; and (b) operably linked and heterologous to the first promoter, a DNA sequence encoding a functional RNA molecule including a Cas12a tracrRNA and a functional RNA moiety. In embodiments, the DNA expression system includes (a) DNA sequence for a first promoter; and (b) operably linked and heterologous to the first promoter, a DNA sequence encoding a functional RNA molecule including a Cas12a tracrRNA and a functional RNA moiety, and (c) a terminator 3' to and operably linked to the DNA encoding a functional RNA molecule.

In embodiments of any one of the first, second, third, fourth, fifth, and sixth engineered systems, the Cas12a tracrRNA is provided as DNA encoding a first RNA molecule including the Cas tracrRNA and including a restriction endonuclease cleavage site that is suitable for insertion of a sequence coding for a functional RNA moiety, and wherein the functional RNA moiety is at least one selected from the group consisting of: (a) a nucleotide sequence for annealing to a donor polynucleotide; (b) a nucleotide sequence for annealing to the crRNA 3' extension; (c) a terminator sequence; (d) an RNA aptamer; (e) an enzymatically active RNA sequence; (f) a detectable label; and (g) an RNA sequence forming at least partially double-stranded RNA. In embodiments of any one of the first, second, fourth, fifth, and sixth engineered systems, the Cas12a tracrRNA is provided as DNA encoding a first RNA molecule including the Cas12a tracrRNA and including a restriction endonuclease cleavage site that is suitable for insertion of a sequence coding for a functional RNA moiety, wherein the functional RNA moiety includes RNA forming at least partially double-stranded RNA capable of silencing a gene (e.g., RNA that forms one or more stem-loops where the stem includes double-stranded RNA of at least about 18 base-pairs designed to silence a target gene, or RNA that has the secondary structure of a microRNA precursor and is processed to a mature microRNA designed to silence a target gene). In embodiments of any one of the first, second, fourth, fifth, and sixth engineered systems, the Cas12a tracrRNA is provided as DNA encoding a first RNA molecule including the Cas12a tracrRNA and including a restriction endonuclease cleavage site that is suitable for insertion of a sequence coding for a functional RNA moiety, wherein the functional RNA moiety includes an RNA sequence for annealing to a donor polynucleotide, and wherein the composition further includes the donor polynucleotide.

In embodiments of any one of the first, second, third, fourth, fifth, and sixth engineered systems, the Cas12a tracrRNA is provided as a functional RNA molecule including the Cas12a tracrRNA and a functional RNA moiety, or as a polynucleotide encoding the functional RNA molecule, and wherein the functional RNA moiety is at least one selected from the group consisting of: (a) a nucleotide sequence for annealing to a donor polynucleotide; (b) a nucleotide sequence for annealing to the crRNA 3' extension; (c) a terminator sequence; (d) an RNA aptamer; (e) an enzymatically active RNA sequence; (f) a detectable label; and (g) an RNA sequence forming at least partially double-stranded RNA. In embodiments of any one of the first, second, third, fourth, fifth, and sixth engineered systems, the Cas12a tracrRNA is provided as a functional RNA molecule including the Cas12a tracrRNA and a functional RNA moiety, or as a polynucleotide encoding the functional RNA molecule, and wherein the functional RNA moiety includes RNA forming at least partially double-stranded RNA capable of silencing a gene (e.g., RNA that forms one or more stem-loops where the stem includes double-stranded RNA of at least about 18 base-pairs designed to silence a target gene, or RNA that has the secondary structure of a microRNA precursor and is processed to a mature microRNA designed to silence a target gene). In embodiments of any one of the first, second, third, fourth, fifth, and sixth engineered systems, the Cas12a tracrRNA is provided as a functional RNA molecule including the Cas12a tracrRNA and a functional RNA moiety, or as a polynucleotide encoding the functional RNA molecule, and wherein the functional RNA moiety includes RNA forming at least partially double-stranded RNA capable of silencing a gene that is involved in one or more small RNA-mediated silencing pathways, e.g., RDR6, SDE3, RDR2, WEX, SGS3, DCL2-4, UPF1, UPF3, HEN1, NRPD1A, NRPD2, DRD1, HDA6, AGO1, and MOP1.

In embodiments of any one of the first, second, third, fourth, fifth, and sixth engineered systems, the Cas12a tracrRNA is provided as a functional RNA molecule including the Cas12a tracrRNA and a functional RNA moiety, or as a polynucleotide encoding the functional RNA molecule, wherein the functional RNA moiety includes an RNA sequence for annealing to a donor polynucleotide, and wherein the system further includes the donor polynucleotide. In embodiments, the donor polynucleotide is single-stranded DNA, or is blunt-ended double-stranded DNA, or is double-stranded DNA with an overhang at least at one terminus, or is an at least partially double-stranded DNA/RNA hybrid. In embodiments of any one of the first, second, third, fourth, fifth, and sixth engineered systems, the Cas12a tracrRNA is provided in a molar excess, relative to the amount of Cas12a nuclease. In embodiments of any one of the first, second, third, fourth, fifth, and sixth engineered systems, the Cas12a tracrRNA is provided in a molar amount that is at least 10-fold greater than the molar amount of the Cas12a nuclease.

A related aspect of the invention includes a delivery particle including the engineered system any one of the first, second, third, fourth, fifth, and sixth engineered systems. In embodiments of the delivery particle, the Cas12a nuclease is complexed with the engineered Cas12a crRNA polynucleotide, e.g., to form a Cas12a ribonucleoprotein. In embodiments of the delivery particle, the Cas12a tracrRNA is present in a molar excess, relative to the amount of Cas12a nuclease (or Cas12a ribonucleoprotein). In embodiments of the delivery particle, the Cas12a tracrRNA is present in a molar amount that is at least 10-fold greater than the molar amount of the Cas12a nuclease (or Cas12a ribonucleoprotein). In embodiments of the delivery particle, the Cas12a nuclease is first complexed with the engineered Cas12a crRNA polynucleotide, e.g., to form a Cas12a ribonucleoprotein, followed by provision, without an annealing step, of the Cas12a tracrRNA in a molar amount that is at least 10-fold greater than the molar amount of the Cas12a nuclease (or Cas12a ribonucleoprotein).

A related aspect of the invention includes a delivery liquid including the engineered system any one of the first, second, third, fourth, fifth, and sixth engineered systems. In embodiments of the delivery liquid, the Cas12a nuclease is complexed with the engineered Cas12a crRNA polynucleotide, e.g., to form a Cas12a ribonucleoprotein. In embodiments of the delivery liquid, the Cas12a tracrRNA is present in a molar excess, relative to the amount of Cas12a nuclease (or Cas12a ribonucleoprotein). In embodiments of the delivery liquid, wherein the Cas12a tracrRNA is present in a molar amount that is at least 10-fold greater than the molar amount of the Cas12a nuclease (or Cas12a ribonucleoprotein). In embodiments of the delivery liquid, the Cas12a nuclease is first complexed with the engineered Cas12a crRNA polynucleotide, e.g., to form a Cas12a ribonucleoprotein, followed by provision, without an annealing step, of the Cas12a tracrRNA in a molar amount that is at least 10-fold greater than the molar amount of the Cas12a nuclease (or Cas12a ribonucleoprotein).

Yet another aspect of the invention includes a method of modifying or editing a target sequence in a locus of interest of a eukaryotic cell including delivering the engineered system according to any one of the first, second, third, fourth, fifth, and sixth engineered systems to the locus of interest, wherein the spacer sequence hybridizes with the target sequence, whereby modification or editing of the locus of interest occurs. Target sequences and eukaryotic cells are described in detail below under the section headed "Related Disclosure". The locus of interest is any specific locus in a DNA molecule, chromosome, or genome obtained from or located within a eukaryotic cell, a eukaryotic tissue, or a eukaryotic organism; in embodiments, the DNA molecule, chromosome, or genome is in vitro, ex vivo, or in vivo. In embodiments of the method, the eukaryotic cell includes a cell of a cell line or a cell of a multicellular organism, and the locus of interest includes a locus of interest in the genome of the eukaryotic cell. In embodiments of the method, the locus of interest is DNA encoding a gene of interest, and can include coding sequence, non-coding sequence, or both coding and non-coding sequence, and can include an intact functional gene (e.g., including untranscribed regions located 3' or 5' to DNA regions encoding a polypeptide, introns, and regulatory elements such as promoters, enhancers, polyadenylation signals, and terminators). In embodiments of the method, the target sequence is a segment of the locus of interest; in embodiments, the target sequence includes about 20 to about 30 contiguous nucleotides and has near perfect or perfect sequence complementarity to the nucleotide sequence of the spacer of the Cas12a crRNA. In embodiments of the method, the eukaryotic cell is a non-human animal cell, a human cell, a plant cell, or a fungal cell. In embodiments of the method, the eukaryotic cell is in vitro, ex vivo, or in vivo. In embodiments of the method, the locus of interest is within a eukaryotic cell, a eukaryotic tissue, or a eukaryotic organism; in embodiments, the locus of interest is within the genome of a non-human animal, a human, a plant, or a fungus, or within the genome of a eukaryotic organelle such as a mitochondrion or a plastid (e.g., a chloroplast). In embodiments of the method, the eukaryotic cell includes a non-human animal or human stem cell or a non-human animal or human stem cell line. In embodiments of the method, the locus of interest is within a eukaryotic DNA molecule in vitro or in a recombinant DNA molecule or recombinant vector.

In embodiments of the method, the eukaryotic cell includes a plant cell, and the modification of the locus of interest is correlated with a modified trait in a plant including cells containing the modification of the locus of interest. In embodiments of the method, the eukaryotic cell includes a plant cell, the modification of the locus of interest is correlated with a modified trait in a plant including cells containing the modification of the locus of interest, and the method further includes obtaining, growing, or regenerating a plant from the plant cell, wherein the plant includes cells containing the modification of the locus of interest, and wherein the plant exhibits the modified trait effected by the modification of the locus of interest. In embodiments of the method, the eukaryotic cell includes a plant cell, and the method further includes identifying a trait of interest in a plant obtained, grown, or regenerated from the plant cell, wherein the trait of interest is effected by the modification of the locus of interest. In embodiments of the method, the eukaryotic cell includes a plant cell, the method further includes identifying a trait of interest in a plant obtained, grown, or regenerated from the plant cell, wherein the trait of interest is effected by the modification of the locus of interest, and the method further includes (a) introducing a nucleotide sequence including the locus of interest into a plant cell, a plant cell line, or a plant germplasm, and generating from the plant cell, the plant cell line, or the plant germplasm a plant including cells containing the nucleotide sequence including the locus of interest; or (b) introducing the modified locus of interest into a plant cell, a plant cell line, or a plant germplasm, and generating from the plant cell, the plant cell line, or the plant germplasm a plant including cells containing the modified locus of interest; or (c) modifying expression of the locus of interest in a plant cell, a plant cell line, or a plant germplasm, and generating from the plant cell, the plant cell line, or the plant germplasm a plant including cells containing the locus of interest having modified expression; or (d) deleting the locus of interest or an endogenous nucleotide sequence including the locus of interest in a plant cell, and generating from the plant cell, the plant cell line, or the plant germplasm a plant including cells in which the locus of interest or the endogenous nucleotide sequence including the locus of interest has been deleted.

In embodiments of the method, the eukaryotic cell includes a non-human animal cell (e.g. a somatic cell or gamete of a non-human animal, in vivo, in vitro, or ex vivo), and the modification of the locus of interest is correlated with a modified trait or characteristic in a non-human animal including cells containing the modification of the locus of interest. In embodiments of the method, the eukaryotic cell includes a non-human animal cell, the modification of the locus of interest is correlated with a modified trait or characteristic in a non-human animal or in a non-human animal cell line including cells containing the modification of the locus of interest, and the method further includes obtaining, growing, regenerating, or breeding a non-human animal or a non-human animal cell line from the non-human animal cell, wherein the non-human animal or a non-human animal cell line includes cells containing the modification of the locus of interest, and wherein the non-human animal or a non-human animal cell line exhibits the modified trait or characteristic effected by the modification of the locus of interest. In embodiments of the method, the eukaryotic cell includes a non-human animal cell, and the method further includes identifying a trait or characteristic of interest in a non-human animal or a non-human animal cell line obtained, grown, regenerated, or bred from the non-human animal cell, wherein the trait or characteristic of interest is effected by the modification of the locus of interest. In embodiments of the method, the eukaryotic cell includes a non-human animal cell, the method further includes identifying a trait or characteristic of interest in a non-human animal or a non-human animal cell line obtained, grown, regenerated, or bred from the non-human animal cell, wherein the trait or characteristic of interest is effected by the modification of the locus of interest, and the method further includes (a) introducing a nucleotide sequence including the locus of interest into a non-human animal cell, a non-human animal cell line, or a non-human animal, and obtaining, growing, regenerating, or breeding from the non-human animal cell, the non-human animal cell line, or the non-human animal a non-human animal or a non-human animal cell line including cells containing the nucleotide sequence including the locus of interest; or (b) introducing the modified locus of interest into a non-human animal cell, a non-human animal cell line, or a non-human animal, and obtaining, growing, regenerating, or breeding from the non-human animal cell, the non-human animal cell line, or the non-human animal a non-human animal or a non-human animal cell line including cells containing the modified locus of interest; or (c) modifying expression of the locus of interest in a non-human animal cell, a non-human animal cell line, or a non-human animal, and obtaining, growing, regenerating, or breeding from the non-human animal cell, the non-human animal cell line, or the non-human animal a non-human animal or a non-human animal cell line including cells containing the locus of interest having modified expression; or (d) deleting the locus of interest or an endogenous nucleotide sequence including the locus of interest in a non-human animal cell, a non-human animal cell line, or a non-human animal, and obtaining, growing, regenerating, or breeding from the non-human animal cell, the non-human animal cell line, or the non-human animal a non-human animal or a non-human animal cell line including cells in which the locus of interest or the endogenous nucleotide sequence including the locus of interest has been deleted.

In embodiments of the method, the engineered system or a component thereof is delivered via delivery particles, delivery vesicles, delivery liquids, or one or more viral or bacterial vectors. In embodiments of the method, the engineered system or a component thereof is delivered via delivery particles such as delivery nanoparticles or delivery microparticles including at least one material or reagent selected from the group consisting of a lipid, a sugar, a metal, or a protein. In embodiments of the method, the system or a component thereof is delivered via delivery exosomes or liposomes. In embodiments of the method, the engineered system or a component thereof is delivered via at least one viral vector selected from the group consisting of adenoviruses, lentiviruses, adeno-associated viruses, retroviruses, geminiviruses, begomoviruses, tobamoviruses, potex viruses, comoviruses, wheat streak mosaic virus, barley stripe mosaic virus, bean yellow dwarf virus, bean pod mottle virus, cabbage leaf curl virus, beet curly top virus, tobacco yellow dwarf virus, tobacco rattle virus, potato virus X, and cowpea mosaic virus. In embodiments of the method, the engineered system or a component thereof is delivered via at least one bacterial vector capable of transforming a plant cell and selected from the group consisting of *Agrobacterium* sp., *Rhizobium* sp., *Sinorhizobium* (Ensifer) sp., *Mesorhizobium* sp., *Bradyrhizobium* sp., *Azobacter* sp., and *Phyllobacterium* sp. Additional information on delivery particles, delivery vesicles, delivery liquids, viral or bacterial vectors, and reagents and methods for their use is found in the section below headed "Delivery Methods and Delivery Agents".

In embodiments of the method, the Cas12a nuclease is: (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag.

In embodiments of the method, the Cas12a tracrRNA has a nucleotide sequence including a sequence selected from the group consisting of SEQ ID NOs:1, 3, 6, 139-146, and 149-169. In embodiments of the method, the tracrRNA is a putative Cas12a tracrRNA that is identified from the same genomic region as the Cas12a nuclease by at least the following steps: (a) identifying in the genomic region flanking the DNA encoding the Cas12a nuclease at least one nucleotide sequence that includes a CRISPR array including direct repeats; (b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat. In embodiments of the method, the Cas12a tracrRNA locus is directly adjacent to the DNA encoding the Cas12a nuclease. In embodiments of the method, there is additional genomic sequence, such as DNA sequence encoding other Cas nucleases, located between the Cas12a tracrRNA locus and the DNA encoding the Cas12a nuclease; see, e.g., FIGS. 1 and 4.

Methods of Editing a Genetic Locus with a Cas12a Nuclease with Increased Efficiency A further aspect of the invention includes a method of editing a genetic locus with a Cas12a nuclease, including contacting DNA that includes the genetic locus with: (a) a Cas12a nuclease; and (b) an engineered Cas12a crRNA that includes a spacer sequence that is designed to hybridize with a target sequence in the genetic locus; and (c) a Cas12a tracrRNA, thereby editing the genetic locus; wherein the efficiency of editing of the genetic locus is increased compared to a control method in which the DNA that includes the genetic locus is contacted with the Cas12a nuclease and the Cas12a crRNA, but not the Cas12a tracrRNA. The method enables editing a genetic locus or target sequence with a Cas12a nuclease with increased efficiency, in comparison to methods previously reported that employ a Cas12a nuclease and a Cas12a crRNA (or "guide RNA") but do not include a Cas12a tracrRNA. Efficiency of editing is increased, e.g., when the percentage of cells containing the expected edit at the genetic locus is increased compared to that seen in a control, or when a given level of editing is obtained using a lower amount of Cas12a nuclease, compared to a control. A related aspect is a method of increasing the efficiency of editing a genetic locus by a Cas12a ribonucleoprotein that includes a Cas12a nuclease and a Cas12a crRNA, by providing together with the Cas12a ribonucleoprotein a Cas12a tracrRNA that is capable of hybridizing to the Cas12a crRNA (e.g., a Cas12a tracrRNA of between about 60 to about 100 nucleotides in length that has at least 50% complementarity to the sequence of the Cas12a crRNA), whereby the efficiency of the editing of the genetic locus is increased, compared to that obtained in a control method where the Cas12a ribonucleoprotein is provided without the Cas12a tracrRNA; in embodiments of the method, the Cas12a tracrRNA is provided in molar excess of the Cas12a ribonucleoprotein.

In embodiments of the methods, the Cas12a nuclease and the engineered Cas12a crRNA are provided as a ribonucleoprotein complex. In embodiments, the Cas12a nuclease is provided as a polynucleotide encoding the Cas12a nuclease. In embodiments, the Cas12a nuclease is: (a) a Cas12a nuclease identified from the genome of a bacterial species selected from the group consisting of Francisella tularensis 1, Prevotella albensis, Lachnospiraceae bacterium MC2017 1, Butyrivibrio proteoclasticus, Peregrinibacteria bacterium GW2011_GWA2_33_10, Parcubacteria bacterium GW2011_GWC2_44_17, Smithella sp. SCADC, Acidaminococcus sp. BV3L6, Lachnospiraceae bacterium MA2020, Candidatus Methanoplasma termitum, Eubacterium eligens, Moraxella bovoculi 237, Leptospira inadai, Lachnospiraceae bacterium ND2006, Porphyromonas crevioricanis 3, Prevotella disiens and Porphyromonas macacae; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag. The methods including use of a tracrRNA as disclosed herein can also be employed with related Cas nucleases, including Csm nucleases, e.g., ObCsm1 (GenBank accession number OGX23684), SmCsm1 (GenBank accession number KF067988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

In embodiments of the methods, the Cas12a tracrRNA is provided: (a) as DNA encoding a first RNA molecule including the Cas12a tracrRNA and including a restriction endonuclease cleavage site that is suitable for insertion of a sequence coding for a functional RNA moiety; or (b) as a functional RNA molecule including the Cas12a tracrRNA and a functional RNA moiety, or as a polynucleotide encoding the functional RNA molecule; or (c) by a DNA expression system comprising (i) DNA sequence for a first promoter; and (ii) operably linked and heterologous to the first promoter, DNA encoding a first RNA molecule comprising a Cas12a tracrRNA and comprising a restriction endonuclease cleavage site that is suitable for insertion of a sequence coding for a functional RNA moiety; and (iii) optionally, a terminator 3' to and operably linked to the DNA encoding the first RNA molecule; or (d) by a DNA expression system comprising: (i) DNA sequence for a first promoter; and (ii) operably linked and heterologous to the first promoter, a DNA encoding a functional RNA molecule comprising a Cas12a tracrRNA and a functional RNA moiety; and (iii) optionally, a terminator 3' to and operably linked to the DNA encoding a functional RNA molecule. In embodiments of the methods, the Cas12a tracrRNA is provided as a synthetic Cas12a tracrRNA, e.g., a Cas12a tracrRNA synthesized in vitro from an expression construct including a heterologous promoter operably linked to DNA encoding the Cas12a tracrRNA and optionally including an operably linked terminator. In embodiments of the methods, the Cas12a tracrRNA is provided as a Cas12a tracrRNA obtained from a naturally occurring source, e.g., isolated from a Cas12a tracrRNA that naturally occurs in genomic DNA, or amplified from a Cas12a tracrRNA that naturally occurs in genomic DNA.

In embodiments of the methods, the Cas12a tracrRNA is a putative tracrRNA. In embodiments, the putative Cas12a tracrRNA is identified from the same genomic region as the Cas12a nuclease by at least the following steps: (a) identifying in the genomic region flanking the DNA encoding the Cas12a nuclease at least one nucleotide sequence that includes a CRISPR array including direct repeats; (b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat. In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4.

In embodiments of the methods, the Cas12a tracrRNA is provided in a molar excess, relative to the Cas12a nuclease. In embodiments, the Cas12a tracrRNA is provided in a molar amount that is at least 10-fold (e.g., at least 10-fold, 15-fold, 20-fold, 30-fold, 50-fold, 90-fold, 100-fold, 150-fold, or 200-fold) greater than the molar amount of the Cas12a nuclease. In embodiments, the Cas12a tracrRNA is added in a molar excess (relative to the Cas12a nuclease) to a composition containing the Cas12a ribonucleoprotein including the Cas12a nuclease and the Cas12a crRNA. In embodiments, the Cas12a tracrRNA has a nucleotide sequence comprising a sequence selected from the group consisting of SEQ ID NOs:1, 3, 6, 139-146, and 149-169.

In embodiments of the methods, the engineered Cas12a crRNA includes a spacer sequence that is designed to hybridize with a target sequence in the genetic locus. In embodiments, the target sequence is a segment of a genetic locus or a gene of interest. In embodiments, the target sequence includes about 20 to about 30 contiguous nucleotides and has near perfect or perfect sequence complementarity to the nucleotide sequence of the spacer of the Cas12a crRNA. In embodiments, the engineered Cas12a crRNA, or a polynucleotide encoding the engineered Cas12a crRNA, further includes at least one direct repeat sequence or fragment thereof capable of associating with the Cas12a nuclease, wherein the at least one direct repeat sequence or fragment thereof is adjacent to and 3' to the spacer sequence. In embodiments, the engineered Cas12a crRNA further includes a 3' extension adjacent to the spacer sequence. In embodiments, the 3' extension includes nucleotides that when base-paired form about one helical turn. In embodiments, the 3' extension includes at least 10 contiguous nucleotides. In embodiments, the Cas12a tracrRNA has a nucleotide sequence having sufficient complementarity to the engineered Cas12a crRNA's 3' extension to allow hybridization between the tracrRNA and the engineered Cas12a crRNA.

In embodiments of the methods, the editing of the genetic locus is effecting an indel in the genetic locus. In embodiments, the editing of the genetic locus is effecting non-homologous end joining (NHEJ) in the genetic locus. In embodiments, the editing of the genetic locus is effecting homology-dependent repair (HDR) in the genetic locus; in such embodiments, the method can further comprise providing a donor polynucleotide encoding a sequence to be integrated at a double-stranded break that is effected by the method in the genetic locus; examples of suitable donor polynucleotides are described above under the heading "A Method of Integrating a Sequence Encoded by a Donor Polynucleotide at a Specific Locus".

In embodiments of the methods, the DNA that includes the genetic locus is genomic DNA. In embodiments, the genetic locus is genomic DNA of a eukaryotic nucleus, or mitochondrial DNA, or plastid DNA. In embodiments, the DNA that includes the genetic locus is in a eukaryotic DNA molecule in vitro. In embodiments, the DNA that includes the genetic locus is in a eukaryotic cell; in embodiments, the eukaryotic cell is an isolated eukaryotic cell, or a eukaryotic cell in culture, or a eukaryotic cell located in a tissue or organ of a eukaryotic organism. In embodiments, the eukaryotic cell is a cell of a non-human animal, an invertebrate, a vertebrate, a mollusk, an arthropod, an insect, a fish, a reptile, an amphibian, a bird, a mammal, a primate, a non-human primate, a human, a plant, or a fungus. In embodiments, the eukaryotic cell includes a cell of a cell line or a cell of a multicellular organism, and wherein the genetic locus to be modified includes a locus of interest in the genome of the eukaryotic cell. In embodiments, the eukaryotic cell is in vitro, ex vivo, or in vivo. In embodiments, the eukaryotic cell includes a non-human animal or human stem cell or a non-human animal or human stem cell line. Target sequences and eukaryotic cells are described in detail below under the section headed "Related Disclosure".

Compositions for Modifying a Genetic Locus

Yet another aspect of the invention provides a composition for modifying a genetic locus in a eukaryotic cell, including: (a) a eukaryotic cell containing a genetic locus to be modified; and (b) a Cas12a nuclease, or a polynucleotide encoding the Cas12a nuclease; and (c) an engineered Cas12a crRNA that includes a spacer sequence that is designed to hybridize with a target sequence in the genetic locus, or a polynucleotide encoding the Cas12a crRNA; and (d) a Cas12a tracrRNA, or a polynucleotide encoding the Cas12a tracrRNA, wherein the Cas12a tracrRNA is provided in molar excess relative to the Cas12a nuclease. In embodiments wherein the genetic locus is to be modified by homology-dependent repair, the composition further includes: (e) a donor polynucleotide encoding a sequence to be integrated at a double-stranded break in the genetic locus; examples of suitable donor polynucleotides are described above under the heading "A Method of Integrating a Sequence Encoded by a Donor Polynucleotide at a Specific Locus".

In embodiments of the composition, the Cas12a tracrRNA is identified from the same genomic region as the Cas12a nuclease by at least the following steps: (a) identifying in the genomic region flanking the DNA encoding the Cas12a nuclease at least one nucleotide sequence that includes a CRISPR array including direct repeats; (b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat. In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4.

In embodiments of the composition, the Cas12a tracrRNA is present in a molar excess, relative to the Cas12a nuclease. In embodiments, the Cas12a tracrRNA is present in a molar amount that is at least 10-fold (e.g., at least 10-fold, 15-fold, 20-fold, 30-fold, 50-fold, 90-fold, 100-fold, 150-fold, or 200-fold) greater than the molar amount of the Cas12a nuclease.

In embodiments of the composition, the eukaryotic cell is a cell of a non-human animal, an invertebrate, a vertebrate, a mollusk, an arthropod, an insect, a fish, a reptile, an amphibian, a bird, a mammal, a primate, a non-human primate, a human, a plant, or a fungus. In embodiments, the eukaryotic cell includes a cell of a cell line or a cell of a multicellular organism, and wherein the genetic locus to be modified includes a locus of interest in the genome of the eukaryotic cell. In embodiments, the eukaryotic cell is in vitro, ex vivo, or in vivo. In embodiments, the eukaryotic cell includes a non-human animal or human stem cell or a non-human animal or human stem cell line.

In embodiments of the composition, the Cas12a nuclease and the engineered Cas12a crRNA are provided as a ribonucleoprotein complex. In embodiments, the Cas12a nuclease is provided as a polynucleotide encoding the Cas12a nuclease. In embodiments, the Cas12a nuclease is: (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag. The compositions including a tracrRNA as disclosed herein can also be employed with related Cas nucleases, including Csm nucleases, e.g., ObCsm1 (GenBank accession number OGX23684), SmCsm1 (GenBank accession number KF067988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

In embodiments of the composition, the engineered Cas12a crRNA includes a spacer sequence that is designed to hybridize with a target sequence in the genetic locus. In embodiments, the target sequence is a segment of a genetic locus or a gene of interest; in embodiments, the target sequence includes about 20 to about 30 contiguous nucleotides and has near perfect or perfect sequence complementarity to the nucleotide sequence of the spacer of the Cas12a crRNA. In embodiments, the engineered Cas12a crRNA, or a polynucleotide encoding the engineered Cas12a crRNA, further includes at least one direct repeat sequence or fragment thereof capable of associating with the Cas12a nuclease, wherein the at least one direct repeat sequence or fragment thereof is adjacent to and 3' to the spacer sequence. In embodiments, the engineered Cas12a crRNA further includes a 3' extension adjacent to the spacer sequence. In embodiments, the 3' extension includes nucleotides that when base-paired form about one helical turn. In embodiments, the 3' extension includes at least 10 contiguous nucleotides. In embodiments, the Cas12a tracrRNA has a nucleotide sequence having sufficient complementarity to the engineered Cas12a crRNA's 3' extension to allow hybridization between the tracrRNA and the engineered Cas12a crRNA.

In embodiments of the composition, the Cas12a tracrRNA is provided: (a) as DNA encoding a first RNA molecule including the Cas12a tracrRNA and including a restriction endonuclease cleavage site that is suitable for insertion of a sequence coding for a functional RNA moiety; or (b) as a functional RNA molecule including the Cas12a tracrRNA and a functional RNA moiety, or as a polynucleotide encoding the functional RNA molecule; or (c) by a DNA expression system comprising (i) DNA sequence for a first promoter; and (ii) operably linked and heterologous to the first promoter, DNA encoding a first RNA molecule comprising a Cas12a tracrRNA and comprising a restriction endonuclease cleavage site that is suitable for insertion of a sequence coding for a functional RNA moiety; and (iii) optionally, a terminator 3' to and operably linked to the DNA encoding the first RNA molecule; or (d) by a DNA expression system comprising: (i) DNA sequence for a first promoter; and (ii) operably linked and heterologous to the first promoter, a DNA encoding a functional RNA molecule comprising a Cas12a tracrRNA and a functional RNA moiety; and (iii) optionally, a terminator 3' to and operably linked to the DNA encoding a functional RNA molecule.

In embodiments of the composition, the Cas12a tracrRNA is provided as DNA encoding a first RNA molecule including the Cas12a tracrRNA and including a restriction endonuclease cleavage site that is suitable for insertion of a sequence coding for a functional RNA moiety, and wherein the functional RNA moiety is at least one selected from the group consisting of: (a) a nucleotide sequence for annealing to a donor polynucleotide; (b) a nucleotide sequence for annealing to the crRNA 3' extension; (c) a terminator sequence; (d) an RNA aptamer; (e) an enzymatically active RNA sequence; (f) a detectable label; and (g) an RNA sequence forming at least partially double-stranded RNA. In embodiments of the composition, the Cas12a tracrRNA is provided as DNA encoding a first RNA molecule including the Cas12a tracrRNA and including a restriction endonuclease cleavage site that is suitable for insertion of a sequence coding for a functional RNA moiety, wherein the functional RNA moiety includes RNA forming at least partially double-stranded RNA capable of silencing a gene (e.g., RNA that forms one or more stem-loops where the stem includes double-stranded RNA of at least about 18 base-pairs designed to silence a target gene, or RNA that has the secondary structure of a microRNA precursor and is processed to a mature microRNA designed to silence a target gene). In embodiments of the composition, the Cas12a tracrRNA is provided as DNA encoding a first RNA molecule including the Cas12a tracrRNA and including a restriction endonuclease cleavage site that is suitable for insertion of a sequence coding for a functional RNA moiety, wherein the functional RNA moiety includes an RNA sequence for annealing to a donor polynucleotide, and wherein the composition further includes the donor polynucleotide. In embodiments of the composition, the Cas12a tracrRNA is provided as a functional RNA molecule including the Cas12a tracrRNA and a functional RNA moiety, or as a polynucleotide encoding the functional RNA molecule, and wherein the functional RNA moiety is at least one selected from the group consisting of: (a) a nucleotide sequence for annealing to a donor polynucleotide; (b) a nucleotide sequence for annealing to the crRNA 3' extension; (c) a terminator sequence; (d) an RNA aptamer; (e) an enzymatically active RNA sequence; (f) a detectable label; and (g) an RNA sequence forming at least partially double-stranded RNA. In embodiments of the composition, the Cas12a tracrRNA is provided as a functional RNA molecule including the Cas12a tracrRNA and a functional RNA moiety, or as a polynucleotide encoding the functional RNA molecule, and wherein the functional RNA moiety includes RNA forming at least partially double-stranded RNA capable of silencing a gene (e.g., RNA that forms one or more stem-loops where the stem includes double-stranded RNA of at least about 18 base-pairs designed to silence a target gene, or RNA that has the secondary structure of a microRNA precursor and is processed to a mature microRNA designed to silence a target gene). In embodiments of the composition, the Cas12a tracrRNA is provided as a functional RNA molecule including the Cas12a tracrRNA and a functional RNA moiety, or as a polynucleotide encoding the functional RNA molecule, wherein the functional RNA moiety includes an RNA sequence for annealing to a donor polynucleotide, and wherein the composition further includes the donor polynucleotide.

In embodiments of the composition, the genetic locus in a eukaryotic cell to be modified is genomic DNA. In embodiments, the genetic locus is in genomic DNA of a eukaryotic nucleus, or mitochondrial DNA, or plastid DNA. In embodiments, the genetic locus is in a eukaryotic DNA molecule in vitro. In embodiments, the genetic locus is in a eukaryotic cell; in embodiments, the eukaryotic cell is an isolated eukaryotic cell, or a eukaryotic cell in culture, or a eukaryotic cell located in a tissue or organ of a eukaryotic organism. In embodiments, the eukaryotic cell is a cell of a non-human animal, an invertebrate, a vertebrate, a mollusk, an arthropod, an insect, a fish, a reptile, an amphibian, a bird, a mammal, a primate, a non-human primate, a human, a plant, or a fungus. In embodiments, the eukaryotic cell includes a cell of a cell line or a cell of a multicellular organism, and wherein the genetic locus to be modified includes a locus of interest in the genome of the eukaryotic cell. In embodiments, the eukaryotic cell is in vitro, ex vivo, or in vivo. In embodiments, the eukaryotic cell includes a non-human animal or human stem cell or a non-human animal or human stem cell line. Target sequences and eukaryotic cells are described in detail below under the section headed "Related Disclosure".

RELATED DISCLOSURE

Target Sequences or Target Genes: Embodiments of the polynucleotides, compositions, engineered systems, and methods disclosed herein are useful in editing or effecting a sequence-specific modification of a target DNA sequence or target gene in a DNA molecule, a chromosome, or a genome. In embodiments, the target sequence or target gene includes coding sequence (DNA encoding a polypeptide, such as a structural protein or an enzyme), non-coding sequence, or both coding and non-coding sequence. In embodiments, the target sequence or target gene is a gene of a pest or pathogen of a non-human animal, a human, or a plant; important target genes include genes of invertebrate pests (e.g., arthropods, nematodes, and mollusks) of plants, and invertebrate parasites of animals. In embodiments, the target sequence or target gene includes regulatory sequence or translatable (coding) sequence for genes encoding transcription factors and genes encoding enzymes involved in the biosynthesis or catabolism of molecules of interest (such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin). In embodiments, the target gene is an endogenous gene of a eukaryotic cell; in other embodiments, the target gene is an exogenous gene (e.g., a transgene) in a eukaryotic cell. In embodiments, the target sequence or target gene is a gene that is involved in one or more small RNA-mediated (sRNA-mediated) silencing pathways, i.e., a gene involved in RNA-mediated sequence-specific inhibition of gene expression wherein silencing may occur at transcription, post-transcription, or translation, and wherein the sRNA-mediated silencing pathways can be classified by the biosynthesis, biogenesis, and recognition of types of regulatory sRNAs, e.g., short interfering RNAs (siRNAs), microRNAs (miRNAs), and phased sRNAs; possible target sequences include DNA encoding a regulatory RNA (e.g., DNA encoding a pre-miRNA or miRNA precursor, or DNA encoding a recognition site for a mature miRNA or an siRNA) and DNA encoding any of the participating sRNA silencing pathway proteins (e.g., RDR6, SDE3, RDR2, WEX, SGS3, DCL2-4, UPF1, UPF3, HEN1, NRPD1A, NRPD2, DRD1, HDA6, AGO1, and MOP1); see, e.g., U.S. Pat. No. 9,222,100, incorporated herein by reference. Examples of non-coding sequences include DNA encoding long non-coding RNAs (lncRNAs), DNA encoding microRNAs (miRNAs), DNA encoding tRNAs or ribosomal RNAs (rRNAs), DNA encoding untranscribed regions that are located 5' to or 3' to DNA encoding a polypeptide, and DNA encoding regulatory elements (e.g., promoters, enhancers, introns, terminators, silencers, insulators). In embodiments, the target DNA is genomic DNA, e.g., genomic DNA or nuclear DNA of a eukaryote. In embodiments, the target DNA is mitochondrial or plastid DNA, e.g., mitochondrial DNA of a non-human animal, an animal, or a plant, or plastid DNA of a plant or eukaryotic alga.

Eukaryotic Cells and Eukaryotic Species of Interest: Embodiments of the polynucleotides, compositions, engineered systems, and methods disclosed herein are useful in genome editing of eukaryotes, cells of eukaryotes, and DNA obtained from eukaryotes. In embodiments, the polynucleotides, compositions, engineered systems, and methods disclosed herein are useful in genome editing of non-human animals and non-human animal cells, non-human animal stem cells, human cells, human stem cells, and human somatic (non-gametic) cells; isolated tissue (e.g., nervous tissue, epithelial tissue, liver, spleen, pancreas, muscle tissue, bone, connective tissue, endocrine system tissues, and tumours) or cells (e.g., blood cells, erythrocytes, leukocytes, lymphocytes, liver cells, bone cells, immune cells, T cells, B cells, dendritic cells, and tumour cells) or cell organelles (e.g., mitochondria or chloroplasts, either isolated or contained within the eukaryotic cell, tissue, or organism) obtained from a non-human animal or from a human; engineered hybridoma cells; fungi, fungal cells, plants, plant tissue, plant cells, and seeds. In embodiments, the polynucleotides, compositions, engineered systems, and methods disclosed herein are useful in genome editing of a non-human animal cell (e.g., a cell of an animal selected from the group consisting of invertebrates, vertebrates, insects, arthropods, mollusks, fish, reptiles, amphibians, birds, mammals, primates, and non-human primates), a human cell, a plant cell, or a fungal cell. In embodiments, the eukaryotic cell, tissue, or cell organelle is obtained from an economically or agriculturally important animal species, such as, but not limited to, bees, fruit flies, shrimp, oysters, clams, mussels, salmon, trout, carp, tilapia, catfish, barramundi, striped bass, pigeons, chickens, turkeys, ducks, geese, goats, sheep, cattle, water buffalo, horses, pigs, dogs, cats, rabbits, mice, and rats. In embodiments, the eukaryotic cell is in vitro, ex vivo, or in vivo. In embodiments, the eukaryotic cell is a non-human animal stem cell or a non-human animal gametic cell, from which a non-animal tissue or even an intact animal can be developed. In embodiments, the polynucleotides, compositions, engineered systems, and methods disclosed herein are useful in editing of eukaryotic DNA (e.g., genomic DNA) in vitro. In embodiments, the polynucleotides encoding the Cas12a nuclease and Cas12a nuclease variants described herein are codon-optimized, in whole or in part, for the eukaryotic species wherein the Cas12a editing system is to be employed. In an embodiment, a codon-optimized polynucleotide encoding a Cas12a nuclease contains one or more codons selected for having a high frequency for specifying a given amino acid in the eukaryotic species in which the codon-optimized polynucleotide is to be introduced or expressed. Codon usage or bias is known in the art for various eukaryotes; see, e.g., Quax et al. (2015) Molecular Cell, 59:149-161. See also U.S. Pat. No. 6,015,891, incorporated herein by reference.

In embodiments, the polynucleotides, compositions, engineered systems, and methods disclosed herein are useful in genome editing of plants, plant tissue (including callus), plant cells, or plant protoplasts obtained from any monocot or dicot plant species of interest, for example, row crop plants, fruit-producing plants and trees, vegetables, trees, and ornamental plants including ornamental flowers, shrubs, trees, groundcovers, and turf grasses. Examples of plants, plant tissue, plant cells, or plant protoplasts that are useful in such genome editing include whole plant, intact nodal bud, shoot apex or shoot apical meristem, root apex or root apical meristem, lateral meristem, intercalary meristem, seedling, whole seed, halved seed or other seed fragment, zygotic embryo, somatic embryo, ovule, pollen, microspore, anther, hypocotyl, cotyledon, leaf, petiole, stem, tuber, root, callus, or plant cell or plant protoplast cultures. Plants or plant tissues or cells can be haploid, inducibly haploid, haploid-inducing, diploid, or polyploid. Plant species of interest include, but are not limited to, alfalfa (*Medicago sativa*), almonds (*Prunus dulcis*), apples (*Malus* x *domestica*), apricots (*Prunus armeniaca, P. brigantine, P. mandshurica, P. mume, P. sibirica*), asparagus (*Asparagus officinalis*), bananas (*Musa* spp.), barley (*Hordeum vulgare*), beans (*Phaseolus* spp.), blueberries and cranberries (*Vaccinium* spp.), cacao (*Theobroma cacao*), canola and rapeseed or oilseed rape, (*Brassica napus*), carnation (*Dianthus caryophyllus*), carrots (*Daucus carota sativus*), cassava (*Manihot esculentum*), cherry (*Prunus avium*), chickpea (*Cider arietinum*), chicory (*Cichorium intybus*), chili peppers and other capsicum peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), eucalyptus (*Eucalyptus* spp.), flax (*Linum usitatissumum* L.), geraniums (*Pelargonium* spp.), grapefruit (*Citrus xparadisi*), grapes (Vitus spp.) including wine grapes (*Vitus vinifera*), guava (*Psidium guajava*), irises (*Iris* spp.), lemon (*Citrus limon*), lettuce (*Lactuca sativa*), limes (*Citrus* spp.), maize (*Zea mays* L.), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), papaya (*Carica papaya*), peaches and nectarines (*Prunus persica*), pear (*Pyrus* spp.), pea (*Pisa sativum*), peanut (*Arachis hypogaea*), peonies (*Paeonia* spp.), petunias (*Petunia* spp.), pineapple (*Ananas comosus*), plantains (*Musa* spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius* L), sesame seed (*Sesame indium*), sorghum (*Sorghum bicolor*), soybean (*Glycine max* L.), squash (*Cucurbita pepo*), strawberries (*Fragaria* spp., *Fragaria* x *ananassa*), sugar beet (*Beta vulgaris*), sugarcanes (*Saccharum* spp.), sunflower (*Helianthus annuus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (*Tulipa* spp.), turnip (*Brassica rapa rapa*), walnuts (*Juglans* spp. L.), watermelon (*Citrulus lanatus*), wheat (*Tritium aestivum*), or yams (*Discorea* spp.).

Nuclease Fusions and Complexes: In embodiments, the Cas12a nuclease is a fusion protein, e.g., wherein the Cas12a nuclease is covalently bound through a peptide bond to a cell-penetrating peptide, a nuclear localization signal peptide, a chloroplast transit peptide, or a mitochondrial targeting peptide; such fusion proteins are conveniently encoded in a single nucleotide sequence, optionally including codons for linking amino acids. In embodiments, the Cas12a nuclease is a fusion protein, wherein the Cas12a nuclease is covalently bound to another polypeptide via a linker polypeptide, for example, via a glycine polymer $(G)_n$, a glycine-serine polymer, a glycine-alanine polymer, and an alanine-serine polymer. In embodiments, the Cas12a nuclease is chemically conjugated to another polypeptide, e.g., via a non-peptide covalent bond. In embodiments, the Cas12a nuclease is associated with another polypeptide via a non-covalent bond. In embodiments, the Cas12a nuclease is a fusion protein, wherein the Cas12a nuclease is covalently bound to a protein (or a domain from a protein) that inhibits transcription (e.g., a protein that represses transcription, recruits transcription inhibitor proteins, modifies a target DNA through a process such as methylation, recruits a DNA modifier, modulates histones associated with a target DNA, recruits a histone modifier such as those that modify acetylation and/or methylation of histones, or similar functions). Examples of proteins (or fragments thereof) that can be used in decrease transcription include but are not limited to: transcriptional repressors such as the Kruppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), MET1, DRM3 (plants), ZMET2, CMT1, CMT2 (plants), and the like; and periphery recruitment elements such as Lamin A, Lamin B, and the like. In embodiments, the Cas12a nuclease is a fusion protein, wherein the Cas12a nuclease is covalently bound to a protein (or a domain from a protein) that increases transcription (e.g., a protein that activates transcription, recruits transcription activator proteins, modifies a target DNA through a process such as demethylation, recruits a DNA modifier, modulates histones associated with a target DNA, recruits a histone modifier such as those that modify acetylation and/or methylation of histones, or similar functions). Examples of proteins (or fragments thereof) that can be used in increase transcription include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCNS, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like. In embodiments, the Cas12a nuclease is a fusion protein, wherein the Cas12a nuclease is covalently bound to a heterologous polypeptide that has enzymatic activity that modifies a target nucleic acid (e.g., ssRNA, dsRNA, ssDNA, dsDNA), for example, nuclease activity such as that provided by a restriction enzyme (e.g., Fokl nuclease), methyltransferase activity such as that provided by a methyltransferase (e.g., Hhal DNA m5c-methyltransferase, M.Hhal), DNA methyltransferase 1 (DNMT1), DNA methyltransferase 3a (DNMT3a), DNA methyltransferase 3b (DNMT3b), MET1, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS 1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity). In embodiments, the Cas12a nuclease is a fusion protein, wherein the Cas12a nuclease is covalently bound to a heterologous polypeptide that has enzymatic activity that modifies a polypeptide (e.g., a histone) associated with a target nucleic acid (e.g., ssRNA, dsRNA, ssDNA, dsDNA), for example, methyltransferase activity such as that provided by a histone methyltransferase (HMT) (e.g., suppressor of variegation 3-9 homolog 1 (SUV39H1, also known as KMTIA), euchromatic histone lysine methyltransferase 2 (G9A, also known as KMT1C and EHMT2), SUV39H2, ESET/SETDB 1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HB01/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity. In embodiments, the Cas12a nuclease is a fusion protein, wherein the Cas12a nuclease is covalently bound to a dihydrofolate reductase (DHFR) destabilization domain (e.g., to generate a chemically controllable chimeric Cas12a nuclease).

In embodiments, the Cas12a nuclease or a polynucleotide that encodes the Cas12a nuclease or a ribonucleoprotein including the Cas12a nuclease is provided as a complex with a cell-penetrating peptide or other transfecting agent. In embodiments, the Cas12a nuclease or a polynucleotide that encodes the Cas12a nuclease or a ribonucleoprotein including the Cas12a nuclease is complexed with, or covalently or non-covalently bound to, a further element, e.g., a carrier molecule, an antibody, an antigen, a viral movement protein, a polymer, a detectable label (e.g., a moiety detectable by fluorescence, radioactivity, or enzymatic or immunochemical reaction), a quantum dot, or a particulate or nanoparticulate.

In some cases, the fusion partner can modulate transcription (e.g., inhibit transcription, increase transcription) of a target DNA. For example, in some cases the fusion partner Vectors: In certain embodiments, a vector or an expression cassette contained in a vector includes additional components, e.g., a polynucleotide encoding a drug resistance or herbicide gene or a polynucleotide encoding a detectable marker such as green fluorescent protein (GFP) or beta-glucuronidase (gus) to allow convenient screening or selection of cells expressing the vector. In embodiments, the vector or expression cassette includes additional elements for improving delivery to a plant cell or plant protoplast or for directing or modifying expression of one or more genome-editing system elements, for example, fusing a sequence encoding a cell-penetrating peptide, localization signal, transit, or targeting peptide to the Cas12a nuclease, or adding a nucleotide sequence to stabilize a guide RNA; such fusion proteins (and the polypeptides encoding such fusion proteins) or combination polypeptides, as well as expression cassettes and vectors for their expression in a cell, are specifically claimed. In embodiments, a Cas12a nuclease is fused to a localization signal, transit, or targeting peptide, e.g., a nuclear localization signal (NLS), a chloroplast transit peptide (CTP), or a mitochondrial targeting peptide (MTP); in a vector or an expression cassette, the nucleotide sequence encoding any of these can be located either 5' and/or 3' to the DNA encoding the nuclease. CRISPR nuclease fusion proteins containing nuclear localization signals and codon-optimized for expression in maize are disclosed in U.S. patent application Ser. No. 15/120,110, published as U.S. Patent Application Publication 2017/0166912, national phase application claiming priority to PCT/US2015/018104 (published as WO/2015/131101 and claiming priority to U.S. Provisional Patent Application 61/945,700), incorporated herein by reference. In another example, a chloroplast-targeting RNA is appended to the 5' end of an mRNA encoding an endonuclease to drive the accumulation of the mRNA in chloroplasts; see Gomez, et al. (2010) *Plant Signal Behav.*, 5: 1517-1519. In an embodiment, a Cas12a nuclease is fused to a nuclear localization signal (NLS), such as the NLS from SV40. In an embodiment, a Cas12a nuclease is fused to a cell-penetrating peptide (CPP), such as octa-arginine or nona-arginine or a homoarginine 12-mer oligopeptide, or a CPP disclosed in the database of cell-penetrating peptides CPPsite 2.0, publicly available at crd[dot]osdd[dot]net/raghava/cppsite/. In an embodiment, a Cas12a nuclease is fused to a chloroplast transit peptide (CTP) sequence. In embodiments, a CTP sequence is obtained from any nuclear gene that encodes a protein that targets a chloroplast, and the isolated or synthesized CTP DNA is appended to the 5' end of the DNA that encodes a Cas12a nuclease targeted for use in a chloroplast. Chloroplast transit peptides and their use are described in U.S. Pat. Nos. 5,188,642, 5,728,925, and 8,420,888, all of which are incorporated herein by reference in their entirety. Specifically, the CTP nucleotide sequences provided with the sequence identifier (SEQ ID) numbers 12-15 and 17-22 of U.S. Pat. No. 8,420,888 are incorporated herein by reference. In an embodiment, a Cas12a nuclease is fused to a mitochondrial targeting peptide (MTP), such as a plant MTP sequence; see, e.g., Jores et al. (2016) *Nature Communications*, 7:12036-12051.

Plasmids designed for use in plants and encoding CRISPR genome editing elements (CRISPR nucleases and guide RNAs) are publicly available from plasmid repositories such as Addgene (Cambridge, Mass.; also see "addgene[dot]com") or can be designed using publicly disclosed sequences, e.g., sequences of CRISPR nucleases. In embodiments, such plasmids are used to co-express both Cas12a nuclease mRNA and guide RNA(s) (Cas12a crRNA(s)); in other embodiments, Cas12a nuclease mRNA and guide RNA (Cas12a crRNA) are encoded on separate plasmids. In embodiments, the plasmids are *Agrobacterium* TI plasmids. Materials and methods for preparing expression cassettes and vectors for CRISPR endonuclease and guide RNA for stably integrated and/or transient plant transformation are disclosed in U.S. patent application Ser. No. 15/120,110, published as U.S. Patent Application Publication 2017/0166912, national phase application claiming priority to PCT/US2015/018104 (published as WO/2015/131101 and claiming priority to U.S. Provisional Patent Application 61/945,700), U.S. Patent Application Publication 2015/0082478 A1, and PCT/US2015/038767 (published as WO/2016/007347 and claiming priority to U.S. Provisional Patent Application 62/023,246), all of which are incorporated herein by reference in their entirety. In embodiments, such expression cassettes are isolated linear fragments, or are part of a larger construct that includes bacterial replication elements and selectable markers; such embodiments are useful, e.g., for particle bombardment or nanoparticle delivery or protoplast transformation. In embodiments, the expression cassette is adjacent to or located between T-DNA borders or contained within a binary vector, e.g., for *Agrobacterium*-mediated transformation. In embodiments, a plasmid encoding a Cas12a nuclease is delivered to a cell (such as a plant cell or a plant protoplast) for stable integration of the Cas12a nuclease into the genome of the cell, or alternatively for transient expression of the Cas12a nuclease. In embodiments, plasmids encoding a Cas12a nuclease are delivered to a plant cell or a plant protoplast to achieve stable or transient expression of the Cas12a nuclease, and one or multiple guide RNAs (Cas12a crRNAs) (such as a library of individual guide RNAs or multiple pooled guide RNAs) or plasmids encoding the guide RNAs are delivered to the plant cell or plant protoplast individually or in combinations, thus providing libraries or arrays of plant cells or plant protoplasts (or of plant callus or whole plants derived therefrom), in which a variety of genome edits are provided by the different guide RNAs (Cas12a crRNAs).

In embodiments, the polynucleotides, ribonucleoproteins, DNA expression systems, and engineered systems are delivered to a eukaryotic cell using a viral vector. Viral vectors especially useful in animal cells include viral vectors based on vaccinia virus; poliovirus; adenovirus (see, e.g., Li et al., Invest Opthalmol Vis Sci 35:2543 2549, 1994; Borras et al, Gene Ther 6:515 524, 1999; Li and Davidson, PNAS 92:7700 7704, 1995; Sakamoto et al., H Gene Ther 5: 1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90: 10613-10617); SV40; herpes simplex virus; human immunodeficiency virus (see, e.g., Miyoshi et al., PNAS 94: 10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector. Viral vectors especially useful in plant cells include geminiviruses, begomoviruses, tobamoviruses, potex viruses, comoviruses, wheat streak mosaic virus, barley stripe mosaic virus, bean yellow dwarf virus, bean pod mottle virus, cabbage leaf curl virus, beet curly top virus, tobacco yellow dwarf virus, tobacco rattle virus, potato virus X, and cowpea mosaic virus.

In embodiments, the polynucleotides, ribonucleoproteins, DNA expression systems, and engineered systems are delivered to a plant cell using a bacterial vector. In embodiments of the method, the engineered system or a component thereof is delivered via at least one bacterial vector capable of transforming a plant cell and selected from the group consisting of *Agrobacterium* sp., *Rhizobium* sp., *Sinorhizobium* (Ensifer) sp., *Mesorhizobium* sp., *Bradyrhizobium* sp., *Azobacter* sp., and *Phyllobacterium* sp.

Delivery Methods and Delivery Agents: The polynucleotides, ribonucleoproteins, DNA expression systems, engineered systems, and vectors (collectively referred to here as "genome editing reagents") that are aspects of the invention can be delivered to a eukaryotic cell, such as a plant cell, using various techniques and agents. In embodiments, one or more treatments is employed to deliver genome editing reagents into a plant cell or plant protoplast, e.g., through barriers such as a cell wall or a plasma membrane or nuclear envelope or other lipid bilayer. In an embodiment, genome editing reagents are delivered directly, for example by direct contact of the polynucleotide composition with a plant cell or plant protoplast. A genome editing reagent-containing composition in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a eukaryotic cell, such as a non-human animal cell, a human cell, a fungal cell, or a plant cell or plant protoplast (e.g., through abrasion or puncture or otherwise disruption of the cell wall or cell membrane, by spraying or dipping or soaking or otherwise directly contacting, by microinjection). For example, a eukaryotic cell, such as a non-human animal cell, a human cell, a fungal cell, or a plant cell or plant protoplast is soaked in a liquid genome editing reagent-containing composition, whereby the genome editing reagent is delivered to the plant cell or plant protoplast. In embodiments, the genome editing reagent-containing composition is delivered using negative or positive pressure, for example, using vacuum infiltration or application of hydrodynamic or fluid pressure. In embodiments, the genome editing reagent-containing composition is introduced into a eukaryotic cell, such as a non-human animal cell, a human cell, a fungal cell, or a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in U.S. Published Patent Application 2014/0287509, incorporated by reference in its entirety herein. Other techniques useful for delivering the genome editing reagent-containing composition to a eukaryotic cell, such as a non-human animal cell, a human cell, a fungal cell, or a plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In embodiments, the genome editing reagent-containing composition is provided to a plant cell or plant protoplast by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the gRNA; see, e.g., Broothaerts et al. (2005) *Nature,* 433:629-633. Any of these techniques or a combination thereof are alternatively employed on the plant part or tissue or intact plant (or seed) from which a plant cell or plant protoplast is optionally subsequently obtained or isolated; in embodiments, the genome editing reagent-containing composition is delivered in a separate step after the plant cell or plant protoplast has been obtained or isolated.

In embodiments, a treatment employed in delivery of a genome editing reagent to a eukaryotic cell, such as a non-human animal cell, a human cell, a fungal cell, or a plant cell or plant protoplast is carried out under a specific thermal regime, which can involve one or more appropriate temperatures, e.g., chilling or cold stress (exposure to temperatures below that at which normal growth of the eukaryotic cell occurs), or heating or heat stress (exposure to temperatures above that at which normal growth of the eukaryotic cell occurs), or treating at a combination of different temperatures. In embodiments, a specific thermal regime is carried out on the eukaryotic cell, such as a non-human animal cell, a human cell, a fungal cell, or plant cell or plant protoplast, in one or more steps separate from the genome editing reagent delivery. In embodiments, a specific thermal regime is carried out on a plant cell or plant protoplast, or on a plant or plant part from which a plant cell or plant protoplast is subsequently obtained or isolated, in one or more steps separate from the genome editing reagent delivery.

A Cas12a nuclease or a polynucleotide that encodes the Cas12a nuclease or a ribonucleoprotein including the Cas12a nuclease can be provided to a cell (e.g., a plant cell) by any suitable technique. In embodiments, the Cas12a nuclease or a polynucleotide that encodes the Cas12a nuclease or a ribonucleoprotein including the Cas12a nuclease is provided in a solution, or is provided in a liposome, micelle, emulsion, reverse emulsion, suspension, or other mixed-phase composition. In embodiments, the Cas12a nuclease or a polynucleotide that encodes the Cas12a nuclease or a ribonucleoprotein including the Cas12a nuclease is provided by directly contacting a plant cell or plant protoplast with the Cas12a nuclease or a polynucleotide that encodes the Cas12a nuclease or a ribonucleoprotein including the Cas12a nuclease. In embodiments, the Cas12a nuclease or a polynucleotide that encodes the Cas12a nuclease or a ribonucleoprotein including the Cas12a nuclease is provided by transporting the Cas12a nuclease or a polynucleotide that encodes the Cas12a nuclease or a ribonucleoprotein including the Cas12a nuclease into a plant cell or plant protoplast using a chemical, enzymatic, or physical agent. In embodiments, the Cas12a nuclease is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of a plant cell or plant protoplast with a polynucleotide encoding the Cas12a nuclease; see, e.g., Broothaerts et al. (2005) *Nature,* 433:629-633. In an embodiment, the Cas12a nuclease is provided by transcription in a plant cell or plant protoplast of a DNA that encodes the Cas12a nuclease and is stably integrated in the genome of the plant cell or plant protoplast or that is provided to the plant cell or plant protoplast in the form of a plasmid or expression vector (e.g., a viral vector) that encodes the Cas12a nuclease. In embodiments, the Cas12a nuclease is provided to the plant cell or plant protoplast as a polynucleotide that encodes the Cas12a nuclease, e.g., in the form of an mRNA encoding the nuclease.

In embodiments, a whole plant or plant part or seed, or an isolated plant cell or plant protoplast, or the plant or plant part from which a plant cell or plant protoplast is obtained or isolated, is treated with one or more delivery agents which can include at least one chemical, enzymatic, or physical agent, or a combination thereof. In embodiments, a genome editing reagent-containing composition further includes one or more one chemical, enzymatic, or physical agent for delivery. Treatment with the chemical, enzymatic or physical agent can be carried out simultaneously with the genome editing reagent delivery, or in one or more separate steps that precede or follow the genome editing reagent delivery. In embodiments, a chemical, enzymatic, or physical agent, or a combination of these, is associated or complexed with a genome editing reagent composition; examples of such associations or complexes include those involving non-covalent interactions (e.g., ionic or electrostatic interactions, hydrophobic or hydrophilic interactions, formation of liposomes, micelles, or other heterogeneous composition) and covalent interactions (e.g., peptide bonds, bonds formed using cross-linking agents). In non-limiting examples, a genome editing reagent is provided as a liposomal complex with a cationic lipid, or as a complex with a carbon nanotube, or as a fusion protein between the nuclease and a cell-penetrating peptide. Examples of agents useful for delivering a genome editing reagent include the various cationic liposomes and polymer nanoparticles reviewed by Zhang et al. (2007) *J. Controlled Release,* 123:1-10, and the cross-linked multilamellar liposomes described in U.S. Patent Application Publication 2014/0356414 A1, incorporated by reference in its entirety herein.

In embodiments, the chemical agent is at least one selected from the group consisting of:

(a) solvents (e.g., water, dimethylsulfoxide, dimethylformamide, acetonitrile, N-pyrrolidine, pyridine, hexamethylphosphoramide, alcohols, alkanes, alkenes, dioxanes, polyethylene glycol, and other solvents miscible or emulsifiable with water or that will dissolve phosphonucleotides in non-aqueous systems);

(b) fluorocarbons (e.g., perfluorodecalin, perfluoromethyldecalin);

(c) glycols or polyols (e.g., propylene glycol, polyethylene glycol);

(d) surfactants, including cationic surfactants, anionic surfactants, non-ionic surfactants, and amphiphilic surfactants, e.g., alkyl or aryl sulfates, phosphates, sulfonates, or carboxylates; primary, secondary, or tertiary amines; quaternary ammonium salts; sultaines, betaines; cationic lipids; phospholipids; tallowamine; bile acids such as cholic acid; long chain alcohols; organosilicone surfactants including nonionic organosilicone surfactants such as trisiloxane ethoxylate surfactants or a silicone polyether copolymer such as a copolymer of polyalkylene oxide modified heptamethyl trisiloxane and allyloxypolypropylene glycol methylether (commercially available as SILWET L-77™ brand surfactant having CAS Number 27306-78-1 and EPA Number CAL. REG. NO. 5905-50073-AA, Momentive Performance Materials, Inc., Albany, N.Y.); specific examples of useful surfactants include sodium lauryl sulfate, the Tween series of surfactants, Triton-X100, Triton-X114, CHAPS and CHAPSO, Tergitol-type NP-40, Nonidet P-40;

(e) lipids, lipoproteins, lipopolysaccharides;

(f) acids, bases, caustic agents;

(g) peptides, proteins, or enzymes (e.g., cellulase, pectolyase, maceroenzyme, pectinase), including cell-penetrating or pore-forming peptides (e.g., (BO100)2K8, Genscript; poly-lysine, poly-arginine, or poly-homoarginine peptides; gamma zein, see U.S. Patent Application publication 2011/0247100, incorporated herein by reference in its entirety; transcription activator of human immunodeficiency virus type 1 ("HIV-1 Tat") and other Tat proteins, see, e.g., www[dot]lifetein[dot]com/Cell_Penetrating_Peptides[dot] html and Järver (2012) *Mol. Therapy—Nucleic Acids*, 1:e27, 1-17); octa-arginine or nona-arginine; poly-homoarginine (see Unnamalai et al. (2004) *FEBS Letters*, 566:307-310); see also the database of cell-penetrating peptides CPPsite 2.0 publicly available at crdd[dot]osdd[dot]net/raghava/cppsite/

(h) RNase inhibitors;

(i) cationic branched or linear polymers such as chitosan, poly-lysine, DEAE-dextran, polyvinylpyrrolidone ("PVP"), or polyethylenimine ("PEI", e.g., PEI, branched, MW 25,000, CAS #9002-98-6; PEI, linear, MW 5000, CAS #9002-98-6; PEI linear, MW 2500, CAS #9002-98-6);

(j) dendrimers (see, e.g., U.S. Patent Application Publication 2011/0093982, incorporated herein by reference in its entirety);

(k) counter-ions, amines or polyamines (e.g., spermine, spermidine, putrescine), osmolytes, buffers, and salts (e.g., calcium phosphate, ammonium phosphate);

(l) polynucleotides (e.g., non-specific double-stranded DNA, salmon sperm DNA);

(m) transfection agents (e.g., Lipofectin®, Lipofectamine®, and Oligofectamine®, and Invivofectamine® (all from Thermo Fisher Scientific, Waltham, Mass.), PepFect (see Ezzat et al. (2011) *Nucleic Acids Res.*, 39:5284-5298), TransIt® transfection reagents (Mirus Bio, LLC, Madison, Wis.), and poly-lysine, poly-homoarginine, and poly-arginine molecules including octa-arginine and nona-arginine as described in Lu et al. (2010) *J. Agric. Food Chem.*, 58:2288-2294);

(n) antibiotics, including non-specific DNA double-strand-break-inducing agents (e.g., phleomycin, bleomycin, talisomycin); and (o) antioxidants (e.g., glutathione, dithiothreitol, ascorbate).

In embodiments, the chemical agent is provided simultaneously with the genome editing reagent. In embodiments, the genome editing reagent is covalently or non-covalently linked or complexed with one or more chemical agent; for example, a polynucleotide genome editing reagent can be covalently linked to a peptide or protein (e.g., a cell-penetrating peptide or a pore-forming peptide) or non-covalently complexed with cationic lipids, polycations (e.g., polyamines), or cationic polymers (e.g., PEI). In embodiments, the genome editing reagent is complexed with one or more chemical agents to form, e.g., a solution, liposome, micelle, emulsion, reverse emulsion, suspension, colloid, or gel.

In embodiments, the physical agent is at least one selected from the group consisting of particles or nanoparticles (e.g., particles or nanoparticles made of materials such as carbon, silicon, silicon carbide, gold, tungsten, polymers, or ceramics) in various size ranges and shapes, magnetic particles or nanoparticles (e.g., silenceMag Magnetotransfection™ agent, OZ Biosciences, San Diego, Calif.), abrasive or scarifying agents, needles or microneedles, matrices, and grids. In embodiments, particulates and nanoparticulates are useful in delivery of the polynucleotide composition or the nuclease or both. Useful particulates and nanoparticles include those made of metals (e.g., gold, silver, tungsten, iron, cerium), ceramics (e.g., aluminum oxide, silicon carbide, silicon nitride, tungsten carbide), polymers (e.g., polystyrene, polydiacetylene, and poly(3,4-ethylenedioxythiophene) hydrate), semiconductors (e.g., quantum dots), silicon (e.g., silicon carbide), carbon (e.g., graphite, graphene, graphene oxide, or carbon nanosheets, nanocomplexes, or nanotubes), and composites (e.g., polyvinylcarbazole/graphene, polystyrene/graphene, platinum/graphene, palladium/graphene nanocomposites). In embodiments, such particulates and nanoparticulates are further covalently or non-covalently functionalized, or further include modifiers or cross-linked materials such as polymers (e.g., linear or branched polyethylenimine, poly-lysine), polynucleotides (e.g., DNA or RNA), polysaccharides, lipids, polyglycols (e.g., polyethylene glycol, thiolated polyethylene glycol), polypeptides or proteins, and detectable labels (e.g., a fluorophore, an antigen, an antibody, or a quantum dot). In various embodiments, such particulates and nanoparticles are neutral, or carry a positive charge, or carry a negative charge. Embodiments of compositions including particulates include those formulated, e.g., as liquids, colloids, dispersions, suspensions, aerosols, gels, and solids. Embodiments include nanoparticles affixed to a surface or support, e.g., an array of carbon nanotubes vertically aligned on a silicon or copper wafer substrate. Embodiments include polynucleotide compositions including particulates (e.g., gold or tungsten or magnetic particles) delivered by a Biolistic-type technique or with magnetic force. The size of the particles used in Biolistics is generally in the "microparticle" range, for example, gold microcarriers in the 0.6, 1.0, and 1.6 micrometer size ranges (see, e.g., instruction manual for the Helios® Gene Gun System, Bio-Rad, Hercules, Calif.; Randolph-Anderson et al. (2015) "Sub-micron gold particles are superior to larger particles for efficient Biolistic® transformation of organelles and some cell types", Bio-Rad US/EG Bulletin 2015), but successful Biolistics delivery using larger (40 nanometer) nanoparticles has been reported in cultured animal cells; see O'Brian and Lummis (2011) *BMC Biotechnol.*, 11:66-71. Other embodiments of useful particulates are nanoparticles, which are generally in the nanometer (nm) size range or less than 1 micrometer, e.g., with a diameter of less than about 1 nm, less than about 3 nm, less than about 5 nm, less than about 10 nm, less than about 20 nm, less than about 40 nm, less than about 60 nm, less than about 80 nm, and less than about 100 nm. Specific, non-limiting embodiments of nanoparticles commercially available (all from Sigma-Aldrich Corp., St. Louis, Mo.) include gold nanoparticles with diameters of 5, 10, or 15 nm; silver nanoparticles with particle sizes of 10, 20, 40, 60, or 100 nm; palladium "nanopowder" of less than 25 nm particle size; single-, double-, and multi-walled carbon nanotubes, e.g., with diameters of 0.7-1.1, 1.3-2.3, 0.7-0.9, or 0.7-1.3 nm, or with nanotube bundle dimensions of 2-10 nm by 1-5 micrometers, 6-9 nm by 5 micrometers, 7-15 nm by 0.5-10 micrometers, 7-12 nm by 0.5-10 micrometers, 110-170 nm by 5-9 micrometers, 6-13 nm by 2.5-20 micrometers. Embodiments include genome editing reagent-containing compositions including materials such as gold, silicon, cerium, or carbon, e.g., gold or gold-coated nanoparticles, silicon carbide whiskers, carborundum, porous silica nanoparticles, gelatin/silica nanoparticles, nanoceria or cerium oxide nanoparticles (CNPs), carbon nanotubes (CNTs) such as single-, double-, or multi-walled carbon nanotubes and their chemically functionalized versions (e.g., carbon nanotubes functionalized with amide, amino, carboxylic acid, sulfonic acid, or polyethylene glycol moieties), and graphene or graphene oxide or graphene complexes; see, for example, Wong et al. (2016) *Nano Lett.*, 16:1161-1172; Giraldo et al. (2014) *Nature Materials*, 13:400-409; Shen et al. (2012) *Theranostics*, 2:283-294; Kim et al. (2011) *Bioconjugate Chem.*, 22:2558-2567; Wang et al. (2010) *J. Am. Chem. Soc. Comm.*, 132:9274-9276; Zhao et al. (2016) *Nanoscale Res. Lett.*, 11:195-203; and Choi et al. (2016) *J. Controlled Release*, 235:222-235. See also, for example, the various types of particles and nanoparticles, their preparation, and methods for their use, e.g., in delivering polynucleotides and polypeptides to cells, disclosed in U.S. Patent Application Publications 2010/0311168, 2012/0023619, 2012/0244569, 2013/0145488, 2013/0185823, 2014/0096284, 2015/0040268, 2015/0047074, and 2015/0208663, all of which are incorporated herein by reference in their entirety.

In embodiments, a genome editing reagent is delivered to plant cells or plant protoplasts prepared or obtained from a plant, plant part, or plant tissue that has been treated with the polynucleotide compositions (and optionally the nuclease). In embodiments, one or more one chemical, enzymatic, or physical agent, separately or in combination with the genome editing reagent, is provided/applied at a location in the plant or plant part other than the plant location, part, or tissue from which the plant cell or plant protoplast is obtained or isolated. In embodiments, the genome editing reagent is applied to adjacent or distal cells or tissues and is transported (e.g., through the vascular system or by cell-to-cell movement) to the meristem from which plant cells or plant protoplasts are subsequently isolated. In embodiments, a genome editing reagent-containing composition is applied by soaking a seed or seed fragment or zygotic or somatic embryo in the genome editing reagent-containing composition, whereby the genome editing reagent is delivered to the seed or seed fragment or zygotic or somatic embryo from which plant cells or plant protoplasts are subsequently isolated. In embodiments, a flower bud or shoot tip is contacted with a genome editing reagent-containing composition, whereby the genome editing reagent is delivered to cells in the flower bud or shoot tip from which plant cells or plant protoplasts are subsequently isolated. In embodiments, a genome editing reagent-containing composition is applied to the surface of a plant or of a part of a plant (e.g., a leaf surface), whereby the genome editing reagent is delivered to tissues of the plant from which plant cells or plant protoplasts are subsequently isolated. In embodiments a whole plant or plant tissue is subjected to particle- or nanoparticle-mediated delivery (e.g., Biolistics or carbon nanotube or nanoparticle delivery) of a genome editing reagent-containing composition, whereby the genome editing reagent is delivered to cells or tissues from which plant cells or plant protoplasts are subsequently isolated.

EXAMPLES

Example 1

This example illustrates techniques for identifying trans-activating CRISPR (tracrRNA) sequences that are useful in compositions and methods of the invention. More specifically, this example provides examples of Cas12a tracrRNA sequences identified from Lachnospiraceae bacterium ND2006 ("Lb") and *Acidaminococcus* sp. BV3L6 ("As").

Steps for identifying tracrRNA sequences have been described, e.g., in U.S. Pat. No. 9,790,490, incorporated here by reference: "Identification of tracr sequences may relate to the following steps: Search for the direct repeats or tracr mate sequences in a database to identify a CRISPR region comprising a CRISPR enzyme. Search for homologous sequences in the CRISPR region flanking the CRISPR enzyme in both the sense and antisense directions. Look for transcriptional terminators and secondary structures. Identify any sequence that is not a direct repeat or a tracr mate sequence but has more than 50% identity to the direct repeat or tracr mate sequence as a potential tracr sequence. Take the potential tracr sequence and analyze for transcriptional terminator sequences associated therewith." RNA sequencing can be used to further characterize such sequences identified as potential or putative tracrRNAs.

Similar techniques are used to identify putative tracrRNA sequences for Cas12a (Cpf1) nucleases from Lachnospiraceae bacterium ND2006 ("Lb") and *Acidaminococcus* sp. BV3L6 ("As"). The techniques employed include: identifying sequences that are located in the CRISPR region flanking the DNA encoding the CRISPR nuclease and that have a nucleotide sequence that permits the transcribed tracrRNA to hybridize to the crRNA (i.e., the transcribed tracrRNA has sufficient complementarity to a crRNA sequence to hybridize to the crRNA), and searching for the presence of a predicted transcriptional terminator in direction of transcription. Sequences having at least 50% sequence identity to the direct repeat in a corresponding CRISPR array are identified as potential tracrRNA sequences; sequences having slightly less than 50% sequence identity to the direct repeat are also evaluated. In this non-limiting example, putative tracrRNA sequences are identified having lengths of between 65 to 84 nucleotides and between 50.0% to 52.8% sequence identity to the direct repeat.

Figure 2:
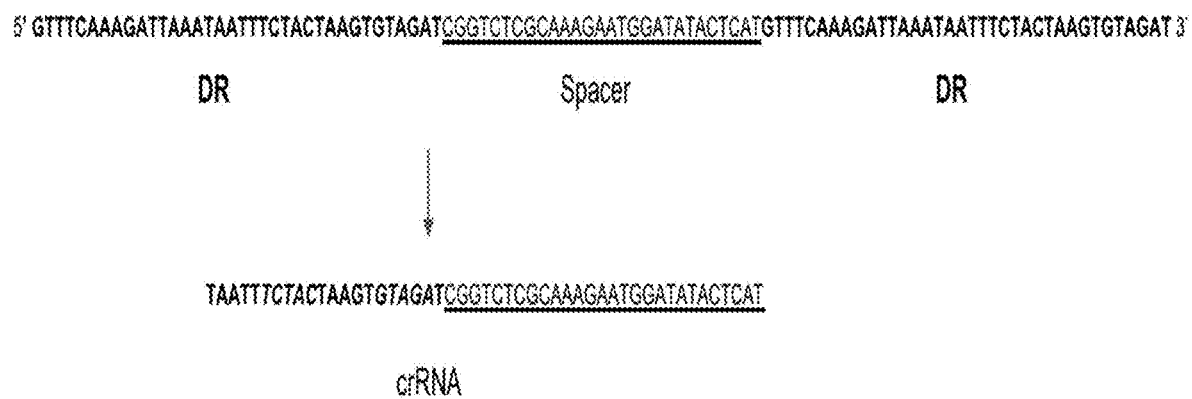
FIG. 2 illustrates a segment of the LbCpf1 CRISPR locus as described in detail in Example 1, showing the arrangement in a CRISPR array of the LbCpf1 direct repeats ("DR", in bold font) (SEQ ID NO:173) flanking a spacer sequence ("spacer", in underlined font) (SEQ ID NO:175), and illustrating the predicted crRNA (SEQ ID NO:176) processing from this CRISPR array. The DR, spacer, and predicted crRNA sequences are provided as DNA equivalents.

FIG. 1 illustrates schematics of the Lachnospiraceae bacterium ND2006 Cas12a ("LbCpf1") CRISPR locus and putative tracrRNA location; the schematics are shown with (upper figure) and without (lower figure) the Cas4 and Cas2 components of the locus. FIG. 2 illustrates a segment of the LbCpf1 CRISPR locus, showing the arrangement in a CRISPR array of the LbCpf1 direct repeats ("DR", in bold font) flanking a spacer sequence ("spacer", in underlined font), and illustrating the predicted crRNA processing from this CRISPR array. The following are identified as putative tracrRNA sequences: LbCpf1 putative tracrRNA 1 (84 nucleotides) having the RNA sequence of SEQ ID NO:1 encoded by the DNA sequence of SEQ ID NO:2, and LbCpf1 putative tracrRNA 2 (65 nucleotides) having the RNA sequence of SEQ ID NO:3 encoded by the DNA sequence of SEQ ID NO:4. FIG. 3 illustrates the alignments of the reverse complement of the LbCpf1 direct repeat (DR) sequence, SEQ ID NO:5, with the LbCpf1 putative tracrRNA 1 (SEQ ID NO:2) (top, showing 52.8% identity between the two sequences) and the LbCpf1 putative tracrRNA 2 (SEQ ID NO:4) (bottom, showing 50.0% identity between the two sequences).

Figure 4:
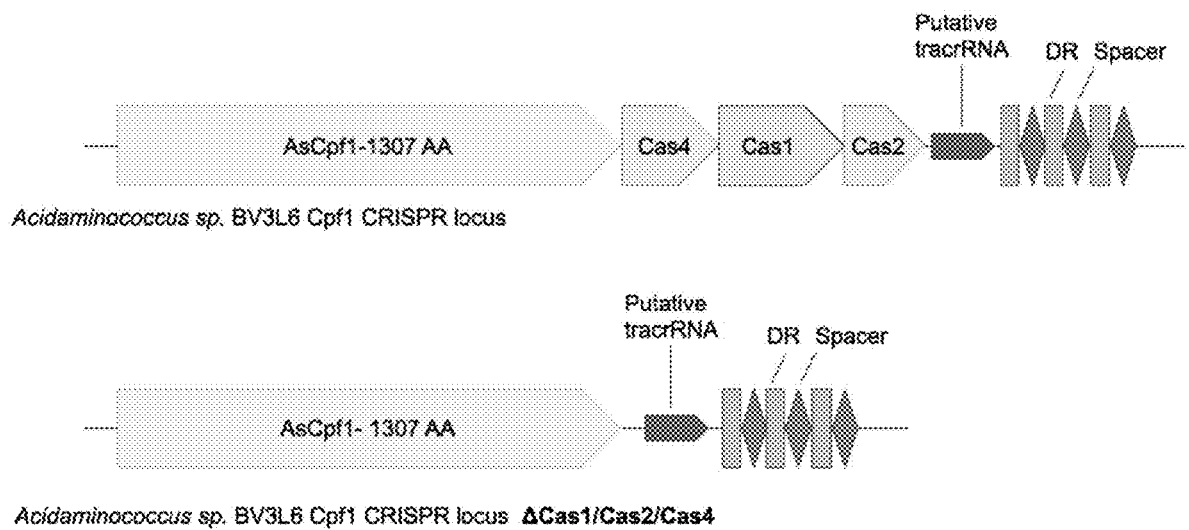
FIG. 4 illustrates schematics of the Acidaminococcus sp. BV3L6 ("As") Cas12a ("AsCpf1") CRISPR locus and tracrRNA ("putative tracrRNA") location as described in detail in Example 1. The schematics are shown with (upper figure) and without (lower figure) the Cas 1, Cas2, and Cas4 components of the locus. The direct repeats ("DR") are indicated by upright rectangles and the spacer sequences are indicated by diamonds.
Figure 5:
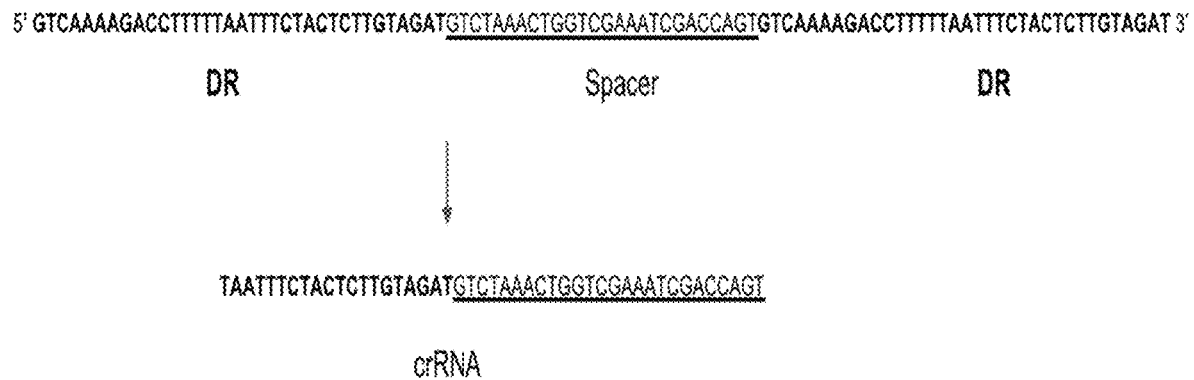
FIG. 5 illustrates a segment of the AsCpf1 CRISPR locus as described in detail in Example 1, showing the arrangement in a CRISPR array of the AsCpf1 direct repeats ("DR", in bold font) (SEQ ID NO:176) flanking a spacer sequence ("spacer", in underlined font) (SEQ ID NO:177), and illustrating the predicted crRNA (SEQ ID NO:178) processing from this CRISPR array. The DR, spacer, and predicted crRNA sequences are provided as DNA equivalents.

FIG. 4 illustrates schematics of the *Acidaminococcus* sp. BV3L6 ("As") Cas12a ("AsCpf1") CRISPR locus and putative tracrRNA location; the schematics are shown with (upper figure) and without (lower figure) the Cas 1, Cas2, and Cas4 components of the locus. FIG. 5 illustrates a segment of the AsCpf1 CRISPR locus, showing the arrangement in a CRISPR array of the AsCpf1 direct repeats ("DR", in bold font) flanking a spacer sequence ("spacer", in underlined font), and illustrating the predicted crRNA processing from this CRISPR array. A putative AsCpf1 tracrRNA (72 nucleotides) is identified as having the RNA sequence of SEQ ID NO:6 encoded by the DNA sequence of SEQ ID NO:7. FIG. 6 illustrates the alignment of the reverse complement of the AsCpf1 direct repeat (DR) sequence, SEQ ID NO:8, with the AsCpf1 putative tracrRNA (SEQ ID NO:7), showing 51.4% identity between the two sequences.

Example 2

This example describes identification of restriction endonuclease recognition and cleavage sites in and adjacent to Cas12a tracrRNA sequences. It is understood that the recognition site to which restriction endonuclease binds may also be where cleavage occurs, or may be a short distance from where cleavage occurs.

Figure 7:
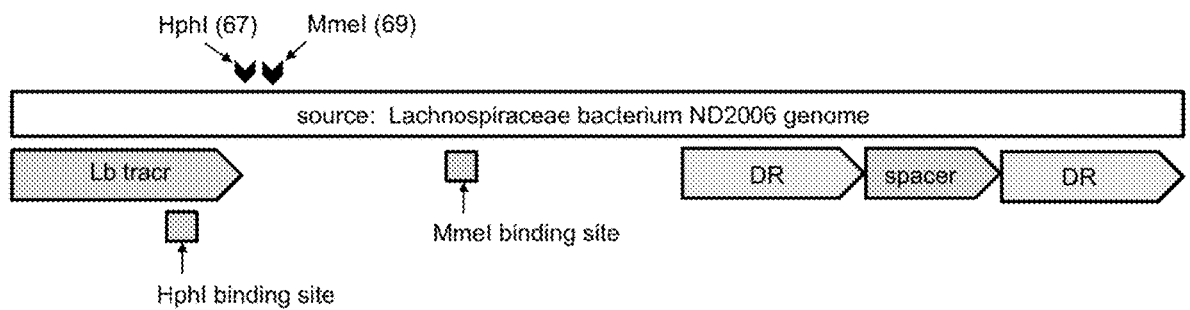
FIG. 7 schematically illustrates the position (not to scale) of some of the restriction endonuclease sites within the Lb Cas12a locus as described in detail in Example 2. Endonuclease recognition and binding sites are indicated by squares; the endonuclease cleavage sites are indicated by arrowheads. "DR" indicates a direct repeat.

Recognition and cleavage sites for commercially available restriction endonucleases are identified in the Lachnospiraceae bacterium ND2006 ("Lb") and *Acidaminococcus* sp. BV3L6 ("As") Cas12a loci, specifically in the region of the putative tracrRNA sequences described in Example 1. Table 1 lists restriction endonuclease sites located in or adjacent to (3' to) the DNA encoding the LbCpf1 putative tracrRNA 2 (65 nucleotides) (see Example 1); FIG. 7 schematically illustrates the position (not to scale) of some of the restriction endonuclease sites within the Lb Cas12a locus.

TABLE 1

| Restriction endonuclease name | Recognition pattern for endonuclease binding | Recognition pattern SEQ ID NO: | Endonuclease cleavage location, relative to the 5' terminus of the Lb tracrRNA 2 sequence |
| --- | --- | --- | --- |
| HphI | GGTGA(8/7) | 183 | 67 |
| AsuHPI | GGTGA(8/7) | 184 | 67 |
| MmeI | TCCRAC(20/18) | 185 | 69 |

Figure 8:
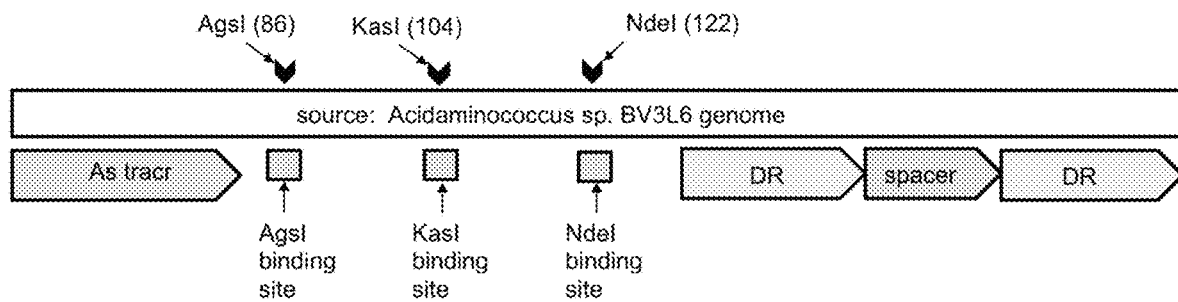
FIG. 8 schematically illustrates the position (not to scale) of some of the restriction endonuclease sites within the As Cas12a locus as described in detail in Example 2. Endonuclease recognition and binding sites are indicated by squares; the endonuclease cleavage sites are indicated by arrowheads. "DR" indicates a direct repeat.

Table 2 lists restriction endonuclease sites located in or adjacent to (3' to) the DNA encoding the AsCpf1 putative tracrRNA (72 nucleotides) (see Example 1); FIG. 8 schematically illustrates the position (not to scale) of some of the restriction endonuclease sites within the As Cas12a locus.

TABLE 2

| Restriction endonuclease name | Recognition pattern for endonuclease binding | Recognition pattern SEQ ID NO: | Endonuclease cleavage location, relative to the 5' terminus of the As tracrRNA sequence |
| --- | --- | --- | --- |
| AgsI | TTS^AA | 186 | 86 |
| MwoI, BstMWI, HpyF10VI | GCNNNNN^NNGC | 187 | 113 |
| Hin6I, HinP1I, HspAI | G^CGC | 188 | 105 |
| HhaI, AspLEI, BstHHI, CfoI | GCG^C | 189 | 107 |
| GlaI | GC^GC | 190 | 106 |
| AcyI, BsaHI, BssNI, BstACI, Hin1I, Hsp92I | GR^CGYC | 191 | 105 |
| HaeII, BfoI, BstH2I | RGCGC^Y | 192 | 108 |
| NlaIV, BmiI, BspLI, PspN4I | GGN^NCC | 193 | 106 |
| KasI, SspDI | G^GCGCC | 194 | 104 |
| NarI, Mly113I | GG^CGCC | 195 | 105 |
| PluTI | GGCGC^C | 196 | 108 |
| DinI, EgeI, EheI, SfoI | GGC^GCC | 197 | 106 |
| AccB1I, BanI, BshNI, BspT107I | G^GYRCC | 198 | 104 |
| EcoT22I, Mph1103I, NsiI, Zsp2I | ATGCA^T | 199 | 118 |
| BsmI, Mva1269I, PctI | GAATGC(1/-1) | 200 | 116 |
| MslI, RseI, SmiMI | CAYNN^NNRTG | 201 | 121 |
| TspDTI | ATGAA(11/9) | 202 | 109 |
| NdeI, FauNDI | CA^TATG | 203 | 122 |

Example 3

This example illustrates non-limiting embodiments of the polynucleotides and ribonucleoproteins useful in carrying out methods of the invention.

Figure 9:
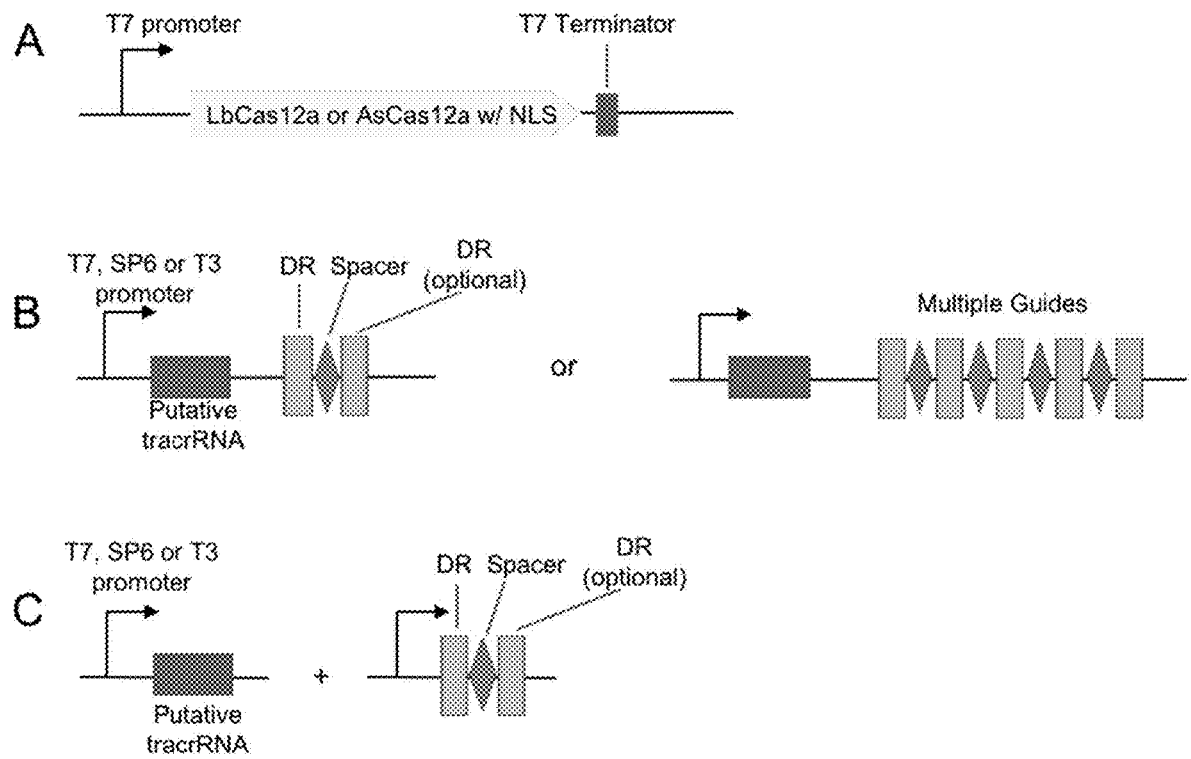
FIG. 9A schematically depicts an expression cassette for expressing a Cas12a nuclease, including a promoter, coding sequence for the Cas12a nuclease, and a terminator, as described in detail in Example 3.
FIG. 9B (left) schematically depicts a DNA expression system including: (a) DNA sequence for a first promoter; (b) operably linked and heterologous to the first promoter, a DNA encoding a first RNA molecule including a Cas12a tracrRNA or putative tracrRNA and including a restriction endonuclease cleavage site that is suitable for insertion of a sequence coding for a functional RNA moiety; and (c) operably linked and heterologous to the first promoter, a DNA encoding a Cas12a crRNA that includes a 3' extension capable of hybridizing with a segment of the first RNA molecule, as described in detail in Example 3.
FIG. 9C (left) schematically depicts a non-limiting example of a DNA expression system including: (a) DNA sequence for a first promoter; and (b) operably linked and heterologous to the first promoter, a DNA sequence encoding a first RNA molecule including a Cas12a tracrRNA or putative tracrRNA and including a restriction endonuclease cleavage site that is suitable for insertion of a sequence coding for a functional RNA moiety, as described in detail in Example 3.

FIG. 9A schematically depicts an expression cassette for expressing a Cas12a nuclease, including a promoter, coding sequence for the Cas12a nuclease, and a terminator. This non-limiting example illustrates a typical bacterial expression vector, wherein the promoter is a T7 promoter, the Cas12a nuclease is a fusion protein including LbCas12a or AsCas12a and at least one copy of a nuclear localization signal (NLS). This T7 expression system can be expressed and purified from E. coli. This or similar expression cassettes are useful, e.g., for expressing a Cas12a nuclease, with one or multiple copies of nuclear localization signal (NLS) for nuclear targeting located at the nuclease's N-terminus or C-terminus or both. The Cas12a nuclease may then be supplied as a protein and assembled with a guide RNA to form a ribonucleoprotein in vitro before delivery into cells.

FIG. 9B (left) schematically depicts a DNA expression system including: (a) DNA sequence for a first promoter; (b) operably linked and heterologous to the first promoter, a DNA sequence encoding a first RNA molecule including a Cas12a tracrRNA (here labelled "putative tracrRNA") and including a restriction endonuclease cleavage site (not specifically indicated) that is suitable for insertion of a sequence coding for a functional RNA moiety; and (c) operably linked and heterologous to the first promoter (and to the optional second promoter, if present), a DNA encoding a Cas12a crRNA (which includes a direct repeat, "DR" and a spacer sequence) that includes a 3' extension capable of hybridizing with a segment of the first RNA molecule. FIG. 9B (right) schematically depicts an alternative design wherein the DNA expression system includes a DNA encoding a Cas12a crRNA including multiple guide RNAs (i.e., multiple direct repeats and multiple spacer sequences), and including a 3' extension capable of hybridizing with a segment of the first RNA molecule. Optional elements that can be used in this system include a DNA sequence for a second promoter, which can be positioned between the DNA sequence encoding a first RNA molecule including a Cas12a tracrRNA and the DNA encoding a Cas12a crRNA; and a terminator, which can be positioned 3' to the DNA encoding a Cas12a crRNA. The 3'-most direct repeat is also optional. This or similar expression systems using e.g., a phage polymerase promoter (such as an SP6, T7, or T3 promoter) permit the tracrRNA and a guide RNA (the Cas12a crRNA) to be transcribed in vitro, together.

FIG. 9C (left) schematically depicts a non-limiting example of a DNA expression system including: (a) DNA sequence for a first promoter; and (b) operably linked and heterologous to the first promoter, a DNA sequence encoding a first RNA molecule including a Cas12a tracrRNA (here labelled "putative tracrRNA") and including a restriction endonuclease cleavage site (not specifically indicated) that is suitable for insertion of a sequence coding for a functional RNA moiety. (A similar expression system can also be used for expressing a DNA sequence encoding a functional RNA molecule including a Cas12a tracrRNA and a functional RNA moiety.) FIG. 9C (right) further schematically depicts an expression construct for expressing a guide RNA (here, a Cas12a crRNA including a direct repeat, "DR", and a spacer sequence); the 3'-most direct repeat is optional. These or similar expression systems using e.g., a phage polymerase promoter (such as an SP6, T7, or T3 promoter) permit the tracrRNA and a guide RNA (the Cas12a crRNA) to be transcribed in vitro, separately.

Figure 10:
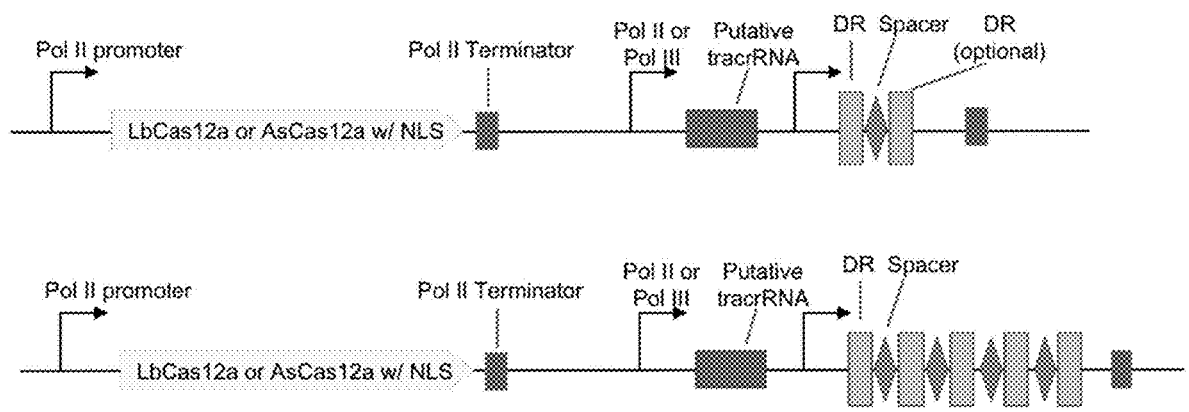
FIG. 10 (top) schematically depicts a DNA expression system, described in detail in Example 3, which includes: (a) DNA sequence for a first promoter; (b) operably linked and heterologous to the first promoter, DNA encoding a Cas12a nuclease; (c) a terminator; (d) a second promoter; (e) operably linked and heterologous to the second promoter, a DNA sequence encoding a functional RNA molecule including a Cas12a tracrRNA or putative tracrRNA and a functional RNA moiety; (f) an optional third promoter; (g) operably linked and heterologous to the second promoter (and to the optional third promoter, if present), a DNA encoding a guide RNA including a Cas12a crRNA that includes a 3' extension capable of hybridizing with a segment of the functional RNA molecule; and (h) a second terminator; the 3'-most direct repeat is optional.

FIG. 10 (top) schematically depicts a DNA expression system including: (a) DNA sequence for a first promoter (here, an RNA polymerase II promoter, such as a maize ubiquitin promoter); (b) operably linked and heterologous to the first promoter, DNA encoding a Cas12a nuclease (here, a fusion protein including LbCas12a or AsCas12a and at least one copy of a nuclear localization signal (NLS)); (c) a pol II terminator; (d) a second promoter (e.g., a pol II or pol III promoter, such as a rice U6 or U3 promoter); (e) operably linked and heterologous to the second promoter, a DNA sequence encoding a functional RNA molecule including a Cas12a tracrRNA (here labelled "putative tracrRNA") and a functional RNA moiety (not specifically indicated); (f) an optional third promoter; (g) operably linked and heterologous to the second promoter (and to the optional third promoter, if present), a DNA encoding a guide RNA including a Cas12a crRNA (which includes a direct repeat, "DR" and a spacer sequence) that includes a 3' extension capable of hybridizing with a segment of the functional RNA molecule; and (h) a second terminator; the 3'-most direct repeat is optional. FIG. 10 (bottom) schematically depicts a second DNA expression system similar to that shown in FIG. 10 (top), except that the guide RNA includes multiple guide RNAs (i.e., multiple direct repeats and multiple spacer sequences), and including a 3' extension capable of hybridizing with a segment of the first RNA molecule; the 3'-most direct repeat is optional. It will be apparent that multiple guide RNAs can alternatively be expressed under the control of multiple promoters. One of skill in the art will appreciate that similar constructs include many of the elements shown in FIG. 10 can be designed for expression of a tracrRNA and a crRNA under either one promoter or two promoters, and that promoters are selected for the type of organism (for example, a dicot plant rather than a monocot plant), tissue, or cell where the encoded nuclease and/or RNAs are to be expressed. Any of these DNA expression systems is conveniently provided on a single plasmid. While FIG. 10 depicts the component expression cassettes orientated in the same direction, it is understood that these can be orientated in opposite directions.

Example 4

This example describes a DNA expression system including: (a) DNA sequence for a first promoter; and (b) operably linked and heterologous to the first promoter, a DNA sequence encoding a functional RNA molecule including a Cas12a tracrRNA and a functional RNA moiety. This example illustrates employing a Cas12a tracrRNA as a scaffold or carrier for a functional RNA moiety (in this case, multiple copies of an aptamer capable of recruiting regulatory proteins as well as RNA for annealing to the crRNA 3' extension), allowing the functional RNA moiety to be incorporated into a Cas12a ribonucleoprotein complex. More specifically, this example illustrates a Cas12a ribonucleoprotein complex including a deactivated Cas12a nuclease, a guide RNA (a Cas12a crRNA having a 3' extension) targeting the promoter region of the maize (Zea mays) Lc gene, and a functional RNA molecule provided by integrating multiple copies of an MS2 aptamer as well as sequence for annealing to the crRNA 3' extension into a Cas12a tracr.

A ternary system is constructed containing a deactivated Cas12a nuclease, a guide RNA (a Cas12a crRNA having a 3' extension) targeting the promoter region of the maize (Zea mays) Lc gene, and a functional RNA molecule provided by integrating multiple copies of an MS2 aptamer and sequence for hybridizing to the crRNA 3' extension into a Cas12a tracr. FIG. 11 (top) schematically depicts construction of the DNA encoding the functional RNA molecule by cleavage at an HphI restriction endonuclease cleavage site (see Example 2 and Table 1) in or adjacent to a tracrRNA identified from the native Lachnospiraceae bacterium ND2006 CRISPR Cas12a locus (see Example 1), insertion of DNA encoding multiple copies of an MS2 aptamer as well as sequence for annealing to the crRNA 3' extension, and ligation to form the DNA encoding the functional RNA molecule, which can be complexed with the Cas12a nuclease to form the ribonucleoprotein depicted in FIG. 11 (bottom). A similar approach is useful for providing functional RNA molecules including a Cas12a tracrRNA and a functional RNA moiety, wherein the functional RNA moiety is one or more RNAs selected from the group consisting of (a) an RNA sequence for annealing to a donor polynucleotide; (b) an RNA sequence for annealing to the crRNA 3' extension; (c) a terminator sequence; (d) an RNA aptamer; (e) a ribozyme; (f) a detectable label; (g) a bar-coding sequence and (h) an RNA sequence forming at least partially double-stranded RNA, for example, RNA forming at least partially double-stranded RNA capable of silencing a gene (e.g., RNA that forms one or more stem-loops where the stem includes double-stranded RNA of at least about 18 base-pairs designed to silence a target gene, or RNA that has the secondary structure of a microRNA precursor and is processed to a mature microRNA designed to silence a target gene). For example, similar approaches are used for providing a functional RNA molecule that includes aptamers engineered to target endogenous proteins, such as transcriptional cofactors.

The DNA encoding the predicted tracrRNA identified from the native Lachnospiraceae bacterium ND2006 CRISPR Cas12a locus has the sequence (SEQ ID NO: 9)
AATTGCAAATCTTTGAAATAATGCAGACTTAAATTTATAAATTCAT

GGAATAAGGTGATTTTATTGTGAAAAAATACTCGTATTTTGTTGGA

AAAACATCTTTTTGTTGTATAATATGATGATATACGG, where the tracrRNA nucleotides are shown in underlined font, the HphI recognition and binding site located within the tracrRNA is shown in bold font, and nucleotides of the native sequence located between the 3' end of the predicted tracrRNA and the 5' end of the CRISPR array are shown in plain font. The DNA encoding the MS2 aptamer stem-loops has the sequence (SEQ ID NO: 10)
GTTTTAGAGCTAGGCCAACATGAGGATCACCCATGTCTGCAGGGCCT

AGCAAGTTAAAATAAGGCTAGTCCGTTATCAACTTGGCCAACATGAG

GATCACCCATGTCTGCAGGGCCAAGTGGCACCGAGTCGGTGCTTTTT.

The deactivated LbCas12a nuclease is encoded by DNA having the sequence of SEQ ID NO:11, which is a D832A mutant of the wild-type Cas12a nuclease having NCBI reference sequence WP_051666128.1 (see www[dot]ncbi [dot]nlm[dot]nih[dot]gov/protein/WP_051666128.1/). In embodiments, the deactivated LbCas12a nuclease optionally includes additional modifications, for example, one or more copies of a nuclear localization signal (NLS), or an affinity tag for later purification of the nuclease, with, if needed, sequences permitting cleavage and removal of the affinity tag. The DNA encoding the Cas12a crRNA with the 3' extension has the sequence GTTTCAAAGATTAAATAATTTCTACTAAGTGTAGATTGGACAGAGCTCCAAGTGACCAAAACCGTATATCAT (SEQ ID NO:12), where the direct repeat is shown in underlined font, the spacer targeting the promoter region of the maize (Zea mays) B104 Lc gene is shown in bold font, and the 3' extension is shown in plain font. The DNA targeted for editing is the maize (Zea mays) Lc gene, specifically the Zm-Lc promoter region having the sequence (SEQ ID NO: 13)
ATAGAGAGAGAAGAGGGGTCGTGTAGTAGTGCTTAAACTGTACATGA

ACAGCAGTAGTGTTACAGAAGCTAAACTCAACCAGAGCTCCACCAAA

GACAAAGAGGGTCTACTTCCATCACCGTCTTGCTCGGTCACTTGGAG

CTCTGTCCATAAATTAAACCCATCGTGGCATATCTGTAGGCATCTAC

CCCGTCTTCGTCGTCCGTTCCTCACTAGCTACCAAGAGGTCGCCATT

ATTGCCAACATAGAGTGTACGTGGATGTCTATATATATGCCTACTTG

CACCCATATGGCATAGGCGTTCGATCCCCTTAGCGCGGAGGAGAGCT

CCTCCGGTTCTTCTCTACCCTTCGCATGGAAGTTCTTGCATTGCTTC

GTTGCTTCTCTAGTTTCTTCCTTCTACGTCTTTCCAGCATACGCATG

CCCCTCGTCCGCCGGTTCACGAGGCATCGTCTGATGATCAGTAGATA

ATAAGCAATATAATACTGATCTAGAATCGAGTTGTTGTACTCTTCGC

AGATAGGTTCGTTCCTTCACATAGAAGCGAGTACAGACTACAGACCA

CACAGTATCAGCTGGCACGAAACGAAAATGGTTACTTGCAAATTGCA

TGCACGAGCTAGAATTATATTCTTCTAATCTTCTTCGTTGACTTTCT

GGCTTCAGCAGGCGCGTGAT, wherein the target sequence that corresponds to the Cas12a crRNA spacer sequence is indicated by bold, underlined font.

The DNA encoding the Lachnospiraceae bacterium ND2006 Cas12a tracrRNA sequence (SEQ ID NO:9) contained within a plasmid vector is cleaved with HphI or by another compatible restriction endonuclease (see Table 1, Example 2) and the DNA encoding the MS2 RNA-binding stem-loops (SEQ ID NO:10) is inserted by ligation to provide DNA encoding the functional RNA molecule (FIG. 11, top); alternatively, the DNA encoding the MS2 RNA-binding stem-loops (SEQ ID NO:10) is inserted into the DNA encoding the Cas12a tracrRNA through another molecular cloning method. This functional RNA molecule is transcribed in vitro and purified. A Cas12a crRNA (SEQ ID NO:12) containing a 3' extension of 10 ribonucleotides complementary to the 3' sequence of the Cas12a tracrRNA is similarly transcribed and purified. The two RNA molecules are mixed with deactivated LbCas12a nuclease (SEQ ID NO:11) in 10:1 molar excess in 50 millimolar HEPES buffer (300 millimolar NaCl, 1 millimolar MgCl2) at room temperature for 20 minutes to provide the ternary ribonucleoprotein for use in modifying the Lc promoter. Ternary RNPs are delivered to maize B104 protoplasts using PEG-mediated transformation. An MS2-tagged transcriptional regulator is co-transfected for multi-copy recruitment to the targeted locus, which is predicted to result in a change in expression of the maize Lc gene. An example of a suitable MS2-tagged transcriptional regulator sequence is an MS2-P65-HSF1 fusion of multiple transcriptional activators (P65 and HSF1) having the sequence of SEQ ID NO:14, which includes an MS2 region (nucleotides 1-390), a nuclear localization signal (NLS) (nucleotides 445-465), a PG5 region (nucleotides 481-1023), and an HSF1 region (nucleotides 1047-1419). In an alternative embodiment, the viral protein-derived transcriptional activator, VP64, with the sequence of SEQ ID NO:15, can be similarly tagged with the MS2 sequence and used to activate transcription of the maize Lc gene.

Example 5

This example illustrates non-limiting embodiments of DNA expression systems that include DNA sequence for a first promoter; and, operably linked and heterologous to the first promoter, a DNA sequence encoding either: (1) a first RNA molecule comprising a Cas12a tracrRNA and comprising a restriction endonuclease cleavage site that is suitable for insertion of a sequence coding for a functional RNA moiety, or (2) a functional RNA molecule comprising a Cas12a tracrRNA and a functional RNA moiety.

In an embodiment, the DNA expression system includes: (a) DNA sequence for a first promoter; and, operably linked and heterologous to the first promoter; (b) a DNA sequence encoding a first RNA molecule comprising a Cas12a tracrRNA and comprising a restriction endonuclease cleavage site that is suitable for insertion of a sequence coding for a functional RNA moiety; and (c) optionally, a terminator. In embodiments, the DNA expression system further comprises: (d) optionally, a DNA sequence for a second promoter; (e) operably linked and heterologous to the first promoter or the second promoter, a DNA encoding a Cas12a crRNA that comprises a 3' extension capable of hybridizing with a segment of the first RNA molecule; and (f) optionally, a terminator. In embodiments of such a DNA expression system, the Cas12a crRNA is capable of complexing with a Cas12a nuclease to form a Cas12a ribonucleoprotein complex. The DNA sequence encoding the first promoter and/or the optional second promoter and or the optional terminator(s) is selected according to the biological system of interest (e.g., for expression in a bacterial cell, a yeast cell, an animal cell, or a plant cell). Non-limiting examples of promoters useful in such DNA expression systems include Pol II promoters and Pol III promoters. Non-limiting examples of promoters useful in the DNA expression systems and engineered systems of this disclosure include promoters functional in prokaryotic cells (e.g., useful for in vitro transcription), such as, but not limited to, promoters from T7 bacteriophage (T7), T7 bacteriophage plus lac operators (T7lac), Sp6 bacteriophage (Sp6, used with SP6 RNA polymerase), arabinose metabolic operon (araBAD), *E. coli* tryptophan operator (trp), lac operon (lac), bacteriophage lambda (pL), and a hybrid promoter of lac and trp (Ptac). Non-limiting examples of promoters useful especially in animal cells include promoters from β-actin (ACTB), cytomegalovirus (CMV), elongation factor-1α, (EF1α), phosphoglycerate kinase (PGK1), ubiquitin C (UbC), herpes simplex virus thymidine kinase (HSV-1 TK), early and late simian vacuolating virus 40 (SV40), long terminal repeats (LTRs) from retrovirus, mouse metallothionein-I, *Drosophila* actin 5c, baculovirus polyhedron, yeast transcription elongation factor (TEF1), alcohol dehydrogenase I (ADH1), glyceraldehyde 3-phosphate dehydrogenase (GAPDH), human polymerase III RNA promoter (H1), human U6 small nuclear promoter (U6), an inducible tetracycline response element promoter, and a CAG hybrid (containing a CMV enhancer, chicken beta actin promoter, and rabbit beta-globin splice acceptor); many other promoters useful in animals, including in humans (e.g., for gene therapeutic applications) are available in the art, see, e.g., Zheng and Baum (2008) *Methods Mol. Biol.*, 434:205-219 (available at doi:10.1007/978-1-60327-248-3_13). Non-limiting examples of promoters useful in such DNA expression systems especially in plant cells include a nopaline synthase (Nos) promoter and a ubiquitin promoter; specific examples include a promoter selected from the group consisting of a TaU3 promoter (SEQ ID NO:16), a Nos promoter (SEQ ID NO:17), a ZmUBI1 promoter (SEQ ID NO:18), and a SlUBI10 promoter (SEQ ID NO:19). Further non-limiting examples of promoters especially useful in plant cells include SEQ ID NOs:20-71; see Table 3. Specific embodiments include a DNA expression system wherein the first promoter has a DNA sequence selected from the group consisting of SEQ ID NOs:16-71, and the Cas12a tracrRNA has the sequence of SEQ ID NOs:1, 3, 6, 139-146, and 149-169. Specific embodiments include a DNA expression system having the optional second promoter, wherein the second promoter has a DNA sequence selected from the group consisting of SEQ ID NOs:16-71. In embodiments, the first promoter and optional second promoter have different sequences; in other embodiments, the first promoter and optional second promoter have identical sequences. In embodiments, the Cas12a crRNA is capable of complexing with a Cas12a nuclease to form a Cas12a ribonucleoprotein complex; in embodiments, the Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum*, *Eubacterium eligens*, *Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A.

In embodiments, the DNA expression system includes: (a) DNA sequence for a first promoter wherein the first promoter has a DNA sequence selected from the group consisting of SEQ ID NOs:16-71; and, operably linked and heterologous to the first promoter; (b) a DNA sequence encoding a first RNA molecule comprising a Cas12a tracrRNA, wherein the Cas12a tracrRNA has a sequence that is selected from SEQ ID NOs:1, 3, 6, 139-146, and 149-169, and that comprises a restriction endonuclease cleavage site that is suitable for insertion of a sequence coding for a functional RNA moiety; and (c) optionally, a terminator, preferably a terminator functional in a eukaryotic cell; in embodiments, the DNA expression system further comprises: (d) optionally, a DNA sequence for a second promoter, e.g., a promoter having a DNA sequence selected from the group consisting of SEQ ID NOs:16-71; (e) operably linked and heterologous to the first promoter or the second promoter, a DNA encoding a Cas12a crRNA that comprises a 3' extension capable of hybridizing with a segment of the first RNA molecule and that is capable of complexing with a Cas12a nuclease to form a Cas12a ribonucleoprotein complex, wherein the Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A; and (f) optionally, a terminator.

In another embodiment, the DNA expression system includes: (a) DNA sequence for a first promoter; and, operably linked and heterologous to the first promoter, (b) a DNA sequence encoding a functional RNA molecule comprising a Cas12a tracrRNA and a functional RNA moiety. In embodiments, the DNA expression system further comprises: (c) optionally, a DNA sequence for a second promoter; (d) operably linked and heterologous to the first promoter or the second promoter, a DNA encoding a Cas12a crRNA that comprises a 3' extension capable of hybridizing with a segment of the functional RNA molecule; and (e) optionally, a terminator. In embodiments of such a DNA expression system, the Cas12a crRNA is capable of complexing with a Cas12a nuclease to form a Cas12a ribonucleoprotein complex. The DNA sequence encoding the first promoter is selected according to the biological system of interest (e.g., for expression in a bacterial cell, a yeast cell, an animal cell, or a plant cell). Non-limiting examples of promoters useful in such DNA expression systems include a nopaline synthase (Nos) promoter and a ubiquitin promoter; specific examples include a promoter selected from the group consisting of a TaU3 promoter (SEQ ID NO:16), a Nos promoter (SEQ ID NO:17), a ZmUBI1 promoter (SEQ ID NO:18), and a SlUBI10 promoter (SEQ ID NO:19). Specific embodiments include a DNA expression system wherein the first promoter has a DNA sequence selected from the group consisting of SEQ ID NOs:16-71, and the functional RNA molecule includes a Cas12a tracrRNA that has the sequence of SEQ ID NO:3. Specific embodiments include a DNA expression system wherein the Cas12a crRNA is capable of complexing with a Cas12a nuclease to form a Cas12a ribonucleoprotein complex, wherein the first promoter has a DNA sequence selected from the group consisting of SEQ ID NOs:16-71 and wherein the Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A; in some embodiments of such DNA expression systems, the Cas12a tracrRNA has the sequence of SEQ ID NOs:1, 3, 6, 139-146, and 149-169.

Embodiments of these various DNA expression systems further include additional expression elements, e.g., expression enhancing elements ("enhancers"), 3' untranslated region elements such as terminators or polyadenylation elements, and introns. The DNA sequences encoding the first promoter, optional second promoter, optional terminator, and any other expression element are generally selected according to the biological system of interest (e.g., for expression in a bacterial cell, a yeast cell, an animal cell, or a plant cell). Terminators useful in DNA expression systems and engineered systems of this disclosure include terminators having a sequence selected from the group consisting of SEQ ID NOs:72-100. Other expression elements useful in DNA expression systems and engineered systems of this disclosure include expression elements having a sequence selected from the group consisting of SEQ ID NOs:101-106.

Promoters useful in plant cells include promoters especially suited to monocot plants and promoters especially suited to dicot plants. Non-limiting examples of these various expression elements are provided in Table 3 and are useful for heterologous expression of Cas12a tracrRNAs, such as a tracrRNA having an RNA sequence selected from SEQ ID NOs:1, 3, 6, 139-146, and 149-169 or the Cas12a tracrRNA sequences disclosed in U.S. Pat. No. 9,790,490 (incorporated herein by reference).

TABLE 3

| Designation | Source | Source ID | Application | Type | SEQ ID NO: |
|---|---|---|---|---|---|
| prAtUbi10 | Arabidopsis thaliana | AT4G05320.2 | Pol II promoter | dicot | 20 |
| prGmUBI8 | Glycine max | Glyma10g051100 | Pol II promoter | dicot | 21 |
| prGmUBI1 | Glycine max | Glyma10g251900 | Pol II promoter | dicot | 22 |
| prGmUBI9 | Glycine max | Glyma13g138600 | Pol II promoter | dicot | 23 |
| prGmUBI4 | Glycine max | Glyma13g176100 | Pol II promoter | dicot | 24 |
| prGmUBI7 | Glycine max | Glyma17g042100 | Pol II promoter | dicot | 25 |
| enTCUP2 | tobacco | JX155386.1 | Pol II promoter | dicot | 26 |
| prSlUbi10 | Solanum lycopersicum | LOC101258282 | Pol II promoter | dicot | 27 |
| prWpUbi10 | White pear | LOC103948134 | Pol II promoter | dicot | 28 |
| prBvUbi10 | Sugar beet | LOC104907074 | Pol II promoter | dicot | 29 |
| prRsUbi10 | Radish | LOC108826774 | Pol II promoter | dicot | 30 |
| prIlUbi10 | Japanese morning glory | LOC109190585 | Pol II promoter | dicot | 31 |
| prCuUbi10 | Cucurbita | LOC111802502 | Pol II promoter | dicot | 32 |
| prHaUBI | Helianthus annuus | OTG28215 | Pol II promoter | dicot | 33 |
| prLAT52 | tomato | X15855 | Pol II promoter | dicot | 34 |
| prHaUbi1 | Helianthus annuus | X57005.1 | Pol II promoter | dicot | 35 |
| prPcUbi4 | Parsley | X64345.1 | Pol II promoter | dicot | 36 |
| SlU6-2 | tomato | | Pol III promoter | dicot | 37 |
| MtU6.6 | Medicago truncatula | | Pol III promoter | dicot | 38 |
| GmU6-9.1 | Glycine max | | Pol III promoter | dicot | 39 |
| AtU6 | Arabidopsis thaliana | | Pol III promoter | dicot | 40 |
| GmU6-10 | Glycine max | | Pol III promoter | dicot | 41 |
| TC-AtU6 | Arabidopsis thaliana | | Pol III promoter | dicot | 42 |
| At7SL | Arabidopsis thaliana | | Pol III promoter | dicot | 43 |
| ZmKN1 | Zea mays | AY312169.1 | Pol II promoter | monocot | 44 |
| prOsACT-B | Oryza sativa | CP018159 | Pol II promoter | monocot | 45 |
| prOsACT-A | Oryza sativa | EU155408.1 | Pol II promoter | monocot | 46 |
| PvUBI1 | Panicum virgatum | HM209467.1 | Pol II promoter | monocot | 47 |
| prOsUbi2 | Oryza sativa | LOC_Os02g06640 | Pol II promoter | monocot | 48 |
| prOsUbi1 | Oryza sativa | LOC_Os06g46770 | Pol II promoter | monocot | 49 |
| prAtaUbi1 | Aegilops tauschii | LOC109747268 | Pol II promoter | monocot | 50 |
| prPhUbi1 | Panicum hallii | LOC112888620 | Pol II promoter | monocot | 51 |
| prZmADP1 | Zea mays | LOC542430 | Pol II promoter | monocot | 52 |
| prZmEF1alpha | Zea mays | LOC542581 | Pol II promoter | monocot | 53 |
| prZmADP2 | Zea mays | LOC542584 | Pol II promoter | monocot | 54 |
| prZmUBI1 | Zea mays | S94464 | Pol II promoter | monocot | 55 |
| prLPT2-A | Hordeum vulgare | X69793 | Pol II promoter | monocot | 56 |
| prLPT2-B | Hordeum vulgare | X69793 | Pol II promoter | monocot | 57 |
| prZmFluory2 | Zea mays | ZEAMMB73_Zm00001d049243 | Pol II promoter | monocot | 58 |
| pZMU6-C1_Short | Zea mays | maize | Pol III promoter | monocot | 59 |
| pOsU6.1 | Oryza sativa | rice | Pol III promoter | monocot | 60 |
| pOsU6.2 | Oryza sativa | rice | Pol III promoter | monocot | 61 |
| pOsU6.1_short | Oryza sativa | rice | Pol III promoter | monocot | 62 |
| pOsU6.2_short | Oryza sativa | rice | Pol III promoter | monocot | 63 |
| OsU6 | Oryza sativa | | Pol III promoter | monocot | 64 |
| TaU3 | wheat | | Pol III promoter | monocot | 65 |
| prM24 | Mirabilis mosaic virus | AF454635.1 | Pol II promoter | dicot or monocot | 66 |
| pr35S | Cauliflower mosaic virus | V00140.1 | Pol II promoter | dicot or monocot | 67 |
| prFMV | figwort mosaic virus | X06166.1 | Pol II promoter | dicot or monocot | 68 |

TABLE 3-continued

| Designation | Source | Source ID | Application | Type | SEQ ID NO: |
|---|---|---|---|---|---|
| prFMV 34S-1/2x | figwort mosaic virus | X16673.1 | Pol II promoter | dicot or monocot | 69 |
| prNOS | Agrobacterium | | Pol II promoter | dicot or monocot | 70 |
| prOCS | Agrobacterium | | Pol II promoter | dicot or monocot | 71 |
| tAtUbi10 | Arabidopsis thaliana | AT4G05320.2 | Pol II terminator | dicot | 72 |
| tAtADH | Arabidopsis thaliana | AY536888 | Pol II terminator | dicot | 73 |
| tNtExt | Nicotiana tabacum | D13951 | Pol II terminator | dicot | 74 |
| tHSP 18.2 | Arabidopsis thaliana | GeneID:836093 | Pol II terminator | dicot | 75 |
| tGmUbi1 | Glycine max | Glyma10g251900 | Pol II terminator | dicot | 76 |
| tSlUbi10 | Solanum lycopersicum | LOC101258282 | Pol II terminator | dicot | 77 |
| tWpUbi10 | White pear | LOC103948134 | Pol II terminator | dicot | 78 |
| tBvUbi10 | Sugar beet | LOC104907074 | Pol II terminator | dicot | 79 |
| tRsUbi10 | Radish | LOC108826774 | Pol II terminator | dicot | 80 |
| tIlUbi10 | Japanese morning glory | LOC109190585 | Pol II terminator | dicot | 81 |
| tCuUbi10 | Cucurbita | LOC111802502 | Pol II terminator | dicot | 82 |
| tHaUBI | Helianthus annuus | OTG28215 | Pol II terminator | dicot | 83 |
| tpea E9 | Pisum sativum | X00806 | Pol II terminator | dicot | 84 |
| tpea 3A | Pisum sativum | X04333.1 | Pol II terminator | dicot | 85 |
| tHaUbil | Helianthus annuus | X57005.1 | Pol II terminator | dicot | 86 |
| tZmKN1 | Zea mays | AY312169.1 | Pol II terminator | monocot | 87 |
| tOsAct1 | Oryza sativa | CP018159 | Pol II terminator | monocot | 88 |
| tOsUbi2 | Oryza sativa | LOC_0s02g06640 | Pol II terminator | monocot | 89 |
| tOsUbi1 | Oryza sativa | LOC_0s06g46770 | Pol II terminator | monocot | 90 |
| tAtaUbi1 | Aegilops tauschii | LOC109747268 | Pol II terminator | monocot | 91 |
| tPhUbi1 | Panicum hallii | LOC112888620 | Pol II terminator | monocot | 92 |
| tZmADP1 | Zea mays | LOC542430 | Pol II terminator | monocot | 93 |
| tZmEF1alpha | Zea mays | LOC542581 | Pol II terminator | monocot | 94 |
| tZmADP2 | Zea mays | LOC542584 | Pol II terminator | monocot | 95 |
| tZmUbi1 | Zea mays | S94464 | Pol II terminator | monocot | 96 |
| tLPT2 | Hordeum vulgare | X69793 | Pol II terminator | monocot | 97 |
| tZmFluory2 | Zea mays | ZEAMMB73_Zm00001d049243 | Pol II terminator | monocot | 98 |
| t35S | Cauliflower mosaic virus | V00140.1 | Pol II terminator | dicot or monocot | 99 |
| tNOS | Agrobacterium | | Pol II terminator | dicot or monocot | 100 |
| TMV translational enhancer | tobacco mosaic virus | | enhancer | dicot | 101 |
| FMV 34S double enhancer | figwort mosaic virus | | enhancer | dicot or monocot | 102 |
| FMV34S/CaMV35S enhancer | figwort and cauliflower mosaic virus/synthetic | | enhancer | dicot or monocot | 103 |
| iGmIDH1 | Glycine max | Gene ID: 606295 | intron | dicot | 104 |
| iZmPEPC | Zea mays | LOC542372 | intron | monocot | 105 |
| MALAT1 | mouse | | 3' end (triple helix) | dicot or monocot | 106 |

Example 6

This example illustrates non-limiting embodiments of Cas12a nucleases and their corresponding tracrRNA sequences. Table 4 provides the protein sequences of several Cas12a nucleases and the RNA sequence of each nuclease's associated tracrRNA. Table 4 further identifies for each tracrRNA one or more native restriction endonuclease cleavage sites that are suitable, e.g., for insertion of a sequence coding for a functional RNA moiety.

TABLE 4

| Species | Protein Accession Number | Protein SEQ ID NO: | tracrRNA SEQ ID NO: | Restriction sites within DNA between tracrRNA and CRISPR array | Restriction sites within DNA encoding the tracrRNA | Putative PAM |
|---|---|---|---|---|---|---|
| Uncultured Clostridium sp. isolate 2789STDY5608795 | SCH45297.1 | 107 | 139 | SgeI, HpyCH4III, MfeI, SspI | DraI | 5' TTTV |
| Uncultured bacterium (gcode 4) ACD_3C00058, whole genome shotgun sequence | EKE28449.1 | 108 | 140 | AvrII | HphI, HpyAV, | 5' TTTV |
| Thiomicrospira sp. XS5 ZB100000 | WP_068647445.1 | 109 | 141 | AjuI, BceAI, HpyCH4III | BseMII, BspHI | 5' TTTV |
| Flavobacterium branchiophilum FL-15 | WP_014085038.1 | 110 | 142 | BtsI, TspRI, FspEI | HindIII, DraI | 5' TTTV |
| Moraxella bovoculi strain 57922 | AKG14689.1 | 111 | 143 | BslI | DraI, ApoI | 5' TTV |
| Candidatus Roizmanbacteria bacterium GW2011_GWA2_37_7 US54_C0016 | KKQ38174.1 | 112 | 144 | DdeI, HgaI, Hpy188I, DrdI, | BbsI, MboII | 5' TTTV |
| Pseudobutyrivibrio xylanivorans | SCZ76797.1 | 113 | 145 | TspRI, FspEI | TspDTI, SmoI, BsuI, BpuEI | 5' TTTV |
| Prevotella bryantii B14 | SER03894.1 | 114 | 146 | TatI, ScaI | EcoRV, PsiI, | 5' TTTV |
| Smithella sp. SCADC | KFO67988.1 | 115 | 147 | PspGI, BstNI, | HhaI | 5' TTTV |
| Smithella sp. SCADC | KFO67988.1 | 115 | 148 | EcoRII | CfoI | 5' TTTV |
| Bacteroidetes bacterium GWF2_33_38 | OFY19591.1 | 116 | 149 | CviQI | DraI | 5' TTTV |
| Candidatus Peribacteria bacterium RIFCSPLOWO2 | OGJ66851.1 | 117 | 150 | AlwNI, EarI, AcuI | EcoRV, NdeI | 5' TTTV |
| Nitrospinae bacterium RIFCSPLOWO2 | OGW03971.1 | 118 | 151 | BstAPI, BsmAI | HaeII | 5' TTTV |
| Candidatus Ryanbacteria bacterium RIFCSPHIGHO2 | OGZ45678.1 | 119 | 152 | BccI, MmeI, Hpy188I | FauI, HpyAV, BseNI | 5' TTTV |
| Candidatus Wildermuthbacteria bacterium RIFCSPHIGHO2 | OHA63117.1 | 120 | 153 | MmeI, BglII, Hpy188I | PsiI, Eco57I, | 5' TTTV |
| Firmicutes bacterium CAG_194_44_15 | OLA30477.1 | 121 | 154 | BsgI | MaeII | 5' TTTV |
| Candidatus Gottesmanbacteria bacterium CG1_02_37_22 | OIO15737.1 | 122 | 155 | FauI, BbvI | PsiI, SspI, BfrI | 5' TTTV |
| Candidatus Gracilibacteria bacterium CG1_02_38_174 | OIO75780.1 | 123 | 156 | BaeI | BseMII, BbsI | 5' TTTV |
| Butyrivibrio fibrisolvens MD2001 | WP_027216152.1 | 124 | 157 | BceAI | PsiI, HphI | 5' TTTV |
| Sneathia amnii strain SN35 | WP_084710347.1 | 125 | 158 | BccI, BspPI | SspI, DraI | 5' TTTV |
| Coprococcus eutactus strain 2789STDY5608843 | WP_082431329.1 | 126 | 159 | PsiI, ApaLI | TspDTI, MaeIII | 5' TTTV |
| Lachnospira pectinoschiza strain 2789STDY5834886 | WP_055306762.1 | 127 | 160 | MseI | BccI, SspI, DraI | 5' TTTV |

TABLE 4-continued

| Species | Protein Accession Number | Protein SEQ ID NO: | tracrRNA SEQ ID NO: | Restriction sites within DNA between tracrRNA and CRISPR array | Restriction sites within DNA encoding the tracrRNA | Putative PAM |
|---|---|---|---|---|---|---|
| Bacteroidetes oral taxon 274 str. F0058 | WP_009217 842.1 | 128 | 161 | BsrGI, AseI, BsrDI | TspDTI, ApoI | 5' TTN |
| Arcobacter butzleri L348 isolate CHRB 125 | WP_052943 011.1 | 129 | 162 | MseI | SspI, HindIII | 5' TTTV |
| Bacteroidales bacterium KA00251 | WP_066040 075.1 | 130 | 163 | BccI, BstXI | EarI | 5' TTTV |
| Acidaminococcus massiliensis strain Marseille-P2828 | WP_075579 848.1 | 131 | 164 | BccI, Bpu10I | PleI, MlyI | 5' TTTV |
| Helcococcus kunzii | WP_005398 606.1 | 132 | 165 | AfeI | EcoRV, NsiI, BsrDI | 5'-YYN |
| Agathobacter rectalis strain 2789STDY5834884 | CUO57667.1 | 133 | 166 | ApoI | PsiI | 5' TTN |
| Acidaminococcus sp. BV3L6 | WP_021736 722.1 | 134 | 167 | KasI, NdeI | MmeI, Bpu10I, BspMI | 5' TTTV |
| Lachnospiraceae bacterium ND2006 | WP_051666 128.1 | 135 | 168 | MmeI, HphI | PsiI, AanI | 5' TTTV |
| Francisella tularensis subsp. novicida U112 | ABK90267.1 | 136 | 169 | | DraI | 5' TTTV |
| Omnitrophica WOR_2 bacterium GWF2_38_59 | OGX23684.1 | 137 | 170 | ApoI | LweI | 5' TTTV |
| Candidatus Roizmanbacteria bacterium GW2011_GWA2_37_7 US54_C0016 | KKQ38176.1 | 138 | 171 | CseI | BbsI | 5' TTTV |

Various DNA expression systems disclosed herein are useful for the expression of these Cas12a tracrRNA sequences. Embodiments include a DNA expression system including (a) DNA sequence for a first promoter; and (b) operably linked and heterologous to the first promoter a DNA sequence encoding a first RNA molecule including a Cas12a tracrRNA and including a restriction endonuclease cleavage site (native or engineered) that is suitable for insertion of a sequence coding for a functional RNA moiety. The functional RNA moiety is characterized by one or more functions. Embodiments of the RNA moiety include RNA sequences for annealing to one or more polynucleotides, RNA sequences that provide structures for binding to other molecules (including proteins or small molecule ligands) or that are catalytically active, or RNA sequences that serve as directly or indirectly detectable labels. Thus, non-limiting embodiments include a DNA expression system including (a) DNA sequence for a first promoter; and (b) operably linked and heterologous to the first promoter a DNA sequence encoding a first RNA molecule including a Cas12a tracrRNA and including a restriction endonuclease cleavage site (native or engineered) that is suitable for insertion of a sequence coding for a functional RNA moiety, wherein the Cas12a tracrRNA has an RNA sequence selected from SEQ ID NOs:1, 3, 6, 139-146, and 149-169; in some embodiments, the first promoter includes a DNA sequence selected from SEQ ID NOs:16-71. In other embodiments, the Cas12a tracrRNA is selected from the Cas12a tracrRNA sequences disclosed in U.S. Pat. No. 9,790,490 (incorporated herein by reference).

In other embodiments, the DNA expression system includes: (a) DNA sequence for a first promoter; (b) operably linked and heterologous to the first promoter a DNA sequence encoding a first RNA molecule including a Cas12a tracrRNA and including a restriction endonuclease cleavage site (native or engineered) that is suitable for insertion of a sequence coding for a functional RNA moiety; (c) optionally, a DNA sequence for a second promoter; (d) operably linked and heterologous to the first promoter or the second promoter, a DNA encoding a Cas12a crRNA that includes a 3' extension capable of hybridizing with a segment of the first RNA molecule; and (e) optionally, a terminator. In non-limiting embodiments, the Cas12a tracrRNA has an RNA sequence selected from the group consisting of SEQ ID NOs:1, 3, 6, 139-146, and 149-169; in some embodiments, the first promoter includes a DNA sequence selected from the group consisting of SEQ ID NOs:16-71; in some embodiments, the optional second promoter includes a DNA sequence selected from the group consisting of SEQ ID NOs:16-71; in some embodiments, the optional terminator includes a DNA sequence selected from the group consisting of SEQ ID NOs:72-100. In embodiments, the first promoter and the DNA encoding the first RNA molecule, and the DNA encoding a Cas12a crRNA that includes a 3' extension are contained in a single construct, and in other embodiments, the first promoter and the DNA encoding the first RNA molecule are contained in a first construct, and the second promoter and the DNA encoding a Cas12a crRNA that includes a 3' extension are contained in a second construct. Where the DNA expression system is provided in a first construct and a second construct, these can be provided in a single vector or in separate vectors. In some embodiments wherein the DNA expression system includes DNA encoding a Cas12a crRNA, the first promoter drives expression of both the DNA encoding the first RNA molecule and the DNA encoding the Cas12a crRNA. In some embodiments, the Cas12a tracrRNA further includes a 5' extension. In many embodiments of the DNA expression system, the Cas12a crRNA is capable of complexing with a Cas12a nuclease to form a Cas12a ribonucleoprotein complex.

Further embodiments of this disclosure include a DNA expression system including: (a) DNA sequence for a first promoter; and (b) operably linked and heterologous to the first promoter, a DNA sequence encoding a functional RNA molecule including a Cas12a tracrRNA and a functional RNA moiety. The functional RNA moiety is characterized by one or more functions. Embodiments of the RNA moiety include RNA sequences for annealing to one or more polynucleotides, RNA sequences that provide structures for binding to other molecules (including proteins or small molecule ligands) or that are catalytically active, or RNA sequences that serve as directly or indirectly detectable labels. In embodiments, the DNA expression system further includes: (c) optionally, a DNA sequence for a second promoter; (d) operably linked and heterologous to the first promoter or the second promoter, a DNA encoding a Cas12a crRNA that includes a 3' extension capable of hybridizing with a segment of the functional RNA molecule; and (e) optionally, a terminator. In embodiments, the functional RNA molecule includes a Cas12a tracrRNA having an RNA sequence selected from the group consisting of SEQ ID NOs:1, 3, 6, 139-146, and 149-169; in some embodiments, the first promoter includes a DNA sequence selected from the group consisting of SEQ ID NOs:16-71; in some embodiments, the optional second promoter includes a DNA sequence selected from the group consisting of SEQ ID NOs:16-71; in some embodiments, the optional terminator includes a DNA sequence selected from the group consisting of SEQ ID NOs:72-100. In embodiments wherein the DNA expression system includes the DNA encoding the Cas12a crRNA, the DNA expression system can be provided in a single construct (e.g., where the first promoter drives expression of both the DNA encoding the functional RNA molecule and the DNA encoding the Cas12a crRNA). In embodiments wherein the DNA expression system includes the second promoter, the second promoter can be operably linked to the DNA encoding the crRNA (e.g., in a second construct). In embodiments where the DNA expression system is provided in two constructs, these can be in a single vector or in separate vectors. In embodiments, the Cas12a tracrRNA further includes a 5' extension. In many embodiments of the DNA expression system, the Cas12a crRNA is capable of complexing with a Cas12a nuclease to form a Cas12a ribonucleoprotein complex.

The various embodiments of the DNA expression systems disclosed herein are useful for expression of a Cas12a tracrRNA that is: (1) contained in a first RNA molecule including a Cas12a tracrRNA and including a restriction endonuclease cleavage site (native or engineered) that is suitable for insertion of a sequence coding for a functional RNA moiety, or (2) contained in a functional RNA molecule including a Cas12a tracrRNA and a functional RNA moiety. In embodiments, a Cas12a nuclease is associated or complexed with a Cas12a crRNA that is previously, simultaneously, or subsequently associated with, complexed with, or tethered to the Cas12a tracrRNA that is (1) contained in a first RNA molecule including a Cas12a tracrRNA and including a restriction endonuclease cleavage site (native or engineered) that is suitable for insertion of a sequence coding for a functional RNA moiety, or (2) contained in a functional RNA molecule including a Cas12a tracrRNA and a functional RNA moiety, thus forming a Cas12a ribonucleoprotein complex. In embodiments, the resulting Cas12a ribonucleoprotein complex contains (1) the Cas12a nuclease complexed with the first RNA molecule including a Cas12a tracrRNA and including a restriction endonuclease cleavage site (native or engineered) that is suitable for insertion of a sequence coding for a functional RNA moiety, or (2) the Cas12a nuclease complexed with the functional RNA molecule including a Cas12a tracrRNA and a functional RNA moiety. In embodiments, the Cas12a nuclease is one having a naturally occurring sequence (e.g., a native sequence of a Cas12a nuclease such as, but not limited to, LbCas12a, AsCas12a, FnCas12a, and an ObCsm1); in other embodiments, the Cas12a nuclease includes a modification, such as an amino acid sequence modification (e.g., the point-mutations provided in Table 5) and/or a chemical modification such as (a) a localization or signal peptide (e.g., a nuclear localization signal (NLS), a chloroplast or plastid transit peptide (CTP), or a mitochondrial targeting peptide (MTP)); (b) a detectable label (e.g., a fluorescent dye); (c) a cell-penetrating peptide; (d) an endosomal escape peptide; and (e) an affinity tag. In embodiments, the Cas12a nuclease is one selected from the Cas12a ("Cpf1") nucleases, Cpf1 orthologues, and Cpf1 variants (including the codon-optimized variants) disclosed in U.S. Pat. No. 9,790,490; the Cas12a ("Cpf1") nuclease sequences disclosed in U.S. Patent Application Publication 2018/0282713 (see, e.g., FIG. 3 and Example 5); and Cas12a ("Cpf1") nuclease sequences disclosed in U.S. Pat. No. 9,896,696; all of these cited patents and patent application publications are incorporated herein by reference. In specific embodiments, the Cas12a nuclease is a Cas12a ("Cpf1") nuclease identified from *Francisella novicida* U112 (FnCas12a or "FnCpf1"), from *Acidaminococcus* sp. BV3L6 (AsCas12a or "AsCpf1"), or from Lachnospiraceae bacterium ND2006 (LbCas12a or "LbCpf1"), or is an orthologue thereof, such as an orthologue having at least 50% sequence identity to FnCas12a ("FnCpf1"); see, e.g., the FnCpf1 nuclease contained in the FnCpf1 locus having SEQ ID NO:211 in U.S. Pat. No. 9,790,490, specifically incorporated herein by reference. In other specific embodiments, the Cas12a nuclease is a Cas12a nuclease having Cas12a nuclease activity and having at least 80%, at least 85%, at least 90%, or at least 95% sequence identity with a sequence selected from the group consisting of SEQ ID NOs:11, 107-114, 116-136, and 172. Table 5 provides non-limiting examples of Cas12a nucleases and sequence variants thereof that are useful with the DNA expression systems and engineered systems provided in this disclosure. Most of the point mutations (those not marked with an * or **) provided in Table 5 are designed to increase the efficiency or efficacy of gene editing by the nuclease (in comparison to the unaltered native nuclease). Increased efficiency or efficacy of gene editing includes but is not limited to: altered translation, folding, and/or stability of the Cas12a nuclease or ribonucleoprotein; altered affinity and/or specificity of target binding; altered Cas12a nuclease efficiency on target and/or non-target strands; altered PAM recognition specificity; and altered DNA repair or modification outcomes (e.g., indel rates). The Ca12a nuclease sequence variants include: (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. The systems and compositions including a tracrRNA and methods of use thereof that are disclosed herein can also be employed with related Cas nucleases, including Csm nucleases, e.g., ObCsm1 (GenBank accession number OGX23684), SmCsm1 (GenBank accession number KF067988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

TABLE 5

| LbCpf1 (WP_051666128) (SEQ ID NO: 135) | AsCpf1 (WP_021736722) (SEQ ID NO: 134) | FnCpf1 (WP_003034647) (SEQ ID NO: 172) | ObCsm1 (OGX23684) (SEQ ID NO: 137) |
|---|---|---|---|
| G309P | L320P | I339P | — |
| Y312F | wt | L342F | — |
| M474I | wt | wt | — |
| D523N | wt | wt | K382N |
| Q531K | wt | Q588K | Q393K |
| C930A | V980A | wt | S925A |
| D937N | Q987N | wt | E933N |
| V954F/Q | T1004F/Q | F1017Q | K943F/Q |
| M975L | wt | wt | K972L |
| A984E | K1035E | K1047E | — |
| I994L | wt | wt | — |
| T1006K | T1057K | wt | wt |
| I1014V | wt | wt | wt |
| V1055N/D | D1107N | N1118D | — |
| L1065F/Y | F1117Y | F1128Y | — |
| Y1180F | wt | wt | wt |
| V1209G | wt | wt | K1064G |
| I1229L | N1291L | wt | — |
| V801I* | wt | L867I* | P670I* |
| Y802I* | wt | wt | N671I* |
| D850A** | D908A** | D917A** | D727A** |
| E943A** | E993A** | E1006A** | E939A** |
| D1198A** | D1263A** | D1255A** | D1053A** |

"wt" = wild type
*mutation expected to increase stabilization of nuclease/crRNA association
**mutation expected to decrease or eliminate endonuclease activity Example 7

This example illustrates compositions and systems including a Cas12a nuclease, a Cas12a crRNA that comprises a 3' extension, and a Cas12a tracrRNA. More specifically, this illustrates an engineered system including a Cas12a crRNA that includes an artificial 3' ribonucleotide extension including a detectable label (a fluorophore) for in vivo identification of cells containing the Cas12a crRNA. The Cas12a crRNA is synthesized for delivery to plant cells as a ribonucleoprotein complex with a Cas12a nuclease, and (2) cloned into a plant expression vector system for co-expression with Cas12a in vivo.

A ZmLc crRNA was designed with the nucleotide sequence of SEQ ID NO:179 including the direct repeat sequence of SEQ ID NO:180 and the spacer sequence of SEQ ID NO:181 for targeting the promoter of the Zea mays Lc gene (GRMZM5G822829); this ZmLc crRNA sequence was modified to contain 11 nucleotides adjacent to and 3' to the spacer region, yielding an engineered 3'-extended ZmLc crRNA. The 3'-extended crRNA sequence is encoded into a dsDNA template downstream of a T7 polymerase binding site and initiator for in vitro transcription using the HiScribe™ T7 High Yield RNA Synthesis Kit (catalogue number E2050S, New England BioLabs, Ipswich, Mass.). Alternatively, the 3'-extended crRNA is chemically synthesized by IDT (Coralville, Iowa), optionally containing chemical modifications or non-natural components. The 3'-extended crRNA is further modified to contain a fluorescent or fluorophore-conjugated nucleotide or nucleotide analog, such as cytidine-5'-phosphate-3'-(6-aminohexyl)phosphate conjugated to Cy5 (NU-1706-CYS, Jena Bioscience, Jena, Germany), at its 3' end using T4 RNA ligase. Alternatively, the 3'-extended crRNA containing one or multiple fluorescent components within or following the polynucleotide extension (e.g., 3' ATTOTM 590 (NHS Ester)) is chemically synthesized by IDT (Coralville, Iowa).

Fluorescent Cas12a ribonucleoprotein complexes (RNPs) are generated with the fluorophore-labelled 3'-extended crRNA, a modified Cas12a nuclease (SEQ ID NO:182), and a Cas12 tracrRNA (SEQ ID NO:3) following the protocols described below in Example 8, incubated with nanoparticles (e.g., 0.6 micrometer gold microcarriers, catalogue number 1652262, BioRad Laboratories, Inc., Hercules, Calif.), and biolistically delivered to meristematic tissue using standard protocols similar to or adapted from Liang et al. (2017) *Nature Communications*, 8:14261, doi:10.1038/ncomms14261. Meristems are further visualized under a fluorescent microscope several hours following delivery to identify and isolate transformed meristem from non-transformed cells or tissue. Optionally, the transformed meristem is grown into callus or plants.

Example 8

This example illustrates compositions and engineered genome editing systems including a Cas12a nuclease, a Cas12acrRNA, and a Cas12a tracrRNA. In addition to the usefulness of an RNA molecule including a Cas12a tracrRNA for, e.g., tethering a donor polynucleotide to a Cas12a nuclease/crRNA ribonucleoprotein (RNP) complex, it was discovered that addition of a molar excess of tracrRNA to an editing system including a Cas12a nuclease/crRNA RNP unexpectedly resulted in an increase of the overall efficiency of genome editing at a given concentration of RNP.

Protoplasts were prepared from leaves of 2-week old maize (*Zea mays*, variety B104) plants, following a protocol previously described (see Example 1 in U.S. patent application Ser. No. 16/480,992 (filed on 25 Jul. 2019 as the national phase application based on PCT/US2018/015793 filed on 29 Jan. 2018 and published as WO2018/140899), incorporated herein by reference.

Reagents were prepared as follows. The modified Cas12a nuclease employed in this experiment had the amino acid sequence of SEQ ID NO:182; included in this sequence are (a) the native Cas12a nuclease sequence (amino acids positions 19-1246 of SEQ ID NO:182), (b) remains of a linker sequence (amino acid positions 1-7 of SEQ ID NO:182), (c) two linker sequences (amino acid positions 15-18 and 1247-1250 of SEQ ID NO:182), (d) an N-terminus nuclear localization signal (NLS) sequence (amino acid positions 8-14 of SEQ ID NO:182), and (e) a C-terminus linker/NLS (amino acid positions 1247-1259 of SEQ ID NO:182). The Cas12a nuclease (5.85 milligrams/milliliter in aqueous buffer containing 25 millimolar Tris-HCl, 300 millimolar NaCl, 0.1 millimolar EDTA, pH 7.4) was diluted with dilution buffer (25 millimolar Tris-HCl, 300 millimolar NaCl, 0.1 millimolar EDTA, 40% glycerol, pH 7.4) to a final concentration of 1.25 milligrams/milliliter nuclease and 31.5% glycerol. A 30 micromolar solution of Cas12a tracrRNA with the nucleotide sequence of SEQ ID NO:3 was prepared in reaction buffer (40 mM HEPES, 200 mM NaCl, 10 mM MgCl2, and 0.2 mM EDTA, pH 6.5). Additional solutions of 40% polyethylene glycol 4000 (PEG), maize washing solution (0.6 molar mannitol, 4 millimolar MES pH 5.7, and 20 millimolar KCl), and PIM containing 50 millimolar $CaCl_2$) (previously described in Table 25, U.S. patent application Ser. No. 16/480,992, filed on 25 Jul. 2019 as the national phase application based on PCT/US2018/015793 filed on 29 Jan. 2018 and published as WO2018/140899, incorporated herein by reference) were prepared. All solutions were aliquoted into 96-well deep plates and sealed until needed for use in a Biomek $FX^P$ automated liquid handler (Beckman Coulter Life Sciences, Indianapolis, Ind.).

Ribonucleoproteins (RNPs) were prepared with a Cas12a nuclease having the sequence of SEQ ID NO:182 and an ZmLc crRNA with the nucleotide sequence of SEQ ID NO:179 including the direct repeat sequence of SEQ ID NO:180 and the spacer sequence of SEQ ID NO:181 for targeting the promoter of the Zea mays Lc gene (GRMZM5G822829). Following a preferred protocol, the ZmLc crRNA was resuspended in reaction buffer to a concentration of 25 micromolar; 1680 microliters of the diluted ZmLc crRNA was mixed with 560 microliters of the Cas12a nuclease solution and incubated 20 minutes at room temperature. To this mixture 1400 microliters of the Cas12a tracrRNA was added and mixed; this "Cas12a nuclease/ZmLc crRNA/tracrRNA editing system" was apportioned in 225 microliter aliquots into 8-strip PCR tubes.

Four mixtures were prepared for use as diluents.

"Diluent 1" (Cas12a nuclease/GmSHAT1-5 crRNA/tracrRNA) was prepared by mixing 420 microliters of 25 micromolar GmSHAT1-5 crRNA (serving as a non-specific Cas12a crRNA, this was designed to target Glycine max SHAT1-5, see www[dot]uniprot[dot]org/uniprot/W8E7P1) in reaction buffer (40 mM HEPES, 200 mM NaCl, 10 mM MgCl2, and 0.2 mM EDTA, pH 6.5) and 140 microliters of the Cas12a nuclease solution, incubating for 20 minutes at room temperature, and then adding 350 microliters of the Cas12a tracrRNA solution. This was apportioned in 225 microliter aliquots into 8-strip PCR tubes.

"Diluent 2" (Cas12a nuclease/GmSHAT1-5 crRNA) was prepared by mixing 420 microliters of 25 micromolar GmSHAT5-1 crRNA in reaction buffer (40 mM HEPES, 200 mM NaCl, 10 mM MgCl2, and 0.2 mM EDTA, pH 6.5) and 140 microliters of the Cas12a nuclease solution, incubating for 20 minutes at room temperature, and then adding 350 microliters of the reaction buffer (40 mM HEPES, 200 mM NaCl, 10 mM MgCl2, and 0.2 mM EDTA, pH 6.5). This was apportioned in 225 microliter aliquots into 8-strip PCR tubes.

"Diluent 3" (Cas12a tracr) was prepared by mixing 350 microliters of the Cas12a tracrRNA solution with 560 microliters of reaction buffer (40 mM HEPES, 200 mM NaCl, 10 mM MgCl2, and 0.2 mM EDTA, pH 6.5). This was apportioned in 225 microliter aliquots into 9-strip PCR tubes.

"Diluent 4" consisted of reaction buffer (40 mM HEPES, 200 mM NaCl, 10 mM MgCl2, and 0.2 mM EDTA, pH 6.5) only. This was apportioned in 225 microliter aliquots into 9-strip PCR tubes.

Transfections of the maize protoplasts were carried out in the Biomek $FX^P$ automated liquid handler. A 16-microliter aliquot of the protoplast suspension was added to each well of a U-Bottom 96 well plate pre-coated with 5% Calf Serum with lid removed. A titration series of the Cas12a nuclease/ZmLc crRNA/tracrRNA editing system was made across twelve wells of a master titration plate using the four different diluents; this was stored on the cold block until transfection. The titrations resulted in a dilution series of the Cas12a nuclease/ZmLc crRNA/tracrRNA editing system, as shown in Table 6, which provides the resulting ratios between the additional Cas12a tracrRNA (provided in the diluent) to Cas12a nuclease (provided in the Cas12a nuclease/ZmLc crRNA/tracrRNA editing system).

TABLE 6

| Cas12a nuclease (pmol) | Cas12a tracrRNA (pmol) | Cas12a tracrRNA: Cas12a nuclease ratio |
| --- | --- | --- |
| 0.00 | 193.70 | — |
| 2.13 | 193.70 | 90.81 |
| 4.06 | 193.70 | 47.71 |
| 5.99 | 193.70 | 32.36 |
| 7.88 | 193.70 | 24.59 |
| 9.80 | 193.70 | 19.76 |
| 11.73 | 193.70 | 16.51 |
| 13.66 | 193.70 | 14.18 |
| 15.58 | 193.70 | 12.43 |
| 17.48 | 193.70 | 11.08 |
| 19.40 | 193.70 | 9.98 |
| 21.33 | 193.70 | 9.08 |

Transfections were performed in triplicate. For transfection, 16 microliters of a given titrated dilution was added to each protoplast-containing well, and mixed; 32 microliters of 40% PEG solution are added and mixed, and the plate incubated 5 minutes at room temperature. Sequential additions of maize washing buffer were dispensed across the plate and mixed, and the plate was removed from the automated liquid handler, covered, and centrifuged. The plate was returned to the automated liquid handler for removal of the majority of the supernatant, and the protoplasts resuspended in 120 microliters PIM containing 50 millimolar $CaCl_2$). The plate was covered and incubated at 27 degrees Celsius in the dark for 48 hours before harvesting. Genomic DNA was isolated from the protoplasts, quantified using QuantiFluor (Promega Corporation, Madison, Wis.), and subjected to PCR amplification followed by amplicon sequencing to detect indel edits.

Figure 12:
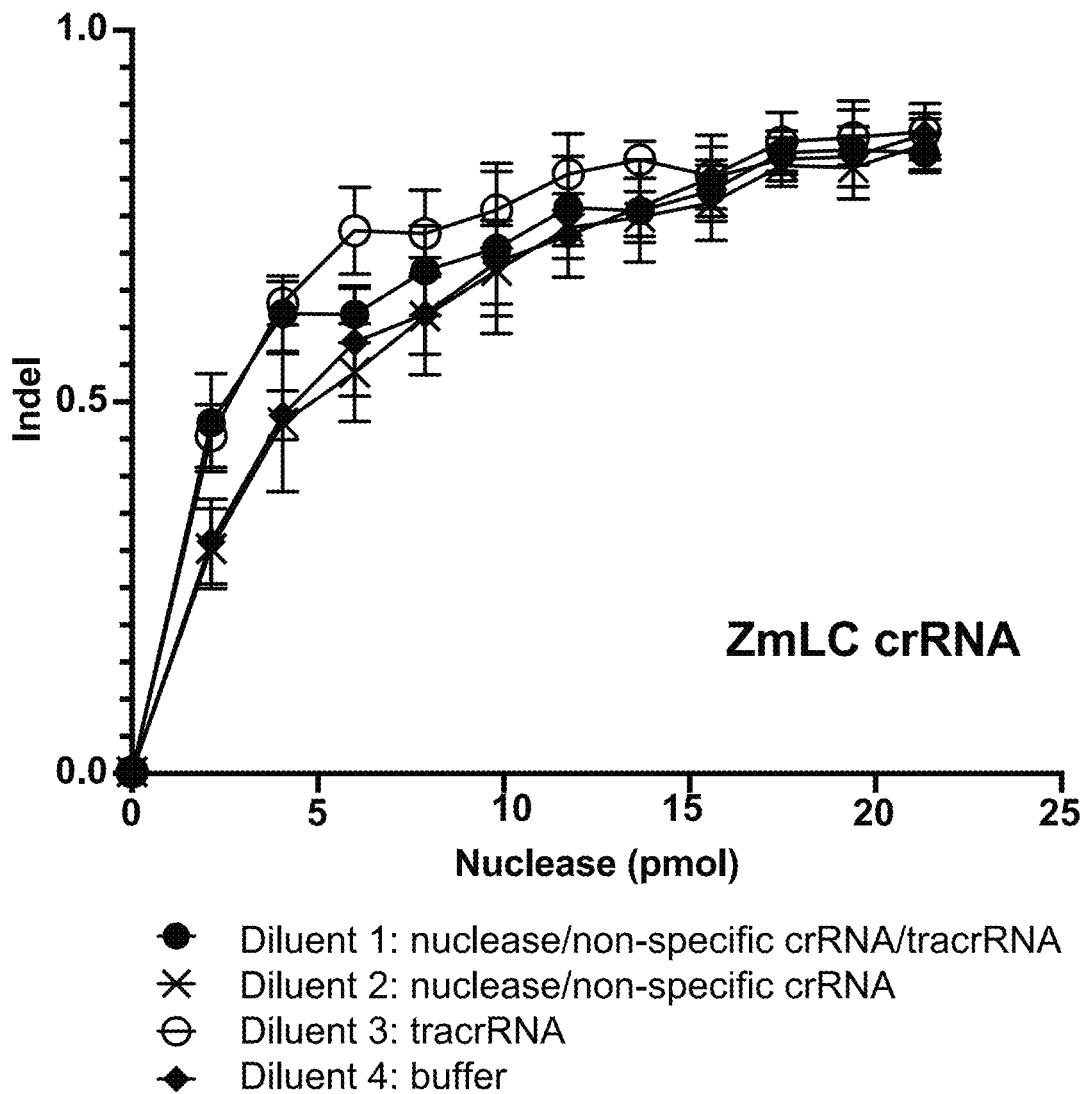
FIG. 12 depicts the results of the experiment described in Example 8 using the GD-30 crRNA. The data are provided as the fraction of edited protoplasts (the number of protoplasts containing an insertion/deletion (indel) at the predicted cleavage site, divided by the total number of protoplasts treated) versus the amount in pmoles of Cas12a nuclease used.

Results, given as the fraction of protoplasts containing an indel at the predicted cleavage site versus the amount of Cas12a nuclease used, are illustrated in FIG. 12. The data indicate that dilutions made with Diluent 2 (Cas12a nuclease/GmSHAT1-5 crRNA in reaction buffer) had no significant effect when compared to the control dilution with Diluent 4 (reaction buffer only). In contrast, dilutions made with Diluent 3 (Cas12a tracrRNA in reaction buffer) markedly increased the editing efficiency at the majority of the nuclease amounts tested; the additional Cas12a tracrRNA appeared to decrease the amount of Cas12a nuclease required to achieve 75% editing to 5.99 pmol, i.e., about a third of the Cas12a nuclease amount needed to achieve the same level of editing efficiency in the control dilution (15.58 pmol). Dilutions made with Diluent 1 (Cas12a nuclease/GmSHAT1-5 crRNA/tracrRNA in reaction buffer) also appeared to slightly increase the editing efficiency of a given amount of Cas12a nuclease; since the difference between Diluent 1 and Diluent 2 was the presence of the Cas12a tracrRNA, it is likely that the increased editing efficiency was due to the Cas12a tracrRNA.

Example 9

This example illustrates compositions and engineered genome editing systems including a Cas12a nuclease, a Cas12acrRNA, and a Cas12a tracrRNA. More specifically, this example illustrates additional experiments that confirmed that addition of a molar excess of tracrRNA to an editing system including a Cas12a nuclease/crRNA RNP unexpectedly resulted in an increase of the overall efficiency of genome editing at a given concentration of RNP.

To further investigate the effects of including a molar excess of Cas12a tracrRNA in a Cas12a nuclease/crRNA/tracrRNA editing system, additional experiments were carried out using different Cas12a crRNAs.

Protoplasts were prepared from etiolated middle leaves of 12-day old maize (*Zea mays*, variety B104) plants, following a protocol previously described (see Example 1 in U.S. patent application Ser. No. 16/480,992 (filed on 25 Jul. 2019 as the national phase application based on PCT/US2018/015793 filed on 29 Jan. 2018 and published as WO2018/140899), incorporated herein by reference.

One experiment tested the effects of various diluents on Cas12a RNPs including a Cas12a nuclease and a "high-performing" Cas12a crRNA, GD-48, which routinely produced indel edits at a frequency between 80-90%. Another experiment tested the effects of various diluents on Cas12a RNPs including a Cas12a nuclease and a "low-performing" Cas12a crRNA, GD-14, which routinely produced indel edits at frequencies below 25%. The nucleotide sequence of both Cas12a crRNAs included, from 5' to 3', a direct repeat sequence (SEQ ID NO:180) and a spacer sequence having perfect complementarity to a specific target sequence in the maize B104 genome.

Experimental procedures were similar to those described in Example 8. The Cas12a nuclease (SEQ ID NO:182) (5.85 milligrams/milliliter in aqueous buffer containing 25 millimolar Tris-HCl, 300 millimolar NaCl, 0.1 millimolar EDTA, pH 7.4) was diluted with dilution buffer (25 millimolar Tris-HCl, 300 millimolar NaCl, 0.1 millimolar EDTA, 40% glycerol, pH 7.4) to a final concentration of 1.25 milligrams/milliliter nuclease and 31.5% glycerol. A 30 micromolar solution of Cas12a tracrRNA (SEQ ID NO:3) was prepared in reaction buffer (40 mM HEPES, 200 mM NaCl, 10 mM MgCl2, and 0.2 mM EDTA, pH 6.5). A 1.25 milligram/milliliter solution of bovine serum albumen (BSA) was prepared in protein storage buffer (25 millimolar Tris-HCl, 300 millimolar NaCl, 0.1 millimolar EDTA, 1 millimolar dithiothreitol, 40% glycerol, pH 7.4). Additional solutions of 40% polyethylene glycol 4000 (PEG), maize washing solution (0.6 molar mannitol, 4 millimolar MES pH 5.7, and 20 millimolar KCl), and PIM containing 50 millimolar $CaCl_2$) (previously described in Table 25, U.S. patent application Ser. No. 16/480,992, filed on 25 Jul. 2019 as the national phase application based on PCT/US2018/015793 filed on 29 Jan. 2018 and published as WO2018/140899, incorporated herein by reference) were prepared. All solutions were aliquoted into 96-well deep plates and sealed until needed for use in a Biomek $FX^P$ automated liquid handler (Beckman Coulter Life Sciences, Indianapolis, Ind.).

Cas12a ribonucleoproteins (RNPs) were prepared with a Cas12a nuclease having the sequence of SEQ ID NO:182 and the "high-performing" Cas12a crRNA, GD-48 as well as the "low-performing" Cas12a crRNA, GD-14. Following a preferred protocol, each Cas12a crRNA was resuspended in reaction buffer to a concentration of 25 micromolar; 1680 microliters of the diluted Cas12a crRNA was mixed with 560 microliters of the Cas12a nuclease solution and incubated 20 minutes at room temperature. To this mixture 1400 microliters of the Cas12a tracrRNA was added and mixed; the resulting "Cas12a nuclease/GD-48 crRNA/tracrRNA editing system" and "Cas12a nuclease/GD-14 crRNA/tracrRNA editing system" were apportioned in 225 microliter aliquots into 8-strip PCR tubes.

Four mixtures were prepared for use as diluents.

"Diluent 1" (Cas12a nuclease/GmSHAT1-5 crRNA/tracrRNA) was prepared by mixing 420 microliters of 25 micromolar GmSHAT1-5 crRNA in reaction buffer (40 mM HEPES, 200 mM NaCl, 10 mM MgCl2, and 0.2 mM EDTA, pH 6.5) and 140 microliters of the Cas12a nuclease solution, incubating for 20 minutes at room temperature, and then adding 350 microliters of the Cas12a tracrRNA solution. This was apportioned in 225 microliter aliquots into 8-strip PCR tubes.

"Diluent 2" (BSA) was prepared by mixing 140 microliters of the BSA stock solution with 770 microliters of reaction buffer (40 mM HEPES, 200 mM NaCl, 10 mM MgCl2, and 0.2 mM EDTA, pH 6.5). This was apportioned in 225 microliter aliquots into 8-strip PCR tubes.

"Diluent 3" (GmSHAT1-5 crRNA/tracrRNA) was prepared by mixing 420 microliters of the GmSHAT1-5 crRNA, 350 microliters of the Cas12a tracrRNA solution, and 140 microliters of reaction buffer (40 mM HEPES, 200 mM NaCl, 10 mM MgCl2, and 0.2 mM EDTA, pH 6.5). This was apportioned in 225 microliter aliquots into 9-strip PCR tubes.

"Diluent 4" consisted of reaction buffer (40 mM HEPES, 200 mM NaCl, 10 mM MgCl2, and 0.2 mM EDTA, pH 6.5) only. This was apportioned in 225 microliter aliquots into 9-strip PCR tubes.

Transfections of the maize protoplasts were carried out in the Biomek $FX^P$ automated liquid handler. A 16-microliter aliquot of the protoplast suspension was added to each well of a U-Bottom 96 well plate pre-coated with 5% Calf Serum with lid removed. A titration series of the Cas12a nuclease/ZmLc crRNA/tracrRNA editing system was made across twelve wells of a master titration plate using the four different diluents; this was stored on the cold block until transfection.

Transfections were performed in triplicate. For transfection, 16 microliters of a given titrated dilution was added to each protoplast-containing well, and mixed; 32 microliters of 40% PEG solution are added and mixed, and the plate incubated 5 minutes at room temperature. Sequential additions of maize washing buffer were dispensed across the plate and mixed, and the plate was removed from the automated liquid handler, covered, and centrifuged. The plate was returned to the automated liquid handler for removal of the majority of the supernatant, and the protoplasts resuspended in 120 microliters PIM containing 50 millimolar $CaCl_2$). The plate was covered and incubated at 27 degrees Celsius in the dark for 36 hours before harvesting. Genomic DNA was isolated from the protoplasts, quantified using QuantiFluor (Promega Corporation, Madison, Wis.), and subjected to PCR amplification followed by amplicon sequencing to detect indel edits.

Figure 13:
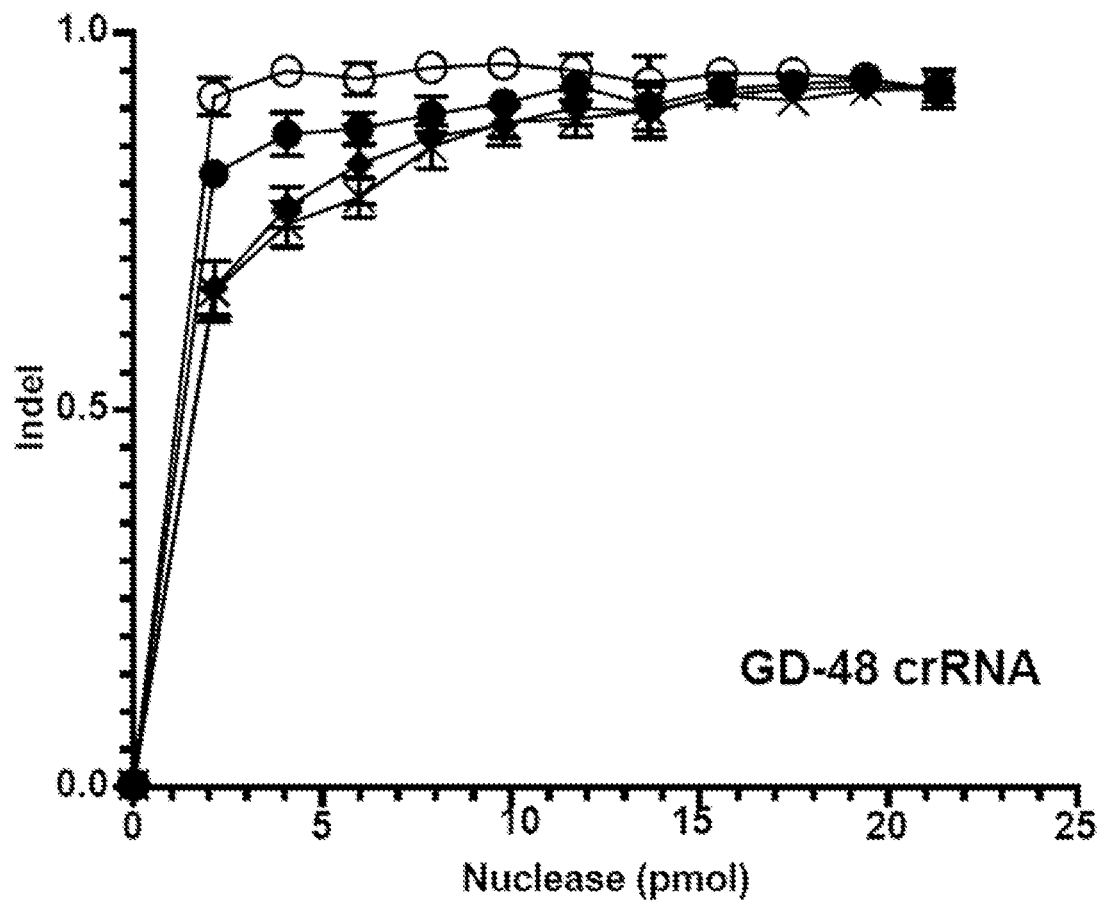
FIG. 13 depicts the results of the experiment using a "high-performing" Cas12a crRNA, GD-48, as described in Example 9. The data are provided as the fraction of edited protoplasts (the number of protoplasts containing an insertion/deletion (indel) at the predicted cleavage site, divided by the total number of protoplasts treated) versus the amount in pmoles of Cas12a nuclease used.
Figure 14:
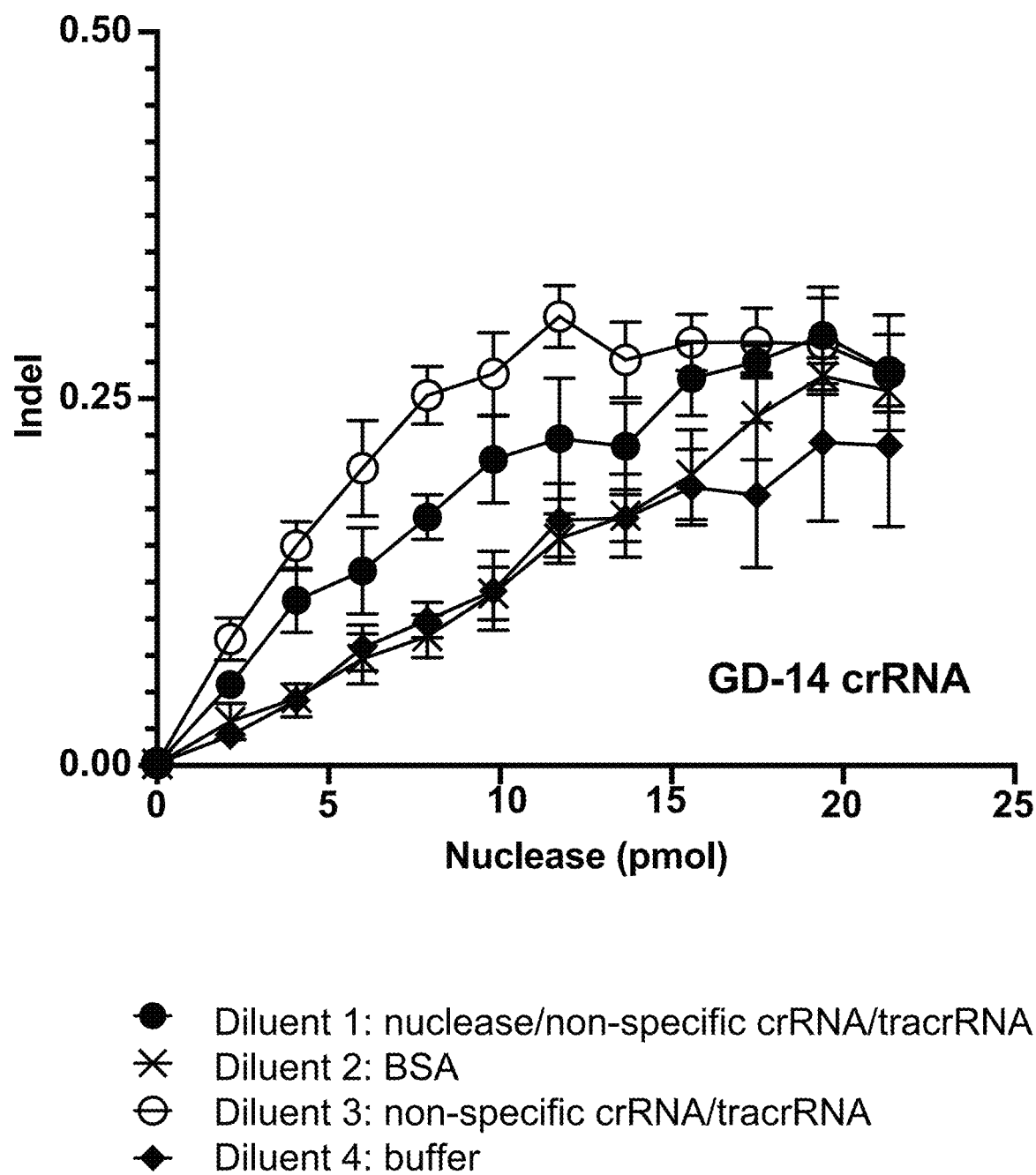
FIG. 14 depicts the results of the experiment using a "low-performing" Cas12a crRNA, GD-14, as described in Example 9. The data are provided as the fraction of edited protoplasts (the number of protoplasts containing an insertion/deletion (indel) at the predicted cleavage site, divided by the total number of protoplasts treated) versus the amount in pmoles of Cas12a nuclease used.

Results, given as the fraction of protoplasts containing an indel at the predicted cleavage site versus the amount of Cas12a nuclease used, are illustrated in FIGS. 13 and 14. The data indicate that dilutions made with Diluent 2 (BSA in reaction buffer) had no significant effect when compared to the control dilution with Diluent 4 (reaction buffer only). In contrast, dilutions made with Diluent 3 (GmSHAT1-5 crRNA/tracrRNA in reaction buffer) markedly increased the editing efficiency at the majority of the Cas12a nuclease amounts tested for both Cas12a crRNAs tested. In the case of the "high-performing" Cas12a crRNA, GD-48, the indel editing frequency reached about maximum (about 90-95%) at much lower Cas12a nuclease concentrations with Diluent 3 than with Diluent 4 (reaction buffer control); use of this Cas12a tracrRNA-containing diluent appeared to decrease the amount of Cas12a nuclease required to achieve about 90% editing to about 2.13 pmol, i.e., about one-seventh the amount of Cas12a nuclease needed to achieve the same level of editing efficiency in the control dilution (15.58 pmol). Dilutions made with Diluent 1 (Cas12a nuclease/ GmSHAT1-5 crRNA/tracrRNA in reaction buffer) also appeared to increase the editing efficiency of a given amount of Cas12a nuclease; use of this diluent appeared to decrease the amount of Cas12a nuclease required to achieve about 90% editing to about 11.73 pmol, i.e., about 75% of the amount of Cas12a nuclease needed to achieve the same level of editing efficiency in the control dilution (15.58 pmol).

In the case of the "low-performing" Cas12a crRNA, GD-14, the indel editing frequency reached about maximum (about 30%) at much lower Cas12a nuclease concentrations with Diluent 3 than with Diluent 4 (the reaction buffer control). Furthermore, use of Diluent 3 resulted in a higher maximum indel editing frequency (about 30%), compared to that obtained with Diluent 4 (only about 20%). Thus, use of Diluent 3 increased overall indel editing efficiency by about fifty percent, and reached maximum editing efficiency at a Cas12a nuclease concentration that was estimated to be at least less than half of the Cas12a nuclease concentration needed to reach the maximum editing efficiency observed in the control dilution. Dilutions made with Diluent 1 (Cas12a nuclease/GmSHAT1-5 crRNA/tracrRNA in reaction buffer) also appeared to increase the editing efficiency of a given amount of Cas12a nuclease; the maximum editing efficiency (about 30%) was also greater than that seen with Diluent 4, and this level was reached with about 15.58 pmol of Cas12a nuclease in Diluent 1.

Example 10

Various embodiments of the systems, methods, and compositions provided herein are included in the following non-limiting list of numbered embodiments.

1. A method of tethering a functional RNA molecule to a Cas12a crRNA, the method comprising hybridizing
   (a) a functional RNA molecule comprising a Cas12a tracrRNA and a functional RNA moiety; and
   (b) a Cas12a crRNA that comprises a 3' extension capable of hybridizing with a segment of the functional RNA molecule;
      thereby tethering the functional RNA molecule to the Cas12a crRNA.
2. The method of embodiment 1, wherein the functional RNA molecule is provided by transcription of a DNA molecule comprising DNA encoding the Cas12a tracrRNA and DNA encoding the functional RNA moiety, wherein the DNA encoding the functional RNA moiety is inserted at a restriction endonuclease cleavage site in or adjacent to the DNA encoding the Cas12a tracrRNA.
3. The method of embodiment 2, wherein the restriction endonuclease cleavage site is native.
4. The method of embodiment 2, wherein the restriction endonuclease cleavage site is artificial.
5. The method of embodiment 1, wherein the crRNA 3' extension comprises nucleotides that when base-paired form about one helical turn.
6. The method of embodiment 1, wherein the crRNA 3' extension comprises at least 10 contiguous nucleotides.
7. The method of any one of embodiments 1 to 6, wherein the functional RNA moiety is at least one selected from the group consisting of:
   (a) an RNA sequence for annealing to a donor polynucleotide;
   (b) an RNA sequence for annealing to the crRNA 3' extension;
   (c) a terminator sequence;
   (d) an RNA aptamer;
   (e) a ribozyme;
   (f) a detectable label;
   (g) a bar-coding sequence; and
   (h) an RNA sequence forming at least partially double-stranded RNA.
8. The method of any one of embodiments 1 to 6, wherein the functional RNA moiety comprises RNA forming at least partially double-stranded RNA capable of silencing a gene.
9. The method of any one of embodiments 1 to 8, wherein the Cas12a crRNA is complexed with, or is capable of complexing with, a Cas12a nuclease to form a Cas12a ribonucleoprotein complex containing the functional RNA molecule.
10. The method of embodiment 9, wherein the Cas12a nuclease is:
    (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum*, *Eubacterium eligens*, *Moraxella bovoculi* 237, *Leptospira inadai*, Lachnospiraceae bacterium ND2006, *Porphyromonas crevioricanis* 3, *Prevotella disiens* and *Porphyromonas macacae*; or
    (b) a Cas12a nuclease selected from the group consisting of LbCas12a, AsCas12a, FnCas12a, and a deactivated Cas12a nuclease; or
    (c) a Cas12a nuclease having at least 80% sequence identity with a sequence selected from the group consisting of SEQ ID NOs:11, 107-114, 116-136, and 172; or
    (d) a Cas12a nuclease variant selected from the group consisting of (1) a variant LbCpf1 that differs from a wild type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134)

in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A.

11. The method of embodiment 9 or embodiment 10, wherein the Cas12a nuclease comprises at least one modification selected from the group consisting of:
   (a) a localization signal;
   (b) a detectable label;
   (c) a cell-penetrating peptide;
   (d) an endosomal escape peptide; and
   (e) an affinity tag.

12. A modified Cas12a ribonucleoprotein complex comprising
   (a) a Cas12a nuclease;
   (b) a functional RNA molecule comprising a Cas12a tracrRNA and a functional RNA moiety; and
   (c) a Cas12a crRNA that comprises a 3' extension capable of hybridizing with a segment of the functional RNA molecule.

13. The modified Cas12a ribonucleoprotein complex of embodiment 12, wherein the Cas12a nuclease is:
   (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum*, *Eubacterium eligens*, *Moraxella bovoculi* 237, *Leptospira inadai*, Lachnospiraceae bacterium ND2006, *Porphyromonas crevioricanis* 3, *Prevotella disiens* and *Porphyromonas macacae*; or
   (b) a Cas12a nuclease selected from the group consisting of LbCas12a, AsCas12a, FnCas12a, and a deactivated Cas12a nuclease; or
   (c) a Cas12a nuclease having at least 80% sequence identity with a sequence selected from the group consisting of SEQ ID NOs:11, 107-114, 116-136, and 172; or
   (d) a Cas12a nuclease variant selected from the group consisting of (1) a variant LbCpf1 that differs from a wild type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A.

14. The modified Cas12a ribonucleoprotein complex of embodiment 12 or embodiment 13, wherein the Cas12a nuclease comprises at least one modification selected from the group consisting of:
   (a) a localization signal;
   (b) a detectable label;
   (c) a cell-penetrating peptide;
   (d) an endosomal escape peptide; and
   (e) an affinity tag.

15. A method of integrating a nucleotide sequence encoded by a donor polynucleotide at a specific locus in a target DNA, the method comprising:
   (a) annealing a donor polynucleotide to the modified Cas12a ribonucleoprotein complex of embodiment 12, wherein the functional RNA moiety comprises an RNA sequence for annealing to the donor polynucleotide, and wherein the Cas12a crRNA comprises a spacer sequence that corresponds to a specific target locus in a target DNA, thus forming a donor:RNP complex; and
   (b) contacting the target DNA with the donor: RNP complex;
   whereby the nucleotide sequence encoded by the donor polynucleotide is integrated at the specific target locus in the target DNA.

16. The method of embodiment 15, wherein the donor polynucleotide comprises single-stranded DNA, optionally comprising chemical modifications.

17. The method of embodiment 15, wherein the donor polynucleotide comprises double-stranded DNA, optionally comprising chemical modifications.

18. A DNA expression system comprising
   (a) DNA sequence for a first promoter; and
   (b) operably linked and heterologous to the first promoter, DNA encoding a first RNA molecule comprising a Cas12a tracrRNA and comprising a restriction endonuclease cleavage site that is suitable for insertion of a sequence coding for a functional RNA moiety; and
   (c) optionally, a terminator 3' to and operably linked to the DNA encoding the first RNA molecule.

19. The DNA expression system of embodiment 18, wherein the restriction endonuclease cleavage site occurs natively in the DNA encoding the Cas12a tracrRNA.

20. The DNA expression system of embodiment 18, wherein the restriction endonuclease cleavage site is artificial.

21. The DNA expression system of embodiment 18, further comprising:
   (d) optionally, a DNA sequence for a second promoter;
   (e) operably linked and heterologous to the first promoter or the second promoter, DNA encoding a Cas12a crRNA that comprises a 3' extension capable of hybridizing with a segment of the first RNA molecule; and
   (f) optionally, a terminator 3' to and operably linked to the DNA encoding the Cas12a crRNA.

22. The DNA expression system of embodiment 21, wherein the first promoter and the DNA encoding the first RNA molecule, and the DNA encoding a Cas12a crRNA that comprises a 3' extension are contained in a single construct.

23. The DNA expression system of embodiment 21, comprising the second promoter, wherein the first promoter and the DNA encoding the first RNA molecule are contained in a first construct, and the second promoter and the DNA encoding a Cas12a crRNA that comprises a 3' extension are contained in a second construct.

24. The DNA expression system of embodiment 23, wherein the first construct and the second construct are provided (a) in a single vector, or (b) in separate vectors.

25. The DNA expression system of embodiment 21, wherein the first promoter drives expression of both the DNA encoding the first RNA molecule and the DNA encoding the Cas12a crRNA that comprises a 3' extension.

26. The DNA expression system of any one of embodiments 21 to 25, wherein the Cas12a tracrRNA further comprises a 5' extension.

27. The DNA expression system of any one of embodiments 21 to 26, wherein the Cas12a crRNA that comprises a 3' extension is capable of complexing with a Cas12a nuclease to form a Cas12a ribonucleoprotein complex.

28. The DNA expression system of embodiment 18, further comprising:
    (d) optionally, a DNA sequence for a second promoter;
    (e) operably linked and heterologous to the first promoter or the second promoter, DNA encoding a Cas12a crRNA capable of hybridizing with a segment of the first RNA molecule; and
    (f) optionally, a terminator 3' to and operably linked to the DNA encoding the Cas12a crRNA.

29. The DNA expression system of embodiment 28, wherein the first promoter and the DNA encoding the first RNA molecule, and the DNA encoding a Cas12a crRNA are contained in a single construct.

30. The DNA expression system of embodiment 28, comprising the second promoter, wherein the first promoter and the DNA encoding the first RNA molecule are contained in a first construct, and the second promoter and the DNA encoding a Cas12a crRNA are contained in a second construct.

31. The DNA expression system of embodiment 30, wherein the first construct and the second construct are provided (a) in a single vector, or (b) in separate vectors.

32. The DNA expression system of embodiment 28, wherein the first promoter drives expression of both the DNA encoding the first RNA molecule and the DNA encoding the Cas12a crRNA.

33. The DNA expression system of any one of embodiments 28 to 32, wherein the Cas12a tracrRNA further comprises a 5' extension.

34. The DNA expression system of any one of embodiments 28 to 33, wherein the Cas12a crRNA is capable of complexing with a Cas12a nuclease to form a Cas12a ribonucleoprotein complex.

35. The DNA expression system of embodiment 27 or embodiment 34, wherein the Cas12a nuclease is:
    (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum*, *Eubacterium eligens*, *Moraxella bovoculi* 237, *Leptospira inadai*, Lachnospiraceae bacterium ND2006, *Porphyromonas crevioricanis* 3, *Prevotella disiens* and *Porphyromonas macacae*; or
    (b) a Cas12a nuclease selected from the group consisting of LbCas12a, AsCas12a, FnCas12a, and a deactivated Cas12a nuclease; or
    (c) a Cas12a nuclease having at least 80% sequence identity with a sequence selected from the group consisting of SEQ ID NOs:11, 107-114, 116-136, and 172; or
    (d) a Cas12a nuclease variant selected from the group consisting of (1) a variant LbCpf1 that differs from a wild type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A.

36. The DNA expression system of any one of embodiments 18 to 35, wherein the first promoter has a DNA sequence selected from the group consisting of SEQ ID NOs:16-71 and wherein the Cas12a tracrRNA has a nucleotide sequence comprising a sequence selected from the group consisting of SEQ ID NOs:1, 3, 6, 139-146, and 149-169.

37. A DNA expression system comprising:
    (a) DNA sequence for a first promoter; and
    (b) operably linked and heterologous to the first promoter, a DNA encoding a functional RNA molecule comprising a Cas12a tracrRNA and a functional RNA moiety; and
    (c) optionally, a terminator 3' to and operably linked to the DNA encoding a functional RNA molecule.

38. The DNA expression system of embodiment 37, further comprising:
    (d) optionally, a DNA sequence for a second promoter;
    (e) operably linked and heterologous to the first promoter or the second promoter, a DNA encoding a Cas12a crRNA that comprises a 3' extension capable of hybridizing with a segment of the functional RNA molecule; and
    (f) optionally, a terminator 3' to and operably linked to the DNA encoding a Cas12 crRNA.

39. The DNA expression system of embodiment 38, wherein the first promoter and the DNA encoding the functional RNA molecule, and the DNA encoding a Cas12a crRNA that comprises a 3' extension are contained in a single construct.

40. The DNA expression system of embodiment 38, comprising the second promoter, wherein the first promoter and the DNA encoding the functional RNA molecule are contained in a first construct, and the second promoter and the DNA encoding a Cas12a crRNA that comprises a 3' extension are contained in a second construct.

41. The DNA expression system of embodiment 40, wherein the first construct and the second construct are provided (a) in a single vector, or (b) in separate vectors.

42. The DNA expression system of embodiment 38, wherein the first promoter drives expression of both the DNA encoding the functional RNA molecule and the DNA encoding the Cas12a crRNA that comprises a 3' extension.

43. The DNA expression system of any one of embodiments 37 to 42, wherein the functional RNA moiety is at least one selected from the group consisting of:

(a) a nucleotide sequence for annealing to a donor polynucleotide;
(b) a nucleotide sequence for annealing to the crRNA 3' extension;
(c) a terminator sequence;
(d) an RNA aptamer;
(e) an enzymatically active RNA sequence;
(f) a detectable label; and
(g) an RNA sequence forming at least partially double-stranded RNA.

44. The DNA expression system of any one of embodiments 37 to 42, wherein the functional RNA moiety comprises RNA forming at least partially double-stranded RNA capable of silencing a gene.

45. The DNA expression system of any one of embodiments 38 to 44, wherein the Cas12a tracrRNA further comprises a 5' extension.

46. The DNA expression system of any one of embodiments 38 to 45, wherein the Cas12a crRNA is capable of complexing with a Cas12a nuclease to form a Cas12a ribonucleoprotein complex containing the functional molecule.

47. The DNA expression system of any one of embodiments 37 to 56, wherein the first promoter has a DNA sequence selected from the group consisting of SEQ ID NOs:16-71 and wherein the Cas12a tracrRNA has a nucleotide sequence comprising a sequence selected from the group consisting of SEQ ID NOs:1, 3, 6, 139-146, and 149-169.

48. The DNA expression system of embodiment 46 or 47, wherein the Cas12a nuclease is:
(a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum*, *Eubacterium eligens*, *Moraxella bovoculi* 237, *Leptospira inadai*, Lachnospiraceae bacterium ND2006, *Porphyromonas crevioricanis* 3, *Prevotella disiens* and *Porphyromonas macacae*; or
(b) a Cas12a nuclease selected from the group consisting of LbCas12a, AsCas12a, FnCas12a, and a deactivated Cas12a nuclease; or
(c) a Cas12a nuclease having at least 80% sequence identity with a sequence selected from the group consisting of SEQ ID NOs:11, 107-114, 116-136, and 172; or
(d) a Cas12a nuclease variant selected from the group consisting of (1) a variant LbCpf1 that differs from a wild type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A.

49. An engineered system comprising:
(a) a Cas12a nuclease; and
(b) at least one engineered Cas12a crRNA, or a polynucleotide encoding the engineered Cas12a crRNA, wherein the engineered Cas12a crRNA comprises
(i) at least one direct repeat sequence or fragment thereof that is capable of associating with the Cas12a nuclease, and
(ii) a spacer sequence that is designed to hybridize with a target sequence in a eukaryotic cell, wherein the at least one direct repeat sequence or fragment thereof is adjacent to and 5' to the spacer sequence; and
(c) a Cas12a tracrRNA comprising a nucleotide sequence that has at least 50% complementarity with, the nucleotide sequence of the at least one direct repeat of the engineered Cas12a crRNA.

50. An engineered system comprising:
(a) a Cas12a nuclease; and
(b) at least one engineered Cas12a crRNA, or a polynucleotide encoding the engineered Cas12a crRNA, wherein the engineered Cas12a crRNA comprises
(i) at least one direct repeat sequence or fragment thereof that is capable of associating with the Cas12a nuclease, and
(ii) a spacer sequence that is designed to hybridize with a target sequence in a eukaryotic cell, wherein the at least one direct repeat sequence or fragment thereof is adjacent to and 5' to the spacer sequence; and
(c) a Cas12a tracrRNA comprising a naturally occurring putative Cas12a tracrRNA sequence that is identified from the same genomic region as the Cas12a nuclease by at least the following steps: (i) identifying in the genomic region flanking the DNA encoding the Cas12a nuclease at least one nucleotide sequence that comprises a CRISPR array including direct repeats, and (ii) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat.

51. The engineered system of embodiment 49 or embodiment 50, wherein the engineered Cas12a crRNA, or the polynucleotide encoding the engineered Cas12a crRNA, further comprises at least one direct repeat sequence or fragment thereof capable of associating with the Cas12a nuclease adjacent to and 3' to the spacer sequence.

52. The engineered system of embodiment 49 or embodiment 50, wherein the engineered Cas12a crRNA further comprises a 3' extension adjacent to the spacer sequence.

53. The engineered system of embodiment 52, wherein the 3' extension comprises nucleotides that when base-paired form about one helical turn.

54. The engineered system of embodiment 52, wherein the 3' extension comprises at least 10 contiguous nucleotides.

55. The engineered system of any one of embodiments 52, 53, and 54, wherein the Cas12a tracrRNA has a nucleotide sequence having sufficient complementarity to the engineered Cas12a crRNA's 3' extension to allow hybridization between the tracrRNA and the engineered Cas12a crRNA.

56. An engineered system comprising:
   (a) one or more nucleotide sequences encoding a Cas12a nuclease; and
   (b) one or more nucleotide sequences encoding at least one engineered Cas12a crRNA that is designed to form a complex with the Cas12a nuclease and that comprises a spacer sequence designed to hybridize with a target sequence in a eukaryotic cell; and
   (c) one or more nucleotide sequences encoding at least one Cas12a tracrRNA.
57. An engineered system comprising:
   (a) a Cas12a nuclease, or one or more nucleotide sequences encoding the Cas12a nuclease; and
   (b) at least one engineered Cas12a crRNA designed to form a complex with the Cas12a nuclease and comprising a spacer sequence designed to hybridize with a target sequence in a eukaryotic cell, or one or more nucleotide sequences encoding the at least one engineered Cas12a crRNA polynucleotide; and
   (c) at least one tracrRNA, or one or more nucleotide sequences encoding the at least one Cas12a tracrRNA.
58. The engineered system of embodiment 56 or embodiment 57, wherein the at least one engineered Cas12a crRNA, or a polynucleotide encoding the at least one engineered Cas12a crRNA, further comprises at least one direct repeat sequence or fragment thereof that is capable of associating with the Cas12a nuclease and is adjacent to and 5' to the spacer sequence.
59. The engineered system of embodiment 56 or embodiment 57, wherein the engineered Cas12a crRNA, or a polynucleotide encoding the engineered Cas12a crRNA, further comprises at least one direct repeat sequence or fragment thereof capable of associating with the Cas12a nuclease adjacent to and 3' to the spacer sequence.
60. The engineered system of embodiment 56 or embodiment 57, wherein the engineered Cas12a crRNA further comprises a 3' extension adjacent to the spacer sequence.
61. The engineered system of embodiment 60, wherein the 3' extension comprises nucleotides that when base-paired form about one helical turn.
62. The engineered system of embodiment 60, wherein the 3' extension comprises at least 10 contiguous nucleotides.
63. The engineered system of any one of embodiments 60, 61, and 62, wherein the Cas12a tracrRNA has a nucleotide sequence having sufficient complementarity to the engineered Cas12a crRNA's 3' extension to allow hybridization between the Cas12a tracrRNA and the engineered Cas12a crRNA.
64. An engineered system comprising one or more vectors comprising:
   (a) a first regulatory element that is heterologous to and operably linked to one or more nucleotide sequences encoding a Cas12a nuclease; and
   (b) a second regulatory element that is heterologous to and operably linked to one or more nucleotide sequences encoding at least one engineered Cas12a crRNA that is designed to form a complex with the Cas12a nuclease and that comprises a spacer sequence designed to hybridize with a target sequence in a eukaryotic cell; and
   (c) a third regulatory element that is heterologous to and operably linked to one or more nucleotide sequences encoding at least one Cas12a tracrRNA;
   wherein components (a) and (b) and (c) are located on the same vector or on different vectors of the system.
65. The engineered system of embodiment 64, wherein the first regulatory element, the second regulatory element, and the third regulatory element each comprise a promoter that is functional in the eukaryotic cell.
66. The engineered system of embodiment 65, wherein the first regulatory element, the second regulatory element, and the third regulatory element each comprise a promoter selected from the group consisting of pol III promoters, pol II promoters, and pol I promoters.
67. The engineered system of embodiment 69, wherein the first regulatory element, the second regulatory element, and the third regulatory element each comprise a promoter selected from the group consisting of a U6 promoter, an H1 promoter, a Rous sarcoma virus (RSV) LTR promoter, a cytomegalovirus (CMV) promoter, an SV40 promoter, a dihydrofolate reductase promoter, a beta-actin promoter, a phosphoglycerol kinase (PGK) promoter, an EF1a promoter.
68. The engineered system of embodiment 64, wherein the eukaryotic cell is a plant cell, and wherein the third regulatory element comprises a promoter having a nucleotide sequence selected from the group consisting of SEQ ID NOs:16-71.
69. The engineered system of any one of embodiments 64-68, wherein the at least one Cas12a tracrRNA is at least one Cas12a tracrRNA having a nucleotide sequence comprising a sequence selected from the group consisting of SEQ ID NOs:1, 3, 6, 139-146, and 149-169.
70. An engineered system comprising one or more vectors comprising:
   (a) a first expression cassette comprising at least a first promoter that is heterologous to and operably linked to one or more nucleotide sequences encoding a Cas12a nuclease and—optionally—a first transcription terminator sequence; and
   (b) a second expression cassette comprising at least a second promoter that is heterologous to operably linked to one or more nucleotide sequences encoding at least one engineered Cas12a crRNA that is designed to form a complex with the Cas12a nuclease and that comprises a spacer sequence designed to hybridize with a target sequence in a eukaryotic cell and—optionally—a second transcription terminator sequence; and
   (c) a third expression cassette comprising at least a third promoter that is heterologous to operably linked to one or more nucleotide sequences encoding at least one Cas12a tracrRNA and—optionally
   a third transcription terminator sequence,
   wherein components (a) and (b) and (c) are located on the same vector or on different vectors of the system.
71. The engineered system of embodiment 70, wherein the first promoter, the second promoter, and the third promoter are each a promoter that is functional in the eukaryotic cell, and wherein the first transcription terminator, the second transcription terminator, and the third transcription terminator are each a transcription terminator that is functional in the eukaryotic cell.
72. The engineered system of embodiment 70, wherein the first promoter, the second promoter, and the third promoter are each a promoter selected from the group consisting of pol III promoters, pol II promoters, and pol I promoters.
73. The engineered system of embodiment 70, wherein the first promoter, the second promoter, and the third promoter are each a promoter selected from the group consisting of a U6 promoter, an H1 promoter, a Rous sarcoma virus (RSV) LTR promoter, a cytomegalovirus (CMV) promoter, an SV40 promoter, a dihydrofolate reductase promoter, a beta-actin promoter, a phosphoglycerol kinase (PGK) promoter, an EF1a promoter.

74. The engineered system of embodiment 70, wherein the first promoter, the second promoter, and the third promoter are each a promoter with a nucleotide sequence selected from the group consisting of SEQ ID NOs:16-71.

75. The engineered system of embodiment 70, wherein the first transcription terminator, the second transcription terminator, and the third transcription terminator are each selected from the group consisting of a U6 poly-T terminator, an SV40 terminator, an hGH terminator, a BGH terminator, an rbGlob terminator, a synthetic terminator functional in a eukaryotic cell, a 3' element from an *Agrobacterium* sp. gene, a 3' element from a non-human animal gene, a 3' element from a human gene, and a 3' element from a plant gene, wherein the 3' element terminate transcription of an RNA transcript located immediately 5' to the 3' element.

76. The engineered system of embodiment 70, wherein the first transcription terminator, the second transcription terminator, and the third transcription terminator are each a transcription terminator having a sequence selected from SEQ ID NOs:72-100.

77. The engineered system of any one of embodiments 49-76, wherein the eukaryotic cell is a non-human animal cell, a human cell, a plant cell, or a fungal cell.

78. The engineered system of any one of embodiments 49-77, wherein the eukaryotic cell is in vitro, ex vivo, or in vivo.

79. The engineered system of any one of embodiments 49-78, wherein the Cas12a nuclease is:
(a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum*, *Eubacterium eligens*, *Moraxella bovoculi* 237, *Leptospira inadai*, Lachnospiraceae bacterium ND2006, *Porphyromonas crevioricanis* 3, *Prevotella disiens* and *Porphyromonas macacae*; or
(b) a Cas12a nuclease selected from the group consisting of LbCas12a, AsCas12a, FnCas12a, and a deactivated Cas12a nuclease; or
(c) a Cas12a nuclease having at least 80% sequence identity with a sequence selected from the group consisting of SEQ ID NOs:11, 107-114, 116-136, and 172; or
(d) a Cas12a nuclease variant selected from the group consisting of (1) a variant LbCpf1 that differs from a wild type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A.

80. The engineered system of any one of embodiments 49-79, wherein the Cas12a nuclease comprises one or more of:
(a) a localization signal;
(b) a detectable label;
(c) a cell-penetrating peptide;
(d) an endosomal escape peptide; and
(e) and affinity tag.

81. The engineered system of any one of embodiments 49-80, wherein the at least one Cas12a tracrRNA has a nucleotide sequence selected from SEQ ID NOs:1, 3, 6, 139-146, and 149-169.

82. The engineered system of any one of embodiments 49-81, wherein the genomic sequence encoding the Cas12a nuclease and the genomic sequence encoding the Cas12a tracrRNA occur naturally within the same region in a genome.

83. The engineered system of any one of embodiments 49, 50, 56, 57, 64, and 68, wherein the target sequence is located 3' of a Protospacer Adjacent Motif (PAM) and the PAM sequence is TTN, where N is A/C/G or T and the Cas12a nuclease is FnCpf1, or the PAM sequence is TTTV, where V is A/C or G and the Cas12a nuclease is PaCpf1p, LbCpf1 or AsCpf1.

84. The engineered system of any one of embodiments 49, 56, 57, 64, and 68, wherein the Cas12a tracrRNA is a putative Cas12a tracrRNA that is identified from the same genomic region as the Cas12a nuclease by at least the following steps:
(a) identifying in the genomic region flanking the DNA encoding the Cas12a nuclease at least one nucleotide sequence that comprises a CRISPR array including direct repeats;
(b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat.

85. The engineered system of any one of embodiments 49, 50, 56, 57, 64, and 68, wherein the Cas12a tracrRNA is provided:
(a) as DNA encoding a first RNA molecule comprising the Cas12a tracrRNA and comprising a restriction endonuclease cleavage site that is suitable for insertion of a sequence coding for a functional RNA moiety; or
(b) as a functional RNA molecule comprising the Cas12a tracrRNA and a functional RNA moiety, or as a polynucleotide encoding the functional RNA molecule; or
(c) by the DNA expression system of embodiment 18; or
(d) by the DNA expression system of embodiment 37.

86. The engineered system of any one of embodiments 49, 50, 56, 57, 64, and 68, wherein the Cas12a tracrRNA is provided as DNA encoding a first RNA molecule comprising the Cas12a tracrRNA and comprising a restriction endonuclease cleavage site that is suitable for insertion of a sequence coding for a functional RNA moiety, and wherein the functional RNA moiety is at least one selected from the group consisting of:
(a) a nucleotide sequence for annealing to a donor polynucleotide;
(b) a nucleotide sequence for annealing to the crRNA 3' extension;
(c) a terminator sequence;

(d) an RNA aptamer;
(e) an enzymatically active RNA sequence;
(f) a detectable label; and
(g) an RNA sequence forming at least partially double-stranded RNA.

87. The engineered system of any one of embodiments 49, 50, 56, 57, 64, and 68, wherein the Cas12a tracrRNA is provided as DNA encoding a first RNA molecule comprising the Cas12a tracrRNA and comprising a restriction endonuclease cleavage site that is suitable for insertion of a sequence coding for a functional RNA moiety, wherein the functional RNA moiety comprises RNA forming at least partially double-stranded RNA capable of silencing a gene.

88. The engineered system of any one of embodiments 49, 50, 56, 57, 64, and 68, wherein the Cas12a tracrRNA is provided as DNA encoding a first RNA molecule comprising the Cas12a tracrRNA and comprising a restriction endonuclease cleavage site that is suitable for insertion of a sequence coding for a functional RNA moiety, wherein the functional RNA moiety comprises an RNA sequence for annealing to a donor polynucleotide, and wherein the composition further comprises the donor polynucleotide.

89. The engineered system of any one of embodiments 49, 50, 56, 57, 64, and 68, wherein the Cas12a tracrRNA is provided as a functional RNA molecule comprising the Cas12a tracrRNA and a functional RNA moiety, or as a polynucleotide encoding the functional RNA molecule, and wherein the functional RNA moiety is at least one selected from the group consisting of:
(a) a nucleotide sequence for annealing to a donor polynucleotide;
(b) a nucleotide sequence for annealing to the crRNA 3' extension;
(c) a terminator sequence;
(d) an RNA aptamer;
(e) an enzymatically active RNA sequence;
(f) a detectable label; and
(g) an RNA sequence forming at least partially double-stranded RNA.

90. The engineered system of any one of embodiments 49, 50, 56, 57, 64, and 68, wherein the Cas12a tracrRNA is provided as a functional RNA molecule comprising the Cas12a tracrRNA and a functional RNA moiety, or as a polynucleotide encoding the functional RNA molecule, and wherein the functional RNA moiety comprises RNA forming at least partially double-stranded RNA capable of silencing a gene.

91. The engineered system of any one of embodiments 49, 50, 56, 57, 64, and 68, wherein the Cas12a tracrRNA is provided as a functional RNA molecule comprising the Cas12a tracrRNA and a functional RNA moiety, or as a polynucleotide encoding the functional RNA molecule, wherein the functional RNA moiety comprises an RNA sequence for annealing to a donor polynucleotide, and wherein the system further comprises the donor polynucleotide.

92. The engineered system of any one of embodiments 49, 50, 56, 57, 64, and 68, wherein the Cas12a tracrRNA is provided in a molar excess, relative to the amount of Cas12a nuclease.

93. The engineered system of any one of embodiments 49, 50, 56, 57, 64, and 68, wherein the Cas12a tracrRNA is provided in a molar amount that is at least 10-fold greater than the molar amount of the Cas12a nuclease.

94. A delivery particle comprising the engineered system of any one of embodiments 49, 50, 56, 57, 64, and 68.

95. The delivery particle of embodiment 94, wherein the Cas12a nuclease is complexed with the engineered Cas12a crRNA polynucleotide.

96. The delivery particle of embodiment 94, wherein the Cas12a tracrRNA is present in a molar excess, relative to the amount of Cas12a nuclease.

97. The delivery particle of embodiment 94, wherein the Cas12a tracrRNA is present in a molar amount that is at least 10-fold greater than the molar amount of the Cas12a nuclease.

98. A delivery liquid comprising the engineered system of any one of embodiments 49, 50, 56, 57, 64, and 68.

99. The delivery liquid of embodiment 98, wherein the Cas12a nuclease is complexed with the engineered Cas12a crRNA polynucleotide.

100. The delivery liquid of embodiment 98, wherein the Cas12a tracrRNA is present in a molar excess, relative to the amount of Cas12a nuclease.

101. The delivery liquid of embodiment 98, wherein the Cas12a tracrRNA is present in a molar amount that is at least 10-fold greater than the molar amount of the Cas12a nuclease.

102. A method of modifying a target sequence in a locus of interest of a eukaryotic cell comprising delivering the engineered system according to any one of embodiments 49, 50, 56, 57, 64, and 68 to the locus of interest, wherein the spacer sequence hybridizes with the target sequence, whereby modification of the locus of interest occurs.

103. The method of embodiment 102, wherein the locus of interest is within a eukaryotic cell.

104. The method of embodiment 102, wherein the eukaryotic cell is a plant cell.

105. The method of embodiment 102, wherein the eukaryotic cell is a non-human animal cell or a human cell.

106. The method of embodiment 102, wherein the engineered system or a component thereof is delivered via delivery particles, delivery vesicles, delivery liquids, or one or more viral or bacterial vectors.

107. The method of embodiment 102, wherein the engineered system or a component thereof is delivered via delivery particles comprising at least one selected from the group consisting of a lipid, a sugar, a metal, or a protein.

108. The method of embodiment 102, wherein the engineered system or a component thereof is delivered via delivery exosomes or liposomes.

109. The method of embodiment 102, wherein the engineered system or a component thereof is delivered via at least one viral vector selected from the group consisting of adenoviruses, lentiviruses, adeno-associated viruses, retroviruses, geminiviruses, begomoviruses, tobamoviruses, potex viruses, comoviruses, wheat streak mosaic virus, barley stripe mosaic virus, bean yellow dwarf virus, bean pod mottle virus, cabbage leaf curl virus, beet curly top virus, tobacco yellow dwarf virus, tobacco rattle virus, potato virus X, and cowpea mosaic virus.

110. The method of embodiment 102, wherein the system or a component thereof is delivered via at least one bacterial vector capable of transforming a plant cell and selected from the group consisting of *Agrobacterium* sp., *Rhizobium* sp., *Sinorhizobium* (Ensifer) sp., *Mesorhizobium* sp., *Bradyrhizobium* sp., *Azobacter* sp., and *Phyllobacterium* sp.

111. The method of embodiment 102, wherein the Cas12a nuclease is:
(a) a Cas12a nuclease identified from the genome of a bacterial species selected from the group consisting of

*Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum*, *Eubacterium eligens*, *Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A.

112. The method of embodiment 102, wherein the Cas12a nuclease comprises one or more of:
(a) a localization signal;
(b) a detectable label;
(c) a cell-penetrating peptide;
(d) an endosomal escape peptide; and
(e) and affinity tag.

113. The method of embodiment 102, wherein the Cas12a tracrRNA has a nucleotide sequence comprising a sequence selected from the group consisting of SEQ ID NOs:1, 3, 6, 139-146, and 149-169.

114. The method of embodiment 102, wherein the tracrRNA is a putative Cas12a tracrRNA that is identified from the same genomic region as the Cas12a nuclease by at least the following steps:
(a) identifying in the genomic region flanking the DNA encoding the Cas12a nuclease at least one nucleotide sequence that comprises a CRISPR array including direct repeats;
(b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with the nucleotide sequence of the direct repeat.

115. The method of embodiment 102, wherein the eukaryotic cell comprises a cell of a cell line or a cell of a multicellular organism, and wherein the locus of interest comprises a locus of interest in the genome of the eukaryotic cell.

116. The method of embodiment 102, wherein the eukaryotic cell is in vitro, ex vivo, or in vivo.

117. The method of embodiment 102, wherein the eukaryotic cell comprises a non-human animal or human stem cell or a non-human animal or human stem cell line.

118. The method of embodiment 102, wherein the locus of interest is within a eukaryotic DNA molecule in vitro.

119. The method of embodiment 102, wherein the eukaryotic cell comprises a plant cell, and wherein the modification of the locus of interest is correlated with a modified trait in a plant comprising cells containing the modification of the locus of interest.

120. The method of embodiment 119, wherein the method further comprises obtaining, growing, or regenerating a plant from the plant cell, wherein the plant comprises cells containing the modification of the locus of interest, and wherein the plant exhibits the modified trait effected by the modification of the locus of interest.

121. The method of embodiment 102, wherein the eukaryotic cell comprises a plant cell, and the method further comprises identifying a trait of interest in a plant obtained, grown, or regenerated from the plant cell, wherein the trait of interest is effected by the modification of the locus of interest.

122. The method of embodiment 121, further comprising:
(a) introducing a nucleotide sequence comprising the locus of interest into a plant cell, a plant cell line, or a plant germplasm, and generating from the plant cell, the plant cell line, or the plant germplasm a plant comprising cells containing the nucleotide sequence comprising the locus of interest; or
(b) introducing the modified locus of interest into a plant cell, a plant cell line, or a plant germplasm, and generating from the plant cell, the plant cell line, or the plant germplasm a plant comprising cells containing the modified locus of interest; or
(c) modifying expression of the locus of interest in a plant cell, a plant cell line, or a plant germplasm, and generating from the plant cell, the plant cell line, or the plant germplasm a plant comprising cells containing the locus of interest having modified expression; or
(d) deleting the locus of interest or an endogenous nucleotide sequence comprising the locus of interest in a plant cell, and generating from the plant cell, the plant cell line, or the plant germplasm a plant comprising cells in which the locus of interest or the endogenous nucleotide sequence comprising the locus of interest has been deleted.

123. A method of editing a genetic locus with a Cas12a nuclease, comprising contacting DNA that comprises the genetic locus with:
(a) a Cas12a nuclease; and
(b) an engineered Cas12a crRNA that includes a spacer sequence that is designed to hybridize with a target sequence in the genetic locus; and
(c) a Cas12a tracrRNA, thereby editing the genetic locus; wherein the efficiency of editing of the genetic locus is increased compared to a control method in which the DNA that comprises the genetic locus is contacted with the Cas12a nuclease and the Cas12a crRNA, but not the Cas12a tracrRNA.

124. The method of embodiment 123, wherein the Cas12a nuclease and the engineered Cas12a crRNA are provided as a ribonucleoprotein complex.

125. The method of embodiment 123, wherein the Cas12a nuclease is provided as a polynucleotide encoding the Cas12a nuclease.
126. The method of embodiment 123, wherein the Cas12a tracrRNA is provided:
    (a) as DNA encoding a first RNA molecule comprising the Cas12a tracrRNA and comprising a restriction endonuclease cleavage site that is suitable for insertion of a sequence coding for a functional RNA moiety; or
    (b) as a functional RNA molecule comprising the Cas12a tracrRNA and a functional RNA moiety, or as a polynucleotide encoding the functional RNA molecule; or
    (c) by the DNA expression system of embodiment 18; or
    (d) by the DNA expression system of embodiment 37.
127. The method of embodiment 123, wherein the DNA that comprises the genetic locus is genomic DNA.
128. The method of embodiment 123, wherein the DNA that comprises the genetic locus is in a eukaryotic DNA molecule in vitro.
129. The method of embodiment 123, wherein the DNA that comprises the genetic locus is in a eukaryotic cell.
130. The method of embodiment 129, wherein the eukaryotic cell is a cell of a non-human animal, an invertebrate, a vertebrate, a mollusk, an arthropod, an insect, a fish, a reptile, an amphibian, a bird, a mammal, a primate, a non-human primate, a human, a plant, or a fungus.
131. The method of embodiment 129, wherein the eukaryotic cell comprises a cell of a cell line or a cell of a multicellular organism, and wherein the genetic locus to be modified comprises a locus of interest in the genome of the eukaryotic cell.
132. The method of embodiment 129, wherein the eukaryotic cell is in vitro, ex vivo, or in vivo.
133. The method of embodiment 129, wherein the eukaryotic cell comprises a non-human animal or human stem cell or a non-human animal or human stem cell line.
134. The method of embodiment 123, wherein the Cas12a tracrRNA is a putative tracrRNA.
135. The method of embodiment 134, wherein the putative Cas12a tracrRNA is identified from the same genomic region as the Cas12a nuclease by at least the following steps:
    (a) identifying in the genomic region flanking the DNA encoding the Cas12a nuclease at least one nucleotide sequence that comprises a CRISPR array including direct repeats;
    (b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat.
136. The method of embodiment 123, wherein the Cas12a tracrRNA is provided in a molar excess, relative to the Cas12a nuclease.
137. The method of embodiment 123, wherein the Cas12a tracrRNA is provided in a molar amount that is at least 10-fold greater than the molar amount of the Cas12a nuclease.
138. The method of embodiment 123, wherein the engineered Cas12a crRNA, or a polynucleotide encoding the engineered Cas12a crRNA, further comprises at least one direct repeat sequence or fragment thereof capable of associating with the Cas12a nuclease adjacent to and 3' to the spacer sequence.
139. The method of embodiment 123, wherein the engineered Cas12a crRNA further comprises a 3' extension adjacent to the spacer sequence.
140. The method of embodiment 123, wherein the 3' extension comprises nucleotides that when base-paired form about one helical turn.
141. The method of embodiment 123, wherein the 3' extension comprises at least 10 contiguous nucleotides.
142. The method of embodiment 123, wherein the Cas12a tracrRNA has a nucleotide sequence having sufficient complementarity to the engineered Cas12a crRNA's 3' extension to allow hybridization between the tracrRNA and the engineered Cas12a crRNA.
143. The method of embodiment 123, wherein the editing of the genetic locus is effecting an indel in the genetic locus.
144. The method of embodiment 123, wherein the editing of the genetic locus is effecting non-homologous end joining (NHEJ) in the genetic locus.
145. The method of embodiment 123, wherein the editing of the genetic locus is effecting homology-dependent repair (HDR) in the genetic locus.
146. A composition for modifying a genetic locus in a eukaryotic cell, comprising:
    (a) a eukaryotic cell containing a genetic locus to be modified; and
    (b) a Cas12a nuclease, or a polynucleotide encoding the Cas12a nuclease; and
    (c) an engineered Cas12a crRNA that includes a spacer sequence corresponding to a specific sequence in the genetic locus, or a polynucleotide encoding the Cas12a crRNA; and
    (d) a Cas12a tracrRNA, or a polynucleotide encoding the Cas12a tracrRNA, wherein the Cas12a tracrRNA is provided in molar excess relative to the Cas12a nuclease.
147. The composition of embodiment 146, wherein the Cas12a tracrRNA is identified from the same genomic region as the Cas12a nuclease by at least the following steps:
    (a) identifying in the genomic region flanking the DNA encoding the Cas12a nuclease at least one nucleotide sequence that comprises a CRISPR array including direct repeats;
    (b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat.
148. The composition of embodiment 146, wherein the Cas12a tracrRNA is present in a molar excess, relative to the Cas12a nuclease.
149. The composition of embodiment 146, wherein the Cas12a tracrRNA is present in a molar amount that is at least 10-fold greater than the molar amount of the Cas12a nuclease.
150. The composition of embodiment 146, wherein the eukaryotic cell is a cell of a non-human animal, an invertebrate, a vertebrate, a mollusk, an arthropod, an insect, a fish, a reptile, an amphibian, a bird, a mammal, a primate, a non-human primate, a human, a plant, or a fungus.
151. The composition of embodiment 146, wherein the eukaryotic cell comprises a cell of a cell line or a cell of a multicellular organism, and wherein the genetic locus to be modified comprises a locus of interest in the genome of the eukaryotic cell.

152. The composition of embodiment 146, wherein the eukaryotic cell is in vitro, ex vivo, or in vivo.

153. The composition of embodiment 146, wherein the eukaryotic cell comprises a non-human animal or human stem cell or a non-human animal or human stem cell line.

154. The composition of embodiment 146, wherein the Cas12a tracrRNA is provided:
    (a) as DNA encoding a first RNA molecule comprising the Cas12a tracrRNA and comprising a restriction endonuclease cleavage site that is suitable for insertion of a sequence coding for a functional RNA moiety; or
    (b) as a functional RNA molecule comprising the Cas12a tracrRNA and a functional RNA moiety, or as a polynucleotide encoding the functional RNA molecule; or
    (c) by the DNA expression system of embodiment 18; or
    (d) by the DNA expression system of embodiment 37.

155. The composition of embodiment 146, wherein the Cas12a tracrRNA is provided as DNA encoding a first RNA molecule comprising the Cas12a tracrRNA and comprising a restriction endonuclease cleavage site that is suitable for insertion of a sequence coding for a functional RNA moiety, and wherein the functional RNA moiety is at least one selected from the group consisting of:
    (a) a nucleotide sequence for annealing to a donor polynucleotide;
    (b) a nucleotide sequence for annealing to the crRNA 3' extension;
    (c) a terminator sequence;
    (d) an RNA aptamer;
    (e) an enzymatically active RNA sequence;
    (f) a detectable label; and
    (g) an RNA sequence forming at least partially double-stranded RNA.

156. The composition of embodiment 146, wherein the Cas12a tracrRNA is provided as DNA encoding a first RNA molecule comprising the Cas12a tracrRNA and comprising a restriction endonuclease cleavage site that is suitable for insertion of a sequence coding for a functional RNA moiety, wherein the functional RNA moiety comprises RNA forming at least partially double-stranded RNA capable of silencing a gene.

157. The composition of embodiment 146, wherein the Cas12a tracrRNA is provided as DNA encoding a first RNA molecule comprising the Cas12a tracrRNA and comprising a restriction endonuclease cleavage site that is suitable for insertion of a sequence coding for a functional RNA moiety, wherein the functional RNA moiety comprises an RNA sequence for annealing to a donor polynucleotide, and wherein the composition further comprises the donor polynucleotide.

158. The composition of embodiment 146, wherein the Cas12a tracrRNA is provided as a functional RNA molecule comprising the Cas12a tracrRNA and a functional RNA moiety, or as a polynucleotide encoding the functional RNA molecule, and wherein the functional RNA moiety is at least one selected from the group consisting of:
    (a) a nucleotide sequence for annealing to a donor polynucleotide;
    (b) a nucleotide sequence for annealing to the crRNA 3' extension;
    (c) a terminator sequence;
    (d) an RNA aptamer;
    (e) an enzymatically active RNA sequence;
    (f) a detectable label; and
    (g) an RNA sequence forming at least partially double-stranded RNA.

159. The composition of embodiment 146, wherein the Cas12a tracrRNA is provided as a functional RNA molecule comprising the Cas12a tracrRNA and a functional RNA moiety, or as a polynucleotide encoding the functional RNA molecule, and wherein the functional RNA moiety comprises RNA forming at least partially double-stranded RNA capable of silencing a gene.

160. The composition of embodiment 146, wherein the Cas12a tracrRNA is provided as a functional RNA molecule comprising the Cas12a tracrRNA and a functional RNA moiety, or as a polynucleotide encoding the functional RNA molecule, wherein the functional RNA moiety comprises an RNA sequence for annealing to a donor polynucleotide, and wherein the composition further comprises the donor polynucleotide.

161. The method of any one of embodiments 102-122, wherein modification of the locus of interest occurs at a greater frequency compared to a control method, wherein a control engineered system identical to the engineered system except for the absence of the Cas12a tracrRNA is delivered to the locus of interest.

162. A method of modifying a target sequence in a locus of interest of a eukaryotic cell comprising delivering the engineered system according to embodiment 92 or 93 to the locus of interest, wherein the spacer sequence hybridizes with the target sequence, whereby modification of the locus of interest occurs at a greater frequency compared to a control method, wherein a control engineered system identical to the engineered system except for the absence of the Cas12a tracrRNA is delivered to the locus of interest.

All cited patents and patent publications referred to in this application are incorporated herein by reference in their entirety. All of the materials and methods disclosed and claimed herein can be made and used without undue experimentation as instructed by the above disclosure and illustrated by the examples. Although the materials and methods of this disclosure have been described in terms of embodiments and illustrative examples, it will be apparent to those of skill in the art that substitutions and variations can be applied to the materials and methods described herein without departing from the concept, spirit, and scope of the invention. For instance, while the particular examples provided illustrate the methods and embodiments described herein using a specific plant, the principles in these examples are applicable to any plant of interest. All such similar substitutes and modifications apparent to those skilled in the art are deemed to be within the spirit, scope, and concept of the invention as encompassed by the embodiments of the inventions recited herein and the specification and appended claims.

What is claimed:
1. A DNA expression system comprising
   (a) DNA sequence for a first promoter; and
   (b) operably linked and heterologous to the first promoter, a DNA encoding a first RNA molecule comprising a Cas12a tracrRNA and comprising a restriction endonuclease cleavage site that is suitable for insertion of a sequence coding for a functional RNA moiety, wherein the Cas12a tracrRNA comprises a sequence selected from the group consisting of SEQ ID NOs:1, 3, 6, 139-146, and 149-169; and
   (c) optionally, a terminator 3' to and operably linked to the DNA encoding the first RNA molecule.
2. The DNA expression system of claim 1, further comprising:
   (d) optionally, a DNA sequence for a second promoter;
   (e) operably linked and heterologous to the first promoter or the second promoter, a DNA encoding a Cas12a crRNA capable of hybridizing with a segment of the first RNA molecule; and
   (f) optionally, a terminator 3' to and operably linked to the DNA encoding the Cas12a crRNA.
3. The DNA expression system of claim 2, wherein the first promoter and the DNA encoding the first RNA molecule and the DNA encoding the Cas12a crRNA are contained in a single construct.
4. The DNA expression system of claim 2, comprising the second promoter operably linked to the Cas12a crRNA, wherein the first promoter and the DNA encoding the first RNA molecule are contained in a first construct, and the second promoter and the DNA encoding the Cas12a crRNA are contained in a second construct, and wherein the first construct and the second construct are provided (a) in a single vector, or (b) in separate vectors.
5. The DNA expression system of claim 2, wherein the DNA encoding the Cas12a crRNA comprises a 3' extension.
6. The DNA expression system of claim 1, wherein the Cas12a tracrRNA further comprises a 5' extension.
7. The DNA expression system of claim 2, wherein the Cas12a crRNA is capable of complexing with a Cas12a nuclease to form a Cas12a ribonucleoprotein complex.
8. The DNA expression system of claim 7, wherein the Cas12a nuclease is:
   (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum*, *Eubacterium eligens*, *Moraxella bovoculi* 237, *Leptospira inadai*, Lachnospiraceae bacterium ND2006, *Porphyromonas crevioricanis* 3, *Prevotella disiens* and *Porphyromonas macacae*; or
   (b) a Cas12a nuclease selected from the group consisting of LbCas12a, AsCas12a, FnCas12a, and a deactivated Cas12a nuclease; or
   (c) a Cas12a nuclease having at least 80% sequence identity with a sequence selected from the group consisting of SEQ ID NOs:11, 107-114, 116-136, and 172; or
   (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801 I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291 L, D908A, E993A, and D1263A; and (3) a variant FnCpf1 that differs from a wild-type FnCpf1 sequence (SEQ ID NO:172) in containing at least one point mutation selected from the group consisting of 1339P, L342F, Q588K, F1017Q, K1047E, N1118D, F1128Y, L867I, D917A, E1006A, and D1255A.
9. The DNA expression system of claim 1, wherein the first promoter has a DNA sequence selected from the group consisting of SEQ ID NOs:16-71.
10. A method of tethering a functional RNA molecule to a Cas12a crRNA, the method comprising hybridizing
    (a) a functional RNA molecule comprising a Cas12a tracrRNA and a functional RNA moiety, wherein the Cas12a tracrRNA comprises a sequence selected from the group consisting of SEQ ID NOs:1, 3, 6, 139-146, and 149-169; and
    (b) a Cas12a crRNA that is capable of hybridizing with a segment of the functional RNA molecule;
    thereby tethering the functional RNA molecule to the Cas12a crRNA.
11. The method of claim 10, wherein the functional RNA molecule is provided by transcription of a DNA molecule comprising a DNA molecule encoding the Cas12a tracrRNA and a DNA molecule encoding the functional RNA moiety, wherein the DNA molecule encoding the functional RNA moiety is or has been inserted at a restriction endonuclease cleavage site in or adjacent to the DNA molecule encoding the Cas12a tracrRNA.
12. The method of claim 10, wherein the functional RNA moiety is
    at least one RNA selected from the group consisting of:
    (a) an RNA sequence for annealing to a donor polynucleotide;
    (b) an RNA sequence for annealing to a 3' extension to the crRNA;
    (c) a terminator sequence;
    (d) an RNA aptamer;
    (e) a ribozyme;
    (f) an RNA comprising a detectable label;
    (g) an RNA bar-coding sequence; and
    (h) an RNA sequence forming at least partially double-stranded RNA.
13. The method of claim 10, wherein the Cas12a crRNA further comprises a 3' extension.
14. The method of claim 10, wherein the Cas12a crRNA is complexed with, or is capable of complexing with, a Cas12a nuclease to form a Cas12a ribonucleoprotein complex containing the functional RNA molecule.
15. The method of claim 14, wherein the Cas12a nuclease is:
    (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacte- rium MA2020, *Candidatus* Methanoplasma *termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801 I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A.

\* \* \* \* \*

SEQUENCE LISTING

<160> NUMBER OF SEQ ID NOS: 203

<210> SEQ ID NO 1
<211> LENGTH: 84
<212> TYPE: RNA
<213> ORGANISM: Unknown
<220> FEATURE:
<223> OTHER INFORMATION: Lachnospiraceae bacterium ND2006

<400> SEQUENCE: 1
acuuauacua aauuuuaacu guauacuuuc ccaaaauacc auaggcucuc ugaaucucuu    60
aacccagauu ccaagggcuu uuuu    84

<210> SEQ ID NO 2
<211> LENGTH: 84
<212> TYPE: DNA
<213> ORGANISM: Unknown
<220> FEATURE:
<223> OTHER INFORMATION: Lachnospiraceae bacterium ND2006

<400> SEQUENCE: 2
acttatacta aattttaact gtatactttc ccaaatacc ataggctctc tgaatctctt    60
aacccagatt ccagggctt tttt    84

<210> SEQ ID NO 3
<211> LENGTH: 65
<212> TYPE: RNA
<213> ORGANISM: Unknown
<220> FEATURE:
<223> OTHER INFORMATION: Lachnospiraceae bacterium ND2006

<400> SEQUENCE: 3
aauugcaaau cuuugaaaua augcagacuu aaauuuauaa auucauggaa uaaggugauu    60
uuauu    65

<210> SEQ ID NO 4
<211> LENGTH: 65
<212> TYPE: DNA
<213> ORGANISM: Unknown
<220> FEATURE:
<223> OTHER INFORMATION: Lachnospiraceae bacterium ND2006

<400> SEQUENCE: 4
aattgcaaat ctttgaaata atgcagactt aaatttataa attcatggaa taaggtgatt    60
ttatt    65

<210> SEQ ID NO 5
<211> LENGTH: 36
<212> TYPE: DNA
<213> ORGANISM: Unknown
<220> FEATURE:
<223> OTHER INFORMATION: Lachnospiraceae bacterium ND2006

<400> SEQUENCE: 5
atctacactt agtagaaatt atttaatctt tgaaac    36

<210> SEQ ID NO 6
<211> LENGTH: 72
<212> TYPE: RNA
<213> ORGANISM: Unknown
<220> FEATURE:
<223> OTHER INFORMATION: Acidaminococcus sp. BV3L6

<400> SEQUENCE: 6

```
cauugucuaa ccugcaaacc uccaacuuac uauugcuaag gaguauauau uuuguauaaa    60
aggucuuuuu uc                                                       72

<210> SEQ ID NO 7
<211> LENGTH: 72
<212> TYPE: DNA
<213> ORGANISM: Unknown
<220> FEATURE:
<223> OTHER INFORMATION: Acidaminococcus sp. BV3L6

<400> SEQUENCE: 7
cattgtctaa cctgcaaacc tccaacttac tattgctaag gagtatatat tttgtataaa    60 aggtctttt tc                                                        72

<210> SEQ ID NO 8
<211> LENGTH: 35
<212> TYPE: DNA
<213> ORGANISM: Unknown
<220> FEATURE:
<223> OTHER INFORMATION: Acidaminococcus sp. BV3L6

<400> SEQUENCE: 8
atctacaaga gtagaaatta aaaggtctt ttgac                               35

<210> SEQ ID NO 9
<211> LENGTH: 128
<212> TYPE: DNA
<213> ORGANISM: Unknown
<220> FEATURE:
<223> OTHER INFORMATION: Lachnospiraceae bacterium ND2006

<400> SEQUENCE: 9
aattgcaaat ctttgaaata atgcagactt aaatttataa attcatggaa taaggtgatt    60
ttattgtgaa aaaatactcg tattttgttg gaaaaacatc ttttgttgt ataatatgat   120 gatatacg                                                          128

<210> SEQ ID NO 10
<211> LENGTH: 141
<212> TYPE: DNA
<213> ORGANISM: Artificial sequence
<220> FEATURE:
<223> OTHER INFORMATION: Synthetic construct

<400> SEQUENCE: 10
gttttagagc taggccaaca tgaggatcac ccatgtctgc agggcctagc aagttaaaat    60
aaggctagtc cgttatcaac ttggccaaca tgaggatcac ccatgtctgc agggccaagt   120
ggcaccgagt cggtgctttt t                                            141

<210> SEQ ID NO 11
<211> LENGTH: 1246
<212> TYPE: PRT
<213> ORGANISM: Artificial sequence
<220> FEATURE:
<223> OTHER INFORMATION: Synthetic construct

<400> SEQUENCE: 11

Met Leu Lys Asn Val Gly Ile Asp Arg Leu Asp Val Glu Lys Gly Arg
 1               5                  10                  15

Lys Asn Met Ser Lys Leu Glu Lys Phe Thr Asn Cys Tyr Ser Leu Ser
                20                  25                  30
```

```
Lys Thr Leu Arg Phe Lys Ala Ile Pro Val Gly Lys Thr Gln Glu Asn
                35                  40                  45

Ile Asp Asn Lys Arg Leu Leu Val Glu Asp Glu Lys Arg Ala Glu Asp
 50                  55                  60

Tyr Lys Gly Val Lys Lys Leu Leu Asp Arg Tyr Tyr Leu Ser Phe Ile
 65                  70                  75                  80

Asn Asp Val Leu His Ser Ile Lys Leu Lys Asn Leu Asn Asn Tyr Ile
                 85                  90                  95

Ser Leu Phe Arg Lys Lys Thr Arg Thr Glu Lys Glu Asn Lys Glu Leu
                100                 105                 110

Glu Asn Leu Glu Ile Asn Leu Arg Lys Glu Ile Ala Lys Ala Phe Lys
                115                 120                 125

Gly Asn Glu Gly Tyr Lys Ser Leu Phe Lys Lys Asp Ile Ile Glu Thr
                130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
                165                 170                 175

Glu Asn Met Phe Ser Glu Glu Ala Lys Ser Thr Ser Ile Ala Phe Arg
                180                 185                 190

Cys Ile Asn Glu Asn Leu Thr Arg Tyr Ile Ser Asn Met Asp Ile Phe
                195                 200                 205

Glu Lys Val Asp Ala Ile Phe Asp Lys His Glu Val Gln Glu Ile Lys
                210                 215                 220

Glu Lys Ile Leu Asn Ser Asp Tyr Asp Val Glu Asp Phe Phe Glu Gly
225                 230                 235                 240

Glu Phe Phe Asn Phe Val Leu Thr Gln Glu Gly Ile Asp Val Tyr Asn
                245                 250                 255

Ala Ile Ile Gly Gly Phe Val Thr Glu Ser Gly Glu Lys Ile Lys Gly
                260                 265                 270

Leu Asn Glu Tyr Ile Asn Leu Tyr Asn Gln Lys Thr Lys Gln Lys Leu
                275                 280                 285

Pro Lys Phe Lys Pro Leu Tyr Lys Gln Val Leu Ser Asp Arg Glu Ser
290                 295                 300

Leu Ser Phe Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
                325                 330                 335

Lys Lys Leu Glu Lys Leu Phe Lys Asn Phe Asp Glu Tyr Ser Ser Ala
                340                 345                 350

Gly Ile Phe Val Lys Asn Gly Pro Ala Ile Ser Thr Ile Ser Lys Asp
                355                 360                 365

Ile Phe Gly Glu Trp Asn Val Ile Arg Asp Lys Trp Asn Ala Glu Tyr
                370                 375                 380

Asp Asp Ile His Leu Lys Lys Lys Ala Val Val Thr Glu Lys Tyr Glu
385                 390                 395                 400

Asp Asp Arg Arg Lys Ser Phe Lys Lys Ile Gly Ser Phe Ser Leu Glu
                405                 410                 415

Gln Leu Gln Glu Tyr Ala Asp Ala Asp Leu Ser Val Val Glu Lys Leu
                420                 425                 430

Lys Glu Ile Ile Ile Gln Lys Val Asp Glu Ile Tyr Lys Val Tyr Gly
                435                 440                 445

Ser Ser Glu Lys Leu Phe Asp Ala Asp Phe Val Leu Glu Lys Ser Leu
```

```
                450             455             460
Lys Lys Asn Asp Ala Val Val Ala Ile Met Lys Asp Leu Leu Asp Ser
465                 470                 475                 480

Val Lys Ser Phe Glu Asn Tyr Ile Lys Ala Phe Phe Gly Glu Gly Lys
                485                 490                 495

Glu Thr Asn Arg Asp Glu Ser Phe Tyr Gly Asp Phe Val Leu Ala Tyr
                500                 505                 510

Asp Ile Leu Leu Lys Val Asp His Ile Tyr Asp Ala Ile Arg Asn Tyr
                515                 520                 525

Val Thr Gln Lys Pro Tyr Ser Lys Asp Lys Phe Lys Leu Tyr Phe Gln
                530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Tyr Leu Ala Ile Met
                565                 570                 575

Asp Lys Lys Tyr Ala Lys Cys Leu Gln Lys Ile Asp Lys Asp Asp Val
                580                 585                 590

Asn Gly Asn Tyr Glu Lys Ile Asn Tyr Lys Leu Leu Pro Gly Pro Asn
                595                 600                 605

Lys Met Leu Pro Lys Val Phe Phe Ser Lys Lys Trp Met Ala Tyr Tyr
                610                 615                 620

Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
                645                 650                 655

Phe Lys Asp Ser Ile Ser Arg Tyr Pro Lys Trp Ser Asn Ala Tyr Asp
                660                 665                 670

Phe Asn Phe Ser Glu Thr Glu Lys Tyr Lys Asp Ile Ala Gly Phe Tyr
                675                 680                 685

Arg Glu Val Glu Glu Gln Gly Tyr Lys Val Ser Phe Glu Ser Ala Ser
                690                 695                 700

Lys Lys Glu Val Asp Lys Leu Val Glu Glu Gly Lys Leu Tyr Met Phe
705                 710                 715                 720

Gln Ile Tyr Asn Lys Asp Phe Ser Asp Lys Ser His Gly Thr Pro Asn
                725                 730                 735

Leu His Thr Met Tyr Phe Lys Leu Leu Phe Asp Glu Asn Asn His Gly
                740                 745                 750

Gln Ile Arg Leu Ser Gly Gly Ala Glu Leu Phe Met Arg Arg Ala Ser
                755                 760                 765

Leu Lys Lys Glu Glu Leu Val Val His Pro Ala Asn Ser Pro Ile Ala
                770                 775                 780

Asn Lys Asn Pro Asp Asn Pro Lys Lys Thr Thr Thr Leu Ser Tyr Asp
785                 790                 795                 800

Val Tyr Lys Asp Lys Arg Phe Ser Glu Asp Gln Tyr Glu Leu His Ile
                805                 810                 815

Pro Ile Ala Ile Asn Lys Cys Pro Lys Asn Ile Phe Lys Ile Asn Thr
                820                 825                 830

Glu Val Arg Val Leu Leu Lys His Asp Asp Asn Pro Tyr Val Ile Gly
                835                 840                 845

Ile Ala Arg Gly Glu Arg Asn Leu Leu Tyr Ile Val Val Val Asp Gly
                850                 855                 860

Lys Gly Asn Ile Val Glu Gln Tyr Ser Leu Asn Glu Ile Ile Asn Asn
865                 870                 875                 880
```

```
Phe Asn Gly Ile Arg Ile Lys Thr Asp Tyr His Ser Leu Leu Asp Lys
            885                 890                 895

Lys Glu Lys Glu Arg Phe Glu Ala Arg Gln Asn Trp Thr Ser Ile Glu
        900                 905                 910

Asn Ile Lys Glu Leu Lys Ala Gly Tyr Ile Ser Gln Val Val His Lys
            915                 920                 925

Ile Cys Glu Leu Val Glu Lys Tyr Asp Ala Val Ile Ala Leu Glu Asp
    930                 935                 940

Leu Asn Ser Gly Phe Lys Asn Ser Arg Val Lys Val Glu Lys Gln Val
945                 950                 955                 960

Tyr Gln Lys Phe Glu Lys Met Leu Ile Asp Lys Leu Asn Tyr Met Val
            965                 970                 975

Asp Lys Lys Ser Asn Pro Cys Ala Thr Gly Gly Ala Leu Lys Gly Tyr
        980                 985                 990

Gln Ile Thr Asn Lys Phe Glu Ser  Phe Lys Ser Met Ser  Thr Gln Asn
            995                 1000                1005

Gly Phe  Ile Phe Tyr Ile Pro  Ala Trp Leu Thr Ser  Lys Ile Asp
        1010                 1015                1020

Pro Ser  Thr Gly Phe Val Asn  Leu Leu Lys Thr Lys  Tyr Thr Ser
    1025                 1030                1035

Ile Ala  Asp Ser Lys Lys Phe  Ile Ser Ser Phe Asp  Arg Ile Met
    1040                 1045                1050

Tyr Val  Pro Glu Glu Asp Leu  Phe Glu Phe Ala Leu  Asp Tyr Lys
    1055                 1060                1065

Asn Phe  Ser Arg Thr Asp Ala  Asp Tyr Ile Lys Lys  Trp Lys Leu
    1070                 1075                1080

Tyr Ser  Tyr Gly Asn Arg Ile  Arg Ile Phe Arg Asn  Pro Lys Lys
    1085                 1090                1095

Asn Asn  Val Phe Asp Trp Glu  Glu Val Cys Leu Thr  Ser Ala Tyr
    1100                 1105                1110

Lys Glu  Leu Phe Asn Lys Tyr  Gly Ile Asn Tyr Gln  Gln Gly Asp
    1115                 1120                1125

Ile Arg  Ala Leu Leu Cys Glu  Gln Ser Asp Lys Ala  Phe Tyr Ser
    1130                 1135                1140

Ser Phe  Met Ala Leu Met Ser  Leu Met Leu Gln Met  Arg Asn Ser
    1145                 1150                1155

Ile Thr  Gly Arg Thr Asp Val  Asp Phe Leu Ile Ser  Pro Val Lys
    1160                 1165                1170

Asn Ser  Asp Gly Ile Phe Tyr  Asp Ser Arg Asn Tyr  Glu Ala Gln
    1175                 1180                1185

Glu Asn  Ala Ile Leu Pro Lys  Asn Ala Asp Ala Asn  Gly Ala Tyr
    1190                 1195                1200

Asn Ile  Ala Arg Lys Val Leu  Trp Ala Ile Gly Gln  Phe Lys Lys
    1205                 1210                1215

Ala Glu  Asp Glu Lys Leu Asp  Lys Val Lys Ile Ala  Ile Ser Asn
    1220                 1225                1230

Lys Glu  Trp Leu Glu Tyr Ala  Gln Thr Ser Val Lys  His
    1235                 1240                1245

<210> SEQ ID NO 12
<211> LENGTH: 72
<212> TYPE: DNA
<213> ORGANISM: Artificial sequence
<220> FEATURE:
```

<223> OTHER INFORMATION: Synthetic construct

<400> SEQUENCE: 12

```
gtttcaaaga ttaaataatt tctactaagt gtagattgga cagagctcca agtgaccaaa    60
accgtatatc at                                                        72
```

<210> SEQ ID NO 13
<211> LENGTH: 678
<212> TYPE: DNA
<213> ORGANISM: Zea mays

<400> SEQUENCE: 13

```
atagagagag aagaggggtc gtgtagtagt gcttaaactg tacatgaaca gcagtagtgt    60
tacagaagct aaactcaacc agagctccac caaagacaaa gagggtctac ttccatcacc   120
gtcttgctcg gtcacttgga gctctgtcca taaattaaac ccatcgtggc atatctgtag   180
gcatctaccc cgtcttcgtc gtccgttcct cactagctac caagaggtcg ccattattgc   240
caacatagag tgtacgtgga tgtctatata tatgcctact tgcacccata tggcataggc   300
gttcgatccc cttagcgcgg aggagagctc ctccggttct tctctaccct tcgcatggaa   360
gttcttgcat tgcttcgttg cttctctagt ttcttccttc tacgtctttc cagcatacgc   420
atgcccctcg tccgccggtt cacgaggcat cgtctgatga tcagtagata ataagcaata   480
taatactgat ctagaatcga gttgttgtac tcttcgcaga taggttcgtt ccttcacata   540
gaagcgagta cagactacag accacacagt atcagctggc acgaaacgaa aatggttact   600
tgcaaattgc atgcacgagc tagaattata ttcttctaat cttcttcgtt gactttctgg   660
cttcagcagg cgcgtgat                                                 678
```

<210> SEQ ID NO 14
<211> LENGTH: 1422
<212> TYPE: DNA
<213> ORGANISM: Artificial sequence
<220> FEATURE:
<223> OTHER INFORMATION: Synthetic construct

<400> SEQUENCE: 14

```
atggcttcaa actttactca gttcgtgctc gtggacaatg gtgggacagg ggatgtgaca    60
gtggctcctt ctaatttcgc taatggggtg gcagagtgga tcagctccaa ctcacggagc   120
caggcctaca aggtgacatg cagcgtcagg cagtctagtg cccagaagag aaagtatacc   180
atcaaggtgg aggtccccaa agtggctacc cagacagtgg gcggagtcga actgcctgtc   240
gccgcttgga ggtcctacct gaacatggag ctcactatcc caattttcgc taccaattct   300
gactgtgaac tcatcgtgaa ggcaatgcag gggctcctca agacggtaa tcctatccct   360
tccgccatcg ccgctaactc aggtatctac agcgctggag gaggtggaag cggaggagga   420
ggaagcggag gaggaggtag cggacctaag aaaaagagga aggtggcggc cgctggatcc   480
ccttcagggc agatcagcaa ccaggccctg gctctggccc ctagctccgc tccagtgctg   540
gcccagacta tggtgcccct cagtgctatg gtgcctctgg cccagccacc tgctccagcc   600
cctgtgctga ccccaggacc accccagtca ctgagcgctc cagtgcccaa gtctacacag   660
gccggcgagg ggactctgag tgaagctctg ctgcacctgc agttcgacgc tgatgaggac   720
ctgggagctc tgctggggaa cagcaccgat cccggagtgt tcacagatct ggcctccgtg   780
gacaactctg agtttcagca gctgctgaat cagggcgtgt ccatgtctca tagtacagcc   840
gaaccaatgc tgatggagta ccccgaagcc attacccggc tggtgaccgg cagccagcgg   900
```

```
cccccccgacc ccgctccaac tccccctggga accagcggcc tgcctaatgg gctgtccgga    960
gatgaagact tctcaagcat cgctgatatg gactttagtg ccctgctgtc acagatttcc   1020
tctagtgggc agggaggagg tggaagcggc ttcagcgtgg acaccagtgc cctgctggac   1080
ctgttcagcc cctcggtgac cgtgcccgac atgagcctgc ctgaccttga cagcagcctg   1140
gccagtatcc aagagctcct gtctccccag gagcccccca ggcctcccga ggcagagaac   1200
agcagcccgg attcagggaa gcagctggtg cactacacag cgcagccgct gttcctgctg   1260
gaccccggct ccgtggacac cgggagcaac gacctgccgg tgctgtttga gctgggagag   1320
ggctcctact tctccgaagg ggacggcttc gccgaggacc ccaccatctc cctgctgaca   1380
ggctcggagc ctcccaaagc caaggacccc actgtctcct ga                      1422
```

<210> SEQ ID NO 15
<211> LENGTH: 138
<212> TYPE: DNA
<213> ORGANISM: Artificial sequence
<220> FEATURE:
<223> OTHER INFORMATION: Synthetic construct

<400> SEQUENCE: 15

```
atggatgctc ttgacgattt tgacctcgat atgctcgacg ctcttgatga ttttgatctc     60
gacatgctcg atgcacttga tgactttgac cttgacatgc tcgacgcact cgatgacttc    120
gacctcgaca tgctttag                                                  138
```

<210> SEQ ID NO 16
<211> LENGTH: 400
<212> TYPE: DNA
<213> ORGANISM: Triticum aestivum

<400> SEQUENCE: 16

```
ggcggcaggg agagttttaa cattgactag cgtgctgata atttgtgaga ataataatt      60 gacaagtaga tactgacatt tgagaagagc ttctgaactg ttattagtaa caaaaatgga    120
aagctgatgc acggaaaaag gaaagaaaaa gccatacttt ttttaggta ggaaaagaaa     180 aagccatacg agactgatgt ctctcagatg ggccgggatc tgtctatcta gcaggcagca    240
gccctaccaa cctcacgggc cagcaattac gagtccttct aaaacgtccc gccgagggcg    300
cgtggccgtg ctgtgcagca gcacgtctaa cattagtccc acctcgccag tttacaggga    360
gcagaaccag cttataagcg gaggcgcggc accaagaagc                          400
```

<210> SEQ ID NO 17
<211> LENGTH: 299
<212> TYPE: DNA
<213> ORGANISM: Agrobacterium tumefaciens

<400> SEQUENCE: 17

```
gatcatgagc ggagaattaa gggagtcacg ttatgacccc cgccgatgac gcgggacaag     60
ccgttttacg tttggaactg acagaaccgc aacgttgaag gagccactca gccgcgggtt    120
tctggagttt aatgagctaa gcacatacgt cagaaaccat tattgcgcgt tcaaaagtcg    180
cctaaggtca ctatcagcta gcaaatattt cttgtcaaaa atgctccact gacgttccat    240 aaattccccct cggtatccaa ttagagtctc atattcactc tcaatccaaa taatctgca    299
```

<210> SEQ ID NO 18
<211> LENGTH: 899
<212> TYPE: DNA

<213> ORGANISM: Zea mays

<400> SEQUENCE: 18

| | | | | | |
|---|---|---|---|---|---|
| tgcagtgcag | cgtgacccgg | tcgtgcccct | ctctagagat | aatgagcatt | gcatgtctaa | 60
| gttataaaaa | attaccacat | atttttttg | tcacacttgt | ttgaagtgca | gtttatctat | 120
| ctttatacat | atatttaaac | tttactctac | gaataatata | atctatagta | ctacaataat | 180
| atcagtgttt | tagagaatca | tataaatgaa | cagttagaca | tggtctaaag | gacaattgag | 240
| tatttgaca | acaggactct | acagttttat | cttttagtg | tgcatgtgtt | ctccttttt | 300
| tttgcaaata | gcttcaccta | tataatactt | catccatttt | attagtacat | ccatttaggg | 360
| tttagggtta | atggttttta | tagactaatt | tttttagtac | atctatttta | ttctatttta | 420
| gcctctaaat | taagaaaact | aaaactctat | tttagtttt | ttatttaata | atttagatat | 480
| aaaatagaat | aaaataaagt | gactaaaaat | taaacaaata | ccctttaaga | aattaaaaaa | 540
| actaaggaaa | cattttctt | gtttcgagta | gataatgcca | gcctgttaaa | cgccgtcgac | 600
| gagtctaacg | gacaccaacc | agcgaaccag | cagcgtcgcg | tcgggccaag | cgaagcagac | 660
| ggcacggcat | ctctgtcgct | gcctctggac | ccctctcgag | agttccgctc | caccgttgga | 720
| cttgctccgc | tgtcggcatc | cagaaattgc | gtggcggagc | ggcagacgtg | agccggcacg | 780
| gcaggcggcc | tcctcctcct | ctcacggcac | cggcagctac | ggggattcc | tttcccaccg | 840
| ctccttcgct | ttcccttcct | cgcccgccgt | aataaataga | cacccctcc | acaccctct | 899

<210> SEQ ID NO 19
<211> LENGTH: 2243
<212> TYPE: DNA
<213> ORGANISM: Solanum lycopersicum

<400> SEQUENCE: 19

| | | | | | |
|---|---|---|---|---|---|
| atcgtatcca | gtgcaccata | tttttggcg | attaccactc | atattattgt | gtttagtaga | 60
| tatttaggt | gcataattga | tctcttcttt | aaaactaggg | gcacttatta | ttatacatcc | 120
| acttgacact | tgctttagtt | ggctattttt | tttattttt | attttttgtc | aactacccca | 180
| attaaattt | tatttgatta | agatattttt | atggacctac | tttataatta | aaaatatttt | 240
| ctatttgaaa | aggaaggaca | aaaatcatac | aattttggtc | caactactcc | tctcttttt | 300
| ttttggctt | tataaaaag | gaaagtgatt | agtaataaat | aattaaataa | tgaaaaaagg | 360
| aggaaataaa | atttttcgaat | taaaatgtaa | aagagaaaaa | ggagagggag | taatcattgt | 420
| ttaactttat | ctaaagtacc | ccaattcgat | tttacatgta | tatcaaatta | tacaaatatt | 480
| ttattaaaat | atagatattg | aataattta | ttattcttga | acatgtaaat | aaaaattatc | 540
| tattatttca | atttttatat | aaactattat | ttgaaatctc | aattatgatt | ttttaatatc | 600
| actttctatc | catgataatt | tcagcttaaa | aagttttgtc | aataattaca | ttaattttgt | 660
| tgatgaggat | gacaagattt | cggtcatcaa | ttacatatac | acaaattgaa | atagtaagca | 720
| acttgatttt | ttttctcata | atgataatga | caaagacacg | aaaagacaat | tcaatattca | 780
| cattgattta | ttttatatg | ataataatta | caataataat | attcttataa | agaaagagat | 840
| caatttgac | tgatccaaaa | atttatttat | ttttactata | ccaacgtcac | taattatatc | 900
| taataatgta | aaacaattca | atcttactta | aatattaatt | tgaataaaac | tattttata | 960
| acgaaattac | taaatttatc | caataacaaa | aaggtcttaa | gaagacataa | attcttttt | 1020
| tgtaatgctc | aaataaattt | gagtaaaaaa | gaatgaaatt | gagtgatttt | ttttaatca | 1080
| taagaaaata | aataattaat | ttcaatataa | taaaacagta | atataatttc | ataaatggaa | 1140

-continued

| | |
|---|---|
| ttcaatactt acctcttaga tataaaaaat aaatataaaa ataaagtgtt tctaataaac | 1200 |
| ccgcaattta aataaaatat ttaatatttt caatcaaatt taaataatta tattaaaata | 1260 |
| tcgtagaaaa agagcaatat ataatacaag aaagaagatt taagtacaat tatcaactat | 1320 |
| tattatactc taattttgtt atatttaatt tcttacggtt aaggtcatgt tcacgataaa | 1380 |
| ctcaaaatac gctgtatgag gacatatttt aaattttaac caataataaa actaagttat | 1440 |
| ttttagtata ttttttttgtt taacgtgact taattttttct tttctagagg agcgtgtaag | 1500 |
| tgtcaacctc attctcctaa ttttcccaac cacataaaaa aaaaataaag gtagcttttg | 1560 |
| cgtgttgatt tggtacacta cacgtcatta ttacacgtgt tttcgtatga ttggttaatc | 1620 |
| catgaggcgg tttcctctag agtcggccat accatctata aaataaagct ttctgcagct | 1680 |
| catttttttca tcttctatct gatttctatt ataatttctc tgaattgcct tcaaatttct | 1740 |
| ctttcaaggt tagaattttt ctctattttt tggttttttgt ttgtttagat tctgagttta | 1800 |
| gttaatcagg tgctgttaaa gccctaaatt ttgagttttt ttcggttgtt ttgatggaaa | 1860 |
| atacctaaca attgagtttt ttcatgttgt tttgtcggag aatgcctaca attggagttc | 1920 |
| ctttcgttgt tttgatgaga aagcccctaa tttgagtgtt tttccgtcga tttgatttta | 1980 |
| aaggtttata ttcgagtttt tttcgtcggt ttaatgagaa ggcctaaaat aggagttttt | 2040 |
| ctggttgatt tgactaaaaa agccatggaa ttttgtgttt ttgatgtcgc tttggttctc | 2100 |
| aaggcctaag atctgagttt ctccggttgt tttgatgaaa aagccctaaa attggagttt | 2160 |
| ttatcttgtg ttttaggttg ttttaatcct tataatttga gttttttcgt tgttctgatt | 2220 |
| gttgttttta tgaatttcct gca | 2243 |

<210> SEQ ID NO 20
<211> LENGTH: 1327
<212> TYPE: DNA
<213> ORGANISM: Arabidopsis thaliana

<400> SEQUENCE: 20

| | |
|---|---|
| gtcgagctgc aggtcaacgg atcaggatat tcttgtttaa gatgttgaac tctatggagg | 60 |
| tttgtatgaa ctgatgatct aggaccggat aagttcccctt cttcatagcg aacttattca | 120 |
| aagaatgttt tgtgtatcat tcttgttaca ttgttattaa tgaaaaaata ttattggtca | 180 |
| ttggactgaa cacgagtgtt aaatatggac caggccccaa ataagatcca ttgatatatg | 240 |
| aattaaataa caagaataaa tcgagtcacc aaaccacttg cctttttttaa cgagacttgt | 300 |
| tcaccaactt gatacaaaag tcattatcct atgcaaatca ataatcatac aaaaatatcc | 360 |
| aataacacta aaaattaaa agaaatggat aatttcacaa tatgttatac gataaagaag | 420 |
| ttacttttcc aagaaattca ctgattttat aagcccactt gcattagata aatggcaaaa | 480 |
| aaaacaaaa aggaaaagaa ataaagcacg aagaattcta gaaaatacga aatacgcttc | 540 |
| aatgcagtgg gacccacggt tcaattattg ccaattttca gctccaccgt atatttaaaa | 600 |
| aataaaacga taatgctaaa aaaatataaa tcgtaacgat cgttaaatct caacggctgg | 660 |
| atcttatgac gaccgttaga aattgtggtt gtcgacgagt cagtaataaa cggcgtcaaa | 720 |
| gtggttgcag ccggcacaca cgagtcgtgt ttatcaactc aaagcacaaa tacttttcct | 780 |
| caacctaaaa ataaggcaat tagccaaaaa caactttgcg tgtaaacaac gctcaataca | 840 |
| cgtgtcattt tattattagc tattgcttca ccgccttagc tttctcgtga cctagtcgtc | 900 |
| ctcgtcttttt cttcttcttc ttctataaaa caatacccaa agagctcttc ttcttcacaa | 960 |

```
ttcagatttc aatttctcaa aatcttaaaa actttctctc aattctctct accgtgatca    1020
aggtaaattt ctgtgttcct tattctctca aaatcttcga ttttgttttc gttcgatccc    1080
aatttcgtat atgttctttg gtttagattc tgttaatctt agatcgaaca cgattttctg    1140
ggtttgatcg ttagatatca tcttaattct cgattagggt ttcatagata tcatccgatt    1200
tgttcaaata atttgagttt tgtcgaataa ttactcttcg atttgtgatt tctatctaga    1260
tctggtgtta gtttctagtt tgtgcgatcg aatttgtcga ttaatctgag ttttttctgat   1320 taacagg                                                               1327

<210> SEQ ID NO 21
<211> LENGTH: 872
<212> TYPE: DNA
<213> ORGANISM: Glycine max

<400> SEQUENCE: 21
tccctaatta atgtgatatt gggaaagata cgtatgcaaa gagaatggta attaatgtga      60
gatgaaactg aaaaatgaca aatgagaaat attggaaaaa tcacacgttg aatgaacgtg     120
agtatatgca tgtagaatta gcaggataat gtaattcaaa atggacgaaa aatgtagaat     180
ggagaactta ttcgctttat taataaaaca aaattaattt acgcatgcat tgaggaagac     240
aaaagttaac cgaatccacc ctaattaatg tgatattgag aaagattttt gttttttggt     300
taatatgata ttgaaaaga tacgttgaaa atataatggt aattaatgtg agaagagact      360
aaaagatgac aaatgagaaa tattggaaaa gtcacgcgtt gaatgaacgg aatataatg     420 caaaatagac gaaagatgta gaatagagaa cttatttgct ttattaataa aatatgaatt    480
tagttaaatt tgacctaaat tgggccatgt acaaattgta cacaaatata cactaagcat    540
agaaacgaaa atataatata ttatttcgga attttgaaca atattttcca aattttcaat    600
aagcaataac attcaaccac gaattctatt tgtttggtca tgacgtcttt agaggccacg    660
catttgactc ctagaatatt ctggacccac cgtaacaact atccgttact tttcttaatc    720
cctaatcttt caagagttct ggattcttct attcgcccta tataaacaac ccctttttct    780
tcgtgcttca ttcatctcaa tcgcaatctc tcaatcgttt tctacataat acaaacctct    840 ctaattttg aagctaatta tacccaatct cg                                    872

<210> SEQ ID NO 22
<211> LENGTH: 1427
<212> TYPE: DNA
<213> ORGANISM: Glycine max

<400> SEQUENCE: 22
aacaattaga tgatacccat tgcccttacg ttttctttaa catcaattat tgttttgtc      60 aacaagctat cttttagttt tatttttattg gtaaaaaata tgtcgccttc aagttgcatc    120
atttaacaca tctcgtcatt agaaaaataa aactcttccc taaacgatta gtagaaaaaa    180
tcattcgata ataaataaga aagaaaaatt agaaaaaaat aacttcattt taaaaaaatc    240
attaaggcta tattttttaa atgactaatt ttatatagac tgtaactaaa agtatacaat    300
ttattatgct atgtatctta aagaattact tataaaaatc tacggaagaa tatcttacaa    360
agtgaaaaac aaatgagaaa gaatttagtg ggatgattat gattttattt gaaaattgaa   420
aaaataatta ttaaagactt tagtggagta agaaagcttt cctattagtc ttttcttatc    480
cataaaaaaa aaaaaaaaaa tctagcgtga cagcttttcc atagatttta ataatgtaaa    540
atactggtag cagccgaccg ttcaggtaat ggacactgtg gtcctaactt gcaacgggtg    600
```

```
cgggcccaat ttaataacgc cgtggtaacg gataaagcca agcgtgaagc ggtgaaggta      660
catctctgac tccgtcaaga ttacgaaacc gtcaactacg aaggactccc cgaaatatca      720
tctgtgtcat aaacaccaag tcacaccata catgggcacg cgtcacaata tgattggaga      780
acggttccac cgcatatgct ataaaatgcc cccacacccc tcgaccctaa tcgcacttca      840
attgcaatca aattagttca ttctctttgc gcagttccct acctctcctt tcaaggttcg      900
tagatttctt ctgtttttt ttcttcttct ttattgtttg ttctacatca gcatgatgtt       960
gatttgattg tgttttctat cgtttcatcg attataaatt ttcataatca gaagattcag     1020
cttttattaa tgcaagaacg tccttaattg atgatttat aaccgtaaat taggtctaat      1080
tagagttttt ttcataaaga ttttcagatc cgtttacaac aagccttaat tgttgattct     1140
gtagtcgtag attaaggttt ttttcatgaa ctacttcaga tccgttaaac aacagcctta     1200
tttgttgata cttcactcgt ttttcaagaa attgttcaga tccgttgata aaagccttat     1260
tcgttgattc tgtatggtat ttcaagagat attgctcagg tcctttagca actacccttat    1320 ttgttgattc tgtggccata gattaggatt tttttttcacg aaattgcttc ttgaaattac    1380
gtgatggatt ttgattctga tttatcttgt gattgttgac tctacag                   1427

<210> SEQ ID NO 23
<211> LENGTH: 1294
<212> TYPE: DNA
<213> ORGANISM: Glycine max

<400> SEQUENCE: 23
tccattattc gggatttagc aaattgtttg tttcttcaat atttgattga atactaattt       60
aaaactaaaa taagagagcg tgacaaatca aaaatatagt gtgttatata atgtttccgt      120
gcaggagatc atataggacc actagttgtt aatcttagtc acaaaacaat acatgtcttg      180
caaagaaaaa atcgtagaca taatctgtta cattttgttt agaaaagttt tgttcagcaa      240
aatgttttca tttaactcga tttgatatgc tgtggttttg gtattttttac acacagtagt    300 ttttttttta attattgtta agcgaattta aaatagttat tattattatt aagaggcttt      360
taaatactga aggtgtaaaa aaaatgcttc aattactttta aactttaga catcttaatt     420 ttaaccaaaa tatggagcta aaatgaatc acgaagaaag tatgaaagaa ttcctccatt       480
tttttagcat tttattttgt cttttaaaaat aagaaataaa gtaatatttt aaaaattatt    540
agccagagta aaaaaaattt attaaggctc tttatattta cattttttta aatcattaat     600
aatattccta aagtctctta tctatgcaag atttagagtg taatatttt taatttatgt       660 gattaaacaa gtgaagttaa tgaattattg aactcttaaa tactcctaat ttataggtat     720
tgagtgttca aggtgttgaa taatccatta atttcaacca accaaaatat tttgatctaa     780 atttattat tattgagta gaattcaacc acattcaaag ttgttttctt atgttagagt      840
aacaactttt ttttttttt tctaaatact cataaatcta atgactcaat tcattcacat      900
gacactttat tttaattatg atgttcaatt tcttagaaaa ttcgaagttt aacttttggg    960
agaccaaatt taaatcaaca tgttattaat tgtatttgac agaaaaaagc ttaaaccaaa    1020
cccattccaa actaaaacat tttaattggt tttggtaata atgagtttta gttaaagtca    1080
acctaaattt gcaatgtacg cgtttgcgtc gccgtcatta gaggccagaa ttgactccta    1140
gaatattcta gacctaccct aacaactatc cgttactttt cttaatccct aatatttcaa    1200
gagttctaga ttcttctatt cgccctatat aaacaacctc attctcgatt gcttcctaca    1260
```

```
ccactaaaat atctctctat tattctcgtt ttca                              1294
```

<210> SEQ ID NO 24
<211> LENGTH: 1176
<212> TYPE: DNA
<213> ORGANISM: Glycine max

<400> SEQUENCE: 24

```
caagcagaac actgagacat agaggaggat tgaagtgcag aaaatatata ttacctctat    60
tctaaaataa gtgtcacatt ttgataaaat aaatcgtttt ttattaaata cactccaatt   120
cttggatttc ttggaattct ccaaaaaaaa aaagagattg tgagatatat taaaaaggtc   180
aataaatctt aaaaaatatt tagttttaaa ataaatttaa aataaattta aaatattgtt   240
agaatgttta tcatcttatt agttggcgac ggataaaaaa atgctattag ttgccgaaaa   300
ggactcataa gccagttgcc ctgtcaacgt gggctcgtgg ttccaattcg tccacgtgtc   360
acaacgtgat tgaaagaggt gcctttgcgt tgctataaaa gcgaagccca caccaaaatc   420
atcatcaatc caaatattta atcctatcct atcgtagcaa agaaagaaag aaagaaaacc   480
ctagcttacc ttttcaactt tcaaggtacc ttctgctcct cttctgtttt cgattaagat   540
ttcgttgtt agggttttat gcttttttt tttatcgatc atcggacctg tcgagctatt    600
tgaattttga tctggatttt ttttcgtgtc tttgatttta ccgtctatat aattacgcaa   660
cctggtatcc gttttgaaac ttttgttgat tatttggctt tgtttcaaat tatttgttga   720
ttgaaagtga tcctgatgtt atgaggttat atatttaatt tgtcagaact tggggcatgt   780
attgtgtatt gtatacaggt aaaatctcta ttgtttagat ttgttaaagg tattttcctc   840
gtctattttg gatatcaatc tgattgattt atttattgga atcgagttat caaaagcgtt   900
gttgtatttt tgttttgtcc tggctttaat tctgtctatg ttgtatatca ctgcacatgt   960
agttttgtaa cttggttttc cttgttatat tgtttgggag ggtttgatgg actaattttt  1020
caatttttt aagctgtaaa tataatgttg gataattttg ctttcagttc tctgatttgt  1080
attgtctttc cattctctgt tcatgaacat tttaatggtt atgataaaga gttggtgact  1140
gattcattta ttttgttgac tgtattgtat atgtag                            1176
```

<210> SEQ ID NO 25
<211> LENGTH: 1427
<212> TYPE: DNA
<213> ORGANISM: Glycine max

<400> SEQUENCE: 25

```
cataccattg agatccttgt tgagtgtttg agtcctcaat cctcagcaac caatctcaac    60
aaatccacat ggcttacgat tggttccttg cccttgcctt tctccatgga gagaaaaacg   120
tttccatctc gataaaaaag atagaggtaa tacgagagaa ggttaatacg agagacagaa   180
aatgaaatat ttgaagagat actcattttt attaattgca tggaatgaga agagtggatg   240
gacgatgtat ggaaaatagg ttttttctact aatgaagttg acaatatata aatgacagaa   300
ttaaaaaata tattattaat agattagttg gtgacttata aataagatca aatatttctt   360
atagaaggtg atcaatatat aagatcggac ggaatacact ttaaaaaaag attaaaaaaa   420
tattttgtga attcaaaaga attaaaagac aaatttaaat ttaaagtatt aaaaaattat   480
tcataattaa tggattaaaa acatatttaa gaaaaaataa aaattataac aaagagataa   540
atttaggttt taggtggcag aaaagcattt tgtcatcgac gacgttagaa gcaaaatgta   600
gaatcttccg gaccattgta gaaacgtaat ccttatcttg ccgtgcgtgt caatgaccac   660
```

-continued

```
caccgtacac gtggcaaatc ttaattcgtt cagtttcgga tattttcgtc attgagacat      720
cgcaccaagc tataagtacg acccottcta cctctaattc atgcatagca attcccaatt      780
cctaattgtt taaacctaat tctcatttct tcatcgttcg attcttctcc tcctaaaggt      840
acggctctgg tttcctctct ctcttgttca ttcttttcgt aatagcaacc ttattagcct      900
tcgtttattg atttttctcc taattacact tcaattttt cgatttgtgt ttgttacgtc       960
aatctgtata tcttttttgt tgtcgtcgaa tccgaaactt tcattcgcc tttctgattc      1020
cgtaaatcgt tgttaagtg caacatcttt ccctgttctt aggtatctga ttgatttctc     1080
tctttctttt tttttttatc agtttgagg aattagggtt cgtgatctga tttgtttctt      1140
taaaatttcc ccggttctta attaggctct gcgatttaat ttcttttatc atatttgaag     1200
aatcatggtt ctttcttggt ttgatttatt gtgcactcag tttctgatat gcaaaatctt     1260
tccctgtttt aattaaggtt tagggtttgc gagttgtcat tttggaaaat agggtttgtg     1320
gtttattgat tgtgtaatcc gtttggttgt aagcagaaac ttctctgttt taaatcattg     1380
tttgtgattt agctctattt tttatggttc tgtttgtgat tgaacag                  1427
```

<210> SEQ ID NO 26
<211> LENGTH: 502
<212> TYPE: DNA
<213> ORGANISM: Nicotiana tabacum

<400> SEQUENCE: 26

```
gggatcttct gcaagcatct ctatttcctg aaggtctaac ctcgaagatt taagatttaa       60
ttacgtttat aattacaaaa ttgattctag tatctttaat ttaatgctta tacattatta      120
attaatttag tactttcaat ttgttttcag aaattatttt actatttttt ataaaataaa      180
agggagaaaa tggctatta aatactagcc tattttattt caattttagc ttaaaatcag      240
ccccaattag ccccaatttc aaattcaaat ggtccagccc aattcctaaa taacccaccc     300
ctaacccgcc cggtttcccc ttttgatcca tgcagtcaac gcccagaatt tccctatata     360
attttttaat tcccaaacac ccctaactct atcccatttc tcaccaaccg ccacatagat     420
ctatcctctt atctctcaaa ctctctcgaa ccttcccta acoctagcag cctctcatca     480
tcctcacctc aaaacccacc gg                                              502
```

<210> SEQ ID NO 27
<211> LENGTH: 2243
<212> TYPE: DNA
<213> ORGANISM: Solanum lycopersicum

<400> SEQUENCE: 27

```
atcgtatcca gtgcaccata ttttttggcg attaccactc atattattgt gtttagtaga       60
tattttaggt gcataattga tctcttcttt aaaactaggg gcacttatta ttatacatcc      120
acttgacact tgcttagtt ggctattttt tttattttt attttttgtc aactaccca        180
atttaaattt tatttgatta agatatttt atggacctac tttataatta aaaatatttt      240
ctatttgaaa aggaaggaca aaaatcatac aattttggtc caactactcc tctcttttt      300
tttttggctt tataaaaaag gaaagtgatt agtaataaat aattaaataa tgaaaaaagg     360
aggaaataaa attttcgaat taaaatgtaa aagagaaaaa ggagagggag taatcattgt     420
ttaactttat ctaagtacc ccaattcgat tttacatgta tatcaaatta tacaaatatt      480
ttattaaaat atagatattg aataatttta ttattcttga acatgtaaat aaaaattatc      540
```

```
tattatttca attttatat aaactattat ttgaaatctc aattatgatt ttttaatatc    600
actttctatc catgataatt tcagcttaaa aagttttgtc aataattaca ttaattttgt    660
tgatgaggat gacaagattt cggtcatcaa ttacatatac acaaattgaa atagtaagca    720
acttgatttt ttttctcata atgataatga caaagacacg aaaagacaat tcaatattca    780
cattgattta tttttatatg ataataatta caataataat attcttataa agaaagagat    840
caattttgac tgatccaaaa atttatttat ttttactata ccaacgtcac taattatatc    900
taataatgta aaacaattca atcttactta aatattaatt tgaaataaac tattttata     960 acgaaattac taaatttatc caataacaaa aaggtcttaa gaagacataa attcttttt    1020 tgtaatgctc aaataaattt gagtaaaaaa gaatgaaatt gagtgatttt ttttaatca    1080 taagaaaata aataattaat ttcaatataa taaacagta atataatttc ataaatggaa     1140
ttcaatactt acctcttaga tataaaaaat aaatataaaa ataaagtgtt tctaataaac    1200
ccgcaattta aataaaatat ttaatatttt caatcaaatt taataatta tattaaaata    1260 tcgtagaaaa agagcaatat ataatacaag aaagaagatt taagtacaat tatcaactat    1320
tattatactc taattttgtt atatttaatt tcttacggtt aaggtcatgt tcacgataaa    1380
ctcaaaatac gctgtatgag gacatatttt aaattttaac caataataaa actaagttat    1440
ttttagtata tttttttgtt taacgtgact taatttttct tttctagagg agcgtgtaag    1500
tgtcaacctc attctcctaa ttttcccaac cacataaaaa aaaataaag gtagcttttg    1560 cgtgttgatt tggtacacta cacgtcatta ttacacgtgt tttcgtatga ttggttaatc    1620
catgaggcgg tttcctctag agtcggccat accatctata aaataaagct ttctgcagct    1680 catttttca tcttctatct gatttctatt ataatttctc tgaattgcct tcaaatttct    1740
ctttcaaggt tagaattttt ctctattttt tggttttgt ttgtttagat tctgagttta    1800
gttaatcagg tgctgttaaa gccctaaatt ttgagttttt ttcggttgtt ttgatggaaa    1860 ataccttaaca attgagttttt ttcatgttgt tttgtcggag aatgcctaca attggagttc    1920 cttcgttgt tttgatgaga aagcccctaa tttgagtgtt tttccgtcga tttgattta    1980 aaggtttata ttcgagtttt tttcgtcggt ttaatgagaa ggcctaaaat aggagttttt    2040
ctggttgatt tgactaaaaa agccatggaa ttttgtgttt ttgatgtcgc tttggttctc    2100
aaggcctaag atctgagttt ctccggttgt tttgatgaaa aagccctaaa attggagttt    2160
ttatcttgtg ttttaggttg ttttaatcct tataaattga gttttttcgt tgttctgatt    2220
gttgttttta tgaatttcct gca                                            2243
```

<210> SEQ ID NO 28
<211> LENGTH: 1833
<212> TYPE: DNA
<213> ORGANISM: Pyrus communis

<400> SEQUENCE: 28

```
ttataataac tttaaccgtt tgattaaatt tcaatggtct ggatctccag atttgataga     60
ctggaaggaa tggatccaga tgatcccct tccttctttt tggcaccacc tcaatggcta    120
atcttgttta atacctaata ctaaattttg ctctgattaa tcgaaggtcc ttgcaataca    180
cgcatacatc atattcaatt gctataaaaa ataaaataca aatttgttta tcttaaattc    240
ttaatcatga tagtatttat attagaaata caatgcaaat gaagtttcaa cacttataaa    300
caacatgaaa tggtgcacaa cctttaaac taatataaat gaaagttgta actggcgcga    360
aagaagtcga ggagtcagga ttttcaaata attgagtcat gttttcgata aaaaaatttt    420
```

```
attagatatt tcgtcgagca cttgttctac atgtcgattt tttacaacat ttcttaaagg    480
cttatgccaa tatatgtcaa taactactat tatatgtaga gtcaaatatg gctatataga    540
atttacagta atattaagaa tggtagaact tgtcatcgga gcatttcgtc aagtatttag    600
tgcgcacaat aggttagatg gcctaatacg aattattggt gattagtgat cgtaataatt    660
cgaagggcaa gtggacagaa aagtataaat actcaaggaa attgttattg gcactccaaa    720
aatctcattt tactctactt ataaatgtat aataagattt tgaagtact acttctcata     780 ctcaatctcg aagataacgc cgtaagggcc ccgtgaagga ggaagtcatt tgagatcacg    840
gactttgata ttatcaaaga aggggactag ataccaggct tgccgttta acccgcgcca     900 tcggcacgtc attccatcca cgtgtcgcta aataagtgga cctcctcgtc acgccaacta    960
caattccgtg acgaagtcgc cttctctaac gctataaatc caggcatcag cctctcccct   1020
tcctcacaat tgcgattgtt ttgcttctca acaatctgaa aaatcctcct ctaaatctct   1080
ctcgaagctc cctcagcctt tcaaggtgtg ttcttttttt cttgtttctt gttaatttct   1140
tgtttggttg ctaggaaagt gtaggaaaat tggagattct gtatttgatt tggttgatgt   1200
ttgagattta tgattaatcg gttggatctg ttaaatttag cattgttttg gcttttgatg   1260
ttagggtttt tttatttatt ggatgcgaaa ttagtaactt ggaaagaaaa tttgcgtcga   1320
atcttgtgtt caattttcac gaattagggg ttttgtgtat tttatctaaa tgatcagcat   1380
gtcttttcga attgaaagta aatttctttg tatcaatttt gacaagtagg ttttattctg   1440
tatccgatat cgaaattgag atttgttaat ggtcaattta attttgctat ttatttttat   1500
tccaaaattg agtaatttta gactaaaatt gtgtctttga tctgtgattt aaagctaaag   1560
cagggttttt ttttccttta cctgatttgc tgaaattcaa tttgcaatct tgatcttgaa   1620
ttgatttatt gtatataaat ggctgttaat attttgttta tataaaaatt gggatttttct  1680 tgaatttctt tgatttctga tgcattagtt tccaaattag gggttttttt tttttttttt   1740
ttttaatctg attttcttat ctgtaattct taattttaat ctaagggat tgttttttt     1800 atgcttaatc ttatggtatt ttggtttctg tag                                1833
```

<210> SEQ ID NO 29
<211> LENGTH: 1631
<212> TYPE: DNA
<213> ORGANISM: Beta vulgaris

<400> SEQUENCE: 29

```
atatgtagcc ctaagggcta tgtatatcat tttcctagat ttattatttg gttgtgcaat     60
ttggtctatt tagataaaat tgagtctatg agacacgggt taagaaatac ttgacataca    120
tttatttagt ttacatatat atacaccaat tacacgcttg gtaactagtc agacaaccca    180
tttactccct ggcccctgcg gtctgtaccc gtttcttttg cacaaagttt caggagaaat    240
aatgttgtgg gacataaaaa gatagagaaa ctattatttt atattaaagt atgtgattac    300
attccaaaac tagaataaaa agaaatgaat aaactaatta aaaacatctc aaaaaagaat    360
acggataaac taataaagac cgaaactagt actccctccg tcccaaaata tagttcccat    420
tacccatttt ttacggtaat ttatgcaagt agaatctaag agggataaca aagatttttt    480
gtttatttaa ataaatgttg tatggaaaaa gatgattta ggagagagaa tggagaatga     540
ttggtgggag agcattaatt gtaacatttt ggttgaataa acaaggaaa aaacaaaatt      600 caagaagcaa ataaatgatg ggacacgatt tttctaggta aattacggaa aaatgtgaaa    660
```

```
ctaaatatga aaatgagaac tatattttg gacacttaaa atggaaatag gaactatatt      720
ttgggacgga gggagtaata aataacgact tggtcgtcta ccgttccaga ccgtcagatt      780
aaaccctcac cataaatctt gtaggtagca cgtactatat aatttcacaa gttcgagaag      840
tcgtgagaat ctccgtctct agttgaaccg cctcaaaagc aaagaaaagt agctttaccc      900
gtgagggcta ggtcaagaca cgtcatacat cacacgtgtc aaacgatgat tggtaaacta      960
gagataattg tcttaattaa gtcggtcaaa caagtcttta aatacagcct attcccttca     1020
ttggtttctc atccttcatt tgaacgtaaa cgatcattca ttttctctc tcctctcttt     1080
caaggtaaat tcctaatttc cttttctctc ttctcagttt tcttcgtaaa ttttcatctc     1140
atttctgtgt aagataacaa gatccaattt agttagtgta agattgattt atctaagaaa     1200
ttcatttgga atttgttct ttttgatttt caatttctca ggattttgtc gacaaaaaat     1260
taatcaaatt ttgtgttttt cagtttcata tagatctttc ttgtgttgtt gaaatacaga     1320
tctgatcatt gttacaattt ctaaaattta ggtttgaaaa ttcgccataa tttctcgtac     1380
ttctgcaatc gattgatttt taattcggaa aaattagtgt taaagatatc gccataattt     1440
atcacaattc tgcaatcgat taaattttcg atctggaaaa atctagggtt aaaatctcgc     1500
cagaatttat cgcaattctc caatcgttta atttctgatt tagtgtattc tagggttaaa     1560
gatctcgtca taaattttc aaaatttcgt aaattgatgt gatttctgat ccttttcttt     1620
cgattttgta g                                                         1631

<210> SEQ ID NO 30
<211> LENGTH: 1441
<212> TYPE: DNA
<213> ORGANISM: Unknown
<220> FEATURE:
<223> OTHER INFORMATION: Raphanus raphanistrum

<400> SEQUENCE: 30
taaaagtaca acaacttttt ttttaggaaa caacaactta gctaacatat gtaacaaaat       60
tgcaaactga gctatctatc taatctgaaa ctgctgcact tcttgccact aaactatctc      120
aggaaaccca acttagtctg taagaagaac catcaacgaa caaaactatt cgaagaggct      180
ttcattgact gaataaaccc gatatcttag aaatgggcca agcccaaaaa agtccgtttg      240
atgtgtgata ccgaatccat tgccttcagc ccatttgcca acttgatacc aaaatcatgc      300
aaatatccaa aaccactaaa aaaagaaaaa aacattatgt tattttttcag gaaatttcct      360
ctattaattg tttgaagaaa aaaaaacaat ttgccaactt gataccacaa tcatgcaata      420
tccaaaacga ctaaaaataa aaaacattat gttatttttca ggaagattcc ttttttattt      480
ttaaaattca aaattaaaaa ccccacctgc atagaaaaag ggaaaattaa agaaaagaaa      540
agataagagc atcgacatag ggggaccatg ggctcaatta ttggcatttt tttagctcca      600
ccgttgatta aaaaaaaaaa gaaagataat aataacaccg atcgtaacga tccgttaaat      660
cacaacgtcg gcttctgtta cggcccgtta gaaactgtgg ttgtcgtgga gttagtaaag      720
aaacggcgtt aaaatagaat gcagccaaca cacgacgggt cgtgggggtt atcaactcaa      780
agcacaaaat atatactttt cctttatacc taaaaaaatc aaaggcgaag gaaagattat      840
cttttccatt aaaaggttgc gtgtaaccaa cgctgaatac acgtcattta acatacgtgt      900
cgaaatccta ttcgctattg cttcaccgcc ataggtttct cgtgaccgag tcctcctcat      960
cctcttgtat aaatcaaacc ctaaacacct cttctccttc acaaatcgaa aaccaattct     1020
tctcaattct caattctcaa ttctcaattc tcaattctct ctctctcgcg aattacgatc     1080
```

```
aaggttagat tcgtgtttct tcttctctcg attagctgtt tcgttcgatc gtaattgatt    1140
aagccccgat agatctcgtc gtgattttga ttattagggt tcaattgtta cgattaaggt    1200
ttgattctgg tttcttcttc atcgattagt tgtttcattc aatcgtatat gtattttcga    1260
atttgaatcg gtttgttgag attaaacgat agaactcgtc gtgattttg  attttccag     1320 atttgtgttg ctacttgat  catatatgat ccgtgtttgt atattgtagc gatctctttg    1380
tattgatttc gcaattgatc cgagtcaaaa gagtattgat cttggctttt gtgaattaca    1440
g                                                                    1441
```

<210> SEQ ID NO 31
<211> LENGTH: 1394
<212> TYPE: DNA
<213> ORGANISM: Ipomoea nil

<400> SEQUENCE: 31

```
attagggaaa atagcacttt tccccctaa  gttatatact tatagcattt tttcccctc       60 aattatttat gtaagtacat tagcccctc  aattattta  aaagtggtgg ttttccccc      120 tgatatatta aattgacatt tctacccta  aagtaaacat tttatttttt tacttctcca    180
acaaattatt gtgtatatgt agcaatgacc acggttcggt tcgaactaaa ccgcacacta    240
tagcaatcga attaaaactt ttcggttata attcagatct agaatccaat atttgaattt    300
caatttatta aatttatgaa ccaaaaaaac tggatcatga accgtgaacc ggcgattata    360
gatccggttc gcaattttga accgtcttta ttttaaaatt ttatttatt  ttttatttta   420 aaatagtcta aattcaacaa taatgtaat  ttatttttc  agttcggaac atgaactggc    480
cattccggtt tgcgatttta ataaactcta aatatcgcat tttgattcta aattgtaatt    540
ggaatatttt ggtttggttg gtatagtatc tgtttggttt gaaccaaatt atagtaataa    600
tttgttggag aagaaaaata aatgaaatat ttattttaag agtaaatatg tccatttaat    660
attttagggg gaaaagaacc acttaaataa ttcaaggaga aaaagtgcta taagtatata    720
actcagggag aaaaagtgtc attttcctt  attatatata tatatatata tatatataaa    780
taaaaaaatg aatagtataa aacaaattta taaattttgc cggatcggat aattatgaag    840
cgcgtaggtt ttgaagtcaa aatcggctac ttgccaaatt gcaatttccg aacctaataa    900
tctccaccac gcaaagaaaa tccgacaaat aatgcaagcc gttgcgtgtg gtattgatca    960
atacacgtaa tatccaacac gtgtccctcc ttcataggtc aacaagataa gcactttctt   1020
cgcaaggcgg tcgagacacg cctttataat cttctcctcc ctcgcccttt ctcatccatc   1080
atacgatttc tctattctat ccaaatttct tcctcctcaa aaccttctct caaggtaacc   1140
acagttttct caatcttcct tccttttgt  ttattgttat tattgttaat gttaattgtt    1200
aattttctgt gttattctta ttcgtgattc gtgaattggg gatctggggg ttgtgttctt   1260
tgatcttcat aaattgcaat tggttttagg gttttttttt tttttttttt ttttggatt    1320 gaattggtgt taattgagga tgttttatgt ttgtatttga tggttaattt gattttgtat   1380
ttggatatat acag                                                      1394
```

<210> SEQ ID NO 32
<211> LENGTH: 1438
<212> TYPE: DNA
<213> ORGANISM: Unknown
<220> FEATURE:
<223> OTHER INFORMATION: Cucurbita sp.

<400> SEQUENCE: 32

```
cttatgtgca acgttacatt tcggttatca tcttagttcc caacaacata actcatgcat      60
caggatgcca ttccatgtct taggacaagt caaccatctt gacttgcttg aacatgtcta     120
tcaagatcaa tctatgtgtc actcatctca ttgtgacatc ctaaacatcc attcatcatg     180
tcattcatac ctatcagggt catccaacac tattttgat agacccattt caaagaaagt      240
tgtccgagac actcgtccac accgcgacac acatatgtgc cacaagatag cccgcttagg     300
ctacatggcc caggaggaga agagagctaa caccatgcct ctcctataat acattttgag     360
ccatttctaa tctttctgga gtagacgtta ttttgacaag tagtcatatt gtagcattga     420
gcgttgtcgg atatccaatt gacacaaatt ttggtgagtt tcatctttta tataatgaa      480
cttaactcta gagccgtatc ccgaaaactc atatagaaat tctgacttct aaggttatga     540
cccagggatc tactcgaccc tcttcgagat tgtcttcgac gctcgtggtt ctctccaacc     600
ttcctaattt ttcaatttga ctttaatgta taccttggt atattagatg atgcatcgtc      660
ctctttcgt atcataacgc gtattggccc gggaaacata atttaaaagt ctccccaagc      720
ctatctttga gtgtggggtc acagcccatc tagagaaaga agaatagtag attcaactca     780
aagacgcgca aaacgtctag aattttcttg agaaccacta gaacctaact ccgttataac     840
gacgttagtt gttgttttgc gtgctattat tgagtcggct tattgctttg aattttggtc     900
cacagattcc atttctgcct tcgcctgcaa gtaacgcgca ttgacagata ataaatgctt     960
acgtggcgga aatgtgtgga taattcatcg cctgccatga cctaattctc cttacaattt    1020
cctataaatt caccccttcc gccctgggtt tctccgcaat tgaatctctc ttctttcatc    1080
gaccaatcta cagcgaattc ttccaaggta ttttctgct ttcttttctt tttcgctttg     1140
attctgttca tctgtttcga gagttctgga tcggtgttgt ttttttcccc ttttgttgtg    1200
gaaattttg aatcgtttat tcttctcgga gatctgatgc tttgtggttg gatccgcttg     1260
gatcgtttga agttttatga tatgtattcg gattgtagtg tgttttgtga gagattggct    1320
tgaaacattg ggattttact gattttatcg aagtgaaatt tagaatttag gttttgact    1380
tgttcgtgtt atcgtttga tagaaattgt cctgattttt gtgtttcctt ctgtatag      1438
```

<210> SEQ ID NO 33
<211> LENGTH: 2560
<212> TYPE: DNA
<213> ORGANISM: Helianthus annuus

<400> SEQUENCE: 33

```
tacacttagg ctattactta acgcgggtcg cgagaggcct gttttcaga ttttaaaat      60
cttttgaaat gattacgaaa tcctggtaat taataacgaa atctttcgta atgatttacc     120
tgacctttcg agtttgaagg ggtaactttg cggtttggcc ctcggttaat tacaactaag     180
gacctcgtgt tatttacccg cgttgttaag tccccgatta gttattaat tactcagaaa     240
gccttcactt tcattattga cgcttttaac ccttctccta cgaattcgat cgtaactttc     300
tcgtttcata acgaaacttc gcgaaattta tatattatat tttagtgagt gtataatacc     360
gttacaaagc cttgggaacg ttaaagggtc actcagaggt ataattaaac atgttgacac     420
ggttaacccc tgtagcttgt aatctctcac tttctttcgt gtttcgcttc tgtacgatct     480
atgatttatt tgtttgaagg ttcaagcatt atttagggtt agtatacagt atatttaccc     540
ttgttgacat ttataaccct cgaatttata tactttcaag gtttgtcaaa attagtcctt    600
tatttaatat taatgccacg tgtaaacaaa tgacacgtgt taacacatca ttggacgcaa     660
```

```
aaattcgagg tgttacagta acagatctga acccttgctt gatgctaagt tgttttcttg      720
taggttttat tatttcaatt atcgctttat tgcttcgttc taaacctgat atgtaagcta      780
tgagattatt cttgtttgtc atatacttac atccgtttgt tattgtgatt tattaactgc      840
gtttaagata tgcgcataaa aagttcagtc aacaattaaa accatactac agccgcctgc      900
attattactt ttaagatatg tgtgttattg cttttgcgac cgaaaattat tatcctgttg      960
gtttaatcgg gtcagagata gtcatatcgg tcgggatcga taaacgggtc ggcatcaact     1020
tgggtcgatc ggatccgggt gtgcatgttt gtggttgtag atgttgcagg tggaaagaga     1080
gagaagtgtg ttgaggtggg gtatggcagg attatttata tatttatgaa atgactaaaa     1140
tgcccttgac agacttaaca catatggatg aagttaagtc agttggacca aaatggcaac     1200
gatgaaatat ttttagatcc agatgttaaa aataaaacct ttgaactaaa ctgttaaaat     1260
gacccaaacc atagggacta aaatgacatt taactcttaa aaaaaaatta gaaacaagat     1320
aagggtcacg caatattta ttccaaaata aaagaagac gccaaaccta aaaatcagcg     1380
actccattaa aaatcaaaac ccatcaacgg ctcttatctt aactttggtg tttggtcacc     1440
aatactttat acacgtggca cattctccac cgattgttat ctaaccgcac cgtcacgtta     1500 accttttcttt gcgtgcaccc ttagctttat tgttctataa attcacccc aatttatccc     1560 cttcattcat caaccaattc tcttatcttc ttcaatttct cagatctctt caatcccttc     1620
aaggtatgtt cctttcgatt tgtgtgtttt gttttgtta atagatctgc tatgtattgt     1680
ttgatctgtt aagttttaga tcgatttgtt tagatttaga tacgctatat cgtttgatcg     1740
gttaggattt tgatcgattt atttaggtct gttatatcgt gtgatctgta agcttttga     1800 ttgatttaga cctaaaattt gatcgtaggt gacttttact atgtatatat tacgtctgat     1860
tgttaggttt tcttttagat ctgtgatatt gtttgatctg taagttttta gattgatcta     1920
gattgaaatt tttaacgta ggtggttttaa tatgcacaat ttaacgtctg attgctagat     1980
tttcgttata gatctgttat attgtctgat ctgttaggtt ttcgatcggt aggtggctaa     2040
atatgtttgt atctgattag atctgatgat tagacaaagg atgatgtgtt ttgatcttga     2100
attcctttcg atttcgcgtt atttataggt ttttgtttca gatcggtgat atatacagtt     2160
ttacgtctga tcattagttt attgttttgg atctgttagt ttattgatcg attaaaacct     2220
acagttgata gtaggtgtct taatatgttt ataattctta gtctgaaccg atttgataag     2280
tacacaacga ttttgaacgg ttaatcgtct agttcttgca gttttgtgga taatgattct     2340
gttttttgta tgatatttga tctgatgatt acataacgtt ttgtggtttt atattatgaa     2400 ttttaacag agattcgtta agattttca gtcctgtttg ttatgatttt gttttggtt     2460 gaaattctgt tttattgagg cgtgtttact tgtatttaaa aagttatttt ggtattgtta     2520
ctgatcttct gttcttatgc ttttcaacag tagcaaaacc                          2560
```

<210> SEQ ID NO 34
<211> LENGTH: 601
<212> TYPE: DNA
<213> ORGANISM: Solanum lycopersicum

<400> SEQUENCE: 34

```
tcgacatact cgactcagaa ggtattgagg aatgatcgat tctgggtcat tgtgtggtt       60 aatcaccctc caaatcaact aagtcatcct gaaggacaat atcctatttt ttctctcgta      120
ggtttatcat ttaaattact atcgcgtgat aattttgtaa cgtagaaaaa taataccatt      180
```

```
aatccaaacg ttatattcat taaaataatt atgatacatt taaaaatatt tcgtgacctc    240
tcaattattg caaattctaa gccatcccaa gttttgaggc tattttttt tactatacta    300 ttttttacaac cacaaaaaca taaaaaataa aaaataaaaa aaataaaccg agtcaattgc   360
tacaatcact tcattattaa ttttaattaa tattatgtgg ttatatatga aactgttaga   420
gaaataatag ctccaccata ttttttttctc aatttatttt cactataaaa aggctatttc   480
attataatca aaacaagaca cacacaaaga gaaggagcaa taaataaaa gtaaacaaca     540 atttgtgtgt ttaaaaaaaa aaaaaaagta cacacaccaa aaaaaaaaat tccaatttaa    600
a                                                                    601

<210> SEQ ID NO 35
<211> LENGTH: 2054
<212> TYPE: DNA
<213> ORGANISM: Helianthus annuus

<400> SEQUENCE: 35
taatcaacat cccgctgcaa cgcgcgggta agcataaact cgttcctata caaattacaa     60
ttccaaatca ttcgatgaat caaatgccac ctaagaagat attaatctca taatcaaatt    120
attataccaa atcattgatc tgggcttttgt attactcgaa ttaatgctgt tatgttttta    180
ttaaacgtat gggcttgctt gaaccaggct taaggcatga gtgtactttt ttttaaacaa    240
ctaacataat caatttcaag cacttttggg acaccgactg gattaaacgc agtactttga    300
aagtaaccca gtccaccta ctcgtagaca caacagtaaa attactggta aaacctgttg     360
gtttccctga gttttctgtc attgtccact aatgcctcat tcttcaccaa atagaagttg    420
aacctgcata atacaataag gctatgggat atactttcac gccccttaac tacacgtagg    480
catcacatca cgtacttgac cctctttcac ttcacttcac aacaaggaaa ttgtttaacg    540
cccattaaca cccccttaaat taaataaaat acatatatat agcatgttgt gtgtgtgtaa   600
attttgcgat gcttgattct ctccctctct ctcctaatta acttcttaac atataaagct    660
tttaataact cttaacactc ttcaggaacg gtataataaa tgttaacgga taccaactag    720
gattacgtga tacaagcctt cctctctaaa acttaagaaa gtcaccaaaa agaaagtcaa    780
agacggcaac ggcaacccag aagctacgtt ctctttctag attctatgcc ctacctaccg    840
tgtggtgcac aacaacttga cccccatcat tgactctcca ccgtacacgt gtcacgatac    900
catttgttgg tctcctacca cttacgtaac attaatattc catccgtgac cgcctcttct    960
tcatcatcct ataaattcac cttcttatct cttccgcttt cattcgttca tcatcatcac   1020
aattaacaac aatccaaagc aatcttctct catattctta tctcttcctg tttcgcttcg   1080
tctctttcaa ggtatctatc atccttttct ctatatatct cttcttgatt attatgtgtt   1140
gtcagatgtt agatctattt agatttggaa ttgtgtgatt gattatatga tttagaattt   1200
tagatgcatg attgatcttc gtaatcatat gagtaatcgt tttcagcgag acggattgta   1260
gatctggacg attgtaggtt tttacgagtt gttattggat cgtttgatga ttgttgttat   1320
ttgttagttt gatctgttta gatgtaaaat tgtgtgaaca taataacgga gagatgactt    1380
gttgataatc gttctcaacg agacagattc atgtttttact ctagatctgg ctaatgtgaa   1440
tttgtgtgtt taattatgtt ttgtatgtat tatatagtga acctatgaag atatggtttg   1500
atgcatgatt attgatatga ataatcctac gagtaatcgt ttttacaag acgacttgtc    1560 tctcactgta gatcatatat gagttgttct tggatcattc gatgactgtt gttgattgat   1620
tcggtttttc tgtgatgata tggtggaact taataatgaa aagatgtttt agatgcatta   1680
```

```
ttgatttgat aatcttgagg agtaatcgat tttaacaaga catatacgaa ttaacgaatt    1740 attgccttt  tatttgttag tttgatatga tttaggtata attcgtcctg tttgattcct    1800
ttttctgtaa tgatatgatg aacttaataa cgtagagatg ttttcgatga attttaattt    1860
taatatttgt tagtgtgatt ttgggtagaa ttcgttgtga tttgggtgtt tgacttagtc    1920
actagttcat gtttgatgat cttacttagt acttcataat ttgctttgtt tctcattcca    1980
gcccatctga tttaagttat tgatggtata atttattgct tagggtatta atctgtttgt    2040 atttttaat  ccag                                                     2054
```

```
<210> SEQ ID NO 36
<211> LENGTH: 983
<212> TYPE: DNA
<213> ORGANISM: Petroselinum crispum

<400> SEQUENCE: 36
gaattcgaat ccaaaaatta cggatatgaa tataggcata tccgtatccg aattatccgt     60
ttgacagcta gcaacgattg tacaattgct tctttaaaaa aggaagaaag aaagaaagaa    120
aagaatcaac atcagcgtta acaaacggcc ccgttacggc ccaaacggtc atatagagta    180
acggcgttaa gcgttgaaag actcctatcg aaatacgtaa ccgcaaacgt gtcatagtca    240 gatccctct  tccttcaccg cctcaaacac aaaaataatc ttctacagcc tatatataca    300
accccccctt ctatctctcc tttctcacaa ttcatcatct ttctttctct accccccaatt   360 ttaagaaatc ctctcttctc ctcttcattt tcaaggtaaa tctctctctc tctctctctc    420
tctgttattc cttgttttaa ttaggtatgt attattgcta gtttgttaat ctgcttatct    480
tatgtatgcc ttatgtgaat atctttatct tgttcatctc atccgtttag aagctataaa    540
tttgttgatt tgactgtgta tctacacgtg gttatgttta tatctaatca gatatgaatt    600
tcttcatatt gttgcgtttg tgtgtaccaa tccgaaatcg ttgatttttt tcatttaatc    660
gtgtagctaa ttgtacgtat acatatggat ctacgtatca attgttcatc tgtttgtgtt    720
tgtatgtata cagatctgaa aacatcactt ctctcatctg attgtgttgt tacatacata    780
gatatagatc tgttatatca ttttttttat taattgtgta tatatatatg tgcatagatc    840
tggattacat gattgtgatt atttacatga ttttgttatt tacgtatgta tatatgtaga    900
tctggacttt ttggagttgt tgacttgatt gtatttgtgt gtgtatatgt gtgttctgat    960
cttgatatgt tatgtatgtg cag                                           983
```

```
<210> SEQ ID NO 37
<211> LENGTH: 585
<212> TYPE: DNA
<213> ORGANISM: Solanum lycopersicum

<400> SEQUENCE: 37
tgtcttttaa tggataatta ctaattttag cggtactttt tatttattat catttataat     60
aatactatgt taaatatgca acatgtatta gaagtgaatt aagtatgcaa tagatatgta    120
tttaaaaata tattatgctt gtttgataag aagttgatgc attgtattat aagtacgtta    180
gaatgtgcaa taaatatatt atctatcatt agaacttgaa ttataagtga ataatagatt    240 atttttttgta atatgaatta aaagtgtatt aaacatgtat taacggtgat caattggtta    300
aaaaaaagtt tattattaaa atgataaatc tttttaatttt atagtatatt tatgtaagtt    360
ttcacgttga gtaaatagcg aagaagttgg gcccaaccaa gtaaaataag aaggccgggc    420
```

```
cattacaatt aagtcgtcac acaactgggc ttcattgaaa aaagcgcaaa accgattcca    480
ggcccgtgtt agcatgaaga ctcaactcaa ccagagattt ctccctcatc gcttacagaa    540
aaaagctata tgctgtttat attgcgaaat ctaacagtgt agttt                    585

<210> SEQ ID NO 38
<211> LENGTH: 352
<212> TYPE: DNA
<213> ORGANISM: Medicago truncatula

<400> SEQUENCE: 38
atgcctatct tatatgatca atgaggcatt taattgggtg catatgatgg tgaaaaaagg     60
tgcagctcct ggcttgggaa tgatgactca tgtggaattt ggtcttaaat ttatcacatc    120
cttttgggat gtgatgattg tatcacttgt tcattttgca aagacaaggt gcactgctac    180
aaactttggt ttaatctgaa ataaaacaaa actcactgag aggaagatgc atcccagtag    240
gtgaaagtcg agaaggattt gcatgttact attacacttg cttttttagtc ccacatcgtc    300 tgaaacataa aatatttcag cgtttaaata cttcaagcga accagtaggc tt            352

<210> SEQ ID NO 39
<211> LENGTH: 472
<212> TYPE: DNA
<213> ORGANISM: Glycine max

<400> SEQUENCE: 39
cccgggttaa gagaattgta agtgtgcttt tatatattta aaattaatat attttgaaat     60
gttaaaatat aaaagaaaat tcaatgtaaa ttaaaaataa ataaatgttt aataaagata    120
aattttaaaa cataaagaa atgtctaac agaggatta agatcctgtg ctcttaaatt    180
tttaggtgtt gaaatcttag ccatacaaaa tatattttat taaaaccaag catgaaaaaa    240
gtcactaaag agctatataa ctcatgcagc tagaaatgaa gtgaagggaa tccagtttgt    300
tctcagtcga aagagtgtct atctttgttc ttttctgcaa ccgagttaag caaaatggga    360
atgcgaggta tcttcctttc gttaggggag caccagatgc atagttagtc ccacattgat    420
gaatataaca agagcttcac agaatatata gcccaggcca cagtaaaagc tt            472

<210> SEQ ID NO 40
<211> LENGTH: 445
<212> TYPE: DNA
<213> ORGANISM: Arabidopsis thaliana

<400> SEQUENCE: 40
cttcgttgaa caacggaaac tcgacttgcc ttccgcacaa tacatcattt cttcttagct     60
ttttttcttc ttcttcgttc atacagtttt tttttgttta tcagcttaca ttttcttgaa    120
ccgtagcttt cgttttcttc tttttaactt tccattcgga gttttttgtat cttgtttcat    180 agtttgtccc aggattagaa tgattaggca tcgaaccttc aagaatttga ttgaataaaa    240
catcttcatt cttaagatat gaagataatc ttcaaaaggc ccctgggaat ctgaaagaag    300
agaagcaggc ccatttatat gggaaagaac aatagtattt cttatatagg cccatttaag    360
ttgaaaacaa tcttcaaaag tcccacatcg cttagataag aaaacgaagc tgagtttata    420
tacagctaga gtcgaagtag tgatt                                          445

<210> SEQ ID NO 41
<211> LENGTH: 306
<212> TYPE: DNA
<213> ORGANISM: Glycine max
```

<400> SEQUENCE: 41

| | | | | | | |
|---|---|---|---|---|---|---|
| aaaataaatg | gtaaaatgtc | aaatcaaaac | taggctgcag | tatgcagagc | agagtcatga | 60 |
| tgatactact | tactacaccg | attcttgtgt | gcagaaaaat | atgttaaaat | aattgaatct | 120 |
| ttctctagcc | aaatttgaca | acaatgtaca | ccgttcatat | tgagagacga | tgcttcttgt | 180 |
| ttgctttcgg | tggaagctgc | atatactcaa | cattactcct | tcagcgagtt | ttccaactga | 240 |
| gtcccacatt | gcccagacct | aacacggtat | tcttgtttat | aatgaaatgt | gccaccacat | 300 |
| ggattg | | | | | | 306 |

<210> SEQ ID NO 42
<211> LENGTH: 445
<212> TYPE: DNA
<213> ORGANISM: Arabidopsis thaliana

<400> SEQUENCE: 42

| | | | | | | |
|---|---|---|---|---|---|---|
| cttcgttgaa | caacggaaac | tcgacttgcc | ttccgcacaa | tacatcattt | cttcttagct | 60 |
| ttttttcttc | ttcttcgttc | atacagtttt | tttttgttta | tcagcttaca | ttttcttgaa | 120 |
| ccgtagcttt | cgtttctttc | tttttaactt | tccattcgga | gtttttgtat | cttgtttcat | 180 |
| agtttgtccc | aggattagaa | tgattaggca | tcgaaccttc | aagaatttga | ttgaataaaa | 240 |
| catcttcatt | cttaagatat | gaagataatc | ttcaaaaggc | ccctgggaat | ctgaaagaag | 300 |
| agaagcaggc | ccatttatat | gggaaagaac | aatagtattt | cttatatagg | cccatttaag | 360 |
| ttgaaaacaa | tcttcaaaag | tcccacatcg | cttagataag | aaaacgaagc | tgagtttata | 420 |
| tacagctaga | gtcgaagtag | tgatt | | | | 445 |

<210> SEQ ID NO 43
<211> LENGTH: 323
<212> TYPE: DNA
<213> ORGANISM: Arabidopsis thaliana

<400> SEQUENCE: 43

| | | | | | | |
|---|---|---|---|---|---|---|
| ccatggatgt | tgttgttacc | agaaagtaaa | taaatgttca | atctctgatg | ttctcaagta | 60 |
| agtgagtttt | attgggaata | atattaactt | atgttcttct | tgcatttgat | ttctttgccg | 120 |
| ctctcttctt | ctatcttaaa | tctgtgtata | ctatttcact | attgggcttt | ttattagtct | 180 |
| ataatgggac | tcaaaataag | gctttggccc | acatcaaaaa | gataagtcac | aaatcaaaac | 240 |
| taaattcaga | gtcttttctc | ccacatcggt | cactgtactc | attttgtgtt | tgtttatata | 300 |
| ttacacgaac | cgatctttgg | tac | | | | 323 |

<210> SEQ ID NO 44
<211> LENGTH: 1982
<212> TYPE: DNA
<213> ORGANISM: Zea mays

<400> SEQUENCE: 44

| | | | | | | |
|---|---|---|---|---|---|---|
| caattaatgc | acgtcggccc | agtaactccc | gtcggccaga | cagggccgac | atgcattaat | 60 |
| ttgtaatccc | cgtcggccag | cggtagccga | cgggagttac | tcggccgatg | tgcattaatt | 120 |
| ggtaatcccc | gtcggccagc | cgtagccgac | aggaattact | aattcccgtc | agtgcccgac | 180 |
| gagaataagc | atatccccaa | catctgatgc | ccgtcggctt | agggtcgacg | ggaattaacc | 240 |
| atataccgac | gagaattagt | aatccctatc | ggtttagtgc | ttattcccgt | cggttctgag | 300 |
| tcggcgggaa | ttaattggat | tcttgtagtg | atgcactgag | ttttactat | aattttaaca | 360 |

-continued

| | |
|---|---|
| agtaaaatga ctaacttgga taaaaaaatg tttcgtgggg cgggtacatg gggaacgtgg | 420 |
| acggtcctcg tgaactacgg ggattaaatt ttctccattt aaatcccgc ggggactaaa | 480 |
| ttagtctcat acccatcccc taatagggga atttccgcg gggaattggg gatcgagtcc | 540 |
| ccattgtcat ctctactctg cgcacgtctg gatggtcgcg cctggggccc gaacggttca | 600 |
| cgatggcgca gagggtctta ttttcacag cagacctaga tcttgcctct cgggagggat | 660 |
| cccgtcgggg aggagagatc ctaggtgtg tcttggtgtc agcaggccac ccaagacgct | 720 |
| tctaatcgat gtagaaccga agaaatgcga agatttaagg tagaggaagg ctaaactaga | 780 |
| gctactccta atacaaaatg taaaaacgat aagtaaattt gatctgatcg aatgtggggg | 840 |
| ttcaatcggc cgtagcccct tatatatata aatgagagat ctgaacccgt tacatgtcgt | 900 |
| ttaccgagtt aatctcgtag atttagctaa caaatcccac aagaaaatcg aaatcctaac | 960 |
| cgattctaca cacaagcgga ccatccatgc catcaccgcg gatcatccgg cctagcgtcc | 1020 |
| cctgcccaaa agtgggctca acaagcctaa atacatataa tttataccac gtgcaacaca | 1080 |
| tttattcatc catatcacat gtcatgcaag gcataagcat catgttaact tagttatact | 1140 |
| gacatacatt tatgagttga gatgtccagg atgtgagcgc atgagcccat tgtccattca | 1200 |
| ggaccaagac aggctactaa gcactttcta cataacttgt atgtgctaac tatagcatgc | 1260 |
| ttatatggct ctctccaaag ttcaaagcta gctcaaatct tttgatttaa taaaacttaa | 1320 |
| atttgtttga tttcagataa actgataatt tttataat ttagagtgag ttgaaaacag | 1380 |
| aaactggccg caaatccacc tcaagccttt tgatttgacc taaaaaaag aagccccac | 1440 |
| aaacaccact ccacactagt gcactgtctc tctccaaagg cagctgcatt ggcctccagc | 1500 |
| cttttcccta ctgtgccgcg cgccctcct tctctctaat gatagcatag ggagagaagg | 1560 |
| catactccga ggcatccttc tcctttccct ctccttcccc aaaccttttt cctctttccc | 1620 |
| tcgccccaag aacttcatct catctccagg cgcccctttt gcgcttgcgc aggagtagct | 1680 |
| cacggggaca gtgggcggat agctcgatcg ctgcaccact acttcactgg aggtccgccc | 1740 |
| actccctagg caagcaagac tagtagccgc agtctaacaa tagctctcct gcttccggtt | 1800 |
| cagctactgc tgctagcgaa gtttggccac atctgatgtc aagagcatgg cgcatgcaca | 1860 |
| tactttctgc ttgcttttac atagcatact atagtttatg catgctgctc atgtagacat | 1920 |
| gtgcatctgg tgttcggaac tttctcaaac ggccgtgggt gtttgcaggt gggggcaaaa | 1980 |
| cc | 1982 |

<210> SEQ ID NO 45
<211> LENGTH: 2051
<212> TYPE: DNA
<213> ORGANISM: Oryza sativa

<400> SEQUENCE: 45

| | |
|---|---|
| tgggccaatg aatccgtgtg atcgcgtctg attggctaga gatatgtttc ttccttgttg | 60 |
| gatgtatttt catacataat catatgcata caaatatttc attcactttt atagaaatgg | 120 |
| tcagtaataa accctatcac tatgtctggt gtttcatttt atttgctttt aaacgaaaat | 180 |
| tgacttcctg attcaatatt taaggatcgt caacggtgtg cagttactaa attctggttt | 240 |
| gtaggaacta tagtaaacta ttcaagtctt cacttattgt gcactcacct ctcgccacat | 300 |
| caccacagat gttattcacg tcttaaattt gaactacaca tcatattgac acaatatttt | 360 |
| ttttaaataa gcgattaaaa cctagcctct atgtcaacaa tggtgtacat aaccagcgaa | 420 |
| gtttagggag taaaaaacat cgccttacac aaagttcgct ttaaaaaata aagagtaaat | 480 |

```
tttactttgg accacccttc aaccaatgtt tcactttaga acgagtaatt ttattattgt      540
cactttggac caccctcaaa tcttttttcc atctacatcc aatttatcat gtcaaagaaa      600
tggtctacat acagctaagg agatttatcg acgaatagta gctagcatac tcgaggtcat      660
tcatatgctt gagaagagag tcgggatagt ccaaaataaa acaaaggtaa gattacctgg      720
tcaaaagtga aaacatcagt taaaaggtgg tataaagtaa aatatcggta ataaaaggtg      780
gcccaaagtg aaatttactc ttttctacta ttataaaaat tgaggatgtt tttgtcggta      840
ctttgatacg tcattttgt atgaattggt ttttaagttt attcgctttt ggaaatgcat       900
atctgtattt gagtcgggtt ttaagttcgt ttgcttttgt aaatacagag ggatttgtat      960
aagaaatatc tttaaaaaaa cccatatgct aatttgacat aattttgag aaaaatatat      1020 attcaggcga attctcacaa tgaacaataa taagattaaa atagctttcc cccgttgcag     1080
cgcatgggta tttttctag taaaaataaa agataaactt agactcaaaa catttacaaa      1140
aacaacccct aaagttccta aagcccaaag tgctatccac gatccatagc aagcccagcc     1200
caacccaacc caacccaacc cacccccagtc cagccaactg gacaatagtc tccacacccc    1260
cccactatca ccgtgagttg tccgcacgca ccgcacgtct cgcagccaaa aaaaaaaaa     1320 gaaagaaaaa aaagaaaaag aaaaaacagc aggtgggtcc gggtcgtggg ggccggaaac    1380
gcgaggagga tcgcgagcca cgacgaggc cggccctccc tccgcttcca aagaaacgcc    1440
ccccatcgcc actatataca tacccccccc tctcctccca tccccccaac cctaccacca   1500
ccaccaccac cacctccacc tcctccccccc tcgctgccgg acgaccagct cctccccccct 1560 ccccctccgc cgccgccgcg ccggtaacca ccccgcccct ctcctctttc tttctccgtt  1620 tttttttcc gtctcggtct cgatctttgg ccttggtagt ttgggtgggc gagaggcggc    1680
ttcgtgcgcg cccagatcgg tgcgcgggag gggcgggatc tcgcggctgg ggctctcgcc  1740
ggcgtggatc cggcccggat ctcgcgggga atggggctct cggatgtaga tctgcgatcc  1800
gccgttgttg ggggagatga tgggggggttt aaaatttccg ccatgctaaa caagatcagg  1860
aagaggggaa aagggcacta tggtttatat ttttatatat ttctgctgct tcgtcaggct    1920
tagatgtgct agatctttct ttcttctttt tgtgggtaga atttgaatcc ctcagcattg    1980
ttcatcggta gttttctttt tcatgatttg tgacaaatgc agcctcgtgc ggagcttttt   2040
tgtaggtaga a                                                        2051
```

<210> SEQ ID NO 46
<211> LENGTH: 842
<212> TYPE: DNA
<213> ORGANISM: Oryza sativa

<400> SEQUENCE: 46

```
tcgaggtcat tcatatgctt gagaagagag tcgggatagt ccaaaataaa acaaaggtaa      60
gattacctgg tcaaaagtga aaacatcagt taaaaggtgg tataaagtaa aatatcggta    120
ataaaaggtg gcccaaagtg aaatttactc ttttctacta ttataaaaat tgaggatgtt    180
tttgtcggta ctttgatacg tcattttgt atgaattggt ttttaagttt attcgctttt     240
ggaaatgcat atctgtattt gagtcgggtt ttaagttcgt ttgcttttgt aaatacagag    300
ggatttgtat aagaaatatc tttaaaaaaa cccatatgct aatttgacat aattttgag    360 aaaaatatat attcaggcga attctcacaa tgaacaataa taagattaaa atagctttcc   420
cccgttgcag cgcatgggta tttttctag taaaaataaa agataaactt agactcaaaa   480
```

| | | |
|---|---|---|
| catttacaaa aacaacccct aaagttccta aagcccaaag tgctatccac gatccatagc | 540 | |
| aagcccagcc caacccaacc caacccaacc caccccagtc cagccaactg gacaatagtc | 600 | |
| tccacacccc cccactatca ccgtgagttg tccgcacgca ccgcacgtct cgcagccaaa | 660 | |
| aaaaaaaaaa gaaagaaaaa aaagaaaaag aaaaacagc aggggtccg ggtcgtgggg | 720 | |
| gccggaaacg cgaggaggat cgcgagccag cgacgaggcc ggccctccct ccgcttccaa | 780 | |
| agaaacgccc cccatcgcca ctatatacat accccccct ctcctcccat cccccaacc | 840 | |
| ct | 842 | |

<210> SEQ ID NO 47
<211> LENGTH: 1973
<212> TYPE: DNA
<213> ORGANISM: Panicum virgatum

<400> SEQUENCE: 47

| | | |
|---|---|---|
| cacgtcagtg tttggtttcc actagcacga gtagcgcaat cagaaaattt tcaatgcatg | 60 | |
| aagtactaaa cgaagtttat ttagaaattt ttttaagaaa tgagtgtaat ttttgcgac | 120 | |
| gaatttaatg acaataatta atcgatgatt gcctacagta atgctacagt aaccaacctc | 180 | |
| taatcatgcg tcgaatgcgt cattagattc gtctcgcaaa atagcacaag aattatgaaa | 240 | |
| ttaattttac aaactatttt tatttaatac taataattaa ctgtcaaagt ttgtgctact | 300 | |
| cgcaagagta gcgcgaacca acacggcct ggaggagcac ggtaacggcg tcgacaaact | 360 | |
| aacggccacc acccgccaac gcaaaggaga cggatgagag ttgacttctt gacggttctc | 420 | |
| cacccctctg tctctctgtc actgggccct gggtcccct ctcgaaagtt cctctggccg | 480 | |
| aaattgcgcg gcggagacga ggcgggcgga accgtcacgg cagaggattc cttccccacc | 540 | |
| ctgcctggcc cggccatata taaacagcca ccgcccctcc ccgttcccca tcgcgtctcg | 600 | |
| tctcgtgttg ttcccagaac acaaccaaaa tccaaatcct cctcctcctc ccgagcctcg | 660 | |
| tcgatccctc acccgcttca aggtacggcg atcctcctct cccttctccc ctcgatcgat | 720 | |
| tatgcgtgtt ccgtttccgt ttccgatcga gcgaatcgat ggttaggacc catggggac | 780 | |
| ccatggggtg tcgtgtggtg gtctggtttg atccgcgata tttctccgtt cgtagtgtag | 840 | |
| atctgatcga atccctggtg aaatcgttga tcgtgctatt cgtgtgaggg ttcttaggtt | 900 | |
| tggagttgtg gaggtagttc tgatcggttt gtaggtgaga ttttccccat gatttgctt | 960 | |
| ggctcgtttg tcttggttag attagatctg cccgcatttt gttcgatatt tctgatgcag | 1020 | |
| atatgatgaa taatttcgtc cttgtatccc gcgtccgtat gtgtattaag tttgcaggtc | 1080 | |
| ctagttaggt ttttcctact gatttgtctt atccattctg tttagcttgc aaggtttggt | 1140 | |
| aatggtccgg catgtttgtc tctatagatt agagtagaat aagattatct caacaagctg | 1200 | |
| ttggcttatc aattttggat ctgcatgtgt ttcgcatcta tatctttgca attaagatgg | 1260 | |
| tagatggaca tatgctcctg ttgagttgat gttgtacctt ttacctgagg tctgaggaac | 1320 | |
| atgcatcctc ctgctacttt gtgcttatac agatcatcaa gattatgcag ctaatattcg | 1380 | |
| atcagtttct agtatctaca tggtaaactt gcatgcactt gctacttatt tttgatatac | 1440 | |
| ttggatgata acatatgctg ctggttgatt cctacctaca tgatgaacat tttacaggcc | 1500 | |
| attagtgtct gtctgtatgt gttgttcctg tttgcttcag tctatttctg tttcattcct | 1560 | |
| agtttattgg ttctctgcta gatacttacc ctgctgggct tagttatcat cttatctcga | 1620 | |
| atgcattttc atgtttatag atgaaatatac actcagatag gtgtagatgt atgctactgt | 1680 | |
| ttctctacgt tgctgtaggt tttacctgtg gcaactgcat actcctgttg cttcgctaga | 1740 | |

-continued

| | | |
|---|---|---|
| tatgtatgtg cttatataga ttaagatatg tgtgatggtt ctttagtata tctgatgatc | 1800 |
| atgtatgctc ttttaacttc ttgctacact tggtaacatg ctgtgatgct gtttgttgat | 1860 |
| tctgtagcac taccaatgat gaccttatct ctctttgtat atgatgtttc tgtttgtttg | 1920 |
| aggcttgtgt tactgctagt tacttaccct gttgcctggc taatcttctg cag | 1973 |

<210> SEQ ID NO 48
<211> LENGTH: 2119
<212> TYPE: DNA
<213> ORGANISM: Oryza sativa

<400> SEQUENCE: 48

| | | |
|---|---|---|
| ccgtcaacaa agaaatcaa aagggaaatg caccatctta tatctccagt ttatatgaac | 60 |
| agattggata agatcataag atcaagtggt ttatattatt ttgaggaata taacatggat | 120 |
| tcatcctaat cactcgtcta ggcagtatgt gtattcatga tggatatggt actatactac | 180 |
| ggagttttt cttcacaaaa taacctgtta ttttgacctc caaccaaaca cgaattatac | 240 |
| caaaaattgg gttatttcat ctatagtaca actctattat aaacatgcag taaattatcc | 300 |
| tacacatata ccaaaattca agtgtaataa tcctaataca cagacttaaa aaacaaacta | 360 |
| tttccttttt aagaaaagga aaaccatttt tttaacggaa ggaaaacaaa ttcgggtcaa | 420 |
| ggcggaagcc agcgcgccac cccacgtcag caaatacgga ggcgcggggt tgacggcgtc | 480 |
| acccggtcct aacggcgacc aacaaaccag ccagaagaaa ttacagtaaa aaaaaagtaa | 540 |
| attgcacttt gatccaccct ttattaccta agtctcaatt tggatcaccc ttaaacctat | 600 |
| cttttcaatt tgggccgggt tgtggtttgg actaccatga acaactttc gtcatgtcta | 660 |
| acttcccttt cagcaaacat atgaaccata tatagaggag atcggccgta tactagagct | 720 |
| gatgtgttta aggtcgttga ttgcacgaga aaaaaaaatc caaatcgcaa caatagcaaa | 780 |
| tttatctggt tcaaagtgaa aagatatgtt taaaggtagt ccaaagtaaa acttatagat | 840 |
| aataaaatgt ggtccaaagc gtaattcact caaaaaaaat caacgagacg tgtaccaaac | 900 |
| ggagacaaac ggcatcttct cgaaatttcc caaccgctcg ctcgcccgcc tcgtcttccc | 960 |
| ggaaaccgcg gtggtttcag cgtggcggat tctccaagca gacggagacg tcacggcacg | 1020 |
| ggactcctcc caccacccaa ccgccataaa taccagcccc ctcatctcct ctcctcgcat | 1080 |
| cagctccacc cccgaaaaat ttctccccaa tctcgcgagg ctctcgtcgt cgaatcgaat | 1140 |
| cctctcgcgt cctcaaggta cgctgcttct cctctcctcg cttcgtttcg attcgatttc | 1200 |
| ggacgggtga ggttgttttg ttgctagatc cgattggtgg ttaggggttgt cgatgtgatt | 1260 |
| atcgtgagat gtttaggggt tgtagatctg atggttgtga tttgggcacg gttggttcga | 1320 |
| taggtggaat cgtggttagg ttttgggatt ggatgttggt tctgatgatt ggggggaatt | 1380 |
| tttacggtta gatgaattgt tggatgattc gattggggaa atcggtgtag atctgttggg | 1440 |
| gaattgtgga actagtcatg cctgagtgat tggtgcgatt tgtagcgtgt tccatcttgt | 1500 |
| aggccttgtt gcgagcatgt tcagatctac tgttccgctc ttgattgagt tattggtgcc | 1560 |
| atgggttggt gcaaacacag gctttaatat gttatatctg ttttgtgttt gatgtagatc | 1620 |
| tgtagggtag ttcttcttag acatggttca attatgtagc ttgtgcgttt cgatttgatt | 1680 |
| tcatatgttc acagattaga taatgatgaa ctctttttaat taattgtcaa tggtaaatag | 1740 |
| gaagtcttgt cgctatatct gtcataatga tctcatgtta ctatctgcca gtaatttatg | 1800 |
| ctaagaacta tattagaata tcatgttaca atctgtagta atatcatgtt acaatctgta | 1860 |

```
gttcatctat ataatctatt gtggtaattt cttttttacta tctgtgtgaa gattattgcc    1920
actagttcat tctacttatt tctgaagttc aggatacgtg tgctgttact acctatctga    1980
atacatgtgt gatgtgcctg ttactatctt tttgaataca tgtatgttct gttggaatat    2040
gtttgctgtt tgatccgttg ttgtgtcctt aatcttgtgc tagttcttac cctatctgtt    2100
tggtgattat ttcttgcag                                                 2119

<210> SEQ ID NO 49
<211> LENGTH: 1830
<212> TYPE: DNA
<213> ORGANISM: Oryza sativa

<400> SEQUENCE: 49
gttatcacgt cggcacgccg acgtcgctgc gcctgcgcgt gggaggccag ggcagatgct      60
acgtgccatc aggaatgtcg acctgatgat tattttgttg atcatgattt tcttttggct     120
atttgatttt ttgaaagata ttttttttccc tgggaagaca cctatgggac gaagatatta    180
tgtttcttat atagcaccaa acaaatttaa tatatatata tatatatata tatatatata    240
tatatatata tatatatata tatatatata tatatatata tatatatata tatcacatca    300
gtctctgcac aaagtgcatc ctgggctgct tcaattataa agccccattc accacatttg    360
ctagatagtc gaaaagcacc atcaatattg agcttcaggt attttttggtt gtgttgtggt    420 tggattgatt ctaatatata ccaaatcaat ataattcact accaaaatat accatagcca    480
tcacaacttt attaattttg gtagcttaag atggtatata taataaccaa ttaacaactg    540
attctaattt tactacggcc cagtatgtac caatacaaaa caacgagtat gttttcttcc    600
atcgtaatcg tacacagtac aaaaaaaacct ggccagcctt tcttgggctg gggctctctt    660
tcgaaaggtc acaaaacgta cacggcagta acgccgcttc gctgcgtgtt aacggccacc    720
aaccccgccg tgagcaaacg gcatcagctt tccacctcct cgatatctcc gcggcgccgt    780 ctggaccccgc cccctttccg ttcctttctt tccttctcgc gtttgcgtgg tggggacgga    840
ctccccaaac cgcctctccc tctctccttt ctttatttgt ctatattctc actgggcccc    900
acccaccgca ccctgggcc cactcacgag tccccccctc cccacctata aatacccccac   960 cccctcctcg cctcttcctc cgtcaatcga accccaaaat cgcagagaaa aaaaaatctc   1020
ccctcgaagc gaagcgtcga atcgccttct caaggtatgc gattttctga tcctctccgt   1080
tcctcgcgtt tgatttgatt tcccggcctg ttcgtgattg tgagatgttg tggttagtct   1140
ccgttttgcg atctgtggta gatttgaaca ggtttagatg gggttcgcgt ggtatgctgg   1200
atctgtgatt atgagcgatg ctgttcgtgg tccaagtatt gattggttcg gatctagaag   1260
tagaactgtg ctagggttgt gatttgttcc gatctgttca attagtagga tttagtctct   1320 gttttttctcg ttgatccaag tagcagcttc aggtatatt tgcttaggtt gttttttgatt  1380 cagtcccctct agttgcatag attctactct gttcatgttt aatctaaggg ctgcgtcttg   1440
ttgattagtg attacatagc atagctttca ggatatttta cttgcttatg cctatcttat    1500
caactgttgc acctgtaaat tctagcctat gttaattaac ctgccttatg tgctctcggg   1560
atagtgctag tagttattga atcagtttgc cgatggaatt ctagtagttc atagacctgc   1620
agattatttt tgtgaactcg agcacggtgc gtctctctat tttgttaggt cactgttggt   1680
gttgataggt acactgatgt tattgtggtt taggtcgtgt atctaacata ttggaataat   1740
ttgattgact gatttctgct gtacttgctt ggtattgtta taatttcatg ttcatagttg   1800
ctgaccatgc ttcggtaatt gtgtgtgcag                                    1830
```

<210> SEQ ID NO 50
<211> LENGTH: 2212
<212> TYPE: DNA
<213> ORGANISM: Aegilops tauschii

<400> SEQUENCE: 50

| | | | | | |
|---|---|---|---|---|---|
| tgcagcgtcc | cggtgccgtc | ggagcttgcc | gcgactactg | tggagatccg | agggagcttc | 60 |
| aatggagtgt | gtcaagggct | gcaatggagc | gccgccgggg | tcgttggagc | ttgtcgtgga | 120 |
| ttcaagcttt | caccggagct | gcaatggagc | gccgtcggag | cttgaagctt | ttttcgcgcc | 180 |
| gcagtgcaac | accgccgtct | atgtgcaact | ttccgcctgt | ttcaatgaag | caccgttgtt | 240 |
| cgtgacacct | ggtgcaacgc | ggcattgccg | tcggacgcac | gagctgagag | ggggtgccat | 300 |
| ggcgctacca | accagggatg | ttgcttttct | ctcccaacgc | aaccacaatc | tgctcagctc | 360 |
| cccacatgca | gcaagctcac | atgccgcacc | tagcacaccg | cgacacgacc | acgtgactgc | 420 |
| tactatcggg | ggccatggcc | agcgagctca | agggttgggg | cagccatatg | ccctgcaaag | 480 |
| ctcaagggtt | gtggcggtca | tggcatgtga | gctctggggc | gagtcgttat | aggcggcgct | 540 |
| acaaccgcgg | aagctgactg | ctacaaccgt | ggtgaccgtg | tgtcgtgacc | ccagtggggg | 600 |
| ctatgctgcg | accgtccggg | tgagaagcta | cgcccccagc | cgaagatgtt | ccgactgaca | 660 |
| tgggcggggg | aggggagcac | gggcgggcgg | cgcagcaatc | gtcggcgaca | ggaaggtgca | 720 |
| aacctcgaca | gccatgctac | aaccttccaa | tatctggagc | tggagacaag | aaggttaccg | 780 |
| gtgtggtgct | cagatcggcc | ggccgatgca | gagcactgtc | caaggcgaat | acaaattcga | 840 |
| gtcaaaattg | tgacaacaca | gtaggcgtgg | ccgtacgagt | tcgagtcacg | catgactaac | 900 |
| gatgctcacg | caccgcacca | acggcgtgag | cgcggcgtcc | aactccaacg | gccaccaacc | 960 |
| agccaaatcc | ccaacagcac | caaacgacgt | cacctttgga | atctcctccc | ctattctggc | 1020 |
| ttttgcgacc | gcctctctct | cctccgcctg | cctatccgct | ccatcctcca | cacgtcaggc | 1080 |
| gtgccgtgtc | tcttcttcct | tctctccctc | cctcccgtcc | gagcctgcta | taaaatccct | 1140 |
| gcccccctccc | gtctcctctc | cacacatccg | atccaatcca | atccagtccc | cgtccaatcg | 1200 |
| aagcgaagcg | aagcgaaggc | tctctcgtcc | tcctcctcaa | ggtatgcgat | gcgagcctcc | 1260 |
| gattttctct | ccgccttctc | gtcatgtgcg | tgcgtgcccc | gggatcattg | ataagactgc | 1320 |
| cctgatcgat | tattggtggt | tcccctcgat | tcctgttagt | aggttggagt | agatctgcgg | 1380 |
| gcgggccgag | tctgttatag | tcgactgatt | gctgctggtt | cgctcagtcg | aggttgatta | 1440 |
| agtctcgatt | ttagattaat | ctctctcgat | tatgcctgga | ttttcgagta | gatctgccga | 1500 |
| ttgggatgcg | attttcttg | gtttcgtcca | tctatatata | tgctgtggtt | agctatgtct | 1560 |
| gctggttgtt | gataaatcgt | cgcagtattc | ttggatttac | gattttgtac | ccctcgtatc | 1620 |
| acaccagcaa | tttgctgttg | ctaacctttg | cttgctgtac | gctgtgcatc | gactttttac | 1680 |
| cttcatattg | ctcccacaag | gctaaagatt | gcttgtagat | ctgctaatat | atttctgttg | 1740 |
| agttctgcta | agatttagca | ctgcatgctc | tgaaatccgt | ttgcttagtc | tagcggattc | 1800 |
| tttgtactgt | ggcctcgttt | atctatagat | tgacttactg | cagatttcat | tattcttgtg | 1860 |
| gtttcggccc | tgtagctact | tgtttagtct | tttgattcaa | ctcttaaata | catgtgggtt | 1920 |
| tgatgatgtt | actgttaata | cgtccatgac | ttgaccagct | tattctgttt | aactgactaa | 1980 |
| taatatatac | tccccatgac | catgaggcta | gagatttcac | tgataataaa | tctgctaata | 2040 |
| tatttgtggt | aggggttctt | ccaaaagtta | gcatcgtcaa | tcatttgatt | agcttattct | 2100 |

| | |
|---|---|
| aagggattcc ttagttacaa ttccatctct gttgtataat ccggttcatg tattgttaca | 2160 |
| gatttctctg taccgtttct aactctggtt ctgtgtgctt tgttgtttac ag | 2212 |

<210> SEQ ID NO 51
<211> LENGTH: 2452
<212> TYPE: DNA
<213> ORGANISM: Unknown
<220> FEATURE:
<223> OTHER INFORMATION: Panicum hallii

<400> SEQUENCE: 51

| | |
|---|---|
| aatcgttggt caactttcct tccattactt tttaatacgt aacaattatc cctaaagcct | 60 |
| aattaagtaa ttcaacttcc gaattcaata ggggatcatc tgggcacgac ctaattgaaa | 120 |
| ggataacaat agcttttcaaa caacatttcc acttgtggta agatttaagg tcttaacatt | 180 |
| gtatagttgt ttttctcacg gccctagact tgagaaaggg acctttttgat atcgttattg | 240 |
| tgctccataa ttttttagttg ggacaaatgt aatttcttat atttacgata aactcgattc | 300 |
| taatgtattg ataactccaa tgccgtgtcc atttatggtg ttatcatttg tttcctgatt | 360 |
| taaagaaaaa atataacaca caaaaaagat gattttggaa gtttacaatc acgttcacca | 420 |
| ttactctcta ccatatcttg gcgttgttgc caagcgtatc tagtaatttc attcttgaaa | 480 |
| gcctctagct cttaaacgta atttatgata cagtactata tttttttttat taagggcaaa | 540 |
| agatcgagag gtaaatggtc tgctccgtaa atttatctta catagaggct ttaaaaagaa | 600 |
| atatcatgta aaatcgcttt tgttagaagc aggtcatgca taaccttcca gggacatgcc | 660 |
| agttgttagt tgcttttttt tagtttctct ttctttttacc tgattataat ctttttaaagt | 720 |
| tatagtcttg tatttctaat atagaaacgc atacgtgtgc gccgttgtta aaaacaaaga | 780 |
| gatcatgcat gattgaagca tcaccataac gacgttaatc ttccgtccag ccattaacgg | 840 |
| ccaccaaccg caggaggcaa acggcgtcac catcctcgat atctccgcgg cggccgctgg | 900 |
| cgttttccgg agaaattgcg cggtggggac ggattccacg agagcctctc gctgctgggc | 960 |
| cccacatcaa tggcgtaacc tcacgggacg cttcctccct cctgcggccc tcccccgcgt | 1020 |
| ataaatagca cccctccctc acctcttcct catccagtcc ccaacccgtc gagaaattct | 1080 |
| cccgagcgat tgcaatcgaa gcgaagaggt ctcccccgat cctctcaagg tatgcgagtc | 1140 |
| ctcgatcccc ttccgatcta tctcgtttct cgcgtgctct ccctgctcgt gttcgtcgtc | 1200 |
| gatctagttt agggtttgat ttggttctga atcgttccct tttcctgctt gcgttcgatt | 1260 |
| tgtcgtcgat tctcgggtag atgtgtggat ctgcggggcg tgatgaggta gtttggtgta | 1320 |
| gattcgtgtt gggcgttcaa tttgcctcta gggttcggct gctgttggca tgcctgtgat | 1380 |
| cgagcggccg gataggatta gttttttta tatatatg ttggatgcct gatttcctgt | 1440 |
| atgttgggtt agattgctgg tacgattcat ctaggcggtg ctttgcagag gaacagcctt | 1500 |
| gctgtttagt atttggtagc tctttctaca ttgattactt ttgatcatag cctgataatg | 1560 |
| atcaccgatt ggtgtggaat taattatttc attgtcgaaa gcatagctga tgtagatata | 1620 |
| gctgcacaat ttcttccttg gctccttact gtctaaattg tagagtatac tgagttactg | 1680 |
| cttctttatc agtttctctg gattgttgta tccagttagg ccagtgttgt caaaatttga | 1740 |
| catggtagtt catctgaaat ttctccggac tgttggtatg ctcgtggcca gacttaattg | 1800 |
| attaggctgt tcttcatgtt ggatcacccc atgtttgtg atacctgttg ggttagattg | 1860 |
| ttggttcgat tgctgtttaa tcttggtagc ttcatctaga tttgtacaac ttttggtcac | 1920 |
| ctgatgatga tcaccgattg ttgtagaatt agttaattca ttgttgatct aggtgtggaa | 1980 |

```
ttaattagtt aattgttaat ctatggcatg gctcatgcag atattgatgc aaattttctt    2040
aactggttcc ttgcttcagt gtgtatctgt ttgtctgtgt tttaggccac atcatatgat    2100
tgtcaaaatt ttaaatggta gtttaatgat aaatgtagtt cagcttactt cagtgttgat    2160
ttgcttcaaa tgtagttttc tgtcctattg aacatagaat cttcatgaga tgttaatgta    2220
ttctcttgtt cagaattgat ctgtttcaat atcacaatat tatgtgtcct gtaaagtttt    2280
ttagtatgat ttgttttaaa tttagttagc ctatcctgtt aatataggat gatgagccgt    2340
gagatgttca ttctcttttg ttcagagcta atcattttca atgttgcaat gttctgtgtc    2400
tagctggatg cttacggtgg tttaactctc ttctgttcct taatgtttgc ag            2452
```

<210> SEQ ID NO 52
<211> LENGTH: 1783
<212> TYPE: DNA
<213> ORGANISM: Zea mays

<400> SEQUENCE: 52

```
gtagattacg ttggttaaat atatatgaat gtgaaacaac aactaaaatt tgaactatta      60
attatgtata attttatctt atttttatat aaaacagaga ggagaggagc gatgactgtg     120
gcgtgtggga acgtggaaac tcgctggccc atctcgaata attttgctgc acttctaata     180
ccttcacgag tctgcacaag catagattgg tgctggttga acggccctga ttcttttttt     240
tcatggctct gcgttcgaga gcatgttttt cgttgaaggc ttctttggtt agaagtgacc     300
tgagtgaatt ggagaggatt agaggcatgt ttggttcact acctcagttg ctacattttg     360
cctaactttt ctgcctaagg ttagttattc aatttgaacg actaacctta gacaaagtgg     420
ggcacattta gccacaaacc aaacaggccc taaatctatt tatatttaat tttaaatatg     480
aataaattta attctattaa tctttgtcga gtgttctttg ccgagtgtta cactcggcaa     540
agcctttgcc gagtgtaaaa tagcatttgc cgagtgtgtt agacactcga caaagaacgc     600
gattccggta gtgttaattt cctctagttt ttatacaaca aagcataaga ggatatattt     660 cttttcttttt actttgatga aacaatttgg ttcttttgga cgagccaaaa cccggatatg     720
gtccaattaa gaccttattc gtttgtccaa aaatgtaaca ggaatcattt cagatgatca     780
aaacttatat aaaattagaga aacaaatcgg ctaggaatta tttcatatct ccattcctga     840
agaaacgaac ggtcctaagg ctccaagcac gggtctatac atcaggttgc gccggtctaa     900
gcccgcacaa cattgggtcg ggtcgtgttc aagcattaat cgtggtatag actggaccat     960
cgtgtcacgg gctatataat acatttgaga atgtagaatt aaatacatac tccccgactc    1020
taaatgacat attcatatac gaggatggta cttctttgga ctatataggg acggaggtcg    1080
ggagggaatt cgcgagagca agaaagcagc tacggtagcc atgcatgacc atatgaaagc    1140
gacgacgcga gaggatgtat ggtttgggct gcttaaatac aatctgcaat agactgtgct    1200
gcattgcaca ttattcttat gaaagagtgt gtttcatctc tatttatgtt gttttggata    1260
aaatgttttg tttatttatg aaggacatat ttccttatca ataattccta cgcccaaatt    1320
aaagaagccc tggaatcagg aactaggaag gggcaccgat gtgattttgt gagccaacga    1380
catggggagc atgagcgtga gcaatgcatg tttgccgagt caaacgttgc cccaccaaca    1440
agcaagtgcg tcgtgcgtgg atcctctcct tcctctctct tggttcctgt tatctctctc    1500
ggctgtccac tccccgtga tgtgagcgcg tttctctccc gtcctctcct ctcctccccc     1560
gcaacaaact cctgcaagct gctctcgatc tctctctccg tcgccatctc tctcgcgcgc    1620
```

| | |
|---|---:|
| gcattacttg cacgtacgtg ctcagaagga aggcagaggc aaaagcagcc taggtgatat | 1680 |
| gataccctcct cctcctcctc ccattagctc ctccgcatgc atcatgcatg ggtacgtgcg | 1740 |
| cgtgctacat tttatttgaa atgaaatggc tggttgtctg cag | 1783 |

<210> SEQ ID NO 53
<211> LENGTH: 3710
<212> TYPE: DNA
<213> ORGANISM: Zea mays

<400> SEQUENCE: 53

| | |
|---|---:|
| gcccgacaag aaagctaatg ggctgggctg ccaaccatgt ttactaggct aggctcattc | 60 |
| ggatgctagc caatcgttcc tgcactgagg ctctagattt catagatagc taatgggctg | 120 |
| ggctgccaac catgtttact aggccataaa atgaactttt ggtttgttta ataatattat | 180 |
| gccgggtttt agaaacccat gggtttgcgg gtatgggtac taggatccca tactcgtacc | 240 |
| ctcatacccg ctgggtttag cttatcaccc attaagaaac ccgtgggttt ggatattagc | 300 |
| ccgtacccgt cccctaatag ggtaaaaacc caccgggttt cgggtttcgg gtacccattg | 360 |
| ccatctctac ctgtcaatga cccatttaaa tagagcccat cgaagcccac taaatattta | 420 |
| acatttttga gctagttgta cttttttcctt ttttaaccca aattttttaat gtggcaccca | 480 |
| caaacaaccc aattttattt tggttatata tgttatgtac ttttatttat gttatttcat | 540 |
| gtgatttgtg ctaacctgac acattaattt tgggttaatt aagttggata ggcacactta | 600 |
| agtattcatg ggttgtgttt tggatcgacg gcttgacgtc ttggtccacg ggctggcaca | 660 |
| ccacgacccg taattgaaat tgtactttag tggactgtgc cttagtggat gtgctttaa | 720 |
| taagcctggg gtgtaccata ttgggctgat ccagatatac atgtacaccg gggagtattt | 780 |
| atctttgaca caaggagtat ttacttatta tgaaaccagc tccaaaaagt ggcttctgag | 840 |
| cctatccacg tcgtccatta atctttcgac cgtaggatcg gattccaacg gctacacgag | 900 |
| tgttctcacg caccaggcgc caggcggcct cctcatgctg gataaatcgt gacgcttcca | 960 |
| gatgatacat ctccctcttg gctgccgggc ggcactctcc atggtgaaga gggtgtcgac | 1020 |
| cgcgatggct acaacgacga cgatggagca cttgacgccc caacagatg cgagccattc | 1080 |
| tcctcctccc tacgtccttt ccccctccac gacaccataa ccgtgcctgc tccgccgaat | 1140 |
| ctaaaggtgt caggatcccc aatccttccc ctcctctccc cctctccacg acgctgcaac | 1200 |
| tgtgctcgca tcgccatccc ctccctccc ctgtctccaa gccaggaatc ccatccccac | 1260 |
| cccaatgtcg cagttctgct cgcgttggcc ggatctgtga atgaagaacc cacggttcca | 1320 |
| cgacctcctc ttcgtggaag cctaaaaggc atcaccccca taagcgagag ggaaaagaca | 1380 |
| cattcctata tattctctta gtttgtccgc tgttgtctag aaacatcatg taatgaggct | 1440 |
| gggaaacgat cccacggagt gctcccgtgt ccgtcgcctc ggttcggcag aggccagcaa | 1500 |
| ccgcggcacc tggtccacag cagcagccac cacgactcgc tagggctagg ccgacctaga | 1560 |
| tgatatgcag tgagctgatg ggagggatgg gcgagcaaga attggtacag taaccggaag | 1620 |
| acgatcttga tttattcctt atgtcatgaa ttcctttta tttacaccca cactttctaa | 1680 |
| ctttcgtaca atgattcgta tatttaaaac aaggctaact tatgttctca tgctttacga | 1740 |
| accctggcat atgtcgcaaa aaatccttac ctaaagaact aactctgcag cctcttcaag | 1800 |
| ctctagattt caattcttat ggcctaagaa gtgttttttt atttcataat ataagctttc | 1860 |
| acaacaatct aattccttgga gtcagattct ataaatacccc aacatttact aacctacatt | 1920 |
| ttttttttcaa ttggtgccat gaccatcaca taatgttgat gagctattcc ctccaagttg | 1980 |

```
ctgattgcat gtggattacc atgcatggct atttgctatt tggttgtctc gacctttctt    2040
aggatctatt ggatgtaata catattatca ttatttagct aatatttgct aactactacc    2100
tagcagagtg gatagtaggt tgtggtgttt atatccataa ctaatgggtt aattaataat    2160
tggagagtaa tgttcctgtt agcccccatt gtttgggtag atagtaagat aatggggatt    2220
tagaaacaat ctaaagttta ttacaatctg ttatctagac ctatttatat ccatagagct    2280
aaagtttagc agattgctac atcctcatta ttagttggga gccaaacatg tcctgattgt    2340
ataatttaaa tgtttatagg agtaaccaat ttgttttagc tttgctattt tacgagtgtc    2400
aagatgctta actatttcat acttgctttg taggaatgtt cgatgccgac aacatcttgc    2460
tctaccagaa ggtaccagct ccaaatcaag aaccaaaatt taggaaaaat acgaactgca    2520
accttatccg tcatctttag taattcatgt gtttatctta tttgcaccaa gaactatgct    2580
ggaggctata aaactatgaa tgttatttgt gacatgtaaa taatactagc ttgtacatgc    2640
atctaaatgc atataagaaa cacaatgcac cttttgtttg cattccatgt aaattataaa    2700
ttaaatccaa acattgaaaa attacaaaac acacacacac aacactatgc gcgcatgggc    2760
gcgcgcaaga cactagtaca taataataac gatattgttc gcttcggatt aaattaaacc    2820
aagcgagtat gcgtgcatgt gtacgtcgga tgctttgttt gttcatttgt ggcccgtgaa    2880
gtaatatttg ggcccaatag cccattcatc catgtcctaa ccctagggcg cgttccttat    2940
aaaacctatc tccattctgt tctcactctc agacaccaga cgcagtcggc tgccgcagac    3000
tggtagtagc ccgcgcgccg tcaccgtatc ctcagatcag aggcgagcag aaaccacacc    3060
actctactga cgcccgacga ggtacacttc cgcgcgcgcg cttctcttcc ttctttttc    3120 gctcgacgag gtactctgct tcacgcgcgg gcgcgcttct cttccttctc ttttcgctct    3180
gccttgagcc tgttcgtttg atgcccagat ctactaggtt tgtcgatcgt cgttatgtgt    3240
gatgagctga gccgattcat gcactgtatt tttaattaag tgtttttttc ctccgccgct    3300
acctttattg tctatgtatg aacttgcagc ttacaactgg ttattgagcc ataaattgta    3360
actgagtttc cgagatctat aatattacgt ggctgaggcg cttcatctct gttttgtttg    3420
tatgacagta ggagtactaa tccaagttta gcttccgctt cttcatctac ctttagtatg    3480
tatttcgtat ataaatacga ttgcagtttg caactgattc tcggccatag atgattaccg    3540
ttgcgttgtt catcgggtct agtttcggat ctctgatgtt gtgtgggtgg ggtacttcga    3600
cttgggtttt cctgcccttt gtttgattac tggtttattg acatatattt atctattgac    3660 ttttatctg ctatgtttga tgtaagcagc agtgtaacat tttcctgcag    3710
```

<210> SEQ ID NO 54
<211> LENGTH: 1645
<212> TYPE: DNA
<213> ORGANISM: Zea mays
<400> SEQUENCE: 54

```
caaagggctt ttggtcatca gccgggagcg cctccatggc cggcttgatg atgttggtag     60
tggagatctt ggtgtgatcc ttaaaaccgg ccatttatgg gccgattttt agcagatcta    120
gacacctatt ccccagcgga gtcgccaaaa gtatgttgac gcttttcgg agcgccaatc     180 actcaagaag aaccggcggc ggtgccctct gcacaggggc ggacggtccg cgcgcagggg    240
ccggacggtc cgcggcctgg tgcgaggcgg cggcgctctc tggttagacg cggacggtcc    300
gcggcacagg gccggacggt ccgcgaccta gtgcaggtgc tcgggttccc tgcctgacgg    360
```

```
ccggacggtc cgcgctctag ggccggacgg tccgcgcgtg cgcaggggcg gcggaagatc    420
gccggcggcg cctggatctc gctcccggga gggaccccgt cggggaggag agatcctagg    480
agttgtctag gctcgggccg gccgacctag actcctctaa tcgacgtaga gtcgaggaga    540
ggcagagaat tgggggattg gaatactaaa ctagggctaa actagaacta gactagaact    600
actcctaatt gtgctgaaaa taaatgcgag atagaagttg tattggttcg attgttgggg    660
gtcaatcggc cgtagccctt catctatata aaggggaggt ctggatccgt ttccaactga    720
tttccgagtt aatcccgcgg ttttaggtaa caaatcccgc gagaaactag gaaccctaac    780
tgactctgcg cacgcgcgga ccgtccgcgc caccaccgcg gacggtccgg accgcggacc    840
gtccggcctc cgggccggac cgtccgcacg gtcattttgg gttcgaacag agtcccaacg    900
aggttagtaa atgtagtgat gaaattaagt tttgtacgaa gtttgtaaat ttaaggacct    960
gttttacata actattggag aagagttttc tctgaaaaat tcttaaattt atatttaggg   1020
agttgtttat ataactattg gcatttgaga tgctctaagg aagcgaagga ataacttgg    1080
cggcgatcct agtcgacaac cgttgaattc gtgagaatca atcattctgt aggagtaaaa   1140
aaataaaata aatatgcat ttcctcgttc ctatacgctt aaattagacg accctggact    1200
ggaaccagga actaggaagg ggcaccgatg tcatttgcga agcaacaaca acatgcgtga   1260
ggacgaccaa gtcaaacgtt gcgtcgcgtt gcctcgccgg cgggccggtc ccaccaagac   1320
gtggcgccat gcaagtgcgt cgtcgaccct cttctctctc tctcttgtag tcttgttcct   1380
gttatctctc tcggctgtcc gctgccccgt gatctgagcg cgtttctctc ccgtcctctc   1440
ttctccctct cccgcaacaa acacctgcta tccgctctcc ctctcccctg ccatctctct   1500
ctatcgcatt gcttgcgcga gcgcagaagg cacacacgta cagcctaggt gatacctcct   1560
cctcctcctc ctcctcctcc tgatctcctc tcctcctccg gcctccgtat acctataact   1620
aaaagatgat catcgtgcga tgcag                                         1645

<210> SEQ ID NO 55
<211> LENGTH: 899
<212> TYPE: DNA
<213> ORGANISM: Zea mays

<400> SEQUENCE: 55
tgcagtgcag cgtgacccgg tcgtgcccct ctctagagat aatgagcatt gcatgtctaa     60
gttataaaaa attaccacat attttttttg tcacacttgt ttgaagtgca gtttatctat    120
ctttatacat atatttaaac tttactctac gaataatata atctatagta ctacaataat    180
atcagtgttt tagagaatca tataaatgaa cagttagaca tggtctaaag gacaattgag    240
tattttgaca acaggactct acagttttat cttttttagtg tgcatgtgtt ctcctttttt    300
tttgcaaata gcttcaccta tataatactt catccatttt attagtacat ccatttaggg    360
tttagggtta atggttttta tagactaatt ttttttagtac atctatttta ttctatttta    420
gcctctaaat taagaaaact aaaactctat tttagttttt ttatttaata atttagatat    480
aaaatagaat aaaataaagt gactaaaaat taaacaaata ccctttaaga aattaaaaaa    540
actaaggaaa catttttctt gtttcgagta gataatgcca gcctgttaaa cgccgtcgac    600
gagtctaacg gacaccaacc agcgaaccag cagcgtcgcg tcgggccaag cgaagcagac    660
ggcacggcat ctctgtcgct gcctctggac ccctctcgag agttccgctc caccgttgga    720
cttgctccgc tgtcggcatc cagaaattgc gtggcggagc ggcagacgtg agccggcacg    780
gcaggcggcc tcctcctcct ctcacggcac cggcagctac gggggattcc tttcccaccg    840
```

```
ctccttcgct ttcccttcct cgcccgccgt aataaataga cacccctcc acaccctct      899
```

<210> SEQ ID NO 56
<211> LENGTH: 807
<212> TYPE: DNA
<213> ORGANISM: Hordeum vulgare

<400> SEQUENCE: 56

```
gatctcgatg tgtagtctac gagaagggtt aaccgtctct tcgtgagaat aaccgtggcc      60
taaaaataag ccgatgagga taaataaaat gtggtggtac agtacttcaa gaggtttact     120
catcaagagg atgcttttcc gatgagctct agtagtacat cggacctcac atacctccat     180
tgtggtgaaa tattttgtgc tcatttagtg atgggtaaat tttgtttatg tcactctagg     240
ttttgacatt tcagttttgc cactcttagg ttttgacaaa taatttccat tccgcggcaa     300
aagcaaaaca atttatttt acttttacca ctcttagctt tcacaatgta tcacaaatgc     360
cactctagaa attctgttta tgccacagaa tgtgaaaaaa acactcact tatttgaagc     420
caaggtgttc atggcatgga aatgtgacat aaagtaacgt tcgtgtataa gaaaaaattg     480
tactcctcgt aacaagagac ggaaacatca tgagacaatc gcgtttggaa ggctttgcat     540
cacctttgga tgatgcgcat gaatggagtc gtctgcttgc tagccttcgc ctaccgccca     600
ctgagtccgg gcggcaacta ccatcggcga acgaccagc tgacctctac cgaccggact     660
tgaatgcgct accttcgtca gcgacgatgg ccgcgtacgc tggcgacgtg ccccgcatg     720
catggcggca catggcgagc tcagaccgtg cgtggctggc tacaaatacg taccccgtga     780
gtgccctagc tagaaactta cacctgc                                          807
```

<210> SEQ ID NO 57
<211> LENGTH: 1084
<212> TYPE: DNA
<213> ORGANISM: Hordeum vulgare

<400> SEQUENCE: 57

```
gggcaagtta aaggccctac tggtggcatg ggtgggcagg ctgaagaccc tactagtggc      60
atgggtgggg agctccctgc caccatgtaa tggaaccttt atgatttact acccctttatg    120
ttgtgtgtga gtgtgacaga gaaacctttc tctgccttat taataataaa taaagcacat    180
cacttgtgtg tgttctgaaa aaagatctc gatgtgtagt ctacgagaag ggttaaccgt    240
ctcttcgtga gaataaccgt ggcctaaaaa taagccgatg aggataaata aaatgtggtg    300
gtacagtact tcaagaggtt tactcatcaa gaggatgctt ttccgatgag ctctagtagt    360
acatcggacc tcacatacct ccattgtggt gaaatatttt gtgctcattt agtgatgggt    420
aaattttgtt tatgtcactc taggttttga catttcagtt ttgccactct taggttttga    480
caaataattt ccattccgcg gcaaaagcaa acaatttta ttttactttt accactctta    540
gctttcacaa tgtatcacaa atgccactct agaaattctg tttatgccac agaatgtgaa    600
aaaaacact cacttatttg aagccaaggt gttcatggca tggaaatgtg acataaagta    660
acgttcgtgt ataagaaaaa attgtactcc tcgtaacaag agacggaaac atcatgagac    720
aatcgcgttt ggaaggcttt gcatcacctt tggatgatgc gcatgaatgg agtcgtctgc    780
ttgctagcct tcgcctaccg cccactgagt ccgggcggca actaccatcg cgaaccacc    840
cagatgacct ctaccgatcg accggacatg aatgcgctac cttcgtcggc gacgatggcc    900
gcgtacgctg gcgacgtgcc cccgcatgca tggcggcaca tggcgagcta ggaacctagg    960
```

```
accgtgcgtg gccgccggct ataaatatcc catggtcgtg agaccactag aaggaagcag    1020
cacctggcac tgcgagagcg agcgtgcagt gagtagatag actagaccaa cgacgacggc    1080
aggc                                                                 1084

<210> SEQ ID NO 58
<211> LENGTH: 3064
<212> TYPE: DNA
<213> ORGANISM: Zea mays

<400> SEQUENCE: 58
gctcgatcca cctaggcttg ttgcacatct ttacccacaa gtcatgttac ccatctgcca      60
aggggtcatg aatcccatac acctctacca tggaagcgag acagggtaac actacgaggc     120
ctttacaaag ttccactagc tttagaaaac ccgctacaag gatccccgt ctgaccgcca      180 tcacagcaaa acccgagaac ctccctacac cgaccactcc cctactatcc ttgccccttt     240
cgggtaagat agtcttccac tagctttcct aattagtcag ccaagggcgt cccataccac     300
ccttatggta gcactgtttt tccgggtggt cgctccatgt tccaattaac ataataatct     360
tatcatgaac aataaataac aaaaaatgat aataaaagca tgatcatgaa taatgtgtat     420
ctcaataccc aaaaccacat aaagcaatag caggtactac ccaaaagttc agtggtaaac     480
aaggtataaa gatagtcaaa ctgggttgac ctattgggtc tcatcaaaat taacctatgc     540
agatcataat gattaacagt aacattattg ggtaaataga agtgatcaag gcacaagtt      600 gccttcaacg agatcctgct cagcagtctc cacctgctga cacctgggt cctcagtggc      660 ttgcttgtct actcgcaaca atacaaacaa acatggtata ggagaaatta acatcacacc     720
aaacagcaga acagaatgca tgataatatt ctacgtgtca taacgagatg gtaggaacaa     780
gaatcactaa attcagagtt acgatttct gaagttatta ggtgcttagt atagaataaa      840
tcaagtggat aattttactc tatgtttat ggctaaacag agttaccaag tgataaacaa      900
tattaataca aaattaatgc aactggaatg gaccaaaaag gagttaaaat ggattttcta     960
tgaattaatc taggttttgg aattgttttt atactaaata ttcattttct cggcttatta    1020
ttaaccctgg tattttattt ggactgcgga cgcaaatgct agaaactaca gggtccaata    1080
tatgaaaatc agggcatgga tgtaattaat ttacaatagc agtggacggc gggttaattc    1140
agtaattccc taggggcact taagcaaata tccatcgcaa aggggtattg ttggatcccg    1200
accgttggat cagatccgaa ggccgagaat agatcgcgcc cacacaactg cgtcgtgcac    1260
tgaccaccct ccggttaaga ttcgacggac caaatttaat gaaatccaaa ccacccacag    1320
ccccacgatc agcaatctac ggtccctctt aacccagatg aatcggtatc cgacttctaa    1380
tctaagcagt tcctcaatcg atcaacgctc cagggccttc ttctatctcc caacgcagat    1440
cgagctacgg tcgcttgcac ccgaggaacg ccgacacagc gagcggcgga ccagcggttc    1500
tgggtaatga tttggagcac aaacaatatt ggcgcgacat aggaatgatg caactatta    1560 ggttgtgacc ttactagtgt cagcggtgtg ggcagggtcg cccacgggaa accagtgcga    1620
cggtgctccc ggcttgttaa tgacggtgtg ctggtcccga cacggtgatg ccccaaacgc    1680
ccccgccgta cgagaacacc gcagacgccc tgctcgact ccgccctcgg cttcccgcgc     1740
ccacctcgca cttcgacggc cgcaccgacc ctctgacctc tccttttctc tcctttctca    1800
ctcctatcgg tagctacaac agaagcgact cccaacgtgg cgcaaaccct cgaagcatac    1860
ggctggggaa ggtggcagcc aggtttatat cctaggcgcc cgaggaaatc gtgtggacgg    1920
ctgttacgtt tcgcccgcgg ggcgcgattc gcgcgaagaa gactgtatgc gaggtagggc    1980
```

```
ccactagcag tgagccatca cccagggaag cgcgcatgca tcgattgaca cgcgaccccca   2040 acagtcaggc gacccgagtg tgcagacggt cgcgatggtg aaagtggcta gctcgcgcgg   2100
acgcgtaggg gcattgggcc gaaatgcgtt tcagcggtcc aacttctttt tttcttgtct   2160
ttttttcttt cctttccttt tctattttta gatttcaaat ttaagttcaa attttttgtg   2220
gtgaattttc taaaaatcca catatcagta tgaaagaat ttatatataa atctatttat   2280
ttatatattt attttttttc tatgttattt ccaatttcta aaatgtaaat taggttaaat   2340
cgccatttgg acactaatat atctttatta gtattactat tattatatgc acaaccaaat   2400
aaactccaac atgatgcatc gattatttgt atgtcattgg ttaattattc actttaaata   2460
tgttccttaa cgattctcat gaaacagaag gccatgcaca taaagatgta tccctttttt   2520
ctatattccc agagttgggt attacaacat tcatctatgc attctaggat ttcaattact   2580
ctcaatcttt tagtatttgt tccttcattg tcaaatcact tctcatctaa ctactatgct   2640
tgtttaacca gcagaacaat actacaacaa tatccattta taaaggcttt aatagcaaac   2700
tttacatatt catatcatgt taaggttgtc acatgtgtaa aggtgaagag atcatgcatg   2760
tcattccaca taaatgaaaa gaattcctat ataaaaatga catgttttgt tgtaggtagt   2820
ggaaattatc tttccagcaa agaccatata atccgataaa gctgataact aaatgtcaaa   2880
atcgagtaag tgccatatca tctatatctt atctgttgtt tggaaaaaga caaaatccaa   2940
aaaaaaatat atgagatctc acatgtataa atagctccca aatcagtagt taatacatct   3000
cccataatat tttcagcatt caaaaacaca ccaagcgaag cgcactagca acgacctaac   3060
acca                                                                3064

<210> SEQ ID NO 59
<211> LENGTH: 178
<212> TYPE: DNA
<213> ORGANISM: Zea mays

<400> SEQUENCE: 59
cacgtgagct tgcgatgtcc actagggagc tccatccact gatccacccc cacgcggcgt    60
ggcgtcgtca ttaacggctt gtggggaagg gaacgagcaa ctaaccgata attagtacca   120
gaccggccag tgaacgatgc caaaaccggc ttataagctc agctgcgaca accgtttt    178

<210> SEQ ID NO 60
<211> LENGTH: 330
<212> TYPE: DNA
<213> ORGANISM: Oryza sativa

<400> SEQUENCE: 60
aagaacgaac taagccggac aaaaaaaaaa aggagcacat atacaaaccg gttttattca    60
tgaatggtca cgatggatga tggggctcag acttgagcta cgaggccgca ggcgagagaa   120
gcctagtgtg ctctctgctt gtttgggccg taacggagga tacggccgac gagcgtgtac   180
taccgcgcgg gatgccgctg ggcgctgcgg gggccgttgg atggggatcg gtgggtcgcg   240
ggagcgttga ggggagacag gtttagtacc acctcgccta ccgaacaatg aagaacccac   300
cttataaccc cgcgcgctgc cgcttgtgtt                                    330

<210> SEQ ID NO 61
<211> LENGTH: 246
<212> TYPE: DNA
<213> ORGANISM: Oryza sativa
```

```
<400> SEQUENCE: 61
ggatcatgaa ccaacggcct ggctgtattt ggtggttgtg tagggagatg gggagaagaa      60
aagcccgatt ctcttcgctg tgatgggctg gatgcatgcg ggggagcggg aggcccaagt     120
acgtgcacgg tgagcggccc acagggcgag tgtgagcgcg agaggcggga ggaacagttt     180
agtaccacat tgcccagcta actcgaacgc gaccaactta taaacccgcg cgctgtcgct     240
tgtgtt                                                                246

<210> SEQ ID NO 62
<211> LENGTH: 187
<212> TYPE: DNA
<213> ORGANISM: Oryza sativa

<400> SEQUENCE: 62
tgggccgtaa cggaggatac ggccgacgag cgtgtactac cgcgcgggat gccgctgggc      60
gctgcggggg ccgttggatg gggatcggtg ggtcgcggga gcgttgaggg gagacaggtt     120
tagtaccacc tcgcctaccg aacaatgaag aacccacctt ataacccgc gcgctgccgc      180 ttgtgtt                                                               187

<210> SEQ ID NO 63
<211> LENGTH: 163
<212> TYPE: DNA
<213> ORGANISM: Oryza sativa

<400> SEQUENCE: 63
tgggctggat gcatgcgggg gagcgggagg cccaagtacg tgcacggtga gcggcccaca      60
gggcgagtgt gagcgcgaga ggcgggagga acagtttagt accacattgc ccagctaact     120
cgaacgcgac caacttataa acccgcgcgc tgtcgcttgt gtt                       163

<210> SEQ ID NO 64
<211> LENGTH: 287
<212> TYPE: DNA
<213> ORGANISM: Oryza sativa

<400> SEQUENCE: 64
ggtaccgagc tcggatccac tagtaacggc cgccagtgtg ctggaattgc ccttggatca      60
tgaaccaacg gcctggctgt atttggtggt tgtgtaggga gatggggaga agaaaagccc     120
gattctcttc gctgtgatgg gctggatgca tgcgggggag cgggaggccc aagtacgtgc     180
acggtgagcg gcccacaggg cgagtgtgag cgcgagaggc gggaggaaca gtttagtacc     240
acattgccca gctaactcga acgcgaccaa cttataaacc cgcgcgc                   287

<210> SEQ ID NO 65
<211> LENGTH: 400
<212> TYPE: DNA
<213> ORGANISM: Triticum aestivum

<400> SEQUENCE: 65
ggcggcaggg agagttttaa cattgactag cgtgctgata atttgtgaga aataataatt      60
gacaagtaga tactgacatt tgagaagagc ttctgaactg ttattagtaa caaaatgga     120 aagctgatgc acggaaaaag gaaagaaaaa gccatacttt tttttaggta ggaaaagaaa     180
aagccatacg agactgatgt ctctcagatg ggccgggatc tgtctatcta gcaggcagca     240
gccctaccaa cctcacgggc cagcaattac gagtccttct aaaacgtccc gccgagggcg     300
cgtggccgtg ctgtgcagca gcacgtctaa cattagtccc acctcgccag tttacaggga     360
```

```
gcagaaccag cttataagcg gaggcgcggc accaagaagc                           400
```

<210> SEQ ID NO 66
<211> LENGTH: 626
<212> TYPE: DNA
<213> ORGANISM: Unknown
<220> FEATURE:
<223> OTHER INFORMATION: Mirabilis mosaic virus

<400> SEQUENCE: 66

```
ttcgtccaca gacatcaaca tcttatcgtc ctttgaagat aagataataa tgttgaagat    60
aagagtggga gccaccacta aaacattgct ttgtcaaaag ctaaaaaaga tgatgcccga   120
cagccacttg tgtgaagcat gtgaagccgg tccctccact aagaaaatta gtgaagcatc   180
ttccagtggt ccctccactc acagctcaat cagtgagcaa caggacgaag gaaatgacgt   240
aagccatgac gtctaatccc cccaacttcg tccacagaca tcaacatctt atcgtccttt   300
gaagataaga taataatgtt gaagataaga gtggagccca ccactaaaac attgctttgt   360
caaaagctaa aaagatgat gcccgacagc cacttgtgtg aagcatgtga agccggtccc   420
tccactaaga aaattagtga agcatcttcc agtggtccct ccactcacag ctcaatcagt   480
gagcaacagg acgaaggaaa tgacgtaagc catgacgtct aatcccacaa gaatttcctt   540
atataaggaa cacaaatcag aaggaagaga tcaatcgaaa tcaaaatcgg aatcgaaatc   600
aaaatcggaa tcgaaatctc tcatct                                        626
```

<210> SEQ ID NO 67
<211> LENGTH: 357
<212> TYPE: DNA
<213> ORGANISM: Cauliflower mosaic virus

<400> SEQUENCE: 67

```
tctggcgcgc ctgagacttt tcaacaaagg gtaatatccg gaaacctcct cggattccat    60
tgcccagcta tctgtcactt catcaaaagg acagtagaaa aggaaggtgg cacctacaaa   120
tgccatcatt gcgataaagg aaaggctatc gttcaagatg cctctgccga cagtggtccc   180
aaagatggac ccccacccac gaggagcatc gtggaaaaag aagacgttcc aaccacgtct   240
tcaaagcaag tggattgatg tgatatctcc actgacgtaa gggatgacgc acaatcccac   300
tatccttcgc aagacccttc ctctatataa ggaagttcat ttcatttgga gagaaca      357
```

<210> SEQ ID NO 68
<211> LENGTH: 510
<212> TYPE: DNA
<213> ORGANISM: Figwort mosaic virus

<400> SEQUENCE: 68

```
cagctggctt gtggggacca gacaaaaaag gaatggtgca gaattgttag gcgcacctac    60
caaaagcatc tttgccttta ttgcaaagat aaagcagatt cctctagtac aagtggggaa   120
caaaataacg tggaaaagag ctgtcctgac agcccactca ctaatgcgta tgacgaacgc   180
agtgacgacc acaaaacagc tggcttgtgg ggaccagaca aaaaggaat ggtgcagaat   240
tgttaggcgc acctaccaaa agcatctttg ccttttattgc aaagataaag cagattcctc   300
tagtacaagt ggggaacaaa ataacgtgga aaagagctgt cctgacagcc cactcactaa   360
tgcgtatgac gaacgcagtg acgaccacaa agaattcccc tctatataag aaggcattca   420
ttcccatttg aaggatcatc agatactgaa ccaatatttc tcactctaag aaattaagag   480
```

| ctttgtattc ttcaatgaga ggctaagacc | 510 |

```
<210> SEQ ID NO 69
<211> LENGTH: 554
<212> TYPE: DNA
<213> ORGANISM: Figwort mosaic virus

<400> SEQUENCE: 69
```

| ctcgagcaag tgtacaaaaa agattaccac ggaagaaatt cacaaggtaa aacttttga | 60 |
| gaaaagattg atcaacatca atcaaatcaa ttgtggagac cacacaaaga aattgtggtg | 120 |
| taaaattcta cagaaaaagt acgaagagca tctttgccag tactgcagtg ggaccaccc | 180 |
| acgtgacaac aaagaagtgg cagacaagtc acctcaaagt ggaacccatc cacgtgataa | 240 |
| aagtatcatg gcagcagcc ggtacaataa tggggaggac agcttgcaaa gcagcccatg | 300 |
| tggaagccca ctcacaaacg cgtattacga acgcagtgac gacatccact caagaattcc | 360 |
| atctatttaa agacggattc attcccattt gaagatcatc aatactcaac caatatttct | 420 |
| cactctaaga aataaagagc tttgtattct tcaatgatag gctaagaccc taagagtct | 480 |
| cgaaagagac atgtagtata gtaagagtcc tcccagtccg ggagattgta ataaagagat | 540 |
| cttgttaagg atcc | 554 |

```
<210> SEQ ID NO 70
<211> LENGTH: 299
<212> TYPE: DNA
<213> ORGANISM: Unknown
<220> FEATURE:
<223> OTHER INFORMATION: Agrobacterium

<400> SEQUENCE: 70
```

| gatcatgagc ggagaattaa gggagtcacg ttatgacccc cgccgatgac gcgggacaag | 60 |
| ccgttttacg tttggaactg acagaaccgc aacgttgaag gagccactca gccgcgggtt | 120 |
| tctggagttt aatgagctaa gcacatacgt cagaaaccat tattgcgcgt tcaaaagtcg | 180 |
| cctaaggtca ctatcagcta gcaaatattt cttgtcaaaa atgctccact gacgttccat | 240 |
| aaattcccct cggtatccaa ttagagtctc atattcactc tcaatccaaa taatctgca | 299 |

```
<210> SEQ ID NO 71
<211> LENGTH: 711
<212> TYPE: DNA
<213> ORGANISM: Unknown
<220> FEATURE:
<223> OTHER INFORMATION: Agrobacterium

<400> SEQUENCE: 71
```

| cctgctttaa tgagatatgc gagacgccta tgatcgcatg atatttgctt tcaattctgt | 60 |
| tgtgcacgtt gtaaaaaacc tgagcatgtg tagctcagat ccttaccgcc ggtttcggtt | 120 |
| cattctaatg aatatatcac ccgttactat cgtatttta tgaataatat tctccgttca | 180 |
| atttactgat tgtaccctac tacttatatg tacaatatta aaatgaaaac aatatattgt | 240 |
| gctgaatagg tttatagcga catctatgat agagcgccac aataacaaac aattgcgttt | 300 |
| tattattaca aatccaattt taaaaaaagc ggcagaaccg gtcaaaccta aaagactgat | 360 |
| tacataaatc ttattcaaat ttcaaaagtg ccccaggggc tagtatctac gacacaccga | 420 |
| gcggcgaact aataacgctc actgaaggga actccggttc ccgccggcg cgcatgggtg | 480 |
| agattccttg aagttgagta ttggccgtcc gctctaccga aagttacggg caccattcaa | 540 |
| cccggtccag cacggcggcc gggtaaccga cttgctgccc cgagaattat gcagcatttt | 600 |

```
tttggtgtat gtgggcccca aatgaagtgc aggtcaaacc ttgacagtga cgacaaatcg    660
ttgggcgggt ccagggcgaa ttttgcgaca acatgtcgag gctcagcagg a            711

<210> SEQ ID NO 72
<211> LENGTH: 708
<212> TYPE: DNA
<213> ORGANISM: Arabidopsis thaliana

<400> SEQUENCE: 72
atctcgtctc tgttatgctt aagaagttca atgtttcgtt tcatgtaaaa ctttggtggt    60
ttgtgttttg gggccttgta taatccctga tgaataagtg ttctactatg tttccgttcc   120
tgttatctct ttcttttctaa tgacaagtcg aacttcttct ttatcatcgc ttcgttttta   180
ttatctgtgc ttcttttgtt taatacgcct gcaaagtgac tcgactctgt ttagtgcagt   240
tctgcgaaac ttgtaaatag tccaattgtt ggcctctagt aatagatgta gcgaaagtgt   300
tgagctgttg ggttctaagg atggcttgaa catgttaatc ttttaggttc tgagtatgat   360
gaacattcgt tgttgctaag aaatgcctgt aatgtcccac aaatgtagaa aatggttcgt   420
acctttgtcc aagcattgat atgtctgatg agaggaaact gcaagatact gagcttggtt   480
taacgaagga gaggcagttt cttccttcca aagcatttca tttgacaatg ccttgatcat   540
cttaagtaga gttctgttg tggaaagttt gaaactttga agaaacgact ctcaagtaaa    600
ttgatgatca caagtgaaag tgtatgttac ataagtggat atttcaccct ttttccatca    660
atcaaaacat catatagtaa tccattggtt tatacaaaca tcaaaata                 708

<210> SEQ ID NO 73
<211> LENGTH: 250
<212> TYPE: DNA
<213> ORGANISM: Arabidopsis thaliana

<400> SEQUENCE: 73
agccattctc tcgcagatga tgttcacttt gtgttttact tcctttatgc attcacagca    60 ataaagaaa gaaatctcca tcgcttttgg ttttcttctc tgtcttaagt tagtcgtttt    120
cgtgtctaat ctattactta tcattgtaat agactcttct tctattgaga tttgaatata   180
aactaaaaca cattccattt tactgtgttc tcaacattca gaatgcaaac ggactaaccg   240
tagtgactcg                                                           250

<210> SEQ ID NO 74
<211> LENGTH: 480
<212> TYPE: DNA
<213> ORGANISM: Nicotiana tabacum

<400> SEQUENCE: 74
aaagcagaat gctgagctaa agaaaggct ttttccattt tcgagagaca atgagaaaag    60
aagaagaaga agaagaagaa gaagaagaag aaaagagtaa ataataaagc cccacaggag   120
gcgaagttct tgtagctcca tgttatctaa gttattgata ttgtttgccc tatattttat   180
ttctgtcatt gtgtatgttt tgttcagttt cgatctcctt gcaaaatgca gagattatga   240
gatgaataaa ctaagttata ttattatacg tgttaatatt ctcctcctct ctctagctag   300
ccttttgttt tctctttttc ttatttgatt ttctttaaat caatccattt taggagaggg   360
ccagggagtg atccagcaaa acatgaagat tagaagaaac ttccctcttt tttttcctga   420
aaacaattta acgtcgagat ttatctcttt ttgtaatgga atcatttcta cagttatgac   480
```

<210> SEQ ID NO 75
<211> LENGTH: 250
<212> TYPE: DNA
<213> ORGANISM: Arabidopsis thaliana

<400> SEQUENCE: 75

```
atatgaagat gaagatgaaa tatttggtgt gtcaaataaa aagcttgtgt gcttaagttt      60
gtgttttttt cttggcttgt tgtgttatga atttgtggct ttttctaata ttaaatgaat     120
gtaagatcac attataatga ataaacaaat gtttctataa tccattgtga atgttttgtt     180
ggatctcttc tgcagcatat aactactgta tgtgctatgg tatggactat ggaatatgat     240
taaagataag                                                           250
```

<210> SEQ ID NO 76
<211> LENGTH: 1000
<212> TYPE: DNA
<213> ORGANISM: Glycine max

<400> SEQUENCE: 76

```
gctggagctg atttctgtgt gatgttcgat gttggatttt cccaaacatt ttaagaagaa      60
atgtgatgtg taatgggtct gtaatgacct ttgaaaataa gtttggtttg tgttgaactc     120
tattgtccca ttaatgttac tactgtttgt tatcaatttg tggagctgat atataattat     180
caactgtatg ctggcatatt gtgtttgaat tttgttctca atccagtgaa ttggcgtata     240
ttagtgggtt ttttattctt catgcttatc acggaggaaa agcagggatg agttgtgtga     300
aggatggtga tcatcccacg aattattaga ttttggtatt ataggttaaa gatatttatt     360
aggtagggag aactcttgga ttagattcta aagtgatatt ttgaaaacac accaaaggat     420
ttttgaacaa acgagagatca tgatccctag tttcaattag ctgccccta ccaagaggta     480
gcaacttaaa aattatgctc gtgaagcata tttggtatcg tatataaatt atgtaagcaa     540
tctgcttcag ttggaacatt aattggcttg cggaatgcac atttagatga tccacacagg     600
tccacataaa aattcctaat caatttagt tatgcaatct ttctgcttca ggtagtcctt     660
gtcttacaga aagcacattg agatgatccc cacacagatc cacataaaaa attcctaatc     720
aataataact tgaaaatcat taaagatgt aatgccatac taatccctaa ttttttgtgca    780
agtttttgta tactggaccc caaaaaatac caaaagaaa aaacaagtta ttcagtgata     840
tttttctgct ccaatataaa tttgattacc aaataccaaa aataaaaac actattcagt     900
ggtattttc tgctccaata ctggaccca aattaatcag aatcggatcc gtttaacaga     960
taaaaacaaa agcgatcggg ttaaaatccc attttttacaa                        1000
```

<210> SEQ ID NO 77
<211> LENGTH: 1000
<212> TYPE: DNA
<213> ORGANISM: Solanum lycopersicum

<400> SEQUENCE: 77

```
gttgtggttg tctggttgcg tctgttgccc gttgtctgtt gcccattgtg gtggttgtgt      60
ttgtatgatg gtcgttaagg atcatcaatg tgttttcgct ttttgttcca ttctgtttct     120
catttgtgaa taataatggt atctttatga atatgcagtt tgtggtttct tttctgattg     180
cagttctgag catttgtttt ttgcttccgt ttactatacc acttacagtt tgcactaatt     240
tagttgatat gcgagccatc tgatgtttga tgattcaaat ggcgtttatg taactcgtac     300
ccgagtggat ggagaagtgc tccattgccg gtttgtttca tgggtggcgg agggcaactc     360
```

```
ctgggaagga acaaaagaaa aaccgtgata cgagttcatg ggtgagtgct ccagcttgat      420
cccttctctg tcgatcaaat ttgaattttt ggatcacggc aggctcacaa gataatccaa      480
agtaaaacat aatgaatagt acttctcaat gatcacttat ttttagcaaa tcagcaattg      540
tgcatgtcaa atgatttcgg tgtaagagaa agagttgatg aatcaaaata tctgtagctg      600
gatcaagaat ctgaggcagt tgtatgtatc aatgatcttt ccgctacaat gatgttagct      660
atccgagtca aattgttgta gaattgcata cttcggcatc acattctgga tgacataata      720
aataggaagt cttcagatcc ctaaaaaatt gagagctaat aacattagtc ctagatgtaa      780
ctgggtgaca accaagaaag agacatgcaa atactacttt tgtttgaagg agcatccctg      840
gtttgacata ttttttctga atatcaaact ttgaaactct acctagtcta atgtctaacg      900
acagatctta ctggtttaac tgcagtgata tctactatct tttggaatgt tttctccttc      960
agttatacat caagttccaa gatgcaggtg tgcttgattg                            1000
```

<210> SEQ ID NO 78
<211> LENGTH: 1000
<212> TYPE: DNA
<213> ORGANISM: Pyrus communis

<400> SEQUENCE: 78

```
gtgctggatg tggccggtgg ccgtcttcta cccgttttcg ttgaattgtt tatgttttta       60
ctgtttttat gtatttaagt ttgatggtac tgtttctgcc tcctgattga ggcatatgga      120
caagtttggt ttatcttta ctatgtttg ataaataaat tccgttctgg ttaaaaactt       180
cgtgtttgaa atttgttgtg aatctcttgg tttaatttgt ttgtttgcat ggtgttgtgt      240
ttgtgaatgg tttgctttca atcgtctgtt taatgttgat tgtgtggtgc ggttgccatc      300
cttgaactgg acctttggta caagactggc atttcaaggt gtgcctcaat ctgtggtttc      360
gattgtggtt tcagattttc cggtgagctc actctagcgt ccggcattta ccccaatcag      420
ttttccggca cggagaggga aattgatatt taccccaatc agttttccgg caacggagag      480
ggaaattgat atatcggagt gaaggtgtcc gactcaacta tggcaagcgt cactctagca      540
tccaacattt agccgaaaac ctaagacttt gacacccaaa agaagagatg ctgttgagtc      600
tattgaaaac acgagttaca ccagttgtgt ggaaagagga gacgtgccgt gtccaatgta      660
tgctaatttg cccctcatat ctgcagccac tataggctgc cgatgaattt caccgtcccc      720
tgatgtatat tttcagtact tgtccacgtt tgaatattga catccacgtt tgaatttcgc      780
tatcctggtg catccgctcc cgactctctt agtcgagttg gaaaaaccca aataagttaa      840
ctggctttgg accttctgta aacgtctatc catttagggc taaccgcgtg gttttgttac      900
aaaatcgctt tagacctccc gtttatatct cggaaaccat ttttagcgat tgaattttat      960
cttttgtacg aaagtattgg acatactaat ccgaagttag                            1000
```

<210> SEQ ID NO 79
<211> LENGTH: 1000
<212> TYPE: DNA
<213> ORGANISM: Beta vulgaris

<400> SEQUENCE: 79

```
gcttgtggtg gttcgtcgtt ggttgttggc cttggaacaa tggctttgtt gggtgtttat       60 cccctataa tctgtgaatt catctatcat ctagtttatg ttgaacaatt ttaatttcag      120
ttggttatca aatgttggtt ttatatcgtc gtatgtctgt tgggttacta tgaactatta      180
```

```
aggttcagtt gtgaataata ttctctgttt gtgtctactt tgttctcctt ttgttgcaac    240
tatgttttta atgtttcact ttatcttcct gatttctaag tggcattatc atgcttcatg    300
ccttgccttg tggagttgtg gagtatgttt gattatattc tccagaatga tattgctcag    360
cttattgtta cctaactttt tgtctggctt tttatgcttg ttgattgtag ataaagggaa    420
caaaatttgt gttcacatag tatgcacaca ttttgtgttt gcagattgtg tgccatttat    480
cttgctacac tcttgtttat ggttttttt ggttgtatac tctgttctca tttgtggttt     540
cacctaaaac aaatgtgatg attttggcaa ggggtgcat ctctgttttt ctggttgttt     600 ttttttttt gatgaccttg agtgatggtg gtgttgatgt atgcgaggag tcgaggactg     660
atgcttttgc acatatgttg tgtctattgt tctggcttgt atgcactgtt acggtatgtc    720
ttgtgagcta ttttgaagta tatttgtaat tgaacattga tctgagagtt cgggctggtg    780
catcttccat tactaccaat gttacagcat tgtaggagtt ccgttagtgt gttgctgatc    840
ccttttgata tctttgaaat gtgattcata acataaatgc cgatggggaa ggaaagatat    900
ttactgttga atctaaatgt gaagagatgc tatgagccta atccattttg ggtaagcctc    960
acctttgctc ataagcttta tgagtcccac tgctgaaaat                         1000

<210> SEQ ID NO 80
<211> LENGTH: 1000
<212> TYPE: DNA
<213> ORGANISM: Unknown
<220> FEATURE:
<223> OTHER INFORMATION: Raphanus raphanistrum

<400> SEQUENCE: 80
gtctctcgtc ctttgtctta tcaaaaatca acaatgtctg cttttagtc tcgttttctt     60 taaaacttat catggtttgt gtgtttgagg cattataagc ctcttttgaa taatcgttga    120
actctgtttc tctcttttcc ttgcaagact tttctatcta tatcctcgtt attcttaaat    180
gctttgtgtt catctttcaa attttgaggt taagttgtcg atgcggtgaa ctttctattt    240
ttgcttagct gttacttctg aaagcacacc tgtaagcttt aacgtgttca cttttcagag    300
ttatgtgaag ttttttagaa cgttcagtct gtacttattg gtcgtctcta caaggaatcg    360
tgtgacaaaa ttgtctgtta ccactagctt gacaagtata gtaatttgga gaattcatcc    420
ttccaaaaga ggttatcagt gatgggttag tctcttggtc ttcatacgca aaattgaatc    480
tggtgaacaa cagaggttag tcgagtttgc aagttaattg gccggatcat aggtcgagtt    540
tgcagatcaa tgggccagat cataggtcgt aattgactgt tttatatcgc tggatcactt    600
cagtaagaaa gaactaccaa agagttcagt gaggtcttaa ttgacagata tgtgaactaa    660
aattaattca gttgctcaaa taatgtttaa ctgcatcaaa cgttttagtg gtgctcgttt    720
tattgatcta aatttaaatt tgtaaagagt tttaaacatg gtgatttatt tggaaacact    780
tttgaatgca ttataaagtg taaactaggt gttttgccgg catttttcaga tttaatagtt    840 tctagaaaaa ttataaaaag gtatattata aaattcaaaa atcttaggat aaaatattgg    900
cccatttggg tgaaaaacca agaacgataa gtttattagg catgtatgca acacataatt    960
taattaggta gtcgtgcaga actctagaat cgaatttact                         1000

<210> SEQ ID NO 81
<211> LENGTH: 1000
<212> TYPE: DNA
<213> ORGANISM: Ipomoea nil

<400> SEQUENCE: 81
```

```
agagcctcac tgtcctgttt gaattgcttg gtttgtgtgt taagtgccaa agctatagta      60
acttggcact gctggtgaat tgtgtttgtt ttgcttttgg ttgatgaacc catgaaggtt     120
atgtttcctt gaataataat aataataata atagcattac tattattatt attaggtcct     180
actattttgt tagccccatt tgttctgaac tctgttact tttagtttaa tgttattaat      240
atattttacc aggtaaaatg taatactatt ttatagaata ctttcgttaa aaatgagtgt     300
taccttcata tctatctcaa gtagtaatca atttgagatc cgtctactgg gagcaacata     360
gcattggcct tcacgagaag gaagggacat tattgctcca accgtggcag gagacattt     420 tataaataat aatctgaact ttataaataa tttgaactta cgtgcagcaa catagctaac     480
aataaagact acatctctag gctctagcca acaataagtg ctttgatgta atttgattat     540
aattgtattg caatttgttt agtcaacaat aagtgccttt ttggttggat gtaatttaaa     600
tgtaattaca ttgcaattca cttttcccat caattacgtt attcaattga atataattca     660
tggaccttat ttaagaatta caattcagtg gtgaaatgga gaaatatatt attgtgaaga     720 cattttacc attatcatta cttatctcat gtcgcccacc gaattacaat ttattctccc      780
taattccttt cttccaacta aaccggtaaa gacttcatct catactatgt gaaactacaa     840
agaaaggttt acttttttaca aggcgtttaa gttggaagaa gagaattaag aaaaaacgag    900
tagtaatttt gttggaaagg aatttaaatt atattgtttg ataggaaaaa atataataat     960
tcttaaatta cattgtttga tagggaagaa taaaatgatt                          1000

<210> SEQ ID NO 82
<211> LENGTH: 1000
<212> TYPE: DNA
<213> ORGANISM: Unknown
<220> FEATURE:
<223> OTHER INFORMATION: Cucurbita sp.

<400> SEQUENCE: 82
attgttcttc tgaagatgga taaatcagca tgcggggtgg ggtggccttg ttgcggccat      60
ttgttatttt cttctgttct ctacttctgg tgttatgttt ttaaatgctc cctgagggtt     120
acagtatggg gagaatatta atataagatg tcatatttca aataaaaatt tcgtttcttg     180
tttaagaatc gtgtccagac ttctcttatc cagattctcc tggttgtttg tcattgggga     240
tgatgatgac taaacatggt tgaagctttg tcctttctgg ataattctta attcatgatg     300
ggacgaacac aatcccctgg tcgtccagag aattgaatag ctaaggaact ctttagtgga     360
gtcgaatcag atctgaatca gatatggctg ccctctcctt ttcccccaag aacccgaaat     420
ctagttcatc tcccccaggt ccatccccgt tccctgtgcc tatctccaaa agtcctccag     480
tcttggctac agcttaaatt atcatcagtg ctagccattt tgatcatatc tgcaaaaagt     540
tgatttcggc ggccatgagt gcatctgtta aaacaagaat gtgtattggg gaaactcact     600
tcatctccat cttgggaaag tgggaagatt tatggggttt ctaggatacc taacttagaa     660
gacataattg aagacaacat attattagtt taacggtgaa ttggaaaggc tttcatattt     720
cttgtgagag gctttcatat ttcttgtgag atcccatttt agtcaactct ctctaaccaa     780
tacaacttct ccttaaccaa ttcattttaa aatgtgagac cgacgacaat aactgttcaa     840
gcagcagcaa tggtggtatg caggtaggaa ggaactctat tatctttgac tctgagtttc     900
aactattaag tgcttatct gctactcaat cacggaatcg attctgtcta agtggaaaga      960 aaagaagag gaagttagtg agcccacacc ctcctttat                            1000
```

<210> SEQ ID NO 83
<211> LENGTH: 1006
<212> TYPE: DNA
<213> ORGANISM: Helianthus annuus

<400> SEQUENCE: 83

| | | | | | |
|---|---|---|---|---|---|
| atgtttgtgg | tggttgtgat | gtttgaagtt | ggtactgttg | ttggtttttta | aatgtctgtg | 60 |
| gttgtggtta | atgtttgaag | ttggaacaat | tgttggatac | agattctcta | tggtttcctt | 120 |
| ctatgattgt | tgaataaatg | aattttatgg | tttaatcttg | ggtttgatca | tggtcattgt | 180 |
| tataaattga | agtctgggtt | gcatattctg | aaaatgattt | gtcagtagtt | tattgtttgg | 240 |
| tttaaatgtt | gattataacg | aaggtagttt | atgatatgct | tagcaactgt | tttgtaagga | 300 |
| catagtgatt | tgtgccaaga | ccaaaagttc | aaagtggtag | gggtggcgtg | aaaaaaaaaa | 360 |
| accaatttta | aagggctagt | gctcttgacc | aataaggttt | tgtcatgtca | tgtgggttgt | 420 |
| ctcgctcaac | gtctaggctg | aaaccccgcc | caaggagtca | cgctgaaacc | caagcccacc | 480 |
| ataccacttt | gaaattccct | tttggtctta | gctagcaaat | ataccatgtc | cttacaaaac | 540 |
| agttgctaag | tcgttttggc | atgtgttttct | gtgtctgaag | atatgttaat | tgcatatttc | 600 |
| ataatcattt | aagcatagaa | acgacggaat | ttaataaaca | cagatcaaat | tatttggtat | 660 |
| ttttggataa | agtccttttt | gagtctttgt | ggtgtgtgca | ttttaactat | ttttgaatct | 720 |
| aaaaatcaaa | cttgtcttga | tttgagtccc | tgtagtttgt | attttttaaca | ctttgattcc | 780 |
| ccgtggtttg | tattttttaac | cttttgaatc | aaacactttt | agtccatgat | ttggatgagg | 840 |
| tttgcgtttt | ggattcaaag | ggttaaaaat | acaaacctac | aaggactcaa | atcaagtcaa | 900 |
| gtttagtttt | tggattcaaa | tagttaaaat | gcacaaacca | caaggactca | aaaaggactt | 960 |
| tactcttttg | gatataacaa | agagtttctt | aaattcctct | gagctc | | 1006 |

<210> SEQ ID NO 84
<211> LENGTH: 306
<212> TYPE: DNA
<213> ORGANISM: Pisum sativum

<400> SEQUENCE: 84

| | | | | | |
|---|---|---|---|---|---|
| gttcgagtat | tatggcattg | ggaaaactgt | ttttcttgta | ccatttgttg | tgcttgtaat | 60 |
| ttactgtgtt | ttttattcgg | ttttcgctat | cgaactgtga | atggaaatg | gatgagaag | 120 |
| agttaatgaa | tgatatggtc | cttttgttca | ttctcaaatt | aatattattt | gttttttctc | 180 |
| ttatttgttg | tgtgttgaat | ttgaaattat | aagagatatg | caaacatttt | gttttgagta | 240 |
| aaaatgtgtc | aaatcgtggc | ctctaatgac | cgaagttaat | atgaggagta | aaacacttgt | 300 |
| agttgt | | | | | | 306 |

<210> SEQ ID NO 85
<211> LENGTH: 469
<212> TYPE: DNA
<213> ORGANISM: Pisum sativum

<400> SEQUENCE: 85

| | | | | | |
|---|---|---|---|---|---|
| caggcctccc | agctttcgtc | cgtatcatcg | gtttcgacaa | cgttcgtcaa | gttcaatgca | 60 |
| tcagtttcat | tgcccacaca | ccagaatcct | actaagtttg | agtattatgg | cattggaaaa | 120 |
| gctgttttct | tctatcattt | gttctgcttg | taattactg | tgttctttca | gttttttgttt | 180 |
| tcggacatca | aaatgcaaat | ggatggataa | gagttaataa | atgatatggt | ccttttgttc | 240 |
| attctcaaat | tattattatc | tgttgttttt | actttaatgg | gttgaattta | agtaagaaag | 300 |

| | |
|---|---|
| gaactaacag tgtgatatta aggtgcaatg ttagacatat aaaacagtct ttcacctctc | 360 |
| tttggttatg tcttgaattg gtttgtttct tcacttatct gtgtaatcaa gtttactatg | 420 |
| agtctatgat caagtaatta tgcaatcaag ttaagtacag tataggctt | 469 |

<210> SEQ ID NO 86
<211> LENGTH: 1000
<212> TYPE: DNA
<213> ORGANISM: Helianthus annuus

<400> SEQUENCE: 86

| | |
|---|---|
| aggatttaag cttgtcttat gtttgaactc ttgtgaaagg tttctgtgac gctactttt | 60 |
| aagtgttggt gcaaatttaa ataaaatcat ggttctataa atacgatgtt tgtatgtaag | 120 |
| tttgaacacc caagttcatt caggtttcaa cagatgtgct tatttaagta cacattggcc | 180 |
| acgtcatcaa gttctcgtgt ttgtgttgct ttgatcttta gttgttcatt gcacgtactt | 240 |
| tggttattga gttgtacaat tacaagtacg gttacaaaaa tcttttaga tacacatcag | 300 |
| gatgattatc acaagacaaa tataacaata ctgatgttga ttgagcaaaa tataaaaaaa | 360 |
| aaagccatca tactaagggg ctgtttggct aagcttattt tagtgactta tttacttatt | 420 |
| tacttttta aaagttaaaa aaggtgtttg gattagctta ttatgtgaga ggaataagta | 480 |
| aataagtcat tccaataagc ttagtcactt tttagataca catcaggatg ttatcacaa | 540 |
| gacaaatata acaataccga tgttgattga gcaaaataat ataaaaaaag ccaccataca | 600 |
| aaagctaagt tttagtcgtg ttactagcca aatttatata aatgtgtaac atactcttta | 660 |
| agatccatat aaagttgaac tcaaaccact ttattttccc tcagccacca tatgactaga | 720 |
| agacattcca gacgacccct ttgaagacat ttaggctagg atcttcaacc ttactatatt | 780 |
| agaggccgca gacaattgcg attttatac aaacgtcatt attatatgct aaacgtataa | 840 |
| acaaccaaaa atttctcaaa atgggcatta tgtcaaatct atagctcaca caatctttcc | 900 |
| tcacttaagt gtcagagcac aacacaagag gctctcacgg tatctcctgc ttgtgtagtg | 960 |
| tggttaacga gttgtacatc tatctcaacg acactttgaa | 1000 |

<210> SEQ ID NO 87
<211> LENGTH: 999
<212> TYPE: DNA
<213> ORGANISM: Zea mays

<400> SEQUENCE: 87

| | |
|---|---|
| ccaccggtat ctcgcttcca tttcacaccc cacggcctag ctataaagac taatggttcc | 60 |
| aggtgtctga agtactgaag acagggggc tagctatcta atgtttgtgc cgcacgcatg | 120 |
| agctgtaagg aggccatgct taattattct gttgccgttg ctactctatc tatatgcgcc | 180 |
| tatgcctccg tgcatgaact atgctttagg tggttgctgc tccacactgt ggtggtgtgc | 240 |
| ttttgctttt gtgtggtcgt attgtatgcg taacctgaca gatggatccc tgattgctac | 300 |
| atgtttgaat aatttgcatg atctagctag tttctgccta atctaatggt acggctcatg | 360 |
| tcttgtcagg tggatttgtt atgtgttttt tttttcaaat tgaggcttgt ttgttttgct | 420 |
| ctcaatccat ccatgtgaat tgggtggaat taaatgagtt taaattccaa agtcagtcaa | 480 |
| aatctgttat aattcttcca atccataacc gaagatcata ggccctgttt ggaatcccta | 540 |
| gaactaatag ttagctagct aatatattat tagtcggtat gagccggctc taataaacta | 600 |
| attgttattt gtgagataac taacaattac taatagttag ctagctaata tattattagc | 660 |

```
tggtttgagc cagctctaat acactaattg ttatttgtga gataactaac aattaattat    720
gatattagct gatgatgttt ggaacctaac aactaatttt taattttatt tctataggtt    780
ctaaacagga ccttagtggc tagtttggat acactaaagt gtcgttcggt tgtttgagat    840
cgatggatcg aaacgattac taatcagatt acttctctaa tttatataaa ctttgattag    900
ctaaaataat ttcgggcgca atctggtaca acgaacaag ccctaatcag gatggcatgc     960
caatttggat tggtgtgggg tcacgcatgg tgaattatg                           999
```

<210> SEQ ID NO 88
<211> LENGTH: 1007
<212> TYPE: DNA
<213> ORGANISM: Oryza sativa

<400> SEQUENCE: 88

```
ttcttcggac ccaagaatgc taagccaaga ggagctgtta tcgccgtcct cctgcttgtt     60
tctctctttt tgttgctgtt tcttcattag cgtggacaaa gttttcaacc ggcctatctg    120
ttatcatttt cttctattca aagactgtaa tacctattgc tacctgtggt tctcacttgt    180
gattttggac acatatgttc ggtttattca aatttaatca gatgcctgat gagggtacca    240
gaaaaaatac gtgttctggt tgttttttgag ttgcgattat tctatgaaat gaataacatc    300
gaagttatca tcccagtatt ttcgcatgaa tgttcttttc ttctgtcttg tgcatcagtg    360
atctagtgca tgggagtttg tattgtgatg ttcgacatca cgtaacttcc actttgcctt    420
tgctgttcga tattttaatg acatgtcaca cacacttctg atacttttct ttcttggcta    480
ttgtgccagc atgatgcaag atgcatcaca gcatcagata tattctcatc gtcaggcttt    540
agcagcacac gagcacgctt tgccgcttaa aagttgtacg gcgcagctta gacatcccct    600
gtagaagtga taatctttc actttccctt aaacaaattg agaggggaaa tggaaccatg     660
tggatcagag aagctttgt ttctttacac aagaatattt ggtacagtgg gggtcctatg     720 ttcgtggggtt cgtggcttgg ctgcctgtct tcaaccaagt gttttcagtt caacatgtta    780
gcgtgtagaa agagcacaat tctgtttatc tccaaggtaa aatgtggcat tctgttaaag    840
aacatgatcc tgccaatttt ttaagtttca atggaagagg aatgtaaagc tttctatggt    900
ttgtgtacac aacacagtgg aagaggagtg caagctttct atggtttgtg tgcgcgttgt    960
gtgtcagcac ttcaatttg ttagaaaatg aaagaaaaaa aaggatg                  1007
```

<210> SEQ ID NO 89
<211> LENGTH: 1000
<212> TYPE: DNA
<213> ORGANISM: Oryza sativa

<400> SEQUENCE: 89

```
tcagccagtt tggtggagct gccgatgtgc ctggtcgtcc cgagcctctg ttcgtcaagt     60
atttgtggtg ctgatgtcta cttgtgtctg gtttaatgga ccatcgagtc cgtatgatat    120
gttagtttta tgaaacagtt tcctgtggga cagcagtatg ctttatgaat aagttggatt    180
tgaacctaaa tatgtgctca atttgctcat ttgcatctca ttcctgttga tgtttttatct    240 gagttgcaag tttgaaaatg ctgcatattc ttattaaatc gtcatttact tttatcttaa    300
tgagctttgc aatggcctat gggatataaa agattattct ggagggaagt gatgctggaa    360
ggactatgct gtcctgattt atatttggag ccactatgag catttgggct ttctttttcag   420 aacgctgtag gcgtgtgttg aaatctttgc gacattcaat ttgatatatg attcgaggta    480
attgggcttt aatttgtcat ctcatgtaac atcttttttgt ttcttcgctg cttgatttct    540
```

-continued

```
ctatttcgta gcattggaag ataatagtag aatgatgata tactccaata cttgcaattt    600
caaaaccgtt agaaagaaag gaaaatcacg gctaggggaa aaattctctc tgatgcgtgc    660
atcaccaaaa tctgattgat tgacataagc attggaacac aaatagaaga tggagaggtg    720
gacatgtttc cgagacatag catttgagct cacattgttt ttgatccgtg gctgtgccat    780
acgcgataat ttactaaact ttcccttgcc ccttggtaat ataaagctta taatgtatac    840
accgaaattg aaaacgtat tagttcactc ttcttccttt ttctcagcaa agcgtgttca     900
tcaattttat tccacatgaa tgtgattgcg aattgtgacc aggaatgcat gatttaacaa    960
tcccgatcaa ccctgttgtc ggtggtggca ctaaaaatta                         1000
```

<210> SEQ ID NO 90
<211> LENGTH: 1000
<212> TYPE: DNA
<213> ORGANISM: Oryza sativa

<400> SEQUENCE: 90

```
gtcctcagcc atggagctgc tgctgttcta gggttcacaa gtctgcctat ttgtcttccc     60
caatggagct atggttgtct ggtctggtcc ttggtcgtgt cccgtttcat tgtgtactat    120
ttacctgtaa tgtgtatcct aagtctggt ttgatggtgt ctgaaacgtt ttgctgtggt    180
agagcagcat ggaagaacta taatgaataa gtgatcccta atcattgtgt ccaaattttg    240
cttctgctat acccttttgt gctgtttctt atgttttgct taaaaatttg atctgacaaa    300
caaatttgtc taaattatgc tcttgttctg actgtgtact gtacacattt gtattgctac    360
cggtttggca catagttttc tctttgattg cagatcaaac ccttctgatt gcagattgct    420
tggctatggc tgatgtgctc actgttcttc tttagcttgt atattgctga tggtggcttg    480
gctacggctg aaaaagttgc tgctgcgccg acttggcaac tgttgctcca gtaatgcttt    540
gtcctctctt cctagccgcc gacttggcac ttggcagctg ttgctcctgt aatgcgttgt    600
tatctcttat ctcttgagat gtactatgat tttgaggctg tttgacttgt gccagattgc    660
cagtgctgat gctatattat ctcaggtttt tatgctagta tatgttttac tgtgtgctgc    720
ctgtgtcgag ttacgtaatc tattgaaccg ctatgcgtgt tgatgccctg ttgttgcttg    780
ccagattgat gccccctgttg cttgcagctt gcaagctgta gtgaaatcct aaaattcgaa    840
gccaaatcta ttctgaactt tgaagatct gtgatgtccg gaagaaaaga ttcaaacaga    900
taaacgggac tctccagaat ctataaaata aatgatcgac aaacgctttg ctttggtagg    960
cttctcatta acccaaacat tctggaagac caatgctgga                        1000
```

<210> SEQ ID NO 91
<211> LENGTH: 1000
<212> TYPE: DNA
<213> ORGANISM: Aegilops tauschii

<400> SEQUENCE: 91

```
gtgcctggca atggagcggc ttctctgcgg gttcacaggt cttgtgtctt cgatatgtcc     60
tccaatggtg catgtgtctg tcgtcctggt cgtttctatg tttctatcgt agtgtgctgc    120
atcgttatgt tcggttgtat ttgagaactg ctgctgttgt gaacagcttt ggtgaacttg    180
ataaataagt gagcccctaa ttgtgtctgc agctgctgag ttatcctgcg ttttcttttg    240
tttgcttcta tctgatgcat ttcatctcta ttcatatgaa tattgtacct tgcatttgtt    300
agttcgacta tatggtactt tgtggcaatt acatcttggt tatcatagag gcttcactct    360
```

| | | |
|---|---|---|
| tttgaggagt agggattggg agggaccgga ctatcattag agataaccgt atcctgtttg | 420 | |
| tcgacaagca gcatggtcgg gcactccggt gggatcatgg ttgaatcgga ctgcattgat | 480 | |
| gtcgtcgagg tgatgcagca aggggttaaa tctgtgggcg atctttgagg aatgtagttt | 540 | |
| cttatgccgt aaattttgat catgtcttgt tcaaccatgt cctgtgaatt gaagatgaat | 600 | |
| ccttagttgt caatcaaaag gataagaaaa acgatgttcc atatgtaata atttgttcat | 660 | |
| aaccaagtaa aagtatctgt gtaactagta gaaaattcag tagatcagaa caacatatgg | 720 | |
| taccaaccca ttttgtacat caaggttgat tgaaaaacat tttaaggaaa atctgttgtg | 780 | |
| attctggtgc gccaactaca aaattatgtg tgtgccttat attataaggt gagaggcatt | 840 | |
| tcggcaatgc aaattgtgtg gaccttcata tatgtattga cttttttttt gcgatgagta | 900 | |
| ttgactggtt tattaagtgc atgaatccct aactttcacc atatgcacaa aacttctgag | 960 | |
| ggttatgtgg gcattatgcc agccagaccg aatcaaatgc | 1000 | |

<210> SEQ ID NO 92
<211> LENGTH: 1000
<212> TYPE: DNA
<213> ORGANISM: Unknown
<220> FEATURE:
<223> OTHER INFORMATION: Panicum hallii

<400> SEQUENCE: 92

| | | |
|---|---|---|
| gtcttgggcc atggagctgc tgttgtccct gggctcacaa gtctggtgcc tgccttgtct | 60 | |
| ctccaatgga gattgtcttg gtgtcctgtg gtcgtgtcct tgtcgtgcct gtctgatgtg | 120 | |
| agtcatgtcg tctggttgtg ttttgtgaac acttgctgct gtgcagcagt ttggttgaac | 180 | |
| tatgcaatga ataagtgagc cctgaagtta ctgtggtaat cttgtcttct ggatgagtcg | 240 | |
| tcattattat atggtttatt catgtttgtg aagtggaagc attaatttcc tcctggtgcg | 300 | |
| ttgcttttgc agttctgctt gtgtcgtgat gttactggtt ttgcaagtat gctgcttcct | 360 | |
| tgatcgcaac ttcattttgg gtcattcttc atttggttat gctggtgctc tggttttaga | 420 | |
| ttcatcatat atttcagatt aatgtagtgt ttataggaac tatcatttta aattttccca | 480 | |
| gatgtcattt gtgctgcctg gttgttgcat acggcgtggt tgtcaaggca ggttaagatt | 540 | |
| gccgatctcc ttttgatcct tgctatctcc agattatttg gaagattttt tttgtttctt | 600 | |
| gaacaggtag attggttgca gctatgaatt cattgaagct atggtgccca aaatgtcatg | 660 | |
| tgctccaaat tttgtagcca ttttgcagat gtagcaacac gttttcagat tatatagtac | 720 | |
| tgcatcaaaa tcaaattgtt ggcgccatag tacattacta tcacactagt aatgaccagg | 780 | |
| aacaatcgca gccagttaac atgccggagt attccacatg gataaacaat ggtgcatttc | 840 | |
| ttgaggagtt gatcagaacc actgaactgc caaacatgtc cgcagaacca tgacaacccc | 900 | |
| ttgcatgaag atgtgctaaa gttgttgaca gaaagtccaa actctatgat atgcacacat | 960 | |
| tatcagcaag agatggggat tgttatttgc caaaaatttc | 1000 | |

<210> SEQ ID NO 93
<211> LENGTH: 1001
<212> TYPE: DNA
<213> ORGANISM: Zea mays

<400> SEQUENCE: 93

| | | |
|---|---|---|
| ccgtcatcgt ccatcaacga ccaagcaaca acacatccac actatatact caattcacat | 60 | |
| tgcaatgcat cgttattatt acatcattta tttcagaccc cccgcccact gctaaccgta | 120 | |
| gtccataaga gattcatcat ccgtggacta tgctcgatct cttccgtacg atacaattct | 180 | |

```
caaatatttc tatttatttc ctaagtgaat tattatatat gtactatttc attccaggtt      240
cattttactt gtgaccattc ttcagttctt ttttctgtaa ggatcggtat atcggagcat      300
atgtgcatgg ctatgccagt tgttgggcgt aagaatgtat ttttttctgt aatatagaaa      360
aaaactattt taagcaacag gttattgtca agttactttg cttgtgaaca aatttcgtac      420
cacgtatata tttgtatgac ctttgtataa aggtgacacg cctagtaaca ttaaccaaac      480
accgaggaaa tattaattct caatccaagg gaactcaagg cggttgagag gattttttagg     540 gctgattcag tgatcagaga tcccgtggat ccctcagga tccctgatca ccaaatcaac      600
ccttaggcta gtttggaaac tcaaatctct tttaggattg aagaagattg gagagaaaat     660
tagttcattt ccacctcaat ctcatttaat cccgaagggg atttgaggtt cccaaagtag    720
cccttactgg gataaaattc cccttaatct ttttcaaggc tactttgatg acaatggaat    780
ttagggagaa aatgaactaa ttcttcacac gatctcctcc aatccttttt aattctctta    840
tatcaccaaa caaggcctca atgtccttgg attggcgagg tcatcccatt ttatctcgtt    900
cacaaaaaca acagcgacat taatagactt aaaaacattt gagatgtcca cggagatatg    960
accaaccgga aacaagtgat attcatggta gctgtcccta c                        1001
```

<210> SEQ ID NO 94
<211> LENGTH: 1000
<212> TYPE: DNA
<213> ORGANISM: Zea mays

<400> SEQUENCE: 94

```
tctatctgtc tggtgctgtg cttgcttgtt ggttacctcg tggaagctta aaatatctcg       60
tcttgttgac atccttgcag ttgtcgcgtg aacaagtaat ctatgatggc aatgtttgcc      120
tggtcatgaa gtattattac tttcgttgaa accgtgatgc tattaagact taattttttt      180
atggaacatc gaatgtaagg catacatggt tatgagtttt gtactaccct ttgcagtgtg      240
ttcctgttta cctttgtgc tgatgattcg cttgtctttg tgtcttcaag ttaatcttgc       300
acttaactgt ttttaatatg ccagatcgtt tcaaaagatt tgaaatttgg attcttccga      360
aacgtttttt tgataataat gtagtcctga aaacatgatt ttgattcttc agaaactatt      420
tttgataaat aatgtagtcc tgacaacatg gtcaatttta cgcttttagt tatcaatgca     480
tttttcatga tttccgaaag ttccgctcca accttttcga aatgccagca tttgagttgt     540
ttttttttct acttttttccg atagcctgaa gtctaattta gttgcaaaaa cataaatgtg    600
gagtaactag agctgtgtct aagggggtaag tgtaaaaatt gccaagagcc ctttttgaag   660
aaggaatgtt tcatgctcta cgatggaggc gaaggaacat ctctacgttg atcagatagc    720
ggtcgtctcc tccagattcg ctgtgcttcg aagatccgcg atcgattcct gctccactca    780
aggtcacctc cactcgagtt ctcaagccta tcctcttcct ctccctgtct ctcacctttc    840
ctcttccctg caagatggat ctgccggcg tggctgccat ggtgaggtca tctccctcat     900
acgaccgtgg ctgctacaac acaagctcgg gtgctccgtc gcctaaggag atcccgctgc   960
caggcgcccg cccgccattc atccatggtg gttcggccgc                          1000
```

<210> SEQ ID NO 95
<211> LENGTH: 1107
<212> TYPE: DNA
<213> ORGANISM: Zea mays

<400> SEQUENCE: 95

```
tcgtcatcgt cctactatca agcaacacga tcgaccacca cctcgattat atatgcatca    60
ttatagtatc gtttattaat ttcagaccca cccactgcta accacatcgt ccacgagaga   120
ttatattcat ccgtggacta cgctctcgat cttacaattt gaaacctttc tattttccta   180
attactatgt attccaggtt cattttgatt gtgaccattc ttcagttctt tctgtaagga   240
tcggagcata ttatatactc tatgtggcta tgccaattat attgttgggt ataagaatgc   300
attttgtttc tgtaatacgg aaaaatatat tttctttaag caacaacaag gtaaaaactt   360
gcctcgttgc atattttctt tatgtcaatc tccttttgtt cgttgtatga tcctctgttt   420
ggaaactgaa tactgatcga caactgatca aggagttaaa acatattgta aatatatata   480
aaaacttgct gtgtacaact cttctttatt gtataagttt cttgaggtaa ccgaaataga   540
tagtaaatcc caatacaaat agattcctcc gttactaact aatctgaaca taaatgctaa   600 taaaaaagt ataaatttct atctgcgtat gtaccttgac cttacccttta ttctattaac   660 tcctgatttt ctattcagat tttgaacggt ctgttacttc cttctatc tgttctggtt     720 tcgtcgtcgt ttgtttccga acggtctgct acttctgatt ttctatttgt tcttacgttt   780
ggttttgccg ttctagtttc ttgcgttttt ccatataaat atagaaacac aaaataaatg   840
taatgttgta gatacttgaa ctatcgatct tttccttttaa aaaatgatat tgctaccact   900
aatgtagttt taattaggaa caaaacttac aaccaatgat caactaatga accggtctag   960
aacagtctat atggacatgg tgagcaagcg tacgtaattc cgggaagcac ttgtcgtccg   1020
gacgcaggct acattactac atagtagcaa aacaaatttt attccgataa tattggttgc   1080
tatacagacc tctgcagaca aaaataa                                       1107

<210> SEQ ID NO 96
<211> LENGTH: 1000
<212> TYPE: DNA
<213> ORGANISM: Zea mays

<400> SEQUENCE: 96
gtcatgggtc gtttaagctg ccgatgtgcc tgcgtcgtct ggtgccctct ctccatatgg    60
aggttgtcaa agtatctgct gttcgtgtca tgagtcgtgt cagtgttggt ttaataatgg   120
accggttgtg ttgtgtgtgc gtactaccca gaactatgac aaatcatgaa taagtttgat   180
gtttgaaatt aaagcctgtg ctcattatgt tctgtctttc agttgtctcc taatatttgc   240
ctgcaggtac tggctatcta ccgtttctta cttaggaggt gtttgaatgc actaaaacta   300
atagttagtg gctaaaatta gttaaaacat ccaaacacca tagctaatag ttgaactatt   360
agctattttt ggaaaattag ttaatagtga ggtagttatt tgttagctag ctaattcaac   420
taacaatttt tagccaacta acaattagtt tcagtgcatt caaacaccccc cttaatgtta   480 acgtggttct atctaccgtc tcctaatata tggttgattg ttcggtttgt tgctatgcta   540
ttgggttctg attgctgcta gttccttgctg aatccagaag ttctcgtagt atagctcaga   600
ttcatattat ttatttgagt gataagtgat ccaggttatt actatgttag ctaggttttt   660
tttacaagga taaattatct gtgatcataa ttcttatgaa agctttatgt ttcctggagg   720
cagtggcatg caatgcatga cagcaacttg atcacaccag ctgaggtaga tacggtaaca   780
aggttcttaa atctgttcac caaatcattg gagaacacac atacacattc ttgccagtct   840
tggttagaga aatttcatga caaaatgcca aagctgtctt gactcttcac ttttggccat   900
gagtcgtgac ttagttttggt ttaatggacc ggttctccta gcttgttcta ctcaaaactg   960
ttgttgatgc gaataagttg tgatggttga tctctggatt                         1000
```

<210> SEQ ID NO 97
<211> LENGTH: 1000
<212> TYPE: DNA
<213> ORGANISM: Hordeum vulgare

<400> SEQUENCE: 97

| | | | | | |
|---|---|---|---|---|---|
| ccgcctagcc | gatcgagggc | tccaggcacg | catgcatgtt | cctgttatgt | ggatgttgga | 60 |
| ataaaatgct | ggtgatctat | ggcggctagc | ttgcttcctg | gctagcagct | gctgtaatga | 120 |
| aatttgtgtt | gcaacttttt | ttttagtccc | atccagagct | cttttctttt | ctttaatttg | 180 |
| ctgtagtaat | caaagtaagg | taggtcgcca | gaaaaattga | gttgggccag | ttaattatgg | 240 |
| gggaatcgat | ttgatccgtt | ggatgacaca | tcttcttcct | ctagtcggct | tcctccttta | 300 |
| aacatatcag | tatcacatcg | cctgctaccg | cctctcacgg | ccgcctcacc | gcaccgccct | 360 |
| tccctgaacc | tcccccaccg | ccgatcttgg | tgccgcccca | tacaatccct | ctaagtcctt | 420 |
| cgaccaccca | aaaaaactcc | ggcgagaggg | ctccaggcat | gcatgcatgc | atgttcctgt | 480 |
| tatgtggttc | caccgatgat | gtgggaataa | aatgatggtg | atctagctac | aggcggtcag | 540 |
| gttgcttctt | tcctggctgc | tgctagtaat | acttttaga | gcctcttttc | ttttcttttg | 600 |
| ctactagtaa | tgaaactaag | ttaagtcacc | aggaaatttg | aattgggcca | gtcaattccg | 660 |
| ggggaatcga | tttgagccgg | tggatgacaa | acgaacggtg | atgctcgcgt | cttcctctgg | 720 |
| tcgatttcct | cctggtattc | tagacgtggt | ctggccgatt | caccgattcc | aaatatcact | 780 |
| ttcacatact | gaaagaagca | acttcacgaa | ttgtaaatca | gcttcactca | ctggaaatat | 840 |
| gagttacact | tctttgaaaa | aacggtttca | cattttgaa | ataatcgttt | caaatatttg | 900 |
| aagaaaatca | attttacgta | ttaaaatata | tgcttcacaa | agagaaacaa | tcccttttcac | 960 |
| atatttgaaa | agagaactgc | gttccacaaa | ctgaaaatat | | | 1000 |

<210> SEQ ID NO 98
<211> LENGTH: 1042
<212> TYPE: DNA
<213> ORGANISM: Zea mays

<400> SEQUENCE: 98

| | | | | | |
|---|---|---|---|---|---|
| attacatatg | agatgtactc | gacaatggtg | ccctcatacc | gacatgtgtt | tcctagaaat | 60 |
| aatcaatata | ttgattgaga | tttatctcga | tatatttctg | aactatgttc | atcatataaa | 120 |
| taattgaaaa | catcaaatca | taatttaaa | ctcatgcttg | gtcaatacat | agataataca | 180 |
| atattacttc | atcatcccaa | tgatgtccta | gcccaaccta | ttgaatgtta | atgtttggtt | 240 |
| gtgtgagggt | gtgtttataa | catagatgtg | attatttgcg | cttttgttg | agtatataca | 300 |
| tatatggtat | gttgatttga | tagggatg | gacacatgct | ttggccttgg | atattcaaat | 360 |
| cacttgtact | tgcacgaagc | aaaacataat | atatagttta | gaagtaaaact | tgtaactatg | 420 |
| tccaaacatg | ctcacacaaa | gtcataccgc | attataattt | tttggtaaat | attcaacaca | 480 |
| tgtattttt | acaagaaccc | aaatttaca | gacaaatgca | gcattgtaga | catgtagaat | 540 |
| tctttgaagc | atgtgaactt | aacaacacca | atgtcattaa | atcaactaga | ccctatgagt | 600 |
| aacaatttcg | atattgcaaa | caccaaatta | tggaacttat | ttgctgaaaa | aattatgatc | 660 |
| aatgtgaagt | ttaaattatt | ataccataaa | tatatcaaag | atttttttga | ggaaggtaaa | 720 |
| aattgcatgg | aatgggctgc | ccaacgtgat | agctcacttt | tatgctaggt | agcattacca | 780 |
| aagatgggaa | cgttctgatg | aacaccaaac | ccactcaaat | aatatttata | tttgggttgt | 840 |

```
ttagttgtaa aagtgaagac ccaagtttaa agtaccaatt ggccaatgcc attcgattgt    900
tttgttcaaa gagcacttgg tacgtcattt ggactcgtat cttagtccaa tatattgcat    960
tttgcttcaa tgtgtagaat ccgacaaagt gcatgttcta aaattgtaaa tctaactaaa   1020
ttagaaagct tgttactaat tt                                            1042
```

<210> SEQ ID NO 99
<211> LENGTH: 191
<212> TYPE: DNA
<213> ORGANISM: Cauliflower mosaic virus

<400> SEQUENCE: 99

```
ctcgagtttc tccataataa tgtgtgagta gttcccagat aagggaatta gggttcctat     60
agggtttcgc tcatgtgttg agcatataag aaacccttag tatgtatttg tatttgtaaa    120
atacttctat caataaaatt tctaattcct aaaaccaaaa tccagtacta aaatccagat    180
cccccgaatt a                                                        191
```

<210> SEQ ID NO 100
<211> LENGTH: 250
<212> TYPE: DNA
<213> ORGANISM: Agrobacterium tumefaciens

<400> SEQUENCE: 100

```
cgttcaaaca tttggcaata aagtttctta agattgaatc ctgttgccgg tcttgcgatg     60
attatcatat atatttctgt tgattacgtt aagcatgtaa taattaacat gtaatgcatg    120
acgttattta tgagatgggt ttttatgatt agagtcccgc aattatacat ttaatacgcg    180
atagaaaaca aaatatagcg cgcaaactag gataaattat cgcgcgcggt gtcatctatg    240
ttactagatc                                                          250
```

<210> SEQ ID NO 101
<211> LENGTH: 68
<212> TYPE: DNA
<213> ORGANISM: Tobacco mosaic virus

<400> SEQUENCE: 101

```
gtatttttac aacaattacc aacaacaaca aacaacaaac aacattacaa ttactattta     60
cataaacc                                                             68
```

<210> SEQ ID NO 102
<211> LENGTH: 510
<212> TYPE: DNA
<213> ORGANISM: Figwort mosaic virus

<400> SEQUENCE: 102

```
cagctggctt gtggggacca gacaaaaaag gaatggtgca gaattgttag gcgcacctac     60
caaaagcatc tttgccttta ttgcaaagat aaagcagatt cctctagtac aagtggggaa    120
caaaataacg tggaaaagag ctgtcctgac agcccactca ctaatgcgta tgacgaacgc    180
agtgacgacc acaaaacagc tggcttgtgg ggaccagaca aaaaggaat ggtgcagaat     240
tgttaggcgc acctaccaaa agcatctttg cctttattgc aaagataaag cagattcctc    300
tagtacaagt ggggaacaaa ataacgtgga aaagagctgt cctgacagcc cactcactaa    360
tgcgtatgac gaacgcagtg acgaccacaa agaattccc tctatataag aaggcattca    420
ttcccatttg aaggatcatc agatactgaa ccaatatttc tcactctaag aaattaagag    480
ctttgtattc ttcaatgaga ggctaagacc                                    510
```

<210> SEQ ID NO 103
<211> LENGTH: 493
<212> TYPE: DNA
<213> ORGANISM: Unknown
<220> FEATURE:
<223> OTHER INFORMATION: figwort and cauliflower mosaic virus/synthetic

<400> SEQUENCE: 103

```
agctgcttgt ggggaccaga caaaaaagga atggtgcaga attgttaggc gcacctacca    60
aaagcatctt tgcctttatt gcaaagataa agcagattcc tctagtacaa gtggggaaca   120
aaataacgtg gaaagagct gtcctgacag cccactcact attgcgtttg acgaacgcag   180
tgacgaccac aaaactcgag actttcaac aagggtaat atccggaaac ctcctcggat   240
tccattgccc agctatctgt cactttattg tgaagatagt ggaaaaggaa ggtggctcct   300
acaaatgcca tcattgcgat aaaggaaagg ctatcgttga agatgcctct gccgacagtg   360
gtcccaaaga tggaccccca cccacgagga gcatcgtgga aaaagaagac gttccaacca   420
cgtcttcaaa gcaagtggat tgatgtgata tctccactga cgtaagggat gacgaacaat   480
cccactatcc ttc                                                     493
```

<210> SEQ ID NO 104
<211> LENGTH: 413
<212> TYPE: DNA
<213> ORGANISM: Glycine max

<400> SEQUENCE: 104

```
gtatgttatg tatctcactc tgctcatctc tttcatatgt gtttctgatc tttctacctc    60
tgggttgtaa ttaatgctaa tagtgtgaga gtgcttaatt ctctatcagt aatgaaaatt   120
ttgtctgctt taattatttt gttcaagtgg ggtctcaatt acaatcaccc cttttcaagt   180
ttgaatatgc ttctagcgtt tttgggactt gagttcatat gggggtctct tcctttctta   240
aattttgtgt ttttccttga ttcaatcatt attgaaaatt aagttcaatt ggggggtctca   300
gtctcagagc atttggcttt tgaatcatat gatctttcga taggtgttta aaaagtaatc   360
gactttcagt ttcttgatct gaataatcag tctttcattg tctgcgcatg tag          413
```

<210> SEQ ID NO 105
<211> LENGTH: 107
<212> TYPE: DNA
<213> ORGANISM: Zea mays

<400> SEQUENCE: 105

```
gtaactaacc actgccgccg cccatttctt cttcgaccgg ttgccgcctg cgcgcggcac    60
tgctcgtacg tctccccgcc agtgcttact gtaatgcatg catgcag                 107
```

<210> SEQ ID NO 106
<211> LENGTH: 110
<212> TYPE: DNA
<213> ORGANISM: Mus musculus

<400> SEQUENCE: 106

```
gattcgtcag tagggttgta aaggttttc ttttcctgag aaacaacct tttgttttct    60
caggttttgc ttttggcct ttccctagct ttaaaaaaaa aaaagcaaaa              110
```

<210> SEQ ID NO 107
<211> LENGTH: 1272
<212> TYPE: PRT

<213> ORGANISM: Unknown
<220> FEATURE:
<223> OTHER INFORMATION: Uncultured Clostridium sp. isolate
      2789STDY5608795

<400> SEQUENCE: 107

```
Met Glu Asp Lys Gln Phe Leu Glu Arg Tyr Lys Glu Phe Ile Gly Leu
1               5                   10                  15

Asn Ser Leu Ser Lys Thr Leu Arg Asn Ser Leu Ile Pro Val Gly Ser
            20                  25                  30

Thr Leu Lys His Ile Gln Glu Tyr Gly Ile Leu Glu Glu Asp Ser Leu
        35                  40                  45

Arg Ala Gln Lys Arg Glu Leu Lys Gly Ile Met Asp Asp Tyr Tyr
50                  55                  60

Arg Asn Tyr Ile Glu Met His Leu Arg Asp Val His Asp Ile Asp Trp
65                  70                  75                  80

Asn Glu Leu Phe Glu Ala Leu Thr Glu Val Lys Lys Asn Gln Thr Asp
                85                  90                  95

Asp Ala Lys Lys Cys Leu Glu Lys Ile Gln Glu Lys Lys Arg Lys Glu
            100                 105                 110

Ile Tyr Gln Tyr Leu Ser Asp Asp Ala Val Phe Ser Glu Met Phe Lys
        115                 120                 125

Glu Lys Met Ile Ser Gly Ile Leu Pro Asp Phe Ile Arg Cys Asn Glu
130                 135                 140

Glu Tyr Ser Glu Glu Glu Lys Glu Glu Lys Leu Lys Thr Val Ala Leu
145                 150                 155                 160

Phe His Arg Phe Thr Ser Ser Phe Asn Asp Phe Leu Asn Arg Lys
                165                 170                 175

Asn Val Phe Thr Lys Glu Ala Ile Ala Thr Ala Ile Gly Tyr Arg Val
            180                 185                 190

Val His Glu Asn Ala Glu Ile Phe Leu Glu Asn Met Val Ala Phe Gln
        195                 200                 205

Asn Ile Gln Lys Ser Ala Glu Ser Gln Ile Ser Ile Glu Arg Lys
210                 215                 220

Asn Glu His Tyr Phe Met Glu Trp Lys Leu Ser His Ile Phe Thr Ala
225                 230                 235                 240

Asp Tyr Tyr Met Met Leu Met Thr Gln Lys Ala Ile Glu His Tyr Asn
                245                 250                 255

Glu Met Cys Gly Val Val Asn Gln His Met Lys Glu Tyr Cys Gln Lys
            260                 265                 270

Glu Lys Lys Asn Trp Asn Leu Tyr Arg Met Lys Arg Leu His Lys Gln
        275                 280                 285

Ile Leu Ser Asn Ala Ser Thr Ser Phe Lys Ile Pro Glu Lys Tyr Glu
290                 295                 300

Asn Asp Ala Glu Val Tyr Glu Ser Val Asn Ser Phe Leu Gln Asn Val
305                 310                 315                 320

Met Glu Lys Thr Val Met Glu Arg Ile Ala Val Leu Lys Asn Asn Thr
                325                 330                 335

Asp Asn Phe Asp Leu Ser Lys Ile Tyr Ile Thr Ala Pro Tyr Tyr Glu
            340                 345                 350

Lys Ile Ser Asn Tyr Leu Cys Gly Ser Trp Asn Thr Ile Ala Asp Cys
        355                 360                 365

Leu Thr His Tyr Tyr Glu Gln Gln Ile Ala Gly Lys Gly Ala Arg Lys
370                 375                 380
```

```
Asp Gln Lys Val Lys Ala Ala Val Lys Ala Asp Lys Trp Lys Ser Leu
385                 390                 395                 400

Ser Glu Ile Glu Gln Leu Leu Lys Glu Tyr Ala Arg Ala Glu Glu Val
            405                 410                 415

Lys Arg Lys Pro Glu Glu Tyr Ile Ala Glu Ile Glu Asn Ile Val Ser
            420                 425                 430

Leu Lys Glu Val His Leu Leu Glu Tyr His Pro Glu Val Asn Leu Ile
        435                 440                 445

Glu Asn Glu Lys Tyr Ala Thr Glu Ile Lys Asp Val Leu Asp Asn Tyr
    450                 455                 460

Met Glu Leu Phe His Trp Met Lys Trp Phe Tyr Ile Glu Glu Ala Val
465                 470                 475                 480

Glu Lys Glu Val Asn Phe Tyr Gly Glu Leu Asp Asp Leu Tyr Glu Glu
            485                 490                 495

Ile Arg Asp Ile Val Pro Leu Tyr Asn Lys Val Arg Asn Tyr Val Thr
            500                 505                 510

Gln Lys Pro Tyr Ser Asp Thr Lys Ile Lys Leu Asn Phe Gly Thr Pro
        515                 520                 525

Thr Leu Ala Asn Gly Trp Ser Lys Ser Lys Glu Tyr Asp Tyr Asn Ala
        530                 535                 540

Ile Leu Leu Gln Lys Asp Gly Lys Tyr Tyr Met Gly Ile Phe Asn Pro
545                 550                 555                 560

Val Gln Lys Pro Glu Lys Glu Ile Ile Glu Gly His Ser His Pro Leu
            565                 570                 575

Glu Gly Asn Glu Tyr Lys Lys Met Val Tyr Tyr Leu Pro Ser Ala
        580                 585                 590

Asn Lys Met Leu Pro Lys Val Leu Leu Ser Lys Gly Met Glu Ile
        595                 600                 605

Tyr Gln Pro Ser Glu Tyr Ile Ile Asn Gly Tyr Lys Glu Arg Arg His
        610                 615                 620

Ile Lys Ser Glu Glu Lys Phe Asp Leu Gln Phe Cys His Asp Leu Ile
625                 630                 635                 640

Asp Tyr Phe Lys Ser Gly Ile Glu Arg Asn Pro Asp Trp Lys Val Phe
            645                 650                 655

Gly Phe His Phe Ser Asp Thr Asp Thr Tyr Gln Asp Ile Ser Gly Phe
            660                 665                 670

Tyr Arg Glu Val Glu Asp Gln Gly Tyr Lys Ile Asp Trp Thr Tyr Ile
        675                 680                 685

Lys Glu Ala Asp Ile Asp Arg Leu Asn Glu Gly Lys Leu Tyr Leu
        690                 695                 700

Phe Gln Ile Tyr Asn Lys Asp Phe Ser Glu Lys Ser Thr Gly Arg Glu
705                 710                 715                 720

Asn Leu His Thr Met Tyr Leu Lys Asn Leu Phe Ser Glu Glu Asn Ile
            725                 730                 735

Arg Glu Gln Val Leu Lys Leu Asn Gly Glu Ala Glu Ile Phe Phe Arg
            740                 745                 750

Lys Ser Ser Val Lys Lys Pro Ile Ile His Lys Lys Gly Thr Met Leu
        755                 760                 765

Val Asn Arg Thr Tyr Met Glu Glu Met His Gly Glu Ser Val Lys Lys
        770                 775                 780

Asn Ile Pro Glu Lys Glu Tyr Gln Glu Ile Tyr Asn Tyr Met Asn His
785                 790                 795                 800

Arg Trp Lys Gly Glu Leu Ser Ala Glu Ala Lys Glu Tyr Leu Lys Lys
```

```
                805                 810                 815
Ala Val Cys His Glu Thr Lys Lys Asp Ile Val Lys Asp Tyr Arg Tyr
            820                 825                 830
Ser Val Asp Lys Phe Phe Ile His Leu Pro Ile Thr Ile Asn Tyr Arg
            835                 840                 845
Ala Ser Gly Lys Glu Ala Leu Asn Ser Val Ala Gln Arg Tyr Ile Ala
            850                 855                 860
His Gln Asn Asp Met His Val Ile Gly Ile Asp Arg Gly Glu Arg Asn
865                 870                 875                 880
Leu Ile Tyr Val Ser Val Ile Asn Met Gln Gly Glu Ile Ile Glu Gln
                885                 890                 895
Lys Ser Phe Asn Val Val Asn Lys Tyr Asn Tyr Lys Glu Lys Leu Lys
                900                 905                 910
Glu Arg Glu Gln Asn Arg Asp Glu Ala Arg Lys Asn Trp Lys Glu Ile
                915                 920                 925
Gly Gln Ile Lys Asp Leu Lys Glu Gly Tyr Leu Ser Gly Val Ile His
                930                 935                 940
Glu Ile Ala Lys Met Met Ile Lys Tyr His Ala Ile Val Ala Met Glu
945                 950                 955                 960
Asp Leu Asn Tyr Gly Phe Lys Arg Gly Arg Phe Lys Val Glu Arg Gln
                965                 970                 975
Val Tyr Gln Lys Phe Glu Asn Met Leu Ile Gln Lys Leu Asn Tyr Leu
                980                 985                 990
Val Phe Lys Asp Arg Ser Ala Asp  Glu Asp Gly Gly Val  Leu Arg Gly
                995                 1000                1005
Tyr Gln  Leu Ala Tyr Ile Pro  Asp Ser Val Lys Lys  Leu Gly Arg
1010                1015                1020
Gln Cys  Gly Met Ile Phe Tyr  Val Pro Ala Ala Phe  Thr Ser Lys
1025                1030                1035
Ile Asp  Pro Ala Thr Gly Phe  Val Asp Ile Phe Asn  His Lys Ala
1040                1045                1050
Tyr Thr  Thr Asp Gln Ala Lys  Arg Glu Phe Ile Leu  Ser Phe Asp
1055                1060                1065
Glu Ile  Cys Tyr Asp Val Glu  Arg Gln Leu Phe Arg  Phe Thr Phe
1070                1075                1080
Asp Tyr  Ala Asn Phe Ala Thr  His Asn Val Thr Leu  Ala Arg Asn
1085                1090                1095
Asn Trp  Thr Ile Tyr Thr Asn  Gly Thr Arg Thr Gln  Lys Glu Phe
1100                1105                1110
Val Asn  Arg Arg Val Arg Asp  Lys Lys Glu Val Phe  Asp Pro Thr
1115                1120                1125
Glu Lys  Met Leu Lys Leu Leu  Glu Leu Glu Gly Val  Glu Tyr Gln
1130                1135                1140
Ser Gly  Ala Asn Leu Leu Pro  Lys Leu Glu Lys Ile  Ser Asp Pro
1145                1150                1155
His Leu  Phe His Glu Leu Gln  Arg Ile Val Arg Phe  Thr Val Gln
1160                1165                1170
Leu Arg  Asn Ser Lys Asn Glu  Glu Asn Asp Val Asp  Tyr Asp His
1175                1180                1185
Val Ile  Ser Pro Val Leu Asn  Glu Glu Gly Lys Phe  Phe Asp Ser
1190                1195                1200
Ser Lys  Tyr Glu Asn Lys Glu  Glu Lys Lys Glu Ser  Leu Leu Pro
1205                1210                1215
```

```
Val Asp Ala Asp Ala Asn Gly Ala Tyr Cys Ile Ala Leu Lys Gly
    1220            1225            1230

Leu Tyr Ile Met Gln Ala Ile Gln Lys Asn Trp Ser Glu Glu Lys
    1235            1240            1245

Ala Leu Ser Pro Asp Val Leu Arg Leu Asn Asn Asn Asp Trp Phe
    1250            1255            1260

Asp Tyr Ile Gln Asn Lys Arg Tyr Arg
    1265            1270

<210> SEQ ID NO 108
<211> LENGTH: 1247
<212> TYPE: PRT
<213> ORGANISM: Unknown
<220> FEATURE:
<223> OTHER INFORMATION: Uncultured bacterium (gcode 4) ACD_3C00058,
      whole genome shotgun sequence

<400> SEQUENCE: 108

Met Phe Lys Gly Asp Ala Phe Thr Gly Leu Tyr Glu Val Gln Lys Thr
1               5                   10                  15

Leu Arg Phe Glu Leu Val Pro Ile Gly Leu Thr Gln Ser Tyr Leu Glu
            20                  25                  30

Asn Asp Trp Val Ile Gln Lys Asp Lys Glu Val Glu Glu Asn Tyr Gly
        35                  40                  45

Lys Ile Lys Ala Tyr Phe Asp Leu Ile His Lys Glu Phe Val Arg Gln
    50                  55                  60

Ser Leu Glu Asn Ala Trp Leu Cys Gln Leu Asp Asp Phe Tyr Glu Lys
65                  70                  75                  80

Tyr Ile Glu Leu His Asn Ser Leu Glu Thr Arg Lys Asp Lys Asn Leu
                85                  90                  95

Ala Lys Gln Phe Glu Lys Val Met Lys Ser Leu Lys Lys Glu Phe Val
            100                 105                 110

Ser Phe Phe Asp Ala Lys Trp Asn Glu Trp Lys Gln Lys Phe Ser Phe
        115                 120                 125

Leu Lys Lys Trp Trp Ile Asp Val Leu Asn Glu Lys Glu Val Leu Asp
    130                 135                 140

Leu Met Ala Glu Phe Tyr Pro Asp Glu Lys Glu Leu Phe Asp Lys Phe
145                 150                 155                 160

Asp Lys Phe Phe Thr Tyr Phe Ser Asn Phe Lys Glu Ser Arg Lys Asn
                165                 170                 175

Phe Tyr Ala Asp Asp Gly Arg Ala Trp Ala Ile Ala Thr Arg Ala Ile
            180                 185                 190

Asp Glu Asn Leu Ile Thr Phe Ile Lys Asn Ile Glu Asp Phe Lys Lys
        195                 200                 205

Leu Asn Ser Ser Phe Arg Glu Phe Val Asn Asp Asn Phe Ser Glu Glu
    210                 215                 220

Asp Lys Gln Ile Phe Glu Ile Asp Phe Tyr Asn Asn Cys Leu Leu Gln
225                 230                 235                 240

Pro Trp Ile Asp Lys Tyr Asn Lys Ile Val Trp Trp Tyr Ser Leu Glu
                245                 250                 255

Asn Trp Glu Lys Val Gln Trp Leu Glu Lys Ile Asn Asn Phe Lys
            260                 265                 270

Gln Asn Gln Asn Lys Ser Asn Ser Lys Asp Leu Lys Phe Pro Arg Met
        275                 280                 285

Lys Leu Leu Tyr Lys Gln Ile Leu Gly Asp Lys Glu Lys Lys Val Tyr
```

-continued

```
            290                 295                 300
Ile Asp Glu Ile Arg Asp Asp Lys Asn Leu Ile Asp Leu Ile Asp Asn
305                 310                 315                 320

Ser Lys Arg Arg Asn Gln Ile Lys Ile Asp Asn Ala Asn Asp Ile Ile
                325                 330                 335

Asn Asp Phe Ile Asn Asn Asn Ala Lys Phe Glu Leu Asp Lys Ile Tyr
                340                 345                 350

Leu Thr Arg Gln Ser Ile Asn Thr Ile Ser Ser Lys Tyr Phe Ser Ser
                355                 360                 365

Trp Asp Tyr Ile Arg Trp Tyr Phe Trp Thr Gly Glu Leu Gln Glu Phe
        370                 375                 380

Val Ser Phe Tyr Asp Leu Lys Glu Thr Phe Trp Lys Ile Glu Tyr Glu
385                 390                 395                 400

Thr Leu Glu Asn Ile Phe Lys Asp Cys Tyr Val Lys Gly Ile Asn Thr
                405                 410                 415

Glu Ser Gln Asn Asn Ile Val Phe Glu Thr Gln Gly Ile Tyr Glu Asn
                420                 425                 430

Phe Leu Asn Ile Phe Lys Phe Glu Phe Asn Gln Asn Ile Ser Gln Ile
                435                 440                 445

Ser Leu Leu Glu Trp Glu Leu Asp Lys Ile Gln Asn Glu Asp Ile Lys
        450                 455                 460

Lys Asn Glu Lys Gln Val Glu Val Ile Lys Asn Tyr Phe Asp Ser Val
465                 470                 475                 480

Met Ser Val Tyr Lys Met Thr Lys Tyr Phe Ser Leu Glu Lys Trp Lys
                485                 490                 495

Lys Arg Val Glu Leu Asp Thr Asp Asn Asn Phe Tyr Asn Asp Phe Asn
                500                 505                 510

Glu Tyr Leu Glu Gly Phe Glu Ile Trp Lys Asp Tyr Asn Leu Val Arg
                515                 520                 525

Asn Tyr Ile Thr Lys Lys Gln Val Asn Thr Asp Lys Ile Lys Leu Asn
        530                 535                 540

Phe Asp Asn Ser Gln Phe Leu Thr Trp Trp Asp Lys Asp Lys Glu Asn
545                 550                 555                 560

Glu Arg Leu Gly Ile Ile Leu Arg Arg Glu Trp Lys Tyr Tyr Leu Trp
                565                 570                 575

Ile Leu Lys Lys Trp Asn Thr Leu Asn Phe Gly Asp Tyr Leu Gln Lys
                580                 585                 590

Glu Trp Glu Ile Phe Tyr Glu Lys Met Asn Tyr Lys Gln Leu Asn Asn
                595                 600                 605

Val Tyr Arg Gln Leu Pro Arg Leu Leu Phe Pro Leu Thr Lys Lys Leu
        610                 615                 620

Asn Glu Leu Lys Trp Asp Glu Leu Lys Lys Tyr Leu Ser Lys Tyr Ile
625                 630                 635                 640

Gln Asn Phe Trp Tyr Asn Glu Glu Ile Ala Gln Ile Lys Ile Glu Phe
                645                 650                 655

Asp Ile Phe Gln Glu Ser Lys Glu Lys Trp Glu Lys Phe Asp Ile Asp
                660                 665                 670

Lys Leu Arg Lys Leu Ile Glu Tyr Tyr Lys Lys Trp Val Leu Ala Leu
                675                 680                 685

Tyr Ser Asp Leu Tyr Asp Leu Glu Phe Ile Lys Tyr Lys Asn Tyr Asp
        690                 695                 700

Asp Leu Ser Ile Phe Tyr Ser Asp Val Glu Lys Lys Met Tyr Asn Leu
705                 710                 715                 720
```

```
Asn Phe Thr Lys Ile Asp Lys Ser Leu Ile Asp Gly Lys Val Lys Ser
            725                 730                 735

Trp Glu Leu Tyr Leu Phe Gln Ile Tyr Asn Lys Asp Phe Ser Glu Ser
            740                 745                 750

Lys Lys Glu Trp Ser Thr Glu Asn Ile His Thr Lys Tyr Phe Lys Leu
            755                 760                 765

Leu Phe Asn Glu Lys Asn Leu Gln Asn Leu Val Val Lys Leu Ser Trp
            770                 775                 780

Trp Ala Asp Ile Phe Phe Arg Asp Lys Thr Glu Asn Leu Lys Phe Lys
785                 790                 795                 800

Lys Asp Lys Asn Gly Gln Glu Ile Leu Asp His Arg Arg Phe Ser Gln
            805                 810                 815

Asp Lys Ile Met Phe His Ile Ser Ile Thr Leu Asn Ala Asn Cys Trp
            820                 825                 830

Asp Lys Tyr Trp Phe Asn Gln Tyr Val Asn Glu Tyr Met Asn Lys Glu
            835                 840                 845

Arg Asp Ile Lys Ile Ile Trp Ile Asp Arg Trp Glu Lys His Leu Ala
            850                 855                 860

Tyr Tyr Cys Val Ile Asp Lys Ser Trp Lys Ile Phe Asn Asn Glu Ile
865                 870                 875                 880

Trp Thr Leu Asn Glu Leu Asn Trp Val Asn Tyr Leu Glu Lys Leu Glu
            885                 890                 895

Lys Ile Glu Ser Ser Arg Lys Asp Ser Arg Ile Ser Trp Trp Glu Ile
            900                 905                 910

Glu Asn Ile Lys Glu Leu Lys Asn Gly Tyr Ile Ser Gln Val Ile Asn
            915                 920                 925

Lys Leu Thr Glu Leu Ile Val Lys Tyr Asn Ala Ile Ile Val Phe Glu
            930                 935                 940

Asp Leu Asn Ile Trp Phe Lys Arg Trp Arg Gln Lys Ile Glu Lys Gln
945                 950                 955                 960

Ile Tyr Gln Lys Leu Glu Leu Ala Leu Ala Lys Lys Leu Asn Tyr Leu
            965                 970                 975

Thr Gln Lys Asp Lys Lys Asp Asp Glu Ile Leu Trp Asn Leu Lys Ala
            980                 985                 990

Leu Gln Leu Val Pro Lys Val Asn Asp Tyr Gln Asp Ile Trp Asn Tyr
            995                 1000                1005

Lys Gln Ser Trp Ile Met Phe Tyr Val Arg Ala Asn Tyr Thr Ser
            1010                1015                1020

Val Thr Cys Pro Asn Cys Trp Leu Arg Lys Asn Leu Tyr Ile Ser
            1025                1030                1035

Asn Ser Ala Thr Lys Glu Asn Gln Lys Lys Ser Leu Asn Ser Ile
            1040                1045                1050

Ala Ile Lys Tyr Asn Asp Trp Lys Phe Ser Phe Ser Tyr Glu Ile
            1055                1060                1065

Asp Asp Lys Ser Trp Lys Gln Lys Gln Ser Leu Asn Lys Lys Lys
            1070                1075                1080

Phe Ile Val Tyr Ser Asp Ile Glu Arg Phe Val Tyr Ser Pro Leu
            1085                1090                1095

Glu Lys Leu Thr Lys Val Ile Asp Val Asn Lys Lys Leu Leu Glu
            1100                1105                1110

Leu Phe Arg Asp Phe Asn Leu Ser Leu Asp Ile Asn Lys Gln Ile
            1115                1120                1125
```

-continued

| | | | | | | | | | | | |
|---|---|---|---|---|---|---|---|---|---|---|---|
|Gln|Glu|Lys|Asp|Leu|Asp|Ser|Val|Phe|Phe|Lys|Ser|Leu|Thr|His|
| |1130| | | |1135| | | | |1140| | | | |

Gln Glu Lys Asp Leu Asp Ser Val Phe Phe Lys Ser Leu Thr His
    1130              1135              1140

Leu Phe Asn Leu Ile Leu Gln Leu Arg Asn Ser Asp Ser Lys Asp
1145              1150              1155

Asn Lys Asp Tyr Ile Ser Cys Pro Ser Cys Tyr Tyr His Ser Asn
    1160              1165              1170

Asn Trp Leu Gln Trp Phe Glu Phe Asn Trp Asp Ala Asn Trp Ala
1175              1180              1185

Tyr Asn Ile Ala Arg Lys Gly Ile Ile Leu Leu Asp Arg Ile Arg
    1190              1195              1200

Lys Asn Gln Glu Lys Pro Asp Leu Tyr Val Ser Asp Ile Asp Trp
1205              1210              1215

Asp Asn Phe Val Gln Ser Asn Gln Phe Pro Asn Thr Ile Ile Pro
    1220              1225              1230

Ile Gln Asn Ile Glu Lys Gln Val Pro Leu Asn Ile Lys Ile
1235              1240              1245

<210> SEQ ID NO 109
<211> LENGTH: 1298
<212> TYPE: PRT
<213> ORGANISM: Unknown
<220> FEATURE:
<223> OTHER INFORMATION: Thiomicrospira sp. XS5 ZB100000

<400> SEQUENCE: 109

Met Thr Lys Thr Phe Asp Ser Glu Phe Phe Asn Leu Tyr Ser Leu Gln
1               5                 10              15

Lys Thr Val Arg Phe Glu Leu Lys Pro Val Gly Glu Thr Ala Ser Phe
          20                 25              30

Val Glu Asp Phe Lys Asn Glu Gly Leu Lys Arg Val Val Ser Glu Asp
              35               40              45

Glu Arg Arg Ala Val Asp Tyr Gln Lys Val Lys Glu Ile Ile Asp Asp
50                 55                 60

Tyr His Arg Asp Phe Ile Glu Glu Ser Leu Asn Tyr Phe Pro Glu Gln
65                70               75              80

Val Ser Lys Asp Ala Leu Glu Gln Ala Phe His Leu Tyr Gln Lys Leu
              85               90              95

Lys Ala Ala Lys Val Glu Glu Arg Glu Lys Ala Leu Lys Glu Trp Glu
          100              105              110

Ala Leu Gln Lys Lys Leu Arg Glu Lys Val Val Lys Cys Phe Ser Asp
         115               120              125

Ser Asn Lys Ala Arg Phe Ser Arg Ile Asp Lys Lys Glu Leu Ile Lys
130               135                140

Glu Asp Leu Ile Asn Trp Leu Val Ala Gln Asn Arg Glu Asp Asp Ile
145                150               155             160

Pro Thr Val Glu Thr Phe Asn Asn Phe Thr Thr Tyr Phe Thr Gly Phe
              165               170            175

His Glu Asn Arg Lys Asn Ile Tyr Ser Lys Asp Asp His Ala Thr Ala
         180               185              190

Ile Ser Phe Arg Leu Ile His Glu Asn Leu Pro Lys Phe Phe Asp Asn
        195               200              205

Val Ile Ser Phe Asn Lys Leu Lys Glu Gly Phe Pro Glu Leu Lys Phe
210               215                220

Asp Lys Val Lys Glu Asp Leu Glu Val Asp Tyr Asp Leu Lys His Ala
225                230               235             240

```
Phe Glu Ile Glu Tyr Phe Val Asn Phe Val Thr Gln Ala Gly Ile Asp
                245                 250                 255
Gln Tyr Asn Tyr Leu Leu Gly Lys Thr Leu Glu Asp Gly Thr Lys
        260                 265                 270
Lys Gln Gly Met Asn Glu Gln Ile Asn Leu Phe Lys Gln Gln Thr
        275                 280                 285
Arg Asp Lys Ala Arg Gln Ile Pro Lys Leu Ile Pro Leu Phe Lys Gln
    290                 295                 300
Ile Leu Ser Glu Arg Thr Glu Ser Gln Ser Phe Ile Pro Lys Gln Phe
305                 310                 315                 320
Glu Ser Asp Gln Glu Leu Phe Asp Ser Leu Gln Lys Leu His Asn Asn
                325                 330                 335
Cys Gln Asp Lys Phe Thr Val Leu Gln Gln Ala Ile Leu Gly Leu Ala
                340                 345                 350
Glu Ala Asp Leu Lys Lys Val Phe Ile Lys Thr Ser Asp Leu Asn Ala
                355                 360                 365
Leu Ser Asn Thr Ile Phe Gly Asn Tyr Ser Val Phe Ser Asp Ala Leu
370                 375                 380
Asn Leu Tyr Lys Glu Ser Leu Lys Thr Lys Lys Ala Gln Glu Ala Phe
385                 390                 395                 400
Glu Lys Leu Pro Ala His Ser Ile His Asp Leu Ile Gln Tyr Leu Glu
                405                 410                 415
Gln Phe Asn Ser Ser Leu Asp Ala Glu Lys Gln Ser Thr Asp Thr
                420                 425                 430
Val Leu Asn Tyr Phe Ile Lys Thr Asp Glu Leu Tyr Ser Arg Phe Ile
                435                 440                 445
Lys Ser Thr Ser Glu Ala Phe Thr Gln Val Gln Pro Leu Phe Glu Leu
450                 455                 460
Glu Ala Leu Ser Ser Lys Arg Arg Pro Glu Ser Glu Asp Glu Gly
465                 470                 475                 480
Ala Lys Gly Gln Glu Gly Phe Glu Gln Ile Lys Arg Ile Lys Ala Tyr
                485                 490                 495
Leu Asp Thr Leu Met Glu Ala Val His Phe Ala Lys Pro Leu Tyr Leu
        500                 505                 510
Val Lys Gly Arg Lys Met Ile Glu Gly Leu Asp Lys Asp Gln Ser Phe
        515                 520                 525
Tyr Glu Ala Phe Glu Met Ala Tyr Gln Glu Leu Glu Ser Leu Ile Ile
        530                 535                 540
Pro Ile Tyr Asn Lys Ala Arg Ser Tyr Leu Ser Arg Lys Pro Phe Lys
545                 550                 555                 560
Ala Asp Lys Phe Lys Ile Asn Phe Asp Asn Asn Thr Leu Leu Ser Gly
                565                 570                 575
Trp Asp Ala Asn Lys Glu Thr Ala Asn Ala Ser Ile Leu Phe Lys Lys
                580                 585                 590
Asp Gly Leu Tyr Tyr Leu Gly Ile Met Pro Lys Gly Lys Thr Phe Leu
                595                 600                 605
Phe Asp Tyr Phe Val Ser Ser Glu Asp Ser Glu Lys Leu Lys Gln Arg
        610                 615                 620
Arg Gln Lys Thr Ala Glu Ala Leu Ala Gln Asp Gly Glu Ser Tyr
625                 630                 635                 640
Phe Glu Lys Ile Arg Tyr Lys Leu Leu Pro Gly Ala Ser Lys Met Leu
                645                 650                 655
Pro Lys Val Phe Phe Ser Asn Lys Asn Ile Gly Phe Tyr Asn Pro Ser
```

```
                660               665               670
Asp Asp Ile Leu Arg Ile Arg Asn Thr Ala Ser His Thr Lys Asn Gly
            675               680               685
Thr Pro Gln Lys Gly His Ser Lys Val Glu Phe Asn Leu Asn Asp Cys
690               695               700
His Lys Met Ile Asp Phe Phe Lys Ser Ser Ile Gln Lys His Pro Glu
705               710               715               720
Trp Gly Ser Phe Gly Phe Thr Phe Ser Asp Thr Ser Asp Phe Glu Asp
                725               730               735
Met Ser Ala Phe Tyr Arg Glu Val Glu Asn Gln Gly Tyr Val Ile Ser
            740               745               750
Phe Asp Lys Ile Lys Glu Thr Tyr Ile Gln Ser Gln Val Glu Gln Gly
            755               760               765
Asn Leu Tyr Leu Phe Gln Ile Tyr Asn Lys Asp Phe Ser Pro Tyr Ser
            770               775               780
Lys Gly Lys Pro Asn Leu His Thr Leu Tyr Trp Lys Ala Leu Phe Glu
785               790               795               800
Glu Ala Asn Leu Asn Asn Val Val Ala Lys Leu Asn Gly Glu Ala Glu
                805               810               815
Ile Phe Phe Arg Arg His Ser Ile Lys Ala Ser Asp Lys Val Val His
                820               825               830
Pro Ala Asn Gln Ala Ile Asp Asn Lys Asn Pro His Thr Glu Lys Thr
            835               840               845
Gln Ser Thr Phe Glu Tyr Asp Leu Val Lys Asp Lys Arg Tyr Thr Gln
            850               855               860
Asp Lys Phe Phe Phe His Val Pro Ile Ser Leu Asn Phe Lys Ala Gln
865               870               875               880
Gly Val Ser Lys Phe Asn Asp Lys Val Asn Gly Phe Leu Lys Gly Asn
                885               890               895
Pro Asp Val Asn Ile Ile Gly Ile Asp Arg Gly Glu Arg His Leu Leu
                900               905               910
Tyr Phe Thr Val Val Asn Gln Lys Gly Glu Ile Leu Val Gln Glu Ser
            915               920               925
Leu Asn Thr Leu Met Ser Asp Lys Gly His Val Asn Asp Tyr Gln Gln
            930               935               940
Lys Leu Asp Lys Lys Glu Gln Glu Arg Asp Ala Ala Arg Lys Ser Trp
945               950               955               960
Thr Thr Val Glu Asn Ile Lys Glu Leu Lys Glu Gly Tyr Leu Ser His
                965               970               975
Val Val His Lys Leu Ala His Leu Ile Ile Lys Tyr Asn Ala Ile Val
                980               985               990
Cys Leu Glu Asp Leu Asn Phe Gly Phe Lys Arg Gly Arg Phe Lys Val
            995               1000              1005
Glu Lys Gln Val Tyr Gln Lys Phe Glu Lys Ala Leu Ile Asp Lys
        1010              1015              1020
Leu Asn Tyr Leu Val Phe Lys Glu Lys Glu Leu Gly Glu Val Gly
        1025              1030              1035
His Tyr Leu Thr Ala Tyr Gln Leu Thr Ala Pro Phe Glu Ser Phe
        1040              1045              1050
Lys Lys Leu Gly Lys Gln Ser Gly Ile Leu Phe Tyr Val Pro Ala
        1055              1060              1065
Asp Tyr Thr Ser Lys Ile Asp Pro Thr Thr Gly Phe Val Asn Phe
        1070              1075              1080
```

```
Leu Asp Leu Arg Tyr Gln Ser Val Glu Lys Ala Lys Gln Leu Leu
    1085                1090                1095

Ser Asp Phe Asn Ala Ile Arg Phe Asn Ser Val Gln Asn Tyr Phe
    1100                1105                1110

Glu Phe Glu Ile Asp Tyr Lys Lys Leu Thr Pro Lys Arg Lys Val
    1115                1120                1125

Gly Thr Gln Ser Lys Trp Val Ile Cys Thr Tyr Gly Asp Val Arg
    1130                1135                1140

Tyr Gln Asn Arg Arg Asn Gln Lys Gly His Trp Glu Thr Glu Glu
    1145                1150                1155

Val Asn Val Thr Glu Lys Leu Lys Ala Leu Phe Ala Ser Asp Ser
    1160                1165                1170

Lys Thr Thr Thr Val Ile Asp Tyr Ala Asn Asp Asp Asn Leu Ile
    1175                1180                1185

Asp Val Ile Leu Glu Gln Asp Lys Ala Ser Phe Phe Lys Glu Leu
    1190                1195                1200

Leu Trp Leu Leu Lys Leu Thr Met Thr Leu Arg His Ser Lys Ile
    1205                1210                1215

Lys Ser Glu Asp Asp Phe Ile Leu Ser Pro Val Lys Asn Glu Gln
    1220                1225                1230

Gly Glu Phe Tyr Asp Ser Arg Lys Ala Gly Glu Val Trp Pro Lys
    1235                1240                1245

Asp Ala Asp Ala Asn Gly Ala Tyr His Ile Ala Leu Lys Gly Leu
    1250                1255                1260

Trp Asn Leu Gln Gln Ile Asn Gln Trp Glu Lys Gly Lys Thr Leu
    1265                1270                1275

Asn Leu Ala Ile Lys Asn Gln Asp Trp Phe Ser Phe Ile Gln Glu
    1280                1285                1290

Lys Pro Tyr Gln Glu
    1295

<210> SEQ ID NO 110
<211> LENGTH: 1318
<212> TYPE: PRT
<213> ORGANISM: Unknown
<220> FEATURE:
<223> OTHER INFORMATION: Flavobacterium branchiophilum FL-15

<400> SEQUENCE: 110

Met Thr Asn Lys Phe Thr Asn Gln Tyr Ser Leu Ser Lys Thr Leu Arg
1               5                   10                  15

Phe Glu Leu Ile Pro Gln Gly Lys Thr Leu Glu Phe Ile Gln Glu Lys
                20                  25                  30

Gly Leu Leu Ser Gln Asp Lys Gln Arg Ala Glu Ser Tyr Gln Glu Met
            35                  40                  45

Lys Lys Thr Ile Asp Lys Phe His Lys Tyr Phe Ile Asp Leu Ala Leu
        50                  55                  60

Ser Asn Ala Lys Leu Thr His Leu Glu Thr Tyr Leu Glu Leu Tyr Asn
65                  70                  75                  80

Lys Ser Ala Glu Thr Lys Lys Glu Gln Lys Phe Lys Asp Asp Leu Lys
                85                  90                  95

Lys Val Gln Asp Asn Leu Arg Lys Glu Ile Val Lys Ser Phe Ser Asp
                100                 105                 110

Gly Asp Ala Lys Ser Ile Phe Ala Ile Leu Asp Lys Lys Glu Leu Ile
            115                 120                 125
```

-continued

```
Thr Val Glu Leu Glu Lys Trp Phe Glu Asn Asn Gln Lys Asp Ile
    130                 135                 140
Tyr Phe Asp Glu Lys Phe Lys Thr Phe Thr Thr Tyr Phe Thr Gly Phe
145                 150                 155                 160
His Gln Asn Arg Lys Asn Met Tyr Ser Val Glu Pro Asn Ser Thr Ala
                165                 170                 175
Ile Ala Tyr Arg Leu Ile His Glu Asn Leu Pro Lys Phe Leu Glu Asn
            180                 185                 190
Ala Lys Ala Phe Glu Lys Ile Lys Gln Val Glu Ser Leu Gln Val Asn
        195                 200                 205
Phe Arg Glu Leu Met Gly Glu Phe Gly Asp Glu Gly Leu Ile Phe Val
    210                 215                 220
Asn Glu Leu Glu Glu Met Phe Gln Ile Asn Tyr Tyr Asn Asp Val Leu
225                 230                 235                 240
Ser Gln Asn Gly Ile Thr Ile Tyr Asn Ser Ile Ile Ser Gly Phe Thr
                245                 250                 255
Lys Asn Asp Ile Lys Tyr Lys Gly Leu Asn Glu Tyr Ile Asn Asn Tyr
            260                 265                 270
Asn Gln Thr Lys Asp Lys Asp Arg Leu Pro Lys Leu Lys Gln Leu
        275                 280                 285
Tyr Lys Gln Ile Leu Ser Asp Arg Ile Ser Leu Ser Phe Leu Pro Asp
    290                 295                 300
Ala Phe Thr Asp Gly Lys Gln Val Leu Lys Ala Ile Phe Asp Phe Tyr
305                 310                 315                 320
Lys Ile Asn Leu Leu Ser Tyr Thr Ile Glu Gly Gln Glu Glu Ser Gln
                325                 330                 335
Asn Leu Leu Leu Leu Ile Arg Gln Thr Ile Glu Asn Leu Ser Ser Phe
            340                 345                 350
Asp Thr Gln Lys Ile Tyr Leu Lys Asn Asp Thr His Leu Thr Thr Ile
        355                 360                 365
Ser Gln Gln Val Phe Gly Asp Phe Ser Val Phe Ser Thr Ala Leu Asn
    370                 375                 380
Tyr Trp Tyr Glu Thr Lys Val Asn Pro Lys Phe Glu Thr Glu Tyr Ser
385                 390                 395                 400
Lys Ala Asn Glu Lys Lys Arg Glu Ile Leu Asp Lys Ala Lys Ala Val
                405                 410                 415
Phe Thr Lys Gln Asp Tyr Phe Ser Ile Ala Phe Leu Gln Glu Val Leu
            420                 425                 430
Ser Glu Tyr Ile Leu Thr Leu Asp His Thr Ser Asp Ile Val Lys Lys
        435                 440                 445
His Ser Ser Asn Cys Ile Ala Asp Tyr Phe Lys Asn His Phe Val Ala
    450                 455                 460
Lys Lys Glu Asn Glu Thr Asp Lys Thr Phe Asp Phe Ile Ala Asn Ile
465                 470                 475                 480
Thr Ala Lys Tyr Gln Cys Ile Gln Gly Ile Leu Glu Asn Ala Asp Gln
                485                 490                 495
Tyr Glu Asp Glu Leu Lys Gln Asp Gln Lys Leu Ile Asp Asn Leu Lys
            500                 505                 510
Phe Phe Leu Asp Ala Ile Leu Glu Leu Leu His Phe Ile Lys Pro Leu
        515                 520                 525
His Leu Lys Ser Glu Ser Ile Thr Glu Lys Asp Thr Ala Phe Tyr Asp
    530                 535                 540
```

```
Val Phe Glu Asn Tyr Tyr Glu Ala Leu Ser Leu Leu Thr Pro Leu Tyr
545                 550                 555                 560

Asn Met Val Arg Asn Tyr Val Thr Gln Lys Pro Tyr Ser Thr Glu Lys
                565                 570                 575

Ile Lys Leu Asn Phe Glu Asn Ala Gln Leu Leu Asn Gly Trp Asp Ala
                580                 585                 590

Asn Lys Glu Gly Asp Tyr Leu Thr Thr Ile Leu Lys Lys Asp Gly Asn
                595                 600                 605

Tyr Phe Leu Ala Ile Met Asp Lys Lys His Asn Lys Ala Phe Gln Lys
            610                 615                 620

Phe Pro Glu Gly Lys Glu Asn Tyr Glu Lys Met Val Tyr Lys Leu Leu
625                 630                 635                 640

Pro Gly Val Asn Lys Met Leu Pro Lys Val Phe Phe Ser Asn Lys Asn
                645                 650                 655

Ile Ala Tyr Phe Asn Pro Ser Lys Glu Leu Leu Glu Asn Tyr Lys Lys
                660                 665                 670

Glu Thr His Lys Lys Gly Asp Thr Phe Asn Leu Glu His Cys His Thr
            675                 680                 685

Leu Ile Asp Phe Phe Lys Asp Ser Leu Asn Lys His Glu Asp Trp Lys
    690                 695                 700

Tyr Phe Asp Phe Gln Phe Ser Glu Thr Lys Ser Tyr Gln Asp Leu Ser
705                 710                 715                 720

Gly Phe Tyr Arg Glu Val Glu His Gln Gly Tyr Lys Ile Asn Phe Lys
                725                 730                 735

Asn Ile Asp Ser Glu Tyr Ile Asp Gly Leu Val Asn Glu Gly Lys Leu
                740                 745                 750

Phe Leu Phe Gln Ile Tyr Ser Lys Asp Phe Ser Pro Phe Ser Lys Gly
            755                 760                 765

Lys Pro Asn Met His Thr Leu Tyr Trp Lys Ala Leu Phe Glu Glu Gln
            770                 775                 780

Asn Leu Gln Asn Val Ile Tyr Lys Leu Asn Gly Gln Ala Glu Ile Phe
785                 790                 795                 800

Phe Arg Lys Ala Ser Ile Lys Pro Lys Asn Ile Ile Leu His Lys Lys
                805                 810                 815

Lys Ile Lys Ile Ala Lys Lys His Phe Ile Asp Lys Thr Lys Thr
            820                 825                 830

Ser Glu Ile Val Pro Val Gln Thr Ile Lys Asn Leu Asn Met Tyr Tyr
    835                 840                 845

Gln Gly Lys Ile Ser Glu Lys Glu Leu Thr Gln Asp Asp Leu Arg Tyr
    850                 855                 860

Ile Asp Asn Phe Ser Ile Phe Asn Glu Lys Asn Lys Thr Ile Asp Ile
865                 870                 875                 880

Ile Lys Asp Lys Arg Phe Thr Val Asp Lys Phe Gln Phe His Val Pro
                885                 890                 895

Ile Thr Met Asn Phe Lys Ala Thr Gly Gly Ser Tyr Ile Asn Gln Thr
            900                 905                 910

Val Leu Glu Tyr Leu Gln Asn Asn Pro Glu Val Lys Ile Ile Gly Leu
        915                 920                 925

Asp Arg Gly Glu Arg His Leu Val Tyr Leu Thr Leu Ile Asp Gln Gln
        930                 935                 940

Gly Asn Ile Leu Lys Gln Glu Ser Leu Asn Thr Ile Thr Asp Ser Lys
945                 950                 955                 960

Ile Ser Thr Pro Tyr His Lys Leu Leu Asp Asn Lys Glu Asn Glu Arg
```

965                 970                 975

Asp Leu Ala Arg Lys Asn Trp Gly Thr Val Glu Asn Ile Lys Glu Leu
                980                 985                 990

Lys Glu Gly Tyr Ile Ser Gln Val Val His Lys Ile Ala Thr Leu Met
            995                1000                1005

Leu Glu Glu Asn Ala Ile Val Met Glu Asp Leu Asn Phe Gly
        1010                1015                1020

Phe Lys Arg Gly Arg Phe Lys Val Glu Lys Gln Ile Tyr Gln Lys
        1025                1030                1035

Leu Glu Lys Met Leu Ile Asp Lys Leu Asn Tyr Leu Val Leu Lys
        1040                1045                1050

Asp Lys Gln Pro Gln Glu Leu Gly Gly Leu Tyr Asn Ala Leu Gln
        1055                1060                1065

Leu Thr Asn Lys Phe Glu Ser Phe Gln Lys Met Gly Lys Gln Ser
        1070                1075                1080

Gly Phe Leu Phe Tyr Val Pro Ala Trp Asn Thr Ser Lys Ile Asp
        1085                1090                1095

Pro Thr Thr Gly Phe Val Asn Tyr Phe Tyr Thr Lys Tyr Glu Asn
        1100                1105                1110

Val Asp Lys Ala Lys Ala Phe Phe Glu Lys Phe Glu Ala Ile Arg
        1115                1120                1125

Phe Asn Ala Glu Lys Lys Tyr Phe Glu Phe Glu Val Lys Lys Tyr
        1130                1135                1140

Ser Asp Phe Asn Pro Lys Ala Glu Gly Thr Gln Gln Ala Trp Thr
        1145                1150                1155

Ile Cys Thr Tyr Gly Glu Arg Ile Glu Thr Lys Arg Gln Lys Asp
        1160                1165                1170

Gln Asn Asn Lys Phe Val Ser Thr Pro Ile Asn Leu Thr Glu Lys
        1175                1180                1185

Ile Glu Asp Phe Leu Gly Lys Asn Gln Ile Val Tyr Gly Asp Gly
        1190                1195                1200

Asn Cys Ile Lys Ser Gln Ile Ala Ser Lys Asp Lys Ala Phe
        1205                1210                1215

Phe Glu Thr Leu Leu Tyr Trp Phe Lys Met Thr Leu Gln Met Arg
        1220                1225                1230

Asn Ser Glu Thr Arg Thr Asp Ile Asp Tyr Leu Ile Ser Pro Val
        1235                1240                1245

Met Asn Asp Asn Gly Thr Phe Tyr Asn Ser Arg Asp Tyr Glu Lys
        1250                1255                1260

Leu Glu Asn Pro Thr Leu Pro Lys Asp Ala Asp Ala Asn Gly Ala
        1265                1270                1275

Tyr His Ile Ala Lys Lys Gly Leu Met Leu Leu Asn Lys Ile Asp
        1280                1285                1290

Gln Ala Asp Leu Thr Lys Lys Val Asp Leu Ser Ile Ser Asn Arg
        1295                1300                1305

Asp Trp Leu Gln Phe Val Gln Lys Asn Lys
        1310                1315

<210> SEQ ID NO 111
<211> LENGTH: 1251
<212> TYPE: PRT
<213> ORGANISM: Unknown
<220> FEATURE:
<223> OTHER INFORMATION: Moraxella bovoculi strain 57922

<400> SEQUENCE: 111

```
Met Leu Phe Gln Asp Phe Thr His Leu Tyr Pro Leu Ser Lys Thr Val
1               5                   10                  15

Arg Phe Glu Leu Lys Pro Ile Gly Arg Thr Leu Glu His Ile His Ala
            20                  25                  30

Lys Asn Phe Leu Ser Gln Asp Glu Thr Met Ala Asp Met Tyr Gln Lys
        35                  40                  45

Val Lys Val Ile Leu Asp Asp Tyr His Arg Asp Phe Ile Ala Asp Met
50                  55                  60

Met Gly Glu Val Lys Leu Thr Lys Leu Ala Glu Phe Tyr Asp Val Tyr
65                  70                  75                  80

Leu Lys Phe Arg Lys Asn Pro Lys Asp Asp Gly Leu Gln Lys Gln Leu
                85                  90                  95

Lys Asp Leu Gln Ala Val Leu Arg Lys Glu Ser Val Lys Pro Ile Gly
            100                 105                 110

Ser Gly Gly Lys Tyr Lys Thr Gly Tyr Asp Arg Leu Phe Gly Ala Lys
        115                 120                 125

Leu Phe Lys Asp Gly Lys Glu Leu Gly Asp Leu Ala Lys Phe Val Ile
130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
            180                 185                 190

His Glu Asn Leu Pro Arg Phe Ile Asp Asn Leu Gln Ile Leu Thr Thr
        195                 200                 205

Ile Lys Gln Lys His Ser Ala Leu Tyr Asp Gln Ile Ile Asn Glu Leu
210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Arg Ile Ile
                245                 250                 255

Gly Glu Val Asn Gly Tyr Thr Asn Lys His Asn Gln Ile Cys His Lys
            260                 265                 270

Ser Glu Arg Ile Ala Lys Leu Arg Pro Leu His Lys Gln Ile Leu Ser
        275                 280                 285

Asp Gly Met Gly Val Ser Phe Leu Pro Ser Lys Phe Ala Asp Asp Ser
290                 295                 300

Glu Met Cys Gln Ala Val Asn Glu Phe Tyr Arg His Tyr Thr Asp Val
305                 310                 315                 320

Phe Ala Lys Val Gln Ser Leu Phe Asp Gly Phe Asp Asp His Gln Lys
                325                 330                 335

Asp Gly Ile Tyr Val Glu His Lys Asn Leu Asn Glu Leu Ser Lys Gln
            340                 345                 350

Ala Phe Gly Asp Phe Ala Leu Leu Gly Arg Val Leu Asp Gly Tyr Tyr
        355                 360                 365

Val Asp Val Val Asn Pro Glu Phe Asn Glu Arg Phe Ala Lys Ala Lys
370                 375                 380

Thr Asp Asn Ala Lys Ala Lys Leu Thr Lys Glu Lys Asp Lys Phe Ile
385                 390                 395                 400

Lys Gly Val His Ser Leu Ala Ser Leu Glu Gln Ala Ile Glu His His
                405                 410                 415
```

```
Thr Ala Arg His Asp Asp Glu Ser Val Gln Ala Gly Lys Leu Gly Gln
                420                 425                 430

Tyr Phe Lys His Gly Leu Ala Gly Val Asp Asn Pro Ile Gln Lys Ile
                435                 440                 445

His Asn Asn His Ser Thr Ile Lys Gly Phe Leu Glu Arg Glu Arg Pro
450                 455                 460

Ala Gly Glu Arg Ala Leu Pro Lys Ile Lys Ser Gly Lys Asn Pro Glu
465                 470                 475                 480

Met Thr Gln Leu Arg Gln Leu Lys Glu Leu Leu Asp Asn Ala Leu Asn
                485                 490                 495

Val Ala His Phe Ala Lys Leu Leu Thr Thr Lys Thr Thr Leu Asp Asn
                500                 505                 510

Gln Asp Gly Asn Phe Tyr Gly Glu Phe Gly Val Leu Tyr Asp Glu Leu
                515                 520                 525

Ala Lys Ile Pro Thr Leu Tyr Asn Lys Val Arg Asp Tyr Leu Ser Gln
                530                 535                 540

Lys Pro Phe Ser Thr Glu Lys Tyr Lys Leu Asn Phe Gly Asn Pro Thr
545                 550                 555                 560

Leu Leu Asn Gly Trp Asp Leu Asn Lys Glu Lys Asp Asn Phe Gly Val
                565                 570                 575

Ile Leu Gln Lys Asp Gly Cys Tyr Tyr Leu Ala Leu Leu Asp Lys Ala
                580                 585                 590

His Lys Lys Val Phe Asp Asn Ala Pro Asn Thr Gly Lys Asn Val Tyr
                595                 600                 605

Gln Lys Met Val Tyr Lys Leu Leu Pro Gly Pro Asn Lys Met Leu Pro
                610                 615                 620

Lys Val Phe Phe Ala Lys Ser Asn Leu Asp Tyr Tyr Asn Pro Ser Ala
625                 630                 635                 640

Glu Leu Leu Asp Lys Tyr Ala Lys Gly Thr His Lys Lys Gly Asp Asn
                645                 650                 655

Phe Asn Leu Lys Asp Cys His Ala Leu Ile Asp Phe Phe Lys Ala Gly
                660                 665                 670

Ile Asn Lys His Pro Glu Trp Gln His Phe Gly Phe Lys Phe Ser Pro
                675                 680                 685

Thr Ser Ser Tyr Arg Asp Leu Ser Asp Phe Tyr Arg Glu Val Glu Pro
690                 695                 700

Gln Gly Tyr Gln Val Lys Phe Val Asp Ile Asn Ala Asp Tyr Ile Asp
705                 710                 715                 720

Glu Leu Val Glu Gln Gly Lys Leu Tyr Leu Phe Gln Ile Tyr Asn Lys
                725                 730                 735

Asp Phe Ser Pro Lys Ala His Gly Lys Pro Asn Leu His Thr Leu Tyr
                740                 745                 750

Phe Lys Ala Leu Phe Ser Glu Asp Asn Leu Ala Asp Pro Ile Tyr Lys
                755                 760                 765

Leu Asn Gly Glu Ala Gln Ile Phe Tyr Arg Lys Ala Ser Leu Asp Met
                770                 775                 780

Asn Glu Thr Thr Ile His Arg Ala Gly Glu Val Leu Glu Asn Lys Asn
785                 790                 795                 800

Pro Asp Asn Pro Lys Lys Arg Gln Phe Val Tyr Asp Ile Ile Lys Asp
                805                 810                 815

Lys Arg Tyr Thr Gln Asp Lys Phe Met Leu His Val Pro Ile Thr Met
                820                 825                 830
```

```
Asn Phe Gly Val Gln Gly Met Thr Ile Lys Glu Phe Asn Lys Lys Val
                835                 840                 845

Asn Gln Ser Ile Gln Gln Tyr Asp Glu Val Asn Val Ile Gly Ile Asp
    850                 855                 860

Arg Gly Glu Arg His Leu Leu Tyr Leu Thr Val Ile Asn Ser Lys Gly
865                 870                 875                 880

Glu Ile Leu Glu Gln Arg Ser Leu Asn Asp Ile Thr Thr Ala Ser Ala
                885                 890                 895

Asn Gly Thr Gln Val Thr Thr Pro Tyr His Lys Ile Leu Asp Lys Arg
            900                 905                 910

Glu Ile Glu Arg Leu Asn Ala Arg Val Gly Trp Gly Glu Ile Glu Thr
        915                 920                 925

Ile Lys Glu Leu Lys Ser Gly Tyr Leu Ser His Val Val His Gln Ile
    930                 935                 940

Asn Gln Leu Met Leu Lys Tyr Asn Ala Ile Val Val Leu Glu Asp Leu
945                 950                 955                 960

Asn Phe Gly Phe Lys Arg Gly Arg Phe Lys Val Glu Lys Gln Ile Tyr
                965                 970                 975

Gln Asn Phe Glu Asn Ala Leu Ile Lys Lys Leu Asn His Leu Val Leu
            980                 985                 990

Lys Asp Lys Ala Asp Asp Glu Ile Gly Ser Tyr Lys Asn Ala Leu Gln
        995                 1000                1005

Leu Thr Asn Asn Phe Thr Asp Leu Lys Ser Ile Gly Lys Gln Thr
    1010                1015                1020

Gly Phe Leu Phe Tyr Val Pro Ala Trp Asn Thr Ser Lys Ile Asp
    1025                1030                1035

Pro Glu Thr Gly Phe Val Asp Leu Leu Lys Pro Arg Tyr Glu Asn
    1040                1045                1050

Ile Ala Gln Ser Gln Ala Phe Phe Gly Lys Phe Asp Lys Ile Cys
    1055                1060                1065

Tyr Asn Thr Asp Lys Gly Tyr Phe Glu Phe His Ile Asp Tyr Ala
    1070                1075                1080

Lys Phe Thr Asp Lys Ala Lys Asn Ser Arg Gln Lys Trp Ala Ile
    1085                1090                1095

Cys Ser His Gly Asp Lys Arg Tyr Val Tyr Asp Lys Thr Ala Asn
    1100                1105                1110

Gln Asn Lys Gly Ala Ala Lys Gly Ile Asn Val Asn Asp Glu Leu
    1115                1120                1125

Lys Ser Leu Phe Ala Arg Tyr His Ile Asn Asp Lys Gln Pro Asn
    1130                1135                1140

Leu Val Met Asp Ile Cys Gln Asn Asn Asp Lys Glu Phe His Lys
    1145                1150                1155

Ser Leu Met Cys Leu Leu Lys Thr Leu Leu Ala Leu Arg Tyr Ser
    1160                1165                1170

Asn Ala Ser Ser Asp Glu Asp Phe Ile Leu Ser Pro Val Ala Asn
    1175                1180                1185

Asp Glu Gly Val Phe Phe Asn Ser Ala Leu Ala Asp Asp Thr Gln
    1190                1195                1200

Pro Gln Asn Ala Asp Ala Asn Gly Ala Tyr His Ile Ala Leu Lys
    1205                1210                1215

Gly Leu Trp Leu Leu Asn Glu Leu Lys Asn Ser Asp Asp Leu Asn
    1220                1225                1230

Lys Val Lys Leu Ala Ile Asp Asn Gln Thr Trp Leu Asn Phe Ala
```

<210> SEQ ID NO 112
<211> LENGTH: 1285
<212> TYPE: PRT
<213> ORGANISM: Unknown
<220> FEATURE:
<223> OTHER INFORMATION: Candidatus Roizmanbacteria bacterium
GW2011_GWA2_37_7 US54_C0016

<400> SEQUENCE: 112

```
Met Lys Ser Phe Asp Ser Phe Thr Asn Leu Tyr Ser Leu Ser Lys Thr
 1               5                  10                  15

Leu Lys Phe Glu Met Arg Pro Val Gly Asn Thr Gln Lys Met Leu Asp
             20                  25                  30

Asn Ala Gly Val Phe Glu Lys Asp Lys Leu Ile Gln Lys Lys Tyr Gly
         35                  40                  45

Lys Thr Lys Pro Tyr Phe Asp Arg Leu His Arg Glu Phe Ile Glu Glu
     50                  55                  60

Ala Leu Thr Gly Val Glu Leu Ile Gly Leu Asp Glu Asn Phe Arg Thr
 65                  70                  75                  80

Leu Val Asp Trp Gln Lys Asp Lys Lys Asn Asn Val Ala Met Lys Ala
                 85                  90                  95

Tyr Glu Asn Ser Leu Gln Arg Leu Arg Thr Glu Ile Gly Lys Ile Phe
            100                 105                 110

Asn Leu Lys Ala Glu Asp Trp Val Lys Asn Lys Tyr Pro Ile Leu Gly
        115                 120                 125

Leu Lys Asn Lys Asn Thr Asp Ile Leu Phe Glu Glu Ala Val Phe Gly
    130                 135                 140

Ile Leu Lys Ala Arg Tyr Gly Glu Glu Lys Asp Thr Phe Ile Glu Val
145                 150                 155                 160

Glu Glu Ile Asp Lys Thr Gly Lys Ser Lys Ile Asn Gln Ile Ser Ile
                165                 170                 175

Phe Asp Ser Trp Lys Gly Phe Thr Gly Tyr Phe Lys Lys Phe Phe Glu
            180                 185                 190

Thr Arg Lys Asn Phe Tyr Lys Asn Asp Gly Thr Ser Thr Ala Ile Ala
        195                 200                 205

Thr Arg Ile Ile Asp Gln Asn Leu Lys Arg Phe Ile Asp Asn Leu Ser
    210                 215                 220

Ile Val Glu Ser Val Arg Gln Lys Val Asp Leu Ala Glu Thr Glu Lys
225                 230                 235                 240

Ser Phe Ser Ile Ser Leu Ser Gln Phe Phe Ser Ile Asp Phe Tyr Asn
                245                 250                 255

Lys Cys Leu Leu Gln Asp Gly Ile Asp Tyr Tyr Asn Lys Ile Ile Gly
            260                 265                 270

Gly Glu Thr Leu Lys Asn Gly Glu Lys Leu Ile Gly Leu Asn Glu Leu
        275                 280                 285

Ile Asn Gln Tyr Arg Gln Asn Asn Lys Asp Gln Lys Ile Pro Phe Phe
    290                 295                 300

Lys Leu Leu Asp Lys Gln Ile Leu Ser Glu Lys Ile Leu Phe Leu Asp
305                 310                 315                 320

Glu Ile Lys Asn Asp Thr Glu Leu Ile Glu Ala Leu Ser Gln Phe Ala
                325                 330                 335
```

```
Lys Thr Ala Glu Glu Lys Thr Lys Ile Val Lys Lys Leu Phe Ala Asp
                340                 345                 350

Phe Val Glu Asn Asn Ser Lys Tyr Asp Leu Ala Gln Ile Tyr Ile Ser
            355                 360                 365

Gln Glu Ala Phe Asn Thr Ile Ser Asn Lys Trp Thr Ser Glu Thr Glu
    370                 375                 380

Thr Phe Ala Lys Tyr Leu Phe Glu Ala Met Lys Ser Gly Lys Leu Ala
385                 390                 395                 400

Lys Tyr Glu Lys Lys Asp Asn Ser Tyr Lys Phe Pro Asp Phe Ile Ala
                405                 410                 415

Leu Ser Gln Met Lys Ser Ala Leu Leu Ser Ile Ser Leu Glu Gly His
            420                 425                 430

Phe Trp Lys Glu Lys Tyr Tyr Lys Ile Ser Lys Phe Gln Glu Lys Thr
    435                 440                 445

Asn Trp Glu Gln Phe Leu Ala Ile Phe Leu Tyr Glu Phe Asn Ser Leu
    450                 455                 460

Phe Ser Asp Lys Ile Asn Thr Lys Asp Gly Glu Thr Lys Gln Val Gly
465                 470                 475                 480

Tyr Tyr Leu Phe Ala Lys Asp Leu His Asn Leu Ile Leu Ser Glu Gln
                485                 490                 495

Ile Asp Ile Pro Lys Asp Ser Lys Val Thr Ile Lys Asp Phe Ala Asp
            500                 505                 510

Ser Val Leu Thr Ile Tyr Gln Met Ala Lys Tyr Phe Ala Val Glu Lys
    515                 520                 525

Lys Arg Ala Trp Leu Ala Glu Tyr Glu Leu Asp Ser Phe Tyr Thr Gln
    530                 535                 540

Pro Asp Thr Gly Tyr Leu Gln Phe Tyr Asp Asn Ala Tyr Glu Asp Ile
545                 550                 555                 560

Val Gln Val Tyr Asn Lys Leu Arg Asn Tyr Leu Thr Lys Lys Pro Tyr
                565                 570                 575

Ser Glu Glu Lys Trp Lys Leu Asn Phe Glu Asn Ser Thr Leu Ala Asn
            580                 585                 590

Gly Trp Asp Lys Asn Lys Glu Ser Asp Asn Ser Ala Val Ile Leu Gln
    595                 600                 605

Lys Gly Gly Lys Tyr Tyr Leu Gly Leu Ile Thr Lys Gly His Asn Lys
    610                 615                 620

Ile Phe Asp Asp Arg Phe Gln Glu Lys Phe Ile Val Gly Ile Glu Gly
625                 630                 635                 640

Gly Lys Tyr Glu Lys Ile Val Tyr Lys Phe Phe Pro Asp Gln Ala Lys
                645                 650                 655

Met Phe Pro Lys Val Cys Phe Ser Ala Lys Gly Leu Glu Phe Phe Arg
            660                 665                 670

Pro Ser Glu Glu Ile Leu Arg Ile Tyr Asn Asn Ala Glu Phe Lys Lys
    675                 680                 685

Gly Glu Thr Tyr Ser Ile Asp Ser Met Gln Lys Leu Ile Asp Phe Tyr
    690                 695                 700

Lys Asp Cys Leu Thr Lys Tyr Glu Gly Trp Ala Cys Tyr Thr Phe Arg
705                 710                 715                 720

His Leu Lys Pro Thr Glu Glu Tyr Gln Asn Asn Ile Gly Glu Phe Phe
                725                 730                 735

Arg Asp Val Ala Glu Asp Gly Tyr Arg Ile Asp Phe Gln Gly Ile Ser
            740                 745                 750

Asp Gln Tyr Ile His Glu Lys Asn Glu Lys Gly Glu Leu His Leu Phe
```

```
            755                 760                 765
Glu Ile His Asn Lys Asp Trp Asn Leu Asp Lys Ala Arg Asp Gly Lys
            770                 775                 780

Ser Lys Thr Thr Gln Lys Asn Leu His Thr Leu Tyr Phe Glu Ser Leu
785                 790                 795                 800

Phe Ser Asn Asp Asn Val Val Gln Asn Phe Pro Ile Lys Leu Asn Gly
                    805                 810                 815

Gln Ala Glu Ile Phe Tyr Arg Pro Lys Thr Glu Lys Asp Lys Leu Glu
                820                 825                 830

Ser Lys Lys Asp Lys Lys Gly Asn Lys Val Ile Asp His Lys Arg Tyr
            835                 840                 845

Ser Glu Asn Lys Ile Phe Phe His Val Pro Leu Thr Leu Asn Arg Thr
850                 855                 860

Lys Asn Asp Ser Tyr Arg Phe Asn Ala Gln Ile Asn Asn Phe Leu Ala
865                 870                 875                 880

Asn Asn Lys Asp Ile Asn Ile Ile Gly Val Asp Arg Gly Glu Lys His
                    885                 890                 895

Leu Val Tyr Tyr Ser Val Ile Thr Gln Ala Ser Asp Ile Leu Glu Ser
                900                 905                 910

Gly Ser Leu Asn Glu Leu Asn Gly Val Asn Tyr Ala Glu Lys Leu Gly
            915                 920                 925

Lys Lys Ala Glu Asn Arg Glu Gln Ala Arg Arg Asp Trp Gln Asp Val
930                 935                 940

Gln Gly Ile Lys Asp Leu Lys Lys Gly Tyr Ile Ser Gln Val Val Arg
945                 950                 955                 960

Lys Leu Ala Asp Leu Ala Ile Lys His Asn Ala Ile Ile Ile Leu Glu
                    965                 970                 975

Asp Leu Asn Met Arg Phe Lys Gln Val Arg Gly Gly Ile Glu Lys Ser
                980                 985                 990

Ile Tyr Gln Gln Leu Glu Lys Ala Leu Ile Asp Lys Leu Ser Phe Leu
            995                 1000                1005

Val Asp Lys Gly Glu Lys Asn Pro Glu Gln Ala Gly His Leu Leu
    1010                1015                1020

Lys Ala Tyr Gln Leu Ser Ala Pro Phe Glu Thr Phe Gln Lys Met
    1025                1030                1035

Gly Lys Gln Thr Gly Ile Ile Phe Tyr Thr Gln Ala Ser Tyr Thr
    1040                1045                1050

Ser Lys Ser Asp Pro Val Thr Gly Trp Arg Pro His Leu Tyr Leu
    1055                1060                1065

Lys Tyr Phe Ser Ala Lys Lys Ala Lys Asp Asp Ile Ala Lys Phe
    1070                1075                1080

Thr Lys Ile Glu Phe Val Asn Asp Arg Phe Glu Leu Thr Tyr Asp
    1085                1090                1095

Ile Lys Asp Phe Gln Gln Ala Lys Glu Tyr Pro Asn Lys Thr Val
    1100                1105                1110

Trp Lys Val Cys Ser Asn Val Glu Arg Phe Arg Trp Asp Lys Asn
    1115                1120                1125

Leu Asn Gln Asn Lys Gly Gly Tyr Thr His Tyr Thr Asn Ile Thr
    1130                1135                1140

Glu Asn Ile Gln Glu Leu Phe Thr Lys Tyr Gly Ile Asp Ile Thr
    1145                1150                1155

Lys Asp Leu Leu Thr Gln Ile Ser Thr Ile Asp Glu Lys Gln Asn
    1160                1165                1170
```

```
Thr Ser Phe Phe Arg Asp Phe Ile Phe Tyr Phe Asn Leu Ile Cys
    1175            1180            1185

Gln Ile Arg Asn Thr Asp Asp Ser Glu Ile Ala Lys Lys Asn Gly
    1190            1195            1200

Lys Asp Asp Phe Ile Leu Ser Pro Val Glu Pro Phe Phe Asp Ser
    1205            1210            1215

Arg Lys Asp Asn Gly Asn Lys Leu Pro Glu Asn Gly Asp Asp Asn
    1220            1225            1230

Gly Ala Tyr Asn Ile Ala Arg Lys Gly Ile Val Ile Leu Asn Lys
    1235            1240            1245

Ile Ser Gln Tyr Ser Glu Lys Asn Glu Asn Cys Glu Lys Met Lys
    1250            1255            1260

Trp Gly Asp Leu Tyr Val Ser Asn Ile Asp Trp Asp Asn Phe Val
    1265            1270            1275

Thr Gln Ala Asn Ala Arg His
    1280            1285

<210> SEQ ID NO 113
<211> LENGTH: 1207
<212> TYPE: PRT
<213> ORGANISM: Unknown
<220> FEATURE:
<223> OTHER INFORMATION: Pseudobutyrivibrio xylanivorans

<400> SEQUENCE: 113

Met Tyr Tyr Gln Asn Leu Thr Lys Met Tyr Pro Ile Ser Lys Thr Leu
1               5                   10                  15

Arg Asn Glu Leu Ile Pro Val Gly Lys Thr Leu Glu Asn Ile Arg Lys
            20                  25                  30

Asn Gly Ile Leu Glu Ala Asp Ile Gln Arg Lys Ala Asp Tyr Glu His
        35                  40                  45

Val Lys Lys Leu Met Asp Asn Tyr His Lys Gln Leu Ile Asn Glu Ala
    50                  55                  60

Leu Gln Gly Val His Leu Ser Asp Leu Ser Ala Tyr Asp Leu Tyr
65                  70                  75                  80

Phe Asn Leu Ser Lys Glu Lys Asn Ser Val Asp Ala Phe Ser Lys Cys
                85                  90                  95

Gln Asp Lys Leu Arg Lys Glu Ile Val Ser Phe Leu Lys Asn His Glu
            100                 105                 110

Asn Phe Pro Lys Ile Gly Asn Lys Glu Ile Ile Lys Leu Ile Gln Ser
        115                 120                 125

Leu Asn Asp Asn Asp Ala Asp Asn Ala Leu Asp Ser Phe Ser Asn
    130                 135                 140

Phe Tyr Thr Tyr Phe Ser Ser Tyr Asn Glu Val Arg Lys Asn Leu Tyr
145                 150                 155                 160

Ser Asp Glu Glu Lys Ser Ser Thr Val Ala Tyr Arg Leu Ile Asn Glu
                165                 170                 175

Asn Leu Pro Lys Ser Leu Asp Asn Ile Lys Ala Tyr Ala Ile Ala Lys
            180                 185                 190

Lys Ala Gly Val Arg Ala Glu Gly Leu Ser Glu Glu Gln Asp Cys
        195                 200                 205

Leu Phe Ile Ile Glu Thr Phe Glu Arg Thr Leu Thr Gln Asp Gly Ile
    210                 215                 220

Asp Asn Tyr Asn Ala Asp Ile Gly Lys Leu Asn Thr Ala Ile Asn Leu
225                 230                 235                 240
```

```
Tyr Asn Gln Gln Asn Lys Lys Gln Glu Gly Phe Arg Lys Val Pro Gln
                245                 250                 255

Met Lys Cys Leu Tyr Lys Gln Ile Leu Ser Asp Arg Glu Glu Ala Phe
            260                 265                 270

Ile Asp Glu Phe Ser Asp Glu Asp Leu Ile Thr Asn Ile Glu Ser
        275                 280                 285

Phe Ala Glu Asn Met Asn Val Phe Leu Asn Ser Glu Ile Ile Thr Asp
    290                 295                 300

Phe Lys Asn Ala Leu Val Glu Ser Asp Gly Ser Leu Val Tyr Ile Lys
305                 310                 315                 320

Asn Asp Val Ser Lys Thr Leu Phe Ser Asn Ile Val Phe Gly Ser Trp
                325                 330                 335

Asn Ala Ile Asp Glu Lys Leu Ser Asp Glu Tyr Asp Leu Ala Asn Ser
                340                 345                 350

Lys Lys Lys Lys Asp Glu Lys Tyr Tyr Glu Lys Arg Gln Lys Glu Leu
                355                 360                 365

Lys Lys Asn Lys Ser Tyr Asp Leu Glu Thr Ile Ile Gly Leu Phe Asp
            370                 375                 380

Asp Ser Ile Asp Val Ile Gly Lys Tyr Ile Glu Lys Leu Glu Ser Asp
385                 390                 395                 400

Ile Thr Ala Ile Ala Glu Ala Lys Asn Asp Phe Asp Glu Ile Val Leu
                405                 410                 415

Arg Lys His Asp Lys Asn Lys Ser Leu Arg Lys Asn Thr Asn Ala Val
                420                 425                 430

Glu Ala Ile Lys Ser Tyr Leu Asp Thr Val Lys Asp Phe Glu Arg Asp
            435                 440                 445

Ile Lys Leu Ile Asn Gly Ser Gly Gln Glu Val Glu Lys Asn Leu Val
            450                 455                 460

Val Tyr Ala Glu Gln Glu Asn Ile Leu Ala Glu Ile Lys Asn Val Asp
465                 470                 475                 480

Ser Leu Tyr Asn Met Ser Arg Asn Tyr Leu Thr Gln Lys Pro Phe Ser
                485                 490                 495

Thr Glu Lys Phe Lys Leu Asn Phe Glu Asn Pro Thr Leu Leu Asn Gly
            500                 505                 510

Trp Asp Arg Asn Lys Glu Lys Asp Tyr Leu Gly Ile Leu Phe Glu Lys
            515                 520                 525

Glu Gly Met Tyr Tyr Leu Gly Ile Ile Asn Asn Asn His Arg Lys Ile
        530                 535                 540

Phe Glu Asn Glu Lys Leu Cys Thr Gly Lys Glu Ser Cys Phe Asn Lys
545                 550                 555                 560

Ile Val Tyr Lys Gln Ile Ser Asn Ala Ala Lys Tyr Leu Ser Ser Lys
                565                 570                 575

Gln Ile Asn Pro Gln Asn Pro Pro Lys Glu Ile Ala Glu Ile Leu Leu
            580                 585                 590

Lys Arg Lys Ala Asp Ser Ser Leu Ser Arg Lys Glu Thr Glu Leu
            595                 600                 605

Phe Ile Asp Tyr Leu Lys Asp Asp Phe Leu Val Asn Tyr Pro Met Ile
    610                 615                 620

Ile Asn Ser Asp Gly Glu Asn Phe Asn Phe His Phe Lys Gln Ala
625                 630                 635                 640

Lys Asp Tyr Gly Ser Leu Gln Glu Phe Phe Lys Glu Val Glu His Gln
                645                 650                 655
```

-continued

Ala Tyr Ser Leu Lys Thr Arg Pro Ile Asp Asp Ser Tyr Ile Tyr Arg
              660                 665                 670

Met Ile Asp Glu Gly Lys Leu Tyr Leu Phe Gln Ile His Asn Lys Asp
          675                 680                 685

Phe Ser Pro Tyr Ser Lys Gly Asn Leu Asn Leu His Thr Ile Tyr Leu
      690                 695                 700

Gln Met Leu Phe Asp Gln Arg Asn Leu Asn Asn Val Val Tyr Lys Leu
705                 710                 715                 720

Asn Gly Glu Ala Glu Val Phe Tyr Arg Pro Ala Ser Ile Asn Asp Glu
              725                 730                 735

Glu Val Ile Ile His Lys Ala Gly Glu Ile Lys Asn Lys Asn Ser
          740                 745                 750

Lys Arg Ala Val Asp Lys Pro Thr Ser Lys Phe Gly Tyr Asp Ile Ile
      755                 760                 765

Lys Asp Arg Arg Tyr Ser Lys Asp Lys Phe Met Leu His Ile Pro Val
770                 775                 780

Thr Met Asn Phe Gly Val Asp Glu Thr Arg Arg Phe Asn Asp Val Val
785                 790                 795                 800

Asn Asp Ala Leu Arg Asn Asp Glu Lys Val Arg Val Ile Gly Ile Asp
              805                 810                 815

Arg Gly Glu Arg Asn Leu Leu Tyr Val Val Val Asp Thr Asp Gly
          820                 825                 830

Thr Ile Leu Glu Gln Ile Ser Leu Asn Ser Ile Ile Asn Asn Glu Tyr
      835                 840                 845

Ser Ile Glu Thr Asp Tyr His Lys Leu Leu Asp Glu Lys Glu Gly Asp
850                 855                 860

Arg Asp Arg Ala Arg Lys Asn Trp Thr Thr Ile Glu Asn Ile Lys Glu
865                 870                 875                 880

Leu Lys Glu Gly Tyr Leu Ser Gln Val Val Asn Val Ile Ala Lys Leu
              885                 890                 895

Val Leu Lys Tyr Asn Ala Ile Ile Cys Leu Glu Asp Leu Asn Phe Gly
          900                 905                 910

Phe Lys Arg Gly Arg Gln Lys Val Glu Lys Gln Val Tyr Gln Lys Phe
      915                 920                 925

Glu Lys Met Leu Ile Asp Lys Leu Asn Tyr Leu Val Ile Asp Lys Ser
930                 935                 940

Arg Lys Gln Glu Lys Pro Glu Glu Phe Gly Gly Ala Leu Asn Ala Leu
945                 950                 955                 960

Gln Leu Thr Ser Lys Phe Thr Ser Phe Lys Asp Met Gly Lys Gln Thr
              965                 970                 975

Gly Ile Ile Tyr Tyr Val Pro Ala Tyr Leu Thr Ser Lys Ile Asp Pro
          980                 985                 990

Thr Thr Gly Phe Ala Asn Leu Phe Tyr Val Lys Tyr Glu Asn Val Glu
      995                 1000                1005

Lys Ala Lys Glu Phe Phe Ser Arg Phe Asp Ser Ile Ser Tyr Asn
      1010                1015                1020

Asn Glu Ser Gly Tyr Phe Glu Phe Ala Phe Asp Tyr Lys Lys Phe
      1025                1030                1035

Thr Asp Arg Ala Cys Gly Ala Arg Ser Gln Trp Thr Val Cys Thr
      1040                1045                1050

Tyr Gly Glu Arg Ile Ile Lys Tyr Arg Asn Ala Asp Lys Asn Asn
      1055                1060                1065

Ser Phe Asp Asp Lys Thr Ile Val Leu Ser Glu Glu Phe Lys Glu

-continued

```
                1070                1075                1080
Leu Phe Ser Ile Tyr Gly Ile Ser Tyr Glu Asp Gly Ala Glu Leu
        1085                1090                1095
Lys Asn Lys Ile Met Ser Val Asp Glu Ala Asp Phe Phe Arg Cys
        1100                1105                1110
Leu Thr Gly Leu Leu Gln Lys Thr Leu Gln Met Arg Asn Ser Ser
        1115                1120                1125
Asn Asp Gly Thr Arg Asp Tyr Ile Ile Ser Pro Ile Met Asn Asp
        1130                1135                1140
Arg Gly Glu Phe Phe Asn Ser Glu Ala Cys Asp Ala Ser Lys Pro
        1145                1150                1155
Lys Asp Ala Asp Ala Asn Gly Ala Phe Asn Ile Ala Arg Lys Gly
        1160                1165                1170
Leu Trp Val Leu Glu Gln Ile Arg Asn Thr Pro Ser Gly Asp Lys
        1175                1180                1185
Leu Asn Leu Ala Met Ser Asn Ala Glu Trp Leu Glu Tyr Ala Gln
        1190                1195                1200
Arg Asn Gln Ile
        1205

<210> SEQ ID NO 114
<211> LENGTH: 1247
<212> TYPE: PRT
<213> ORGANISM: Unknown
<220> FEATURE:
<223> OTHER INFORMATION: Prevotella bryantii B14

<400> SEQUENCE: 114

Met Lys Phe Thr Asp Phe Thr Gly Leu Tyr Ser Leu Ser Lys Thr Leu
1               5                   10                  15
Arg Phe Glu Leu Lys Pro Ile Gly Lys Thr Leu Glu Asn Ile Lys Lys
            20                  25                  30
Ala Gly Leu Leu Glu Gln Asp Gln His Arg Ala Asp Ser Tyr Lys Lys
        35                  40                  45
Val Lys Lys Ile Ile Asp Glu Tyr His Lys Ala Phe Ile Glu Lys Ser
    50                  55                  60
Leu Ser Asn Phe Glu Leu Lys Tyr Gln Ser Glu Asp Lys Leu Asp Ser
65                  70                  75                  80
Leu Glu Glu Tyr Leu Met Tyr Tyr Ser Met Lys Arg Ile Glu Lys Thr
                85                  90                  95
Glu Lys Asp Lys Phe Ala Lys Ile Gln Asp Asn Leu Arg Lys Gln Ile
            100                 105                 110
Ala Asp His Leu Lys Gly Asp Glu Ser Tyr Lys Thr Ile Phe Ser Lys
        115                 120                 125
Asp Leu Ile Arg Lys Asn Leu Pro Asp Phe Val Lys Ser Asp Glu Glu
    130                 135                 140
Arg Thr Leu Ile Lys Glu Phe Lys Asp Phe Thr Thr Tyr Phe Lys Gly
145                 150                 155                 160
Phe Tyr Glu Asn Arg Glu Asn Met Tyr Ser Ala Glu Asp Lys Ser Thr
                165                 170                 175
Ala Ile Ser His Arg Ile Ile His Glu Asn Leu Pro Lys Phe Val Asp
            180                 185                 190
Asn Ile Asn Ala Phe Ser Lys Ile Ile Leu Ile Pro Glu Leu Arg Glu
        195                 200                 205
Lys Leu Asn Gln Ile Tyr Gln Asp Phe Glu Glu Tyr Leu Asn Val Glu
```

```
                210                 215                 220
Ser Ile Asp Glu Ile Phe His Leu Asp Tyr Phe Ser Met Val Met Thr
225                 230                 235                 240

Gln Lys Gln Ile Glu Val Tyr Asn Ala Ile Gly Gly Lys Ser Thr
                245                 250                 255

Asn Asp Lys Lys Ile Gln Gly Leu Asn Glu Tyr Ile Asn Leu Tyr Asn
                260                 265                 270

Gln Lys His Lys Asp Cys Lys Leu Pro Lys Leu Lys Leu Leu Phe Lys
                275                 280                 285

Gln Ile Leu Ser Asp Arg Ile Ala Ile Ser Trp Leu Pro Asp Asn Phe
290                 295                 300

Lys Asp Asp Gln Glu Ala Leu Asp Ser Ile Asp Thr Cys Tyr Lys Asn
305                 310                 315                 320

Leu Leu Asn Asp Gly Asn Val Leu Gly Glu Gly Asn Leu Lys Leu Leu
                325                 330                 335

Leu Glu Asn Ile Asp Thr Tyr Asn Leu Lys Gly Ile Phe Ile Arg Asn
                340                 345                 350

Asp Leu Gln Leu Thr Asp Ile Ser Gln Lys Met Tyr Ala Ser Trp Asn
                355                 360                 365

Val Ile Gln Asp Ala Val Ile Leu Asp Leu Lys Lys Gln Val Ser Arg
                370                 375                 380

Lys Lys Lys Glu Ser Ala Glu Asp Tyr Asn Asp Arg Leu Lys Lys Leu
385                 390                 395                 400

Tyr Thr Ser Gln Glu Ser Phe Ser Ile Gln Tyr Leu Asn Asp Cys Leu
                405                 410                 415

Arg Ala Tyr Gly Lys Thr Glu Asn Ile Gln Asp Tyr Phe Ala Lys Leu
                420                 425                 430

Gly Ala Val Asn Asn Glu His Glu Gln Thr Ile Asn Leu Phe Ala Gln
                435                 440                 445

Val Arg Asn Ala Tyr Thr Ser Val Gln Ala Ile Leu Thr Thr Pro Tyr
                450                 455                 460

Pro Glu Asn Ala Asn Leu Ala Gln Asp Lys Glu Thr Val Ala Leu Ile
465                 470                 475                 480

Lys Asn Leu Leu Asp Ser Leu Lys Arg Leu Gln Arg Phe Ile Lys Pro
                485                 490                 495

Leu Leu Gly Lys Gly Asp Glu Ser Asp Lys Asp Glu Arg Phe Tyr Gly
                500                 505                 510

Asp Phe Thr Pro Leu Trp Glu Thr Leu Asn Gln Ile Thr Pro Leu Tyr
                515                 520                 525

Asn Met Val Arg Asn Tyr Met Thr Arg Lys Pro Tyr Ser Gln Glu Lys
                530                 535                 540

Ile Lys Leu Asn Phe Glu Asn Ser Thr Leu Leu Gly Gly Trp Asp Leu
545                 550                 555                 560

Asn Lys Glu His Asp Asn Thr Ala Ile Ile Leu Arg Lys Asn Gly Leu
                565                 570                 575

Tyr Tyr Leu Ala Ile Met Lys Lys Ser Ala Asn Lys Ile Phe Asp Lys
                580                 585                 590

Asp Lys Leu Asp Asn Ser Gly Asp Cys Tyr Glu Lys Met Val Tyr Lys
                595                 600                 605

Leu Leu Pro Gly Ala Asn Lys Met Leu Pro Lys Val Phe Phe Ser Lys
                610                 615                 620

Ser Arg Ile Asp Glu Phe Lys Pro Ser Glu Asn Ile Ile Glu Asn Tyr
625                 630                 635                 640
```

-continued

Lys Lys Gly Thr His Lys Lys Gly Ala Asn Phe Asn Leu Ala Asp Cys
                    645                 650                 655

His Asn Leu Ile Asp Phe Phe Lys Ser Ile Ser Lys His Glu Asp
                660                 665                 670

Trp Ser Lys Phe Asn Phe His Phe Ser Asp Thr Ser Ser Tyr Glu Asp
            675                 680                 685

Leu Ser Asp Phe Tyr Arg Glu Val Glu Gln Gln Gly Tyr Ser Ile Ser
        690                 695                 700

Phe Cys Asp Val Ser Val Glu Tyr Ile Asn Lys Met Val Glu Lys Gly
705                 710                 715                 720

Asp Leu Tyr Leu Phe Gln Ile Tyr Asn Lys Asp Phe Ser Glu Phe Ser
                725                 730                 735

Lys Gly Thr Pro Asn Met His Thr Leu Tyr Trp Asn Ser Leu Phe Ser
                740                 745                 750

Lys Glu Asn Leu Asn Asn Ile Ile Tyr Lys Leu Asn Gly Gln Ala Glu
                755                 760                 765

Ile Phe Phe Arg Lys Lys Ser Leu Asn Tyr Lys Arg Pro Thr His Pro
770                 775                 780

Ala His Gln Ala Ile Lys Asn Lys Asn Lys Cys Asn Glu Lys Lys Glu
785                 790                 795                 800

Ser Ile Phe Asp Tyr Asp Leu Val Lys Asp Lys Arg Tyr Thr Val Asp
                805                 810                 815

Lys Phe Gln Phe His Val Pro Ile Thr Met Asn Phe Lys Ser Thr Gly
                820                 825                 830

Asn Thr Asn Ile Asn Gln Gln Val Ile Asp Tyr Leu Arg Thr Glu Asp
            835                 840                 845

Asp Thr His Ile Ile Gly Ile Asp Arg Gly Glu Arg His Leu Leu Tyr
            850                 855                 860

Leu Val Val Ile Asp Ser His Gly Lys Ile Val Glu Gln Phe Thr Leu
865                 870                 875                 880

Asn Glu Ile Val Asn Glu Tyr Gly Gly Asn Ile Tyr Arg Thr Asn Tyr
                885                 890                 895

His Asp Leu Leu Asp Thr Arg Glu Gln Asn Arg Glu Lys Ala Arg Glu
                900                 905                 910

Ser Trp Gln Thr Ile Glu Asn Ile Lys Glu Leu Lys Glu Gly Tyr Ile
            915                 920                 925

Ser Gln Val Ile His Lys Ile Thr Asp Leu Met Gln Lys Tyr His Ala
        930                 935                 940

Val Val Val Leu Glu Asp Leu Asn Met Gly Phe Met Arg Gly Arg Gln
945                 950                 955                 960

Lys Val Glu Lys Gln Val Tyr Gln Lys Phe Glu Glu Met Leu Ile Asn
                965                 970                 975

Lys Leu Asn Tyr Leu Val Asn Lys Lys Ala Asp Gln Asn Ser Ala Gly
                980                 985                 990

Gly Leu Leu His Ala Tyr Gln Leu Thr Ser Lys Phe Glu Ser Phe Gln
            995                 1000                1005

Lys Leu Gly Lys Gln Ser Gly Phe Leu Phe Tyr Ile Pro Ala Trp
        1010                1015                1020

Asn Thr Ser Lys Ile Asp Pro Val Thr Gly Phe Val Asn Leu Phe
        1025                1030                1035

Asp Thr Arg Tyr Glu Ser Ile Asp Lys Ala Lys Ala Phe Phe Gly
        1040                1045                1050

```
Lys Phe Asp Ser Ile Arg Tyr Asn Ala Asp Lys Asp Trp Phe Glu
    1055                1060                1065

Phe Ala Phe Asp Tyr Asn Asn Phe Thr Thr Lys Ala Glu Gly Thr
    1070                1075                1080

Arg Thr Asn Trp Thr Ile Cys Thr Tyr Gly Ser Arg Ile Arg Thr
    1085                1090                1095

Phe Arg Asn Gln Ala Lys Asn Ser Gln Trp Asp Asn Glu Glu Ile
    1100                1105                1110

Asp Leu Thr Lys Ala Tyr Lys Ala Phe Phe Ala Lys His Gly Ile
    1115                1120                1125

Asn Ile Tyr Asp Asn Ile Lys Glu Ala Ile Ala Met Glu Thr Glu
    1130                1135                1140

Lys Ser Phe Phe Glu Asp Leu Leu His Leu Leu Lys Leu Thr Leu
    1145                1150                1155

Gln Met Arg Asn Ser Ile Thr Gly Thr Thr Thr Asp Tyr Leu Ile
    1160                1165                1170

Ser Pro Val His Asp Ser Lys Gly Asn Phe Tyr Asp Ser Arg Ile
    1175                1180                1185

Cys Asp Asn Ser Leu Pro Ala Asn Ala Asp Ala Asn Gly Ala Tyr
    1190                1195                1200

Asn Ile Ala Arg Lys Gly Leu Met Leu Ile Gln Gln Ile Lys Asp
    1205                1210                1215

Ser Thr Ser Ser Asn Arg Phe Lys Phe Ser Pro Ile Thr Asn Lys
    1220                1225                1230

Asp Trp Leu Ile Phe Ala Gln Glu Lys Pro Tyr Leu Asn Asp
    1235                1240                1245

<210> SEQ ID NO 115
<211> LENGTH: 1064
<212> TYPE: PRT
<213> ORGANISM: Unknown
<220> FEATURE:
<223> OTHER INFORMATION: Smithella sp. SCADC

<400> SEQUENCE: 115

Met Glu Lys Tyr Lys Ile Thr Lys Thr Ile Arg Phe Lys Leu Leu Pro
1               5                   10                  15

Asp Lys Ile Gln Asp Ile Ser Arg Gln Val Ala Val Leu Gln Asn Ser
            20                  25                  30

Thr Asn Ala Glu Lys Lys Asn Asn Leu Leu Arg Leu Val Gln Arg Gly
        35                  40                  45

Gln Glu Leu Pro Lys Leu Leu Asn Glu Tyr Ile Arg Tyr Ser Asp Asn
    50                  55                  60

His Lys Leu Lys Ser Asn Val Thr Val His Phe Arg Trp Leu Arg Leu
65                  70                  75                  80

Phe Thr Lys Asp Leu Phe Tyr Asn Trp Lys Lys Asp Asn Thr Glu Lys
                85                  90                  95

Lys Ile Lys Ile Ser Asp Val Val Tyr Leu Ser His Val Phe Glu Ala
            100                 105                 110

Phe Leu Lys Glu Trp Glu Ser Thr Ile Glu Arg Val Asn Ala Asp Cys
        115                 120                 125

Asn Lys Pro Glu Glu Ser Lys Thr Arg Asp Ala Glu Ile Ala Leu Ser
    130                 135                 140

Ile Arg Lys Leu Gly Ile Lys His Gln Leu Pro Phe Ile Lys Gly Phe
145                 150                 155                 160
```

Val Asp Asn Ser Asn Asp Lys Asn Ser Glu Asp Thr Lys Ser Lys Leu
              165                 170                 175

Thr Ala Leu Leu Ser Glu Phe Glu Ala Val Leu Lys Ile Cys Glu Gln
        180                 185                 190

Asn Tyr Leu Pro Ser Gln Ser Ser Gly Ile Ala Ile Ala Lys Ala Ser
            195                 200                 205

Phe Asn Tyr Tyr Thr Ile Asn Lys Lys Gln Lys Asp Phe Glu Ala Glu
    210                 215                 220

Ile Val Ala Leu Lys Lys Gln Leu His Ala Arg Tyr Gly Asn Lys Lys
225                 230                 235                 240

Tyr Asp Gln Leu Leu Arg Glu Leu Asn Leu Ile Pro Leu Lys Glu Leu
                245                 250                 255

Pro Leu Lys Glu Leu Pro Leu Ile Glu Phe Tyr Ser Glu Ile Lys Lys
            260                 265                 270

Arg Lys Ser Thr Lys Lys Ser Glu Phe Leu Glu Ala Val Ser Asn Gly
        275                 280                 285

Leu Val Phe Asp Asp Leu Lys Ser Lys Phe Pro Leu Phe Gln Thr Glu
    290                 295                 300

Ser Asn Lys Tyr Asp Glu Tyr Leu Lys Leu Ser Asn Lys Ile Thr Gln
305                 310                 315                 320

Lys Ser Thr Ala Lys Ser Leu Leu Ser Lys Asp Ser Pro Glu Ala Gln
                325                 330                 335

Lys Leu Gln Thr Glu Ile Thr Lys Leu Lys Lys Asn Arg Gly Glu Tyr
            340                 345                 350

Phe Lys Lys Ala Phe Gly Lys Tyr Val Gln Leu Cys Glu Leu Tyr Lys
    355                 360                 365

Glu Ile Ala Gly Lys Arg Gly Lys Leu Lys Gly Gln Ile Lys Gly Ile
370                 375                 380

Glu Asn Glu Arg Ile Asp Ser Gln Arg Leu Gln Tyr Trp Ala Leu Val
385                 390                 395                 400

Leu Glu Asp Asn Leu Lys His Ser Leu Ile Leu Ile Pro Lys Glu Lys
                405                 410                 415

Thr Asn Glu Leu Tyr Arg Lys Val Trp Gly Ala Lys Asp Asp Gly Ala
            420                 425                 430

Ser Ser Ser Ser Ser Ser Thr Leu Tyr Tyr Phe Glu Ser Met Thr Tyr
    435                 440                 445

Arg Ala Leu Arg Lys Leu Cys Phe Gly Ile Asn Gly Asn Thr Phe Leu
        450                 455                 460

Pro Glu Ile Gln Lys Glu Leu Pro Gln Tyr Asn Gln Lys Glu Phe Gly
465                 470                 475                 480

Glu Phe Cys Phe His Lys Ser Asn Asp Lys Glu Ile Asp Glu Pro
                485                 490                 495

Lys Leu Ile Ser Phe Tyr Gln Ser Val Leu Lys Thr Asp Phe Val Lys
            500                 505                 510

Asn Thr Leu Ala Leu Pro Gln Ser Val Phe Asn Glu Val Ala Ile Gln
        515                 520                 525

Ser Phe Glu Thr Arg Gln Asp Phe Gln Ile Ala Leu Glu Lys Cys Cys
    530                 535                 540

Tyr Ala Lys Lys Gln Ile Ile Ser Glu Ser Leu Lys Lys Glu Ile Leu
545                 550                 555                 560

Glu Asn Tyr Asn Thr Gln Ile Phe Lys Ile Thr Ser Leu Asp Leu Gln
                565                 570                 575

Arg Ser Glu Gln Lys Asn Leu Lys Gly His Thr Arg Ile Trp Asn Arg

-continued

```
            580             585             590
Phe Trp Thr Lys Gln Asn Glu Glu Ile Asn Tyr Asn Leu Arg Leu Asn
            595             600             605

Pro Glu Ile Ala Ile Val Trp Arg Lys Ala Lys Lys Thr Arg Ile Glu
            610             615             620

Lys Tyr Gly Glu Arg Ser Val Leu Tyr Glu Pro Lys Arg Asn Arg
625             630             635             640

Tyr Leu His Glu Gln Tyr Thr Leu Cys Thr Thr Val Thr Asp Asn Ala
            645             650             655

Leu Asn Asn Glu Ile Thr Phe Ala Phe Glu Asp Thr Lys Lys Lys Gly
            660             665             670

Thr Glu Ile Val Lys Tyr Asn Glu Lys Ile Asn Gln Thr Leu Lys Lys
            675             680             685

Glu Phe Asn Lys Asn Gln Leu Trp Phe Tyr Gly Ile Asp Ala Gly Glu
            690             695             700

Ile Glu Leu Ala Thr Leu Ala Leu Met Asn Lys Asp Lys Glu Pro Gln
705             710             715             720

Leu Phe Thr Val Tyr Glu Leu Lys Lys Leu Asp Phe Lys His Gly
            725             730             735

Tyr Ile Tyr Asn Lys Glu Arg Glu Leu Val Ile Arg Glu Lys Pro Tyr
            740             745             750

Lys Ala Ile Gln Asn Leu Ser Tyr Phe Leu Asn Glu Glu Leu Tyr Glu
            755             760             765

Lys Thr Phe Arg Asp Gly Lys Phe Asn Glu Thr Tyr Asn Glu Leu Phe
            770             775             780

Lys Glu Lys His Val Ser Ala Ile Asp Leu Thr Thr Ala Lys Val Ile
785             790             795             800

Asn Gly Lys Ile Ile Leu Asn Gly Asp Met Ile Thr Phe Leu Asn Leu
            805             810             815

Arg Ile Leu His Ala Gln Arg Lys Ile Tyr Glu Glu Leu Ile Glu Asn
            820             825             830

Pro His Ala Glu Leu Lys Glu Lys Asp Tyr Lys Leu Tyr Phe Glu Ile
            835             840             845

Glu Gly Lys Asp Lys Asp Ile Tyr Ile Ser Arg Leu Asp Phe Glu Tyr
            850             855             860

Ile Lys Pro Tyr Gln Glu Ile Ser Asn Tyr Leu Phe Ala Tyr Phe Ala
865             870             875             880

Ser Gln Gln Ile Asn Glu Ala Arg Glu Glu Gln Ile Asn Gln Thr
            885             890             895

Lys Arg Ala Leu Ala Gly Asn Met Ile Gly Val Ile Tyr Tyr Leu Tyr
            900             905             910

Gln Lys Tyr Arg Gly Ile Ile Ser Ile Glu Asp Leu Lys Gln Thr Lys
            915             920             925

Val Glu Ser Asp Arg Asn Lys Phe Glu Gly Asn Ile Glu Arg Pro Leu
            930             935             940

Glu Trp Ala Leu Tyr Arg Lys Phe Gln Gln Glu Gly Tyr Val Pro Pro
945             950             955             960

Ile Ser Glu Leu Ile Lys Leu Arg Glu Leu Glu Lys Phe Pro Leu Lys
            965             970             975

Asp Val Lys Gln Pro Lys Tyr Glu Asn Ile Gln Gln Phe Gly Ile Ile
            980             985             990

Lys Phe Val Ser Pro Glu Glu Thr Ser Thr Thr Cys Pro Lys Cys Leu
            995            1000            1005
```

```
Arg Arg Phe Lys Asp Tyr Asp Lys Asn Lys Gln Glu Gly Phe Cys
    1010                1015                1020

Lys Cys Gln Cys Gly Phe Asp Thr Arg Asn Asp Leu Lys Gly Phe
    1025                1030                1035

Glu Gly Leu Asn Asp Pro Asp Lys Val Ala Ala Phe Asn Ile Ala
    1040                1045                1050

Lys Arg Gly Phe Glu Asp Leu Gln Lys Tyr Lys
    1055                1060

<210> SEQ ID NO 116
<211> LENGTH: 1251
<212> TYPE: PRT
<213> ORGANISM: Unknown
<220> FEATURE:
<223> OTHER INFORMATION: Bacteroidetes bacterium GWF2_33_38

<400> SEQUENCE: 116

Met Asn His Met Lys Gln Phe Thr Asn Gln Phe Ser Leu Ser Lys Thr
1               5                   10                  15

Leu Arg Phe Glu Leu Ile Pro Gln Gly Lys Thr Lys Glu Phe Ile Glu
            20                  25                  30

Ile Asn Gly Leu Ile Glu Lys Asp Asn Glu Arg Ala Val Ser Tyr Lys
        35                  40                  45

Lys Val Lys Lys Ile Ile Asp Glu Tyr His Lys Tyr Phe Ile Glu Met
50                  55                  60

Val Leu Cys Asp Phe Lys Leu His Gly Leu Thr Tyr Glu Thr Ile
65                  70                  75              80

Phe Asn Lys Lys Glu Lys Asp Thr Asp Lys Lys Glu Phe Asp Asn
                85                  90                  95

Ile Arg Asn Ser Leu Arg Lys Gln Ile Ala Asp Ala Phe Ala Lys Asn
            100                 105                 110

Pro Asn Asp Glu Ile Lys Glu Arg Phe Lys Asn Leu Phe Ala Lys Glu
        115                 120                 125

Leu Ile Lys Gln Asp Leu Leu Asn Phe Val Asp Glu Gln Lys Glu
130                 135                 140

Leu Val Asn Glu Phe Lys Asp Phe Thr Thr Tyr Phe Thr Gly Phe His
145                 150                 155                 160

Gln Asn Arg Arg Asn Met Tyr Val Ala Asp Glu Lys Ala Thr Ala Ile
                165                 170                 175

Ala Tyr Arg Leu Val Asn Glu Asn Leu Pro Lys Phe Ile Asp Asn Leu
            180                 185                 190

Lys Ile Tyr Glu Lys Ile Lys Lys Asp Ala Pro Glu Leu Ile Ser Asp
        195                 200                 205

Leu Asn Lys Thr Leu Val Glu Met Glu Glu Ile Val Gln Gly Lys Thr
210                 215                 220

Leu Asp Glu Ile Phe Ser Leu Ser Phe Phe Asn Gln Thr Leu Thr Gln
225                 230                 235                 240

Thr Gly Ile Glu Leu Tyr Asn Ile Val Ile Gly Gly Arg Thr Ala Asp
                245                 250                 255

Glu Gly Lys Thr Lys Ile Lys Gly Leu Asn Glu Tyr Ile Asn Thr Asp
            260                 265                 270

Tyr Asn Gln Lys Gln Thr Asp Lys Lys Lys Gln Ala Lys Phe Lys
        275                 280                 285

Gln Leu Tyr Lys Gln Ile Leu Ser Asp Arg His Ser Val Ser Phe Val
290                 295                 300
```

```
Ala Glu Thr Phe Glu Thr Asp Ala Gln Leu Leu Glu Asn Ile Glu Gln
305                 310                 315                 320

Phe Tyr Ser Ser Val Leu Cys Asn Tyr Glu Asp Asp Gly His Thr Thr
            325                 330                 335

Asn Ile Phe Glu Ala Ile Lys Asn Leu Ile Ile Gly Leu Lys Thr Phe
            340                 345                 350

Asp Leu Ser Lys Ile Tyr Leu Arg Asn Asp Thr Ser Leu Thr Asp Ile
            355                 360                 365

Ser Gln Lys Leu Phe Gly Asp Trp Ser Ile Ile Ser Ser Ala Leu Asn
370                 375                 380

Asp Tyr Tyr Glu Lys Gln Asn Pro Ile Ser Ser Lys Glu Lys Gln Glu
385                 390                 395                 400

Lys Tyr Asp Glu Arg Lys Ala Lys Trp Leu Lys Gln Asp Phe Asn Ile
                405                 410                 415

Glu Thr Ile Gln Thr Ala Leu Asn Glu Cys Asp Ser Glu Ile Ile Lys
            420                 425                 430

Glu Lys Asn Asn Lys Asn Ile Val Ser Glu Tyr Phe Ala Lys Leu Gly
            435                 440                 445

Leu Asp Lys Asp Asn Lys Ile Asp Leu Leu Gln Lys Ile His His Asn
450                 455                 460

Tyr Val Val Ile Lys Asp Leu Leu Asn Glu Pro Tyr Pro Glu Asn Ile
465                 470                 475                 480

Lys Leu Gly Asn Gln Lys Glu Gln Val Ser Gln Ile Lys Asp Phe Leu
                485                 490                 495

Asp Ser Ile Leu Asn Leu Ile His Phe Leu Lys Pro Leu Ser Leu Lys
            500                 505                 510

Asp Lys Asp Lys Glu Lys Asp Glu Leu Phe Tyr Ser Leu Phe Thr Ala
            515                 520                 525

Leu Phe Glu His Leu Ser Gln Thr Ile Ser Ile Tyr Asn Lys Val Arg
530                 535                 540

Asn Tyr Leu Thr Gln Lys Ala Tyr Ser Thr Glu Lys Ile Lys Leu Asn
545                 550                 555                 560

Phe Glu Asn Ser Thr Leu Leu Asn Gly Trp Asp Val Asn Lys Glu Pro
                565                 570                 575

Val Asn Thr Ser Val Ile Phe Arg Lys Asn Gly Leu Phe Tyr Leu Gly
            580                 585                 590

Ile Met Ser Lys Ser Asn Asn Arg Ile Phe Glu Arg Asn Val Pro Val
            595                 600                 605

Cys Lys Asn Glu Glu Thr Ala Phe Glu Lys Met Asn Tyr Lys Leu Leu
            610                 615                 620

Pro Gly Ala Asn Lys Met Leu Pro Lys Val Phe Leu Ser Ala Lys Gly
625                 630                 635                 640

Ile Glu Ser Phe Gln Pro Ser Ala Glu Ile Gln Ser Lys Tyr Gln Lys
                645                 650                 655

Glu Thr His Lys Lys Gly Asp Ala Phe Val Arg Lys Asp Met Glu Asn
            660                 665                 670

Leu Ile Asp Phe Phe Lys Gln Ser Ile Ala Lys His Thr Asp Trp Lys
            675                 680                 685

His Phe Asn His Gln Phe Ser Lys Thr Glu Thr Tyr Asn Asp Leu Ser
            690                 695                 700

Glu Phe Tyr Lys Glu Val Glu Lys Gln Gly Tyr Lys Leu Thr Phe Thr
705                 710                 715                 720
```

```
Lys Leu Asp Glu Thr Tyr Ile Asn Gln Leu Val Asp Glu Gly Lys Leu
                725                 730                 735

Tyr Leu Phe Gln Ile Tyr Asn Lys Asp Phe Ser Pro Phe Ser Lys Gly
        740                 745                 750

Lys Pro Asn Met His Thr Leu Tyr Trp Lys Met Leu Phe Asp Glu Gln
        755                 760                 765

Asn Leu Gln Asn Val Val Tyr Lys Leu Asn Gly Glu Ala Glu Val Phe
        770                 775                 780

Phe Arg Gln Ser Ser Ile Lys Gln Thr Asp Arg Ile Ile His Lys Ala
785                 790                 795                 800

Asn Gln Ala Ile Asp Asn Lys Asn Pro Leu Asn Asn Lys Lys Gln Ser
                805                 810                 815

Ser Phe Asn Tyr Asp Leu Ile Lys Asp Lys Arg Phe Thr Leu Asp Lys
            820                 825                 830

Phe Gln Phe His Val Pro Ile Thr Leu Asn Phe Lys Ala Glu Gly Asn
        835                 840                 845

Glu Tyr Leu Asn Thr Lys Val Asn Glu Tyr Leu Lys Ser Asn Ser Asp
        850                 855                 860

Val Lys Ile Ile Gly Leu Asp Arg Gly Glu Arg His Leu Ile Tyr Leu
865                 870                 875                 880

Thr Leu Ile Asn Gln Lys Gly Glu Leu Leu Lys Gln Gln Ser Leu Asn
                885                 890                 895

Val Ile Ala Thr Ser Gln Glu His Glu Thr Asp Tyr Lys Asn Leu Leu
            900                 905                 910

Val Asn Lys Glu Asn Glu Arg Ala Asn Ala Arg Gln Asp Trp Lys Thr
        915                 920                 925

Ile Glu Thr Ile Lys Glu Leu Lys Glu Gly Tyr Leu Ser Gln Val Val
        930                 935                 940

His Gln Ile Ala Thr Met Met Val Asp Glu Asn Ala Ile Val Val Met
945                 950                 955                 960

Glu Asp Leu Asn Ala Gly Phe Met Arg Gly Arg Gln Lys Val Glu Arg
                965                 970                 975

Gln Val Tyr Gln Lys Leu Glu Lys Met Leu Ile Glu Lys Leu Asn Tyr
            980                 985                 990

Leu Val Phe Lys Asn Asn Asp Val Asn Glu Thr Ala Gly Val Leu Asn
        995                 1000                1005

Ala Leu Gln Leu Thr Asn Lys Phe Glu Ser Phe Glu Lys Met Gly
        1010                1015                1020

Lys Gln Ser Gly Phe Leu Phe Tyr Val Pro Ala Trp Asn Thr Ser
        1025                1030                1035

Lys Ile Asp Pro Ala Thr Gly Phe Val Asp Phe Leu Lys Pro Lys
        1040                1045                1050

Tyr Glu Ser Val Glu Lys Ala Lys Leu Phe Phe Glu Lys Phe Glu
        1055                1060                1065

Ser Ile Lys Phe Asn Ala Asp Lys Asn Tyr Phe Glu Phe Glu Phe
        1070                1075                1080

Asp Tyr Lys Lys Phe Thr Glu Lys Ala Glu Gly Ser Gln Thr Lys
        1085                1090                1095

Trp Thr Val Cys Thr His Ser Asp Val Arg Tyr Arg Tyr Asn Pro
        1100                1105                1110

Gln Thr Lys Ala Ser Asp Glu Val Asn Val Thr Asn Glu Leu Lys
        1115                1120                1125

Leu Ile Phe Asp Lys Phe Lys Ile Glu Tyr Lys Asn Gly Lys Asn
```

-continued

```
            1130                1135                1140

Leu Lys Thr Glu Leu Leu Leu Gln Asp Asp Lys Gln Leu Phe Ser
    1145                1150                1155

Lys Leu Leu His Tyr Leu Ala Leu Thr Leu Met Leu Arg Gln Ser
    1160                1165                1170

Lys Ser Gly Thr Asp Ile Asp Phe Ile Leu Ser Pro Val Ala Lys
    1175                1180                1185

Asn Gly Val Phe Tyr Asp Ser Arg Asn Ala Met Pro Asn Leu Pro
    1190                1195                1200

Lys Asp Ala Asp Ala Asn Gly Ala Phe His Ile Ala Leu Lys Gly
    1205                1210                1215

Leu Trp Cys Val Gln Gln Ile Lys Lys Ala Asp Asp Leu Lys Lys
    1220                1225                1230

Ile Lys Leu Ala Ile Ser Asn Lys Glu Trp Leu Ser Phe Val Gln
    1235                1240                1245

Asn Leu Lys
    1250

<210> SEQ ID NO 117
<211> LENGTH: 1353
<212> TYPE: PRT
<213> ORGANISM: Unknown
<220> FEATURE:
<223> OTHER INFORMATION: Candidatus Peribacteria bacterium RIFCSPLOWO2

<400> SEQUENCE: 117

Met Ala Asn Asp Ile Tyr Ala Gln Phe Thr Arg Lys Tyr Ala Leu Ser
1               5                   10                  15

Lys Thr Leu Arg Phe Glu Leu Lys Pro Val Gly Lys Thr Leu Asp Asn
                20                  25                  30

Met Arg Lys His Leu Glu Tyr Asp Pro Glu Leu Arg Thr Phe Leu Lys
            35                  40                  45

Asp Gln Cys Ile Glu Asp Ala Tyr Gln Ala Leu Lys Pro Lys Val Asp
        50                  55                  60

Glu Leu His Gln Arg Phe Ile Asn Leu Ala Leu Gly Ser Ala Arg Ala
65                  70                  75                  80

Lys Ser Met Glu Phe Ser Pro Phe Phe Glu Ile Arg Arg Gln Leu Leu
                85                  90                  95

Glu Leu Lys Met Lys Ala Lys Glu Lys Gly Val Gly Asp Lys Asp Ile
                100                 105                 110

Gln Asn Leu Glu Gly Glu Leu Asp Gly Ala Gly Glu Thr Leu Arg Lys
            115                 120                 125

Ala Phe Gly Asp Ile Phe Lys Asp Ala Gly Ala Arg Trp Lys Glu Leu
        130                 135                 140

Tyr Gly Ala Tyr Gly Trp Lys Lys Gly Lys Glu Thr Lys Gly Ser
145                 150                 155                 160

Ala Val Leu Ser Cys Pro Asp Val Leu Lys Val Ile Asp Glu Asn
                165                 170                 175

Glu Lys Lys Glu Leu Pro Glu Gln Cys Val Arg Asp Ala Ile Lys Ala
                180                 185                 190

Leu Glu Gly Phe Phe Thr Tyr Leu Gly Gly Phe Asn Gln Asn Arg Glu
            195                 200                 205

Asn Tyr Tyr Glu Thr Ala Lys Glu Ala Ala Thr Ala Ile Ala Thr Arg
        210                 215                 220

Ile Val His Glu Asn Leu Pro Arg Phe Thr Asp Asn Ala Leu Thr Phe
```

```
            225                 230                 235                 240
Glu Ser Gly Asn Lys Glu Tyr Leu Asp Ala Tyr Arg Phe Leu Lys Asp
                245                 250                 255

Ala Gly Lys Val Ile Gln Arg Lys Asp Glu Lys Pro Val Thr Pro Ile
                260                 265                 270

Ser Glu Ala Ile Phe Cys Gln Asn Tyr Phe Gly Asn Cys Leu Thr Gln
                275                 280                 285

Glu Glu Ile Glu Arg Tyr Asn Glu Glu Ile Gly Asn Cys Asn Leu Val
            290                 295                 300

Ile Asn Leu Tyr Asn Gln Thr Glu Asp Glu Glu Gly Phe Arg Arg Leu
305                 310                 315                 320

Pro Ile Phe Lys Val Leu Tyr Lys Gln Ile Gly Cys Gly Lys Lys Asp
                325                 330                 335

Ala Leu Phe Phe Arg Leu Thr His Glu Lys Lys Glu Asp Ala Asp Ala
                340                 345                 350

Ala Arg Arg Glu Asn Pro Asn Lys Gln Phe Asp Ser Val Glu Glu Ile
            355                 360                 365

Leu Glu Arg Ala Arg Thr Ala Gly Glu Lys Tyr Phe Gln Pro Asn Lys
    370                 375                 380

Thr Ala Asp Met Asp Thr Leu Ser Glu Phe Ile Arg Tyr Leu Lys Glu
385                 390                 395                 400

Arg Lys Asp Tyr Ser Gly Phe Tyr Trp Ser Lys Asn Ala Leu Asn Thr
                405                 410                 415

Ile Ser Asn Lys Tyr Phe Ala Asn Trp His Ala Leu Lys Asp Arg Leu
                420                 425                 430

Lys Glu Thr Gly Val Phe Lys Lys Gly Gly Lys Asp Asp Glu Glu Tyr
            435                 440                 445

Val Lys Ile Pro Asp Ala Ile Glu Leu Gln Pro Phe Phe Glu Leu Leu
            450                 455                 460

Asp Val Thr Lys Asp Trp Arg Lys Thr Leu Phe Lys Leu Ser Gln Arg
465                 470                 475                 480

Asn Gly Ser Glu Glu Ile Glu Lys Met Arg Ile Ile Asp Asn Ala Lys
                485                 490                 495

Thr Pro His Glu Ala Leu Leu Gly Met Leu Thr Leu Asp Val Ala Asp
                500                 505                 510

Arg Ala Glu Lys Phe Val Asn Gly Ala Ala Gly Val Met Arg Val Thr
            515                 520                 525

Arg Glu Tyr Phe Ala Asn Ala Asp Lys Met Lys Glu Glu Arg Arg Arg
            530                 535                 540

Val Trp Lys Glu Glu Ile Lys Gln Trp Met Asp His Ala Leu Ala Val
545                 550                 555                 560

Asn Arg Met Leu Lys Tyr Phe Lys Val Arg Glu Ser Lys Val Lys Gly
                565                 570                 575

Ala Pro Ile Asp Ala Thr Leu Thr Lys Ala Leu Gly Ile Leu Leu Tyr
                580                 585                 590

Gly Lys Asp Gly Asp Ala Glu Trp Phe Lys Trp Tyr Asp Thr Leu Arg
            595                 600                 605

Asn Phe Leu Thr Lys Lys Pro Gln Asp Asp Ala Lys Glu Asn Lys Leu
            610                 615                 620

Lys Leu Asn Phe Glu Asn Gly Ser Leu Leu Gly Gly Trp Ser Asp Gly
625                 630                 635                 640

Gln Glu Lys Asn Lys Ala Ala Val Leu Leu Arg Lys Asp Gly Leu Tyr
                645                 650                 655
```

-continued

Tyr Leu Gly Ile Leu Lys Lys Lys Ser Leu Phe Asp Thr Lys Gln Glu
                660             665             670

Asn Asn Pro Met Tyr Glu His Phe Thr Gln Gly Cys Glu Arg Leu Ile
            675             680             685

Leu Thr Asn Leu Lys Phe Gln Thr Leu Ala Gly Lys Gly Phe Ser Arg
        690             695             700

Lys Phe Arg Ile Ala Tyr Gly Ala Met Gly Lys Gln Asp Pro Gln Lys
705             710             715             720

Ala Ile Ile Ser Leu Gln Asp Ile Met Lys Glu Arg Tyr Leu Asn Lys
                725             730             735

Tyr Pro Leu Leu Ser Pro Ile Ala Ser Ala Ser Tyr Thr Asp Lys Lys
            740             745             750

Lys Phe Asp Lys Glu Val Gln Glu Ala Leu Lys Glu Ser Tyr Asp Cys
        755             760             765

Lys Phe Arg Lys Ile Asn Trp Asn Glu Ile Glu Gln Tyr Thr Lys Ser
        770             775             780

Gly Asp Met Tyr Leu Phe Gln Ile His Ser Lys Asp Phe Ala Pro Gly
785             790             795             800

Ala Ser Gly Lys Lys Asp Leu Gln Thr Ile Tyr Trp Gln Ser Leu Phe
                805             810             815

Asp Ser Asn Gly Ser His Gln Leu Asn Gly Gly Glu Ile Phe Tyr
            820             825             830

Arg Lys Gln Ala Leu Arg Asp Lys His Val Lys Lys Gly Tyr Glu Gln
        835             840             845

Lys Pro Trp Ile Ile Glu Ser Arg Arg Phe Thr Leu Glu Ser Gly Lys
850             855             860

Phe Met Phe His Cys Pro Ile Lys Leu Asn Tyr Lys Ser Ser Ala Gln
865             870             875             880

Ser Asp Pro Lys Tyr Ala Phe Pro Phe Val Asn Lys Tyr Ile Asn Glu
            885             890             895

His Phe Ala Gly Asn Ala Asp Ile Cys Phe Leu Gly Ile Asp Arg Gly
            900             905             910

Glu Lys His Leu Ala Tyr Tyr Ser Leu Val Asp Ser Arg Gly Thr Ile
        915             920             925

Val Asp Gln Gly Thr Leu Asn Ile Pro Phe Thr Asp Ser Lys Gly Asn
930             935             940

Pro Arg Thr Val Arg Ala Ile Lys Arg Thr Leu Asp Lys Asn Gly His
945             950             955             960

Glu Trp Val Glu Glu Val Glu Cys Ser Asn Tyr Asn Asp Leu Leu Ala
            965             970             975

Ala Arg Ala Gly Asp Arg Asp Tyr Ala Arg Lys Asn Trp Gln Thr Ile
            980             985             990

Gly Thr Ile Lys Glu Leu Lys Glu Gly Tyr Ile Ser Gln Val Ile His
        995             1000            1005

Lys Ile Val Arg Leu Ala Ala Leu Asp Ser Asp Lys Pro Met Phe
    1010            1015            1020

Ile Val Leu Glu Asp Leu Ser Ile Gly Phe Met Arg Gly Arg Gln
    1025            1030            1035

Lys Ile Glu Lys Ser Val Tyr Lys Gln Phe Glu Val Ala Leu Ala
    1040            1045            1050

Lys Lys Leu Ser Phe Leu Val Asp Lys Ser Lys Asp Gly Lys Tyr
    1055            1060            1065

```
Gly Glu Val Gly Ser Val Thr Ala Ala Leu Gln Leu Thr Pro Pro
    1070                1075                1080

Ile Lys Asn Phe Asp Glu Leu Lys Glu Arg Gly Lys Gln Ala Gly
    1085                1090                1095

Val Met Leu Phe Val Arg Pro Asp Tyr Thr Ser Gln Thr Asp Pro
    1100                1105                1110

Val Thr Gly Trp Arg Lys Arg Ile Tyr Ile Asp Ser Gly Ser Glu
    1115                1120                1125

Leu Thr Ile Arg Lys Lys Val Thr Glu Ser Phe Glu Asp Ile Ala
    1130                1135                1140

Phe Asp Gly Lys Asp Tyr Val Phe Val Tyr Lys Asp Val Val Thr
    1145                1150                1155

Gly Lys Cys Trp Ser Met Tyr Ser Gly Lys Asp Gly Glu Ser Leu
    1160                1165                1170

Lys Arg Phe His Arg Val Arg Ser Val Asp Lys Asp Glu Trp Lys
    1175                1180                1185

Ser Glu Pro Gln Asn Leu Ala Glu Met Leu Asp Cys Leu Phe Lys
    1190                1195                1200

Asp Phe Asp Lys Asp Arg Ser Leu Leu Ser Gln Ile Val Asp Glu
    1205                1210                1215

Gly Met Gln Pro Lys Lys Val Asn Glu His Ser Ala Trp Glu Ser
    1220                1225                1230

Phe Arg Phe Val Ile Lys Leu Ile Gln Gln Ile Arg Asn Thr Asp
    1235                1240                1245

Gly Gly Asp Gly Gly Arg Glu Ser Asp Phe Leu Leu Ser Pro Val
    1250                1255                1260

Arg Glu His Gly Asn His Phe Asp Ser Arg Pro Tyr Trp Asp Glu
    1265                1270                1275

Glu Gln Arg Thr Gly His Pro Ala Leu Leu Pro Ser Cys Gly Asp
    1280                1285                1290

Ala Asn Gly Ala Tyr Asn Ile Ala Arg Lys Gly Ile Ile Leu His
    1295                1300                1305

Glu His Met Lys Arg Asp Phe Lys Leu Tyr Val Arg Asp Glu Glu
    1310                1315                1320

Trp Asp Ser Trp Leu Ala Gly Lys Glu Thr Trp Asp Asn Trp Leu
    1325                1330                1335

Arg Asn His Glu Lys Asp Leu Arg Lys Thr Pro Arg Lys Gly Gly
    1340                1345                1350

<210> SEQ ID NO 118
<211> LENGTH: 1289
<212> TYPE: PRT
<213> ORGANISM: Unknown
<220> FEATURE:
<223> OTHER INFORMATION: Nitrospinae bacterium RIFCSPLOWO2

<400> SEQUENCE: 118

Met Glu Asn Lys Glu Leu Phe Asn Ser Phe Thr Lys Lys Cys Gln Leu
1               5                   10                  15

Ser Lys Thr Leu Arg Phe Glu Leu Val Pro Gln Gly Glu Thr Glu Lys
            20                  25                  30

Phe Ile Lys Lys Lys Gly Leu Leu Lys Gln Asp Lys Asp Arg Ala Asp
        35                  40                  45

Asp Tyr Arg Lys Ala Lys Lys Leu Ile Asp Glu Tyr His Lys Asp Phe
    50                  55                  60
```

```
Ile Glu His Ala Leu Ser Gly Lys Gln Leu Lys Leu Gln Ala Tyr
 65                  70                  75                  80

Tyr Asp Glu Phe Thr Ala Leu Leu Gly Lys Pro Ala Lys Glu Arg Asp
                 85                  90                  95

Thr Arg Val Leu Ser Asn Ile Ser Glu Ala Leu Arg Lys Glu Ile Ala
            100                 105                 110

Gly Trp Leu Lys Asp Asn Pro Ile Lys Asp Glu Lys Lys Leu Ile Lys
            115                 120                 125

Glu Ile Val Pro Asn Phe Leu Lys Ser Lys Asp Arg Asn Asp Asp Ala
        130                 135                 140

Ala Leu Val Leu Lys Phe Lys Gly Phe Thr Thr Tyr Phe Gly Gly Phe
145                 150                 155                 160

Asn Glu Asn Arg Arg Asn Met Tyr Ser Ala Glu Glu Lys Ser Thr Ala
                165                 170                 175

Ile Ala Tyr Arg Ile Val His Glu Asn Leu Pro Lys Phe Ile Ser Asn
            180                 185                 190

Met Lys Thr Phe Gln Arg Leu Thr Glu Asn His Lys Ile Asp Phe Leu
        195                 200                 205

Glu Val Glu Thr Gln Met Asn Asp Glu Leu Asp Gly Asn Lys Leu Lys
        210                 215                 220

Asp Val Phe Ser Ile Asp Tyr Phe Asn Gln Cys Leu Thr Gln Ser Gly
225                 230                 235                 240

Ile Asp Arg Tyr Asn Thr Ile Leu Gly Gly Lys Thr Asp Ser Arg Gly
                245                 250                 255

Ala Gln Ile Gln Gly Val Asn Ile Lys Ile Asn Leu Phe Gly Gln Lys
            260                 265                 270

Asn Asn Leu Lys Ser Lys Asp Ala Pro Val Leu Ala Arg Leu Tyr Lys
        275                 280                 285

Gln Ile Leu Ser Asp Arg Thr Ser Ala Ser Phe Leu Pro Glu Lys Phe
        290                 295                 300

Glu Thr Ala Lys Glu Leu Ile Ala Ser Ile Arg Glu Phe Tyr Glu Lys
305                 310                 315                 320

Ala Ile Asn Gly Phe Ile Lys Asn Asn Glu Arg Lys Asn Val Ile Asp
                325                 330                 335

Glu Ile Glu Ser Leu Phe Asn Lys Lys Leu Asn Pro Thr Asp Cys Asp
            340                 345                 350

Leu Ser Gln Ile Tyr Ile Arg Asn Ile Phe Ile Ser Ala Val Ser Gln
        355                 360                 365

Gln Ile Phe Gly Ser Tyr Ser Val Ile Thr Ser Ala Leu Asn Ala Phe
        370                 375                 380

Ile Asp Lys Thr Tyr Lys Thr Lys Lys Glu Lys Glu Lys Gln Gln Lys
385                 390                 395                 400

Lys Ser Tyr Phe Gly Ile Ala Glu Ile Glu Ala Ala Leu Lys Ala Tyr
                405                 410                 415

Leu Gln Glu Thr Glu Ile Glu Asn Lys Glu Lys Arg Glu Glu Val Leu
            420                 425                 430

Lys His Ala Asn Pro Val Leu Gln Tyr Leu Asn Ser Leu Thr Thr Asn
        435                 440                 445

Ile Glu Ile Asn Asn Lys Lys Glu Lys Ala Asn Val Ile Val Arg Phe
        450                 455                 460

Arg Gln Gln His Glu Ala Val Gln Ser Val Leu Asn Lys Glu Tyr Gly
465                 470                 475                 480

Asn Asn Ser Glu Leu Ile Gln Asp Lys Asn Ala Val Ala Ala Ile Lys
```

```
              485                 490                 495
Asp Tyr Leu Asp Ser Cys Gln His Ile Leu His Phe Val Lys Pro Leu
                500                 505                 510
Phe Val Pro Pro Lys Lys Glu Asn Ala Glu Leu Pro Asp Lys Asp
            515                 520                 525
Ala Phe Tyr Ser Glu Phe Asp Glu Leu Phe Glu Gln Leu Lys Ser Val
            530                 535                 540
Thr Pro Leu Tyr Asn Met Val Arg Asn Phe Leu Thr Gln Lys Pro Tyr
545                 550                 555                 560
Ser Thr Glu Lys Ile Lys Leu Asn Phe Glu Asn Val Ser Leu Leu Ser
                565                 570                 575
Gly Trp Asp Val Asn Lys Glu Thr Asp Asn Thr Ser Val Ile Phe Arg
            580                 585                 590
Lys Asp Ser Leu Tyr Tyr Leu Gly Ile Met Asp Lys Lys His Asn Lys
            595                 600                 605
Val Phe His Asp Ile Pro Ala Ser Ser Asp Asn Asp Phe Tyr Glu Lys
            610                 615                 620
Met Asn Tyr Lys Leu Leu Pro Gly Ala Asn Lys Met Leu Pro Lys Val
625                 630                 635                 640
Ile Phe Ser Asp Arg Trp Ile Glu Tyr Phe Asn Pro Ser Lys Glu Leu
                645                 650                 655
Ile Glu Lys Tyr Lys Lys Gly Thr His Lys Lys Gly Glu Ile Phe Ser
                660                 665                 670
Leu Ser Asp Cys His Ala Leu Ile Asp Phe Phe Lys Thr Ser Ile Ala
            675                 680                 685
Lys His Glu Asp Trp Lys Gln Phe Asn Phe Gln Phe Ser Pro Thr Lys
            690                 695                 700
Thr Tyr Gln Asp Ile Asn Glu Phe Tyr Arg Glu Val Glu His Gln Gly
705                 710                 715                 720
Tyr Lys Ile Ser Phe Gln Asn Val Ser Ala Lys Tyr Ile His Gln Leu
                725                 730                 735
Val Ser Glu Gly Lys Leu Phe Leu Phe Lys Ile Tyr Asn Lys Asp Phe
            740                 745                 750
Ser Pro Tyr Ser Lys Gly Lys Pro Asn Leu His Thr Leu Tyr Trp Lys
            755                 760                 765
Ala Val Phe Asp Lys Glu Asn Leu Lys Asp Val Val Lys Leu Asn
            770                 775                 780
Gly Glu Ala Glu Val Phe Tyr Arg Pro Gln Ser Ile Pro Lys Lys Ser
785                 790                 795                 800
Lys Ile Val His Lys Lys Asn Lys Pro Ile Val Asn Lys Asn Pro Asn
                805                 810                 815
Asn Pro Lys Lys Gln Ser Leu Phe Glu Tyr Asp Ile Val Lys Asp
            820                 825                 830
Lys Arg Tyr Thr Glu Asp Lys Tyr His Phe His Val Pro Ile Thr Leu
            835                 840                 845
Asn Phe Lys Glu Ala Lys Val Pro Ser Glu Asn Asp Arg Lys Lys Ala
850                 855                 860
Phe Ala Tyr Thr Phe Asn Lys Gly Ala Asn Glu Thr Leu Lys Glu Asn
865                 870                 875                 880
Phe Pro Asn Ile Ile Gly Ile Asp Arg Gly Glu Arg His Leu Ala Tyr
                885                 890                 895
Tyr Ser Leu Ile Asn Ser Lys Gly Glu Ile Leu Glu Gln Gly Ser Phe
            900                 905                 910
```

```
Asn Val Ile Lys Asn Glu Phe Asn Gly Thr Lys His Glu Thr Asp Tyr
            915                 920                 925

Tyr Ala Ser Leu Val Glu Lys Glu Lys Ala Arg Asp Ala Ala Arg Lys
            930                 935                 940

Ser Trp Asp Thr Ile Gly Lys Ile Lys Glu Leu Lys Glu Gly Tyr Leu
945                 950                 955                 960

Ser Gln Val Val His Lys Ile Ala Arg Met Met Ile Glu His Asn Ala
            965                 970                 975

Ile Ile Val Leu Glu Asp Leu Thr Met Lys Phe Lys Asp Ile Arg Lys
            980                 985                 990

Lys Val Glu Arg Gln Val Tyr Gln Lys Leu Glu Lys Met Leu Ile Asp
            995                1000                1005

Lys Leu Asn Tyr Leu Val Phe Lys Asp Arg Glu Ala Tyr Glu Pro
            1010                1015                1020

Gly Gly Val Leu Asn Ala Tyr Gln Leu Ala Ala Pro Phe Thr Ser
            1025                1030                1035

Phe Lys Asp Met Gly Lys Gln Thr Gly Phe Ile Phe Tyr Val Pro
            1040                1045                1050

Ala Ala Asn Thr Ser Lys Ile Asp Tyr Ala Thr Gly Phe Met Asn
            1055                1060                1065

Phe Ile Tyr Pro Lys Ile Glu Asp Ala Val Glu Phe Phe Gln Lys
            1070                1075                1080

Phe Glu Tyr Ile Arg Phe Asn Pro Asp Lys Asn Tyr Phe Glu Phe
            1085                1090                1095

Ala Ala Arg Tyr Asn Asn Phe Val Lys Asp Asp Glu Ala Lys Leu
            1100                1105                1110

Pro Asp Glu Tyr Asn Glu Pro Trp Ile Ile Cys Thr His Gly Glu
            1115                1120                1125

Gln Arg Phe Gln Tyr Gln Pro Ser Tyr Lys Ser Phe Lys Glu Val
            1130                1135                1140

Asn Val Thr Gln Glu Leu Gln Asp Leu Phe Ser Lys His Ala Ile
            1145                1150                1155

Met Pro Tyr Ala His Gly Asn Asp Leu Ser Pro Gln Ile Lys Asp
            1160                1165                1170

Lys Gly Asn Thr Ser Phe Tyr Lys Gly Leu Ile Ala Leu Leu Arg
            1175                1180                1185

Leu Val Leu Gln Met Arg Tyr Thr Asp Gly Lys Gly Arg Asp Phe
            1190                1195                1200

Ile Leu Ser Pro Val Ala Asn Asp Glu Gly Val Phe Phe Asn Ser
            1205                1210                1215

Glu Lys Ala Lys Glu Thr Glu Pro Asn Asp Ala Asp Ala Asn Gly
            1220                1225                1230

Ala Tyr His Ile Ala Leu Lys Gly Leu Leu Leu Lys Arg Ile
            1235                1240                1245

Lys Gly Glu Phe Lys Lys Glu Lys Thr Gly Lys Lys Thr
            1250                1255                1260

Gln Lys Glu Asn Trp Ile Asp Leu Ser Ile Ser Asn Lys Glu Trp
            1265                1270                1275

Tyr Glu Phe Ala Gln Lys Lys Glu Tyr Arg Lys
            1280                1285

<210> SEQ ID NO 119
<211> LENGTH: 1342
```

<212> TYPE: PRT
<213> ORGANISM: Unknown
<220> FEATURE:
<223> OTHER INFORMATION: Candidatus Ryanbacteria bacterium RIFCSPHIGHO2

<400> SEQUENCE: 119

Met Ala Asn Glu Lys Lys Glu Lys Ser Ile Phe Asp Glu Phe Thr Gly
1               5                   10                  15

Lys Tyr Ser Leu Ser Lys Thr Leu Lys Phe Glu Leu Arg Pro Val Gly
            20                  25                  30

Lys Thr Leu Glu Asn Met Arg Gln His Leu Gly Tyr Asp Lys Asn Leu
        35                  40                  45

Gln Thr Phe Leu Ala Asp Gln Lys Ile Glu Asp Ala Tyr Gln Ser Leu
    50                  55                  60

Lys Pro Ile Phe Asp Phe Leu His Glu Lys Phe Ile Thr Glu Ser Leu
65                  70                  75                  80

Glu Ser Asp Val Ala Arg Lys Ile Asp Phe Thr Glu Tyr Phe Glu Lys
                85                  90                  95

Tyr Lys Arg Arg Lys Asp Leu Ser Glu Lys Asp Phe Val Gly Val Glu
            100                 105                 110

Lys Ser Leu Arg Asp Glu Phe Leu Lys Ala Tyr Asp Glu Thr Ala Glu
        115                 120                 125

Ser Leu Arg Ile Lys Ala Gly Lys Asn Glu Lys Gly Lys Phe Ile Leu
    130                 135                 140

Ser Glu Asn Gly His Lys Ile Leu Thr Glu His Gly Ile Leu Glu Tyr
145                 150                 155                 160

Ile Lys Lys Asn Ile Asp Glu Phe Val Glu Ile Thr Pro Glu Arg Glu
                165                 170                 175

Ile Glu Lys Ser Leu Ala Ala Phe Glu Gly Phe Phe Thr Tyr Phe Gly
            180                 185                 190

Gly Phe Asn Gln Asn Arg Glu Asn Tyr Tyr Glu Thr Lys Lys Glu Thr
        195                 200                 205

Ala Thr Ser Val Ala Thr Arg Val Ile His Glu Asn Leu Pro Lys Phe
    210                 215                 220

Cys Asp Asn Ile Leu Ala Phe Asp Gly Arg Ser Arg Asp Tyr Lys Asn
225                 230                 235                 240

Ala Tyr Ser Ile Leu Gln Lys Leu Gly Arg Thr Leu Val Asp Lys Glu
                245                 250                 255

Gly Lys Glu Leu Ile Pro Ile Glu Glu Asn Ile Phe Lys Ile Glu Tyr
            260                 265                 270

Phe Asn Ser Cys Met Ser Gln Arg Gly Val Glu Lys Tyr Asn Asp Gln
        275                 280                 285

Ile Gly Asn Ala Asn Phe Leu Ile Asn Leu Tyr Asn Gln Ala Lys Lys
    290                 295                 300

Glu Glu Asn Gly Phe Lys Lys Leu Pro Leu Leu Lys Thr Leu Tyr Lys
305                 310                 315                 320

Gln Ile Gly Cys Gly Glu Lys Arg Ser Leu Phe Ala Ile Asn Tyr
                325                 330                 335

Asp Gln Ala Asp Glu Cys Lys Lys Gln Glu Asn Asn Thr Glu Ile Arg
            340                 345                 350

Ser Leu Glu Glu Val Leu Asn Leu Ala Asn Lys Ala Gly Lys Lys Tyr
        355                 360                 365

Phe Lys Gly Lys Ser Asp Asp Gly Met Ile Asn Thr Leu Pro Glu Phe
    370                 375                 380

```
Leu Glu Tyr Leu Lys Asn Arg Glu Asn Tyr Leu Gly Val Tyr Trp Ser
385                 390                 395                 400

Lys Thr Ala Leu Asn Thr Ile Ser Ser Lys Tyr Phe Thr Asn Trp His
            405                 410                 415

Thr Leu Lys Glu Arg Leu Lys Glu Ala Lys Val Phe Lys Lys Ala Gly
        420                 425                 430

Lys Asp Ser Glu Glu Glu Ile Met Ile Pro Glu Ala Val Glu Leu Glu
    435                 440                 445

Gly Phe Phe Ser Val Leu Asp Val Val Glu Asn Trp Lys Asp Glu Gly
450                 455                 460

Val Leu Phe Lys Gln Asn Leu Thr Glu Ala Gln Lys Gly Ala Gln Gly
465                 470                 475                 480

Glu Asp Lys Asn Lys Ala Arg Lys Asp Ile Ile Leu Asn Ala Ser Ile
            485                 490                 495

Pro Ser Glu Ala Leu Leu Asn Leu Ile Phe Leu Gly Ile Glu Gln His
        500                 505                 510

Ala Lys Ala Phe Leu Asp Arg Ala Pro Glu Val Leu Ala Leu Lys Glu
    515                 520                 525

Tyr Lys Asn Ala Thr Ser Lys Glu Val Ile Lys Ser Trp Met Asp His
530                 535                 540

Ala Leu Ser Ile Thr Gln Met Leu Lys Tyr Phe Leu Val Lys Glu Ser
545                 550                 555                 560

Lys Val Lys Gly Thr Ala Leu Asp Ser Thr Ile Ser Gln Ala Leu Glu
            565                 570                 575

Val Phe Leu Gln Ser Asp Asp Ala Asp Trp Phe Gly Trp Tyr Asp Ala
        580                 585                 590

Leu Arg Asn Tyr Leu Thr Lys Lys Pro Gln Asp Asp Leu Lys Glu Asn
    595                 600                 605

Lys Leu Lys Leu Asn Phe Glu Asn Ser Thr Leu Ala Ser Gly Trp Asp
610                 615                 620

Val Ser Lys Glu Pro Asp Asn Tyr Cys Val Ile Phe Gln Asn Pro Glu
625                 630                 635                 640

Gly Glu Lys Phe Leu Ala Ile Ile Ala Arg Lys Lys Asp Arg Lys Gly
            645                 650                 655

Phe Asn Lys Ile Phe Glu Lys Asn Asn His Asn Arg Leu Tyr Thr Val
        660                 665                 670

Ser Gly Asn Lys Asn Trp Lys Lys Ile Glu Tyr Lys Leu Leu Pro Gly
    675                 680                 685

Pro Asn Lys Met Leu Pro Lys Cys Leu Met Pro Lys Ser Asp Arg Phe
690                 695                 700

Lys Tyr Gly Ala Thr Gln Glu Ile Leu Asp Ile Tyr Asp Glu Gly Ser
705                 710                 715                 720

Phe Lys Lys Asn Glu Val Ser Phe Ser Ile Gln Lys Leu Tyr Lys Met
            725                 730                 735

Ile Asp Phe Tyr Lys Met Ala Leu Glu Arg Tyr Lys Asp Trp Gly Cys
        740                 745                 750

Phe Asn Phe Ser Phe Gln Glu Thr Ser Lys Tyr Gln Asp Ile Ser Gln
    755                 760                 765

Phe Tyr Asn Asp Val Glu Lys Gln Gly Tyr Lys Leu Asp Val Val Asp
770                 775                 780

Ile Asn Lys Ser Ile Val Asp Ser Leu Val Glu Asp Gly Ser Ile Tyr
785                 790                 795                 800

Leu Phe Glu Ile Lys Asn Gln Asp Ser Asn Gln Gly Lys Lys Glu Asn
```

-continued

His Arg Asp Asn Leu His Thr Ile Tyr Trp Arg Ala Val Phe Glu Ser
      805                 810                 815

Val Glu Asn Arg Pro Lys Leu Asn Gly Gly Ala Glu Ile Phe Tyr Arg
      820                 825                 830

Lys Ala Leu Leu Pro Glu Lys Leu Glu Arg Asn Glu Asp Arg Lys Gly
      835                 840                 845

Lys Lys Ile Ile Lys Asn Pro Arg Phe Ser Lys Glu Lys Phe Leu Phe
850                 855                 860                 865

His Val Pro Ile Thr Leu Asn Phe Ser Ser Lys Asn Thr Arg Ile Asn
      870                 875                 880

Asp Leu Val Asn Asp Ile Leu Ser Arg Tyr Gly Asp Val His Phe Leu
      885                 890                 895

Gly Ile Asp Arg Gly Glu Lys His Leu Ala Tyr Tyr Ser Leu Val Asp
      900                 905                 910

Gln Asn Gly Arg Ile Lys Asp His Gly Thr Leu Asn Ile Pro Phe Leu
      915                 920                 925

Asp Lys Asp Gly Asn Ser Arg Met Val Arg Ala Lys Lys Arg Thr Leu
945                 950                 955                 960

Gly Lys Asp Gly Lys Glu Gln Ile Glu Met Val Glu Cys Lys Asp Tyr
                965                 970                 975

Asn Glu Leu Leu Asp Ala Arg Ala Gly Asp Arg Asp Tyr Ala Arg Lys
      980                 985                 990

Asn Trp Gln Thr Ile Gly Thr Ile Lys Asp Leu Lys Asp Gly Tyr Ile
                995                1000                 1005

Ser Gln Val Val Arg Thr Ile Ala Asp Leu Ala Leu Ala Asn Asn
      1010                1015                 1020

Ala Phe Ile Val Leu Glu Ser Leu Asp Thr Gly Phe Lys Arg Gly
      1025                1030                 1035

Arg Gln Lys Ile Glu Lys Ser Val Tyr Gln Lys Leu Glu Leu Ala
      1040                1045                 1050

Leu Ala Lys Lys Leu Asn Phe Leu Val Asp Lys Lys Ala Lys Phe
      1055                1060                 1065

Gly Glu Ile Gly Ser Val Thr Asn Ala Leu Gln Leu Thr Pro Pro
      1070                1075                 1080

Val Ala Asn Tyr Gly Asp Ile Glu Asn Arg Lys Gln Leu Gly Val
      1085                1090                 1095

Met Leu Tyr Val Lys Ala Asp Tyr Thr Ser Gln Thr Asp Pro Ile
      1100                1105                 1110

Thr Gly Trp Arg Lys Ser Ile Tyr Leu Lys Lys Gly Ser Glu Glu
      1115                1120                 1125

Tyr Ile Arg Ser Gln Ile Arg Asp Gly Phe Ser Asp Ile Ser Phe
      1130                1135                 1140

Asp Gly Lys Asp Tyr Val Phe Thr Tyr Glu Asp Lys Asn Thr His
      1145                1150                 1155

Lys Gln Trp Lys Leu Tyr Ser Gly Lys Asn Gly Lys Ser Leu Asp
      1160                1165                 1170

Arg Tyr His Arg Glu Lys Gly Glu Thr Arg Asn Ser Trp Asp Pro
      1175                1180                 1185

Ile Arg Lys Asp Val Thr Glu Met Leu Asn Gly Ile Phe Glu Asn
      1190                1195                 1200

Phe Asn Arg Ser Asn Ser Ile His Ser Gln Ile Val Asp Glu Gly
      1205                1210                 1215

```
Val Glu  Leu Lys Lys Ile  Asp Ser Ala His  Thr Ala  Trp Glu Ser
    1220         1225             1230

Leu Arg  Phe Thr Ile Asp  Leu Ile Gln Gln  Ile Arg  Asn Thr Gly
    1235         1240             1245

Thr Ala  Lys Glu Asp Asp  Asp Phe Ile Leu  Ser Pro  Val Arg Asp
    1250         1255             1260

Glu Asn  Gly Asn His Phe  Asp Ser Arg Lys  Thr Ile  Lys Tyr Gln
    1265         1270             1275

Pro Asn  Ser Gly Asp Ala  Asn Gly Ala Tyr  Asn Ile  Ala Arg Lys
    1280         1285             1290

Gly Ile  Val Leu Asn Glu  His Ile Lys Arg  Gly Tyr  Arg Leu Phe
    1295         1300             1305

Ile Ser  Asp Glu Glu Trp  Asp Ala Trp Leu  Ala Gly  Lys Glu Arg
    1310         1315             1320

Trp Glu  Lys Trp Ile Ser  His Lys Lys Asp  Leu Ala  Lys Lys
    1325         1330             1335

Gln Thr  Ala Gln
    1340

<210> SEQ ID NO 120
<211> LENGTH: 1390
<212> TYPE: PRT
<213> ORGANISM: Unknown
<220> FEATURE:
<223> OTHER INFORMATION: Candidatus Wildermuthbacteria bacterium
      RIFCSPHIGHO2

<400> SEQUENCE: 120

Met Ile Asp Asn Thr Lys  Glu Lys Lys Glu  Gly Ser Val Phe Asp Gly
1               5                10                  15

Phe Thr Arg Lys Tyr Gln  Leu Ser Lys Thr  Leu Arg Phe Glu Leu Arg
            20                  25                  30

Pro Ile Leu Asn Thr Pro  Lys Met Leu Asp  Asp Glu Gln Val Ile Lys
        35                  40                  45

Asn Asp Glu Thr Arg Arg  Lys Lys Tyr Glu  Ala Val Lys Pro Trp Phe
50                  55                  60

Asp Gln Leu His Arg Glu  Phe Ile Glu Asp  Ala Leu Lys Ser Phe Lys
65                  70                  75                  80

Phe Lys Asn Leu Ala Ile  Tyr Gln Asp Thr  Phe Gln Thr Trp Gln Lys
                85                  90                  95

Asp Arg Lys Ser Lys Gln  Lys Lys Asp Thr  Leu Val Lys Ile Glu Val
            100                 105                 110

Gly Leu Arg Glu Glu Ile  Val Arg Arg Phe  Glu Glu Val Ala Asn Ile
        115                 120                 125

Trp Val Arg Ser Glu Gln  Tyr Lys Leu Leu  Gly Ile Lys Lys Glu Gly
    130                 135                 140

Leu Gly Met Leu Phe Glu  Ala Gly Val Phe  Arg Leu Leu Lys Glu Arg
145                 150                 155                 160

Phe Lys Asn Glu Lys Asp  Thr Thr Val Asp  Gly Asn Asn Ile Phe Asp
                165                 170                 175

Glu Trp Thr Arg Trp Thr  Gly Tyr Phe Lys  Lys Phe Phe Glu Thr Arg
            180                 185                 190

Lys Asn Phe Tyr Lys Ser  Asp Asp Thr Ser  Thr Ala Ile Ala Tyr Arg
        195                 200                 205

Val Ile Asn Gln Asn Leu  Arg Arg Phe Cys  Glu Asn Ile Gln Ile Phe
```

```
               210                 215                 220
Glu Lys Ile Ser Glu Lys Ile Glu Phe Ser Glu Val Glu Lys Ser Phe
225                 230                 235                 240

Asp Ile Ser Cys Ala Gly Ile Phe Ser Leu Ala Tyr Asn Ala Cys
                245                 250                 255

Leu Leu Gln Gly Gly Ile Asp Thr Tyr Asn Lys Ile Ile Gly Gly Glu
                260                 265                 270

Val Asp Glu Lys Asp Lys Lys Ile Pro Gly Ile Asn Glu Leu Ile Asn
                275                 280                 285

Lys Tyr Arg Gln Asp Asn Ser Gly Glu Lys Ile Pro Phe Leu Lys Gln
                290                 295                 300

Leu Asp Lys Gln Ile His Ser Ala Lys Glu Ala Phe Ile Glu Ser Ile
305                 310                 315                 320

Glu Thr Asn Lys Glu Leu Val Gly Lys Leu Lys Thr Phe Tyr Glu Asn
                325                 330                 335

Ala Glu Val Lys Ile Gln Ser Phe Arg Asn Leu Ile Ala Asp Ile Val
                340                 345                 350

Thr Asp Tyr Ser Gly Tyr Asp Ile Asp Lys Ile Tyr Leu Thr Lys Glu
                355                 360                 365

Ala Val Ser His Asn Ala Ser Arg Trp Phe Ala Ser Phe Glu Ser Phe
                370                 375                 380

Glu Arg Asp Leu Phe Ala Val Val Ala Glu Lys Gln Asn Lys Leu Val
385                 390                 395                 400

Tyr Glu Leu Leu Arg Thr His Lys Asn Asp Ser Lys Ile Ser Asp Lys
                405                 410                 415

Asp Gly Lys Phe Ser Phe Pro Asp Phe Ile Lys Cys Ser His Ile Lys
                420                 425                 430

Arg Ala Leu Glu Lys Gln Glu Gly Arg Ile Trp Lys Gly Glu Tyr Tyr
                435                 440                 445

Glu Asp Ile Val Asp Phe Glu Lys Ile Lys Asp Val Phe Thr Gln Phe
                450                 455                 460

Leu Cys Val Phe Lys Phe Glu Leu Glu Gln Gln Phe Phe Arg Lys Thr
465                 470                 475                 480

Thr Ser Ala Gln Thr Gly Glu Gln Thr Lys Ile Gly Tyr Glu Ile Phe
                485                 490                 495

Val Thr Lys Ile Asn Glu Leu Ile Thr Arg Glu Asn Pro Val Ile Asp
                500                 505                 510

Leu Glu Glu Lys Ile Ala Ile Lys Asn Phe Ala Asp Ala Thr Leu Leu
                515                 520                 525

Ile Tyr Gln Ile Ala Lys Tyr Phe Ala Val Glu Lys Arg Arg Gly Trp
                530                 535                 540

Leu Asp Asn Tyr Asp Leu Asp Asp Arg Phe Tyr Lys Ser Ser Asp Ile
545                 550                 555                 560

Gly Tyr Leu Asn Phe Tyr Arg Asp Ala Phe Glu Gln Ile Val Arg Pro
                565                 570                 575

Tyr Asn Leu Phe Arg Asn Tyr Leu Thr Lys Lys Pro Tyr Asn Thr Asn
                580                 585                 590

Lys Trp Val Leu Ser Phe Glu Asn Pro Thr Leu Ala Asp Gly Trp Asp
                595                 600                 605

Lys Asn Lys Glu Lys Thr Asn Ala Ala Val Ile Leu Arg Lys Asp Gly
                610                 615                 620

Arg Tyr Tyr Leu Gly Ile Ile Lys Glu Asp Cys Lys Ser Leu Phe Ala
625                 630                 635                 640
```

-continued

Asp Arg Tyr Ser Lys Glu Met Ser Glu Gly Ile Ser Gly Ser Phe
                645                 650                 655

Gln Lys Met Ala Tyr Lys Phe Phe Pro Glu Ala Ser Lys Met Ile Pro
            660                 665                 670

Lys Cys Ser Thr Gln Thr Lys Asn Val Lys Glu His Phe Arg Lys Ser
        675                 680                 685

Ser Ser Asp Tyr Asn Leu Phe His Glu Lys Asp Tyr Lys Ile Ser Val
    690                 695                 700

Ala Ile Thr Lys Asn Ile Tyr Glu Leu Asn Asn Val Phe Tyr Arg Lys
705                 710                 715                 720

Asp Asn Ile Glu Glu Ser Phe Val Pro Lys Asn Asp Phe Glu Lys Lys
                725                 730                 735

Leu Gly Val Lys Lys Phe Gln Arg Gln Tyr Leu Glu Ile Ser Arg Asp
            740                 745                 750

Asn Asn Gly Tyr Lys Gln Ala Leu Ala Gln Trp Ile Glu Phe Cys Ile
        755                 760                 765

Arg Phe Leu Lys Ala Tyr Lys Ser Thr Thr Ile Phe Asp Tyr Ser Arg
    770                 775                 780

Leu Arg Glu Ala Lys Glu Tyr Glu Ser Leu Asp Ala Phe Tyr Gln Asp
785                 790                 795                 800

Ile Asn Ala Leu Thr Tyr Asn Ile Ser Phe Val Pro Ile Ser Glu Gln
                805                 810                 815

Tyr Ile Lys Glu Lys Asn Asp Asn Gly Glu Leu Phe Leu Phe Glu Ile
            820                 825                 830

Tyr Asn Lys Asp Trp Ser Leu Gly Pro Met Asp Lys Asn Arg Lys Arg
        835                 840                 845

Thr Lys Asn Leu His Thr Leu Tyr Phe Glu Gln Leu Phe Ser Lys Glu
    850                 855                 860

Asn Glu Gln Glu Asn Phe Leu Phe Gln Leu Asn Gly Glu Ala Glu Leu
865                 870                 875                 880

Phe Phe Arg Pro Lys Thr Glu Glu Lys Arg Leu Gly Tyr Lys Val Trp
                885                 890                 895

Asp Ala Gly Glu Lys Lys Trp Val Lys Ala Lys Glu Lys Glu Asp Gly
            900                 905                 910

Ala Val Ile Asp Arg Lys Arg Tyr Ala Lys Asp Ile Ile Leu Phe His
        915                 920                 925

Cys Pro Ile Thr Leu Asn Arg Val Ser Glu Ser Lys Thr Lys Arg Glu
    930                 935                 940

Met Asp Val Glu Ile Arg Glu Val Leu Ser Ser Thr Pro Gly Val His
945                 950                 955                 960

Ile Ile Gly Val Asp Arg Gly Glu Lys His Leu Ala Tyr Tyr Ser Val
                965                 970                 975

Ile Asp Gln Asn Gly Lys Ile Ile Glu Thr Asp Thr Leu Asn Ser Ile
            980                 985                 990

Gly Lys Asp Gly Arg Gly Lys Pro Val Glu Tyr Ala Ser Lys Leu Glu
        995                 1000                1005

Lys Arg Ala Gln Glu Arg Glu Ala Ser Arg Arg Asp Trp Glu Glu
    1010                1015                1020

Val Glu Ala Ile Lys Asp Leu Lys Lys Gly Tyr Ile Ser Gln Val
    1025                1030                1035

Ile Arg Asn Leu Ala Asp Leu Ile Ile Lys His Asn Ala Ile Ile
    1040                1045                1050

Val Phe Glu Asp Leu Asn Met Arg Phe Lys Gln Ile Arg Gly Gly
1055                1060                1065

Ile Glu Lys Ser Ala Tyr Gln Gln Leu Glu Arg Ala Leu Ile Asp
1070                1075                1080

Lys Leu Ser Phe Leu Val Lys Lys Gly Glu Glu Asp Pro Lys Gln
1085                1090                1095

Thr Gly His Ile Leu Arg Ala Tyr Gln Leu Ala Ala Pro Val Ile
1100                1105                1110

Ala Phe Lys Asp Met Gly Lys Gln Thr Gly Leu Ile Phe Tyr Thr
1115                1120                1125

Gln Ala Gly Tyr Thr Ser Lys Thr Cys Pro Glu Cys Gly Tyr Arg
1130                1135                1140

Arg Asn Ile Lys Cys Leu Phe Glu Asn Ile Glu Gln Ala Lys Thr
1145                1150                1155

Leu Ile Glu Asn Leu Glu Ser Ile Asn Tyr Asn Lys Lys Glu Asp
1160                1165                1170

Val Phe Gln Ile Ser Tyr Ser Leu Glu Lys Leu Ser Ser Lys Asp
1175                1180                1185

Gln Lys Lys Glu Lys Val Ser Asn Glu Leu Tyr Ala Lys Thr
1190                1195                1200

Leu Lys Lys Asp Ile Phe Ile Leu Thr Thr Lys Asn Ala Leu Arg
1205                1210                1215

Tyr Lys Trp Tyr Asp Arg Tyr Ser Glu Lys Ala Lys Val Ala Lys
1220                1225                1230

Arg Gly Ile Asp Glu Tyr Lys Gly Glu Val Asn Glu Ser Glu Thr
1235                1240                1245

Lys Lys Gly Val Val Lys Glu Phe Asn Leu Thr Glu Tyr Leu Lys
1250                1255                1260

Gly Leu Leu Lys Thr Tyr Glu Ile Asp Tyr Glu His Gly Gly Ile
1265                1270                1275

Arg Glu Gln Ile Leu Ser Val Ala Arg Gly Arg Glu Phe Tyr Lys
1280                1285                1290

Asp Phe Leu Tyr Ala Leu Phe Leu Leu Thr Glu Thr Arg His Ser
1295                1300                1305

Ile Ser Gly Arg Asn Thr Asp Tyr Ile Gln Cys Pro Glu Cys Glu
1310                1315                1320

Phe Asp Ser Arg Lys Gly Phe Lys Asp Ile Lys Glu Phe Asn Gly
1325                1330                1335

Asp Ala Asn Gly Ala Tyr Asn Ile Ala Arg Lys Gly Ile Met Ile
1340                1345                1350

Leu Glu Lys Ile Lys Gln Phe Lys Lys Asp Asn Asp Gly Asn Leu
1355                1360                1365

Glu Lys Met Gly Trp Gly Asp Leu Ser Ile Ser Ile Glu Glu Trp
1370                1375                1380

Asp Lys Phe Thr Gln Lys Glu
1385                1390

<210> SEQ ID NO 121
<211> LENGTH: 1265
<212> TYPE: PRT
<213> ORGANISM: Unknown
<220> FEATURE:
<223> OTHER INFORMATION: Firmicutes bacterium CAG_194_44_15

<400> SEQUENCE: 121

-continued

```
Met Glu Arg Lys Asp Phe Ile Asn Tyr Asp Gln Val Ser Lys Thr Ile
1               5                   10                  15
Arg Asn Gly Leu Ile Pro Thr Glu Tyr Thr Leu Lys Asn Ile Glu Glu
            20                  25                  30
Thr Gly Val Leu Val Ser Asp Glu Tyr Arg Ala Glu Val Arg Asn Val
        35                  40                  45
Leu Lys Lys Ile Met Asp Asp Tyr Tyr Lys Glu Tyr Ile Asn Met Cys
50                  55                  60
Leu Asn Arg Glu Ile Lys Met Asp Trp Arg Pro Leu Phe Asp Ala Tyr
65                  70                  75                  80
Glu Leu Val Lys Lys Gly Lys Met Lys Pro Lys Glu Ile Glu Asn Ile
                85                  90                  95
Gln Asp Glu Lys Arg Lys Glu Ile Tyr Asp Ile Leu Ser Ala His Asp
            100                 105                 110
Glu Phe Lys Lys Met Phe Ser Ala Lys Met Ile Thr Glu Leu Leu Pro
        115                 120                 125
Gln Phe Ile Ser Gln Ser Thr Gly Tyr Asn Glu Asp Glu Lys Lys Gln
130                 135                 140
Tyr Glu Glu Val Ile His Ile Tyr Ser Arg Phe Thr Ser Asp Phe Thr
145                 150                 155                 160
Asp Phe Phe Gln Asn Arg Lys Asn Val Phe Ser Ser Ala Gly Ile Ala
                165                 170                 175
Thr Ser Ile Cys Asn Arg Ile Val Asn Glu Asn Ala Glu Ile Phe Ser
            180                 185                 190
Asp Asn Lys Ser Thr Phe Asp Arg Ile Lys Lys Asp Ile Ser Tyr Ile
        195                 200                 205
Asp Glu Ile Ile Asp Ser Asp Leu Lys Thr Tyr Leu Asp Gly Trp Glu
210                 215                 220
Leu Glu Gln Ile Tyr Ser Val Asp Phe Tyr Ser Arg Leu Met Ser Gln
225                 230                 235                 240
Ser Gly Ile Asp Phe Tyr Asn Met Ile Ser Gly Ala Val Asn Lys Ala
                245                 250                 255
Val Asn Glu Tyr Cys Gln Lys Asn Gly Leu Asn Lys Asn Lys Tyr Leu
            260                 265                 270
Leu Arg Lys Leu Arg Lys Gln Ile Leu Ser Asn Ser Glu Ser Thr Phe
        275                 280                 285
Gln Ile Pro Glu Lys Phe Leu Ala Asp Glu Glu Val Tyr Lys Ala Val
290                 295                 300
Gly Gln Phe Ile Asp Asn Ile Lys Ser Lys Asn Val Ile Glu Ile Leu
305                 310                 315                 320
Lys Asp Ile Gly Ser Asn Cys Glu Asn Tyr Asp Leu Arg Arg Ile Tyr
                325                 330                 335
Ile Ala Glu Ser Ala Tyr Glu Asp Val Ser Ile Phe Met Gly Tyr Gly
            340                 345                 350
Trp Asn Gly Ile Lys Gly Cys Leu Glu Lys Tyr Glu Lys Glu Ile
        355                 360                 365
Ala Pro Gly Lys Ala Lys Asp Ile Lys Ile Lys Leu Ile Ser Gln
370                 375                 380
Glu Lys Glu Arg Ser Ile Gly Glu Ile Asp Glu Leu Phe His Ile Tyr
385                 390                 395                 400
Gly Glu Glu Lys Asp Gly Lys Ala Ala Ile Gln Tyr Ile Glu Glu Val
                405                 410                 415
Val Glu Leu Cys Asn Glu Val Pro Thr Arg Leu Val Tyr Asp Ser Ser
```

-continued

```
            420                 425                 430
Glu Lys Leu Thr Glu Asn Asp Asn Lys Ala Ala Glu Ile Lys Asn Val
            435                 440                 445

Leu Asp Tyr Tyr Phe Lys Ile Phe His Trp Ile Lys Thr Phe Ile Thr
450                 455                 460

Asp Asp Ile Leu Asp Lys Asp Ile Val Phe Tyr Ser Gly Ile Glu Phe
465                 470                 475                 480

Ala Tyr Glu Glu Ile Lys Asp Ile Val Pro Leu Tyr Asn Lys Val Arg
                485                 490                 495

Asn Tyr Val Thr Gln Lys Pro Tyr Ser Ser Glu Lys Ile Lys Leu Lys
                500                 505                 510

Phe Gly Thr Pro Thr Leu Ala Asn Gly Trp Ser Lys Ser Lys Glu Phe
            515                 520                 525

Asp Asn Asn Ala Ile Leu Leu Val Arg Asp Asn Lys Tyr Tyr Leu Gly
        530                 535                 540

Ile Phe Asn Val Leu Asn Lys Pro Asp Lys Lys Ile Met Ala Gly Tyr
545                 550                 555                 560

Ala Asn Lys Lys Asn Ser Ser Asp Tyr Ala Lys Met Val Tyr Asn Leu
                565                 570                 575

Leu Pro Gly Pro Ser Lys Met Leu Pro Lys Val Cys Leu Ser Gln Lys
            580                 585                 590

Gly Lys Asp Thr Tyr His Pro Ser Ala Tyr Ile Val Asp Asn Tyr Glu
        595                 600                 605

Arg Lys Ala His Val Lys Ser Ser Glu His Phe Ser Ile Gln Tyr Cys
    610                 615                 620

His Asp Leu Ile Asp Tyr Phe Lys Glu Cys Ile Lys Arg Asn Asp Asp
625                 630                 635                 640

Trp Lys Cys Phe Asp Phe Lys Phe Ser Asp Thr Glu Gln Tyr Asn Asp
                645                 650                 655

Ile Ser Glu Phe Tyr Lys Glu Val Glu Leu Gln Gly Tyr Ser Ile Gly
            660                 665                 670

Trp Thr Tyr Ile Ser Gly Glu Asp Ile Glu Ala Leu Asp Lys Glu Gly
        675                 680                 685

Lys Leu Tyr Leu Phe Gln Ile Tyr Asn Lys Asp Phe Ser Glu Gln Ser
    690                 695                 700

His Gly Thr Asp Asn Leu His Thr Met Tyr Leu Lys Asn Leu Phe Ser
705                 710                 715                 720

Pro Glu Asn Leu Asn Asn Ile Val Leu Lys Leu Asn Gly Glu Ala Glu
                725                 730                 735

Leu Phe Tyr Arg Lys Ser Ser Ile Lys Lys Pro Val Val His Lys Lys
            740                 745                 750

Gly Ser Ile Leu Val Asn Lys Thr Tyr Thr Glu Lys Thr Gly Asn Gly
        755                 760                 765

Glu Glu Val Arg Arg Pro Val Pro Asp Val Tyr Leu Glu Leu Val
    770                 775                 780

Asn Tyr Tyr Asn Gly Glu Gln Lys Ala Ile Leu Ser Asp Glu Ala Lys
785                 790                 795                 800

Lys Tyr Met Lys Val Val Glu His His Glu Ala Val Lys Asp Ile Thr
                805                 810                 815

Lys Asp Tyr Arg Tyr Thr Val Asn Lys Phe Phe Ile His Leu Pro Ile
            820                 825                 830

Thr Ile Asn Phe Lys Ala Glu His Thr Gly Asn Leu Asn Glu Met Val
        835                 840                 845
```

```
Ile Gln Tyr Ile Ala Lys Gln Glu Asn Met His Val Ile Gly Ile Asp
    850                 855                 860

Arg Gly Glu Arg Asn Leu Ile Tyr Val Ser Val Ile Asp Met Asn Gly
865                 870                 875                 880

Lys Ile Lys Glu Gln Lys Ser Phe Asn Ile Val Asn Ser Tyr Asn Tyr
                885                 890                 895

Gln Glu Lys Leu Arg Gly Arg Glu Lys Asp Arg Leu Asn Ala Arg Lys
            900                 905                 910

Asn Trp Lys Gln Ile Ala Asn Ile Lys Glu Met Lys Glu Gly Tyr Leu
        915                 920                 925

Ser Leu Val Ile His Glu Ile Thr Glu Met Met Lys Tyr Asn Ala
    930                 935                 940

Ile Ile Ala Met Glu Asp Leu Asn Tyr Gly Phe Lys Arg Gly Arg Phe
945                 950                 955                 960

Lys Val Glu Arg Gln Val Tyr Gln Lys Phe Glu Thr Met Leu Ile Ser
                965                 970                 975

Lys Leu Asn Tyr Leu Val Asp Lys His Lys Lys Val Asp Glu Pro Gly
            980                 985                 990

Gly Leu Leu Arg Gly Tyr Gln Phe Ala Tyr Val Pro Ala Ser Leu Asp
        995                 1000                1005

Arg Leu Gly Arg Gln Cys Gly Phe Ile Phe Tyr Val Pro Ala Ala
    1010                1015                1020

Tyr Thr Ser Lys Ile Asp Pro Thr Thr Gly Phe Val Asp Leu Phe
    1025                1030                1035

Asn His Ser Glu Leu Ile Lys Ala Gly Lys Arg Arg Asp Asn Leu
    1040                1045                1050

Ser Lys Phe Asp Gly Ile Tyr Tyr Asp Glu Gln Lys Asp Met Phe
    1055                1060                1065

Cys Tyr Ala Phe Asp Tyr Lys Asn Phe Val Thr His Asn Thr Asp
    1070                1075                1080

Ile Tyr Gln Asn Ser Trp Glu Ile Tyr Thr Asn Lys Glu Arg Leu
    1085                1090                1095

Arg Lys Ile Phe Gly Asn Gly Arg Pro Thr Gly Lys Thr Glu Lys
    1100                1105                1110

Ile Glu Leu Thr Gln Met Met Lys Glu Val Leu Thr Gly Ala Gly
    1115                1120                1125

Val Glu Tyr Lys Asp Gly His Asn Leu Ile Asp Ile Leu Asn
    1130                1135                1140

Ser Asn Asp Asn Cys Ile Lys Gln Val Leu Asp Ile Phe Leu Tyr
    1145                1150                1155

Ser Ile Gln Leu Arg Asn Ser Lys Gly Glu Asn Glu Asp Ser Lys
    1160                1165                1170

Glu Ser Asp Tyr Asp Arg Ile Ile Ser Pro Val Leu Asn Gln Glu
    1175                1180                1185

Asn Glu Phe Phe Asp Ser Val Val Tyr Ala Asp Lys Tyr Lys Lys
    1190                1195                1200

Asp Glu Lys Leu Ala Asp Lys Pro Ile Asp Ala Asp Ala Asn Gly
    1205                1210                1215

Ala Tyr Cys Ile Ala Leu Lys Gly Leu Tyr Glu Ile Leu Gln Ile
    1220                1225                1230

Lys Asn Asn Trp Lys Glu Gly Glu Val Phe Ser Arg Asp Thr Leu
    1235                1240                1245
```

Lys Ile Thr Asn Ala Asp Trp Leu Arg Phe Met Gln Ser Arg Gly
 1250                1255                1260

Phe Glu
    1265

<210> SEQ ID NO 122
<211> LENGTH: 1322
<212> TYPE: PRT
<213> ORGANISM: Unknown
<220> FEATURE:
<223> OTHER INFORMATION: Candidatus Gottesmanbacteria bacterium
      CG1_02_37_22

<400> SEQUENCE: 122

Met Thr Gly Ile Phe Lys Asp Phe Thr His Leu Tyr Glu Leu Gln Lys
1               5                   10                  15

Thr Leu Arg Phe Glu Leu Ile Pro Val Gly Arg Thr Lys Glu Leu Leu
            20                  25                  30

Glu Lys Asn His Val Phe Glu Lys Asp Glu Lys Ile Ala Glu Asn Tyr
        35                  40                  45

Lys Asp Val Lys Lys Tyr Phe Asp Arg Leu His Lys Glu Phe Ile Lys
50                  55                  60

Asp Ala Phe Ser His Thr Asn Leu Pro Glu Asn Leu Leu Glu Gly Tyr
65                  70                  75                  80

Glu Gln Lys Tyr Phe Ser His Lys Leu Asn Pro Ser Arg Ala Ser Arg
                85                  90                  95

Ile Asp Leu Glu Lys Ile Ala Lys Arg Leu Arg Thr Ile Leu Leu Lys
            100                 105                 110

Ser Phe Asn Thr Glu Ala Asp Gln Trp Lys Asn Arg Tyr Leu Lys Asn
        115                 120                 125

Ile Glu Gln Thr Leu Lys Asn Lys Asn Glu Lys Gln Gln Lys Lys Glu
130                 135                 140

Leu Glu Lys Lys Leu Lys Lys Ile Lys Glu Gly Thr Lys Gly Ile Glu
145                 150                 155                 160

Leu Phe Phe Lys Val Glu Val Phe Asp Phe Leu Lys Tyr Lys Tyr Pro
                165                 170                 175

Glu Ala Gln Ile Asn Gly Lys Ser Ile Phe Asp Pro Phe Asn Lys Phe
            180                 185                 190

Gly Cys Tyr Phe Lys Lys Phe His Glu Thr Arg Ile Asn Phe Tyr Lys
        195                 200                 205

Asp Asp Gly Thr Ser Thr Ala Ile Pro Thr Arg Ile Ile Asn Asp Asn
210                 215                 220

Leu Ser Ile Phe Leu Glu Asn Lys Lys Ile Phe Glu Ser Lys Tyr Ser
225                 230                 235                 240

Lys Lys His Lys Ser Val Phe Ala Lys Asn Glu Leu Arg Ile Phe Val
                245                 250                 255

Leu Phe Tyr Phe Asn Asn Cys Phe Ser Gln Lys Gln Ile Asp Gly Tyr
            260                 265                 270

Asn Asn Thr Ile Ala Leu Ile Asn Ser Asn Val Asn Gln Leu Arg Gln
        275                 280                 285

Asn Asn Pro Glu Val Ser Lys Lys Asp Leu Pro Phe Phe Lys Arg Leu
290                 295                 300

Phe Lys Gln Ile Leu Ser Gln Pro Ser Lys Gln Glu Ile Glu Gln Asp
305                 310                 315                 320

Ser Phe Ile Glu Ile Phe Gln Asp Glu Asp Val Phe Pro Thr Met Gln
                325                 330                 335

```
Lys Phe Ile Asn Glu Asn Lys Ile Cys Ile Pro Lys Ala Lys Ser Ile
                340                 345                 350

Phe Lys Lys Phe Ile Ser Ser Gln Lys Val Lys Ser Asp Glu Tyr Asn
            355                 360                 365

Ile Ser Gln Ile Tyr Val Ala Lys Arg Phe Ile Asn Thr Ile Ser Asn
        370                 375                 380

Lys Trp Phe Ser Asn Trp Asn Thr Ile Arg Asn Leu Leu Ile Pro Lys
385                 390                 395                 400

Asp Lys Lys Asn Ile Pro Asp Phe Ile Ser Val Thr Ser Leu Lys Ala
                405                 410                 415

Ala Leu Gln Lys Thr Gln Asn Ile Val Glu Val Asn Asp Leu Phe Arg
            420                 425                 430

Lys Glu Tyr Arg Asp Ile Leu Glu Glu Gly Ser Asp Phe Tyr Gln Ile
        435                 440                 445

Phe Leu Lys Ile Trp Glu Lys Glu Phe Glu Lys Ala Thr Asp Ile Tyr
450                 455                 460

Leu Asn Glu Thr Lys Glu Ile Glu Lys Met Ile Thr Glu Asp Lys Lys
465                 470                 475                 480

Tyr Leu Pro Asn Lys Lys Gly Arg Leu Lys Ser Gly Lys Lys Gly Ser
                485                 490                 495

Ile Gln Lys Glu Lys Phe Leu Asp Tyr Thr Gln Ser Val Phe Asp Ile
            500                 505                 510

Tyr Leu Met Met Lys Tyr Phe Ser Leu Glu Lys Gly Lys Glu Arg Val
        515                 520                 525

Trp Asn Pro Glu Ala Leu Asp Glu Asp Ala Ile Gly Gly Phe Tyr Glu
530                 535                 540

Lys Phe Lys Glu Tyr Tyr Glu Asn Ile Asn Thr Trp Lys Tyr Phe Asn
545                 550                 555                 560

Val Phe Arg Asn Tyr Leu Thr Lys Lys Pro Tyr Asn Ser Glu Lys Ile
                565                 570                 575

Lys Leu Asn Phe Glu Cys Ser Ser Leu Leu Ser Gly Trp Ser Lys Asn
            580                 585                 590

Tyr Asp Ser Tyr Gly Ala Leu Ile Phe Glu Lys Asn Glu Lys Tyr Tyr
        595                 600                 605

Leu Gly Ile Ile Asn Gly Thr Lys Phe Thr Lys Asp Glu Ile Glu Gln
610                 615                 620

Leu Tyr Leu Asp Ile Arg Asn Asn Asn Ile Ser Leu Arg Leu Val Tyr
625                 630                 635                 640

Asn Tyr Gln Lys Pro Asp Phe Lys Asn Phe Pro Lys Leu Phe Ile Arg
                645                 650                 655

Ser Ser Gly Ser Asn Phe Ala Pro Ala Val Lys Lys Tyr Asn Leu Pro
            660                 665                 670

Ile Asp Ser Val Leu Asn Ile Tyr Asp Lys Gly Leu Phe Lys Thr Ser
        675                 680                 685

Asn Lys Ser Ser Gln Asn Tyr His Glu Ser Leu Lys Lys Ile Ile Asp
690                 695                 700

Tyr Phe Lys Leu Gly Ile Ser Gln His Glu Ser Tyr Lys Gly Phe Ser
705                 710                 715                 720

Phe Lys Trp Gln Glu Thr Ser Glu Tyr Asp Asn Ile Ser Asp Phe Tyr
                725                 730                 735

Lys Asp Ala Thr Arg Ser Cys Tyr Lys Val Thr Trp Glu Asn Ile Asn
            740                 745                 750
```

```
Phe Ser Lys Leu Tyr Glu Leu Ile Glu Ser Gly Arg Leu Tyr Leu Phe
        755                 760                 765

Gln Ile Tyr Asn Lys Asp Phe Glu Leu Asp Glu Asn Ile Ala Pro Lys
    770                 775                 780

Gly Tyr Asn Phe Lys Asp Lys Asn Gly Arg Arg Asn Leu His Ser Ile
785                 790                 795                 800

Tyr Trp Lys Ala Leu Phe Ser Asn Thr Asn Phe Lys Lys Thr Ile Leu
                805                 810                 815

Lys Leu Asn Gly Gly Ala Glu Leu Phe Tyr Arg Lys Leu Thr Lys Asn
            820                 825                 830

Leu Thr Lys Asp Pro Ile Ile Thr Val Lys Asn Gln Ile Lys Ile Ile
            835                 840                 845

Lys Lys Asn Asn Asn Ile Phe His Lys Lys Arg Phe Thr Gln Asn Lys
        850                 855                 860

Ile Tyr Phe His Cys Pro Val Ser Ile Asn Phe Thr Glu Asn Asp Trp
865                 870                 875                 880

Lys Ile Asn Thr Lys Ile Cys Asn Thr Ile Arg Asn Asn Ser Lys Val
                885                 890                 895

Lys Ile Ile Gly Ile Asp Arg Gly Glu Lys Asn Leu Ala Tyr Tyr Ser
            900                 905                 910

Val Ile Asp His Gln Gly Asn Ile Leu Glu Thr Asp Ser Phe Asn Glu
        915                 920                 925

Val Gln Glu Arg Glu Asp Arg Glu Pro Thr Asp Tyr Gln Lys Lys Leu
    930                 935                 940

Asp Gln Ile Gln Lys Glu Arg Asp Trp Gln Arg Lys Ser Trp Gln Glu
945                 950                 955                 960

Ile Ser Ser Ile Lys Glu Met Lys Lys Gly Tyr Ile Ser Gln Val Val
                965                 970                 975

His Gln Ile Cys Lys Leu Ile Arg Lys Tyr Glu Ala Ile Val Val Phe
            980                 985                 990

Glu Asp Leu Asn Ile Gly Phe Lys Arg Gly Arg Phe Ala Ile Glu Lys
        995                1000                1005

Gln Ile Tyr Gln Asn Leu Glu Leu Ala Leu Ala Lys Lys Leu Asn
   1010                1015                1020

Tyr Met Val Phe Lys Asp Ala Lys Glu Glu Thr Gly His Phe
   1025                1030                1035

Leu Gln Ala Tyr Gln Leu Thr Pro Pro Val Ile Asn Phe Gln Asp
   1040                1045                1050

Ile Gly Lys Gln Cys Gly Ile Ile Phe Tyr Val Pro Ala Ser Tyr
   1055                1060                1065

Thr Ser Ala Ile Cys Pro Ala Cys Gly Phe Arg Lys Asn Ile Ser
   1070                1075                1080

Thr Ser Val Glu Lys Ile Glu Lys Asn Ile Asp Leu Ile Asn Lys
   1085                1090                1095

Phe Asn Ile Val Tyr Asp Pro Asp Lys Asp Arg Phe Cys Phe Arg
   1100                1105                1110

Tyr Lys Arg Ser Asp Phe Ile Lys Ser Glu Lys Glu Lys Glu Asp
   1115                1120                1125

Asp Ser Lys Val Lys Leu Tyr Ser Asn Thr Lys Leu Pro Asp Asp
   1130                1135                1140

Phe Thr Phe Tyr Ser Asn Val Glu Arg Phe Lys Tyr Ile Arg Asp
   1145                1150                1155

Gln Asn Asn Arg Gly Gly Lys Val Glu Leu Lys Tyr Pro Asn Asp
```

```
              1160                1165                1170

Ser Leu Lys Lys Leu Phe His Glu Asn Gly Ile Asn  Phe Gln Asn
    1175                1180                1185

Phe Ser Asn Ile Ser Gln Leu Ile Lys Thr Arg Asn  Phe Glu Asn
    1190                1195                1200

Glu Asn Phe Tyr Lys Pro Phe Ile Tyr Ile Ile Ser  Leu Ile Leu
    1205                1210                1215

Gln Leu Arg Asn Thr Thr Ile Glu Ile Asn Gln Asn  Glu Asn Asn
    1220                1225                1230

Glu Lys Tyr Arg Asp Phe Ile Ser Cys Pro His Cys  Tyr Phe His
    1235                1240                1245

Ser Glu Asn Asn Leu Ile Thr Leu Thr Lys Arg Tyr  Lys Gly Lys
    1250                1255                1260

Lys Pro Phe Glu Phe Asn Gly Asp Ala Asn Gly Ala  Tyr Asn Ile
    1265                1270                1275

Ala Arg Lys Gly Ile Leu Ile Leu Gln Lys Ile Asn  Lys Ala Lys
    1280                1285                1290

Arg Leu Glu Glu Ile Glu Tyr Gly Gly Leu Thr Val  Thr Gln Gln
    1295                1300                1305

Glu Tyr Asp Lys Tyr Leu Ala Leu Val Ser Ser Lys  Lys Ala
    1310                1315                1320

<210> SEQ ID NO 123
<211> LENGTH: 1329
<212> TYPE: PRT
<213> ORGANISM: Unknown
<220> FEATURE:
<223> OTHER INFORMATION: Candidatus Gracilibacteria bacterium
      CG1_02_38_174

<400> SEQUENCE: 123

Met Ser Asn Asn Phe Gln Glu Phe Thr Gln Lys Tyr Ala Leu Ser Lys
1               5                   10                  15

Thr Leu Arg Phe Glu Leu Lys Pro Val Gly Lys Thr Lys Glu Ile Leu
            20                  25                  30

Glu Lys Glu Met Pro Met Tyr Gln Ile Ile Asn Ala Asp Lys Asn Ile
        35                  40                  45

Lys Ala Lys Tyr Ile Gln Thr Lys Pro Phe Phe Asp Gln Leu His Arg
    50                  55                  60

Asp Phe Ile Lys Glu Ala Phe Glu Asn Val Glu Leu Ser Gly Leu Ser
65                  70                  75                  80

Asp Phe Phe Glu Asn Trp Lys Ile Tyr Lys Gln Asp Lys Lys Ala Asn
                85                  90                  95

Glu Lys Ile Tyr Lys Lys Ser Ala Glu Asn Leu Arg Lys Glu Val Val
            100                 105                 110

Ser Phe Leu Asn Ala Lys Gly Lys Asp Trp Ala Glu Lys Tyr His Ser
        115                 120                 125

Ser Gly Leu Lys Lys Ala Asp Ile Glu Ile Leu Phe Glu Glu Gly Ile
    130                 135                 140

Phe Lys Val Leu Glu Ile Arg Tyr Gly Thr Asp Thr Asn Ser Phe Ile
145                 150                 155                 160

Thr Asn Ala Thr Thr Gly Glu Ile Thr Ser Ile Phe Gln Gly Trp Lys
                165                 170                 175

Gly Phe Thr Gly Tyr Phe Leu Lys Phe Trp Asn Thr Arg Glu Asn Tyr
            180                 185                 190
```

```
Tyr Lys Thr Asp Gly Thr Ser Thr Ala Ile Ala Thr Arg Ile Val Asp
            195                 200                 205

Gln Asn Leu Pro Arg Tyr Leu Glu Asn Leu Glu Ile Phe Glu Lys Met
        210                 215                 220

Lys Gly Lys Ile Asp Phe Glu Ser Val Arg Gly Asp Phe Ser Asp Phe
225                 230                 235                 240

Glu Lys Ile Gly Thr Val Glu Tyr Tyr Ser Thr Cys Leu Leu Gln Glu
                245                 250                 255

Gly Ile Asp Gly Tyr Asn Arg Ile Gly Gly Tyr Thr Tyr Glu Asn
            260                 265                 270

Gly Glu Lys Ile Lys Gly Ile Asn Glu Ile Ile Asn Leu Tyr Arg Gln
        275                 280                 285

Thr His Lys Asp Glu Lys Val Pro Phe Leu Lys Thr Leu Asp Lys Gln
    290                 295                 300

Ile Gly Ser Glu Lys Ile Ala Phe Met Glu Thr Ile Asp Thr Pro Glu
305                 310                 315                 320

Glu Phe Arg Lys Ile Phe Glu Glu Phe Val Leu Lys Ser Ser Glu Lys
                325                 330                 335

Val Val Leu Leu Lys Gln Cys Leu Asn His Leu Phe Glu Asn Glu Leu
            340                 345                 350

Thr Asp Gly Val Phe Leu Ser Lys Glu Ser Leu Asn Thr Ile Ser His
        355                 360                 365

Lys Trp Ile Asp Ile Gly Asn Met Lys Leu Phe His Glu Ser Leu Phe
    370                 375                 380

Thr Ile Leu Lys Lys Glu Gly Ala Lys Tyr Asp Ser Lys Glu Asp Glu
385                 390                 395                 400

Tyr Lys Phe Pro Asp Phe Ile Arg Ile Ser Asp Ile Lys Thr Ala Leu
                405                 410                 415

Val Lys Ile Thr Thr Glu Ser Phe Phe Trp Lys Asn Arg Tyr Leu Tyr
            420                 425                 430

Glu Lys Asp Glu Asn Pro Thr Gly Phe Leu Thr Ser Asp Asn Ser Leu
        435                 440                 445

Trp Glu Gly Phe Ile Gln Ile Phe Ser His Glu Phe Ser Ser Leu Phe
    450                 455                 460

Glu Arg Thr Glu Lys Asp Glu Glu Gly Lys Asp Ile Gln Trp Gly Tyr
465                 470                 475                 480

Asp Ile Ser Leu Leu Asn Ile Gln Lys Leu Leu Glu Asn Asn Glu Tyr
                485                 490                 495

Asn Pro Asn Asp Glu Lys Asn Lys Ile Ile Lys Ser Phe Ala Asp
            500                 505                 510

Asp Ile Leu Arg Ile Tyr Gln Met Gly Lys Tyr Phe Ala Leu Glu Lys
        515                 520                 525

Lys Arg Gln Trp Asn Pro Asp Asn Leu Glu Ile Gly Glu Phe Tyr Ser
    530                 535                 540

His Pro Glu Ile Gly Tyr Asp Lys Phe Tyr Phe Asp Ser Tyr Lys Ile
545                 550                 555                 560

Ile Val Gln Gly Tyr Asn Asp Ile Arg Asn Tyr Leu Thr Lys Asn Pro
                565                 570                 575

Trp Ser Glu Glu Lys Trp Lys Leu Asn Phe Glu Asn Pro Thr Leu Ala
            580                 585                 590

Asn Gly Trp Asp Lys Asn Lys Glu Thr Asp Asn Ser Cys Ile Phe Leu
        595                 600                 605

Lys Arg Asp Asn Lys Phe Phe Leu Ala Leu Met Ser Arg Gly Asn Asn
```

-continued

```
            610                 615                 620
Gln Val Phe Asp Glu Arg Asn Ile Gln Lys Phe Ala Gln Asn Ile Glu
625                 630                 635                 640

Gln Gly Lys Tyr Glu Lys Met Val Tyr Lys Met Lys Asp Val Ala
                    645                 650                 655

Leu Gly Ile Pro Lys Ala Thr Thr Gln Leu Asn Ala Val Gln Glu His
                660                 665                 670

Phe Phe Gln Ser Asp Lys Asp Tyr Ile Ile Thr Lys Gly Gly Ser Ser
                675                 680                 685

Ile Gly Glu Phe Ile Lys Pro Leu Arg Val Thr Lys Arg Ile Phe Glu
690                 695                 700

Leu Asn Asn Arg Ile Tyr Pro Lys Asp Asn Leu Gly Ile Ser Phe Leu
705                 710                 715                 720

Arg Asn Gln Val Asn Glu Lys Glu Gln Lys Asn Tyr Ile Lys Ile Phe
                725                 730                 735

Gln Lys Glu Phe Ile Thr Leu Gly Gly Asp Glu Val Val Tyr Lys Lys
                740                 745                 750

Ala Val His Asp Trp Ile Asp Phe Cys Lys Glu Tyr Thr Lys Ser Tyr
                755                 760                 765

Pro Ser Cys Ala Tyr Phe Asp Tyr Ser Gly Leu Lys Asp Thr Lys Glu
770                 775                 780

Tyr Ser Ser Ile Asp Glu Phe Tyr Asn Asp Leu Asp Ser Phe Gly Tyr
785                 790                 795                 800

Gln Ile Ser Trp Gln Asp Ile Ser Ser Tyr Ile Asp Glu Leu Val
                805                 810                 815

Glu Ser Gly Lys Leu Tyr Leu Phe Glu Ile Tyr Asn Gln Asp Phe Ser
                820                 825                 830

Asn Gly Lys Thr Gly Ala Lys Asn Leu His Thr Leu Tyr Phe Glu His
                835                 840                 845

Ile Phe Ser Lys Glu Asn Gln Glu Val Asn Phe Pro Leu Lys Leu Asn
850                 855                 860

Gly Gln Ala Glu Leu Phe Phe Arg Pro Lys Ser Ile Glu Ala Lys Gly
865                 870                 875                 880

Glu Asn Arg Lys Phe Asn Arg Glu Ile Ile Ala Lys Lys Arg Tyr Thr
                885                 890                 895

Glu Asp Lys Ile Phe Phe His Val Pro Leu Thr Leu Asn Arg Thr Glu
                900                 905                 910

Gly Asp Ile Tyr Gly Phe Asn Thr Glu Ile Asn Asn Phe Leu Ala His
                915                 920                 925

Asn Pro Asp Ile Asn Ile Ile Gly Ile Asp Arg Gly Glu Lys His Leu
930                 935                 940

Ala Tyr Tyr Ser Val Ile Asp Gln Lys Gly Asn Ile Ile Glu Ser Asp
945                 950                 955                 960

Ser Leu Asn Thr Val Asn Glu Ile Asn Tyr Gly Glu Lys Leu Thr Asp
                965                 970                 975

Thr Ala Glu Lys Arg Lys Gln Ala Arg Gln Asp Trp Gln Ala Val Glu
                980                 985                 990

Gly Ile Lys Asn Leu Lys Lys Gly Tyr Ile Ser Ala Val Val His Lys
                995                 1000                1005

Leu Thr Asp Leu Ile Ile Lys Tyr Asn Ala Ile Val Ile Phe Glu
        1010                1015                1020

Asp Leu Asn Met Arg Phe Lys Gln Ile Arg Gly Gly Ile Glu Lys
        1025                1030                1035
```

Ser Val Tyr Gln Gln Leu Glu Lys Ala Leu Ile Glu Lys Leu Asn
         1040                1045                1050

Tyr Leu Val Glu Lys Gly Glu Ile Asn Pro Glu Lys Ala Gly His
         1055                1060                1065

Leu Leu Asn Ala Tyr Gln Leu Thr Ala Pro Phe Glu Thr Phe Lys
         1070                1075                1080

Asp Met Gly Lys Gln Thr Gly Ile Val Phe Tyr Gln Ala Ala
         1085                1090                1095

Tyr Thr Ser Lys Ile Asp Pro Val Thr Gly Trp Arg Pro His Leu
         1100                1105                1110

Tyr Leu Lys Tyr Ser Ser Ala Glu Gln Val Lys Lys Glu Ile Ala
         1115                1120                1125

Lys Phe Ser Asn Ile Ile Trp Asn Asn Thr Glu Lys Arg Phe Asp
         1130                1135                1140

Phe Met Tyr Asp Ile Arg Asn Phe Ser Thr Gln Lys Glu Tyr Pro
         1145                1150                1155

Lys Asn Asn Ile Trp Thr Val Cys Ser Ser Val Glu Arg Tyr Arg
         1160                1165                1170

Trp Asp Lys Thr Leu Asn Gln Asn Lys Gly Asp Tyr Val His Tyr
         1175                1180                1185

Lys Ser Ile Thr Pro Glu Phe Glu Lys Leu Phe Ser Asp Phe Gln
         1190                1195                1200

Ile Asp Gly Thr Lys Asn Ile Leu Glu Gln Ile Asn Arg Met Glu
         1205                1210                1215

Thr Lys Gly Asn Glu Lys Phe Phe Lys Ser Phe Ile Phe Phe Phe
         1220                1225                1230

Gly Leu Ile Cys Gln Ile Arg Asn Thr Asn Lys Ala Asp Ser Asp
         1235                1240                1245

Glu Asn Lys Gln Asp Phe Ile Leu Ser Pro Val Pro Phe Phe
         1250                1255                1260

Asp Ser Arg Asp Ser Glu Asn Thr Lys Asn Gly Leu Pro Arg Asn
         1265                1270                1275

Gly Asp Glu Asn Gly Ala Tyr Asn Ile Ala Arg Lys Gly Leu Ile
         1280                1285                1290

Ile Leu Gln Lys Ile Asn Glu Phe Ser Asp Glu Asn Gly Asn Cys
         1295                1300                1305

Asp Lys Leu Gly Trp Lys Glu Leu Ser Ile Ser Gln Val Asp Trp
         1310                1315                1320

Asp Asn Tyr Ile Lys Thr
         1325

<210> SEQ ID NO 124
<211> LENGTH: 1231
<212> TYPE: PRT
<213> ORGANISM: Unknown
<220> FEATURE:
<223> OTHER INFORMATION: Butyrivibrio fibrisolvens MD2001

<400> SEQUENCE: 124

Met Tyr Tyr Glu Ser Leu Thr Lys Leu Tyr Pro Ile Lys Lys Thr Ile
1               5                   10                  15

Arg Asn Glu Leu Val Pro Ile Gly Lys Thr Leu Glu Asn Ile Lys Lys
            20                  25                  30

Asn Asn Ile Leu Glu Ala Asp Gly Asp Arg Lys Ile Ala Tyr Ile Arg
        35                  40                  45

```
Val Lys Ala Ile Met Asp Asp Tyr His Lys Arg Leu Ile Asn Glu Ala
    50                  55                  60

Leu Ser Gly Phe Ala Leu Ile Asp Leu Asp Lys Ala Ala Asn Leu Tyr
65                  70                  75                  80

Leu Ser Arg Ser Lys Ser Ala Asp Asp Ile Glu Ser Phe Ser Arg Phe
                85                  90                  95

Gln Asp Lys Leu Arg Lys Ala Ile Ala Lys Arg Leu Arg Glu His Glu
            100                 105                 110

Asn Phe Gly Lys Ile Gly Asn Lys Asp Ile Ile Pro Leu Leu Gln Lys
        115                 120                 125

Leu Ser Glu Asn Glu Asp Asp Tyr Asn Ala Leu Glu Ser Phe Lys Asn
    130                 135                 140

Phe Tyr Thr Tyr Phe Glu Ser Tyr Asn Asp Val Arg Leu Asn Leu Tyr
145                 150                 155                 160

Ser Asp Lys Glu Lys Ser Ser Thr Val Ala Tyr Arg Leu Ile Asn Glu
                165                 170                 175

Asn Leu Pro Arg Phe Leu Asp Asn Ile Arg Ala Tyr Asp Ala Val Gln
            180                 185                 190

Lys Ala Gly Ile Thr Ser Glu Glu Leu Ser Ser Glu Ala Gln Asp Gly
        195                 200                 205

Leu Phe Leu Val Asn Thr Phe Asn Asn Val Leu Ile Gln Asp Gly Ile
    210                 215                 220

Asn Thr Tyr Asn Glu Asp Ile Gly Lys Leu Asn Val Ala Ile Asn Leu
225                 230                 235                 240

Tyr Asn Gln Lys Asn Ala Ser Val Gln Gly Phe Arg Lys Val Pro Lys
                245                 250                 255

Met Lys Val Leu Tyr Lys Gln Ile Leu Ser Asp Arg Glu Glu Ser Phe
            260                 265                 270

Ile Asp Glu Phe Glu Ser Asp Thr Glu Leu Leu Asp Ser Leu Glu Ser
        275                 280                 285

His Tyr Ala Asn Leu Ala Lys Tyr Phe Gly Ser Asn Lys Val Gln Leu
    290                 295                 300

Leu Phe Thr Ala Leu Arg Glu Ser Lys Gly Val Asn Val Tyr Val Lys
305                 310                 315                 320

Asn Asp Ile Ala Lys Thr Ser Phe Ser Asn Val Val Phe Gly Ser Trp
                325                 330                 335

Ser Arg Ile Asp Glu Leu Ile Asn Gly Glu Tyr Asp Asp Asn Asn Asn
            340                 345                 350

Arg Lys Lys Asp Glu Lys Tyr Tyr Asp Lys Arg Gln Lys Glu Leu Lys
        355                 360                 365

Lys Asn Lys Ser Tyr Thr Ile Glu Lys Ile Ile Thr Leu Ser Thr Glu
    370                 375                 380

Asp Val Asp Val Ile Gly Lys Tyr Ile Glu Lys Leu Glu Ser Asp Ile
385                 390                 395                 400

Asp Asp Ile Arg Phe Lys Gly Lys Asn Phe Tyr Glu Ala Val Leu Cys
                405                 410                 415

Gly His Asp Arg Ser Lys Lys Leu Ser Lys Asn Lys Gly Ala Val Glu
            420                 425                 430

Ala Ile Lys Gly Tyr Leu Asp Ser Val Lys Asp Phe Glu Arg Asp Leu
        435                 440                 445

Lys Leu Ile Asn Gly Ser Gly Gln Glu Leu Glu Lys Asn Leu Val Val
    450                 455                 460
```

```
Tyr Gly Glu Gln Glu Ala Val Leu Ser Glu Leu Ser Gly Ile Asp Ser
465                 470                 475                 480

Leu Tyr Asn Met Thr Arg Asn Tyr Leu Thr Lys Lys Pro Phe Ser Thr
            485                 490                 495

Glu Lys Ile Lys Leu Asn Phe Asn Lys Pro Thr Phe Leu Asp Gly Trp
                500                 505                 510

Asp Tyr Gly Asn Glu Glu Ala Tyr Leu Gly Phe Phe Met Ile Lys Glu
            515                 520                 525

Gly Asn Tyr Phe Leu Ala Val Met Asp Ala Asn Trp Asn Lys Glu Phe
        530                 535                 540

Arg Asn Ile Pro Ser Val Asp Lys Ser Asp Cys Tyr Lys Lys Val Ile
545                 550                 555                 560

Tyr Lys Gln Ile Ser Ser Pro Glu Lys Ser Ile Gln Asn Leu Met Val
                565                 570                 575

Ile Asp Gly Lys Thr Val Lys Lys Asn Gly Arg Lys Glu Lys Glu Gly
            580                 585                 590

Ile His Ser Gly Glu Asn Leu Ile Leu Glu Glu Leu Lys Asn Thr Tyr
        595                 600                 605

Leu Pro Lys Lys Ile Asn Asp Ile Arg Lys Arg Arg Ser Tyr Leu Asn
610                 615                 620

Gly Asp Thr Phe Ser Lys Lys Asp Leu Thr Glu Phe Ile Gly Tyr Tyr
625                 630                 635                 640

Lys Gln Arg Val Ile Glu Tyr Tyr Asn Gly Tyr Ser Phe Tyr Phe Lys
                645                 650                 655

Ser Asp Asp Asp Tyr Ala Ser Phe Lys Glu Phe Gln Glu Asp Val Gly
            660                 665                 670

Arg Gln Ala Tyr Gln Ile Ser Tyr Val Asp Val Pro Val Ser Phe Val
        675                 680                 685

Asp Asp Leu Ile Asn Ser Gly Lys Leu Tyr Leu Phe Arg Val Tyr Asn
        690                 695                 700

Lys Asp Phe Ser Glu Tyr Ser Lys Gly Arg Leu Asn Leu His Thr Leu
705                 710                 715                 720

Tyr Phe Lys Met Leu Phe Asp Glu Arg Asn Leu Lys Asn Val Val Tyr
                725                 730                 735

Lys Leu Asn Gly Gln Ala Glu Val Phe Tyr Arg Pro Ser Ser Ile Lys
            740                 745                 750

Lys Glu Glu Leu Ile Val His Arg Ala Gly Glu Glu Ile Lys Asn Lys
        755                 760                 765

Asn Pro Lys Arg Ala Ala Gln Lys Pro Thr Arg Leu Asp Tyr Asp
770                 775                 780

Ile Val Lys Asp Arg Arg Tyr Ser Gln Asp Lys Phe Met Leu His Thr
785                 790                 795                 800

Ser Ile Ile Met Asn Phe Gly Ala Glu Glu Asn Val Ser Phe Asn Asp
                805                 810                 815

Ile Val Asn Gly Val Leu Arg Asn Glu Asp Lys Val Asn Val Ile Gly
            820                 825                 830

Ile Asp Arg Gly Glu Arg Asn Leu Leu Tyr Val Val Ile Asp Pro
        835                 840                 845

Glu Gly Lys Ile Leu Glu Gln Arg Ser Leu Asn Cys Ile Thr Asp Ser
        850                 855                 860

Asn Leu Asp Ile Glu Thr Asp Tyr His Arg Leu Leu Asp Glu Lys Glu
865                 870                 875                 880

Ser Asp Arg Lys Ile Ala Arg Arg Asp Trp Thr Thr Ile Glu Asn Ile
```

885                 890                 895

Lys Glu Leu Lys Ala Gly Tyr Leu Ser Gln Val Val His Ile Val Ala
                900                 905                 910

Glu Leu Val Leu Lys Tyr Asn Ala Ile Ile Cys Leu Glu Asp Leu Asn
                915                 920                 925

Phe Gly Phe Lys Arg Gly Arg Gln Lys Val Glu Lys Gln Val Tyr Gln
930                 935                 940

Lys Phe Glu Lys Met Leu Ile Asp Lys Leu Asn Tyr Leu Val Met Asp
945                 950                 955                 960

Lys Ser Arg Glu Gln Leu Ser Pro Glu Lys Ile Ser Gly Ala Leu Asn
                965                 970                 975

Ala Leu Gln Leu Thr Pro Asp Phe Lys Ser Phe Lys Val Leu Gly Lys
                980                 985                 990

Gln Thr Gly Ile Ile Tyr Tyr Val Pro Ala Tyr Leu Thr Ser Lys Ile
                995                 1000                1005

Asp Pro Met Thr Gly Phe Ala Asn Leu Phe Tyr Val Lys Tyr Glu
        1010                1015                1020

Asn Val Asp Lys Ala Lys Glu Phe Phe Ser Lys Phe Asp Ser Ile
        1025                1030                1035

Lys Tyr Asn Lys Asp Gly Lys Asn Trp Asn Thr Lys Gly Tyr Phe
        1040                1045                1050

Glu Phe Ala Phe Asp Tyr Lys Lys Phe Thr Asp Arg Ala Tyr Gly
        1055                1060                1065

Arg Val Ser Glu Trp Thr Val Cys Thr Val Gly Glu Arg Ile Ile
        1070                1075                1080

Lys Phe Lys Asn Lys Glu Lys Asn Asn Ser Tyr Asp Asp Lys Val
        1085                1090                1095

Ile Asp Leu Thr Asn Ser Leu Lys Glu Leu Phe Asp Ser Tyr Lys
        1100                1105                1110

Val Thr Tyr Glu Ser Glu Val Asp Leu Lys Asp Ala Ile Leu Ala
        1115                1120                1125

Ile Asp Asp Pro Ala Phe Tyr Arg Asp Leu Thr Arg Arg Leu Gln
        1130                1135                1140

Gln Thr Leu Gln Met Arg Asn Ser Ser Cys Asp Gly Ser Arg Asp
        1145                1150                1155

Tyr Ile Ile Ser Pro Val Lys Asn Ser Lys Gly Glu Phe Phe Cys
        1160                1165                1170

Ser Asp Asn Asn Asp Asp Thr Thr Pro Asn Asp Ala Asp Ala Asn
        1175                1180                1185

Gly Ala Phe Asn Ile Ala Arg Lys Gly Leu Trp Val Leu Asn Glu
        1190                1195                1200

Ile Arg Asn Ser Glu Glu Gly Ser Lys Ile Asn Leu Ala Met Ser
        1205                1210                1215

Asn Ala Gln Trp Leu Glu Tyr Ala Gln Asp Asn Thr Ile
        1220                1225                1230

<210> SEQ ID NO 125
<211> LENGTH: 999
<212> TYPE: PRT
<213> ORGANISM: Unknown
<220> FEATURE:
<223> OTHER INFORMATION: Sneathia amnii strain SN35

<400> SEQUENCE: 125

Met Asn Leu Leu Ile Asn Glu Val Asn Gln Lys Tyr Lys Ser Lys Leu

-continued

```
1               5                   10                  15
Asn Val Phe Asn Ser Leu Tyr Lys Gln Ile Leu Thr Glu Glu Asp Thr
                20                  25                  30
Lys Ser Phe Val Asp Glu Ile Leu Leu Thr Pro Glu Ser Val Ile Lys
                35                  40                  45
Thr Ile Asp Asn Phe Ile Asp Ser Ile Ile Met Asn Asp Ile Glu Gly
                50                  55                  60
Leu Lys Glu Glu Phe Leu Lys Ile Ser Leu Glu Asn Phe Glu Gly Ile
65                  70                  75                  80
Tyr Ile Ser Asn Lys Lys Leu Asn Glu Ile Ser Asn Arg Lys Phe Gly
                85                  90                  95
Asp Tyr Asn Ser Ile Asn Met Met Ile Lys Gln Ser Met Asn Glu Lys
                100                 105                 110
Gly Ile Leu Ser Lys Lys Glu Ile Asn Glu Leu Ile Pro Asp Leu Glu
                115                 120                 125
Asn Ile Asn Lys Pro Lys Val Lys Ser Phe Asn Leu Ser Phe Ile Phe
                130                 135                 140
Glu Asn Leu Thr Lys Glu His Lys Glu Leu Ile Ile Asp Tyr Ile Arg
145                 150                 155                 160
Glu Asn Ile Cys Asn Val Ile Glu Asn Val Lys Ile Thr Ile Glu Lys
                165                 170                 175
Tyr Arg Asn Ile Asp Asn Lys Ile Glu Phe Lys Asn Asn Ala Glu Lys
                180                 185                 190
Val Ser Lys Ile Lys Glu Met Leu Glu Ser Ile Asn Glu Leu Cys Lys
                195                 200                 205
Leu Ile Lys Glu Phe Asn Thr Asp Glu Ile Glu Lys Asn Asn Glu Phe
210                 215                 220
Tyr Asn Ile Leu Asn Lys Asn Phe Glu Ile Phe Glu Ser Ser Tyr Lys
225                 230                 235                 240
Val Leu Asn Lys Val Arg Asn Phe Val Thr Lys Lys Glu Val Ile Glu
                245                 250                 255
Asn Lys Met Lys Leu Asn Phe Ser Asn Tyr Gln Leu Gly Asn Gly Trp
                260                 265                 270
His Lys Asn Lys Glu Lys Asp Cys Ser Ile Ile Leu Phe Arg Lys Arg
                275                 280                 285
Asn Asn Glu Arg Trp Ile Tyr Tyr Leu Gly Ile Leu Lys His Gly Thr
                290                 295                 300
Lys Ile Lys Glu Asn Asp Tyr Leu Ser Ser Val Asp Thr Gly Phe Tyr
305                 310                 315                 320
Lys Met Asp Tyr Tyr Ala Gln Asn Ser Leu Ser Lys Met Ile Pro Lys
                325                 330                 335
Cys Ser Ile Thr Val Lys Asn Val Lys Asn Ala Pro Glu Asp Glu Ser
                340                 345                 350
Val Ile Leu Asn Asp Ser Lys Lys Phe Asn Glu Pro Leu Glu Ile Thr
                355                 360                 365
Pro Glu Ile Arg Lys Leu Tyr Gly Asn Asn Glu His Ile Lys Gly Asp
                370                 375                 380
Lys Phe Lys Lys Glu Ser Leu Val Lys Trp Ile Asp Phe Cys Lys Glu
385                 390                 395                 400
Phe Leu Leu Lys Tyr Lys Ser Phe Glu Lys Ala Lys Lys Glu Ile Leu
                405                 410                 415
Lys Leu Lys Glu Ser Asn Leu Tyr Glu Asn Leu Glu Glu Phe Tyr Ser
                420                 425                 430
```

```
Asp Ala Glu Glu Lys Ala Tyr Phe Leu Glu Phe Ile Asn Ile Asp Glu
            435                 440                 445

Asp Lys Ile Lys Lys Leu Val Lys Glu Lys Asn Leu Tyr Leu Phe Gln
450                 455                 460

Ile Tyr Asn Lys Asp Phe Ser Ala Tyr Ser Thr Gly Asn Lys Asn Leu
465                 470                 475                 480

His Thr Met Tyr Phe Glu Glu Leu Phe Thr Asp Glu Asn Leu Lys Lys
                    485                 490                 495

Pro Val Phe Lys Leu Asn Gly Asn Thr Glu Val Phe Tyr Arg Ile Ala
                500                 505                 510

Ser Ser Lys Pro Lys Ile Val His Asn Lys Gly Glu Lys Leu Val Asn
            515                 520                 525

Lys Thr Tyr Leu Asp Asp Gly Ile Ile Lys Thr Ile Pro Asp Ser Val
        530                 535                 540

Tyr Glu Glu Ile Ser Glu Lys Val Lys Asn Asn Glu Asp Tyr Ser Lys
545                 550                 555                 560

Leu Leu Glu Glu Asn Asn Ile Lys Asn Leu Glu Ile Lys Val Ala Thr
                    565                 570                 575

His Glu Ile Val Lys Asp Lys Arg Tyr Phe Glu Asn Lys Phe Leu Phe
                580                 585                 590

Tyr Leu Pro Ile Thr Leu Asn Lys Lys Val Ser Asn Lys Asn Thr Asn
            595                 600                 605

Lys Asn Ile Asn Lys Asn Val Ile Asp Glu Ile Lys Asp Cys Asn Glu
        610                 615                 620

Tyr Asn Val Ile Gly Ile Asp Arg Gly Glu Arg Asn Leu Ile Ser Leu
625                 630                 635                 640

Cys Ile Ile Asn Gln Asn Gly Glu Ile Ile Leu Gln Lys Glu Met Asn
                    645                 650                 655

Ile Ile Gln Ser Ser Asp Lys Tyr Asn Val Asp Tyr Asn Glu Lys Leu
                660                 665                 670

Glu Ile Lys Ser Lys Glu Arg Asp Asn Ala Lys Lys Asn Trp Ser Glu
            675                 680                 685

Ile Gly Lys Ile Lys Asp Leu Lys Ser Gly Tyr Leu Ser Ala Val Val
        690                 695                 700

His Glu Ile Val Lys Leu Ala Ile Glu Tyr Asn Ala Val Ile Ile Leu
705                 710                 715                 720

Glu Asp Leu Asn Asn Gly Phe Lys Asn Ser Arg Lys Lys Val Asp Lys
                    725                 730                 735

Gln Ile Tyr Gln Lys Phe Glu Arg Ala Leu Ile Glu Lys Leu Gln Phe
                740                 745                 750

Leu Ile Phe Lys Asn Tyr Asp Lys Asn Glu Lys Gly Gly Leu Arg Asn
            755                 760                 765

Ala Phe Gln Leu Thr Pro Glu Leu Lys Asn Ile Thr Lys Val Ala Ser
        770                 775                 780

Gln Gln Gly Ile Ile Tyr Thr Asn Pro Ala Tyr Thr Ser Lys Ile
785                 790                 795                 800

Asp Pro Thr Thr Gly Tyr Ala Asn Ile Ile Lys Lys Ser Asn Asn
                    805                 810                 815

Glu Glu Ser Ile Val Lys Ala Ile Asp Lys Ile Ser Tyr Asp Lys Glu
                820                 825                 830

Lys Asp Met Phe Tyr Phe Asp Ile Asn Leu Ser Asn Ser Ser Phe Asn
            835                 840                 845
```

```
Leu Thr Val Lys Asn Val Leu Lys Lys Glu Trp Arg Ile Tyr Thr Asn
    850                 855                 860

Gly Glu Arg Ile Ile Tyr Lys Asp Arg Lys Tyr Ile Thr Leu Asn Ile
865                 870                 875                 880

Thr Gln Glu Met Lys Asp Ile Leu Ser Lys Cys Gly Ile Asp Tyr Leu
                885                 890                 895

Asn Ile Asp Asn Leu Lys Gln Asp Ile Leu Lys Asn Lys Leu His Lys
                900                 905                 910

Lys Val Tyr Tyr Ile Phe Glu Leu Ala Asn Lys Met Arg Asn Glu Asn
            915                 920                 925

Lys Asp Val Asp Tyr Ile Ile Ser Pro Val Leu Asn Lys Asp Gly Lys
            930                 935                 940

Phe Phe Met Thr Gln Glu Ile Asn Glu Leu Thr Pro Lys Asp Ala Asp
945                 950                 955                 960

Leu Asn Gly Ala Tyr Asn Ile Ala Leu Lys Gly Lys Leu Met Ile Asp
                965                 970                 975

Asn Leu Asn Lys Lys Glu Lys Phe Val Phe Leu Ser Asn Glu Asp Trp
                980                 985                 990

Leu Asn Phe Ile Gln Gly Arg
        995
```

<210> SEQ ID NO 126
<211> LENGTH: 1287
<212> TYPE: PRT
<213> ORGANISM: Unknown
<220> FEATURE:
<223> OTHER INFORMATION: Coprococcus eutactus strain 2789STDY5608843

<400> SEQUENCE: 126

```
Met Asn Asn Thr Asn Ser Phe Glu Pro Phe Ile Gly Gly Asn
1               5                   10                  15

Ser Val Ser Lys Thr Leu Arg Asn Glu Leu Arg Val Gly Ser Glu Tyr
            20                  25                  30

Thr Gly Lys His Ile Lys Glu Cys Ala Ile Ile Ala Glu Asp Ala Val
        35                  40                  45

Lys Ala Glu Asn Gln Tyr Ile Val Lys Glu Met Met Asp Asp Phe Tyr
    50                  55                  60

Arg Asp Phe Ile Asn Arg Lys Leu Asp Ala Leu Gln Gly Ile Asn Trp
65                  70                  75                  80

Glu Gln Leu Phe Asp Ile Met Lys Lys Ala Lys Leu Asp Lys Ser Asn
                85                  90                  95

Lys Val Ser Lys Glu Leu Asp Lys Ile Gln Glu Ser Thr Arg Lys Glu
            100                 105                 110

Ile Val Lys Ile Phe Ser Ser Asp Pro Ile Tyr Lys Asp Met Leu Lys
        115                 120                 125

Ala Asp Met Ile Ser Lys Ile Leu Pro Glu Tyr Ile Val Asp Lys Tyr
    130                 135                 140

Gly Asp Ala Ala Ser Arg Ile Glu Ala Val Lys Val Phe Tyr Gly Phe
145                 150                 155                 160

Ser Gly Tyr Phe Ile Asp Phe Trp Ala Ser Arg Lys Asn Val Phe Ser
                165                 170                 175

Asp Lys Asn Ile Ala Ser Ala Ile Pro His Arg Ile Val Asn Val Asn
            180                 185                 190

Ala Arg Ile His Leu Asp Asn Ile Thr Ala Phe Asn Arg Ile Ala Glu
        195                 200                 205
```

-continued

Ile Ala Gly Asp Glu Val Ala Gly Ile Ala Glu Asp Ala Cys Ala Tyr
    210                 215                 220

Leu Gln Asn Met Ser Leu Glu Asp Val Phe Thr Gly Ala Cys Tyr Gly
225                 230                 235                 240

Glu Phe Ile Cys Gln Lys Asp Ile Asp Arg Tyr Asn Asn Ile Cys Gly
                245                 250                 255

Val Ile Asn Gln His Met Asn Gln Tyr Cys Gln Asn Lys Lys Ile Ser
            260                 265                 270

Arg Ser Lys Phe Lys Met Glu Arg Leu His Lys Gln Ile Leu Cys Arg
        275                 280                 285

Ser Glu Ser Gly Phe Glu Ile Pro Ile Gly Phe Gln Thr Asp Gly Glu
    290                 295                 300

Val Ile Asp Ala Ile Asn Ser Phe Ser Thr Ile Leu Glu Glu Lys Asp
305                 310                 315                 320

Ile Leu Asp Arg Leu Arg Thr Leu Ser Gln Glu Val Thr Gly Tyr Asp
                325                 330                 335

Met Glu Arg Ile Tyr Val Ser Ser Lys Ala Phe Glu Ser Val Ser Lys
            340                 345                 350

Tyr Ile Asp His Lys Trp Asp Val Ile Ala Ser Ser Met Tyr Asn Tyr
        355                 360                 365

Phe Ser Gly Ala Val Arg Gly Lys Asp Lys Lys Asp Ala Lys Ile
370                 375                 380

Gln Thr Glu Ile Lys Lys Ile Lys Ser Cys Ser Leu Leu Asp Leu Lys
385                 390                 395                 400

Lys Leu Val Asp Met Tyr Tyr Lys Met Asp Gly Met Cys Leu Glu His
                405                 410                 415

Glu Ala Thr Glu Tyr Val Ala Gly Ile Thr Glu Ile Leu Val Asp Phe
            420                 425                 430

Asn Tyr Lys Thr Phe Asp Met Asp Asp Ser Val Lys Met Ile Gln Asn
        435                 440                 445

Glu His Met Ile Asn Glu Ile Lys Glu Tyr Leu Asp Thr Tyr Met Ser
    450                 455                 460

Ile Tyr His Trp Ala Lys Asp Phe Met Ile Asp Glu Leu Val Asp Arg
465                 470                 475                 480

Asp Met Glu Phe Tyr Ser Glu Leu Asp Glu Ile Tyr Tyr Asp Leu Ser
                485                 490                 495

Asp Ile Val Pro Leu Tyr Asn Lys Val Arg Asn Tyr Val Thr Gln Lys
            500                 505                 510

Pro Tyr Ser Gln Asp Lys Ile Lys Leu Asn Phe Gly Ser Pro Thr Leu
        515                 520                 525

Ala Asn Gly Trp Ser Lys Ser Lys Glu Phe Asp Asn Asn Val Val Val
    530                 535                 540

Leu Leu Arg Asp Glu Lys Ile Tyr Leu Ala Ile Leu Asn Val Gly Asn
545                 550                 555                 560

Lys Pro Ser Lys Asp Ile Met Ala Gly Glu Asp Arg Arg Arg Ser Asp
                565                 570                 575

Thr Asp Tyr Lys Lys Met Asn Tyr Tyr Leu Leu Pro Gly Ala Ser Lys
            580                 585                 590

Thr Leu Pro His Val Phe Ile Ser Ser Asn Ala Trp Lys Lys Ser His
        595                 600                 605

Gly Ile Pro Asp Glu Ile Met Tyr Gly Tyr Asn Gln Asn Lys His Leu
    610                 615                 620

Lys Ser Ser Pro Asn Phe Asp Leu Glu Phe Cys Arg Lys Leu Ile Asp

```
                625                 630                 635                 640
Tyr Tyr Lys Glu Cys Ile Asp Ser Tyr Pro Asn Tyr Gln Ile Phe Asn
                        645                 650                 655

Phe Lys Phe Ala Ala Thr Glu Thr Tyr Asn Asp Ile Ser Glu Phe Tyr
                660                 665                 670

Lys Asp Val Glu Arg Gln Gly Tyr Lys Ile Glu Trp Ser Tyr Ile Ser
                675                 680                 685

Glu Asp Asp Ile Asn Gln Met Asp Arg Asp Gly Gln Ile Tyr Leu Phe
            690                 695                 700

Gln Ile Tyr Asn Lys Asp Phe Ala Pro Asn Ser Lys Gly Met Gln Asn
705                 710                 715                 720

Leu His Thr Leu Tyr Leu Lys Asn Ile Phe Ser Glu Glu Asn Leu Ser
                    725                 730                 735

Asp Val Val Ile Lys Leu Asn Gly Glu Ala Glu Leu Phe Phe Arg Lys
                740                 745                 750

Ser Ser Ile Gln His Lys Arg Gly His Lys Lys Gly Ser Val Leu Val
            755                 760                 765

Asn Lys Thr Tyr Lys Thr Thr Glu Lys Thr Glu Asn Gly Gln Gly Glu
770                 775                 780

Ile Glu Val Ile Glu Ser Val Pro Asp Gln Cys Tyr Leu Glu Leu Val
785                 790                 795                 800

Lys Tyr Trp Ser Glu Gly Gly Val Gly Gln Leu Ser Glu Glu Ala Ser
                805                 810                 815

Lys Tyr Lys Asp Lys Val Ser His Tyr Ala Ala Thr Met Asp Ile Val
                820                 825                 830

Lys Asp Arg Arg Tyr Thr Glu Asp Lys Phe Phe Ile His Met Pro Ile
            835                 840                 845

Thr Ile Asn Phe Lys Ala Asp Asn Arg Asn Asn Val Asn Glu Lys Val
        850                 855                 860

Leu Lys Phe Ile Ala Glu Asn Asp Asp Leu His Val Ile Gly Ile Asp
865                 870                 875                 880

Arg Gly Glu Arg Asn Leu Leu Tyr Val Ser Val Ile Asp Ser Arg Gly
                885                 890                 895

Arg Ile Val Glu Gln Lys Ser Phe Asn Ile Val Glu Asn Tyr Glu Ser
            900                 905                 910

Ser Lys Asn Val Ile Arg Arg His Asp Tyr Lys Gly Lys Leu Val Asn
        915                 920                 925

Lys Glu His Tyr Arg Asn Glu Ala Arg Lys Ser Trp Lys Glu Ile Gly
    930                 935                 940

Lys Ile Lys Glu Ile Lys Glu Gly Tyr Leu Ser Gln Val Ile His Glu
945                 950                 955                 960

Ile Ser Lys Leu Val Leu Lys Tyr Asn Ala Ile Ile Val Met Glu Asp
                965                 970                 975

Leu Asn Tyr Gly Phe Lys Arg Gly Arg Phe Lys Val Glu Arg Gln Val
            980                 985                 990

Tyr Gln Lys Phe Glu Thr Met Leu  Ile Asn Lys Leu Ala  Tyr Leu Val
        995                 1000                1005

Asp Lys  Ser Arg Ala Val Asp  Glu Pro Gly Gly Leu  Leu Lys Gly
    1010                1015                1020

Tyr Gln Leu Thr Tyr Val Pro  Asp Asn Leu Gly Glu  Leu Gly Ser
        1025                1030                1035

Gln Cys  Gly Ile Ile Phe Tyr  Val Pro Ala Ala Tyr  Thr Ser Lys
    1040                1045                1050
```

```
Ile Asp Pro Val Thr Gly Phe Val Asp Val Phe Asp Phe Lys Ala
    1055                1060                1065

Tyr Ser Asn Ala Glu Ala Arg Leu Asp Phe Ile Asn Lys Leu Asp
    1070                1075                1080

Cys Ile Arg Tyr Asp Ala Ser Arg Asn Lys Phe Glu Ile Ala Phe
    1085                1090                1095

Asp Tyr Gly Asn Phe Arg Thr His His Thr Thr Leu Ala Lys Thr
    1100                1105                1110

Ser Trp Thr Ile Phe Ile His Gly Asp Arg Ile Lys Lys Glu Arg
    1115                1120                1125

Gly Ser Tyr Gly Trp Lys Asp Glu Ile Ile Asp Ile Glu Ala Arg
    1130                1135                1140

Ile Arg Lys Leu Phe Glu Asp Thr Asp Ile Glu Tyr Ala Asp Gly
    1145                1150                1155

His Asn Leu Ile Gly Asp Ile Asn Glu Leu Glu Ser Pro Ile Gln
    1160                1165                1170

Lys Lys Phe Val Gly Glu Leu Phe Asp Ile Ile Arg Phe Thr Val
    1175                1180                1185

Gln Leu Arg Asn Ser Lys Ser Glu Lys Tyr Asp Gly Thr Glu Lys
    1190                1195                1200

Glu Tyr Asp Lys Ile Ile Ser Pro Val Met Asp Glu Glu Gly Val
    1205                1210                1215

Phe Phe Thr Thr Asp Ser Tyr Ile Arg Ala Asp Gly Thr Glu Leu
    1220                1225                1230

Pro Lys Asp Ala Asp Ala Asn Gly Ala Tyr Cys Ile Ala Leu Lys
    1235                1240                1245

Gly Leu Tyr Asp Val Leu Ala Val Lys Lys Tyr Trp Lys Glu Gly
    1250                1255                1260

Glu Lys Phe Asp Arg Lys Leu Leu Ala Ile Thr Asn Tyr Asn Trp
    1265                1270                1275

Phe Asp Phe Ile Gln Asn Arg Arg Phe
    1280                1285

<210> SEQ ID NO 127
<211> LENGTH: 1305
<212> TYPE: PRT
<213> ORGANISM: Unknown
<220> FEATURE:
<223> OTHER INFORMATION: Lachnospira pectinoschiza strain
      2789STDY5834886

<400> SEQUENCE: 127

Met Asn Lys Ala Ala Asp Asn Tyr Thr Gly Gly Asn Tyr Asp Glu Phe
1               5                   10                  15

Ile Ala Leu Ser Lys Val Gln Lys Thr Leu Arg Asn Glu Leu Lys Pro
                20                  25                  30

Thr Pro Phe Thr Ala Glu His Ile Lys Gln Arg Gly Ile Ile Ser Glu
            35                  40                  45

Asp Glu Tyr Arg Ala Gln Gln Ser Leu Glu Leu Lys Lys Ile Ala Asp
        50                  55                  60

Glu Tyr Tyr Arg Asn Tyr Ile Thr His Lys Leu Asn Asp Ile Asn Asn
65                  70                  75                  80

Leu Asp Phe Tyr Asn Leu Phe Asp Ala Ile Glu Glu Lys Tyr Lys Lys
                85                  90                  95

Asn Asp Lys Asp Asn Arg Asp Lys Leu Asp Leu Val Glu Lys Ser Lys
```

```
            100             105              110
Arg Gly Glu Ile Ala Lys Met Leu Ser Ala Asp Asp Asn Phe Lys Ser
            115             120             125

Met Phe Glu Ala Lys Leu Ile Thr Lys Leu Leu Pro Asp Tyr Val Glu
            130             135             140

Arg Asn Tyr Thr Gly Glu Asp Lys Glu Lys Ala Leu Glu Thr Leu Ala
145             150             155             160

Leu Phe Lys Gly Phe Thr Thr Tyr Phe Lys Gly Tyr Phe Lys Thr Arg
                165             170             175

Lys Asn Met Phe Ser Gly Glu Gly Ala Ser Ser Ile Cys His Arg
            180             185             190

Ile Val Asn Val Asn Ala Ser Ile Phe Tyr Asp Asn Leu Lys Thr Phe
            195             200             205

Met Arg Ile Gln Glu Lys Ala Gly Asp Glu Ile Ala Leu Ile Glu Glu
            210             215             220

Glu Leu Thr Glu Lys Leu Asp Gly Trp Arg Leu Glu His Ile Phe Ser
225             230             235             240

Arg Asp Tyr Tyr Asn Glu Val Leu Ala Gln Lys Gly Ile Asp Tyr Tyr
                245             250             255

Asn Gln Ile Cys Gly Asp Ile Asn Lys His Met Asn Leu Tyr Cys Gln
            260             265             270

Gln Asn Lys Phe Lys Ala Asn Ile Phe Lys Met Met Lys Leu Gln Lys
            275             280             285

Gln Ile Met Gly Ile Ser Glu Lys Val Phe Glu Ile Pro Pro Met Tyr
            290             295             300

Gln Asn Asp Glu Glu Val Tyr Ala Ser Phe Asn Glu Phe Ile Ser Arg
305             310             315             320

Leu Glu Glu Val Lys Leu Thr Asp Arg Leu Arg Asn Ile Leu Gln Asn
                325             330             335

Ile Asn Ile Tyr Asn Thr Ala Lys Ile Tyr Ile Asn Ala Arg Tyr Tyr
            340             345             350

Thr Asn Val Ser Thr Tyr Val Tyr Gly Gly Trp Gly Val Ile Glu Ser
            355             360             365

Ala Ile Glu Arg Tyr Leu Cys Asn Thr Ile Ala Gly Lys Gly Gln Ser
            370             375             380

Lys Val Lys Lys Ile Glu Asn Ala Lys Lys Asp Asn Lys Phe Met Ser
385             390             395             400

Val Lys Glu Leu Asp Ser Ile Val Ala Glu Tyr Glu Pro Asp Tyr Phe
                405             410             415

Asn Ala Pro Tyr Ile Asp Asp Asp Asn Ala Val Lys Val Phe Gly
            420             425             430

Gly Gln Gly Val Leu Gly Tyr Phe Asn Lys Met Ser Glu Leu Leu Ala
            435             440             445

Asp Val Ser Leu Tyr Thr Ile Asp Tyr Asn Ser Asp Asp Ser Leu Ile
            450             455             460

Glu Asn Lys Glu Ser Ala Leu Arg Ile Lys Lys Gln Leu Asp Asp Ile
465             470             475             480

Met Ser Leu Tyr His Trp Leu Gln Thr Phe Ile Ile Asp Glu Val Val
                485             490             495

Glu Lys Asp Asn Ala Phe Tyr Ala Glu Leu Glu Asp Ile Cys Cys Glu
            500             505             510

Leu Glu Asn Val Val Thr Leu Tyr Asp Arg Ile Arg Asn Tyr Val Thr
            515             520             525
```

```
Arg Lys Pro Tyr Ser Thr Gln Lys Phe Lys Leu Asn Phe Ala Ser Pro
    530                 535                 540

Thr Leu Ala Ser Gly Trp Ser Arg Ser Lys Glu Phe Asp Asn Asn Ala
545                 550                 555                 560

Ile Ile Leu Leu Arg Asn Asn Lys Tyr Tyr Ile Ala Ile Phe Asn Val
                565                 570                 575

Asn Asn Lys Pro Asp Lys Gln Ile Ile Lys Gly Ser Glu Glu Gln Arg
            580                 585                 590

Leu Ser Thr Asp Tyr Lys Lys Met Val Tyr Asn Leu Leu Pro Gly Pro
        595                 600                 605

Asn Lys Met Leu Pro Lys Val Phe Ile Lys Ser Asp Thr Gly Lys Arg
    610                 615                 620

Asp Tyr Asn Pro Ser Ser Tyr Ile Leu Glu Gly Tyr Glu Lys Asn Arg
625                 630                 635                 640

His Ile Lys Ser Ser Gly Asn Phe Asp Ile Asn Tyr Cys His Asp Leu
                645                 650                 655

Ile Asp Tyr Tyr Lys Ala Cys Ile Asn Lys His Pro Glu Trp Lys Asn
            660                 665                 670

Tyr Gly Phe Lys Phe Lys Glu Thr Asn Gln Tyr Asn Asp Ile Gly Gln
        675                 680                 685

Phe Tyr Lys Asp Val Glu Lys Gln Gly Tyr Ser Ile Ser Trp Ala Tyr
    690                 695                 700

Ile Ser Glu Glu Asp Ile Asn Lys Leu Asp Glu Gly Lys Ile Tyr
705                 710                 715                 720

Leu Phe Glu Ile Tyr Asn Lys Asp Leu Ser Ala His Ser Thr Gly Arg
                725                 730                 735

Asp Asn Leu His Thr Met Tyr Leu Lys Asn Ile Phe Ser Glu Asp Asn
            740                 745                 750

Leu Lys Asn Ile Cys Ile Glu Leu Asn Gly Glu Ala Glu Leu Phe Tyr
        755                 760                 765

Arg Lys Ser Ser Met Lys Ser Asn Ile Thr His Lys Lys Asp Thr Ile
    770                 775                 780

Leu Val Asn Lys Thr Tyr Ile Asn Glu Thr Gly Val Arg Val Ser Leu
785                 790                 795                 800

Ser Asp Glu Asp Tyr Met Lys Val Tyr Asn Tyr Tyr Asn Asn Asn Tyr
                805                 810                 815

Val Ile Asp Thr Glu Asn Asp Lys Asn Leu Ile Asp Ile Glu Lys
            820                 825                 830

Ile Gly His Arg Lys Ser Lys Ile Asp Ile Val Lys Asp Lys Arg Tyr
        835                 840                 845

Thr Glu Asp Lys Tyr Phe Leu Tyr Leu Pro Ile Thr Ile Asn Tyr Gly
    850                 855                 860

Ile Glu Asp Glu Asn Val Asn Ser Lys Ile Ile Glu Tyr Ile Ala Lys
865                 870                 875                 880

Gln Asp Asn Met Asn Val Ile Gly Ile Asp Arg Gly Glu Arg Asn Leu
                885                 890                 895

Ile Tyr Ile Ser Val Ile Asp Asn Lys Gly Asn Ile Ile Glu Gln Lys
            900                 905                 910

Ser Phe Asn Leu Val Asn Asn Tyr Asp Tyr Lys Asn Lys Leu Lys Asn
        915                 920                 925

Met Glu Lys Thr Arg Asp Asn Ala Arg Lys Asn Trp Gln Glu Ile Gly
    930                 935                 940
```

```
Lys Ile Lys Asp Val Lys Ser Gly Tyr Leu Ser Gly Val Ile Ser Lys
945                 950                 955                 960

Ile Ala Arg Met Val Ile Asp Tyr Asn Ala Ile Ile Val Met Glu Asp
                965                 970                 975

Leu Asn Lys Gly Phe Lys Arg Gly Arg Phe Lys Val Glu Arg Gln Val
            980                 985                 990

Tyr Gln Lys Phe Glu Asn Met Leu Ile Ser Lys Leu Asn Tyr Leu Val
        995                 1000                1005

Phe Lys Glu Arg Lys Ala Asp Glu Asn Gly Gly Ile Leu Arg Gly
    1010                1015                1020

Tyr Gln Leu Thr Tyr Ile Pro Lys Ser Ile Lys Asn Val Gly Lys
    1025                1030                1035

Gln Cys Gly Cys Ile Phe Tyr Val Pro Ala Ala Tyr Thr Ser Lys
    1040                1045                1050

Ile Asp Pro Ala Thr Gly Phe Ile Asn Ile Phe Asp Phe Lys Lys
    1055                1060                1065

Tyr Ser Gly Ser Gly Ile Asn Ala Lys Val Lys Asp Lys Lys Glu
    1070                1075                1080

Phe Leu Met Ser Met Asn Ser Ile Arg Tyr Ile Asn Glu Gly Ser
    1085                1090                1095

Glu Glu Tyr Glu Lys Ile Gly His Arg Glu Leu Phe Ala Phe Ser
    1100                1105                1110

Phe Asp Tyr Asn Asn Phe Lys Thr Tyr Asn Val Ser Ser Pro Val
    1115                1120                1125

Asn Glu Trp Thr Ala Tyr Thr Tyr Gly Glu Arg Ile Lys Lys Leu
    1130                1135                1140

Tyr Lys Asp Gly Arg Trp Leu Arg Ser Glu Val Leu Asn Leu Thr
    1145                1150                1155

Glu Asn Leu Ile Lys Leu Met Glu Gln Tyr Asn Ile Glu Tyr Lys
    1160                1165                1170

Asp Gly His Asp Ile Arg Glu Asp Ile Ser His Met Asp Glu Thr
    1175                1180                1185

Arg Asn Ala Asp Phe Ile Cys Ser Leu Phe Glu Glu Leu Lys Tyr
    1190                1195                1200

Thr Val Gln Leu Arg Asn Ser Lys Ser Glu Ala Glu Asp Glu Asn
    1205                1210                1215

Tyr Asp Arg Leu Val Ser Pro Ile Leu Asn Ser Ser Asn Gly Phe
    1220                1225                1230

Tyr Asp Ser Ser Asp Tyr Met Glu Asn Glu Asn Thr Thr His
    1235                1240                1245

Thr Met Pro Lys Asp Ala Asp Ala Asn Gly Ala Tyr Cys Ile Ala
    1250                1255                1260

Leu Lys Gly Leu Tyr Glu Ile Asn Lys Ile Lys Gln Asn Trp Ser
    1265                1270                1275

Asp Asp Lys Lys Phe Lys Glu Asn Glu Leu Tyr Ile Asn Val Thr
    1280                1285                1290

Glu Trp Leu Asp Tyr Ile Gln Asn Arg Arg Phe Glu
    1295                1300                1305

<210> SEQ ID NO 128
<211> LENGTH: 1262
<212> TYPE: PRT
<213> ORGANISM: Unknown
<220> FEATURE:
<223> OTHER INFORMATION: Bacteroidetes oral taxon 274 str. F0058
```

<400> SEQUENCE: 128

| | | | | | | | | | | | | | | |
|---|---|---|---|---|---|---|---|---|---|---|---|---|---|---|
|Met|Arg|Lys|Phe|Asn|Glu|Phe|Val|Gly|Leu|Tyr|Pro|Ile|Ser|Lys|Thr
1| | | | 5| | | | | 10| | | | | 15| |

Leu Arg Phe Glu Leu Lys Pro Ile Gly Lys Thr Leu Glu His Ile Gln
           20                  25                  30

Arg Asn Lys Leu Leu Glu His Asp Ala Val Arg Ala Asp Asp Tyr Val
       35                  40                  45

Lys Val Lys Lys Ile Ile Asp Lys Tyr His Lys Cys Leu Ile Asp Glu
   50                  55                  60

Ala Leu Ser Gly Phe Thr Phe Asp Thr Glu Ala Asp Gly Arg Ser Asn
65                  70                  75                  80

Asn Ser Leu Ser Glu Tyr Tyr Leu Tyr Asn Leu Lys Lys Arg Asn
               85                  90                  95

Glu Gln Glu Gln Lys Thr Phe Lys Thr Ile Gln Asn Asn Leu Arg Lys
               100                 105                 110

Gln Ile Val Asn Lys Leu Thr Gln Ser Glu Lys Tyr Lys Arg Ile Asp
           115                 120                 125

Lys Lys Glu Leu Ile Thr Thr Asp Leu Pro Asp Phe Leu Thr Asn Glu
130                 135                 140

Ser Glu Lys Glu Leu Val Glu Lys Phe Lys Asn Phe Thr Thr Tyr Phe
145                 150                 155                 160

Thr Glu Phe His Lys Asn Arg Lys Asn Met Tyr Ser Lys Glu Glu Lys
                   165                 170                 175

Ser Thr Ala Ile Ala Phe Arg Leu Ile Asn Glu Asn Leu Pro Lys Phe
               180                 185                 190

Val Asp Asn Ile Ala Ala Phe Glu Lys Val Val Ser Pro Leu Ala
           195                 200                 205

Glu Lys Ile Asn Ala Leu Tyr Glu Asp Phe Lys Glu Tyr Leu Asn Val
       210                 215                 220

Glu Glu Ile Ser Arg Val Phe Arg Leu Asp Tyr Tyr Asp Glu Leu Leu
225                 230                 235                 240

Thr Gln Lys Gln Ile Asp Leu Tyr Asn Ala Ile Val Gly Gly Arg Thr
                   245                 250                 255

Glu Glu Asp Asn Lys Ile Gln Ile Lys Gly Leu Asn Gln Tyr Ile Asn
               260                 265                 270

Glu Tyr Asn Gln Gln Thr Asp Arg Ser Asn Arg Leu Pro Lys Leu
           275                 280                 285

Lys Pro Leu Tyr Lys Gln Ile Leu Ser Asp Arg Glu Ser Val Ser Trp
290                 295                 300

Leu Pro Pro Lys Phe Asp Ser Asp Lys Asn Leu Leu Ile Lys Ile Lys
305                 310                 315                 320

Glu Cys Tyr Asp Ala Leu Ser Glu Lys Glu Lys Val Phe Asp Lys Leu
                   325                 330                 335

Glu Ser Ile Leu Lys Ser Leu Thr Tyr Asp Leu Ser Lys Ile Tyr
               340                 345                 350

Ile Ser Asn Asp Ser Gln Leu Ser Tyr Ile Ser Gln Lys Met Phe Gly
           355                 360                 365

Arg Trp Asp Ile Ile Ser Lys Ala Ile Arg Glu Asp Cys Ala Lys Arg
       370                 375                 380

Asn Pro Gln Lys Ser Arg Glu Ser Leu Glu Lys Phe Ala Glu Arg Ile
385                 390                 395                 400

Asp Lys Lys Leu Lys Thr Ile Asp Ser Ile Ser Ile Gly Asp Val Asp

```
                    405                 410                 415
Glu Cys Leu Ala Gln Leu Gly Glu Thr Tyr Val Lys Arg Val Glu Asp
                420                 425                 430
Tyr Phe Val Ala Met Gly Glu Ser Glu Ile Asp Asp Glu Gln Thr Asp
                435                 440                 445
Thr Thr Ser Phe Lys Lys Asn Ile Glu Gly Ala Tyr Glu Ser Val Lys
            450                 455                 460
Glu Leu Leu Asn Asn Ala Asp Asn Ile Thr Asp Asn Asn Leu Met Gln
465                 470                 475                 480
Asp Lys Gly Asn Val Glu Lys Ile Lys Thr Leu Leu Asp Ala Ile Lys
                485                 490                 495
Asp Leu Gln Arg Phe Ile Lys Pro Leu Leu Gly Lys Gly Asp Glu Ala
                500                 505                 510
Asp Lys Asp Gly Val Phe Tyr Gly Glu Phe Thr Ser Leu Trp Thr Lys
            515                 520                 525
Leu Asp Gln Val Thr Pro Leu Tyr Asn Met Val Arg Asn Tyr Leu Thr
530                 535                 540
Ser Lys Pro Tyr Ser Thr Lys Ile Lys Leu Asn Phe Glu Asn Ser
545                 550                 555                 560
Thr Leu Met Asp Gly Trp Asp Leu Asn Lys Glu Pro Asp Asn Thr Thr
                565                 570                 575
Val Ile Phe Cys Lys Asp Gly Leu Tyr Tyr Leu Gly Ile Met Gly Lys
                580                 585                 590
Lys Tyr Asn Arg Val Phe Val Asp Arg Glu Asp Leu Pro His Asp Gly
                595                 600                 605
Glu Cys Tyr Asp Lys Met Glu Tyr Lys Leu Leu Pro Gly Ala Asn Lys
            610                 615                 620
Met Leu Pro Lys Val Phe Phe Ser Glu Thr Gly Ile Gln Arg Phe Leu
625                 630                 635                 640
Pro Ser Glu Glu Leu Leu Gly Lys Tyr Glu Arg Gly Thr His Lys Lys
                645                 650                 655
Gly Ala Gly Phe Asp Leu Gly Asp Cys Arg Ala Leu Ile Asp Phe Phe
                660                 665                 670
Lys Lys Ser Ile Glu Arg His Asp Asp Trp Lys Lys Phe Asp Phe Lys
            675                 680                 685
Phe Ser Asp Thr Ser Thr Tyr Gln Asp Ile Ser Glu Phe Tyr Arg Glu
            690                 695                 700
Val Glu Gln Gln Gly Tyr Lys Met Ser Phe Arg Lys Val Ser Val Asp
705                 710                 715                 720
Tyr Ile Lys Ser Leu Val Glu Glu Gly Lys Leu Tyr Leu Phe Gln Ile
                725                 730                 735
Tyr Asn Lys Asp Phe Ser Ala His Ser Lys Gly Thr Pro Asn Met His
            740                 745                 750
Thr Leu Tyr Trp Lys Met Leu Phe Asp Glu Glu Asn Leu Lys Asp Val
            755                 760                 765
Val Tyr Lys Leu Asn Gly Glu Ala Glu Val Phe Phe Arg Lys Ser Ser
            770                 775                 780
Ile Thr Val Gln Ser Pro Thr His Pro Ala Asn Ser Pro Ile Lys Asn
785                 790                 795                 800
Lys Asn Lys Asp Asn Gln Lys Lys Glu Ser Lys Phe Glu Tyr Asp Leu
                805                 810                 815
Ile Lys Asp Arg Arg Tyr Thr Val Asp Lys Phe Leu Phe His Val Pro
                820                 825                 830
```

-continued

```
Ile Thr Met Asn Phe Lys Ser Val Gly Gly Ser Asn Ile Asn Gln Leu
        835                 840                 845

Val Lys Arg His Ile Arg Ser Ala Thr Asp Leu His Ile Ile Gly Ile
850                 855                 860

Asp Arg Gly Glu Arg His Leu Leu Tyr Leu Thr Val Ile Asp Ser Arg
865                 870                 875                 880

Gly Asn Ile Lys Glu Gln Phe Ser Leu Asn Glu Ile Val Asn Glu Tyr
                885                 890                 895

Asn Gly Asn Thr Tyr Arg Thr Asp Tyr His Glu Leu Leu Asp Thr Arg
                900                 905                 910

Glu Gly Glu Arg Thr Glu Ala Arg Arg Asn Trp Gln Thr Ile Gln Asn
        915                 920                 925

Ile Arg Glu Leu Lys Glu Gly Tyr Leu Ser Gln Val Ile His Lys Ile
    930                 935                 940

Ser Glu Leu Ala Ile Lys Tyr Asn Ala Val Ile Val Leu Glu Asp Leu
945                 950                 955                 960

Asn Phe Gly Phe Met Arg Ser Arg Gln Lys Val Glu Lys Gln Val Tyr
                965                 970                 975

Gln Lys Phe Glu Lys Met Leu Ile Asp Lys Leu Asn Tyr Leu Val Asp
        980                 985                 990

Lys Lys Lys Pro Val Ala Glu Thr Gly Gly Leu Leu Arg Ala Tyr Gln
    995                 1000                1005

Leu Thr Gly Glu Phe Glu Ser Phe Lys Thr Leu Gly Lys Gln Ser
    1010                1015                1020

Gly Ile Leu Phe Tyr Val Pro Ala Trp Asn Thr Ser Lys Ile Asp
    1025                1030                1035

Pro Val Thr Gly Phe Val Asn Leu Phe Asp Thr His Tyr Glu Asn
    1040                1045                1050

Ile Glu Lys Ala Lys Val Phe Phe Asp Lys Phe Lys Ser Ile Arg
    1055                1060                1065

Tyr Asn Ser Asp Lys Asp Trp Phe Glu Phe Val Val Asp Asp Tyr
    1070                1075                1080

Thr Arg Phe Ser Pro Lys Ala Glu Gly Thr Arg Arg Asp Trp Thr
    1085                1090                1095

Ile Cys Thr Gln Gly Lys Arg Ile Gln Ile Cys Arg Asn His Gln
    1100                1105                1110

Arg Asn Asn Glu Trp Glu Gly Gln Glu Ile Asp Leu Thr Lys Ala
    1115                1120                1125

Phe Lys Glu His Phe Glu Ala Tyr Gly Val Asp Ile Ser Lys Asp
    1130                1135                1140

Leu Arg Glu Gln Ile Asn Thr Gln Asn Lys Lys Glu Phe Phe Glu
    1145                1150                1155

Glu Leu Leu Arg Leu Leu Arg Leu Thr Leu Gln Met Arg Asn Ser
    1160                1165                1170

Met Pro Ser Ser Asp Ile Asp Tyr Leu Ile Ser Pro Val Ala Asn
    1175                1180                1185

Asp Thr Gly Cys Phe Phe Asp Ser Arg Lys Gln Ala Glu Leu Lys
    1190                1195                1200

Glu Asn Ala Val Leu Pro Met Asn Ala Asp Ala Asn Gly Ala Tyr
    1205                1210                1215

Asn Ile Ala Arg Lys Gly Leu Leu Ala Ile Arg Lys Met Lys Gln
    1220                1225                1230
```

-continued

Glu Glu Asn Asp Ser Ala Lys Ile Ser Leu Ala Ile Ser Asn Lys
　　1235　　　　　　　　1240　　　　　　　　1245

Glu Trp Leu Lys Phe Ala Gln Thr Lys Pro Tyr Leu Glu Asp
　　1250　　　　　　　　1255　　　　　　　　1260

<210> SEQ ID NO 129
<211> LENGTH: 998
<212> TYPE: PRT
<213> ORGANISM: Unknown
<220> FEATURE:
<223> OTHER INFORMATION: Arcobacter butzleri L348 isolate CHRB125

<400> SEQUENCE: 129

Met Gly Leu Leu Glu His Leu Glu Gly Ala Ile Val Glu Asp Met Phe
1　　　　　　　　　5　　　　　　　　　　10　　　　　　　　　15

Ser Leu Asp Tyr Phe Ser Leu Thr Leu Ser Gln Arg Tyr Ile Asp Ile
　　　　　　　20　　　　　　　　　　25　　　　　　　　　　30

Tyr Asn Thr Met Ile Gly Gly Asn Thr Leu Ala Asp Gly Thr Lys Val
　　　　35　　　　　　　　　　40　　　　　　　　　　45

Gln Gly Ile Asn Glu Asn Ile Asn Ile Tyr Arg Gln Lys Asn Asn Ile
　　50　　　　　　　　　　55　　　　　　　　　　60

Asp Arg Lys Asn Leu Pro Thr Leu Lys Pro Leu His Lys Gln Leu Leu
65　　　　　　　　　　70　　　　　　　　　　75　　　　　　　　　　80

Ser Asp Arg Glu Thr Leu Ser Trp Ile Pro Glu Ala Phe Lys Thr Lys
　　　　　　　　　85　　　　　　　　　　90　　　　　　　　　　95

Glu Glu Val Val Gly Ala Ile Glu Asp Phe Tyr Lys Asn Asn Ile Ile
　　　　　　　100　　　　　　　　　　105　　　　　　　　　　110

Ser Phe Lys Cys Cys Asp Asn Ile Val Asp Ile Thr Lys Gln Phe Ile
　　　　　115　　　　　　　　　　120　　　　　　　　　　125

Asp Ile Phe Ser Leu Asn Glu Asp Tyr Glu Leu Asn Lys Ile Phe Ile
　　　130　　　　　　　　　　135　　　　　　　　　　140

Lys Asn Asp Ile Ser Ile Thr Ser Ile Ser Gln Asp Ile Phe Lys Asp
145　　　　　　　　　　150　　　　　　　　　　155　　　　　　　　　160

Tyr Arg Ile Ile Lys Glu Ala Leu Trp Gln Lys His Ile Asn Glu Asn
　　　　　　　　　165　　　　　　　　　　170　　　　　　　　　175

Pro Lys Ala Ala Lys Ser Lys Asp Leu Thr Gly Asp Lys Glu Lys Tyr
　　　　　　　180　　　　　　　　　　185　　　　　　　　　　190

Phe Ser Arg Lys Asn Ser Phe Phe Ser Phe Glu Glu Ile Ile Ser Ser
　　　　　195　　　　　　　　　　200　　　　　　　　　　205

Leu Lys Leu Met Gly Arg Lys Ile Asp Leu Phe Ser Tyr Phe Lys Asp
　　　210　　　　　　　　　　215　　　　　　　　　　220

Asn Val Glu Tyr Arg Ala His Ser Ile Glu Thr Thr Phe Ile Lys Trp
225　　　　　　　　　　230　　　　　　　　　　235　　　　　　　　　240

Gln Lys Asn Lys Asn Asp Lys Lys Thr Thr Lys Glu Leu Leu Asp Asn
　　　　　　　　　245　　　　　　　　　　250　　　　　　　　　255

Ile Leu Asn Leu Gln Arg Val Leu Lys Pro Leu Tyr Leu Lys Ala Glu
　　　　　　　260　　　　　　　　　　265　　　　　　　　　　270

Val Glu Lys Asp Ile Leu Phe Tyr Ser Ile Phe Asp Ile Tyr Phe Glu
　　　　　275　　　　　　　　　　280　　　　　　　　　　285

Ser Leu Asn Glu Ile Val Lys Leu Tyr Asn Lys Val Arg Asp Phe Glu
　　　290　　　　　　　　　　295　　　　　　　　　　300

Ser Lys Lys Pro Tyr Ser Leu Glu Lys Phe Lys Leu Asn Phe Gln Asn
305　　　　　　　　　　310　　　　　　　　　　315　　　　　　　　　320

Ser Thr Leu Leu Ser Gly Trp Asp Val Asn Lys Glu Pro Asp Asn Thr
　　　　　　　　　325　　　　　　　　　　330　　　　　　　　　335

```
Ser Ile Leu Leu Lys Lys Asp Gly Leu Tyr Tyr Leu Gly Ile Met Asp
                340                 345                 350

Lys Lys His Asn Arg Val Phe Lys Asn Leu Glu Ser Ser Lys Gly Gly
            355                 360                 365

Tyr Glu Lys Ile Glu Tyr Lys Leu Leu Ser Gly Pro Asn Lys Met Leu
        370                 375                 380

Pro Lys Val Phe Phe Ser Asn Lys Ser Ile Gly Tyr Tyr Asn Pro Ser
385                 390                 395                 400

Pro Ala Leu Leu Glu Lys Tyr Lys Ser Gly Val His Lys Lys Gly Glu
                405                 410                 415

Ser Phe Asp Leu Asn Phe Cys His Glu Leu Ile Asp Phe Phe Lys Ala
            420                 425                 430

Ser Ile Asp Lys His Glu Asp Trp Lys Asn Phe Asn Phe Lys Phe Ser
        435                 440                 445

Asp Thr Ser Glu Tyr Ala Asp Ile Ser Gly Phe Tyr Arg Glu Val Glu
    450                 455                 460

Gln Gln Gly Tyr Lys Ile Thr Phe Lys Asn Ile Asp Glu Glu Phe Ile
465                 470                 475                 480

Asn Thr Leu Ile Asn Glu Gly Lys Leu Tyr Leu Phe Gln Ile Tyr Asn
                485                 490                 495

Lys Asp Phe Ser Thr Phe Ser Lys Gly Thr Lys Asn Leu His Thr Leu
            500                 505                 510

Tyr Trp Glu Met Ile Phe Asn Glu Glu Asn Leu Lys Asn Val Val Tyr
        515                 520                 525

Lys Leu Asn Gly Glu Ala Glu Ile Phe Tyr Arg Lys Lys Ser Ile Glu
    530                 535                 540

Tyr Ser Glu Asp Lys Met Lys Tyr Gly His His Tyr Glu Glu Leu Lys
545                 550                 555                 560

Asp Lys Phe Asn Tyr Pro Ile Ile Lys Asp Lys Arg Phe Thr Met Asp
                565                 570                 575

Lys Phe Gln Phe His Val Pro Ile Thr Met Asn Phe Lys Ala Thr Gly
            580                 585                 590

Arg Ser Tyr Ile Asn Glu Glu Val Asn Asp Phe Leu Arg Gln Asn Ser
        595                 600                 605

Lys Asp Val Lys Ile Ile Gly Ile Asn Arg Gly Glu Arg His Leu Ile
    610                 615                 620

Tyr Leu Thr Met Ile Asn Ala Lys Gly Glu Ile Ile Gln Gln Tyr Ser
625                 630                 635                 640

Leu Asn Glu Ile Val Asn Ser Tyr Asn Lys Asn Phe Thr Val Asn
                645                 650                 655

Tyr Asn Glu Lys Leu Ser Lys Lys Glu Gly Glu Arg Ala Ile Ala Arg
            660                 665                 670

Glu Asn Trp Gly Val Val Glu Asn Ile Lys Glu Leu Lys Glu Gly Tyr
        675                 680                 685

Leu Ser His Ala Ile His Thr Ile Ser Asn Leu Ile Val Glu Asn Asn
    690                 695                 700

Ala Ile Val Val Leu Glu Asp Leu Asn Phe Glu Phe Lys Arg Glu Arg
705                 710                 715                 720

Leu Lys Val Glu Lys Ser Ile Tyr Gln Lys Phe Glu Lys Met Leu Ile
                725                 730                 735

Asp Lys Leu Asn Tyr Leu Val Asp Lys Lys Asp Ile Asn Glu Asn
            740                 745                 750

Gly Gly Leu Leu Lys Ala Leu Gln Leu Thr Asn Lys Phe Glu Ser Phe
```

```
                755                 760                 765
Glu Lys Ile Gly Lys Gln Asn Gly Phe Leu Phe Phe Val Asn Ala Trp
        770                 775                 780

Asn Ile Thr Lys Ile Cys Pro Val Thr Gly Phe Val Ser Leu Phe Asp
785                 790                 795                 800

Thr Arg Tyr Gln Ser Val Asp Lys Ala Arg Glu Phe Phe Ser Lys Phe
                805                 810                 815

Asp Ser Ile Lys Tyr Asn Glu Lys Glu His Tyr Glu Phe Val Phe
        820                 825                 830

Asp Tyr Ser Asn Phe Thr Asp Lys Ala Lys Asp Thr Lys Thr Lys Trp
        835                 840                 845

Thr Val Cys Ser Tyr Gly Thr Arg Ile Lys Thr Phe Arg Asn Ser Glu
        850                 855                 860

Lys Asn Asn Asn Trp Asp Asn Lys Thr Val Ser Pro Thr Glu Asp Leu
865                 870                 875                 880

Ser Lys Leu Leu Lys Ser Cys Asp Arg Asp Ile Lys Glu Phe Ile Ile
                885                 890                 895

Ser Gln Asp Lys Lys Glu Phe Phe Val Glu Leu Leu Glu Ile Phe Ser
        900                 905                 910

Leu Ile Val Gln Met Lys Asn Ser Ile Ile Asn Ser Glu Ile Asp Tyr
        915                 920                 925

Ile Ile Ser Pro Val Ala Asn Glu Asn Gly Glu Phe Phe Asp Ser Arg
        930                 935                 940

Phe Ala Asn Ser Ser Leu Pro Lys Asn Ala Asp Ala Asn Ala Ala Tyr
945                 950                 955                 960

Asn Thr Ala Arg Lys Gly Leu Met Leu Leu Glu Lys Ile Arg Asp Ser
                965                 970                 975

Glu Ile Gly Lys Lys Ile Asp Met Lys Ile Thr Asn Thr Glu Trp Leu
        980                 985                 990

Asn Phe Val Gln Glu Arg
        995

<210> SEQ ID NO 130
<211> LENGTH: 1242
<212> TYPE: PRT
<213> ORGANISM: Unknown
<220> FEATURE:
<223> OTHER INFORMATION: Bacteroidales bacterium KA00251

<400> SEQUENCE: 130

Met Lys Lys Phe Thr Asn Leu Tyr Pro Val Gln Lys Thr Leu Arg Phe
1               5                   10                  15

Glu Leu Ile Pro Gln Gly Asn Thr Ser Lys His Leu Cys Lys Ile Ile
            20                  25                  30

Gln Glu Asp Glu Gln Ile Ala Glu Asp Ser Gln Glu Val Lys Lys Leu
        35                  40                  45

Leu Asp Arg Tyr His Lys Glu Phe Ile Ala Ile Ala Leu Ser Ser Phe
    50                  55                  60

Pro Thr Ser Pro Leu Ala Lys Glu Ile Ile Pro Lys Leu Lys Glu Phe
65                  70                  75                  80

Ala Gln Ile Arg Ala Thr Gly Asp Ala Lys Gln Ile Ser Thr Ile Gln
                85                  90                  95

Asp Glu Leu Arg Glu Leu Val Val Lys Gly Phe Lys Gly Glu Gly Glu
            100                 105                 110

Gln Glu Arg Arg Tyr Lys Ile Leu Ile Gly Ala Lys Gly Asn Pro Asn
```

```
                115                 120                 125
Ala Asp Glu Leu Phe Asn Thr Glu Leu Ile Asn Phe Leu Lys Asp Pro
130                 135                 140
Ala Glu Gln Ala Leu Val Lys Lys Phe Gln Lys His Thr Gly Tyr Phe
145                 150                 155                 160
Leu Gly Phe Asn Glu Asn Arg Lys Asn Met Tyr Ser Ala Lys Ala Gln
                165                 170                 175
Ser Thr Ala Ile Ala Tyr Arg Leu Ile His Glu Asn Leu Pro Arg Phe
                180                 185                 190
Leu Asp Asn Ile Thr Thr Tyr Glu Lys Val Lys Thr Tyr Leu Lys Glu
                195                 200                 205
Glu Ile Pro Gln Leu Glu Lys Glu Leu Val Arg Ala Gly Ala Ser Leu
210                 215                 220
Val Ser His Val Asp Ser Val Phe Thr Ile Asp Phe Phe Leu Glu Val
225                 230                 235                 240
Phe Thr Gln Ser Gly Ile Asp Gln Tyr Asn Ala Leu Ile Gly Lys Ile
                245                 250                 255
Val Asn Gln Glu Gln Gly Glu Val Lys Gly Leu Asn Glu Arg Ile Asn
                260                 265                 270
Leu Tyr Asn Gln Gln His Lys Gln Glu Ala Lys Leu Pro Leu Phe Lys
                275                 280                 285
Pro Leu Tyr Lys Gln Ile Leu Ser Asp Arg Glu Gln Leu Ser Trp Leu
                290                 295                 300
Ala Glu Ala Tyr Asn Ser Asp Lys Asp Leu Leu Asp Ser Ile Gln Lys
305                 310                 315                 320
Tyr Tyr Gln Leu Leu Ile Asp Asn Gln Ile Phe Glu Arg Ile Pro Arg
                325                 330                 335
Leu Met His Thr Leu Glu Lys Ala Pro Leu Asp Lys Ile Trp Ile Thr
                340                 345                 350
Tyr Asp Thr Gln Leu Thr Ser Ile Ser Asn Thr Leu Tyr Gly Ser Trp
                355                 360                 365
Arg Val Ile Gly Glu Ala Leu Gly Arg Asn Ala Lys Ser Glu Lys Glu
370                 375                 380
Arg Lys Ser Ser Gln Lys Lys Ala Leu Asn Tyr Ser Leu Glu Ser Ile
385                 390                 395                 400
Asn Gln Ala Ile Ala Lys Met Pro Ser Asp Glu Glu Leu Pro Pro Ile
                405                 410                 415
Gln Lys Tyr Phe Ile Ala Leu Gly Ser Asn Pro Ser Lys Lys Asp Ala
                420                 425                 430
Ser Ser Gly Thr Leu Val Asp Lys Val Arg Ser Ser Tyr Lys Ala Cys
                435                 440                 445
Gln Asp Ile Leu Thr Asn Pro Asp His Thr Gly Lys Lys Leu Ile Gln
                450                 455                 460
Asp Lys Lys Gln Val Asp Leu Leu Lys Gln Leu Leu Asp Asp Leu Leu
465                 470                 475                 480
Ile Leu Gln Arg Phe Ile Lys Pro Leu Leu Tyr Ser Asn Asn Glu Asn
                485                 490                 495
Glu Thr His Lys Asp Glu Val Phe Tyr Thr Glu Leu Thr Asp Ile Met
                500                 505                 510
Asp Leu Leu Asn Pro Ile Val Gly Leu Tyr Asn Lys Val Arg Asn Tyr
                515                 520                 525
Leu Thr Gln Lys Pro Tyr Ser Thr Glu Lys Phe Lys Ile Asn Phe Lys
                530                 535                 540
```

```
Ser Ser Ser Leu Leu Ala Gly Trp Asp Arg Asn Lys Glu Lys Asp Asn
545                 550                 555                 560

Leu Gly Val Ile Leu Lys Arg Glu Asp Lys Tyr Tyr Leu Ala Ile Met
                565                 570                 575

Asp Lys Ala His Asn Ala Thr Phe Lys Asn Lys Ser Leu Pro Thr Gln
            580                 585                 590

Gly Glu Cys Tyr Glu Lys Met Glu Tyr Lys Leu Leu Pro Gly Ala Asn
        595                 600                 605

Lys Met Leu Pro Lys Val Tyr Ile Thr Ser Lys Lys Gly Ile Glu Ser
    610                 615                 620

Phe His Pro Ser Glu Glu Leu Gln Lys Lys Tyr Lys Leu Gly Thr His
625                 630                 635                 640

Lys Lys Gly Ala Ser Phe Asn Leu Ser Asp Met Arg Ala Leu Ile Asp
                645                 650                 655

Tyr Phe Lys Glu Ser Leu Glu Lys His Glu Glu His Ser Gln Phe Gly
                660                 665                 670

Phe His Phe Ser Asp Thr Ser Thr Tyr Glu Asp Ile Ser Gly Phe Tyr
            675                 680                 685

Arg Glu Val Glu Gln Gln Ala Tyr Lys Ile Thr Phe Arg Lys Val Ser
        690                 695                 700

Val Glu Tyr Ile Asp Gln Leu Val Asn Glu Gly Lys Leu Tyr Leu Phe
705                 710                 715                 720

Gln Ile Tyr Asn Lys Asp Phe Ser Pro Tyr Ser Lys Gly Thr Pro Asn
                725                 730                 735

Leu His Thr Leu Tyr Trp Lys Met Leu Phe Asp Pro Ala Asn Leu Gln
                740                 745                 750

Asp Ile Val Tyr Lys Leu Asn Gly Glu Ala Glu Val Phe Phe Arg Lys
            755                 760                 765

Lys Ser Leu Gln Tyr Asp Arg Pro Thr His Pro Lys Gly Gln Pro Ile
        770                 775                 780

Asn Lys Lys Ser Leu Leu Asn Glu Gly Glu Thr Ser Leu Phe Asp Tyr
785                 790                 795                 800

Asp Leu Ile Lys Asp Arg Arg Phe Thr Val Asp Lys Phe Gln Phe His
                805                 810                 815

Val Pro Ile Thr Met Asn Phe Lys Ala Thr Gln Gly Thr Lys Val Asn
                820                 825                 830

Gln Met Val Gln Glu Glu Val Lys Lys Ser Lys Gly Phe His Leu Ile
        835                 840                 845

Gly Ile Asp Arg Gly Glu Arg Asn Leu Leu Tyr Ile Val Val Ile Asn
850                 855                 860

Glu Arg Gly Glu Ile Ile Glu Gln Cys Ser Leu Asn Lys Ile Val Asn
865                 870                 875                 880

Thr Tyr Gln Glu Lys Glu His Thr Val Asp Tyr Lys Ala Leu Leu Glu
                885                 890                 895

Lys Arg Ser Gln Ser Arg Leu Glu Glu Arg Lys Ser Trp Gln Thr Ile
            900                 905                 910

Glu Asn Ile Lys Glu Leu Lys Gly Gly Tyr Leu Ser Gln Val Val His
            915                 920                 925

Lys Ile Ala Gln Leu Met Ile Lys Tyr Asn Ala Ile Ala Val Leu Glu
        930                 935                 940

Asp Leu Asn Phe Gly Phe Ile Arg Thr Arg Lys Lys Phe Glu Phe Ser
945                 950                 955                 960
```

```
Val Tyr Gln Glu Phe Glu Lys Lys Leu Ile Asp Lys Leu Gly Tyr Val
            965                 970                 975

Val Asp Lys Lys Ala Pro Ile Gln Gln Glu Gly Gly Leu Leu Gln Ala
        980                 985                 990

Tyr Gln Leu Thr Ala Pro Phe Lys  Ser Phe Arg Glu Met  Gly Lys Gln
        995                 1000                1005

Asn Gly Phe Leu Phe Tyr Val  Pro Ala Trp Asn Thr  Ser Ala Ile
    1010                1015                1020

Asp Pro Arg Thr Gly Phe Val  Asn Leu Leu Asp Thr  Arg Tyr Glu
    1025                1030                1035

Ser Ile Ala Lys Thr Lys Glu  Leu Ile Lys Lys Leu  Lys Asp Ile
    1040                1045                1050

Arg Tyr Asn Ser Gln Lys Asp  Trp Phe Glu Ile Asp  Leu Asp Tyr
    1055                1060                1065

Asn Ala Phe Gly Asn Arg Ala  Lys Gly Ser Arg Ser  Lys Trp Arg
    1070                1075                1080

Leu Cys Ser Tyr Gly Glu Arg  Ile Glu His Thr Arg  Lys Gln Asp
    1085                1090                1095

Ser Asn Gly Gln Glu Glu Ser  Asp Ser Met Val Val  Leu Thr Glu
    1100                1105                1110

Ala Phe Lys Asp Val Phe Thr  Lys Tyr Gln Ile Asp  Tyr Arg Glu
    1115                1120                1125

Asn Leu Lys Glu Gln Leu Leu  Leu Gln Ser Asp Lys  Ala Phe Phe
    1130                1135                1140

Val Asp Phe Leu Ser Leu Leu  Arg Leu Thr Leu Gln  Leu Arg Asn
    1145                1150                1155

Ser Leu Ser Asn Ser Leu Ile  Asp Tyr Ile Leu Ser  Pro Val Ala
    1160                1165                1170

Asp Glu Asn Gly Glu Phe Phe  Asp Ser Arg Lys Ala  Leu Ser Asn
    1175                1180                1185

Glu Pro Gln Asp Ala Asp Ala  Asn Gly Ala Tyr His  Ile Ala Leu
    1190                1195                1200

Lys Gly Leu Trp Val Leu Asp  Lys Ile Arg Lys Thr  Glu Lys Val
    1205                1210                1215

Thr Pro Ala Lys Leu Ala Leu  Ser Asn Gln Glu Trp  Leu Ser Phe
    1220                1225                1230

Ala Gln Glu Lys Pro Phe Phe  Asn Glu
    1235                1240

<210> SEQ ID NO 131
<211> LENGTH: 1302
<212> TYPE: PRT
<213> ORGANISM: Unknown
<220> FEATURE:
<223> OTHER INFORMATION: Acidaminococcus massiliensis strain
      Marseille-P2828

<400> SEQUENCE: 131

Met Ala Ala Phe Asp Lys Phe Ile His Gln Tyr Gln Val Ser Lys Thr
1               5                   10                  15

Leu Arg Phe Ala Leu Ile Pro Gln Gly Lys Thr Leu Glu Asn Thr Lys
                20                  25                  30

Asn Asn Val Leu Gln Glu Asp Asp Glu Arg Gln Lys Asn Tyr Glu Lys
            35                  40                  45

Val Lys Pro Ile Leu Asp Arg Ile Tyr Lys Val Phe Ala Glu Glu Ser
        50                  55                  60
```

-continued

```
Leu Lys Asp Cys Ser Val Asp Trp Asn Asp Leu Asn Ala Cys Leu Asp
 65                  70                  75                  80

Ala Tyr Gln Lys Asn Pro Ser Ala Asp Lys Arg Gln Lys Val Lys Ala
                 85                  90                  95

Ala Gln Asp Ala Leu Arg Asp Glu Ile Ala Gly Tyr Phe Thr Gly Lys
                100                 105                 110

Gln Tyr Ala Asn Gly Lys Asn Lys Asn Ala Val Lys Glu Lys Glu Gln
                115                 120                 125

Ala Glu Leu Tyr Lys Asp Ile Phe Ser Lys Lys Ile Phe Asp Gly Thr
130                 135                 140

Val Thr Asn Asn Lys Leu Pro Gln Val Asn Leu Ser Ala Glu Glu Thr
145                 150                 155                 160

Glu Leu Leu Gly Cys Phe Asp Lys Phe Thr Thr Tyr Phe Val Gly Phe
                165                 170                 175

Tyr Gln Asn Arg Glu Asn Val Phe Ser Gly Glu Asp Ile Ala Thr Ala
                180                 185                 190

Ile Pro His Arg Ile Val Gln Asp Asn Phe Pro Lys Phe Arg Glu Asn
                195                 200                 205

Cys Arg Ile Tyr Gln Asp Leu Ile Lys Asn Glu Pro Ala Leu Lys Pro
210                 215                 220

Leu Leu Gln Gln Ala Ala Ala Ala Val Met Ala Gln Asn Pro Lys Gly
225                 230                 235                 240

Ile Tyr Gln Pro Arg Lys Ser Leu Asp Asp Ile Phe Val Ile Pro Phe
                245                 250                 255

Tyr Asn His Leu Leu Gln Asp Asp Ile Asp Tyr Phe Asn Gln Ile
                260                 265                 270

Leu Gly Gly Ile Ser Gly Ala Ala Gly Gln Lys Lys Ile Gln Gly Leu
                275                 280                 285

Asn Glu Thr Ile Asn Leu Phe Met Gln Gln His Pro Gln Glu Ala Asp
290                 295                 300

Lys Leu Lys Lys Lys Lys Ile Arg His Arg Phe Ile Pro Leu Tyr Lys
305                 310                 315                 320

Gln Ile Leu Ser Asp Arg Thr Ser Phe Ser Phe Ile Pro Glu Ala Phe
                325                 330                 335

Ser Asn Ser Gln Glu Ala Leu Asp Gly Ile Glu Thr Phe Lys Lys Ser
                340                 345                 350

Leu Lys Lys Asn Asp Thr Phe Gly Ala Leu Glu Arg Leu Ile Gln Asn
                355                 360                 365

Leu Ala Ser Leu Asp Leu Lys Tyr Val Tyr Leu Ser Asn Lys Lys Val
                370                 375                 380

Asn Glu Ile Ser Gln Ala Leu Tyr Gly Glu Trp His Cys Ile Gln Asp
385                 390                 395                 400

Val Leu Lys Gln Asp Phe Ser Leu Glu Ser Leu Ile Gln Ile Asn Pro
                405                 410                 415

Gln Asn Ser Ser Asn Gly Phe Leu Ala Thr Leu Thr Asp Glu Gly Lys
                420                 425                 430

Lys Arg Ile Ser Gln Cys Arg Asn Val Leu Gly Asn Pro Leu Pro Val
                435                 440                 445

Lys Leu Ala Asp Asp Gln Asp Lys Ala Gln Val Lys Asn Gln Leu Asp
                450                 455                 460

Thr Leu Leu Ala Ala Val His Tyr Leu Glu Trp Phe Lys Ala Asp Pro
465                 470                 475                 480
```

```
Asp Leu Glu Thr Asp Pro Asn Phe Thr Val Pro Phe Glu Lys Ile Trp
                485                 490                 495

Glu Glu Leu Val Pro Leu Leu Ser Leu Tyr Ser Lys Val Arg Asn Phe
            500                 505                 510

Val Thr Lys Lys Pro Tyr Ser Thr Ala Lys Phe Lys Leu Asn Phe Ala
        515                 520                 525

Asn Pro Thr Leu Ala Asp Gly Trp Asp Ile His Lys Glu Ser Asp Asn
    530                 535                 540

Gly Ala Leu Leu Phe Glu Lys Gly Leu Tyr Leu Gly Ile Met
545                 550                 555                 560

Asn Pro Lys Asp Lys Pro Asn Phe Lys Ser Tyr Gln Gly Ala Glu Pro
                565                 570                 575

Tyr Tyr Gln Lys Met Val Tyr Arg Phe Phe Pro Asp Cys Ser Lys Thr
            580                 585                 590

Ile Pro Lys Cys Ser Thr Gln Arg Lys Asp Val Lys Lys Tyr Phe Glu
        595                 600                 605

Asp His Pro Gln Ala Thr Ser Tyr Gln Ile His Asp Ser Lys Lys Glu
    610                 615                 620

Lys Phe Arg Gln Asp Phe Phe Glu Ile Pro Arg Glu Ile Tyr Glu Leu
625                 630                 635                 640

Asn Asn Thr Thr Tyr Gly Thr Gly Lys Ser Lys Tyr Lys Lys Phe Gln
                645                 650                 655

Thr Gln Tyr Tyr Gln Lys Thr Gln Asp Lys Ser Gly Tyr Gln Lys Ala
            660                 665                 670

Leu Arg Lys Trp Ile Asp Phe Ser Lys Phe Leu Gln Thr Tyr Val
        675                 680                 685

Ser Thr Ser Ile Phe Asp Phe Lys Gly Leu Arg Pro Ser Lys Asp Tyr
    690                 695                 700

Gln Asp Leu Gly Glu Phe Tyr Lys Asp Val Asn Ser Arg Cys Tyr Arg
705                 710                 715                 720

Val Thr Phe Glu Lys Ile Arg Val Gln Asp Ile His Glu Ala Val Lys
                725                 730                 735

Asn Gly Gln Leu Tyr Leu Phe Gln Leu Tyr Asn Lys Asp Phe Ser Pro
            740                 745                 750

Lys Ser His Gly Leu Pro Asn Leu His Thr Leu Tyr Trp Lys Ala Val
        755                 760                 765

Phe Asp Pro Glu Asn Leu Lys Asp Pro Ile Val Lys Leu Asn Gly Gln
    770                 775                 780

Ala Glu Leu Phe Tyr Arg Pro Lys Ser Asn Met Gln Ile Ile Gln His
785                 790                 795                 800

Lys Thr Gly Glu Glu Ile Val Asn Lys Lys Leu Lys Asp Gly Thr Pro
                805                 810                 815

Val Pro Asp Asp Ile Tyr Arg Glu Ile Ser Ala Tyr Val Gln Gly Lys
            820                 825                 830

Cys Gln Gly Asn Leu Ser Pro Glu Ala Glu Lys Trp Leu Pro Ser Val
        835                 840                 845

Thr Ile Lys Lys Ala Ala His Asp Ile Thr Lys Asp Arg Arg Phe Thr
    850                 855                 860

Glu Asp Lys Phe Phe Phe His Val Pro Ile Thr Leu Asn Tyr Gln Ser
865                 870                 875                 880

Ser Gly Lys Pro Thr Ala Phe Asn Ser Gln Val Asn Asp Phe Leu Thr
                885                 890                 895

Glu His Pro Glu Thr Asn Ile Ile Gly Ile Asp Arg Gly Glu Arg Asn
```

```
                        900                905                910
Leu Ile Tyr Ala Val Ile Thr Pro Asp Gly Lys Ile Leu Glu Gln
        915                920                925
Lys Ser Phe Asn Val Ile His Asp Phe Asp Tyr His Glu Ser Leu Ser
        930                935                940
Gln Arg Glu Lys Gln Arg Val Ala Ala Arg Gln Ala Trp Thr Ala Ile
945                950                955                960
Gly Arg Ile Lys Asp Leu Lys Glu Gly Tyr Leu Ser Leu Val Val His
                965                970                975
Glu Ile Ala Gln Met Met Ile Lys Tyr Gln Ala Val Val Leu Glu
                980                985                990
Asn Leu Asn Thr Gly Phe Lys Arg Val Arg Gly Gly Ile Ser Glu Lys
        995                1000                1005
Ala Val Tyr Gln Gln Phe Glu Lys Met Leu Ile Glu Lys Leu Asn
    1010                1015                1020
Phe Leu Val Phe Lys Asp Arg Ala Ile Asn Gln Glu Gly Gly Val
    1025                1030                1035
Leu Lys Ala Tyr Gln Leu Thr Asp Ser Phe Thr Ser Phe Ala Lys
    1040                1045                1050
Leu Gly Asn Gln Ser Gly Phe Leu Phe Tyr Ile Pro Ser Ala Tyr
    1055                1060                1065
Thr Ser Lys Ile Asp Pro Gly Thr Gly Phe Val Asp Pro Phe Ile
    1070                1075                1080
Trp Ser His Val Thr Ala Ser Glu Glu Asn Arg Asn Glu Phe Leu
    1085                1090                1095
Lys Gly Phe Asp Ser Leu Lys Tyr Asp Ala Gln Ser Ser Ala Phe
    1100                1105                1110
Val Leu His Phe Lys Met Lys Ser Asn Lys Gln Phe Gln Lys Asn
    1115                1120                1125
Asn Val Glu Gly Phe Met Pro Glu Trp Asp Ile Cys Phe Glu Lys
    1130                1135                1140
Asn Glu Glu Lys Ile Ser Leu Gln Gly Ser Lys Tyr Thr Ala Gly
    1145                1150                1155
Lys Arg Ile Ile Phe Asp Ser Lys Lys Lys Gln Tyr Met Glu Cys
    1160                1165                1170
Phe Pro Gln Asn Glu Leu Met Lys Ala Leu Gln Asp Val Gly Ile
    1175                1180                1185
Thr Trp Asn Thr Gly Asn Asp Ile Trp Gln Asp Val Leu Lys Gln
    1190                1195                1200
Ala Ser Thr Asp Thr Gly Phe Arg His Arg Met Ile Asn Leu Ile
    1205                1210                1215
Arg Ser Val Leu Gln Met Arg Ser Ser Asn Gly Ala Thr Gly Glu
    1220                1225                1230
Asp Tyr Ile Asn Ser Pro Val Met Asp Leu Asp Gly Arg Phe Phe
    1235                1240                1245
Asp Thr Arg Ala Gly Ile Arg Asp Leu Pro Leu Asp Ala Asp Ala
    1250                1255                1260
Asn Gly Ala Tyr His Ile Ala Leu Lys Gly Arg Met Val Leu Glu
    1265                1270                1275
Arg Ile Arg Ser Gln Lys Asn Thr Ala Ile Lys Asn Thr Asp Trp
    1280                1285                1290
Leu Tyr Ala Ile Gln Glu Glu Arg Asn
    1295                1300
```

```
<210> SEQ ID NO 132
<211> LENGTH: 1310
<212> TYPE: PRT
<213> ORGANISM: Helcococcus kunzii

<400> SEQUENCE: 132

Met Phe Glu Lys Leu Ser Asn Ile Val Ser Ile Ser Lys Thr Ile Arg
1               5                   10                  15

Phe Lys Leu Ile Pro Val Gly Lys Thr Leu Glu Asn Ile Glu Lys Leu
            20                  25                  30

Gly Lys Leu Glu Lys Asp Phe Glu Arg Ser Asp Phe Tyr Pro Ile Leu
        35                  40                  45

Lys Asn Ile Ser Asp Asp Tyr Tyr Arg Gln Tyr Ile Lys Glu Lys Leu
    50                  55                  60

Ser Asp Leu Asn Leu Asp Trp Gln Lys Leu Tyr Asp Ala His Glu Leu
65                  70                  75                  80

Leu Asp Ser Ser Lys Lys Glu Ser Gln Lys Asn Leu Glu Met Ile Gln
                85                  90                  95

Ala Gln Tyr Arg Lys Val Leu Phe Asn Ile Leu Ser Gly Glu Leu Asp
            100                 105                 110

Lys Ser Gly Glu Lys Asn Ser Lys Asp Leu Ile Lys Asn Asn Lys Ala
        115                 120                 125

Leu Tyr Gly Lys Leu Phe Lys Gln Phe Ile Leu Glu Val Leu Pro
    130                 135                 140

Asp Phe Val Asn Asn Asp Ser Tyr Ser Glu Glu Asp Leu Glu Gly
145                 150                 155                 160

Leu Asn Leu Tyr Ser Lys Phe Thr Thr Arg Leu Lys Asn Phe Trp Glu
                165                 170                 175

Thr Arg Lys Asn Val Phe Thr Asp Lys Asp Ile Val Thr Ala Ile Pro
            180                 185                 190

Phe Arg Ala Val Asn Glu Asn Phe Gly Phe Tyr Tyr Asp Asn Ile Lys
        195                 200                 205

Ile Phe Asn Lys Asn Ile Glu Tyr Leu Glu Asn Lys Ile Pro Asn Leu
    210                 215                 220

Glu Asn Glu Leu Lys Glu Ala Asp Ile Leu Asp Asp Asn Arg Ser Val
225                 230                 235                 240

Lys Asp Tyr Phe Thr Pro Asn Gly Phe Asn Tyr Val Ile Thr Gln Asp
                245                 250                 255

Gly Ile Asp Val Tyr Gln Ala Ile Arg Gly Gly Phe Thr Lys Glu Asn
            260                 265                 270

Gly Glu Lys Val Gln Gly Ile Asn Glu Ile Leu Asn Leu Thr Gln Gln
        275                 280                 285

Gln Leu Arg Arg Lys Pro Glu Thr Lys Asn Val Lys Leu Gly Val Leu
    290                 295                 300

Thr Lys Leu Arg Lys Gln Ile Leu Glu Tyr Ser Glu Ser Thr Ser Phe
305                 310                 315                 320

Leu Ile Asp Gln Ile Glu Asp Asp Asn Asp Leu Val Asp Arg Ile Asn
                325                 330                 335

Lys Phe Asn Val Ser Phe Phe Glu Ser Thr Glu Val Ser Pro Ser Leu
            340                 345                 350

Phe Glu Gln Ile Glu Arg Leu Tyr Asn Ala Leu Lys Ser Ile Lys Lys
        355                 360                 365

Glu Glu Val Tyr Ile Asp Ala Arg Asn Thr Gln Lys Phe Ser Gln Met
```

```
              370                 375                 380
Leu Phe Gly Gln Trp Asp Val Ile Arg Arg Gly Tyr Thr Val Lys Ile
385                 390                 395                 400

Thr Glu Gly Ser Lys Glu Lys Lys Lys Tyr Lys Glu Tyr Leu Glu
                405                 410                 415

Leu Asp Glu Thr Ser Lys Ala Lys Arg Tyr Leu Asn Ile Arg Glu Ile
                420                 425                 430

Glu Glu Leu Val Asn Leu Val Glu Gly Phe Glu Glu Val Asp Val Phe
            435                 440                 445

Ser Val Leu Leu Glu Lys Phe Lys Met Asn Asn Ile Glu Arg Ser Glu
        450                 455                 460

Phe Glu Ala Pro Ile Tyr Gly Ser Pro Ile Lys Leu Glu Ala Ile Lys
465                 470                 475                 480

Glu Tyr Leu Glu Lys His Leu Glu Glu Tyr His Lys Trp Lys Leu Leu
                485                 490                 495

Leu Ile Gly Asn Asp Asp Leu Asp Thr Asp Glu Thr Phe Tyr Pro Leu
                500                 505                 510

Leu Asn Glu Val Ile Ser Asp Tyr Tyr Ile Ile Pro Leu Tyr Asn Leu
            515                 520                 525

Thr Arg Asn Tyr Leu Thr Arg Lys His Ser Asp Lys Asp Lys Ile Lys
        530                 535                 540

Val Asn Phe Asp Phe Pro Thr Leu Ala Asp Gly Trp Ser Glu Ser Lys
545                 550                 555                 560

Ile Ser Asp Asn Arg Ser Ile Ile Leu Arg Lys Gly Gly Tyr Tyr Tyr
                565                 570                 575

Leu Gly Ile Leu Ile Asp Asn Lys Leu Leu Ile Asn Lys Lys Asn Lys
                580                 585                 590

Ser Lys Lys Ile Tyr Glu Ile Leu Ile Tyr Asn Gln Ile Pro Glu Phe
            595                 600                 605

Ser Lys Ser Ile Pro Asn Tyr Pro Phe Thr Lys Val Lys Glu His
        610                 615                 620

Phe Lys Asn Asn Val Ser Asp Phe Gln Leu Ile Asp Gly Tyr Val Ser
625                 630                 635                 640

Pro Leu Ile Ile Thr Lys Glu Ile Tyr Asp Ile Lys Lys Glu Lys Lys
                645                 650                 655

Tyr Lys Lys Asp Phe Tyr Lys Asp Asn Thr Asn Lys Asn Tyr Leu
                660                 665                 670

Tyr Thr Ile Tyr Lys Trp Ile Glu Phe Cys Lys Gln Phe Leu Tyr Lys
            675                 680                 685

Tyr Lys Gly Pro Asn Lys Glu Ser Tyr Lys Glu Met Tyr Asp Phe Ser
        690                 695                 700

Thr Leu Lys Asp Thr Ser Leu Tyr Val Asn Leu Asn Asp Phe Tyr Ala
705                 710                 715                 720

Asp Val Asn Ser Cys Ala Tyr Arg Val Leu Phe Asn Lys Ile Asp Glu
                725                 730                 735

Asn Thr Ile Asp Asn Ala Val Glu Asp Gly Lys Leu Leu Leu Phe Gln
                740                 745                 750

Ile Tyr Asn Lys Asp Phe Ser Pro Glu Ser Lys Gly Lys Lys Asn Leu
            755                 760                 765

His Thr Leu Tyr Trp Leu Ser Met Phe Ser Glu Glu Asn Leu Arg Thr
        770                 775                 780

Arg Lys Leu Lys Leu Asn Gly Gln Ala Glu Ile Phe Tyr Arg Lys Lys
785                 790                 795                 800
```

-continued

Leu Glu Lys Lys Pro Ile Ile His Lys Glu Gly Ser Ile Leu Leu Asn
                805                 810                 815

Lys Ile Asp Lys Glu Gly Asn Thr Ile Pro Glu Asn Ile Tyr His Glu
            820                 825                 830

Cys Tyr Arg Tyr Leu Asn Lys Lys Ile Gly Arg Glu Asp Leu Ser Asp
            835                 840                 845

Glu Ala Ile Ala Leu Phe Asn Lys Asp Val Leu Lys Tyr Lys Glu Ala
        850                 855                 860

Arg Phe Asp Ile Ile Lys Asp Arg Arg Tyr Ser Glu Ser Gln Phe Phe
865                 870                 875                 880

Phe His Val Pro Ile Thr Phe Asn Trp Asp Ile Lys Thr Asn Lys Asn
                885                 890                 895

Val Asn Gln Ile Val Gln Gly Met Ile Lys Asp Gly Glu Ile Lys His
            900                 905                 910

Ile Ile Gly Ile Asp Arg Gly Glu Arg His Leu Leu Tyr Tyr Ser Val
            915                 920                 925

Ile Asp Leu Glu Gly Asn Ile Val Glu Gln Gly Ser Leu Asn Thr Leu
        930                 935                 940

Glu Gln Asn Arg Phe Asp Asn Ser Thr Val Lys Val Asp Tyr Gln Asn
945                 950                 955                 960

Lys Leu Arg Thr Arg Glu Glu Asp Arg Asp Arg Ala Arg Lys Asn Trp
                965                 970                 975

Thr Asn Ile Asn Lys Ile Lys Glu Leu Lys Asp Gly Tyr Leu Ser His
            980                 985                 990

Val Val His Lys Leu Ser Arg Leu Ile Ile Lys Tyr Glu Ala Ile Val
            995                 1000                1005

Ile Met Glu Asn Leu Asn Gln Gly Phe Lys Arg Gly Arg Phe Lys
    1010                1015                1020

Val Glu Arg Gln Val Tyr Gln Lys Phe Glu Leu Ala Leu Met Asn
    1025                1030                1035

Lys Leu Ser Ala Leu Ser Phe Lys Glu Lys Tyr Asp Glu Arg Lys
    1040                1045                1050

Asn Leu Glu Pro Ser Gly Ile Leu Asn Pro Ile Gln Ala Cys Tyr
    1055                1060                1065

Pro Val Asp Ala Tyr Gln Leu Gln Gly Gln Asn Gly Ile Val
    1070                1075                1080

Phe Tyr Leu Pro Ala Ala Tyr Thr Ser Val Ile Asp Pro Val Thr
    1085                1090                1095

Gly Phe Thr Asn Leu Phe Arg Leu Lys Ser Ile Asn Ser Ser Lys
    1100                1105                1110

Tyr Glu Glu Phe Ile Lys Lys Phe Lys Asn Ile Tyr Phe Asp Asn
    1115                1120                1125

Glu Glu Glu Asp Phe Lys Phe Ile Phe Asn Tyr Lys Asp Phe Ala
    1130                1135                1140

Lys Ala Asn Leu Val Ile Leu Asn Asn Ile Lys Ser Lys Asp Trp
    1145                1150                1155

Lys Ile Ser Thr Arg Gly Glu Arg Ile Ser Tyr Asn Ser Lys Lys
    1160                1165                1170

Lys Glu Tyr Phe Tyr Val Gln Pro Thr Glu Phe Leu Ile Asn Lys
    1175                1180                1185

Leu Lys Glu Leu Asn Ile Asp Tyr Glu Asn Ile Asp Ile Ile Pro
    1190                1195                1200

Leu Ile Asp Asn Leu Glu Glu Lys Ala Lys Arg Lys Ile Leu Lys
1205                1210                1215

Ala Leu Phe Asp Thr Phe Lys Tyr Ser Val Gln Leu Arg Asn Tyr
1220                1225                1230

Asp Phe Glu Asn Asp Tyr Ile Ile Ser Pro Thr Ala Asp Asp Asn
1235                1240                1245

Gly Asn Tyr Tyr Asn Ser Asn Glu Ile Asp Ile Asp Lys Thr Asn
1250                1255                1260

Leu Pro Asn Asn Gly Asp Ala Asn Gly Ala Phe Asn Ile Ala Arg
1265                1270                1275

Lys Gly Leu Leu Leu Lys Asp Arg Ile Val Asn Ser Asn Glu Ser
1280                1285                1290

Lys Val Asp Leu Lys Ile Lys Asn Glu Asp Trp Ile Asn Phe Ile
1295                1300                1305

Ile Ser
1310

<210> SEQ ID NO 133
<211> LENGTH: 1263
<212> TYPE: PRT
<213> ORGANISM: Unknown
<220> FEATURE:
<223> OTHER INFORMATION: Agathobacter rectalis strain 2789STDY5834884

<400> SEQUENCE: 133

Met Asn Asn Gly Thr Asn Asn Phe Gln Asn Phe Ile Gly Ile Ser Ser
1               5                   10                  15

Leu Gln Lys Thr Leu Arg Asn Ala Leu Thr Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Ala Gly Lys Arg Lys Ala Ile Tyr Lys Lys
            100                 105                 110

Phe Ala Asp Asp Asp Arg Phe Lys Asn Met Phe Ser Ala Lys Leu Ile
        115                 120                 125

Ser Asp Ile Leu Pro Glu Phe Val Ile His Asn Asn Tyr Ser Ala
    130                 135                 140

Ser Glu Lys Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Asn Leu Ser Asn Asp Asp Ile Asn Lys Ile Ser Gly Asp Met Lys Asp
    210                 215                 220

Ser Leu Lys Lys Met Ser Leu Glu Lys Ile Tyr Ser Tyr Glu Lys Tyr
225                 230                 235                 240

```
Gly Glu Phe Ile Thr Gln Glu Gly Ile Ser Phe Tyr Asn Asp Ile Cys
                245                 250                 255
Gly Lys Val Asn Ser Phe Met Asn Leu Tyr Cys Gln Lys Asn Lys Glu
            260                 265                 270
Asn Lys Asn Leu Tyr Lys Leu Arg Lys Leu His Lys Gln Ile Leu Cys
        275                 280                 285
Ile Ala Asp Thr Ser Tyr Glu Val Pro Tyr Lys Phe Glu Ser Asp Glu
    290                 295                 300
Glu Val Tyr Gln Ser Val Asn Gly Phe Leu Asp Asn Ile Ser Ser Lys
305                 310                 315                 320
His Ile Val Glu Arg Leu Arg Lys Ile Gly Asp Asn Tyr Asn Gly Tyr
                325                 330                 335
Asn Leu Asp Lys Ile Tyr Ile Val Ser Lys Phe Tyr Glu Ser Val Ser
            340                 345                 350
Gln Lys Thr Tyr Arg Asp Trp Glu Thr Ile Asn Thr Ala Leu Glu Ile
        355                 360                 365
His Tyr Asn Asn Ile Leu Pro Gly Asn Gly Lys Ser Lys Ala Asp Lys
    370                 375                 380
Val Lys Lys Ala Val Lys Asn Asp Leu Gln Lys Ser Ile Thr Glu Ile
385                 390                 395                 400
Asn Glu Leu Val Ser Asn Tyr Lys Leu Cys Pro Asp Asp Asn Ile Lys
                405                 410                 415
Ala Glu Thr Tyr Ile His Glu Ile Ser His Ile Leu Asn Asn Phe Glu
            420                 425                 430
Ala Gln Glu Leu Lys Tyr Asn Pro Glu Ile His Leu Val Glu Ser Glu
        435                 440                 445
Leu Lys Ala Ser Glu Leu Lys Asn Val Leu Asp Val Ile Met Asn Ala
    450                 455                 460
Phe His Trp Cys Ser Val Phe Met Thr Glu Glu Leu Val Asp Lys Asp
465                 470                 475                 480
Asn Asn Phe Tyr Ala Glu Leu Glu Glu Ile Tyr Asp Glu Ile Tyr Pro
                485                 490                 495
Val Ile Ser Leu Tyr Asn Leu Val Arg Asn Tyr Val Thr Gln Lys Pro
            500                 505                 510
Tyr Ser Thr Lys Lys Ile Lys Leu Asn Phe Gly Ile Pro Thr Leu Ala
        515                 520                 525
Asp Gly Trp Ser Lys Ser Lys Glu Tyr Ser Asn Asn Ala Ile Ile Leu
    530                 535                 540
Met Arg Asp Asn Leu Tyr Tyr Leu Gly Ile Phe Asn Ala Lys Asn Lys
545                 550                 555                 560
Pro Glu Lys Lys Ile Ile Glu Gly Asn Thr Ser Glu Asn Lys Gly Asp
                565                 570                 575
Tyr Lys Lys Met Ile Tyr Asn Leu Leu Pro Gly Pro Asn Lys Met Ile
            580                 585                 590
Pro Lys Val Phe Leu Ser Ser Lys Thr Gly Val Glu Thr Tyr Lys Pro
        595                 600                 605
Ser Ala Tyr Ile Leu Glu Gly Tyr Lys Gln Asn Lys His Leu Lys Ser
    610                 615                 620
Ser Lys Asp Phe Asp Ile Thr Phe Cys Arg Asp Leu Ile Asp Tyr Phe
625                 630                 635                 640
Lys Asn Cys Ile Ala Ile His Pro Glu Trp Lys Asn Phe Gly Phe Asp
                645                 650                 655
Phe Ser Asp Thr Ser Thr Tyr Glu Asp Ile Ser Gly Phe Tyr Arg Glu
```

-continued

```
                660                 665                 670
Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
            690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Val
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
            755                 760                 765

Thr Tyr Glu Ala Glu Glu Lys Asp Gln Phe Gly Asn Ile Gln Ile Val
            770                 775                 780

Arg Lys Thr Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Ala Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
            835                 840                 845

Phe Lys Ala Asn Lys Thr Ser Phe Ile Asn Asp Arg Ile Leu Gln Tyr
            850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
            930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
            995                 1000                1005

Lys Gly Tyr Gln Leu Thr Tyr Ile Pro Glu Lys Leu Lys Asn Val
            1010                1015                1020

Gly His Gln Cys Gly Cys Ile Phe Tyr Val Pro Ala Ala Tyr Thr
            1025                1030                1035

Ser Lys Ile Asp Pro Thr Thr Gly Phe Val Asn Ile Phe Lys Phe
            1040                1045                1050

Lys Asp Leu Thr Val Asp Ala Lys Arg Glu Phe Ile Lys Lys Phe
            1055                1060                1065

Asp Ser Ile Arg Tyr Asp Ser Asp Lys Asn Leu Phe Cys Phe Thr
            1070                1075                1080
```

-continued

```
Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Lys Leu Thr Val Gln Met Arg
    1160                1165                1170

Asn Ser Leu Ser Glu Leu Glu Asp Arg Asn Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260

<210> SEQ ID NO 134
<211> LENGTH: 1307
<212> TYPE: PRT
<213> ORGANISM: Unknown
<220> FEATURE:
<223> OTHER INFORMATION: Acidaminococcus sp. BV3L6

<400> SEQUENCE: 134

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
                20                  25                  30

Glu Gln Gly Phe Ile Glu Glu Asp Lys Ala Arg Asn Asp His Tyr Lys
            35                  40                  45

Glu Leu Lys Pro Ile Ile Asp Arg Ile Tyr Lys Thr Tyr Ala Asp Gln
        50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175
```

```
Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590
```

Met Tyr Tyr Asp Tyr Phe Pro Asp Ala Ala Lys Met Ile Pro Lys Cys
                    595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys Ser Lys Arg Thr Gly Ile Ala Glu
        995                 1000                1005

Lys Ala Val Tyr Gln Gln Phe Glu Lys Met Leu Ile Asp Lys Leu

-continued

```
            1010                1015                1020
Asn Cys Leu Val Leu Lys Asp Tyr Pro Ala Glu Lys Val Gly Gly
        1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
    1085                1090                1095

Glu Gly Phe Asp Phe Leu His Tyr Asp Val Lys Thr Gly Asp Phe
    1100                1105                1110

Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185

Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn
    1295                1300                1305
```

<210> SEQ ID NO 135
<211> LENGTH: 1246
<212> TYPE: PRT
<213> ORGANISM: Unknown
<220> FEATURE:
<223> OTHER INFORMATION: Lachnospiraceae bacterium ND2006

<400> SEQUENCE: 135

```
Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
                20                  25                  30

Lys Thr Leu Arg Phe Lys Ala Ile Pro Val Gly Lys Thr Gln Glu Asn
        35                  40                  45

Ile Asp Asn Lys Arg Leu Leu Val Glu Asp Glu Lys Arg Ala Glu Asp
```

```
            50                  55                  60
Tyr Lys Gly Val Lys Lys Leu Leu Asp Arg Tyr Tyr Leu Ser Phe Ile
 65                  70                  75                  80

Asn Asp Val Leu His Ser Ile Lys Leu Lys Asn Leu Asn Asn Tyr Ile
                     85                  90                  95

Ser Leu Phe Arg Lys Lys Thr Arg Thr Glu Lys Glu Asn Lys Glu Leu
                100                 105                 110

Glu Asn Leu Glu Ile Asn Leu Arg Lys Glu Ile Ala Lys Ala Phe Lys
                115                 120                 125

Gly Asn Glu Gly Tyr Lys Ser Leu Phe Lys Lys Asp Ile Ile Glu Thr
130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
                165                 170                 175

Glu Asn Met Phe Ser Glu Glu Ala Lys Ser Thr Ser Ile Ala Phe Arg
                180                 185                 190

Cys Ile Asn Glu Asn Leu Thr Arg Tyr Ile Ser Asn Met Asp Ile Phe
                195                 200                 205

Glu Lys Val Asp Ala Ile Phe Asp Lys His Glu Val Gln Glu Ile Lys
210                 215                 220

Glu Lys Ile Leu Asn Ser Asp Tyr Asp Val Glu Asp Phe Phe Glu Gly
225                 230                 235                 240

Glu Phe Phe Asn Phe Val Leu Thr Gln Glu Gly Ile Asp Val Tyr Asn
                245                 250                 255

Ala Ile Ile Gly Gly Phe Val Thr Glu Ser Gly Glu Lys Ile Lys Gly
                260                 265                 270

Leu Asn Glu Tyr Ile Asn Leu Tyr Asn Gln Lys Thr Lys Gln Lys Leu
                275                 280                 285

Pro Lys Phe Lys Pro Leu Tyr Lys Gln Val Leu Ser Asp Arg Glu Ser
                290                 295                 300

Leu Ser Phe Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
                325                 330                 335

Lys Lys Leu Glu Lys Leu Phe Lys Asn Phe Asp Glu Tyr Ser Ser Ala
                340                 345                 350

Gly Ile Phe Val Lys Asn Gly Pro Ala Ile Ser Thr Ile Ser Lys Asp
                355                 360                 365

Ile Phe Gly Glu Trp Asn Val Ile Arg Asp Lys Trp Asn Ala Glu Tyr
370                 375                 380

Asp Asp Ile His Leu Lys Lys Lys Ala Val Val Thr Glu Lys Tyr Glu
385                 390                 395                 400

Asp Asp Arg Arg Lys Ser Phe Lys Lys Ile Gly Ser Phe Ser Leu Glu
                405                 410                 415

Gln Leu Gln Glu Tyr Ala Asp Ala Asp Leu Ser Val Val Glu Lys Leu
                420                 425                 430

Lys Glu Ile Ile Ile Gln Lys Val Asp Glu Ile Tyr Lys Val Tyr Gly
                435                 440                 445

Ser Ser Glu Lys Leu Phe Asp Ala Asp Phe Val Leu Glu Lys Ser Leu
450                 455                 460

Lys Lys Asn Asp Ala Val Val Ala Ile Met Lys Asp Leu Leu Asp Ser
465                 470                 475                 480
```

```
Val Lys Ser Phe Glu Asn Tyr Ile Lys Ala Phe Phe Gly Glu Gly Lys
                485                 490                 495

Glu Thr Asn Arg Asp Glu Ser Phe Tyr Gly Asp Phe Val Leu Ala Tyr
            500                 505                 510

Asp Ile Leu Leu Lys Val Asp His Ile Tyr Asp Ala Ile Arg Asn Tyr
            515                 520                 525

Val Thr Gln Lys Pro Tyr Ser Lys Asp Lys Phe Lys Leu Tyr Phe Gln
            530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Tyr Leu Ala Ile Met
                565                 570                 575

Asp Lys Lys Tyr Ala Lys Cys Leu Gln Lys Ile Asp Lys Asp Asp Val
                580                 585                 590

Asn Gly Asn Tyr Glu Lys Ile Asn Tyr Lys Leu Leu Pro Gly Pro Asn
                595                 600                 605

Lys Met Leu Pro Lys Val Phe Phe Ser Lys Lys Trp Met Ala Tyr Tyr
                610                 615                 620

Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
                645                 650                 655

Phe Lys Asp Ser Ile Ser Arg Tyr Pro Lys Trp Ser Asn Ala Tyr Asp
                660                 665                 670

Phe Asn Phe Ser Glu Thr Glu Lys Tyr Lys Asp Ile Ala Gly Phe Tyr
                675                 680                 685

Arg Glu Val Glu Glu Gln Gly Tyr Lys Val Ser Phe Glu Ser Ala Ser
                690                 695                 700

Lys Lys Glu Val Asp Lys Leu Val Glu Glu Gly Lys Leu Tyr Met Phe
705                 710                 715                 720

Gln Ile Tyr Asn Lys Asp Phe Ser Asp Lys Ser His Gly Thr Pro Asn
                725                 730                 735

Leu His Thr Met Tyr Phe Lys Leu Leu Phe Asp Glu Asn Asn His Gly
                740                 745                 750

Gln Ile Arg Leu Ser Gly Gly Ala Glu Leu Phe Met Arg Arg Ala Ser
                755                 760                 765

Leu Lys Lys Glu Glu Leu Val Val His Pro Ala Asn Ser Pro Ile Ala
770                 775                 780

Asn Lys Asn Pro Asp Asn Pro Lys Lys Thr Thr Thr Leu Ser Tyr Asp
785                 790                 795                 800

Val Tyr Lys Asp Lys Arg Phe Ser Glu Asp Gln Tyr Glu Leu His Ile
                805                 810                 815

Pro Ile Ala Ile Asn Lys Cys Pro Lys Asn Ile Phe Lys Ile Asn Thr
                820                 825                 830

Glu Val Arg Val Leu Leu Lys His Asp Asp Asn Pro Tyr Val Ile Gly
                835                 840                 845

Ile Asp Arg Gly Glu Arg Asn Leu Leu Tyr Ile Val Val Val Asp Gly
                850                 855                 860

Lys Gly Asn Ile Val Glu Gln Tyr Ser Leu Asn Glu Ile Ile Asn Asn
865                 870                 875                 880

Phe Asn Gly Ile Arg Ile Lys Thr Asp Tyr His Ser Leu Leu Asp Lys
                885                 890                 895
```

```
Lys Glu Lys Glu Arg Phe Glu Ala Arg Gln Asn Trp Thr Ser Ile Glu
                900                 905                 910

Asn Ile Lys Glu Leu Lys Ala Gly Tyr Ile Ser Gln Val Val His Lys
        915                 920                 925

Ile Cys Glu Leu Val Glu Lys Tyr Asp Ala Val Ile Ala Leu Glu Asp
        930                 935                 940

Leu Asn Ser Gly Phe Lys Asn Ser Arg Val Lys Val Glu Lys Gln Val
945                 950                 955                 960

Tyr Gln Lys Phe Glu Lys Met Leu Ile Asp Lys Leu Asn Tyr Met Val
                965                 970                 975

Asp Lys Lys Ser Asn Pro Cys Ala Thr Gly Gly Ala Leu Lys Gly Tyr
            980                 985                 990

Gln Ile Thr Asn Lys Phe Glu Ser Phe Lys Ser Met Ser Thr Gln Asn
        995                 1000                1005

Gly Phe Ile Phe Tyr Ile Pro Ala Trp Leu Thr Ser Lys Ile Asp
        1010                1015                1020

Pro Ser Thr Gly Phe Val Asn Leu Leu Lys Thr Lys Tyr Thr Ser
        1025                1030                1035

Ile Ala Asp Ser Lys Lys Phe Ile Ser Ser Phe Asp Arg Ile Met
        1040                1045                1050

Tyr Val Pro Glu Glu Asp Leu Phe Glu Phe Ala Leu Asp Tyr Lys
        1055                1060                1065

Asn Phe Ser Arg Thr Asp Ala Asp Tyr Ile Lys Lys Trp Lys Leu
        1070                1075                1080

Tyr Ser Tyr Gly Asn Arg Ile Arg Ile Phe Arg Asn Pro Lys Lys
        1085                1090                1095

Asn Asn Val Phe Asp Trp Glu Glu Val Cys Leu Thr Ser Ala Tyr
        1100                1105                1110

Lys Glu Leu Phe Asn Lys Tyr Gly Ile Asn Tyr Gln Gln Gly Asp
        1115                1120                1125

Ile Arg Ala Leu Leu Cys Glu Gln Ser Asp Lys Ala Phe Tyr Ser
        1130                1135                1140

Ser Phe Met Ala Leu Met Ser Leu Met Leu Gln Met Arg Asn Ser
        1145                1150                1155

Ile Thr Gly Arg Thr Asp Val Asp Phe Leu Ile Ser Pro Val Lys
        1160                1165                1170

Asn Ser Asp Gly Ile Phe Tyr Asp Ser Arg Asn Tyr Glu Ala Gln
        1175                1180                1185

Glu Asn Ala Ile Leu Pro Lys Asn Ala Asp Ala Asn Gly Ala Tyr
        1190                1195                1200

Asn Ile Ala Arg Lys Val Leu Trp Ala Ile Gly Gln Phe Lys Lys
        1205                1210                1215

Ala Glu Asp Glu Lys Leu Asp Lys Val Lys Ile Ala Ile Ser Asn
        1220                1225                1230

Lys Glu Trp Leu Glu Tyr Ala Gln Thr Ser Val Lys His
        1235                1240                1245

<210> SEQ ID NO 136
<211> LENGTH: 1300
<212> TYPE: PRT
<213> ORGANISM: Unknown
<220> FEATURE:
<223> OTHER INFORMATION: Francisella tularensis subsp. novicida U112

<400> SEQUENCE: 136
```

```
Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
            35                  40                  45

Lys Ala Lys Gln Ile Ile Asp Lys Tyr His Gln Phe Phe Ile Glu Glu
        50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
        130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
            165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
        210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
            245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
        290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
            325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
            405                 410                 415

Val Leu Glu Tyr Ile Thr Gln Gln Ile Ala Pro Lys Asn Leu Asp Asn
```

```
              420             425              430
Pro Ser Lys Lys Glu Gln Glu Leu Ile Ala Lys Lys Thr Glu Lys Ala
        435             440             445
Lys Tyr Leu Ser Leu Glu Thr Ile Lys Leu Ala Leu Glu Glu Phe Asn
        450             455             460
Lys His Arg Asp Ile Asp Lys Gln Cys Arg Phe Glu Glu Ile Leu Ala
465             470             475             480
Asn Phe Ala Ala Ile Pro Met Ile Phe Asp Glu Ile Ala Gln Asn Lys
                    485             490             495
Asp Asn Leu Ala Gln Ile Ser Ile Lys Tyr Gln Asn Gln Gly Lys Lys
            500             505             510
Asp Leu Leu Gln Ala Ser Ala Glu Asp Val Lys Ala Ile Lys Asp
        515             520             525
Leu Leu Asp Gln Thr Asn Asn Leu Leu His Lys Leu Lys Ile Phe His
        530             535             540
Ile Ser Gln Ser Glu Asp Lys Ala Asn Ile Leu Asp Lys Asp Glu His
545             550             555             560
Phe Tyr Leu Val Phe Glu Glu Cys Tyr Phe Glu Leu Ala Asn Ile Val
                565             570             575
Pro Leu Tyr Asn Lys Ile Arg Asn Tyr Ile Thr Gln Lys Pro Tyr Ser
            580             585             590
Asp Glu Lys Phe Lys Leu Asn Phe Glu Asn Ser Thr Leu Ala Asn Gly
        595             600             605
Trp Asp Lys Asn Lys Glu Pro Asp Asn Thr Ala Ile Leu Phe Ile Lys
        610             615             620
Asp Asp Lys Tyr Tyr Leu Gly Val Met Asn Lys Lys Asn Asn Lys Ile
625             630             635             640
Phe Asp Asp Lys Ala Ile Lys Glu Asn Lys Gly Glu Gly Tyr Lys Lys
                645             650             655
Ile Val Tyr Lys Leu Leu Pro Gly Ala Asn Lys Met Leu Pro Lys Val
            660             665             670
Phe Phe Ser Ala Lys Ser Ile Lys Phe Tyr Asn Pro Ser Glu Asp Ile
        675             680             685
Leu Arg Ile Arg Asn His Ser Thr His Thr Lys Asn Gly Ser Pro Gln
        690             695             700
Lys Gly Tyr Glu Lys Phe Glu Phe Asn Ile Glu Asp Cys Arg Lys Phe
705             710             715             720
Ile Asp Phe Tyr Lys Gln Ser Ile Ser Lys His Pro Glu Trp Lys Asp
                725             730             735
Phe Gly Phe Arg Phe Ser Asp Thr Gln Arg Tyr Asn Ser Ile Asp Glu
            740             745             750
Phe Tyr Arg Glu Val Glu Asn Gln Gly Tyr Lys Leu Thr Phe Glu Asn
        755             760             765
Ile Ser Glu Ser Tyr Ile Asp Ser Val Val Asn Gln Gly Lys Leu Tyr
        770             775             780
Leu Phe Gln Ile Tyr Asn Lys Asp Phe Ser Ala Tyr Ser Lys Gly Arg
785             790             795             800
Pro Asn Leu His Thr Leu Tyr Trp Lys Ala Leu Phe Asp Glu Arg Asn
                805             810             815
Leu Gln Asp Val Val Tyr Lys Leu Asn Gly Glu Ala Glu Leu Phe Tyr
            820             825             830
Arg Lys Gln Ser Ile Pro Lys Lys Ile Thr His Pro Ala Lys Glu Ala
        835             840             845
```

```
Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Glu Asp Leu
        995                 1000                1005

Asn Phe Gly Phe Lys Arg Gly Arg Phe Lys Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245
```

```
Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn
    1295                1300

<210> SEQ ID NO 137
<211> LENGTH: 1067
<212> TYPE: PRT
<213> ORGANISM: Unknown
<220> FEATURE:
<223> OTHER INFORMATION: Omnitrophica WOR_2 bacterium GWF2_38_59

<400> SEQUENCE: 137

Met Lys Asn Gly Ile Asn Leu Phe Lys Thr Lys Thr Thr Lys Thr Lys
1               5                   10                  15

Gly Val Asp Met Glu Lys Tyr Gln Ile Thr Lys Thr Ile Arg Phe Lys
            20                  25                  30

Leu Leu Pro Asp Asn Ala His Glu Ile Val Glu Lys Val Lys Ser Leu
        35                  40                  45

Lys Thr Ser Asn Val Asp Glu Leu Met Asp Glu Val Lys Asn Val His
    50                  55                  60

Leu Lys Gly Leu Glu Leu Leu Phe Ala Leu Lys Lys Tyr Phe Tyr Phe
65                  70                  75                  80

Asp Gly Asn Gln Cys Lys Ser Phe Lys Ser Thr Leu Glu Ile Lys Ala
                85                  90                  95

Arg Trp Leu Arg Leu Tyr Thr Pro Asp Gln Tyr Tyr Leu Lys Lys Ser
            100                 105                 110

Ser Lys Asn Ser Tyr Gln Leu Lys Ser Leu Ser Tyr Phe Lys Asp Val
        115                 120                 125

Phe Asn Asp Trp Leu Phe Asn Trp Glu Glu Ser Val Ser Glu Leu Ala
    130                 135                 140

Ile Ile Tyr Glu Lys Tyr Lys Ile Cys Gln His Gln Arg Asp Ser Arg
145                 150                 155                 160

Ala Asp Ile Ala Leu Leu Ile Lys Lys Leu Ser Met Lys Glu Tyr Phe
                165                 170                 175

Pro Phe Ile Ser Asp Leu Ile Asp Cys Val Asn Asp Lys Asn Ser Asn
            180                 185                 190

Lys Thr Phe Leu Met Lys Leu Ser Glu Glu Leu Ser Val Leu Leu Glu
        195                 200                 205

Lys Cys Asn Ser Arg Ala Leu Pro Tyr Gln Ser Asn Gly Ile Val Val
    210                 215                 220

Gly Lys Ala Ser Leu Asn Tyr Tyr Thr Val Ser Lys Ser Glu Lys Met
225                 230                 235                 240

Leu Gln Asn Glu Tyr Glu Asp Val Cys Gln Ser Leu Asp Lys Asn Tyr
                245                 250                 255

Asp Ile Thr Glu Met Lys Val Ile Leu Tyr Lys Glu Lys Leu Asp Asn
            260                 265                 270

Leu Asn Phe Lys Asp Val Thr Ile Ala Asn Ala Tyr Asn Leu Leu Lys
        275                 280                 285

Glu Asn Lys Ala Leu Gln Lys Arg Leu Phe Ser Glu Tyr Val Ser Gln
    290                 295                 300
```

-continued

```
Gly Lys Val Leu Ser Leu Ile Lys Thr Glu Leu Pro Leu Phe Ser Asn
305                 310                 315                 320

Ile Asn Asp Asn Asp Phe Glu Lys Tyr Lys Glu Trp Ser Asn Glu Ile
                325                 330                 335

Lys Lys Leu Ala Asp Lys Lys Asn Thr Phe Cys Lys Lys Thr Gln Gln
            340                 345                 350

Asp Lys Ile Lys Asp Ile Gln Asn Lys Ile Ser Glu Leu Lys Lys Lys
        355                 360                 365

Arg Gly Ala Leu Phe Gln Tyr Lys Phe Thr Ser Phe Gln Lys His Cys
    370                 375                 380

Asp Asn Tyr Lys Lys Val Ala Val Gln Tyr Gly Lys Leu Lys Ala Arg
385                 390                 395                 400

Lys Lys Ala Ile Glu Lys Asp Glu Ile Glu Ala Asn Leu Leu Arg Tyr
                405                 410                 415

Trp Ser Val Ile Leu Glu Gln Glu Asp Lys His Ser Leu Val Leu Ile
            420                 425                 430

Pro Lys Asn Asn Ala Lys Asp Ala Lys Gln Tyr Ile Glu Thr Ile Asn
        435                 440                 445

Thr Lys Gly Gly Lys Tyr Ile Ile His His Leu Asp Ser Leu Thr Leu
    450                 455                 460

Arg Ala Leu Asn Lys Leu Cys Phe Asn Ala Val Asp Ile Glu Lys Gly
465                 470                 475                 480

Gln Met Val Arg Glu Asn Thr Phe Tyr Gln Gly Ile Lys Glu Glu Phe
                485                 490                 495

Glu Arg Asn Lys Ile Asn Cys Asp Asn Gln Gly Val Leu Lys Ile Gln
            500                 505                 510

Gly Leu Tyr Ser Phe Lys Thr Glu Gly Gly Gln Ile Asn Glu Lys Glu
        515                 520                 525

Ala Val Glu Phe Phe Lys Glu Val Leu Lys Ser Asn Tyr Ala Arg Glu
    530                 535                 540

Val Leu Asn Leu Pro Tyr Asp Leu Glu Ser Asn Ile Phe Gln Lys Glu
545                 550                 555                 560

Tyr Thr Asn Leu Asp Gln Phe Arg Gln Asp Leu Glu Lys Cys Cys Tyr
                565                 570                 575

Ala Leu His Ser Lys Ile Gly Lys Asp Asp Leu Asp Glu Phe Thr Arg
            580                 585                 590

Arg Phe Glu Ala Gln Val Phe Asp Ile Thr Ser Ile Asp Leu Lys Ser
        595                 600                 605

Lys Lys Glu Lys Thr Lys Thr Thr Gly Glu Met Lys Lys His Thr Gln
    610                 615                 620

Leu Trp Leu Glu Phe Trp Lys Gly Ala Ile Glu Gln Asn Phe Ala Thr
625                 630                 635                 640

Arg Val Asn Pro Glu Leu Ser Ile Phe Trp Arg Ala Pro Lys Ser Ser
                645                 650                 655

Arg Glu Lys Lys Tyr Gly Lys Gly Ser Asp Leu Tyr Asp Pro Asn Lys
            660                 665                 670

Asn Asn Arg Tyr Leu Tyr Glu Gln Tyr Thr Leu Ala Leu Thr Ile Thr
        675                 680                 685

Glu Asn Ala Gly Ser His Phe Lys Asp Ile Ala Phe Lys Asp Thr Ser
    690                 695                 700

Lys Ile Lys Glu Ala Ile Lys Glu Phe Asn Met Ser Leu Ser Gln Ser
705                 710                 715                 720

Lys Tyr Cys Phe Gly Ile Asp Arg Gly Asn Ala Glu Leu Val Ser Leu
```

```
                    725                 730                 735

Cys Leu Ile Lys Asn Glu Lys Asp Phe Pro Phe Glu Lys Phe Pro Val
            740                 745                 750

Tyr Arg Leu Arg Asp Leu Thr Tyr Gln Gly Asp Phe Lys Asp Lys His
            755                 760                 765

Asp Gln Met Arg Tyr Gly Val Ala Ile Lys Asn Ile Ser Tyr Phe Ile
            770                 775                 780

Asp Gln Glu Asp Leu Phe Glu Lys Asn Asn Leu Ser Ala Ile Asp Met
785                 790                 795                 800

Thr Thr Ala Lys Leu Ile Lys Asn Lys Ile Val Leu Asn Gly Asp Val
                    805                 810                 815

Leu Thr Tyr Leu Lys Leu Lys Glu Glu Thr Ala Lys His Lys Leu Thr
                    820                 825                 830

Gln Phe Phe Gln Gly Ser Ser Ile Asn Lys Asn Ser Arg Val Tyr Phe
                    835                 840                 845

Asp Glu Asp Glu Asn Val Phe Lys Ile Thr Thr Asn Arg Asn His Asn
            850                 855                 860

Pro Glu Glu Ile Ile Tyr Phe Tyr Arg Gly Glu Tyr Gly Ala Ile Lys
865                 870                 875                 880

Asn Lys Asn Asp Leu Glu Asp Ile Leu Asn Glu Tyr Leu Cys Lys Met
                    885                 890                 895

Glu Thr Gly Glu Ser Glu Ile Val Leu Leu Asn Arg Val Asn His Leu
            900                 905                 910

Arg Asp Ala Ile Ser Ala Asn Ile Val Gly Ile Leu Ser Tyr Leu Ile
                    915                 920                 925

Asp Leu Phe Pro Glu Thr Ile Val Ala Leu Glu Asn Leu Ala Lys Gly
            930                 935                 940

Thr Ile Asp Arg His Val Ser Gln Ser Tyr Glu Asn Ile Thr Arg Arg
945                 950                 955                 960

Phe Glu Trp Ala Leu Tyr Arg Lys Leu Leu Asn Lys Gln Leu Ala Pro
                    965                 970                 975

Pro Glu Leu Lys Glu Asn Ile Leu Leu Arg Glu Gly Asp Asp Lys Ile
            980                 985                 990

Asp Gln Phe Gly Ile Ile His Phe  Val Glu Glu Lys Asn  Thr Ser Lys
            995                1000                 1005

Asp Cys Pro Asn Cys Arg Lys  Thr Thr Gln Gln Thr  Asn Asp Asn
        1010                1015                1020

Lys Phe Lys Glu Lys Lys Phe  Val Cys Lys Ser Cys  Gly Phe Asp
        1025                1030                1035

Thr Ser  Lys Asp Arg Lys Gly  Met Asp Ser Leu Asn  Ser Pro Asp
        1040                1045                1050

Thr Val  Ala Ala Tyr Asn Val  Ala Arg Lys Lys Phe  Glu Ser
        1055                1060                1065

<210> SEQ ID NO 138
<211> LENGTH: 1057
<212> TYPE: PRT
<213> ORGANISM: Unknown
<220> FEATURE:
<223> OTHER INFORMATION: Candidatus Roizmanbacteria bacterium
      GW2011_GWA2_37_7 US54_C0016

<400> SEQUENCE: 138

Met Glu Ile Gln Glu Leu Lys Asn Leu Tyr Glu Val Lys Lys Thr Val
1               5                   10                  15
```

-continued

Arg Phe Glu Leu Lys Pro Ser Lys Lys Ile Phe Glu Gly Gly Asp
            20              25              30

Val Ile Lys Leu Gln Lys Asp Phe Glu Lys Val Gln Lys Phe Phe Leu
        35              40              45

Asp Ile Phe Val Tyr Lys Asn Glu His Thr Lys Leu Glu Phe Lys Lys
        50              55              60

Lys Arg Glu Ile Lys Tyr Thr Trp Leu Arg Thr Asn Thr Lys Asn Glu
65              70              75              80

Phe Tyr Asn Trp Arg Gly Lys Ser Asp Thr Gly Lys Asn Tyr Ala Leu
            85              90              95

Asn Lys Ile Gly Phe Leu Ala Glu Ile Leu Arg Trp Leu Asn Glu
            100             105             110

Trp Gln Glu Leu Thr Lys Ser Leu Lys Asp Leu Thr Gln Arg Glu Glu
            115             120             125

His Lys Gln Glu Arg Lys Ser Asp Ile Ala Phe Val Leu Arg Asn Phe
            130             135             140

Leu Lys Arg Gln Asn Leu Pro Phe Ile Lys Asp Phe Phe Asn Ala Val
145             150             155             160

Ile Asp Ile Gln Gly Lys Gln Gly Lys Glu Ser Asp Asp Lys Ile Arg
            165             170             175

Lys Phe Arg Glu Glu Ile Lys Glu Ile Glu Lys Asn Leu Asn Ala Cys
            180             185             190

Ser Arg Glu Tyr Leu Pro Thr Gln Ser Asn Gly Val Leu Leu Tyr Lys
            195             200             205

Ala Ser Phe Ser Tyr Tyr Thr Leu Asn Lys Thr Pro Lys Glu Tyr Glu
210             215             220

Asp Leu Lys Lys Glu Lys Glu Ser Glu Leu Ser Ser Val Leu Leu Lys
225             230             235             240

Glu Ile Tyr Arg Arg Lys Arg Phe Asn Arg Thr Thr Asn Gln Lys Asp
            245             250             255

Thr Leu Phe Glu Cys Thr Ser Asp Trp Leu Val Lys Ile Lys Leu Gly
            260             265             270

Lys Asp Ile Tyr Glu Trp Thr Leu Asp Glu Ala Tyr Gln Lys Met Lys
            275             280             285

Ile Trp Lys Ala Asn Gln Lys Ser Asn Phe Ile Glu Ala Val Ala Gly
            290             295             300

Asp Lys Leu Thr His Gln Asn Phe Arg Lys Gln Phe Pro Leu Phe Asp
305             310             315             320

Ala Ser Asp Glu Asp Phe Glu Thr Phe Tyr Arg Leu Thr Lys Ala Leu
            325             330             335

Asp Lys Asn Pro Glu Asn Ala Lys Lys Ile Ala Gln Lys Arg Gly Lys
            340             345             350

Phe Phe Asn Ala Pro Asn Glu Thr Val Gln Thr Lys Asn Tyr His Glu
            355             360             365

Leu Cys Glu Leu Tyr Lys Arg Ile Ala Val Lys Arg Gly Lys Ile Ile
            370             375             380

Ala Glu Ile Lys Gly Ile Glu Asn Glu Val Gln Ser Gln Leu Leu
385             390             395             400

Thr His Trp Ala Val Ile Ala Glu Glu Arg Asp Lys Lys Phe Ile Val
            405             410             415

Leu Ile Pro Arg Lys Asn Gly Gly Lys Leu Glu Asn His Lys Asn Ala
            420             425             430

His Ala Phe Leu Gln Glu Lys Asp Arg Lys Glu Pro Asn Asp Ile Lys

-continued

```
            435                 440                 445
Val Tyr His Phe Lys Ser Leu Thr Leu Arg Ser Leu Glu Lys Leu Cys
450                 455                 460

Phe Lys Glu Ala Lys Asn Thr Phe Ala Pro Glu Ile Lys Lys Glu Thr
465                 470                 475                 480

Asn Pro Lys Ile Trp Phe Pro Thr Tyr Lys Gln Glu Trp Asn Ser Thr
                    485                 490                 495

Pro Glu Arg Leu Ile Lys Phe Tyr Lys Gln Val Leu Gln Ser Asn Tyr
                500                 505                 510

Ala Gln Thr Tyr Leu Asp Leu Val Asp Phe Gly Asn Leu Asn Thr Phe
                515                 520                 525

Leu Glu Thr His Phe Thr Thr Leu Glu Glu Phe Glu Ser Asp Leu Glu
                530                 535                 540

Lys Thr Cys Tyr Thr Lys Val Pro Val Tyr Phe Ala Lys Lys Glu Leu
545                 550                 555                 560

Glu Thr Phe Ala Asp Glu Phe Glu Ala Glu Val Phe Glu Ile Thr Thr
                    565                 570                 575

Arg Ser Ile Ser Thr Glu Ser Lys Arg Lys Glu Asn Ala His Ala Glu
                580                 585                 590

Ile Trp Arg Asp Phe Trp Ser Arg Glu Asn Glu Glu Asn His Ile
                595                 600                 605

Thr Arg Leu Asn Pro Glu Val Ser Val Leu Tyr Arg Asp Glu Ile Lys
610                 615                 620

Glu Lys Ser Asn Thr Ser Arg Lys Asn Arg Lys Ser Asn Ala Asn Asn
625                 630                 635                 640

Arg Phe Ser Asp Pro Arg Phe Thr Leu Ala Thr Ile Thr Leu Asn
                    645                 650                 655

Ala Asp Lys Lys Lys Ser Asn Leu Ala Phe Lys Thr Val Glu Asp Ile
                660                 665                 670

Asn Ile His Ile Asp Asn Phe Asn Lys Lys Phe Ser Lys Asn Phe Ser
                675                 680                 685

Gly Glu Trp Val Tyr Gly Ile Asp Arg Gly Leu Lys Glu Leu Ala Thr
690                 695                 700

Leu Asn Val Val Lys Phe Ser Asp Val Lys Asn Val Phe Gly Val Ser
705                 710                 715                 720

Gln Pro Lys Glu Phe Ala Lys Ile Pro Ile Tyr Lys Leu Arg Asp Glu
                    725                 730                 735

Lys Ala Ile Leu Lys Asp Glu Asn Gly Leu Ser Leu Lys Asn Ala Lys
                740                 745                 750

Gly Glu Ala Arg Lys Val Ile Asp Asn Ile Ser Asp Val Leu Glu Glu
                755                 760                 765

Gly Lys Glu Pro Asp Ser Thr Leu Phe Glu Lys Arg Glu Val Ser Ser
                770                 775                 780

Ile Asp Leu Thr Arg Ala Lys Leu Ile Lys Gly His Ile Ile Ser Asn
785                 790                 795                 800

Gly Asp Gln Lys Thr Tyr Leu Lys Leu Lys Glu Thr Ser Ala Lys Arg
                    805                 810                 815

Arg Ile Phe Glu Leu Phe Ser Thr Ala Lys Ile Asp Lys Ser Ser Gln
                820                 825                 830

Phe His Val Arg Lys Thr Ile Glu Leu Ser Gly Thr Lys Ile Tyr Trp
                835                 840                 845

Leu Cys Glu Trp Gln Arg Gln Asp Ser Trp Arg Thr Glu Lys Val Ser
850                 855                 860
```

Leu Arg Asn Thr Leu Lys Gly Tyr Leu Gln Asn Leu Asp Leu Lys Asn
865                 870                 875                 880

Arg Phe Glu Asn Ile Glu Thr Ile Glu Lys Ile Asn His Leu Arg Asp
            885                 890                 895

Ala Ile Thr Ala Asn Met Val Gly Ile Leu Ser His Leu Gln Asn Lys
        900                 905                 910

Leu Glu Met Gln Gly Val Ile Ala Leu Glu Asn Leu Asp Thr Val Arg
    915                 920                 925

Glu Gln Ser Asn Lys Lys Met Ile Asp Glu His Phe Glu Gln Ser Asn
930                 935                 940

Glu His Val Ser Arg Arg Leu Glu Trp Ala Leu Tyr Cys Lys Phe Ala
945                 950                 955                 960

Asn Thr Gly Glu Val Pro Pro Gln Ile Lys Glu Ser Ile Phe Leu Arg
            965                 970                 975

Asp Glu Phe Lys Val Cys Gln Ile Gly Ile Leu Asn Phe Ile Asp Val
        980                 985                 990

Lys Gly Thr Ser Ser Asn Cys Pro Asn Cys Asp Gln Glu Ser Arg Lys
    995                 1000                1005

Thr Gly Ser His Phe Ile Cys Asn Phe Gln Asn Asn Cys Ile Phe
    1010                1015                1020

Ser Ser Lys Glu Asn Arg Asn Leu Leu Glu Gln Asn Leu His Asn
    1025                1030                1035

Ser Asp Asp Val Ala Ala Phe Asn Ile Ala Lys Arg Gly Leu Glu
    1040                1045                1050

Ile Val Lys Val
    1055

<210> SEQ ID NO 139
<211> LENGTH: 78
<212> TYPE: RNA
<213> ORGANISM: Unknown
<220> FEATURE:
<223> OTHER INFORMATION: Uncultured Clostridium sp. isolate
      2789STDY5608795

<400> SEQUENCE: 139
cagucuuaau aaacgaaaaa gaauauauua cuuaaccaga ugugugcaaa ugugauaaaa      60
agaauaaguu uaaauaag                                                   78

<210> SEQ ID NO 140
<211> LENGTH: 67
<212> TYPE: RNA
<213> ORGANISM: Unknown
<220> FEATURE:
<223> OTHER INFORMATION: Uncultured bacterium (gcode 4) ACD_3C00058,
      whole genome shotgun sequence

<400> SEQUENCE: 140
agagaaaaau gcaaaccuaa gucuuaauuu uuucaccuuc cuacagauaa gccaaaaguc      60
guaauuu                                                               67

<210> SEQ ID NO 141
<211> LENGTH: 81
<212> TYPE: RNA
<213> ORGANISM: Unknown
<220> FEATURE:
<223> OTHER INFORMATION: Thiomicrospira sp. XS5 ZB100000

<400> SEQUENCE: 141
uucucugaua aaauaauuaa cucaggucuu uucgagaaaa aacugcaaac cuuggucuua    60
augagaaaaa ucaugaaaaa a    81

<210> SEQ ID NO 142
<211> LENGTH: 82
<212> TYPE: RNA
<213> ORGANISM: Unknown
<220> FEATURE:
<223> OTHER INFORMATION: Flavobacterium branchiophilum FL-15

<400> SEQUENCE: 142
caugaaaaca agcuuucgaa ugcuguuuuu uuauuuaaaa gcaaccaaaa acgguaaaaa    60
aggguuguuu uugugucauu uu    82

<210> SEQ ID NO 143
<211> LENGTH: 63
<212> TYPE: RNA
<213> ORGANISM: Unknown
<220> FEATURE:
<223> OTHER INFORMATION: Moraxella bovoculi strain 57922

<400> SEQUENCE: 143
gucuaacgac cuuuuaaauu ucacuguuu guagauauuc gugcguauuu gauuucuuug    60
ugu    63

<210> SEQ ID NO 144
<211> LENGTH: 85
<212> TYPE: RNA
<213> ORGANISM: Unknown
<220> FEATURE:
<223> OTHER INFORMATION: Candidatus Roizmanbacteria bacterium
    GW2011_GWA2_37_7 US54_C0016

<400> SEQUENCE: 144
aauggaaaaa guggaaauug uauuaucagu acaaaaccua agucuuuauu uuuugaaga    60 cgauguagag uuguagucua augag    85

<210> SEQ ID NO 145
<211> LENGTH: 84
<212> TYPE: RNA
<213> ORGANISM: Unknown
<220> FEATURE:
<223> OTHER INFORMATION: Pseudobutyrivibrio xylanivorans

<400> SEQUENCE: 145
accuauaacu uaauuugugg auacuaaguc uugagugaug aaaauggcag uuuuguuagu    60
aaauaaacau aauaauauga ugaa    84

<210> SEQ ID NO 146
<211> LENGTH: 83
<212> TYPE: RNA
<213> ORGANISM: Unknown
<220> FEATURE:
<223> OTHER INFORMATION: Prevotella bryantii B14

<400> SEQUENCE: 146
auauacgaua uuauguuuua gccuacauuu ucauaaaguu cugauaucaa acacauuaua    60
aacuuuuaua uaacaaucaa gaa    83

<210> SEQ ID NO 147
<211> LENGTH: 63

```
<212> TYPE: RNA
<213> ORGANISM: Unknown
<220> FEATURE:
<223> OTHER INFORMATION: Smithella sp. SCADC

<400> SEQUENCE: 147 uuauugguguu ucagcaauuu aaucuugcgc gugaaagaaa aaugugcuua uuaaacaacu      60
aua                                                                   63

<210> SEQ ID NO 148
<211> LENGTH: 57
<212> TYPE: RNA
<213> ORGANISM: Unknown
<220> FEATURE:
<223> OTHER INFORMATION: Smithella sp. SCADC

<400> SEQUENCE: 148
aaaaauuggc ugauuuuaug guguuucagc aauuuaaucu ugcgcgugaa agaaaaa         57

<210> SEQ ID NO 149
<211> LENGTH: 82
<212> TYPE: RNA
<213> ORGANISM: Unknown
<220> FEATURE:
<223> OTHER INFORMATION: Bacteroidetes bacterium GWF2_33_38

<400> SEQUENCE: 149
gcacaaagaa gcaaagcuuu uuuaaaaagc uuugcuucua aaacaauuag uuauuugaaa      60
uaguuguauu uuuuuuuuac ga                                              82

<210> SEQ ID NO 150
<211> LENGTH: 74
<212> TYPE: RNA
<213> ORGANISM: Unknown
<220> FEATURE:
<223> OTHER INFORMATION: Candidatus Peribacteria bacterium RIFCSPLOWO2

<400> SEQUENCE: 150
aaauccauau guggauaucu caucuugcag accaucgucc uuauuucuu aagaagaccu       60 cuucaaacca aaaa                                                       74

<210> SEQ ID NO 151
<211> LENGTH: 74
<212> TYPE: RNA
<213> ORGANISM: Unknown
<220> FEATURE:
<223> OTHER INFORMATION: Nitrospinae bacterium RIFCSPLOWO2

<400> SEQUENCE: 151
uucuacuauu guagaucaaa ccucggucuu aauguaaaaa auggcgcuug gacuggcggu      60
caaaaccaca aaaa                                                       74

<210> SEQ ID NO 152
<211> LENGTH: 67
<212> TYPE: RNA
<213> ORGANISM: Unknown
<220> FEATURE:
<223> OTHER INFORMATION: Candidatus Ryanbacteria bacterium RIFCSPHIGHO2

<400> SEQUENCE: 152
cucgugaaag guggaaaucc agugaaggua uuugguuuaa uauguauauu acgagauaug      60
cgggaaa                                                               67
```

<210> SEQ ID NO 153
<211> LENGTH: 85
<212> TYPE: RNA
<213> ORGANISM: Unknown
<220> FEATURE:
<223> OTHER INFORMATION: Candidatus Wildermuthbacteria bacterium
      RIFCSPHIGHO2

<400> SEQUENCE: 153
uuauacugaa gcauaaagua uaaauugcgu guggauauua auuuagacuc aauauauaac      60
gguggaaaac cuuugccuuu auaaa                                           85

<210> SEQ ID NO 154
<211> LENGTH: 59
<212> TYPE: RNA
<213> ORGANISM: Unknown
<220> FEATURE:
<223> OTHER INFORMATION: Firmicutes bacterium CAG_194_44_15

<400> SEQUENCE: 154
gucuuucuau uuaguuuuaa uuuuaggguua cuugacaaua ugguaauaau aaacaaaau     59

<210> SEQ ID NO 155
<211> LENGTH: 83
<212> TYPE: RNA
<213> ORGANISM: Unknown
<220> FEATURE:
<223> OTHER INFORMATION: Candidatus Gottesmanbacteria bacterium
      CG1_02_37_22

<400> SEQUENCE: 155
auuauaaaag cagaagugaa acuguuaaua uuugagaaaa cuuaagucuu uaugagccug      60
uuucuugcua uuuuacgccu aaa                                             83

<210> SEQ ID NO 156
<211> LENGTH: 87
<212> TYPE: RNA
<213> ORGANISM: Unknown
<220> FEATURE:
<223> OTHER INFORMATION: Candidatus Gracilibacteria bacterium
      CG1_02_38_174

<400> SEQUENCE: 156
aacaagggug gaaaucuuua uguuggguuu uacgaaaacu gcaaaccuca gucuucauuu      60
uuugcgagua ccguuuuaag ccaagaa                                         87

<210> SEQ ID NO 157
<211> LENGTH: 76
<212> TYPE: RNA
<213> ORGANISM: Unknown
<220> FEATURE:
<223> OTHER INFORMATION: Butyrivibrio fibrisolvens MD2001

<400> SEQUENCE: 157
aaccuccgau uugauuuuua uuuauggguu cuuggaaaua auauaugggc aaauuauugg      60
ugauaaguua uaaaaa                                                     76

<210> SEQ ID NO 158
<211> LENGTH: 60
<212> TYPE: RNA
<213> ORGANISM: Unknown
<220> FEATURE:
<223> OTHER INFORMATION: Sneathia amnii strain SN35

```
<400> SEQUENCE: 158
aaucaaggug uuaauauuuu uaaaaugcga aaaaaucaaa ucucucaaau guaaaaaaaa        60

<210> SEQ ID NO 159
<211> LENGTH: 73
<212> TYPE: RNA
<213> ORGANISM: Unknown
<220> FEATURE:
<223> OTHER INFORMATION: Coprococcus eutactus strain 2789STDY5608843

<400> SEQUENCE: 159
cagucuuucu gaggaaaaau uaaggggguua cucaacagau augaacauaa caaacaaaaa        60
aagaauguau aua                                                           73

<210> SEQ ID NO 160
<211> LENGTH: 65
<212> TYPE: RNA
<213> ORGANISM: Unknown
<220> FEATURE:
<223> OTHER INFORMATION: Lachnospira pectinoschiza strain
      2789STDY5834886

<400> SEQUENCE: 160
ugaccuuaau auuuaaaauu agaugggguua cuuaauauaa uauguguaua uugcauaaaa        60
aauaa                                                                    65

<210> SEQ ID NO 161
<211> LENGTH: 80
<212> TYPE: RNA
<213> ORGANISM: Unknown
<220> FEATURE:
<223> OTHER INFORMATION: Bacteroidetes oral taxon 274 str. F0058

<400> SEQUENCE: 161
auggagaaua caaaguuuga uuauugucuu gauaauaaau aaacuaugaa aauuuguuuu        60
uugcaggggg ggauaaaaua                                                    80

<210> SEQ ID NO 162
<211> LENGTH: 63
<212> TYPE: RNA
<213> ORGANISM: Unknown
<220> FEATURE:
<223> OTHER INFORMATION: Arcobacter butzleri L348 isolate CHRB125

<400> SEQUENCE: 162
uauggaaaua uuguuaaaaa auauaaauuu uaagagggua aauaagcuuu uuuaauauga        60
uuu                                                                      63

<210> SEQ ID NO 163
<211> LENGTH: 65
<212> TYPE: RNA
<213> ORGANISM: Unknown
<220> FEATURE:
<223> OTHER INFORMATION: Bacteroidales bacterium KA00251

<400> SEQUENCE: 163
acucccuauu auucaacuaa aaaaggccau uuuccccgau cauuuagaag agagaggggg        60
ggaaa                                                                    65

<210> SEQ ID NO 164
<211> LENGTH: 67
<212> TYPE: RNA
```

<213> ORGANISM: Unknown
<220> FEATURE:
<223> OTHER INFORMATION: Acidaminococcus massiliensis strain
Marseille-P2828

<400> SEQUENCE: 164
agugaaaauc guggaaaauc acuugguaca auggacggga acacuauaua uuguggcaga 60
cuccaag 67

<210> SEQ ID NO 165
<211> LENGTH: 71
<212> TYPE: RNA
<213> ORGANISM: Helcococcus kunzii

<400> SEQUENCE: 165
uucuuaaagg auaucuaaaa auguauucau uaaaugagag uuuaugcauu gcaauacuaa 60
cuauagugac a 71

<210> SEQ ID NO 166
<211> LENGTH: 57
<212> TYPE: RNA
<213> ORGANISM: Unknown
<220> FEATURE:
<223> OTHER INFORMATION: Agathobacter rectalis strain 2789STDY5834884

<400> SEQUENCE: 166
uggaccuuaa uuuuauaaua aucuauauua cuuaacauau uuugugcaaa uguuaua 57

<210> SEQ ID NO 167
<211> LENGTH: 72
<212> TYPE: RNA
<213> ORGANISM: Unknown
<220> FEATURE:
<223> OTHER INFORMATION: Acidaminococcus sp. BV3L6

<400> SEQUENCE: 167
cauugucuaa ccugcaaacc uccaacuuac uauugcuaag gaguauauau uuuguauaaa 60
aggucuuuuu uc 72

<210> SEQ ID NO 168
<211> LENGTH: 65
<212> TYPE: RNA
<213> ORGANISM: Unknown
<220> FEATURE:
<223> OTHER INFORMATION: Lachnospiraceae bacterium ND2006

<400> SEQUENCE: 168
aauugcaaau cuuugaaaua augcagacuu aaauuuauaa auucauggaa uaaggugauu 60
uuauu 65

<210> SEQ ID NO 169
<211> LENGTH: 81
<212> TYPE: RNA
<213> ORGANISM: Unknown
<220> FEATURE:
<223> OTHER INFORMATION: Francisella tularensis subsp. novicida U112

<400> SEQUENCE: 169
aaguucuuag agauauuuaa aaauaugacu guuguuauau aucaaaaugc uaaaaaaauc 60
auagauuuua ggucuuuuuu u 81

<210> SEQ ID NO 170

<211> LENGTH: 72
<212> TYPE: RNA
<213> ORGANISM: Unknown
<220> FEATURE:
<223> OTHER INFORMATION: Omnitrophica WOR_2 bacterium GWF2_38_59

<400> SEQUENCE: 170
gccuuuauuu auuggacuua cgaaaauacu cuuaaaaacu augaugcugu aaauuguugg    60
gguaucguuu gu    72

<210> SEQ ID NO 171
<211> LENGTH: 69
<212> TYPE: RNA
<213> ORGANISM: Unknown
<220> FEATURE:
<223> OTHER INFORMATION: Candidatus Roizmanbacteria bacterium
      GW2011_GWA2_37_7 US54_C0016

<400> SEQUENCE: 171
auggaaaaag uggaaauugu auuaucagua caaaaccuaa gucuuuauuu uuuugaagac    60
gauguagag    69

<210> SEQ ID NO 172
<211> LENGTH: 1300
<212> TYPE: PRT
<213> ORGANISM: Francisella tularensis

<400> SEQUENCE: 172

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
            85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
            165                 170                 175

Thr Tyr Phe Lys Gly Phe His Glu Asn Arg Lys Asn Val Tyr Ser Ser
            180                 185                 190

Asp Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

```
Glu Leu Thr Phe Asp Ile Asp Tyr Lys Thr Ser Val Asn Gln Arg
            245                 250                 255

Val Phe Ser Leu Asp Glu Val Phe Glu Ile Ala Asn Phe Asn Asn Tyr
        260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
        290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
            325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
            355                 360                 365

Ser Ile Lys Glu Thr Leu Ser Leu Leu Phe Asp Asp Leu Lys Ala Gln
        370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
            405                 410                 415

Val Leu Glu Tyr Ile Thr Gln Gln Val Ala Pro Lys Asn Leu Asp Asn
            420                 425                 430

Pro Ser Lys Lys Glu Gln Asp Leu Ile Ala Lys Lys Thr Glu Lys Ala
            435                 440                 445

Lys Tyr Leu Ser Leu Glu Thr Ile Lys Leu Ala Leu Glu Glu Phe Asn
            450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Leu Lys Tyr Gln Asn Gly Lys Lys
            500                 505                 510

Asp Leu Leu Gln Ala Ser Ala Glu Glu Asp Val Lys Ala Ile Lys Asp
            515                 520                 525

Leu Leu Asp Gln Thr Asn Asn Leu Leu His Arg Leu Lys Ile Phe His
        530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
        610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655
```

-continued

```
Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
            675                 680                 685

Leu Arg Ile Arg Asn His Ser Thr His Thr Lys Asn Gly Asn Pro Gln
690                 695                 700

Lys Gly Tyr Glu Lys Phe Glu Phe Asn Ile Glu Asp Cys Arg Lys Phe
705                 710                 715                 720

Ile Asp Phe Tyr Lys Glu Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
            755                 760                 765

Ile Ser Glu Ser Tyr Ile Asp Ser Val Val Asn Gln Gly Lys Leu Tyr
            770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
                835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
            915                 920                 925

Val Asp Gly Lys Gly Asn Ile Ile Lys Gln Asp Thr Phe Asn Ile Ile
930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu His Asn Ala Ile Val Val Phe Glu Asp Leu
            995                1000                1005

Asn Phe Gly Phe Lys Arg Gly Arg Phe Lys Val Glu Lys Gln Val
            1010                1015                1020

Tyr Gln Lys Leu Glu Lys Met Leu Ile Glu Lys Leu Asn Tyr Leu
            1025                1030                1035

Val Phe Lys Asp Asn Glu Phe Asp Lys Thr Gly Gly Val Leu Arg
            1040                1045                1050

Ala Tyr Gln Leu Thr Ala Pro Phe Glu Thr Phe Lys Lys Met Gly
            1055                1060                1065

Lys Gln Thr Gly Ile Ile Tyr Tyr Val Pro Ala Gly Phe Thr Ser
```

Lys Ile Cys Pro Val Thr Gly Phe Val Asn Gln Leu Tyr Pro Lys
1085                1090                1095

Tyr Glu Ser Val Ser Lys Ser Gln Glu Phe Phe Ser Lys Phe Asp
1100                1105                1110

Lys Ile Cys Tyr Asn Leu Asp Lys Gly Tyr Phe Glu Phe Ser Phe
1115                1120                1125

Asp Tyr Lys Asn Phe Gly Asp Lys Ala Ala Lys Gly Lys Trp Thr
1130                1135                1140

Ile Ala Ser Phe Gly Ser Arg Leu Ile Asn Phe Arg Asn Ser Asp
1145                1150                1155

Lys Asn His Asn Trp Asp Thr Arg Glu Val Tyr Pro Thr Lys Glu
1160                1165                1170

Leu Glu Lys Leu Leu Lys Asp Tyr Ser Ile Glu Tyr Gly His Gly
1175                1180                1185

Glu Cys Ile Lys Ala Ala Ile Cys Gly Glu Ser Asp Lys Lys Phe
1190                1195                1200

Phe Ala Lys Leu Thr Ser Val Leu Asn Thr Ile Leu Gln Met Arg
1205                1210                1215

Asn Ser Lys Thr Gly Thr Glu Leu Asp Tyr Leu Ile Ser Pro Val
1220                1225                1230

Ala Asp Val Asn Gly Asn Phe Phe Asp Ser Arg Gln Ala Pro Lys
1235                1240                1245

Asn Met Pro Gln Asp Ala Asp Ala Asn Gly Ala Tyr His Ile Gly
1250                1255                1260

Leu Lys Gly Leu Met Leu Leu Asp Arg Ile Lys Asn Asn Gln Glu
1265                1270                1275

Gly Lys Lys Leu Asn Leu Val Ile Lys Asn Glu Glu Tyr Phe Glu
1280                1285                1290

Phe Val Gln Asn Arg Asn Asn
1295                1300

<210> SEQ ID NO 173
<211> LENGTH: 36
<212> TYPE: DNA
<213> ORGANISM: Unknown
<220> FEATURE:
<223> OTHER INFORMATION: Lachnospiraceae bacterium ND2006

<400> SEQUENCE: 173
gtttcaaaga ttaaataatt tctactaagt gtagat                          36

<210> SEQ ID NO 174
<211> LENGTH: 28
<212> TYPE: DNA
<213> ORGANISM: Unknown
<220> FEATURE:
<223> OTHER INFORMATION: Lachnospiraceae bacterium ND2006

<400> SEQUENCE: 174
cggtctcgca aagaatggat atactcat                                    28

<210> SEQ ID NO 175
<211> LENGTH: 49
<212> TYPE: DNA
<213> ORGANISM: Unknown
<220> FEATURE:
<223> OTHER INFORMATION: Lachnospiraceae bacterium ND2006

```
<400> SEQUENCE: 175
taatttctac taagtgtaga tcggtctcgc aaagaatgga tatactcat                49

<210> SEQ ID NO 176
<211> LENGTH: 35
<212> TYPE: DNA
<213> ORGANISM: Unknown
<220> FEATURE:
<223> OTHER INFORMATION: Acidaminococcus sp. BV3L6

<400> SEQUENCE: 176
gtcaaaagac ctttttaatt tctactcttg tagat                               35

<210> SEQ ID NO 177
<211> LENGTH: 26
<212> TYPE: DNA
<213> ORGANISM: Unknown
<220> FEATURE:
<223> OTHER INFORMATION: Acidaminococcus sp. BV3L6

<400> SEQUENCE: 177
gtctaaactg gtcgaaatcg accagt                                         26

<210> SEQ ID NO 178
<211> LENGTH: 46
<212> TYPE: DNA
<213> ORGANISM: Unknown
<220> FEATURE:
<223> OTHER INFORMATION: Acidaminococcus sp. BV3L6

<400> SEQUENCE: 178
taatttctac tcttgtagat gtctaaactg gtcgaaatcg accagt                   46

<210> SEQ ID NO 179
<211> LENGTH: 41
<212> TYPE: RNA
<213> ORGANISM: Artificial sequence
<220> FEATURE:
<223> OTHER INFORMATION: Synthetic construct

<400> SEQUENCE: 179
uaauuucuac ucuuguagau uggacagagc uccaagugac c                        41

<210> SEQ ID NO 180
<211> LENGTH: 19
<212> TYPE: RNA
<213> ORGANISM: Artificial sequence
<220> FEATURE:
<223> OTHER INFORMATION: Synthetic construct

<400> SEQUENCE: 180
uaauuucuac ucuuguaga                                                 19

<210> SEQ ID NO 181
<211> LENGTH: 21
<212> TYPE: RNA
<213> ORGANISM: Artificial sequence
<220> FEATURE:
<223> OTHER INFORMATION: Synthetic construct

<400> SEQUENCE: 181
uggacagagc uccaagugac c                                              21

<210> SEQ ID NO 182
<211> LENGTH: 1259
```

-continued

```
<212> TYPE: PRT
<213> ORGANISM: Artificial sequence
<220> FEATURE:
<223> OTHER INFORMATION: Synthetic construct

<400> SEQUENCE: 182
```

Gly Pro Ala Gly Ser Gly Gly Pro Lys Lys Arg Lys Val Gly Gly
1               5                   10                  15

Ser Gly Met Ser Lys Leu Glu Lys Phe Thr Asn Cys Tyr Ser Leu Ser
            20                  25                  30

Lys Thr Leu Arg Phe Lys Ala Ile Pro Val Gly Lys Thr Gln Glu Asn
        35                  40                  45

Ile Asp Asn Lys Arg Leu Leu Val Glu Asp Glu Lys Arg Ala Glu Asp
50                  55                  60

Tyr Lys Gly Val Lys Lys Leu Leu Asp Arg Tyr Tyr Leu Ser Phe Ile
65                  70                  75                  80

Asn Asp Val Leu His Ser Ile Lys Leu Lys Asn Leu Asn Asn Tyr Ile
                85                  90                  95

Ser Leu Phe Arg Lys Lys Thr Arg Thr Glu Lys Glu Asn Lys Glu Leu
            100                 105                 110

Glu Asn Leu Glu Ile Asn Leu Arg Lys Glu Ile Ala Lys Ala Phe Lys
        115                 120                 125

Gly Asn Glu Gly Tyr Lys Ser Leu Phe Lys Lys Asp Ile Ile Glu Thr
130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
                165                 170                 175

Glu Asn Met Phe Ser Glu Glu Ala Lys Ser Thr Ser Ile Ala Phe Arg
            180                 185                 190

Cys Ile Asn Glu Asn Leu Thr Arg Tyr Ile Ser Asn Met Asp Ile Phe
        195                 200                 205

Glu Lys Val Asp Ala Ile Phe Asp Lys His Glu Val Gln Glu Ile Lys
210                 215                 220

Glu Lys Ile Leu Asn Ser Asp Tyr Asp Val Glu Asp Phe Phe Glu Gly
225                 230                 235                 240

Glu Phe Phe Asn Phe Val Leu Thr Gln Glu Gly Ile Asp Val Tyr Asn
                245                 250                 255

Ala Ile Ile Gly Gly Phe Val Thr Glu Ser Gly Glu Lys Ile Lys Gly
            260                 265                 270

Leu Asn Glu Tyr Ile Asn Leu Tyr Asn Gln Lys Thr Lys Gln Lys Leu
        275                 280                 285

Pro Lys Phe Lys Pro Leu Tyr Lys Gln Val Leu Ser Asp Arg Glu Ser
290                 295                 300

Leu Ser Phe Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
                325                 330                 335

Lys Lys Leu Glu Lys Leu Phe Lys Asn Phe Asp Glu Tyr Ser Ser Ala
            340                 345                 350

Gly Ile Phe Val Lys Asn Gly Pro Ala Ile Ser Thr Ile Ser Lys Asp
        355                 360                 365

Ile Phe Gly Glu Trp Asn Val Ile Arg Asp Lys Trp Asn Ala Glu Tyr
370                 375                 380

```
Asp Asp Ile His Leu Lys Lys Lys Ala Val Val Thr Glu Lys Tyr Glu
385                 390                 395                 400

Asp Asp Arg Arg Lys Ser Phe Lys Lys Ile Gly Ser Phe Ser Leu Glu
            405                 410                 415

Gln Leu Gln Glu Tyr Ala Asp Ala Asp Leu Ser Val Val Glu Lys Leu
        420                 425                 430

Lys Glu Ile Ile Ile Gln Lys Val Asp Glu Ile Tyr Lys Val Tyr Gly
    435                 440                 445

Ser Ser Glu Lys Leu Phe Asp Ala Asp Phe Val Leu Glu Lys Ser Leu
450                 455                 460

Lys Lys Asn Asp Ala Val Val Ala Ile Met Lys Asp Leu Leu Asp Ser
465                 470                 475                 480

Val Lys Ser Phe Glu Asn Tyr Ile Lys Ala Phe Phe Gly Gly Lys
            485                 490                 495

Glu Thr Asn Arg Asp Glu Ser Phe Tyr Gly Asp Phe Val Leu Ala Tyr
                500                 505                 510

Asp Ile Leu Leu Lys Val Asp His Ile Tyr Asp Ala Ile Arg Asn Tyr
        515                 520                 525

Val Thr Gln Lys Pro Tyr Ser Lys Asp Lys Phe Lys Leu Tyr Phe Gln
    530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Tyr Leu Ala Ile Met
                565                 570                 575

Asp Lys Lys Tyr Ala Lys Cys Leu Gln Lys Ile Asp Lys Asp Asp Val
        580                 585                 590

Asn Gly Asn Tyr Glu Lys Ile Asn Tyr Lys Leu Leu Pro Gly Pro Asn
    595                 600                 605

Lys Met Leu Pro Lys Val Phe Phe Ser Lys Lys Trp Met Ala Tyr Tyr
610                 615                 620

Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
                645                 650                 655

Phe Lys Asp Ser Ile Ser Arg Tyr Pro Lys Trp Ser Asn Ala Tyr Asp
        660                 665                 670

Phe Asn Phe Ser Glu Thr Glu Lys Tyr Lys Asp Ile Ala Gly Phe Tyr
    675                 680                 685

Arg Glu Val Glu Glu Gln Gly Tyr Lys Val Ser Phe Glu Ser Ala Ser
690                 695                 700

Lys Lys Glu Val Asp Lys Leu Val Glu Glu Gly Lys Leu Tyr Met Phe
705                 710                 715                 720

Gln Ile Tyr Asn Lys Asp Phe Ser Asp Lys Ser His Gly Thr Pro Asn
                725                 730                 735

Leu His Thr Met Tyr Phe Lys Leu Leu Phe Asp Glu Asn Asn His Gly
        740                 745                 750

Gln Ile Arg Leu Ser Gly Gly Ala Glu Leu Phe Met Arg Arg Ala Ser
    755                 760                 765

Leu Lys Lys Glu Glu Leu Val Val His Pro Ala Asn Ser Pro Ile Ala
770                 775                 780

Asn Lys Asn Pro Asp Asn Pro Lys Lys Thr Thr Thr Leu Ser Tyr Asp
785                 790                 795                 800

Val Tyr Lys Asp Lys Arg Phe Ser Glu Asp Gln Tyr Glu Leu His Ile
```

-continued

Pro Ile Ala Ile Asn Lys Cys Pro Lys Asn Ile Phe Lys Ile Asn Thr
         805                 810                 815
Glu Val Arg Val Leu Lys His Asp Asp Asn Pro Tyr Val Ile Gly
    820                 825                 830
Ile Asp Arg Gly Glu Arg Asn Leu Leu Tyr Ile Val Val Asp Gly
    835                 840                 845
Lys Gly Asn Ile Val Glu Gln Tyr Ser Leu Asn Glu Ile Ile Asn Asn
850                 855                 860
Phe Asn Gly Ile Arg Ile Lys Thr Asp Tyr His Ser Leu Leu Asp Lys
    865                 870                 875                 880
Lys Glu Lys Glu Arg Phe Glu Ala Arg Gln Asn Trp Thr Ser Ile Glu
            885                 890                 895
Asn Ile Lys Glu Leu Lys Ala Gly Tyr Ile Ser Gln Val Val His Lys
    900                 905                 910
Ile Cys Glu Leu Val Glu Lys Tyr Asp Ala Val Ile Ala Leu Glu Asp
    915                 920                 925
Leu Asn Ser Gly Phe Lys Asn Ser Arg Val Lys Val Glu Lys Gln Val
930                 935                 940
Tyr Gln Lys Phe Glu Lys Met Leu Ile Asp Lys Leu Asn Tyr Met Val
            945                 950                 955                 960
Asp Lys Lys Ser Asn Pro Cys Ala Thr Gly Gly Ala Leu Lys Gly Tyr
    965                 970                 975
Gln Ile Thr Asn Lys Phe Glu Ser Phe Lys Ser Met Ser Thr Gln Asn
    980                 985                 990
Gly Phe Ile Phe Tyr Ile Pro Ala Trp Leu Thr Ser Lys Ile Asp
    995                 1000                1005
Pro Ser Thr Gly Phe Val Asn Leu Leu Lys Thr Lys Tyr Thr Ser
    1010                1015                1020
Ile Ala Asp Ser Lys Lys Phe Ile Ser Ser Phe Asp Arg Ile Met
    1025                1030                1035
Tyr Val Pro Glu Glu Asp Leu Phe Glu Phe Ala Leu Asp Tyr Lys
    1040                1045                1050
Asn Phe Ser Arg Thr Asp Ala Asp Tyr Ile Lys Lys Trp Lys Leu
    1055                1060                1065
Tyr Ser Tyr Gly Asn Arg Ile Arg Ile Phe Arg Asn Pro Lys Lys
    1070                1075                1080
Asn Asn Val Phe Asp Trp Glu Glu Val Cys Leu Thr Ser Ala Tyr
    1085                1090                1095
Lys Glu Leu Phe Asn Lys Tyr Gly Ile Asn Tyr Gln Gln Gly Asp
    1100                1105                1110
Ile Arg Ala Leu Leu Cys Glu Gln Ser Asp Lys Ala Phe Tyr Ser
    1115                1120                1125
Ser Phe Met Ala Leu Met Ser Leu Met Leu Gln Met Arg Asn Ser
    1130                1135                1140
Ile Thr Gly Arg Thr Asp Val Asp Phe Leu Ile Ser Pro Val Lys
    1145                1150                1155
Asn Ser Asp Gly Ile Phe Tyr Asp Ser Arg Asn Tyr Glu Ala Gln
    1160                1165                1170
Glu Asn Ala Ile Leu Pro Lys Asn Ala Asp Ala Asn Gly Ala Tyr
    1175                1180                1185
Asn Ile Ala Arg Lys Val Leu Trp Ala Ile Gly Gln Phe Lys Lys
    1190                1195                1200
                1205                1210                1215

```
Ala Glu Asp Glu Lys Leu Asp Lys Val Lys Ile Ala Ile Ser Asn
    1220            1225                1230

Lys Glu Trp Leu Glu Tyr Ala Gln Thr Ser Val Lys His Gly Gly
    1235            1240                1245

Ser Gly Pro Lys Lys Arg Lys Val Gly Gly
    1250            1255
```

```
<210> SEQ ID NO 183
<211> LENGTH: 5
<212> TYPE: DNA
<213> ORGANISM: Artificial sequence
<220> FEATURE:
<223> OTHER INFORMATION: Synthetic construct

<400> SEQUENCE: 183 ggtga                                                          5

<210> SEQ ID NO 184
<211> LENGTH: 5
<212> TYPE: DNA
<213> ORGANISM: Artificial sequence
<220> FEATURE:
<223> OTHER INFORMATION: Synthetic construct

<400> SEQUENCE: 184 ggtga                                                          5

<210> SEQ ID NO 185
<211> LENGTH: 6
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: R is A or G

<400> SEQUENCE: 185 tccrac                                                         6

<210> SEQ ID NO 186
<211> LENGTH: 5
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: S is G or C

<400> SEQUENCE: 186 ttsaa                                                          5

<210> SEQ ID NO 187
<211> LENGTH: 11
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(9)
<223> OTHER INFORMATION: N is A, C, G, or T

<400> SEQUENCE: 187
```

-continued

```
gcnnnnnnng c                                                            11

<210> SEQ ID NO 188
<211> LENGTH: 4
<212> TYPE: DNA
<213> ORGANISM: Artificial sequence
<220> FEATURE:
<223> OTHER INFORMATION: Synthetic construct

<400> SEQUENCE: 188 gcgc                                                                     4

<210> SEQ ID NO 189
<211> LENGTH: 4
<212> TYPE: DNA
<213> ORGANISM: Artificial sequence
<220> FEATURE:
<223> OTHER INFORMATION: Synthetic construct

<400> SEQUENCE: 189 gcgc                                                                     4

<210> SEQ ID NO 190
<211> LENGTH: 4
<212> TYPE: DNA
<213> ORGANISM: Artificial sequence
<220> FEATURE:
<223> OTHER INFORMATION: Synthetic construct

<400> SEQUENCE: 190 gcgc                                                                     4

<210> SEQ ID NO 191
<211> LENGTH: 6
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: R is A or G
<220> FEATURE:
<221> NAME/KEY: misc_feature
<222> LOCATION: (5)..(5)
<223> OTHER INFORMATION: Y is C or T

<400> SEQUENCE: 191 grcgyc                                                                   6

<210> SEQ ID NO 192
<211> LENGTH: 6
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: R is A or G
<220> FEATURE:
<221> NAME/KEY: misc_feature
<222> LOCATION: (6)..(6)
<223> OTHER INFORMATION: Y is C or T

<400> SEQUENCE: 192 rgcgcy                                                                   6
```

```
<210> SEQ ID NO 193
<211> LENGTH: 6
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(4)
<223> OTHER INFORMATION: N is A, C, G, or T

<400> SEQUENCE: 193 ggnncc                                                                     6

<210> SEQ ID NO 194
<211> LENGTH: 6
<212> TYPE: DNA
<213> ORGANISM: Artificial sequence
<220> FEATURE:
<223> OTHER INFORMATION: Synthetic construct

<400> SEQUENCE: 194 ggcgcc                                                                     6

<210> SEQ ID NO 195
<211> LENGTH: 6
<212> TYPE: DNA
<213> ORGANISM: Artificial sequence
<220> FEATURE:
<223> OTHER INFORMATION: Synthetic construct

<400> SEQUENCE: 195 ggcgcc                                                                     6

<210> SEQ ID NO 196
<211> LENGTH: 6
<212> TYPE: DNA
<213> ORGANISM: Artificial sequence
<220> FEATURE:
<223> OTHER INFORMATION: Synthetic construct

<400> SEQUENCE: 196 ggcgcc                                                                     6

<210> SEQ ID NO 197
<211> LENGTH: 6
<212> TYPE: DNA
<213> ORGANISM: Artificial sequence
<220> FEATURE:
<223> OTHER INFORMATION: Synthetic construct

<400> SEQUENCE: 197 ggcgcc                                                                     6

<210> SEQ ID NO 198
<211> LENGTH: 6
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Y is C or T
<220> FEATURE:
<221> NAME/KEY: misc_feature
<222> LOCATION: (4)..(4)
<223> OTHER INFORMATION: R is A or G
```

```
<400> SEQUENCE: 198 ggyrcc                                                                    6

<210> SEQ ID NO 199
<211> LENGTH: 6
<212> TYPE: DNA
<213> ORGANISM: Artificial sequence
<220> FEATURE:
<223> OTHER INFORMATION: Synthetic construct

<400> SEQUENCE: 199 atgcat                                                                    6

<210> SEQ ID NO 200
<211> LENGTH: 6
<212> TYPE: DNA
<213> ORGANISM: Artificial sequence
<220> FEATURE:
<223> OTHER INFORMATION: Synthetic construct

<400> SEQUENCE: 200 gaatgc                                                                    6

<210> SEQ ID NO 201
<211> LENGTH: 10
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Y is C or T
<220> FEATURE:
<221> NAME/KEY: misc_feature
<222> LOCATION: (4)..(7)
<223> OTHER INFORMATION: N is A, C, G, or T
<220> FEATURE:
<221> NAME/KEY: misc_feature
<222> LOCATION: (8)..(8)
<223> OTHER INFORMATION: R is A or G

<400> SEQUENCE: 201 caynnnnrtg                                                               10

<210> SEQ ID NO 202
<211> LENGTH: 5
<212> TYPE: DNA
<213> ORGANISM: Artificial sequence
<220> FEATURE:
<223> OTHER INFORMATION: Synthetic construct

<400> SEQUENCE: 202 atgaa                                                                     5

<210> SEQ ID NO 203
<211> LENGTH: 6
<212> TYPE: DNA
<213> ORGANISM: Artificial sequence
<220> FEATURE:
<223> OTHER INFORMATION: Synthetic construct

<400> SEQUENCE: 203 catatg                                                                    6
```